US012497462B2

(12) United States Patent
Wong et al.

(10) Patent No.: US 12,497,462 B2
(45) Date of Patent: Dec. 16, 2025

(54) ANTI-CD26 PROTEINS AND USES THEREOF

(71) Applicant: ImmunityBio, Inc., San Diego, CA (US)

(72) Inventors: Hing C. Wong, Miramar, FL (US); Bai Liu, Miramar, FL (US); Lin Kong, Miramar, FL (US); Xiaoyun Zhu, Miramar, FL (US); Catherine Spanoudis, Miramar, FL (US)

(73) Assignee: ImmunityBio, Inc., San Diego, CA (US)

(*) Notice: Subject to any disclaimer, the term of this patent is extended or adjusted under 35 U.S.C. 154(b) by 617 days.

(21) Appl. No.: 17/922,067

(22) PCT Filed: Apr. 29, 2021

(86) PCT No.: PCT/US2021/029920

§ 371 (c)(1),
(2) Date: Oct. 28, 2022

(87) PCT Pub. No.: WO2021/222587

PCT Pub. Date: Nov. 4, 2021

(65) Prior Publication Data

US 2023/0174666 A1 Jun. 8, 2023

Related U.S. Application Data

(60) Provisional application No. 63/017,467, filed on Apr. 29, 2020.

(51) Int. Cl.

| | |
|---|---|
| ***C07K 16/28*** | (2006.01) |
| ***A61K 35/17*** | (2025.01) |
| ***A61K 38/17*** | (2006.01) |
| ***A61K 39/00*** | (2006.01) |
| ***A61K 40/11*** | (2025.01) |
| ***A61K 40/31*** | (2025.01) |
| ***A61K 40/42*** | (2025.01) |
| ***C07K 16/40*** | (2006.01) |
| ***C12N 5/10*** | (2006.01) |

(52) U.S. Cl.

CPC .......... *C07K 16/2896* (2013.01); *A61K 35/17* (2013.01); *A61K 38/1774* (2013.01); *A61K 39/001154* (2018.08); *A61K 40/31* (2025.01); *A61K 40/4224* (2025.01); *A61K 39/00* (2013.01); *A61K 40/11* (2025.01); *A61K 40/4244* (2025.01); *C07K 16/40* (2013.01); *C07K 2317/21* (2013.01); *C07K 2317/24* (2013.01); *C07K 2317/622* (2013.01); *C12N 5/10* (2013.01); *C12N 2510/00* (2013.01); *C12N 2800/00* (2013.01)

(58) Field of Classification Search

CPC ........... C07K 16/2896; C07K 2317/21; C07K 2317/24; C07K 2317/622; A61K 35/17; A61K 38/1774; A61K 39/001154; A61K 40/31; A61K 40/4224; A61K 39/00; A61K 40/11; C12N 5/10; C12N 2510/00; C12N 2800/00

See application file for complete search history.

(56) References Cited

U.S. PATENT DOCUMENTS

| | | | |
|---|---|---|---|
| 6,117,980 | A | 9/2000 | Gonzalez et al. |
| 7,452,537 | B2 | 11/2008 | Bauer et al. |
| 7,482,436 | B2 | 1/2009 | Sugimura et al. |
| 7,488,802 | B2 | 2/2009 | Collins et al. |
| 7,521,051 | B2 | 4/2009 | Collins et al. |
| 7,612,181 | B2 | 11/2009 | Wu et al. |
| 7,691,380 | B2 | 4/2010 | Thorpe et al. |
| 7,723,482 | B2 | 5/2010 | Soulillou et al. |
| 7,968,094 | B2 | 6/2011 | Jiao et al. |
| 8,007,795 | B2 | 8/2011 | Jiao et al. |
| 8,133,485 | B2 | 3/2012 | Levi-Schaffer et al. |
| 8,217,149 | B2 | 7/2012 | Irving et al. |
| 8,258,268 | B2 | 9/2012 | Wu et al. |
| 8,475,792 | B2 | 7/2013 | Dall'Acqua et al. |
| 8,552,156 | B2 | 10/2013 | Takayanagi et al. |
| 8,586,714 | B2 | 11/2013 | Ghayur et al. |
| 8,716,450 | B2 | 5/2014 | Ghayur et al. |
| 8,722,855 | B2 | 5/2014 | Ghayur et al. |
| 8,735,546 | B2 | 5/2014 | Ghayur et al. |
| 8,741,604 | B2 | 6/2014 | Campbell et al. |

(Continued)

FOREIGN PATENT DOCUMENTS

| | | |
|---|---|---|
| CN | 1844150 | 10/2006 |
| CN | 101653603 | 2/2010 |

(Continued)

OTHER PUBLICATIONS

Inamoto T, Yamada T, Ohnuma K, Kina S, Takahashi N, Yamochi T, Inamoto S, Katsuoka Y, Hosono O, Tanaka H, Dang NH, Morimoto C. Humanized anti-CD26 monoclonal antibody as a treatment for malignant mesothelioma tumors. Clin Cancer Res. Jul. 15, 2007;13(14):4191-200. doi: 10.1158/1078-0432.CCR-07-0110. (Year: 2007).*

(Continued)

*Primary Examiner* — Janet L Andres

*Assistant Examiner* — Carol Ann Chase

(74) *Attorney, Agent, or Firm* — Sheridan Ross P.C.

(57) ABSTRACT

Provided herein are proteins comprising an anti-CD26 antigen-binding domain. Also provided herein are methods of treating an aging-related disease or an inflammatory disease in a subject that include administering to the subject one of these proteins or a cell expressing one of these proteins.

21 Claims, 20 Drawing Sheets

Specification includes a Sequence Listing.

(56) References Cited

U.S. PATENT DOCUMENTS

| | | | |
|---|---|---|---|
| 8,753,640 | B2 | 6/2014 | Wu et al. |
| 8,759,494 | B2 | 6/2014 | Bachmann et al. |
| 8,822,645 | B2 | 9/2014 | Ghayur et al. |
| 9,035,026 | B2 | 5/2015 | Hoffmann et al. |
| 9,067,997 | B2 | 6/2015 | Romagne et al. |
| 9,085,623 | B2 | 7/2015 | Rother et al. |
| 9,090,684 | B2 | 7/2015 | Borras et al. |
| 9,226,962 | B2 | 1/2016 | Le Gall et al. |
| 9,238,084 | B2 | 1/2016 | Liu et al. |
| 9,273,136 | B2 | 3/2016 | Rader et al. |
| 9,371,395 | B2 | 6/2016 | Takahashi et al. |
| 9,441,034 | B2 | 9/2016 | Sivakumar et al. |
| 9,505,843 | B2 | 11/2016 | Kim et al. |
| 9,617,345 | B2 | 4/2017 | Berne et al. |
| 9,701,758 | B2 | 7/2017 | Cooper et al. |
| 9,920,135 | B2 * | 3/2018 | Morimoto ........ G01N 33/57419 |
| 11,518,792 | B2 | 12/2022 | Wong |
| 11,672,826 | B2 | 6/2023 | Wong |
| 11,730,762 | B2 | 8/2023 | Wong |
| 11,738,052 | B2 | 8/2023 | Wong |
| 12,018,071 | B2 | 6/2024 | Wong |
| 12,024,545 | B2 | 7/2024 | Wong et al. |
| 2001/0044427 | A1 | 11/2001 | Mazel et al. |
| 2003/0124678 | A1 | 7/2003 | Epstein et al. |
| 2003/0219441 | A1 | 11/2003 | Thorpe et al. |
| 2005/0014224 | A1 | 1/2005 | Collins et al. |
| 2006/0159655 | A1 | 7/2006 | Collins et al. |
| 2007/0160579 | A1 | 7/2007 | Schmitz et al. |
| 2008/0025979 | A1 | 1/2008 | Honjo et al. |
| 2009/0148942 | A1 | 6/2009 | McDonagh et al. |
| 2012/0171197 | A1 | 7/2012 | Eriksson et al. |
| 2012/0264920 | A1 | 10/2012 | Wang et al. |
| 2013/0274446 | A1 | 10/2013 | Kumagai et al. |
| 2014/0242077 | A1 | 8/2014 | Choi |
| 2015/0218274 | A1 | 8/2015 | Sabatos-Peyton et al. |
| 2015/0259429 | A1 | 9/2015 | Benaroch et al. |
| 2016/0175397 | A1 | 6/2016 | Umana et al. |
| 2016/0340413 | A1 | 11/2016 | Duerner et al. |
| 2016/0367664 | A1 | 12/2016 | Wang et al. |
| 2017/0051063 | A1 | 2/2017 | Baum et al. |
| 2017/0198042 | A1 | 7/2017 | Williams et al. |
| 2017/0283499 | A1 | 10/2017 | Delhem et al. |
| 2018/0200366 | A1 | 7/2018 | Wong |
| 2019/0078082 | A1 | 3/2019 | Amorese et al. |
| 2019/0092846 | A1 | 3/2019 | Ibebunjo et al. |
| 2019/0177406 | A1 | 6/2019 | Ledbetter et al. |
| 2019/0315850 | A1 | 10/2019 | Bedinger et al. |
| 2020/0071374 | A1 | 3/2020 | Wong |
| 2020/0123607 | A1 | 4/2020 | Serrano Marugan et al. |
| 2020/0190174 | A1 | 6/2020 | Wong |
| 2020/0392221 | A1 | 12/2020 | Van Snick et al. |
| 2020/0399358 | A1 | 12/2020 | Shapiro et al. |
| 2021/0060064 | A1 | 3/2021 | Wong |
| 2021/0061897 | A1 | 3/2021 | Ledbetter et al. |
| 2021/0070825 | A1 | 3/2021 | Wong |
| 2021/0070826 | A1 | 3/2021 | Wong |
| 2021/0100840 | A1 | 4/2021 | Wong et al. |
| 2021/0137981 | A1 | 5/2021 | Wong |
| 2021/0268022 | A1 | 9/2021 | Wong et al. |
| 2021/0277054 | A1 | 9/2021 | Wong et al. |
| 2021/0338724 | A1 | 11/2021 | Wong |
| 2021/0355204 | A1 | 11/2021 | Bedinger et al. |
| 2021/0403545 | A1 | 12/2021 | Van Snick et al. |
| 2022/0073578 | A1 | 3/2022 | Wong et al. |
| 2023/0023389 | A1 | 1/2023 | Wong |
| 2023/0039157 | A1 | 2/2023 | Wong |
| 2023/0128292 | A1 | 4/2023 | Wong |
| 2023/0272027 | A1 | 8/2023 | Wong |
| 2023/0372399 | A1 | 11/2023 | Wong |
| 2023/0372444 | A1 | 11/2023 | Wong et al. |
| 2023/0381238 | A1 | 11/2023 | Wong |
| 2023/0398151 | A1 | 12/2023 | Wong |
| 2024/0124543 | A1 | 4/2024 | Wong |
| 2024/0124544 | A1 | 4/2024 | Wong |
| 2024/0132561 | A1 | 4/2024 | Wong |

FOREIGN PATENT DOCUMENTS

| | | |
|---|---|---|
| CN | 101965364 | 2/2011 |
| CN | 102153653 | 8/2011 |
| CN | 106255703 | 12/2016 |
| CN | 109513003 | 3/2019 |
| EP | 1245676 | 10/2002 |
| EP | 1719528 | 11/2006 |
| EP | 2537933 | 12/2012 |
| EP | 3029069 | 6/2016 |
| EP | 3348276 | 7/2018 |
| JP | 2005-124568 | 5/2005 |
| JP | 2008-536487 | 9/2008 |
| JP | 2009-512433 | 3/2009 |
| JP | 4361133 | 8/2009 |
| KR | 2016/0127688 | 11/2016 |
| KR | 101778439 | 9/2017 |
| WO | WO 1995/015341 | 6/1995 |
| WO | WO 1996/001653 | 1/1996 |
| WO | WO 2001/083755 | 11/2001 |
| WO | WO 2002/083152 | 10/2002 |
| WO | WO 2003/037911 | 5/2003 |
| WO | WO 2003/104425 | 12/2003 |
| WO | WO 2004/076488 | 9/2004 |
| WO | WO 2006/096828 | 9/2006 |
| WO | WO 2006/097743 | 9/2006 |
| WO | WO 2006/119897 | 11/2006 |
| WO | WO 2008/096158 | 8/2008 |
| WO | WO 2011/127324 | 10/2011 |
| WO | WO 2012/040323 | 3/2012 |
| WO | WO 2012/120125 | 9/2012 |
| WO | WO 2012/170470 | 12/2012 |
| WO | WO 2012/175222 | 12/2012 |
| WO | WO 2012/175692 | 12/2012 |
| WO | WO 2013/068946 | 5/2013 |
| WO | WO 2014/007513 | 1/2014 |
| WO | WO 2014/026054 | 2/2014 |
| WO | WO 2014/095808 | 6/2014 |
| WO | WO 2014/130635 | 8/2014 |
| WO | WO 2014/159531 | 10/2014 |
| WO | WO 2015/089881 | 6/2015 |
| WO | WO 2016/106221 | 6/2016 |
| WO | WO 2016/154585 | 9/2016 |
| WO | WO 2016/166348 | 10/2016 |
| WO | WO 2017/053748 | 3/2017 |
| WO | WO 2017/083612 | 5/2017 |
| WO | WO 2017/149538 | 9/2017 |
| WO | WO 2017/189526 | 11/2017 |
| WO | WO 2018/067825 | 4/2018 |
| WO | WO 2018/075989 | 4/2018 |
| WO | WO 2018/129007 | 7/2018 |
| WO | WO 2018/158350 | 9/2018 |
| WO | WO 2018/183169 | 10/2018 |
| WO | WO 2018/165208 | 12/2018 |
| WO | WO 2019/046313 | 3/2019 |
| WO | WO 2020/047299 | 3/2020 |
| WO | WO 2020/047333 | 3/2020 |
| WO | WO 2020/047462 | 3/2020 |
| WO | WO 2020/047473 | 3/2020 |
| WO | WO 2021/163369 | 8/2021 |

OTHER PUBLICATIONS

Abbott et al., "Genomic organization, exact localization, and tissue expression of the human CD26 (dipeptidyl peptidase IV) gene," Immunogentics, Sep. 1994, 40(5):331-338.

Abdul-Aziz et al., "Acute myeloid leukemia induces protumoral p16INK4a-driven senescence in the bone marrow microenvironment," Blood, Jan. 31, 2019, 133(5):446-456.

Aertgeerts et al., "Crystal structure of human dipeptidyl peptidase IV in complex with a decapeptide reveals details on substrate specificity and tetrahedral intermediate formation," Protein Science, Feb. 2004, 13(2):412-421.

Ait-Oufella el al., "Natural regulatory T cells control the development of atherosclerosis in mice," Nature Medicine, Feb. 5, 2006, 12:178-180.

(56) References Cited

OTHER PUBLICATIONS

Akbari, et al., "Design, expression and evaluation of a novel humanized single chain antibody against epidermal growth factor receptor (EGFR)," Protein Expr. Purif., 2016, 127:8-15.
Ali et al., "Regulatory T cells in skin," Immunology, Jul. 12, 2017, 152(3):372-381.
Angevin et al., "First-in-human phase 1 of YS110, a monoclonal antibody directed against CD26 in advanced CD26-expressing cancers," British Journal of Cancer, Mar. 14, 2017, 116(9):1126-1134.
Bachelet et al., "Mast Cell Costimulation by CD226/CD112 (DNAM-1/Nectin-2) a Novel Interface in the Allergic Process," Journal of Biological Chemistry, Sep. 15, 2006, 281(37):27190-6.
Baker et al., "Chronic treatment with the beta(2)-adrenoceptor agonist prodrug BRL-47672 impairs rat skeletal muscle function by inducing a comprehensive shift to a faster muscle phenotype," J Pharmacol Exp Ther., Oct. 2006, 319(1):439-446.
Baker et al., "Effects of conjugated linoleic acid (CLA) on tissue composition parameters in a murine cachexia model," The FASEB Journal, Mar. 2006, 20(4), 2 pages (Abstract Only).
Baker, et al., "Clearance of p16Ink4a-positive senescent cells delays ageing-associated disorders," Nature, 2011, 479(7372):232-236.
Bennett et al., "Erratum: Killing the old: cell senescence in atherosclerosis," Nature Reviews Cardiology, Jan. 12, 2017, 14(3):132.
Bennett et al., "Killing the old: cell senescence in atherosclerosis," Nature Reviews Cardiology, Dec. 12, 2016, 14(1):8-9, 2 pages.
Bentebibel et al., "A First-in-Human Study and Biomarker Analysis of NKTR-214, a Novel IL2Raf Biased Cytokine, in Patients with Advanced or Metastatic Solid Tumors," Cancer Discovery, Jun. 2019, 9(6):711-721.
Berry et al., "Cancer Anorexia and Cachexia: Screening in an Ambulatory Infusion Service and Nutrition Consultation," Clin J Oncol Nurs., 2018, 22(1):63-68.
Bhat et al., "Astrocyte Senescence as a Component of Alzheimer's Disease," PLoS One, Sep. 12, 2012, 7(9):e45069, 10 pages.
Biran et al., "Senescent cells communicate via intercellular protein transfer," Genes & Development, Apr. 8, 2015, 29(8):791-802, 13 pages.
Borea et al., "Pharmacology of Adenosine Receptors: The State of the Art," Physiological Reviews, May 31, 2018, 98(3):1591-1625.
Borgerding et al., "B-lymphoma cells escape rituximab-triggered elimination by NK cells through increased HLA class I expression," Experimental Hematology, Mar. 1, 2010, 38(3):213-21.
Bork, "Powers and Pitfalls in Sequence Analysis: The 70% Hurdle," Genome Research, 2000, 10:398-400.
Bourgeois et al., "Regulation of cellular senescence via the FOXO4-p53 axis," FEBS Lett., 2018, 592(12): 2083-2097.
Bowie et al., "Deciphering the Message in Protein Sequences: Tolerance to Amino Acid Substitutions," Science, 1990, 247:1306-1310.
Boyman et al., "IL-7/Anti-IL-7 mAb Complexes Restore T Cell Development and Induce Homeostatic T Cell Expansion without Lymphopenia," The Journal of Immunology, Jun. 1, 2008, 180:7265-7275.
Boyman et al., "Selective Stimulation of T Cell Subsets with Antibody-Cytokine Immune Complexes," Science, Mar. 31, 2006, 311(5769):1924-1927.
Brennan et al., "Structural determination of lipid antigens captured at the CD1d-T-cell receptor interface," PNAS, 2017, 114(31):8348-8353.
Brighton et al., "Clearance of senescent decidual cells by uterine natural killer cells in cycling human endometrium," Elife, Dec. 11, 2017, 6:e31274, 23 pages.
Brooks et al., "Combined inhibition of PD1 and CD96 checkpoints improves survival in a resectable murine model of pancreatic cancer," European Journal of Cancer, Jul. 1, 2016, 61:S189, 1 page.
Broxmeyer et al., "Modulation of Hematopoietic Chemokine Effects In Vitro and In Vivo by DPP-4/CD26," Stem Cells and Development, Mar. 4, 2016, 25(8):575-585.
Brunstein et al., "Infusion of Ex Vivo Expanded T Regulatory Cells in Adults Transplanted with Umbilical Cord Blood: Safety Profile and Detection Kinetics," Blood, Jan. 20, 2011, 117(3):1061-1070.
Brunstein et al., "Umbilical cord blood-derived T regulatory cells to prevent GVHD:kinetics, toxicity profile, and clinical effect," Blood, Feb. 25, 2016, 127(8):1044-1051.
Buhling et al., "Functional role of CD26 on human B lymphocytes," Immunology Letters, Feb. 1995, 45(1-2):47-51.
Burgess et al., "Possible Dissociation of the Heparin-binding and Mitogenic Activities of Heparin-binding (Acidic Fibroblast) GrowthFactor-1 from Its Receptor-binding Activities by Site-directed Mutagenesis of a Single Lysine Residue," J. Cell Biol., 1990, 111:2129-2138.
Bussian et al., "Clearance of senescent glial cells prevents tau-dependent pathology and cognitive decline," Nature, Sep. 19, 2018, 562(7728):578-582, 21 pages.
Cai et al., "Chibby suppresses aerobic glycolysis and proliferation of nasopharyngeal carcinoma via the Wnt/β-catenin-Lin28/let7-PDK1 cascade," Journal of Experimental & Clinical Cancer Research, Dec. 1, 2018, 37(1):104.
Cao et al., "Expression and characterization of recombinant humanized anti-HER2 single-chain antibody in Pichia pastoris for targeted cancer therapy," Biotechnology Letters, Jul. 1, 2015, 37(7):1347-54.
Cao, "Self-regulation and cross-regulation of pattern-recognition receptor signaling in health and disease," Nature Reviews Immunology, Dec. 29, 2015, 16(1):35-50.
Carr et al., "NK Cell-Mediated Lysis of Autologous HCMV-Infected Skin Fibroblasts Is Highly Variable among NK Cell Clones and Polyclonal NK Cell Lines," Clinical Immunology, Nov. 2002, 105(2):126-140.
Catania et al., "The tumor-targeting immunocytokine F16-IL2 in combination with doxorubicin: dose escalation in patients with advanced solid tumors and expansion into patients with metastatic breast cancer," Cell Adhesion and Migration, Jan.-Apr. 2015, 9(1-2):14-21.
Cavinato et al., "Molecular mechanisms of UVB-induced senescence of dermal fibroblasts and its relevance for photoaging of the human skin," Experimental Gerontology. Aug. 2017, 94:78-82.
Chalan et al., "Expression of Lectin-Like Transcript 1, the Ligand for CD161, in Rheumatoid Arthritis," PLoS ONE, 2015, 10(7):e0132436.
Chambers et al., "Can blocking inflammation enhance immunity during aging?," Journal of Allergy and Clinical Immunology, May 2020, 145(5):1323-1331.
Chance et al., "A simple and rapid assay of oxidative phosphorylation," Nature, Jun. 1955, 175(4469):1120-1121.
Chandrudu et al., "Chemical methods for peptide and protein production," Molecules, 2013, 18(4):4373-4388.
Chang et al., "Association Between Sarcopenia and Cognitive Impairment: A Systematic Review and Meta-Analysis," J Am Med Dir Assoc., Dec. 1, 2016, 17(12):1164e7-1164e15, 9 pages.
Chattopadyhay et al., "Structural Basis of Inducible Costimulator Ligand Costimulatory Function: Determination of the Cell Surface Oligomeric State and Functional Mapping of the Receptor Binding Site of the Protein1," J Immunol., 2006, 3920-3929.
Chen et al., "Circulating levels of resistin and risk of type 2 diabetes in men and women: results from two prospective cohorts," Diabetes Care, Feb. 2009, 32(2):329-334.
Chen et al., "Sterile inflammation: sensing and reacting to damage," Nature Reviews Immunology, Nov. 19, 2010, 10(12):826-837.
Chichili et al., "Linkers in the structural biology of protein-protein interactions," Protein Science, Feb. 2013, 22(2):153-67.
Childs et al., "Senescent cells: an emerging target for diseases of ageing," Nature Reviews Drug Discovery, Jul. 21, 2017, 16(10):718-735, 18 pages.
Childs et al., "Senescent intimal foam cells are deleterious at all stages of atherosclerosis," Science, Oct. 28, 2016, 354(6311):472-477.
Chinta, et al., "Cellular senescence is induced by the environmental neurotoxin paraquat and bontributes to neuropathology linked to Parkinson's Disease," Cell Rep., 2018, 22(4): 930-940.
Chong et al., "CD36 initiates the secretory phenotype during the establishment of cellular senescence," EMBO Rep., May 18, 2018, 19(6):e45274, 13 pages.

(56) References Cited

OTHER PUBLICATIONS

Ciaglia et al., "Recognition by natural killer cells of N6-isopentenyladensoine-treated human glioma cell lines," Int. J. Cancer, 2018 142(1): 176-190.
Cichocki et al., "GSK3 inhibition drives maturation of NK cells and enhances their antitumor activity," Cancer Research, Oct. 15, 2017, 77(20):5664-75.
Cifaldi et al., "Boosting Natural Killer Cell-Based Immunotherapy with Anticancer Drugs: a Perspective," Trends Molecular Medicine, Dec. 2017, 23(12):1156-1175, 20 pages.
Cipriani et al., "Hippocampal Radial Glial Subtypes and Their Neurogenic Potential in Human Fetuses and Healthy and Alzheimer's Disease Adults," Cerebral Cortex, May 2, 2018, 28(7):2458-2478, 21 pages.
Clayton et al., "Soluble T Cell Immunoglobulin Mucin Domain 3 Is Shed from CD8 T Cells by the Sheddase ADAM10, Is Increased in Plasma during Untreated HIV Infection, and Correlates with HIV Disease Progression," J Viral., 2015, 89(7):3723-3736.
Collado et al., "Senescence in tumours: evidence from mice and humans," Nature Reviews Cancer, Jan. 2010, 10(1):51-57.
Conarello et al., "Mice lacking dipeptidyl peptidase IV are protected against obesity and insulin resistance," Proc. Natl. Acad. Sci. U.S.A., May 27, 2003, 100(11):6825-6830.
Conlon et al., "Abstract CT082: Phase (Ph) I/Ib study of NIZ985 with and without spartalizumab (PDR001) in patients (pts) with metastatic/unresectable solid tumors," Cancer Res. 79(13 Suppl. ):CT082, Jul. 1, 2019, 2 pages.
Coppe et al., "Tumor Suppressor and Aging Biomarker p16INK4a Induces Cellular Senescence without the Associated Inflammatory Secretory Phenotype," Journal of Biological Chemistry, Oct. 21, 2011, 286(42): 36396-36403.
Cosgrove et al., "Usher protein functions in hair cells and photoreceptors," Int J Biochem Cell Biol., Jan. 2014, 46:80-89.
Cosman et al., "ULBPs, novel MHC class I-related molecules, bind to CMV glycoprotein UL16 and stimulate NK cytotoxicity through the NKG2D receptor," Immunity, Feb. 1, 2001, 14(2):123-33.
Costa et al., "Targeting the epidermal growth factor receptor can counteract the inhibition of natural killer cell function exerted by colorectal tumor-associated fibroblasts," Frontiers in Immunology, May 29, 2018, 9:1150, 14 pages.
Crews et al., "Molecular mechanisms of neurodegeneration in Alzheimer's disease," Human Molecular Genetics, Apr. 22, 2010, 19(R1):R12-R20, 9 pages.
Cromie et al., "Nanobodies and their use in GPCR drug discovery," Current Topics in Medicinal Chemistry, Dec. 1, 2015, 15(24):2543-57.
Czaja et al., "A comprehensive analysis of the binding of anti-KIR antibodies to activating KIRs," Genes and Immunity, Jan. 2014, 15(1), 15 pages.
Da Silva et al., "Dipeptidylpeptidase 4 inhibition enhances lymphocyte trafficking, improving both naturally occurring tumor immunity and immunotherapy," Nature Immunology, Jun. 15, 2015, 16(8):850-858, 11 pages.
Dall'Era et al., "Adoptive Regulatory T Cell Therapy in a Patient with Systemic Lupus Erythematosus," Arthritis Rheumatology, Mar. 2019, 71(3):431-440.
De Crescenzo et al., "Engineering TGF-β Traps: Artificially Dimerized Receptor Ectodomains as High-affinity Blockers of TGF-β Action," Transforming Growth Factor-β in Cancer Therapy, vol. II, 2008, Humana Press, 671-84.
De Genst et al., "Antibody repertoire development in camelids," Developmental & Comparative Immunology, Jan. 1, 2006, 30(1-2):187-98.
De Meyer et al., "Nanobody-based products as research and diagnostic tools," Trends in Biotechnology, May 1, 2014, 32(5):263-70.
De Stefano et al., "Establishing pathological cut-offs of brain atrophy rates in multiple sclerosis," Journal of Neurology, Neurosurgery, and Psychiatry, Jan. 2016, 87(1):93-99.
Deacon, "Physiology and Pharmacology of DPP-4 in Glucose Homeostasis and the Treatment of Type 2 Diabetes," Frontiers in Endocrinology, Feb. 2019, 10:80, 14 pages.
Deaglio et al., "Adenosine generation catalyzed by CD39 and CD73 expressed on regulatory T cells mediates immune suppression," Journal of Experimental Medicine, May 14, 2007, 204(6):1257-1265.
Demaria et al., "An Essential Role for Senescent Cellsin Optimal Wound Healing through Secretion of PDGF-AA," Developmental Cell, Dec. 22, 2014, 31(6):722-733.
Deyev et al., "Design of multivalent complexes using the barnase• barstar module," Nature Biotechnology, Dec. 2003, 21(12):1486-92.
Di Ianni et al., "Tregs prevent GVHD and promote immune reconstitution inHLA-haploidentical transplantation," Blood, Apr. 7, 2011, 117(14):3921-3928.
Dietel et al., "Decreased numbers of regulatory T cells are associated with human atherosclerotic lesion vulnerability and inversely correlate with infiltrated mature dendritic cells," Atherosclerosis, Sep. 2013, 230:92-99.
DiGiammarino et al., "Design and generation of DVD-Ig™ molecules for dual-specific targeting," Therapeutic Proteins: Methods and Protocols, Methods in Molecular Biology, 2012, Humana Press, Totowa, NJ., 899:145-516.
Dikov et al., "New fluorescent method for the histochemical detection of tripeptidyl peptidase I using glycyl-1-prolyl-1-met-2-anthraquinonyl hydrazide as substrate," Cellular and Molecular Biology, Jan. 1, 2004, 50 Online Pub: OL565-568, 1 page (Abstract Only).
Dimri et al., "A biomarker that identifies senescent human cells in culture and in aging skin in vivo," Proceedings of the National Academy of Sciences, Sep. 29, 1995, 92(20):9363-9367.
Dinarello, "Interleukin 1 and interleukin 18 as mediators of inflammation and the aging process," The American Journal of Clinical Nutrition, Feb. 1, 2006, 83(2):447S-455S.
Docagne et al., "A soluble transforming growth factor-β (TGF-β) type I receptor mimics TGF-β responses," Journal of Biological Chemistry, Dec. 7, 2001, 276(49):46243-50.
Dong et al., "Characterization of adenosine deaminase binding to human CD26 on T cells and its biologic role in immune response," Journal of Immunology, Feb. 15, 1996, 156(4):1349-1355.
Dong et al., "Determination of adenosine deaminase binding domain on CD26 and its immunoregulatory effect on T cell activation," Journal of Immunology, Dec. 15, 1997, 159(12):6070-6076.
Dong et al., "Loss of methylation at theIFNGpromoter and CNS-1 is associated with the development of functional IFN-γ memory in human CD4+T lymphocytes," European Journal of Immunology, 2013, 43(3), 793-804.
Dou et al., "Cytoplasmic chromatin triggers inflammation in senescence and cancer," Nature, Oct. 4, 2017, 550(7676):402-406, 21 pages.
Drees et al., "Soluble production of a biologically active single-chain antibody against murine PD-L1 in *Escherichia coli*," Protein Express. Purif., 2014, 94:60-66.
Dubois et al., "Preassociation of IL-15 with IL-15Rα-IgG1-Fc Enhances Its Activity on Proliferation of NK and CD8+/CD44high T Cells and Its Antitumor Action," The Journal of Immunology, Feb. 15, 2008, 180:2099-2106.
Edwardraja et al., "Redesigning of anti-c-met single chain Fv antibody for the cytoplasmic folding and its structural analysis," Biotechnology and Bioengineering, Jun. 15, 2010, 106(3):367-75.
Eisenhut et al., "Ion Channels in Inflammation," Pflugers Archive, Jan. 29, 2011, 461(4):401-421.
Elgueta et al., "Molecular mechanism and function of CD40/CD40L engagement in the immune system," Immunological Reviews, 2009, 229(1):152-172.
Elpek et al., "Mature natural killer cells with phenotypic and functional alterations accumulate upon sustained stimulation with IL-15/IL-15Rα complexes," Proceedings of the National Academy of Science, Dec. 14, 2010, 107: 21647-21652.

(56) References Cited

OTHER PUBLICATIONS

Engel et al., "The crystal structure of dipeptidyl peptidase IV (CD26) reveals its functional regulation and enzymatic mechanism," Proc. Natl. Acad. Sci. U.S.A., Apr. 29, 2003, 100(9):5063-5068.
Epardaud et al., "Interleukin-15/Interleukin-15RA Complexes Promote Destruction of Established Tumors by Reviving Tumor-Resident CD8+ T Cells," Cancer Research 68: Apr. 15, 2008, 2972-2983.
Esensten et al., "Regulatory T-cell therapy for autoimmune and autoinflammatory diseases: The next frontier," The Journal of Allergy and Clinical Immunology, Dec. 1, 2018, 142(6):1710-1718.
Farr et al., "Targeting cellular senescence prevents age-related bone loss in mice," Nat. Med., 2017, 23(9): 1072-1079.
Fehniger et al., "A Phase 1 Trial of CNDO-109-Activated Natural Killer Cells in Patients with High-Risk Acute Myeloid Leukemia," Biology of Blood and Marrow Transplantation, Aug. 2018, 24(8):1581-1589.
Feng et al., "The yin and yang functions of extracellular ATP and adenosine in tumor immunity," Cancer Cell International, Apr. 7, 2020, 20:110, 11 pages.
Ferreira et al., "Next-generation regulatory T cell therapy," Nature Reviews Drug Discovery, Sep. 20, 2019, 18(10):749-769, 21 pages.
Ferrucci et al., "The origins of age-related proinflammatory state," Blood, Mar. 15, 2005, 105(6):2294-2299.
Finkelman et al., "Anti-cytokine antibodies as carrier proteins. Prolongation of in vivo effects of exogenous cytokines by injection of cytokine-anti-cytokine antibody complexes," The Journal of Immunology, Aug. 1, 1993, 151:1235-1244.
Finkelstein et al., "Obesity and Severe Obesity Forecasts Through 2030," American Journal of Preventative Medicine, Jun. 2012, 42(6):563-570.
Ford et al., "TREM and TREM-like receptors in inflammation and disease," Current Opinion in Immunology, Feb. 21, 2009, 21(1):38-46.
Franceschi et al., "Inflamm-aging. An evolutionary perspective on immunosenescence," Annals of the New York Academy of Sciences, Jun. 2000, 908:244-254.
Frutoso et al., "Emergence of NK Cell Hyporesponsiveness after Two IL-15 Stimulation Cycles," Journal of Immunology, May 30, 2018, 201: 493-506.
Ganesh et al., "TGF-β Inhibition and Immunotherapy: Checkmate," Immunity, Apr. 17, 2018, 48(4):626-628.
Garber, "Bispecific antibodies rise again," Nat. Rev. Drug Discov., 2014, 13:799-801.
Gaulton et al., "Characterization of a monoclonal rat anti-mouse interleukin 2 (IL-2) receptor antibody and its use in the biochemical characterization of the murine IL-2 receptor," Clinical Immunology and Immunopathology, Jul. 1, 1985, 36(1):18-29.
Gejima et al., "Human single-chain Fv (scFv) antibody specific to human IL-6 with the inhibitory activity on IL-6-signaling," Human Antibodies, Jan. 1, 2002, 11(4):121-9.
Geng et al., "A novel anti-TNF scFv constructed with human antibody frameworks and antagonistic peptides," Immunol. Res. 62(3):377-385, 2015.
Georgilis et al., "PTBP1-Mediated Alternative Splicing Regulates the Inflammatory Secretome and the Pro-tumorigenic Effects of Senescent Cells," Cancer Cell, Jul. 9, 2018, 34(1):85-102.
Ghosh et al., "The Senescence-Associated Secretory Phenotype: Critical Effector in SkinCancer and Aging," Journal of Investigative Dermatology, Nov. 2016, 136(11):2133-2139.
Gibbs et al., "Identification of the factor VIIa binding site on tissue factor by homologous loop swap and alanine scanning mutagenesis," Biochemistry, Nov. 1, 1994, 33(47):14003-10.
Gong et al., "DAMP-sensing receptors in sterile inflammation and inflammatory diseases," Nature Reviews Immunology, Sep. 26, 2019, 20(2):95-112.
Gorrell et al., "Expression of the rat CD26 Antigen (dipeptidyl peptidase IV) on subpopulations of rat lymphocytes," Cellular Immunology, Apr. 15, 1991, 134(1):205-215.
Greenspan et al., "Defining epitopes: Its not as easy as it seems," Nature Biotechnology, 1999, 17:936-937.
Grupp et al., "Chimeric Antigen Receptor-Modified T Cells for Acute Lymphoid Leukemia," The New England Journal of Medicine, Apr. 18, 2013, 368(16):1509-1518.
Gu et al., "Human CD39hi regulatory T cells present stronger stability and function under inflammatory conditions," Cellular and Molecular Immunology, Jul. 4, 2016, 14(6):521-528.
Guo et al., "Immunobiology of the IL-15-IL-15R complex as an antitumor and antiviral agent," 2017, Cytokine & Growth Factor Reviews, 38:10-21.
Gutschmidt et al., "A quantitative histochemical study of dipeptidyl peptidase IV (DPP IV)," Histochemistry, 1981, 73(2):285-304.
Haile et al., "Soluble CD80 Restores T Cell Activation and Overcomes Tumor Cell Programmed Death Ligand 1-Mediated Immune Suppression," J. Immunol., 2013, 191(5):2829-2836.
Hayflick et al., "The serial cultivation of human diploid cell strains," Experimental Cell Research, Dec. 1961, 25:585-621.
He et al., "Senescence in Health and Disease," Cell, Jun. 1, 2017, 169(6):1000-1011.
Hebbar et al., "Detection of circulating soluble CD28 in patients with systemic lupus erythematosus, primary Sjögren's syndrome and systemic sclerosis," Clinical & Experimental Immunology, May 2004, 136(2):388-92.
Helfrich et al., "A rapid and versatile method for harnessing scFv antibody fragments with varous biological effector functions," Journal of Immunological methods, 2000, 237(1-2):131-145.
Helman et al., "Effects of ageing and senescence on pancreatic β-cell function," Diabetes Obes Metab., Sep. 2016, 18(Suppl. 1):58-62.
Heneka et al., "Inflammasome signaling in brain function and neurodegenerative disease," Nature Reviews Neuroscience, Sep. 11, 2018, 19(10):610-621.
Heneka et al., "NLRP3 is activated in Alzheimer's disease and contributes to pathology in APP/PS1 mice," Nature, Jan. 31, 2013, 493(7434):674-678, 8 pages.
Heng et al., "G Protein-Coupled Receptors Revisited: Therapeutic Applications Inspired by Synthetic Biology," Annual Review of Pharmacology and Toxicology, Jan. 2014, 54:227-249.
Heng et al., "Multiple soluble TGF-β receptors in addition to soluble endoglin are elevated in preeclamptic serum and they synergistically inhibit TGF-β signalling." Placenta, 2017 57:320 (1 page).
Highfill et al., "Overcoming Challenges in Process Development of Cellular Therapies," Current Hematologic Malignancy Reports, Jul. 6, 2019, 14(4):269-277, 9 pages.
Hoare et al., "The Power Behind the Throne: Senescence and the Hallmarks of Cancer," Annual Review of Cancer Biology, 2018, 2:175-194.
Hoffmann et al., "Large-scale in vitro expansion of polyclonal human CD4+CD25high regulatory T Cells," Blood, Aug. 2004, 104(3):895-903.
Hollande et al., "Inhibition of the dipeptidyl peptidase DPP4 (CD26) reveals IL-33-dependent eosinophil-mediated control of tumor growth," Nature Immunology, Feb. 18, 2019, 20(3):257-264.
Hombach et al., "Generation of the single chain antibody fragment conserves the idiotypic profile of the anti-CD30 monoclonal antibody HRS3," Scandinavian Journal of Immunology, Nov. 1998, 48(5):497-501.
Hu et al., "Discovery of a novel IL-15 based protein with improved developability and efficacy for cancer immunotherapy," Scientific Reports, 2018, 8:7675, 11 pages.
Huang et al., "Substrate recognition by tissue factor-factor VIIa Evidence for interaction of residues Lys165 and Lys166 of tissue factor with the 4-carboxyglutamate-rich domain of factor X," Journal of Biological Chemistry, Sep. 6, 1996, 271(36):21752-7.
Huang et al., "Targeting the vasculature of colorectal carcinoma with a fused protein of (RGD) 3-tTF" The Scientific World Journal, 2013(637086): 1-11, 2013.
Hudak et al., "Glycocalyx engineering reveals a Siglec-based mechanism for NK cell immunoevasion," Nature Chemical Biology, Jan. 2014, 10(1), 20 pages.

(56) References Cited

OTHER PUBLICATIONS

Hudson et al., "Targeting RAGE Signaling in Inflammatory Disease," Annual Review of Medicine, Jan. 2018, 69:349-364, 16 pages.
Huell et al., "Interleukin-6 is present in early stages of plaque formation and is restricted to the brains of Alzheimer's disease patients," Acta Neuropathologica, Nov. 1995, 89(6):544-551.
Hughes et al., "Transfer of a TCR gene derived from a patient with a marked antitumor response conveys highly active T-cell effector functions," Hum. Gene Ther., 2005, 16:457-72.
Hynes et al., "In vitro analysis of cell metabolism using a long-decay pH-sensitive lanthanide probe and extracellular acidification assay," Analytical biochemistry, Jul. 1, 2009, 390(1):21-28.
Iannello et al., "p53-dependent chemokine production by senescent tumor cells supports NKG2D-dependent tumor elimination by natural killer cells," Journal of Experimental Medicine, Sep. 23, 2013, 210(10):2057-69.
Iihoshi et al., "Aclarubicin, an anthracycline anti-cancer drug, fluorescently contrasts mitochondria and reduces the oxygen consumption rate in living human cells," Toxicology Letters, Aug. 5, 2017, 277:109-114, 22 pages.
International Preliminary Report on Patentability in International Appln. No. PCT/US2019/048881, dated Mar. 11, 2021, 7 pages.
International Preliminary Report on Patentability in International Appln. No. PCT/US2019/048930, dated Mar. 11, 2021, 9 pages.
International Preliminary Report on Patentability in International Appln. No. PCT/US2019/049142, dated Mar. 11, 2021, 11 pages.
International Preliminary Report on Patentability in International Appln. No. PCT/US2019/049158, dated Mar. 11, 2021, 8 pages.
International Preliminary Report on Patentability in International Appln. No. PCT/US2020/035598, mailed Dec. 6, 2022, 7 pages.
International Preliminary Report on Patentability in International Appln. No. PCT/US2020/038717, dated Dec. 30, 2021, 9 pages.
International Preliminary Report on Patentability in International Appln. No. PCT/US2021/017620, dated Aug. 25, 2022, 12 pages.
International Preliminary Report on Patentability in International Appln. No. PCT/US2021/017621, dated Aug. 25, 2022, 8 pages.
International Preliminary Report on Patentability in International Appln. No. PCT/US2021/017714, dated Aug. 25, 2022, 12 pages.
International Preliminary Report on Patentability in International Appln. No. PCT/US2021/029920, dated Nov. 10, 2022, 11 pages.
International Preliminary Report on Patentability in International Appln. No. PCT/US2021/035285, mailed Dec. 15, 2022, 7 pages.
International Search Report and Written Opinion in International Appln. No. PCT/US2019/048881, dated Nov. 9, 2019, 16 pages.
International Search Report and Written Opinion in International Appln. No. PCT/US2019/048930, dated Nov. 20, 2019, 18 pages.
International Search Report and Written Opinion in International Appln. No. PCT/US2019/04912, dated Jun. 23, 2020, 20 pages.
International Search Report and Written Opinion in International Appln. No. PCT/US2019/049158, dated Jan. 20, 2020, 17 pages.
International Search Report and Written Opinion in International Appln. No. PCT/US2020/035598, dated Feb. 18, 2021, 12 pages.
International Search Report and Written Opinion in International Appln. No. PCT/US2020/038717, dated Oct. 16, 2020, 17 pages.
International Search Report and Written Opinion in International Appln. No. PCT/US2021/017620, dated Aug. 6, 2021, 22 pages.
International Search Report and Written Opinion in International Appln. No. PCT/US2021/017621, dated Jun. 9, 2021, 15 pages.
International Search Report and Written Opinion in International Appln. No. PCT/US2021/017714, dated Aug. 27, 2021, 22 pages.
International Search Report and Written Opinion in International Appln. No. PCT/US2021/029920, dated Oct. 6, 2021, 21 pages.
International Search Report and Written Opinion in International Appln. No. PCT/US2021/035285, dated Oct. 18, 2021, 14 pages.
Inzucchi et al., "New Drugs for the Treatment of Diabetes, Part II: Incretin-Based Therapy and Beyond," Circulation, Jan. 29, 2008, 117(4):574-584, 21 pages.
Jain et al., "Mitochondrial Reactive Oxygen Species Regulate Transforming Growth Factor-β Signaling," Journal of Biological Chemistry, Jan. 11, 2013, 288(2):770-777.
Jakob et al., "Structure reveals function of the dual variable domain immunoglobulin (DVD-Ig™) molecule," Mabs, May 1, 2013, Taylor & Francis, 5(3):358-63.
Janeway, "Approaching the Asymptote? Evolution and Revolution in Immunology," Cold Spring Harbor Symposia on Quantitative Biology, 1989, 54 Pt 1:1-13.
Jeannin et al., "Soluble CD86 Is a Costimulatory Moleculefor Human T Lymphocytes," Immunity, 2000, 13(3):303-312.
Jeon et al., "Local clearance of senescent cells attenuates the development of post-traumatic osteoarthritis and creates a pro-regenerative environment," Nat Med., Jun. 2017, 23(6):775-781.
Jin et al., "Novel Insights Into the NLRP3 Inflammasome in Atherosclerosis," Journal of the American Heart Association, Jun. 11, 2019, 8(12):e012219, 12 pages.
Justice et al., "Senolytics in idiopathic pulmonary fibrosis: Results from a first-in-human, open-label, pilot study," EBioMedicine, Feb. 2019, 40:554-563.
Kain et al., "The identification of the endogenous ligands of natural killer T cells reveals the presence of mammalian α-linked glycosylceramides," Immunity, Oct. 16, 2014, 41(4):543-54.
Karin et al., "Senescent cell turnover slows with age providing an explanation for the Gompertz law," Nature Communications, 10:5495, 2019, 9 pages.
Karkera et al., "The anti-interleukin-6 antibody siltuximab down-regulates genes implicated in tumorigenesis in prostate cancer patients from a phase I study," The Prostate, Feb. 14, 2011, 71(13):1455-1465.
Katsuumi et al., "Vascular Senescence in Cardiovascular and Metabolic Diseases," Frontiers in Cardiovascular Medicine, 5:18, 2018, 13 pages.
Kellner et al., "Enhancing natural killer cell-mediated lysis of lymphoma cells by combining therapeutic antibodies with CD20-specific immunoligands engaging NKG2D or NKp30," Oncoimmunology, Jan. 2, 2016, 5(1):e1058459, 12 pages.
Kijanka et al., "Nanobody-based cancer therapy of solid tumors," Nanomedicine, Jan. 2015, 10(1):161-74.
Kim et al., "Experimental malaria infection triggers early expansion of natural killer cells," Infection and Immunity, Dec. 1, 2008, 76(12):5873-82.
Kim et al., "Identification of senescent cell surface targetable protein DPP4," Genes & Development, 2017, 31(15):1529-1534.
Kim et al., "Insulin resistance, inflammation, and nonalcoholic fatty liver disease in non-obese adults without metabolic syndrome components," Hepatol Int., Jun. 2013, 7(2):586-591.
Kim et al., "SCAMP4 enhances the senescent cell secretome," Genes & Development, 2018, 32(13-14):909-914.
Kirchhofer et al., "The tissue factor region that interacts with substrates factor IX and factor X," Biochemistry, Jun. 27, 2000, 39(25):7380-7.
Kirkland et al., "Cellular Senescence: A Translational Perspective," EBioMedicine, Jul. 2017, 21:21-28.
Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology, 2017 6(3):e1277306, 15 pages.
Klein et al., "Design and characterization of structured protein linkers with differing flexibilities," Protein Engineering, Design & Selection, 2014, 27(10):325-30.
Klemann et al., "Cut to the chase: a review of CD26/dipeptidyl peptidase-4's (DPP4) entanglement in the immune system," Clinical and Experimental Immunology, Feb. 25, 2016, 185(1):1-21.
Klingenberg et al., "Depletion of FOXP3+ regulatory T cells promotes hypercholesterolemia and atherosclerosis," The Journal of Clinical Investigation, Feb. 15, 2013, 123:1323-1334.
Kondo et al., "Requirements for the functional expression of OX40 ligand on human activated CD4+ and CD8+ T cells," Human Immunology, 2007, 68(7):563-571.

(56) References Cited

OTHER PUBLICATIONS

Kovaleva et al., "Shark variable new antigen receptor biologics—a novel technology platform for therapeutic drug development," Expert Opinion on Biological Therapy, Oct. 1, 2014, 14(10):1527-39.
Krah et al., "Single-domain antibodies for biomedical applications," Immunopharmacology and Immunotoxicology, Jan. 2, 2016, 38(1):21-8.
Kritsilis et al., "Ageing, Cellular Senescence and Neurodegenerative Disease," International Journal of Molecular Sciences, Sep. 27, 2018, 19(10):2937, 37 pages.
Krizhanovsky et al., "Senescence of activated stellate cells limits liver fibrosis," Cell, Aug. 22, 2008, 134(4):657-67.
Kumagai et al., "Monitoring of glutamate-induced excitotoxicity by mitochondrial oxygen consumption," Synapse, Jan. 2019, 73(1):e22067, 24 Pages.
Kuyinu et al., "Animal models of osteoarthritis: classification, update, and measurement of outcomes," J Orthop Surg Res., Feb. 2, 2016, 11:19, 27 pages.
Lambeir et al., "Dipeptidyl-Peptidase IV from Bench to Bedside: An Update on Structural Properties, Functions, and Clinical Aspects of the Enzyme DPP IV," Critical Reviews in Clinical Laboratory Sciences, Sep. 29, 2003, 40(3):209-294.
Lamkanfi et al., "Mechanisms and Functions of Inflammasomes," Cell, May 22, 2014, 157(5):1013-1022.
Lansigan et al., "DI-Leu16-IL2, an Anti-CD20-Interleukin-2 Immunocytokine, Is Safe and Active in Patients with Relapsed and Refractory B-Cell Lymphoma: A Report of Maximum Tolerated Dose, Optimal Biologic Dose, and Recommended Phase 2 Dose," Blood, Dec. 2, 2016, 128(22):620, 3 pages (Abstract Only).
Latz et al., "Activation and regulation of the inflammasomes," Nature Reviews Immunology, May 24, 2013, 13(6):397-411.
Latz et al., "NLRP3 inflammasome activation in inflammaging," Seminars in Immunology, Dec. 2018, 40:61-73, 13 pages.
Lau et al., "RNA-associated autoantigens activate B cells by combined B cell antigen receptor/Toll-like receptor 7 engagement," The Journal of Experimental Medicine, Oct. 31, 2005, 202(9):1171-1177.
Lazar et al., "Transforming Growth Factor Alpha: Mutation of Aspartic Acid 47 and Leucine 48 Results in Different Biological Activities," Mol. Cell. Biol., 1988, 8:1247-1252.
Li et al., "A Novel I L2-based Irrmunotherapeutic Protein Prevents the Development of Atherosclerosis in ApoE-/mice and LDLR-/-mice," Journal of Immunology, May 1, 2020, 204(1):Supplement (Abstract Only), 2 pages.
Li et al., "Adoptive transfer of natural killer cells in combination with chemotherapy improves outcomes of patients with locally advanced colon carcinoma," Cytotherapy, Jan. 2018, 20(1):134-148, 15 pages.
Li et al., "The cGAS-cGAMP-STING pathway connects DNA damage to inflammation, senescence, and cancer," Journal of Experimental Medicine, Apr. 5, 2018, 215(5):1287-1299.
Li et al., "Transforming Growth Factor-β Regulation of Immune Responses," Annu. Rev. Immunol., 2006, 24:99-146.
Liton et al., "Cellular senescence in the glaucomatous outflow pathway," Experimental Gerontology, Aug.-Sep. 2005, 40(8-9):745-748.
Liu et al., "A Novel Fusion of ALT-803 (IL-15 Superagonist) with an Antibody Demonstrates Antigen-specific Antitumor Responses," Journal of Biological Chemistry, 2016, 291(46):23869-23881.
Liu et al., "Evaluation of the biological activities of the IL-15 superagonist complex, ALT-803, following intravenous versus subcutaneous administration in murine models," Cytokine, Jul. 2018, 107: 105-112, 8 pages.
Loster et al., "The Cysteine-Rich Region of Dipeptidyl Peptidase IV (CD 26) Is the Collagen Binding Site," Biochemical and Biophysical Research Communications, Dec. 5, 1995, 217(1):341-348.
Lu et al., "Molecular basis of binding between novel human coronavirus MERS-CoV and its receptor CD26," Nature, Jul. 7, 2013, 500(7461):227-231.
Lujambio et al., "Non-Cell-Autonomous Tumor Suppression by p53," Cell, Apr. 11, 2013, 153(2):449-460.
Maeda et al., "Original Ligand for LTβR Is Light: Insight into Evolution of the LT/LTβR System," J Immunol., 2018, 201(1):202-214.
Maganto-García et al., "Dynamic Changes in Regulatory T Cells Are Linked to Levels of Diet-Induced Hypercholesterolemia," Circulation, Jun. 20, 2011, 124:185-195.
Mandelboim et al., "Recognition of haemagglutinins on virus-infected cells by NKp46 activates lysis by human NK cells," Nature, Feb. 2001, 409(6823):1055.
Marguet et al., "Enhanced insulin secretion and improved glucose tolerance in mice lacking CD26," Proc. Natl. Acad. Sci. U.S.A., Jun. 6, 2000, 97(12):6874-6879.
Martelli et al., "HLA-haploidentical transplantation with regulatory and conventionalT-cell adoptive immunotherapy prevents acute leukemia relapse," Blood, Jul. 24, 2014, 124(4):638-644.
Masoumi et al., "The role of hypoxia as the driving force for non-erythroid production of globin chains in preeclamptic placentas," Placenta. 2017;57:320.
McCarron et al., "TGF-β prevents T follicular helper cell accumulation and B cell autoreactivity," J Clin Invest., 2014, 124(10):4375-4386.
McHugh et al., "Senescence and aging: Causes, consequences, and therapeutic avenues," Journal of Cellular Biology, Nov. 7, 2017, 217(1):65-77.
Mehta et al., "Why do trials for Alzheimer's disease drugs keep failing? A discontinued drug perspective for 2010-2015," Expert Opinion on Investigational Drugs, May 2017, 26(6):735-739.
Melk et al., "Expression of p16INK4a and other cell cycle regulator and senescence associated genes in aging human kidney," Kidney Int., Feb. 2004, 65(2):510-520.
Melk et al., "Senescence of renal cells: molecular basis and clinical implications," Nephrology Dialysis Transplantation, Dec. 2003, 18(12):2474-2478.
Menshawy et al., "CD58; leucocyte function adhesion-3 (LFA-3) could be used as a differentiating marker between immune and non-immune thyroid disorders," Comparative Clinical Pathology, 2018, 27(3), 721-727, doi.org/10.1007/s00580-018-2657-x.
Mentlein et al., "Dipeptidyl-peptidase IV (CD26)-role in the inactivation of regulatory peptides," Regulatory Peptides, Nov. 30, 1999, 85(1):9-24.
Miah et al., "KIR2DL4 differentially signals downstream functions in human NK cells through distinct structural modules," The Journal of Immunology, Mar. 1, 2008, 180(5):2922-32.
Michelet et al., "Metabolic reprogramming of natural killer cells in obesity limits antitumor responses," Nature Immunology, Nov. 12, 2018, 19(12):1330-1340.
Mikayama et al., "Molecular cloning and functional expression of a cDNA encoding glycosylation-inhibiting factor," Proc. Natl. Acad. Sci. USA, Nov. 1, 1993, 90(21):10056-10060.
Milanovic et al., "Senescence-associated reprogramming promotes cancer stemness," Nature, Dec. 20, 2017, 553(7686):96-100.
Milanovic et al., "The Senescence-Stemness Alliance—A Cancer-Hijacked Regeneration Principle," Trends in Cellular Biology, Dec. 2018, 28(12):1049-1061, 13 pages.
Miller et al., "Soluble CD70: a novel immunotherapeutic agent for experimental glioblastoma," J Neurosurg., 2010, 113(2):280-285.
Miller et al., "Successful adoptive transfer and in vivo expansion of human haploidentical NK cells in patients with cancer," Blood, Apr. 15, 2005, 105(8):3051-3057.
Minamino et al., "A crucial role for adipose tissue p53 in the regulation of insulin resistance," Nature Medicine, Aug. 30, 2009, 15(9):1082-1087.
Mitterberger et al., "Adipogenic Differentiation Is Impaired in Replicative Senescent Human Subcutaneous Adipose-Derived Stromal/Progenitor Cells," The Journals of Gerontology: Series A, Biological Sciences and Medical Sciences, Jan. 2014, 69(1):13-24.
Miyazaki et al., "Abstract 3265: NKTR-255, a polymer-conjugated IL-15 enhances anti-tumor NK cell responses and synergizes with monoclonal antibodies to provide long-term survival in human lymphoma model," Proceedings: AACR Annual Meeting 2019, Atlanta, GA, Mar. 29-Apr. 3, 2019, 1 page.

(56) References Cited

OTHER PUBLICATIONS

Moesta et al., "Targeting CD39 in cancer," Nature Reviews Immunology, Jul. 29, 2020, 20(12):739-755, 17 pages.
Moiseeva et al., "Metformin inhibits the senescence-associated secretory phenotype by interfering with IKK/NF-κB activation," Aging Cell, Mar. 23, 2013, 12(3):489-498.
Molema et al., "The use of bispecific antibodies in tumor cell and tumor vasculature directed immunotherapy," Journal of Controlled Release, 2000, 64(1-3):229-239.
Molgora et al., "Regulatory role of IL-1R8 in immunity and disease," Frontiers in Immunology, Apr. 20, 2016, 7:149.
Mookerjee et al., "Measurement and Analysis of Extracellular Acid Production to Determine Glycolytic Rate," Journal of Visualized Experiments : Jove, Dec. 2015, (106):e53464, 9 Pages.
Moore et al., "Macrophages in atherosclerosis: a dynamic balance," Nature Reviews Immunology, Sep. 2, 2013, 13:709-721, 13 pages.
Moreno et al., "Molecular Evidence of Adenosine Deaminase Linking Adenosine A2A Receptor and CD26 Proteins," Frontiers in Pharmacology, Feb. 15, 2018, 9:106, 18 pages.
Moretta et al., "CD69-mediated pathway of lymphocyte activation: anti-CD69 monoclonal antibodies trigger the cytolytic activity of different lymphoid effector cells with the exception of cytolytic T lymphocytes expressing T cell receptor alpha/beta," Journal of Experimental Medicine, Dec. 1, 1991, 174(6):1393-8.
Mujić-Delić et al., "GPCR-targeting nanobodies: attractive research tools, diagnostics, and therapeutics," Trends in Pharmacological Sciences, May 1, 2014, 35(5):247-55.
Muller et al., "Antibody fusions with immunomodulatory proteins for cancer therapy," Pharmacology and Therapeutics, 2015, 154:57-66.
Mulvihill et al., "Pharmacology, Physiology, and Mechanisms of Action of Dipeptidyl Peptidase-4 Inhibitors," Endocrine Reviews, Dec. 1, 2014, 35(6):992-1019.
Munoz-Espin et al., "Cellular senescence: from physiology to pathology," Nature Reviews Molecular Cellular Biology, Jun. 23, 2014, 15(7):482-496.
Munoz-Espin et al., "Programmed Cell Senescence during Mammalian Embryonic Development," Cell, Nov. 21, 2013, 155(5):1104-1118.
Musi et al., "Tau protein aggregation is associated with cellular senescence in the brain," Aging Cell, Aug. 20, 2018, 17(6):e12840, 13 pages.
Must et al., "The Disease Burden Associated with Overweight and Obesity," Endotext, Feingold et al. (eds.), South Dartmouth, MA, 2000, 35 pages.
Muyldermans et al., "Recognition of antigens by single-domain antibody fragments: the superfluous luxury of paired domains," Trends in Biochemical Sciences, Apr. 1, 2001, 26(4):230-5.
Muyldermans, "Nanobodies: natural single-domain antibodies," Annual Review of Biochemistry, Jun. 2, 2013, 82:775-97.
Muyldermans, "Single domain camel antibodies: current status," Reviews in Molecular Biotechnology, Jun. 1, 2001, 74(4):277-302.
Myung et al., "Evidence of DNA damage in Alzheimer disease: phosphorylation of histone H2AX in astrocytes," Age, Apr. 23, 2008, 30(4):209-215.
Nag et al., "Soluble MHC II-peptide complexes induce antigen-specific apoptosis in T cells," Cellular Immunology, May 25, 1996, 170(1):25-33.
Nayyar et al., "Overcoming Resistance to Natural Killer Cell Based Immunotherapies for Solid Tumors," Frontiers in Oncology, 2019, 9: 28 pages.
Nelson et al., "A senescent cell bystander effect: senescence-induced senescence," Aging Cell, Feb. 9, 2012, 11(2):345-349.
Nilsson et al., "Targeted delivery of tissue factor to the ED-B domain of fibronectin, a marker of angiogenesis, mediates the infarction of solid tumors in mice," Cancer Research, American Association for Cancer Researc, Proceddings: AACR 107th Annual Meeting, 2016, Apr. 16-20, 2016, New Orleans, LA 61(2):711-716.
Nishida et al., "CD26 is a potential therapeutic target by humanized monoclonal antibody for the treatment of multiple myeloma," Blood Cancer Journal, Oct. 22, 2018, 8(11):99, 17 pages.
O'Sullivan et al., "Natural Killer Cell Memory," Immunity, Oct. 20, 2015, 43(4):634-645.
Oberle et al., "Rapid Suppression of Cytokine Transcription in Human CD4+CD25-T Cells by CD4+Foxp3+ Regulatory T Cells: Independence of IL-2 Consumption, TGF-β, and Various Inhibitors of TCR Signaling," The Journal of Immunology, Sep. 15, 2007, 179(6):3578-3587.
Ogrodnik et al., "Cellular senescence drives age-dependent hepatic steatosis," Nat Commun. Jun. 13, 2017;8:15691, 12 pages.
Ogrodnik et al., "Obesity-Induced Cellular Senescence Drives Anxiety and Impairs Neurogenesis," Cell Metabolism, May 2019, 29(5):1061-1077, 25 pages.
Ohnuma et al., "Blockade of CD26-mediated T cell costimulation with soluble caveolin-1-Ig fusion protein induces anergy in CD4+T cells," Biochemical and Biophysics Research Communications, Aug. 21, 2009, 386(2):327-332.
Ohnuma et al., "CD26 Mediates Dissociation of Tollip and IRAK-1 from Caveolin-1 and Induces Upregulation of CD86 on Antigen-Presenting Cells," Molecular and Cellular Biology, Sep. 1, 2005, 25(17):7743-7757.
Ohnuma et al., "CD26 up-regulates expression of CD86 on antigen-presenting cells by means of caveolin-1," Proc. Natl. Acad. Sci. U.S.A., Sep. 28, 2004, 101(39):14186-14191.
Ohnuma et al., "Role of CD26/dipeptidyl peptidase IV in human T cell activation and function," Frontiers in Bioscience, Jan. 1, 2008, 13:2299-2310.
Ohnuma et al., "Soluble CD26/Dipeptidyl Peptidase IV Induces T Cell Proliferation Through CD86 Up-Regulation on APCs," Journal of Immunology, Dec. 15, 2001, 167(12):6745-6755.
Ovadya et al., "Strategies targeting cellular senescence," The Journal of Clinical Investigation, Apr. 2, 2018, 128(4):1247-54.
Owicki et al., "Biosensors based on the energy metabolism of living cells: the physical chemistry and cell biology of extracellular acidification," Biosensors and Bioelectronics, Jan. 1, 1992, 7(4):255-272.
Padutsch et al., "Superior Treg-Expanding Properties of a Novel Dual-Acting Cytokine Fusion Protein," Frontiers in Pharmacology, Dec. 18, 2019, 10:1490, 10 pages.
Palmer et al., "Cellular Senescence in Type 2 Diabetes: A Therapeutic Opportunity," Diabetes, Jul. 2015, 64(7):2289-2298.
Parker et al., "Design, production, and characterization of a single-chain variable fragment (ScFv) derived from the prostate specific membrane antigen (PSMA) monoclonal antibody J591," Protein Expression and Purification, Jun. 1, 2013, 89(2):136-45.
Peipp et al., "HER2-specific immunoligands engaging NKp30 or NKp80 trigger NK-cell-mediated lysis of tumor cells and enhance antibody-dependent cell-mediated cytotoxicity," Oncotarget, Oct. 13, 2015, 6(31):32075.
Pittayapruek et al., "Role of Matrix Metalloproteinases in Photoaging and Photocarcinogenesis," International Journal of Molecular Sciences, 2016, 17(6):868, 20 pages.
Price et al., "Comparison of collagenase-cleaved articular cartilage collagen in mice in the naturally occurring STR/ort model of osteoarthritis and in collagen-induced arthritis," Osteoarthritis Cartilage, Mar. 2002, 10(3):172-179.
Priyanka et al., "Linkers in the structural biology of protein-protein interactions," Protein Sci., 2013, 22(2):153-167.
Purohit et al., "Smad3-dependent regulation of type I collagen in human dermal fibroblasts: Impact on human skin connective tissue aging," Journal of Dermatological Science, Jul. 2016, 83(1):80-83.
Qin et al., "Critical Role of P2Y12 Receptor in Regulation of Th17 Differentiation and Experimental Autoimmune Encephalomyelitis Pathogenesis," The Journal of Immunology, Jul. 1, 2017, 199(1):72-81.
Rafei et al., "Off-the-shelf virus specific T-cells for therapy of adenovirus disease in immunosuppressed patients," Journal of Clinical Oncology, May 26, 2019, 37(15 Suppl.):7008, 2 pages.
Rahbarizadeh et al., "Nanobody; an old concept and new vehicle for immunotargeting," Immunological Investigations, Jan. 1, 2011, 40(3):299-338.

(56) References Cited

OTHER PUBLICATIONS

Raj et al., "Adenosine Deaminase Acts as a Natural Antagonist for Dipeptidyl Peptidase 4-Mediated Entry of the Middle East Respiratory Syndrome Coronavirus," Journal of Virology, Feb. 2014, 88(3):1834-1838, 7 pages.
Ranganathan et al., "Pinpointing the putative heparin/sialic acid-binding residues in the 'sushi' domain 7 of factor H: a molecular modeling study," Biocomputing 2000, 1999, 155-67.
Rao et al., "Purification and characterization of rabbit tissue factor," Thrombosis Research, Oct. 1, 1989, 56(1):109-118.
Rasmussen et al., "Crystal structure of human dipeptidyl peptidase IV/CD26 in complex with a substrate analog," Nature Structural and Molecular Biology, 2003, 10(1):19-25.
Raz et al., "Efficacy and safety of the dipeptidyl peptidase-4 inhibitor sitagliptin as monotherapy in patients with type 2 diabetes mellitus," Diabetologia, Sep. 26, 2006, 49(11):2564-2571.
Resta et al., "Ecto-enzyme and signaling functions of lymphocyte CD 7 3," Immunological Reviews, 1998, 161:95-109.
Rhein et al., "Characterization of Human and Murine T-Cell Immunoglobulin Mucin Domain 4 (TIM-4) IgV Domain Residues Critical for Ebola Virus Entry," J Viral., 2016, 90(13):6097-6111.
Rippmann et al., "Fusion of the Tissue Factor Extracellular Domain to a Tumor Stromaspecific Single-Chain Fragment Variable Antibody Results in an Antigen-Specific Coagulation-Promoting Molecule," Biochemical Journal, 2000, 349(3):805-812.
Rittie et al., "Natural and Sun-Induced Aging of Human Skin," Cold Spring Harbor Perspective in Medicine, 2015, 5(1):a015370, 15 pages.
Rocha et al., "A novel immunofluorescent assay to investigate oxidative phosphorylation deficiency in mitochondrial myopathy: understanding mechanisms and improving diagnosis," Scientific reports, Oct. 15, 2015, 5:15037, 17 Pages.
Rodier et al., "Persistent DNA damage signaling triggers senescence-associated inflammatory cytokine secretion," Nature Cell Biology, Jul. 13, 2009, 11(8): 15 pages.
Rogge et al., "Antibodies to the IL-12 receptor B2 chain mark human Th1 but not Th2 cells in vitro and in vivo," The Journal of Immunology, Apr. 1, 1999, 162(7):3926-32.
Roh et al., "Damage-Associated Molecular Patterns in Inflammatory Diseases," Immune Network, Aug. 2018, 18(4):e27, 14 pages.
Romano et al., "Past, Present, and Future of Regulatory T Cell Therapy in Transplantation and Autoimmunity," Frontiers in Immunology, Jan. 1, 2019, 10:43, 14 pages.
Romee et al., "Cytokine activation induces human memory-like NK cells," Blood, Dec. 6, 2012, 120(24):4751-4760.
Rossi et al., "Complex and defined biostructures with the dock-and-lock method," Trends in Pharmacological Sciences, Sep. 1, 2012, 33(9):474-81.
Rossi et al., "Stably tethered multifunctional structures of defined composition made by the dock and lock method for use in cancer targeting," Proceedings of the National Academy of Sciences, May 2, 2006, 103(18):6841-6.
Rubinstein et al., "Converting IL-15 to a superagonist by binding to soluble IL-15Rα," Proceedings of the National Academy of Sciences U.S.A., Jun. 13, 2006, 103(24):9166-9171.
Ruf et al., "Cofactor residues lysine 165 and 166 are critical for protein substrate recognition by the tissue factor-factor VIIa protease complex," Journal of Biological Chemistry, Mar. 25, 1992, 267(9):6375-81.
Ruf et al., "Tissue factor residues 157-167 are required for efficient proteolytic activation of factor X and factor VII," Journal of Biological Chemistry, Nov. 5, 1992, 267(31):22206-10.
Ruscetti et al., "NK cell-mediated cytotoxicity contributes to tumor control by a cytostatic drug combination," Science, Dec. 21, 2018, 362(6421):1416-1422, 8 pages.
Sagiv et al., "Granule exocytosis mediates immune surveillance of senescent cells," Oncogene, 2013, 32(15):1971-1977.
Sakaguchi et al., "Regulatory T Cells and Human Disease," Annual Review of Immunology, Apr. 26, 2020, 38:541-566.
Sakaguchi et al., "Regulatory T Cells and Immune Tolerance," Cell, May 30, 2008, 133(5):775-787.
Sakaguchi et al., "Regulatory T cells: how do they suppress immune responses?" International Immunology, Sep. 7, 2009, 21(10):1105-1111.
Sakamoto et al., "Phase I clinical trial of autologous NK cell therapy using novel expansion method in patients with advanced digestive cancer," Journal of Translational Medicine, Aug. 25, 2015, 13:277, 13 pages.
Sakamuri et al., "Measurement of respiratory function in isolated cardiac mitochondria using Seahorse XFe24 Analyzer: applications for aging research," Geroscience, Jun. 1, 2018, 40(3):347-356.
Salminen et al., "Emerging role of NF-κB signaling in the induction of senescence-associated secretory phenotype (SASP)," Cellular Signaling, Apr. 2012, 24(4):835-845.
Sandusky et al., "Regulation of 2B4 (CD244)-mediated NK cell activation by ligand-induced receptor modulation," European Journal of Immunology, Dec. 2006, 36(12):3268-76.
Sato et al., "Recombinant soluble murine IL-4 receptor can inhibit or enhance IgE responses in vivo," The Journal of Immunology, Apr. 1, 1993, 150:2717-2723.
Schafer et al., "Cellular senescence mediates fibrotic pulmonary disease," Nat Commun., Feb. 2017, 8:14532, 11 pages.
Schullek et al., "Key ligand interface residues in tissue factor contribute independently to factor VIIa binding," Journal of Biological Chemistry, Jul. 29, 1994, 269(30):19399-403.
Schwoppe et al., "Tissue-factor fusion proteins induce occlusion of tumor vessels," Thrombosis Research, Apr. 1, 2010, 125:S143-S150.
Seo et al., "Positive Feedback Loop between Plasminogen Activator Inhibitor-1 and Transforming Growth Factor-Beta1 during Renal Fibrosis in Diabetes," American Journal of Nephrology, Sep. 25, 2009, 30:481-490.
Sharkey et al., "Improved Therapeutic Results by Pretargeted Radioimmunotherapy of Non-Hodgkin's Lymphoma with a New Recombinant, Trivalent, Anti-CD20, Bispecific Antibody," Cancer Research, Jul. 1, 2008, 68(13):5282-90.
Sharma et al., "Regulatory T Cells License Macrophage Pro Resolving Functions During Atherosclerosis Regression," Circulation Research, Apr. 27, 2020, 127:335-353.
Smith et al., "Antigen Nature and Complexity Influence Human Antibody Light Chain Usage and Specificity," Vaccine, 2016, 34(25): 2813-2820.
Smith et al., "Development and evaluation of an optimal human single-chain variable fragment-derived BCMA-targeted CAR T cell vector," Molecular Therapy, Jun. 6, 2018, 26(6):1447-56.
Soerensen et al., "Safety, PK/PD, and anti-tumor activity of RO6874281, an engineered variant of interleukin-2 (IL-2v) targeted to tumor-associated fibroblasts via binding to fibroblast activation protein (FAP)," Journal of Clinical Oncology, Jun. 1, 2018, 36(No. 15 Suppl.):e15155, 2 pages.
Sondel et al., "Combination Therapy with Interleukin-2 and Anti-tumor Monoclonal Antibodies," Cancer Journal from Scientific American, Jan. 1, 1997, 3(Suppl. 1):S121-S127.
Sone et al., "Pancreatic beta cell senescence contributes to the pathogenesis of type 2 diabetes in high-fat diet-induced diabetic mice," Diabetologia, 2005, 48(1):58-67.
Song et al., "IL-12/IL-18-preactivated donor NK cells enhance GVL effects and mitigate GvHD after allogeneic hematopoietic stem cell transplantation," European Journal of Immunology, Apr. 2018, 48(4):670-682.
Soriani et al., "ATM-ATR-dependent up-regulation of DNAM-1 and NKG2D ligands on multiple myeloma cells by therapeutic agents results in enhanced NK-cell susceptibility and is associated with a senescent phenotype," Blood, Apr. 9, 2009, 113(15):3503-11.
Sousa-Victor et al., "Geroconversion of aged muscle stem cells under regenerative pressure," Cell Cycle, Oct. 15, 2014, 13(20):3183-3190.
Spiess et al., "Alternative molecular formats and therapeutic applications for bispecific antibodies," Molecular Immunology, Oct. 1, 2015, 67(2):95-106.

(56) References Cited

OTHER PUBLICATIONS

Stoklasek et al., "Combined IL-15/IL-15Rα Immunotherapy Maximizes IL-15 Activity In Vivo," The Journal of Immunology, Nov. 1, 2006, 177(9):6072-6080.
Storer et al., "Senescence Is a Developmental Mechanism that Contributes to Embryonic Growth and Patterning," Cell, Nov. 21, 2013, 155(5):1119-1130.
Stryer, Biochemistry Fourth Edition, W. H. Freeman and Company, New York, 1995, pp. 18-23, 8 pages.
Swanson et al., "The NLRP3 inflammasome: molecular activation and regulation to therapeutics," Nature Reviews Immunology, Apr. 29, 2019, 19(8):477-489, 13 pages.
Szalay et al., "Cutting edge: anti-CD1 monoclonal antibody treatment reverses the production patterns of TGF-β2 and Th1 cytokines and ameliorates listeriosis in mice," The Journal of Immunology, Jun. 15, 1999, 162(12):6955-8.
Tahara-Hanaoka et al., "Functional characterization of DNAM-1 (CD226) interaction with its ligands PVR (CD155) and nectin-2 (PRR-2/CD112)," International Immunology, Apr. 1, 2004, 16(4):533-8.
Takahashi et al., "Downregulation of cytoplasmic DNases is implicated in cytoplasmic DNA accumulation and SASP in senescent cells," Nature Communications, Mar. 28, 2018, 9:1249, 12 pages.
Takahashi et al., "Simple and inexpensive technique for measuring oxygen consumption rate in adherent cultured cells," The Journal of Physiological Sciences, Nov. 2017, 67(6):731-737.
Takeda et al., "Phase I study of YS110, a recombinant humanized monoclonal antibody to CD26, in Japanese patients with advanced malignant pleural mesothelioma," Lung Cancer, Nov. 2019, 137:64-70.
Tam et al., "Methods and strategies of peptide ligation," Peptide Science: Original Research on Biomolecules, 2001, 60(3):194-205.
Tanaka et al., "Cloning and functional expression of the T cell activation antigen CD26," Journal of Immunology, Jul. 15, 1992, 149(2):481-486.
Tang et al., "The Foxp3+ regulatory T cell: a jack of all trades, master of regulation," Nature Immunology, Feb. 19, 2008, 9(3):239-244.
Teissier et al., "The receptor for advanced glycation end-products (RAGE) is an important pattern recognition receptor (PRR) for inflammaging," Biogerontology, Apr. 9, 2019, 20(3):279-301, 23 pages.
Teng et al., "Structural assessment of the effects of amino acid substitutions on protein stability and protein proteininteraction," International journal of computational biology and drug design, Feb. 7, 2011, 3(4):334-349.
Theil et al., "Adoptive transfer of allogeneic regulatory T cells into patients with chronic graft-versus-host disease," Cytotherapy, Apr. 2015, 17(4):473-486, 14 pages.
Thonhoff et al., "Expanded autologous regulatory T-lymphocyte infusions in ALS," Neurology Neuroimmunology Neuroinflammation, May 18, 2018, 5(4):e465, 8 pages.
Tobin et al., "NK cells in childhood obesity are activated, metabolically stressed, and functionally deficient," JCI Insight, Dec. 21, 2017, 2(24):e94939, 9 pages.
Tomala et al., "In Vivo Expansion of Activated Naive CD8+ T Cells and NK Cells Driven by Complexes of IL-2 and Anti-IL-2 Monoclonal Antibody as Novel Approach of Cancer Immunotherapy," The Journal of Immunology, Oct. 15, 2009, 183:4904-4912.
Tominaga et al., "TGF-β Signaling in Cellular Senescence and Aging-Related Pathology," International Journal of Molecular Sciences, Oct. 10, 2019, 20(20):5002, 18 pages.
Trevani et al., "Extracellular acidification induces human neutrophil activation," The Journal of Immunology, Apr. 15, 1999, 162(8):4849-4857.
Tse et al., "ABT-263: A Potent and Orally Bioavailable Bcl-2 Family Inhibitor," Cancer Research, May 2008, 68(9):3421-3428.
Uryga et al., "Ageing induced vascular smooth muscle cell senescence in atherosclerosis," Journal of Physiology, Apr. 15, 2016, 594(8):2115-2124.
Vaishampayan et al., "A phase I trial of ALKS 4230, an engineered cytokine activator of NK and effector T cells, in patients with advanced solid tumors," Journal of Clinical Oncology, 2017, 35(15 Suppl.):TPS3111, 4 pages (Abstract Only).
Van Audenhove et al., "Nanobodies as versatile tools to understand, diagnose, visualize and treat cancer," EBioMedicine, Jun. 1, 2016, 8:40-8.
Van den Bergh et al., "IL-15 receptor alpha as the magic wand to boost the success of IL-15 antitumor therapies: The upswing of IL-15 transpresentation," Pharmacology and Therapeutics, 2017, 170:73-79.
Van Deursen, "The role of senescent cells in ageing," Nature, May 21, 2014, 509(7501):439-446.
Vankadari et al., "Emerging COVID-19 coronavirus: glycan shield and structure prediction of spike glycoprotein and its interaction with human CD26," Emerging Microbes and Infection, Mar. 17, 2020, 9(1):601-604.
Vidarsson et al., "IgG subclasses and allotypes: from structure to effector functions," Frontiers in immunology, Oct. 20, 2014, 5:520, 17 Pages.
Vincke et al., "Introduction to heavy chain antibodies and derived Nanobodies," Single Domain Antibodies, Humana Press, Totowa, NJ, 2012, pp. 15-26.
Voelker et al., "Anti-TGF-β1 Antibody Therapy in Patients with Diabetic Nephropathy," J Am Soc Nephrol., 2017, 28:953-962.
Voet et al., Biochemistry, John Wiley & Sons, Inc., 1990, pp. 126-128 and 228-234, 12 pages.
Von Kobbe, "Cellular senescence: a view throughout organismal life," Cellular and Molecular Life Sciences, Jul. 20, 2018, 75:3553-3567, 15 pages.
Waaijer et al., "Do senescence markers correlate in vitro and in situ within individual human donors?," Aging Feb. 2018, 10(2):278-289.
Wallace et al., "B lymphocytes confer immune tolerance via cell surface GARP-TGF-β B complex," JCI Insight., 2018, 3(7):e99863, 19 pages.
Walsh et al., "Inflammasomes in the CNS," Nature Reviews Neuroscience, Jan. 8, 2014, 15(2):84-97, 14 pages.
Wang et al., A New Recombinant Single Chain Trispecific Antibody Recruits T Lymphocytes to Kill CEA (Carcinoma Embryonic Antigen) Positive Tumor Cells In Vitro Efficiently, Journal of Biochemisty, 2004, 135(4):555-565.
Wang et al., "Biomarkers of Cellular Senescence and Skin Aging," Frontiers in Genetics, Aug. 23, 2018, 9:247, 14 pages.
Wang et al., "Loss of lamin B1 is a biomarker to quantify cellular senescence in photoaged skin," Scientific Reports, Nov. 15, 2017, 7(1):15678, 8 pages.
Wang et al., "Recombinant human CD137L for cancer immunotherapy: effects of different fusions and linkers on its activity," Cancer Immunol Immunother., 2012, 61(4):489-495.
Washburn et al., "A potential role for shed soluble major histocompatibility class I molecules as modulators of neurite outgrowth," PLoS One, Mar. 31, 2011, 6(3):e18439.
Weber et al., "Specific low-affinity recognition of major histocompatibility complex plus peptide by soluble T-cell receptor," Nature, Apr. 1992, 356(6372):793.
Weihermann et al., "Elastin structure and its involvement in skin photoageing," International Journal of Cosmetic Science, Jun. 2017, 39(3):241-247.
Weihofen et al., "Crystal Structure of CD26/Dipeptidyl-peptidase IV in Complex with Adenosine Deaminase Reveals a Highly Amphiphilic Interface," Journal of Biological Chemistry, Oct. 2004, 279(41):43330-43335.
Weiner et al., "Antibody-based immunotherapy of cancer," Cell, Mar. 16, 2012, 148(6):1081-4.
Weiss et al., "Formyl-Peptide Receptors in Infection, Inflammation, and Cancer," Trends in Immunology, Oct. 2018, 39(10):815-829, 15 pages.
Wesolowski et al., "Single domain antibodies: promising experimental and therapeutic tools in infection and immunity," Medical Microbiology and Immunology. Aug. 1, 2009, 198(3):157-74.

(56) References Cited

OTHER PUBLICATIONS

Wiemann et al., "Hepatocyte telomere shortening and senescence are general markers of human liver cirrhosis," The FASEB Journal, Jul. 2002, 16(9):935-942.
Wiley et al., "Mitochondrial Dysfunction Induces Senescence with a Distinct Secretory Phenotype," Cell Metabolism, Feb. 9, 2016, 23(2):303-314.
Witkowsa et al., "Soluble intercellular adhesion molecule-1 (sICAM-1): an overview," Eur Cytokine Netw. 2004, 15(2):91-98.
Xiong et al., "Maternal uterine NK cell-activating receptor KIR2DS1 enhances placentation," The Journal of Clinical Investigation, Oct. 1, 2013, 123(10):4264-72.
Xu et al., "Celecoxib attenuates cachectic events in mice by modulating the expression of vascular endothelial growth factor," Mol Med Rep., Jan. 2015, 11(1):289-294.
Xu et al., "JAK inhibition alleviates the cellular senescence-associated secretory phenotype and frailty in old age," Proceedings of the National Academy of Sciences U.S.A., Nov. 17, 2015, 112(46):E6301-6310, 10 pages.
Xu et al., "Senolytics improve physical function and increase lifespan in old age," Nature Medicine, Aug. 2018, 24(8):1246, 15 pages.
Xu et al., "Transplanted senescent cells induce an osteoarthritis-like condition in mice," The Journals of Gerontology: Series A, Jun. 1, 2017, 72(6):780-5.
Yamamoto et al., "Measurement of glucose uptake in cultured cells," Curr Protoc Pharmacol, Dec. 2011, Chapter 12:12.14.1-12.14.22.
Yamazaki et al., "Vascular Cell Senescence Contributes to Blood-Brain Barrier Breakdown," Stroke, Feb. 16, 2016, 47(4):1068-1077, 15 pages.
Yan et al., "Obesity- and aging-induced excess of central transforming growth factor-β potentiates diabetic development via an RNA stress response," Nature Medicine, Aug. 3, 2014, 20:1001-1008, 9 pages.
Yanai et al., "Cellular senescence-like features of lung fibroblasts derived from idiopathic pulmonary fibrosis patients," Aging (Albany NY), Sep. 2015, 7(9):664-672.
Yigit et al., "A combination of an anti-SLAMF6 antibody and ibrutinib efficiently abrogates expansion of chronic lymphocytic leukemia cells," Oncotarget, May 3, 2016, 7(18):26346.
Yousefzadeh et al., "An aged immune system drives senescence and ageing of solid organs," Nature, May 12, 2021, 594:100-105, 34 pages.
Yu et al., "Targeting the Senescence-Overriding Cooperative Activity of Structurally Unrelated H3K9 Demethylases in Melanoma," Cancer Cell, Feb. 12, 2018, 33(2):322-336, 23 pages.
Yu et al., "The dipeptidyl peptidase IV family in cancer and cell biology," FEBS Journal, Feb. 5, 2010, 277(5):1126-1144.
Yun et al., "Recurrent turnover of senescent cells during regeneration of a complex structure," Elife, May 5, 2015, 4:e05505, 16 pages.
Yung et al., "A selective transforming growth factor-β ligand trap attenuates pulmonary hypertension," American Journal of Respiratory and Critical Care Medicine, Nov. 1, 2016, 194(9):1140-51.
Zhang et al., "AAED1 modulates proliferation and glycolysis in gastric cancer," Oncology Reports, Aug. 1, 2018, 40(2):1156-1164.
Zhang et al., "The bone anabolic effects of irisin are through preferential stimulation of aerobic glycolysis," Bone, Sep. 1, 2018, 114:150-160.
Zhao et al., "Histone Deacetylase-3 Modification of MicroRNA-31 Promotes Cell Proliferation and Aerobic Glycolysis in Breast Cancer and Is Predictive of Poor Prognosis," Journal of breast cancer, Jun. 1, 2018, 21(2):112-123.
Zheng et al., "Acquisition of Suppressive Function by Activated Human CD4+CD25-T Cells Is Associated with the Expression of CTLA-4 Not FoxP3," The Journal of Immunology, Aug. 1, 2008, 181(3):1683-1691.
Zhong et al., "A Potential Role for Dendritic Cell/Macrophage-Expressing DPP4 in Obesity-Induced Visceral Inflammation," Diabetes, Jan. 2013, 62(1):149-157.
Zhou et al., "A novel chimeric antigen receptor redirecting T-cell specificity towards CD26cancer cells," Leukemia, Apr. 2020, 35(1):119-129, 11 pages.
Zhu et al., "New agents that target senescent cells: the flavone, fisetin, and the BCL-XL inhibitors, A1331852 and A1155463," Aging (Albany NY), Mar. 2017, 9(3):955-963.
Zhu et al., "Novel Human Interleukin-15 Agonists," The Journal of Immunology, Sep. 15, 2009, 183(6):3598-3607.
Zou et al., "2-NBDG as a fluorescent indicator for direct glucose uptake measurement," Journal of biochemical and biophysical methods, Sep. 30, 2005, 64(3):207-215.
Zwaagstra et al., "Engineering and therapeutic application of single-chain bivalent TGF-β family traps," Molecular Cancer Therapeutics, Jul. 1, 2012, 11(7):1477-87.
Shen et al., "Engineering peptide linkers for scFv immunosensors," Anal Chem., Mar. 2008, 80(6):1910-1917.
Chan et al., "Molecular mechanisms of natural killer cell activation in response to cellular stress," Cell Death & Differentiation, Jan. 2014, 21(1):5-14.
Chang et al., "The dock and lock method: a novel platform technology for building multivalent, multifunctional structures of defined composition with retained bioactivity," Clinical cancer research, Sep. 15, 2007, 13(18):5586s-5591s.
Hui et al., "Butyrate inhibit collagen-induced arthritis via Treg/IL-10/Th17 axis," International immunopharmacology, Mar. 1, 2019, 68: Abstract 1 page.
Li et al., "Lipid metabolism fuels cancer's spread," Cell metabolism, Feb. 7, 2017, 25(2):228-230.
Wilchek et al., "Essentials of biorecognition: The (strept) avidin-biotin system as a model for protein-protein and protein-ligand interaction," Immunology letters, Feb. 28, 2006, 103(1): Abstract 2 pages.
Zhang et al., "Depletion of NK cells improves cognitive function in the Alzheimer disease mouse model," The Journal of Immunology, Jul. 15, 2020, 205(2): 10pages.
Fernando et al., "Targeting tumor endothelial marker 8 in the tumor vasculature of colorectal carcinomas in mice," Cancer Research, Jun. 15, 2009, 69(12):5126-5132.
Mortier et al., "Soluble interleukin-15 receptor α (IL-15Rα)-sushi as a selective and potent agonist of IL-15 action through IL-15Rβ/γ: hyperagonist IL-15• IL-15Rα fusion proteins," Journal of Biological Chemistry, Jan. 20, 2006, 281(3):1612-1619.
Wong et al., "Interleukin-15: Interleukin-15 receptor a scaffold for creation of multivalent targeted immune molecules," Protein Engineering, Design & Selection, Apr. 1, 2011, 24(4):373-383.
Bartscht et al., "Dasatinib blocks transcriptional and promigratory responses to transforming growth factor-beta in pancreatic adenocarcinoma cells through inhibition of Smad signalling: implications for in vivo mode of action," Molecular Cancer, Dec. 2015, 14(199):1-12.
Bird et al., "TGFβ inhibition restores a regenerative response in acute liver injury by suppressing paracrine senescence," Science translational medicine, Aug. 15, 2018, 10(454):eaan 1230, 15 pages.
Cai et al., "Quercetin inhibits transforming growth factor β1-induced epithelial-mesenchymal transition in human retinal pigment epithelial cells via the Smad pathway," Drug design, development and therapy, Dec. 6, 2018, 12:4149-4161.
Chen et al., "A novel idea for establishing Parkinson's disease mouse model by intranasal administration of paraquat" Neurological Research, 43(4):267-277, 2021.
Igarashi et al., "VEGF-C and TGF-β reciprocally regulate mesenchymal stem cell commitment to differentiation into lymphatic endothelial or osteoblastic phenotypes," International journal of molecular medicine, 37(4):1005-1013, Apr. 1, 2016.
Infante-Duarte et al., "New developments in understanding and treating neuroinflammation" Journal of Molecular Medicine, 86:975-985, Sep. 2008.
International Search Report and Written Opinion in International Appln. No. PCT/US2023/065745, mailed on Jun. 26, 2023, 14 pages.

(56) References Cited

OTHER PUBLICATIONS

Janeway et al., “The interaction of the antibody molecule with specific antigen” in Immunobiology: The Immune System in Health and Disease, 5th edition, 5 pages, 2001.
Matsuura et al., “Pole test is a useful method for evaluating the mouse movement disorder caused by striatal dopamine depletion” Journal of neuroscience methods, 73(1):45-48, 1997.
Reddy et al., “Linkers in the structural biology of protein-protein interactions” Protein science, 22(2):153-167, 2013.
Ross et al., “Signaling and function of interleukin-2 in T lymphocytes” Annual review of immunology, 36:411-433, 2018.
Van Bockstaele et al., “The development of nanobodies for therapeutic applications” Current opinion in investigational drugs, 10(11):1212-1224, 2009.
[No Author Listed], “CN Br-activated Sepharose 4 Fast Flow,” 1999, Affinity Chromatography, 4 pages.
Brämer et al., “Membrane adsorber for the fast purification of a monoclonal antibody using protein a chromatography,” Membranes, Nov. 27, 2019, 9(12):159, 15 pages.
Chabannon et al., “Manufacturing natural killer cells as medicinal products,” Frontiers in Immunology, Nov. 15, 2016, 7(504): 1-9.
Guha et al., “Affinity purification of human tissue factor: interaction of factor VII and tissue factor in detergent micelles,” Proceedings of the National Academy of Sciences, Jan. 1986, 83(2):299-302.
Hélie et al., “Application of the Protein Maker as a platform purification system for therapeutic antibody research and development,” Computational and Structural Biotechnology Journal, Jan. 1, 2016, 14:238-244.
info.gbiosciences.com [Online], “G-Biosciences, The Basics of Affinity Purification/Affinity Chromatography,” Jul. 31, 2018, retrieved on Apr. 18, 2023, retrieved from URL<https://info.gbiosciences.com/blog/the-basics-of-affinity-purification/affinity-chromatography?utm_campaign=G-Bio+Search+Ads&utm_term=&utm_source=adwords&utm_medium=ppc&hsa_src=g&hsa_ver-3&hsa_cam=737902488&hsa_kw-&hsa_ad=621736020174&hsa_tgt=dsa-460355902483&hsa_mt=&hsa_acc-6752996364&hsa_grp=92226101427&hsa_net=adwords&gclid-CjwKCAjw_ihBhADEiwAXEazJvXifVFgeRGV_W99XbY72eRROhWnHtdd695ydPgyh8qdvTwd9ikGIRoCdecQAvD_BwE>, 5 pages.
Klingemann et al., “Natural killer cells for immunotherapy-advantages of the NK-92 cell line over blood NK cells,” Frontiers in Immunology, Mar. 14, 2016, 7(91): 1-7.
Kozlowska et al., “Adoptive transfer of osteoclast-expanded natural killer cells for immunotherapy targeting cancer stem-like cells in humanized mice,” Cancer Immunology, Immunotherapy, Jul. 2016, 65:835-845.
Putnam et al., “Clinical grade manufacturing of human alloantigen-reactive regulatory T cells for use in transplantation,” American Journal of Transplantation, Nov. 1, 2013, 13(11):3010-3020.
ThermoFisher.com [Online], “Covalent Immobilization of Affinity Ligands,” 2018, retrieved on Apr. 18, 2023, retrieved from <URLhttps://www.thermofisher.com/us/en/home/life-science/protein-biology/protein-biology-learning-center/protein-biology-resource-library/pierce-protein-methods/covalent-immobilization-affinity-ligands.html>, 13 pages.
Uppendahl et al., “Natural killer cell-based immunotherapy in gynecologic malignancy: a review,” Frontiers in Immunology, Jan. 5, 2018, 8(1825): 1-15.
Urh et al., “Affinity chromatography: general methods,” Methods in Enzymology, Jan. 1, 2009, 463: 23 pages.
Veluchamy et al., “The rise of allogeneic natural killer cells as a platform for cancer immunotherapy: recent innovations and future developments,” Frontiers in Immunology, May 31, 2017, 8(631): 1-20.
Zhou, “Emerging mechanisms and applications of low-dose IL-2 therapy in autoimmunity,” Cytokine & Growth Factor Reviews, Jun. 30, 2022, 67: 80-88.

* cited by examiner

CD26
| | 1 | 2 | 3 | 4 | 5 | 6 | 7 | 8 | | 10 | 11 | 12 |
|---|---|---|---|---|---|---|---|---|---|---|---|---|
| A | 0.041 | 0.817 | 0.297 | 2.924 | 0.375 | 0.960 | 0.357 | 1.017 | 0.644 | 0.040 | 0.905 | 1.006 |
| B | 0.049 | 0.056 | 2.251 | 1.806 | 0.329 | 1.425 | 0.727 | 1.162 | 0.054 | 0.680 | 0.868 | 0.043 |
| C | 0.893 | 0.892 | 0.894 | 0.844 | 0.379 | 0.506 | 0.526 | 0.884 | 0.930 | 1.037 | 2.684 | 0.729 |
| D | 0.948 | 0.988 | 0.902 | 0.316 | 0.918 | 1.015 | 2.814 | 0.967 | 2.901 | 0.604 | 0.043 | 3.020 |
| E | 0.887 | 0.882 | 0.896 | 0.905 | 0.044 | 0.419 | 0.636 | 1.002 | 0.487 | 1.030 | 2.666 | 0.936 |
| F | 2.755 | 0.801 | 2.673 | 0.270 | 2.981 | 0.889 | 0.419 | 2.053 | 0.967 | 0.924 | 0.936 | 0.935 |
| G | 0.881 | 0.826 | 0.859 | 0.868 | 0.381 | 0.047 | 2.125 | 0.369 | 0.966 | 0.043 | 0.916 | 0.877 |
| H | 0.911 | 0.313 | 1.953 | 0.952 | 0.881 | 0.933 | 2.715 | 0.949 | 2.622 | 2.580 | 1.931 | 0.930 |
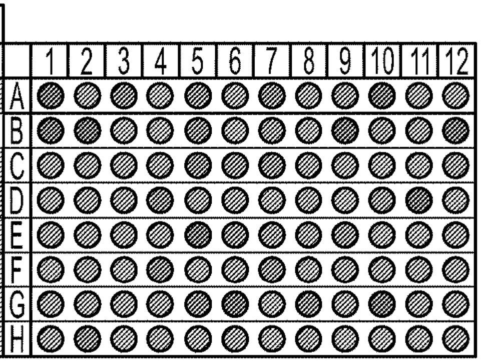
IgG Control
| | 1 | 2 | 3 | 4 | 5 | 6 | 7 | 8 | 9 | 10 | 11 | 12 |
|---|---|---|---|---|---|---|---|---|---|---|---|---|
| A | 0.046 | 0.046 | 0.044 | 0.069 | 0.242 | 0.083 | 0.067 | 0.046 | 0.047 | 0.045 | 0.050 | 0.048 |
| B | 0.045 | 0.045 | 0.045 | 0.259 | 0.450 | 0.074 | 0.191 | 0.056 | 0.088 | 0.046 | 0.047 | 0.044 |
| C | 0.047 | 0.045 | 0.046 | 0.051 | 0.145 | 0.136 | 0.051 | 0.045 | 0.046 | 0.046 | 0.046 | 0.046 |
| D | 0.050 | 0.052 | 0.046 | 0.216 | 0.261 | 0.095 | 0.046 | 0.046 | 0.067 | 0.046 | 0.044 | 0.051 |
| E | 0.047 | 0.045 | 0.046 | 0.053 | 0.094 | 0.050 | 0.048 | 0.047 | 0.044 | 0.045 | 0.045 | 0.046 |
| F | 0.049 | 0.046 | 0.079 | 0.073 | 0.089 | 0.158 | 0.046 | 0.158 | 0.046 | 0.046 | 0.046 | 0.047 |
| G | 0.047 | 0.073 | 0.222 | 0.117 | 0.068 | 0.153 | 0.168 | 0.045 | 0.055 | 0.059 | 0.047 | 0.046 |
| H | 0.053 | 0.073 | 0.194 | 0.051 | 0.057 | 0.127 | 0.047 | 0.050 | 0.048 | 0.047 | 0.214 | 0.046 |
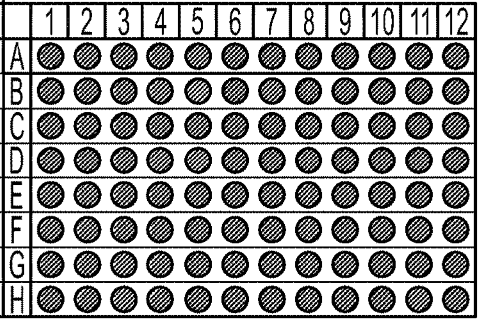
ProL/A-HRP*
| | 1 | 2 | 3 | 4 | 5 | 6 | 7 | 8 | 9 | 10 | 11 | 12 |
|---|---|---|---|---|---|---|---|---|---|---|---|---|
| A | 0.040 | 3.109 | 3.084 | 3.107 | 3.104 | 3.090 | 3.081 | 3.067 | 3.056 | 0.042 | 3.027 | 3.073 |
| B | 0.041 | 2.304 | 3.140 | 3.133 | 3.813 | 3.116 | 3.102 | 3.090 | 0.043 | 3.029 | 3.089 | 0.042 |
| C | 3.144 | 3.163 | 3.150 | 3.136 | 3.120 | 3.141 | 3.107 | 3.062 | 3.034 | 3.013 | 3.051 | 3.062 |
| D | 3.128 | 3.152 | 3.140 | 3.118 | 3.093 | 3.091 | 3.094 | 3.046 | 3.057 | 3.042 | 0.045 | 3.054 |
| E | 3.143 | 3.135 | 3.181 | 3.020 | 0.044 | 3.092 | 3.092 | 3.057 | 3.057 | 3.049 | 3.052 | 3.042 |
| F | 3.172 | 3.092 | 3.160 | 3.074 | 3.111 | 3.090 | 3.105 | 3.110 | 3.060 | 3.034 | 3.064 | 3.051 |
| G | 3.150 | 3.164 | 3.160 | 3.132 | 3.150 | 0.045 | 3.127 | 3.094 | 3.081 | 0.046 | 3.042 | 3.073 |
| H | 3.127 | 3.127 | 3.065 | 3.132 | 3.135 | 3.138 | 3.133 | 3.109 | 3.108 | 3.094 | 3.096 | 3.083 |
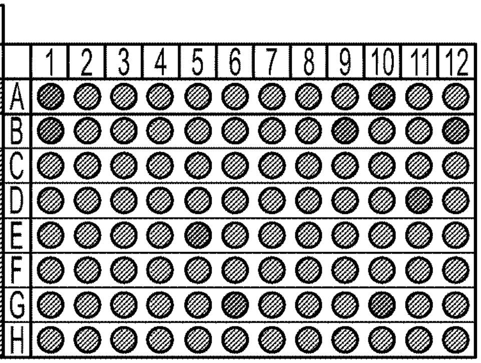
*ProL/ProA-HRP tests were used for scFv quality check.
FIG. 1

| No. | formal name | CDR-L1 | CDR-L2 | CDR-L3 | CDR-H1 | CDR-H2 | CDR-H3 | ELISA $OD_{450}$ | | | GH libraries |
|---|---|---|---|---|---|---|---|---|---|---|---|
| | | | | | | | | CD26 | ProL/ProA-HRP | AH2n | |
| 1 | CD26-01D | RASQDVNSNVA (SEQ ID NO:4) | FGSGGLYS (SEQ ID NO:5) | QQYSSYPL (SEQ ID NO:6) | TINDSYIH (SEQ ID NO:1) | WIWPYGGFTY (SEQ ID NO:2) | ARFLGSSSIMDY (SEQ ID NO:3) | 0.948 | 3.128 | 0.050 | GH02-12 |
| 2 | CD26-04A | RASQDVSGGVA (SEQ ID NO:10) | YGTSGLYS (SEQ ID NO:11) | QQGGDWPI (SEQ ID NO:262) | AINNYSIH (SEQ ID NO:7) | SIWPYGGFTS (SEQ ID NO:8) | ARFFSSYGDMDY (SEQ ID NO:9) | 2.924 | 3.107 | 0.069 | GH02-12 |
| 3 | CD26-10B | RASQDVWGYVA (SEQ ID NO:16) | FASGALYS (SEQ ID NO:17) | QQYFNWPI (SEQ ID NO:18) | TISDYSIH (SEQ ID NO:13) | SIWPYGGFTS (SEQ ID NO:56) | ARFHSSSGDMDY (SEQ ID NO:57) | 0.680 | 3.029 | 0.046 | GH02-12 |
| 4 | CD26-12D | RASQDVYSWVA (SEQ ID NO:22) | YGPGSLYS (SEQ ID NO:23) | QQYYNYPL (SEQ ID NO:24) | TINSSYIH (SEQ ID NO:19) | GIGPYWGFTS (SEQ ID NO:20) | ARFYSSYGFMDY (SEQ ID NO:21) | 3.020 | 3.054 | 0.051 | GH02-12 |
| 5 | CD26-03B | RASQDVYYFVA (SEQ ID NO:28) | SWPTGLYS (SEQ ID NO:29) | QQYFSYPI (SEQ ID NO:30) | TIGNSYIH (SEQ ID NO:25) | GIGPYWGFTS (SEQ ID NO:26) | ARFNGSSGFMDY (SEQ ID NO:27) | 2.251 | 3.140 | 0.045 | GH02-12 |

FIG. 2

GH2 (HHJ)

CD26/ scFv/ Etag-HRP

| P1-CD26 | 1 | 2 | 3 | 4 |
|---|---|---|---|---|
| A | 0.047 | 0.046 | 0.047 | 0.046 |
| B | 0.050 | 0.047 | 0.047 | 0.048 |
| C | 0.055 | 0.048 | 0.048 | 0.048 |
| D | 0.050 | 0.050 | 0.050 | 0.048 |
| E | 0.048 | 0.049 | 0.048 | 3.065 |
| F | 0.050 | 0.049 | 0.048 | 0.049 |
| G | 0.051 | 0.049 | 3.083 | 0.052 |
| H | 0.051 | 0.050 | 0.050 | 0.054 |

PrI/ scFv/ PrA-HRP

| P1-PrLA | 1 | 2 | 3 | 4 |
|---|---|---|---|---|
| A | 0.064 | 0.048 | 0.048 | 0.047 |
| B | 0.047 | 0.048 | 0.049 | 0.048 |
| C | 0.047 | 0.048 | 0.048 | 3.073 |
| D | 0.047 | 0.049 | 0.050 | 0.049 |
| E | 0.051 | 0.051 | 0.049 | 3.082 |
| F | 0.047 | 0.048 | 0.049 | 0.050 |
| G | 0.048 | 0.049 | 3.161 | 0.048 |
| H | 0.049 | 0.048 | 0.048 | 0.048 |

IgG/ scFv/ Etag-HRP

| P1-IgG | 1 | 2 | 3 | 4 |
|---|---|---|---|---|
| A | 0.049 | 0.049 | 0.048 | 0.050 |
| B | 0.050 | 0.049 | 0.049 | 0.049 |
| C | 0.050 | 0.050 | 0.049 | 0.049 |
| D | 0.049 | 0.050 | 0.048 | 0.049 |
| E | 0.050 | 0.049 | 0.052 | 0.050 |
| F | 0.050 | 0.049 | 0.049 | 0.049 |
| G | 0.054 | 0.049 | 0.050 | 0.049 |
| H | 0.053 | 0.051 | 0.052 | 0.050 |

FIG. 5

| Plate2 | | | | | | | | | | | |
|---|---|---|---|---|---|---|---|---|---|---|---|
| CD26 | | | | | | | | | | | |
| 2.185 | 1.327 | 2.785 | 2.643 | 1.063 | 2.563 | 0.042 | 0.042 | 0.042 | 1.597 | 0.042 | 1.227 |
| 2.203 | 2.739 | 2.468 | 2.772 | 2.692 | 1.006 | 0.041 | 0.043 | 0.051 | 0.048 | 0.042 | 2.501 |
| 2.427 | 2.724 | 2.798 | 2.472 | 1.519 | 2.721 | 2.312 | 0.043 | 0.042 | 0.052 | 0.042 | 2.741 |
| 1.910 | 2.692 | 0.993 | 2.860 | 1.246 | 2.677 | 0.043 | 2.303 | 0.044 | 0.042 | 0.043 | 2.675 |
| 2.423 | 2.764 | 2.670 | 2.721 | 1.234 | 2.819 | 0.042 | 0.043 | 0.042 | 0.042 | 0.042 | 2.371 |
| 1.287 | 2.843 | 2.544 | 0.129 | 1.289 | 2.832 | 0.042 | 0.042 | 0.043 | 0.043 | 0.043 | 2.638 |
| 2.497 | 1.038 | 2.623 | 2.377 | 2.676 | 2.683 | 0.043 | 0.042 | 0.042 | 0.052 | 0.042 | 2.658 |
| 2.293 | 0.832 | 2.320 | 0.963 | 2.412 | 2.733 | 2.300 | 0.043 | 0.043 | 1.148 | 0.056 | 2.828 |
| ProL/ProA-HRP | | | | | | | | | | | |
| 2.810 | 2.985 | 2.887 | 2.782 | 2.769 | 2.841 | 0.048 | 0.466 | 0.049 | 2.823 | 0.048 | 2.469 |
| 2.694 | 2.961 | 3.003 | 2.938 | 2.826 | 2.877 | 0.051 | 2.824 | 0.051 | 0.049 | 0.050 | 2.415 |
| 2.904 | 2.905 | 2.995 | 2.992 | 2.888 | 2.900 | 2.829 | 2.947 | 0.052 | 0.381 | 0.043 | 2.709 |
| 2.690 | 2.916 | 2.942 | 2.913 | 2.897 | 2.923 | 0.049 | 2.954 | 0.045 | 0.046 | 0.046 | 2.644 |
| 2.683 | 2.964 | 2.889 | 2.966 | 2.865 | 2.845 | 0.046 | 0.045 | 0.046 | 0.048 | 0.044 | 2.760 |
| 2.713 | 2.907 | 2.924 | 0.058 | 2.898 | 2.985 | 0.058 | 2.983 | 0.052 | 0.053 | 0.051 | 2.637 |
| 2.742 | 3.034 | 2.920 | 2.984 | 2.920 | 2.880 | 0.049 | 0.050 | 2.307 | 0.051 | 0.050 | 2.751 |
| 2.311 | 2.924 | 2.812 | 2.811 | 2.928 | 2.881 | 2.735 | 0.044 | 0.043 | 2.597 | 0.045 | 2.605 |
| IgG | | | | | | | | | | | |
| 0.045 | 0.052 | 0.046 | 0.046 | 0.044 | 0.046 | 0.044 | 0.044 | 0.044 | 0.047 | 0.044 | 0.054 |
| 0.046 | 0.048 | 0.053 | 0.056 | 0.050 | 0.054 | 0.047 | 0.048 | 0.045 | 0.045 | 0.044 | 0.049 |
| 0.047 | 0.046 | 0.048 | 0.058 | 0.056 | 0.047 | 0.049 | 0.047 | 0.046 | 0.136 | 0.045 | 0.049 |
| 0.049 | 0.052 | 0.055 | 0.048 | 0.057 | 0.064 | 0.045 | 0.049 | 0.044 | 0.045 | 0.045 | 0.051 |
| 0.047 | 0.047 | 0.056 | 0.054 | 0.052 | 0.061 | 0.045 | 0.046 | 0.047 | 0.046 | 0.046 | 0.047 |
| 0.045 | 0.046 | 0.050 | 0.053 | 0.046 | 0.049 | 0.047 | 0.059 | 0.047 | 0.049 | 0.063 | 0.083 |
| 0.047 | 0.062 | 0.048 | 0.051 | 0.053 | 0.048 | 0.047 | 0.046 | 0.046 | 0.045 | 0.048 | 0.051 |
| 0.046 | 0.046 | 0.048 | 0.048 | 0.046 | 0.048 | 0.047 | 0.045 | 0.045 | 0.050 | 0.044 | 0.051 |

| No. | formal name | CDR-L1 | CDR-L2 | CDR-L3 | CDR-H1 | CDR-H2 | CDR-H3 | ELISA $OD_{450}$ | | | Date | Repeats |
|---|---|---|---|---|---|---|---|---|---|---|---|---|
| | | | | | | | | CD26 | ProL/ProA -HRP | AH2n IgG | | |
| 1 | CD26-01D | RASQDVNSNVA (SEQ ID NO: 4) | FGSGGLYS (SEQ ID NO:5) | QQYSSYPL (SEQ ID NO:6) | TINDSYIH (SEQ ID NO:1) | WIWPYGGFTY (SEQ ID NO:2) | ARFLGSSSIMDY (SEQ ID NO:3) | 0.948 | 3.128 | 0.050 | 2019/12/4 | 5 |
| 2 | CD26-04A | RASQDVSGGVA (SEQ ID NO:10) | YGTSGLYS (SEQ ID NO:11) | QQGGDWPI (SEQ ID NO:262) | AINNYSIH (SEQ ID NO:7) | SIWPYGGFTS (SEQ ID NO:8) | ARFFSSYGDMDY (SEQ ID NO:9) | 2.924 | 3.107 | 0.069 | 2019/12/4 | 2 |
| 3 | CD26-10B | RASQDVWGYVA (SEQ ID NO:16) | FASGALYS (SEQ ID NO:17) | QQYFNWPI (SEQ ID NO:18) | TISDYSIH (SEQ ID NO:13) | SIWPYGGFTS (SEQ ID NO:56) | ARFHSSSGDMDY (SEQ ID NO:15) | 0.680 | 3.029 | 0.046 | 2019/12/4 | 2 |
| 4 | CD26-12D | RASQDVYSWVA (SEQ ID NO:22) | YGPGSLYS (SEQ ID NO:23) | QQYYNYPL (SEQ ID NO:24) | TINSSYIH (SEQ ID NO:19) | GIGPYWGFTS (SEQ ID NO:20) | ARFYSSYGFMDY (SEQ ID NO:21) | 3.020 | 3.054 | 0.051 | 2019/12/4 | 1 |
| 5 | CD26-03B | RASQDVYYFVA (SEQ ID NO:28) | SWPTGLYS (SEQ ID NO:29) | QQYFSYPI (SEQ ID NO:30) | TIGNSYIH (SEQ ID NO:25) | GIGPYWGFTS (SEQ ID NO:20) | ARFNGSSGFMDY (SEQ ID NO:27) | 2.251 | 3.140 | 0.045 | 2019/12/4 | 8 |

FIG. 7

| | | | | | | | | | | | | |
|---|---|---|---|---|---|---|---|---|---|---|---|---|
| 6 | CD26-07H | KSNQNLLYSHGRTYLN (SEQ ID NO:34) | FGTSHLYS (SEQ ID NO:35) | YQGYHVPF (SEQ ID NO:36) | KASGYTFARFGMY (SEQ ID NO:31) | FIAPNHGYTF (SEQ ID NO:32) | ARGHWYHGYMDY (SEQ ID NO:33) | 2.300 | 2.735 | 0.047 | 2020/3/9 | 2 |
| 7 | CD26-01G | RASQDVNNSVA (SEQ ID NO:40) | FSPTGLYS (SEQ ID NO:41) | QQYFDFPL (SEQ ID NO:42) | AASGFTIGNYGIH (SEQ ID NO:37) | WIGPSGGYTF (SEQ ID NO:38 | ARFDVHGFHGMDY (SEQ ID NO:39) | 2.491 | 2.926 | 0.047 | 2020/3/10 | 3 |
| 8 | CD26-04E | RASQDVNDGVA (SEQ ID NO:46) | YWASYLYS (SEQ ID NO:47) | QQSWNFPL (SEQ ID NO:48) | AASGFTINNDGFIH (SEQ ID NO:263) | GIWPFGGSTS (SEQ ID NO:44) | ARFDVVDWGVMDY (SEQ ID NO:45) | 2.897 | 3.066 | 0.057 | 2020/3/4 | 8 |
| 9 | CD26-03G | RASQDVSSSVA (SEQ ID NO:52) | SYPGWLYS (SEQ ID NO:53) | QQFGDFPM (SEQ ID NO:54) | AASGFTIGNYGIH (SEQ ID NO:37) | WIGPYGGYTF (SEQ ID NO:50) | ARFNNLLWNGMDY (SEQ ID NO:51) | 3.062 | 3.068 | 0.060 | 2020/3/4 | 11 |
| 10 | CD26-01F | RASQDVWGYVA (SEQ ID NO:16) | FSSRSLYS (SEQ ID NO:59) | QQYFNWPI (SEQ ID NO:60) | AASGFTISDYSIH (SEQ ID NO:55) | SIWPYGGFTS (SEQ ID NO:56) | ARFHSSSGDMDY (SEQ ID NO:15) | 1.287 | 2.713 | 0.045 | 2020/3/9 | 4 |

FIG. 7 - Continued

ANTI-CD26 PROTEINS AND USES THEREOF

CROSS-REFERENCE TO RELATED APPLICATIONS

This application is a National Stage Application under 35 U.S.C. 371 of International Patent Application No. PCT/US2021/029920, filed on Apr. 29, 2021, which claims priority to U.S. Provisional Application Ser. No. 63/017,467, filed on Apr. 29, 2020, each of which is incorporated herein by reference in its entirety.

REFERENCE TO SEQUENCE LISTING

This application contains a Sequence Listing that has been submitted electronically as an ASCII text file named "20221025 47039-0021US1_SL_ST25_Replacement.txt". The ASCII text file, created on Sep. 29, 2025, is 325,694 bytes in size. The material in the ASCII text file is hereby incorporated by reference in its entirety.

TECHNICAL FIELD

The present disclosure relates to the field of biotechnology, and more specifically, to anti-CD26 antibodies and uses thereof.

BACKGROUND

CD26 (DPP4, also known as Dipeptidyl-peptidase-4, DDP4) is a transmembrane glycoprotein, anchored to the membrane by its signal peptide, that forms a homodimer or tetramer on the plasma membrane. CD26 is an amino peptidase that primarily cleaves N-terminal dipeptides from peptides or small proteins (e.g., below 80-100 amino acid residues) with proline or alanine as the penultimate amino acid.

CD26 is expressed in numerous tissues including intestinal and renal brush border membranes, vascular endothelium, liver and pancreas, glandular epithelial cells, and by cells of the immune system (Gutschmidt et al., Histochemistry 73 (2): 285-304, 1982; Gorrell et al., Cell. Immunol. 134 (1): 205-215, 1991; Tanaka et al., J. Immunol. 149 (2): 481-486, 1992; Abbott et al., Immunogentics 40 (5): 331-338, 1994; Buhling et al., Immunol. Lett. 45 (1-2): 47-51, 1995; Dikov et al., Cell. Mol. Biol. 50 Online Pub: OL565-568, 2004; Broxmeyer et al., Stem Cells Dev. 25 (8): 575-585, 2016; Hollande et al., Nat. Immunol. 20 (3): 257-264, 2019). CD26 was also found to function as a binding site for the chemokine CXCR4 receptor, the T-cell differentiation antigen CD45, and the sodium-hydrogen exchanger-3 (Mentlein et al., Regul. Pept. 85 (1): 9-24, 1999; Lambeir et al., Crit. Rev. Clin. Lab. Sci. 40 (3): 209-294, 2003). Thus, CD26 can be viewed as a multi-functional protein with a variety of actions which go beyond its role as a proteinase. Its role as a receptor or ligand for a variety of different molecules, either alone or in combination with its enzymatic activity, enable it to affect physiological processes such as the interaction between cells and the extracellular matrix involved in cell migration, activation, and proliferation.

CD26 also plays a major role in glucose metabolism. Incretin peptides such as gastric inhibitory polypeptide (GIP) and glucagon-like peptide (GLP-1) are responsible for the modulation of postprandial blood glucose by promoting insulin secretion from pancreatic B cells and via glucagon static effects. These peptides are rapidly inactivated by CD26 resulting in a short half-life. Besides incretin peptides, CD26 also cleaves a number of other proteins. The physiologic targets include GLP1, GLP2, brain natriuretic peptide, peptide YY, stromal-cell-derived factor, erythropoietin, granulocyte colony-stimulating factor, and substance P. Pharmacological targets include gastric-releasing peptide, growth-hormone-releasing factor, macrophage derived chemokine, eotaxin, IFN-Y-induced protein-10, granulocyte-macrophage colony-stimulating factor, erythropoietin, IL-3, neuropeptide Y, B-type natriuretic peptide, and peptide YY (Mulvihill et al., Endocr. Rev. 35 (6): 992-1019, 2014). Furthermore, CD26 is known to modulate the functionality of chemokines, such as CXCR3, through post-translational cleavage of X-Pro or X-Ala motifs, which leads to amino-terminal dipeptide truncation of chemokines and altered biological functions (Broxmeyer et al., Stem Cells Dev. 25 (8): 575-585, 2016). CD26 also mediates amino-terminal cleavage of the chemokine CXCL10, limiting the migration of CXCR3 natural killer (NK) and T cells and diminution of anti-tumor immunity in preclinical models of melanoma and colorectal carcinoma (Barreira et al., Nat. Immunol. 16 (8): 850-858, 2015). Combined immunotherapy using checkpoint blockade in the presence of the CD26 inhibitor sitagliptin was also shown to decrease tumor growth by enhancing anti-tumor activities of T cells and eosinophils in preclinical mouse models of hepatocellular carcinoma and breast cancer (Hollande et al., Nat. Immunol. 20 (3): 257-264, 2019).

In summary, CD26 exerts its physiological roles either via its enzymatic activity by regulating many peptides or via its interactions with a variety of binding partners. Consequently, altered expression, and/or activity of CD26 have been implicated in several pathological processes, including inflammation, viral infection, immune-mediated diseases, tumor growth, cellular senescence, and metabolic diseases (Mentlein et al., Regul. Pept. 85 (1): 9-24, 1999; Lambeir et al., Crit. Rev. Clin. Lab. Sci. 40 (3): 209-294, 2003; Yu et al., FEBSJ. 277 (5): 1126-1144, 2010; Kim et al., Genes Dev. 31 (15): 1529-1534, 2017; Deacon, Front. Endocrinol. 10:80, 2019. Thus, CD26 is a cell-surface targetable protein for drug development to treat a variety of diseases including viral infections and aging-related pathologies

SUMMARY

Provided herein are proteins comprising an anti-CD26 antigen-binding domain, wherein the anti-CD26 antigen-binding domain comprises: (a) a heavy chain variable domain comprising a CDR1 comprising SEQ ID NO: 1, a CDR2 comprising SEQ ID NO: 2, and a CDR3 comprising SEQ ID NO: 3, and a light chain variable domain comprising a CDR1 comprising SEQ ID NO: 4, a CDR2 comprising SEQ ID NO: 5, and a CDR3 comprising SEQ ID NO: 6; (b) a heavy chain variable domain comprising a CDR1 comprising SEQ ID NO: 7, a CDR2 comprising SEQ ID NO: 8, and a CDR3 comprising SEQ ID NO: 9, and a light chain variable domain comprising a CDR1 comprising SEQ ID NO: 10, a CDR2 comprising SEQ ID NO: 11, and a CDR3 comprising SEQ ID NO: 12; (c) a heavy chain variable domain comprising a CDR1 comprising SEQ ID NO: 13, a CDR2 comprising SEQ ID NO: 14, and a CDR3 comprising SEQ ID NO: 15, and a light chain variable domain comprising a CDR1 comprising SEQ ID NO: 16, a CDR2 comprising SEQ ID NO: 17, and a CDR3 comprising SEQ ID NO: 18; (d) a heavy chain variable domain comprising a CDR1 comprising SEQ ID NO: 19, a CDR2 comprising SEQ ID NO: 20, and a CDR3 comprising SEQ ID NO: 21, and a light chain variable domain comprising a CDR1 comprising SEQ ID NO: 22, a CDR2 comprising SEQ ID NO: 23, and a CDR3 comprising SEQ ID NO: 24; (e) a heavy chain variable domain comprising a CDR1 comprising SEQ ID NO: 25, a CDR2 comprising SEQ ID NO: 26, and a CDR3 comprising SEQ ID NO: 27, and a light chain variable domain comprising a CDR1 comprising SEQ ID NO: 28, a CDR2 comprising SEQ ID NO: 29, and a CDR3 comprising SEQ ID NO: 30; (f) a heavy chain variable domain comprising a CDR1 comprising SEQ ID NO: 31, a CDR2 comprising SEQ ID NO: 32, and a CDR3 comprising SEQ ID NO: 33, and a light chain variable domain comprising a CDR1 comprising SEQ ID NO: 34, a CDR2 comprising SEQ ID NO: 35, and a CDR3 comprising SEQ ID NO: 36; (g) a heavy chain variable domain comprising a CDR1 comprising SEQ ID NO: 37, a CDR2 comprising SEQ ID NO: 38, and a CDR3 comprising SEQ ID NO: 39, and a light chain variable domain comprising a CDR1 comprising SEQ ID NO: 40, a CDR2 comprising SEQ ID NO: 41, and a CDR3 comprising SEQ ID NO: 42; (h) a heavy chain variable domain comprising a CDR1 comprising SEQ ID NO: 43, a CDR2 comprising SEQ ID NO: 44, and a CDR3 comprising SEQ ID NO: 45, and a light chain variable domain comprising a CDR1 comprising SEQ ID NO: 46, a CDR2 comprising SEQ ID NO: 47, and a CDR3 comprising SEQ ID NO: 48; (i) a heavy chain variable domain comprising a CDR1 comprising SEQ ID NO: 49, a CDR2 comprising SEQ ID NO: 50, and a CDR3 comprising SEQ ID NO: 51, and a light chain variable domain comprising a CDR1 comprising SEQ ID NO: 52, a CDR2 comprising SEQ ID NO: 53, and a CDR3 comprising SEQ ID NO: 54; or (j) a heavy chain variable domain comprising a CDR1 comprising SEQ ID NO: 55, a CDR2 comprising SEQ ID NO: 56, and a CDR3 comprising SEQ ID NO: 57, and a light chain variable domain comprising a CDR1 comprising SEQ ID NO: 58, a CDR2 comprising SEQ ID NO: 59, and a CDR3 comprising SEQ ID NO: 60.

In some embodiments, the antigen-binding domain comprises a heavy chain variable domain comprising a CDR1 comprising SEQ ID NO: 1, a CDR2 comprising SEQ ID NO: 2, and a CDR3 comprising SEQ ID NO: 3, and a light chain variable domain comprising a CDR1 comprising SEQ ID NO: 4, a CDR2 comprising SEQ ID NO: 5, and a CDR3 comprising SEQ ID NO: 6. In some embodiments, the heavy chain variable domain comprises a sequence that is at least 80% identical to SEQ ID NO: 61. In some embodiments, the heavy chain variable domain comprises a sequence that is at least 90% identical to SEQ ID NO: 61. In some embodiments, the heavy chain variable domain comprises a sequence that is at least 95% identical to SEQ ID NO: 61. In some embodiments, the light chain variable domain comprises a sequence that is at least 80% identical to SEQ ID NO: 62. In some embodiments, the light chain variable domain comprises a sequence that is at least 90% identical to SEQ ID NO: 62. In some embodiments, the light chain variable domain comprises a sequence that is at least 95% identical to SEQ ID NO: 62.

In some embodiments, the antigen-binding domain comprises a heavy chain variable domain comprising a CDR1 comprising SEQ ID NO: 7, a CDR2 comprising SEQ ID NO: 8, and a CDR3 comprising SEQ ID NO: 9, and a light chain variable domain comprising a CDR1 comprising SEQ ID NO: 10, a CDR2 comprising SEQ ID NO: 11, and a CDR3 comprising SEQ ID NO: 12. In some embodiments, the heavy chain variable domain comprises a sequence that is at least 80% identical to SEQ ID NO: 63. In some embodiments, the heavy chain variable domain comprises a sequence that is at least 90% identical to SEQ ID NO: 63. In some embodiments, the heavy chain variable domain comprises a sequence that is at least 95% identical to SEQ ID NO: 63. In some embodiments, the light chain variable domain comprises a sequence that is at least 80% identical to SEQ ID NO: 64. In some embodiments, the light chain variable domain comprises a sequence that is at least 90% identical to SEQ ID NO: 64. In some embodiments, the light chain variable domain comprises a sequence that is at least 95% identical to SEQ ID NO: 64.

In some embodiments, the antigen-binding domain comprises a heavy chain variable domain comprising a CDR1 comprising SEQ ID NO: 13, a CDR2 comprising SEQ ID NO: 14, and a CDR3 comprising SEQ ID NO: 15, and a light chain variable domain comprising a CDR1 comprising SEQ ID NO: 16, a CDR2 comprising SEQ ID NO: 17, and a CDR3 comprising SEQ ID NO: 18. In some embodiments, the heavy chain variable domain comprises a sequence that is at least 80% identical to SEQ ID NO: 65. In some embodiments, the heavy chain variable domain comprises a sequence that is at least 90% identical to SEQ ID NO: 65. In some embodiments, the heavy chain variable domain comprises a sequence that is at least 95% identical to SEQ ID NO: 65. In some embodiments, the light chain variable domain comprises a sequence that is at least 80% identical to SEQ ID NO: 66. In some embodiments, the light chain variable domain comprises a sequence that is at least 90% identical to SEQ ID NO: 66. In some embodiments, the light chain variable domain comprises a sequence that is at least 95% identical to SEQ ID NO: 66.

In some embodiments, the antigen-binding domain comprises a heavy chain variable domain comprising a CDR1 comprising SEQ ID NO: 19, a CDR2 comprising SEQ ID NO: 20, and a CDR3 comprising SEQ ID NO: 21, and a light chain variable domain comprising a CDR1 comprising SEQ ID NO: 22, a CDR2 comprising SEQ ID NO: 23, and a CDR3 comprising SEQ ID NO: 24. In some embodiments, the heavy chain variable domain comprises a sequence that is at least 80% identical to SEQ ID NO: 67. In some embodiments, the heavy chain variable domain comprises a sequence that is at least 90% identical to SEQ ID NO: 67. In some embodiments, the heavy chain variable domain comprises a sequence that is at least 95% identical to SEQ ID NO: 67. In some embodiments, the light chain variable domain comprises a sequence that is at least 80% identical to SEQ ID NO: 68. In some embodiments, the light chain variable domain comprises a sequence that is at least 90% identical to SEQ ID NO: 68. In some embodiments, the light chain variable domain comprises a sequence that is at least 95% identical to SEQ ID NO: 68.

In some embodiments, the antigen-binding domain comprises a heavy chain variable domain comprising a CDR1 comprising SEQ ID NO: 25, a CDR2 comprising SEQ ID NO: 26, and a CDR3 comprising SEQ ID NO: 27, and a light chain variable domain comprising a CDR1 comprising SEQ ID NO: 28, a CDR2 comprising SEQ ID NO: 29, and a CDR3 comprising SEQ ID NO: 30. In some embodiments, the heavy chain variable domain comprises a sequence that is at least 80% identical to SEQ ID NO: 69. In some embodiments, the heavy chain variable domain comprises a sequence that is at least 90% identical to SEQ ID NO: 69. In some embodiments, the heavy chain variable domain comprises a sequence that is at least 95% identical to SEQ ID NO: 69. In some embodiments, the light chain variable domain comprises a sequence that is at least 80% identical to SEQ ID NO: 70. In some embodiments, the light chain variable domain comprises a sequence that is at least 90% identical to SEQ ID NO: 70. In some embodiments, the light chain variable domain comprises a sequence that is at least 95% identical to SEQ ID NO: 70.

In some embodiments, the antigen-binding domain comprises a heavy chain variable domain comprising a CDR1 comprising SEQ ID NO: 31, a CDR2 comprising SEQ ID NO: 32, and a CDR3 comprising SEQ ID NO: 33, and a light chain variable domain comprising a CDR1 comprising SEQ ID NO: 34, a CDR2 comprising SEQ ID NO: 35, and a CDR3 comprising SEQ ID NO: 36. In some embodiments, the heavy chain variable domain comprises a sequence that is at least 80% identical to SEQ ID NO: 71. In some embodiments, the heavy chain variable domain comprises a sequence that is at least 90% identical to SEQ ID NO: 71. In some embodiments, the heavy chain variable domain comprises a sequence that is at least 95% identical to SEQ ID NO: 71. In some embodiments, the light chain variable domain comprises a sequence that is at least 80% identical to SEQ ID NO: 72. In some embodiments, the light chain variable domain comprises a sequence that is at least 90% identical to SEQ ID NO: 72. In some embodiments, the light chain variable domain comprises a sequence that is at least 95% identical to SEQ ID NO: 72.

In some embodiments, the antigen-binding domain comprises a heavy chain variable domain comprising a CDR1 comprising SEQ ID NO: 37, a CDR2 comprising SEQ ID NO: 38, and a CDR3 comprising SEQ ID NO: 39, and a light chain variable domain comprising a CDR1 comprising SEQ ID NO: 40, a CDR2 comprising SEQ ID NO: 41, and a CDR3 comprising SEQ ID NO: 42. In some embodiments, the heavy chain variable domain comprises a sequence that is at least 80% identical to SEQ ID NO: 73. In some embodiments, the heavy chain variable domain comprises a sequence that is at least 90% identical to SEQ ID NO: 73. In some embodiments, the heavy chain variable domain comprises a sequence that is at least 95% identical to SEQ ID NO: 73. In some embodiments, the light chain variable domain comprises a sequence that is at least 80% identical to SEQ ID NO: 74. In some embodiments, the light chain variable domain comprises a sequence that is at least 90% identical to SEQ ID NO: 74. In some embodiments, the light chain variable domain comprises a sequence that is at least 95% identical to SEQ ID NO: 74.

In some embodiments, the antigen-binding domain comprises a heavy chain variable domain comprising a CDR1 comprising SEQ ID NO: 43, a CDR2 comprising SEQ ID NO: 44, and a CDR3 comprising SEQ ID NO: 45, and a light chain variable domain comprising a CDR1 comprising SEQ ID NO: 46, a CDR2 comprising SEQ ID NO: 47, and a CDR3 comprising SEQ ID NO: 48. In some embodiments, the heavy chain variable domain comprises a sequence that is at least 80% identical to SEQ ID NO: 75. In some embodiments, the heavy chain variable domain comprises a sequence that is at least 90% identical to SEQ ID NO: 75. In some embodiments, the heavy chain variable domain comprises a sequence that is at least 95% identical to SEQ ID NO: 75. In some embodiments, the light chain variable domain comprises a sequence that is at least 80% identical to SEQ ID NO: 76. In some embodiments, the light chain variable domain comprises a sequence that is at least 90% identical to SEQ ID NO: 76. In some embodiments, the light chain variable domain comprises a sequence that is at least 95% identical to SEQ ID NO: 76.

In some embodiments, the antigen-binding domain comprises a heavy chain variable domain comprising a CDR1 comprising SEQ ID NO: 49, a CDR2 comprising SEQ ID NO: 50, and a CDR3 comprising SEQ ID NO: 51, and a light chain variable domain comprising a CDR1 comprising SEQ ID NO: 52, a CDR2 comprising SEQ ID NO: 53, and a CDR3 comprising SEQ ID NO: 54. In some embodiments, the heavy chain variable domain comprises a sequence that is at least 80% identical to SEQ ID NO: 77. In some embodiments, the heavy chain variable domain comprises a sequence that is at least 90% identical to SEQ ID NO: 77. In some embodiments, the heavy chain variable domain comprises a sequence that is at least 95% identical to SEQ ID NO: 77. In some embodiments, the light chain variable domain comprises a sequence that is at least 80% identical to SEQ ID NO: 78. In some embodiments, the light chain variable domain comprises a sequence that is at least 90% identical to SEQ ID NO: 78. In some embodiments, the light chain variable domain comprises a sequence that is at least 95% identical to SEQ ID NO: 78.

In some embodiments, the antigen-binding domain comprises a heavy chain variable domain comprising a CDR1 comprising SEQ ID NO: 55, a CDR2 comprising SEQ ID NO: 56, and a CDR3 comprising SEQ ID NO: 57, and a light chain variable domain comprising a CDR1 comprising SEQ ID NO: 58, a CDR2 comprising SEQ ID NO: 59, and a CDR3 comprising SEQ ID NO: 60. In some embodiments, the heavy chain variable domain comprises a sequence that is at least 80% identical to SEQ ID NO: 79. In some embodiments, the heavy chain variable domain comprises a sequence that is at least 90% identical to SEQ ID NO: 79. In some embodiments, the heavy chain variable domain comprises a sequence that is at least 95% identical to SEQ ID NO: 79. In some embodiments, the light chain variable domain comprises a sequence that is at least 80% identical to SEQ ID NO: 80. In some embodiments, the light chain variable domain comprises a sequence that is at least 90% identical to SEQ ID NO: 80. In some embodiments, the light chain variable domain comprises a sequence that is at least 95% identical to SEQ ID NO: 80.

In some embodiments, the protein is a multi-chain protein. In some embodiments, the protein is a single-chain protein. In some embodiments, the protein is an antibody or an antigen-binding antibody fragment. In some embodiments, the antibody is an IgG1 antibody, an IgG2 antibody, an IgG3 antibody, or an IgG4 antibody. In some embodiments, the antibody is humanized. In some embodiments, the antibody is human. In some embodiments, the protein is a scFv. In some embodiments, the protein is a chimeric antigen receptor (CAR).

Also provided herein are pharmaceutical compositions comprising any one of the proteins described herein and a pharmaceutically acceptable carrier. Also provided herein are kits comprising any one of the pharmaceutical compositions described herein. Also provided herein are nucleic acids encoding any one of the proteins described herein. Also provided herein are vectors comprising any one of the nucleic acids described herein. Also provided herein are pharmaceutical compositions comprising any one of the nucleic acids described herein or any one of the vectors described herein. Also provided herein are kits comprising any one of the pharmaceutical compositions described herein.

Provided herein are cells comprising any one of the nucleic acids described herein or any one of the vectors described herein. In some embodiments, the cell is an immune cell. In some embodiments, the immune cell is a T cell, a B cell, or a natural killer (NK) cell. In some embodiments, the immune cell is a regulatory T (Treg) cell. In some embodiments, the immune cell is an autologous cell. In some embodiments, the immune cell is an allogeneic cell.

Also provided herein are pharmaceutical compositions comprising any one of the cells described herein and a pharmaceutically acceptable carrier. Also provided herein are kits comprising any one of the pharmaceutical compositions described herein.

Provided herein are methods of treating an age-related disease or an inflammatory disease in a subject that include administering to the subject a therapeutically effective amount of any one of the proteins described herein or any one of the pharmaceutical compositions described herein. Also provided herein are methods of treating an aging-related disease or an inflammatory disease in a subject that include administering to the subject a therapeutically effective amount of any one of the nucleic acids described herein, any one of the vectors described herein, or any one of the pharmaceutical compositions described herein. Also provided herein are methods of treating an aging-related disease or an inflammatory disease in a subject, the method comprising administering to the subject a therapeutically effective amount of any one of the cells described herein or any one of the pharmaceutical compositions described herein.

In some embodiments, the aging-related disease is inflamm-aging related. In some embodiments, the subject is further administered (i) a therapeutically effective amount of an NK cell activating agent and/or an NK cell and/or a monoclonal antibody; and/or (ii) a therapeutically effective amount of a Treg cell activating agent and/or a Treg cell and/or a monoclonal antibody and/or an advanced glycation end product (AGE) inhibitor.

In some embodiments, the method comprises administering a therapeutically effective amount of an NK cell to the subject. In some embodiments, the NK cell is an autologous, haploidentical or allogeneic NK cell isolated from peripheral blood, umbilical cord blood, or isolated and differentiated from iPSC. In some embodiments, the method further comprises: isolating the NK cell from the subject; culturing the isolated NK cell in a liquid culture medium under conditions sufficient to induce or increase proliferation of the NK cell, wherein following the isolating and culturing steps, the NK cell is administered to the subject. In some embodiments, the liquid culture medium comprises a multi-chain chimeric polypeptide. In some embodiments, the NK cell comprises a chimeric antigen receptor. In some embodiments, the protein is any one of the chimeric antigen receptors described herein.

In some embodiments, the method comprises administering a therapeutically effective amount of an NK cell activating agent and/or monoclonal antibody to the subject. In some embodiments, the NK cell activating agent is one or more multi-chain chimeric polypeptide(s). In some embodiments, the monoclonal antibody is any one of the anti-tissue factor antibodies or antibodies described herein. In some embodiments, the NK cell activating agent comprises one or more multi-chain chimeric polypeptide(s) and the monoclonal antibody comprises one or more of any one of the anti-tissue factor antibodies and/or antibodies described herein.

In some embodiments, the method comprises administering a therapeutically effective amount of a Treg cell to the subject. In some embodiments, the Treg cell is an autologous Treg cell, a haploidentical Treg cell, or an allogeneic Treg cell isolated from peripheral blood or umbilical cord blood. In some embodiments, the method further comprises: isolating the Treg cell from the subject; culturing the isolated Treg cell in a liquid culture medium under conditions sufficient to induce or increase proliferation of the Treg cell, wherein following the isolating and culturing steps, the Treg cell is administered to the subject. In some embodiments, the liquid culture medium comprises one or more single-chain chimeric polypeptide(s). In some embodiments, the Treg cell comprises a chimeric antigen receptor. In some embodiments, the chimeric antigen receptor comprises an extracellular domain that binds specifically to tissue factor, CD26 (e.g., any of the anti-CD26 antigen-binding domains described herein), or CD36. In some embodiments, the method comprises administering a therapeutically effective amount of a Treg cell activating agent and/or monoclonal antibody and/or AGE inhibitor to the subject. In some embodiments, the Treg cell activating agent is one or more single-chain chimeric polypeptide(s). In some embodiments, the monoclonal antibody is one or both of an anti-tissue factor antibody, an anti-CD26 antibody (e.g., any of the anti-CD26 antibodies described herein), and/or an anti-CD36 antibody. In some embodiments, the AGE inhibitor is a soluble RAGE trap. In some embodiments, the Treg cell activating agent comprises one or more single-chain chimeric polypeptide(s), the monoclonal antibody comprises one or more of an anti-tissue factor antibody, an anti-CD26 antibody (e.g., any of the anti-CD26 antibodies described herein), and/or an anti-CD36 antibody, and the AGE inhibitor comprises one or more soluble RAGE trap.

In some embodiments, the multi-chain chimeric polypeptide comprises: (a) a first chimeric polypeptide comprising: (i) a first target-binding domain; (ii) a soluble tissue factor domain; and (iii) a first domain of a pair of affinity domains; (b) a second chimeric polypeptide comprising: (i) a second domain of a pair of affinity domains; and (ii) a second target-binding domain, wherein the first chimeric polypeptide and the second chimeric polypeptide associate through the binding of the first domain and the second domain of the pair of affinity domains.

In some embodiments, the single-chain chimeric polypeptide comprises: (i) a first target-binding domain; (ii) a soluble tissue factor domain; and (iii) a second target-binding domain.

In some embodiments, the aging-related disorder is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, neurodegeneration, stroke, cancer, dementia, vascular disease, infection susceptibility, chronic inflammation, and renal dysfunction.

In some embodiments, the inflammatory disease is selected from the group of: rheumatoid arthritis, inflammatory bowel disease, lupus erythematosus, lupus nephritis, diabetic nephropathy, CNS injury, Alzheimer's disease, Parkinson's disease, amyotrophic lateral sclerosis, Crohn's disease, multiple sclerosis, Guillain-Barre syndrome, psoriasis, Grave's disease, ulcerative colitis, nonalcoholic steatohepatitis, and mood disorders.

In some embodiments, the age-related disease is a cancer selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Also provided herein are methods of treating cancer in a subject that include administering to the subject a therapeutically effective amount of any one of the proteins described herein.

Also provided herein are methods of treating infectious disease in a subject that include administering to the subject a therapeutically effective amount of any one of the proteins described herein.

Also provided herein are methods of treating an infectious disease in a subject that include administering to the subject a therapeutically effective amount of any one of the proteins described herein or any one of the pharmaceutical compositions described herein.

An "antigen-binding domain" is one or more protein domain(s) (e.g., formed from amino acids from a single polypeptide or formed from amino acids from two or more polypeptides (e.g., the same or different polypeptides) that is capable of specifically binding to an antigen. In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins, e.g., human IgG (e.g., human IgG1, human IgG2, human IgG3, human IgG4)), antibody fragments, and multi-specific antibodies. One example of an antigen-binding domain is an antigen-binding domain formed by a VH-VL dimer. Additional examples of an antibody are described herein. Additional examples of an antibody are known in the art.

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$)). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an antigen-binding domain and its corresponding antigen or epitope are known in the art.

A "single-chain protein" as used herein to refers to a single protein chain.

A "multi-chain protein" as used herein to refers to a polypeptide comprising two or more (e.g., three, four, five, six, seven, eight, nine, or ten) protein chains (e.g., at least a first chimeric polypeptide and a second polypeptide), where the two or more proteins chains associate through non-covalent bonds to form a quaternary structure.

The term "pair of affinity domains" is two different protein domain(s) that bind specifically to each other with a $K_D$ of less than of less than $1\times10^{-7}$ M (e.g., less than $1\times10^{-8}$ M, less than $1\times10^{-9}$ M, less than $1\times10^{-10}$ M, or less than $1\times10^{-11}$ M). In some examples, a pair of affinity domains can be a pair of naturally-occurring proteins. In some embodiments, a pair of affinity domains can be a pair of synthetic proteins. Non-limiting examples of pairs of affinity domains are described herein.

The term "epitope" means a portion of an antigen that specifically binds to an antigen-binding domain. Epitopes can, e.g., consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. Methods for identifying an epitope to which an antigen-binding domain binds are known in the art.

The term "treatment" means to ameliorate at least one symptom of a disorder. In some examples, the disorder being treated is cancer and to ameliorate at least one symptom of cancer includes reducing aberrant proliferation, gene expression, signaling, translation, and/or secretion of factors. Generally, the methods of treatment include administering a therapeutically effective amount of composition that reduces at least one symptom of a disorder to a subject who is in need of, or who has been determined to be in need of such treatment.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 1 shows ELISA binding analysis of selected scFv clones, where a plate of scFv clones were tested and their binding to CD26, Fc, and proA/L were tested, and DNA was prepared for scFv constructs then sent for DNA sequencing to determine LC/HC variable domain sequences.

FIG. 2 shows sequence analysis of five unique scFv binding clones, where the unique clones were identified and sequencing results indicate that their LC and HC variable domains are intact and the sequences of CDR-L1, CDR-L2, CDR-L3, CDR-H1, CDR-H2, and CDR-H3 are unique from each other.

FIG. 5 shows the screening of CD26-binding scFvs, where clone CD26-03G and CD26-04E are shown in circled spots.

FIG. 7 shows the sequences of selected scFvs.

DETAILED DESCRIPTION

Figure 3:
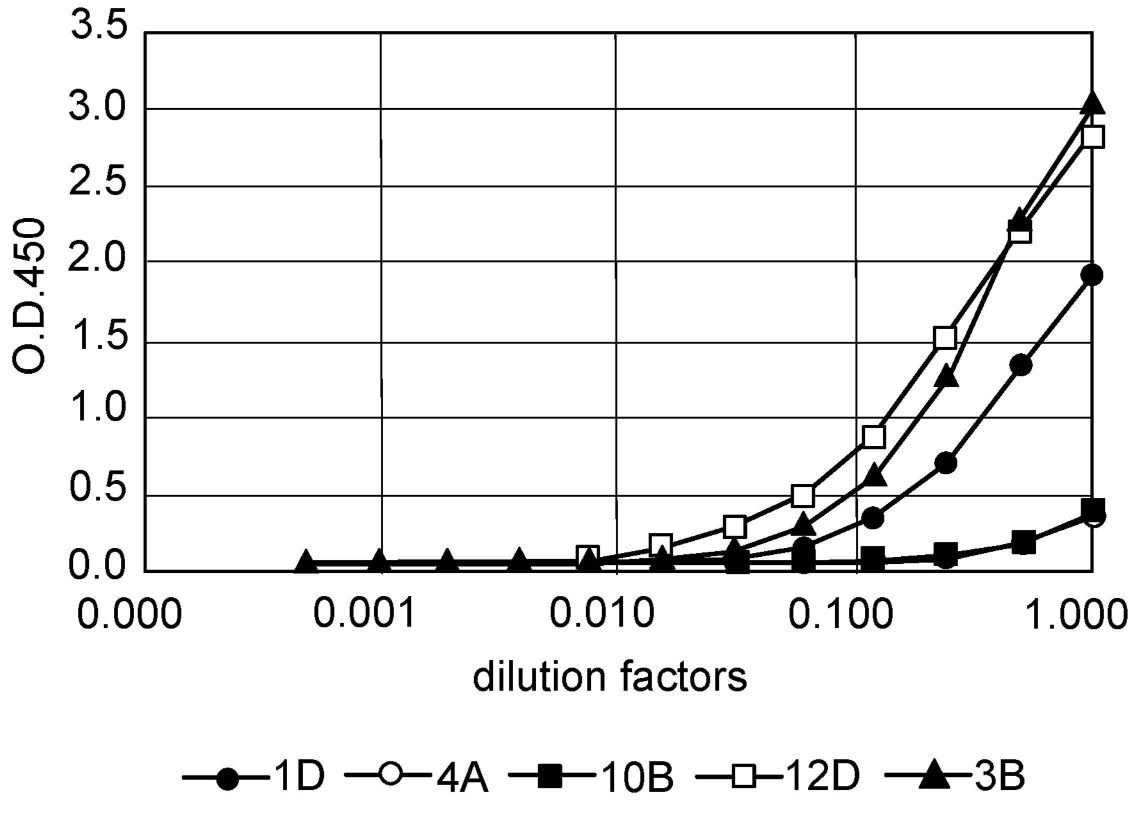
FIG. 3 shows the binding of scFv supernatants to CD26 with serial dilution of scFv supernatants.

Provided herein are proteins that include an anti-CD26 antigen-binding domain, nucleic acids encoding the same, cells including any of these nucleic acids or proteins, compositions including any of these proteins, nucleic acids, and cells, and methods of treating a subject having an aging-related disease or an inflammatory disease using any of the compositions described herein.

Non-limiting aspects of these proteins, nucleic acids, cells, compositions, and methods are described below. CD26

CD26 (DPP4, also known as Dipeptidyl-peptidase-4, DDP4) is a transmembrane glycoprotein, anchored to the membrane by its signal peptide, that forms a homodimer or tetramer on the plasma membrane. CD26 is an amino peptidase that primarily cleaves N-terminal dipeptides from peptides or small proteins (below 80-100 amino acid residues) with proline or alanine as the penultimate amino acid. Protein substrates with glycine, serine, valine, or leucine can also be cleaved but at a slower rate. The enzyme is unable to cleave substrates with proline at position three.

CD26 is expressed in numerous tissues including intestinal and renal brush border membranes, vascular endothelium, liver and pancreas, glandular epithelial cells, and by cells of the immune system (Gutschmidt et al., Histochemistry 73(2):285-304, 1981; Gorrell et al., Cell Immunol. 134(1):205-215, 1991; Tanaka et al., J. Immunol. 149(2): 481-486, 1992; Abbott et al., Immunogenetics 40(5):331-338, 1994; Buhling et al., Immunol. Lett. 45(1-2):47-51, 1995; Dikov et al., Cell. Mol. Biol. 50 Online Pub: OL565-568, 2004; Broxmeyer et al., Stem Cells Dev. 25(8):575-585, 2016; Hollande et al., Nat. Immunol. 20(3):257-264, 2019). The primary structure of CD26 consists of a six-amino acid cytoplasmic domain, a 22-amino acid transmembrane domain, and a 738-amino acid extracellular portion.

The extracellular portion is comprised of the C-terminal catalytic region with the catalytic active site triad Ser630, Asp708, and His740, a cysteine-rich area, and a large glycosylation-rich region linked by a flexible stalk to the transmembrane segment (Klemann et al., (lin. Exp. Immunol. 185(1):1-21, 2016). The crystal structure of human CD26 reveals two domains: an eight-bladed propeller and an α/β-hydrolase domain (Engel et al., Proc. Natl. Acad. Sci. U.S.A. 100(9):5063-5068, 2003). The propeller is open and consists of subdomains made up of blades II-V and VI-VIII for the glycosylation-rich and cysteine-rich regions, respectively. Adenosine deaminase (ADA) and cavelolin-1 bind to the glycosylation-rich domain of human CD26, and collagen, fibronectin, plasminogen, and streptokinase bind to the cysteine-rich region (Klemann et al., Clin. Exp. Immunol. 185(1):1-21, 2016). There are two openings for substrate interactions: a side opening and a propeller tunnel (Rasmussen et al., Nat. Struct. Biol. 10(1):19-25, 2003; Weihofen et al., J. Biol. Chem. 279(41):43330-43335, 2004). The CD26 substrate neuropeptide Y was found to enter CD26 at the side opening (Aertgeerts et al., Protein Sci. 13(2):412-421, 2004). CD26 was also found to function as binding sites for the chemokine CXCR4 receptor, the T-cell differentiation antigen CD45, and the sodium-hydrogen exchanger-3 (Mentlein et al., Regul. Pept. 85(1):9-24, 1999; Lambeir et al., Crit. Rev. Clin. Lab. Sci. 40(3):209-294, 2003). Thus, CD26 can be viewed as a multi-functional protein with a variety of actions which go beyond its role as a proteinase. Its role as a receptor or ligand for a variety of different molecules, either alone or in combination with its enzymatic activity, enable it to affect physiological processes, such as the interaction between cells and the extracellular matrix involved in cell migration, activation, and proliferation.

CD26 plays a major role in glucose metabolism. Incretin peptides, such as gastric inhibitory polypeptide (GIP) and glucagon-like peptide (GLP-1), are responsible for the modulation of postprandial blood glucose by promoting insulin secretion from pancreatic B cells and via glucagon static effects. These peptides are rapidly inactivated by CD26 resulting in a short half-life. $CD26^{-/-}$ mice are protected from the development of diet-induced obesity and demonstrate improved postprandial glucose control due to the prolonged half-life of the incretin peptides. $CD26^{-/-}$ mice also demonstrate improved insulin sensitivity, reduced pancreatic islet hypertrophy, and protection against streptozotocin-induced B cell loss and hyperglycemia (Marguet et al., Proc. Natl. Acad. Sci. U.S.A. 97(12):6874-6879, 2000; Conarello et al., Proc. Natl. Acad. Sci. U.S.A. 100(11):6825-6830, 2003). There are several CD26 inhibitors approved by the US FDA as antidiabetic drugs, such as sitagliptin, saxagliptin, linagliptin, vildagliptin, and alogliptin. Most clinical trials with CD26 inhibitors show approximately a 0.6-0.8% lowering of HbA1C in patients with a baseline level around 8% (Inzucchi et al., Circulation 117(4):574-584, 2008). In general, most studies also corroborate improvements in homeostasis model assessment β cell function index (HOMA-β) and fasting proinsulin: insulin ratio, suggesting improvement in β cell function (Raz et al., Diabetologia 49(11):2564-2571, 2006). The incidence of side effects and hypoglycemia are very low with these agents (Raz et al., Diabetologia 49(11):2564-2571, 2006; Lambeir et al., Crit. Rev. Clin. Lab. Sci. 40(3):209-294, 2003).

Besides incretin peptides, CD26 also cleaves a number of other proteins. The physiologic targets include GLP1, GLP2, brain natriuretic peptide, peptide YY, stromal-cell-derived factor, erythropoietin, granulocyte colony-stimulating factor, and substance P. Pharmacological targets include gastric-releasing peptide, growth-hormone-releasing factor, macrophage derived chemokine, eotaxin, IFN-γ-induced protein-10, granulocyte-macrophage colony-stimulating factor, erythropoietin, IL-3, neuropeptide Y, B-type natriuretic peptide, and peptide YY (Mulvihill et al., Endocr. Rev. 35(6):992-1019, 2014).

CD26 is known to modulate the functionality of chemokines, such as CXCR3, through post-translational cleavage of X-Pro or X-Ala motifs, which leads to amino-terminal dipeptide truncation of chemokines and altered biological function (Broxmeyer et al., Stem Cells Dev. 25 (8): 575-585, 2016). CD26 also mediates amino-terminal cleavage of the chemokine CXCL10, limiting the migration of CXCR3 natural killer (NK) and T cells and diminution of anti-tumor immunity in preclinical models of melanoma and colorectal carcinoma (Barreira da Silva et al., Nat. Immunol. 16(8): 850-858, 2015). Combined immunotherapy using checkpoint blockade in the presence of the CD26 inhibitor sitagliptin was also shown to decrease tumor growth by enhancing anti-tumor activities of T cells and eosinophils in pre-clinical mouse models of hepatocellular carcinoma and breast cancer (Hollande et al., Nat. Immunol. 20(3):257-264, 2019).

As mentioned above, CD26 interacts also with a range of ligands. By interacting with these ligands, CD26 plays a role in a variety of processes such as enhancing T-cell activation and functional modulation of antigen presenting cells (APCs). CD26 is able to trigger direct T cell activation and proliferation via CARMA1-mediated nuclear factor NF-κB in T cells (Ohnuma et al., J. Immunol. 167(12):6745-6755, 2001; Ohnuma et al., Proc. Natl. Acad. Sci. U.S.A. 101(39): 14186-14191, 2004). CD26 on T cells interacts directly with APCs via caveolin-1. Upon linkage, Tollip and interleukin-1-receptor associated kinase 1 (1RAK-1) disengage from caveolin-1 leading to subsequent 1RAK-1 phosphorylation (Ohnuma et al., Mol. Cell. Biol. 25(17):7743-7757, 2005; Ohnuma et al., Front. Biosci. 13:2299-2310, 2008). This results in an up-regulation of the co-stimulatory molecule CD86, which enhances the binding of T cells and APCs at the immunological synapse (Ohnuma et al., Proc. Natl. Acad. Sci. U.S.A. 101(39):14186-14191, 2004). Blocking CD26-mediated T cell co-stimulation with soluble caveolin-1-Ig fusion protein induces anergy in CD4 T cells (Ohhuma et al., Biochem. Biophys. Res. Comm. 386(2):327-332, 2009.

Interaction between CD26 and ADA also facilitate T-cell activation by providing a suitable microenvironment for T-cell proliferation. Extracellular ATP or ADP is initially converted to AMP by CD39 and CD73 to produce adenosine (Deaglio et al., J. Exp. Med. 204(6):1257-1265, 2007). Adenosine is then processed by ADA and converted to inosine (Resta et al., Immunol. Rev. 161:95-109, 1998). Adenosine has multiple physiological effects both within the central nervous system, immune system, and on peripheral tissues that are mediated by the G-protein coupled adenosine receptors identified as A1, A2A, A2B, and A3 (Borea et al., Physiol. Rev. 98(3):1591-1625, 2018). By anchoring ADA onto the surface, CD26 modulates pericellular adenosine levels and thus regulates T-cell activation. Absence of ADA activity results in the accumulation of adenosine, which inhibits T-cell proliferation in a dose-dependent manner. Jurkat cells expressing a CD26 mutant devoid of ADA binding activity are sensitive to adenosine-mediated inhibition of T-cell proliferation (Dong et al., J. Immunol. 159 (12):6070-6076, 1997). Cells expressing ADA and CD26 on the surface are much more resistant to the inhibitory effect of adenosine (Dong et al., J. Immunol. 156(4):1349-1355, 1996; Dong et al., J. Immunol. 159(12):6070-6076, 1997; Zhong et al., Diabetes 62(1):149-157, 2013). Evidence indicates that ADA co-localizing with adenosine receptors on dendritic cells and interacts with CD26 that is expressed on lymphocytes (Moreno et al., Front. Pharmacol. 9:106, 2018). This capacity of ADA functions as a costimulatory signal that potentiates T-cell activation and induces the production of the T-helper cell (Th1) pro-inflammatory cytokines.

CD26 binds multiple components of extracellular matrix such as collagen, fibronectin, and HIV-1 Tat protein (Loster et al., Biochem. Biophys. Res. Comm. 217(1):341-348, 1995; Zhong et al., Diabetes 62(1):149-157, 2013). Interactions with these matrix components may play a role in sequestration of CD26 and allows additional functions, such as matrix remodeling, metastasis, and chemotaxis. Research on anti-CD26 antibodies currently in development demonstrate a promising approach for cancer. In a preclinical study, a humanized monoclonal antibody targeting human CD26 was shown to be effectively against multiple myeloma in vitro and in vivo via the mechanism of antibody-dependent cell-mediated cytotoxicity (ADCC) (Nishida et al., Blood Cancer J. 8(11):99, 2018). A humanized monoclonal antibody to CD26 showed promising antitumor efficacy and was well tolerated in a recently reported Phase I clinical study in patients with advanced malignant pleural mesothelioma (Takeda et al., Lung Cancer 137:64-70, 2019).

CD26 is also implicated in cellular senescence, a hallmark of aging. Senescent cell accumulation in tissues is strongly linked to age-associated pathologies (Childs et al., Nat. Rev. Drug Discov. 16(10):718-735, 2017; Kirkland et al., EBioMedicine 21:21-28, 2017). Mass spectrometry analysis revealed that CD26 was upregulated on the surface of human senescent diploid fibroblasts (Kim et al., Genes Dev. 31(15):1529-1534, 2017). Increased CD26 expression on senescent, but not dividing, fibroblasts sensitized the fibroblasts to NK-mediated ADCC by anti-CD26 antibody (Kim et al., Genes Dev. 31(15):1529-1534, 2017).

Senescence is a form of irreversible growth arrest accompanied by phenotypic changes, resistance to apoptosis and activation of damage-sensing signaling pathways. Cellular senescence was first described in cultured human fibroblast cells that lost their ability to proliferate, reaching permanent arrest after about 50 population doublings (referred to as the Hayflick limit). Senescence is considered a stress response that can be induced by a wide range of intrinsic and extrinsic insults, including oxidative and genotoxic stress, DNA damage, telomere attrition, oncogenic activation, mitochondrial dysfunction, or chemotherapeutic agents.

Senescent cells remain metabolically active and can influence the tissue hemostasis, disease and aging through their secretory phenotype. Senescence is considered as a physiologic process and is important in promoting wound healing, tissue homeostasis, regeneration, and fibrosis regulation. For instance, transient induction of senescent cells is observed during would healing and contributes to wound resolution. Perhaps one of the most important roles of senescence is its role in tumor suppression. However, the accumulation of senescent cells also drives aging and aging-related diseases and conditions. The senescent phenotype also can trigger chronic inflammatory responses and consequently augment chronic inflammatory conditions to promote tumor growth. The connection between senescence and aging was initially based on observations that senescent cells accumulate in aged tissue. The use of transgenic models has enabled the detection of senescent cells systematically in many age-related pathologies. Strategies to selectively eliminate senescent cells have demonstrated that senescent cells can indeed play a causal role in aging and related pathologies.

Senescent cells display important and unique properties which include changes in morphology, chromatin organization, gene expression, and metabolism. There are several biochemical and functional properties associated with cellular senescence, such as (i) increased expression of p16 and p21, inhibitors of cyclin-dependent kinases, (ii) presence of senescence-associated β-galactosidase, a marker of lysosomal activity, (iii) appearance of senescence-associated heterochromatin foci and downregulation of lamin B1 levels, (iv) resistance to apoptosis caused by an increased expression of anti-apoptotic BCL-family protein, and (v) upregulation of CD26 (DPP4), CD36 (Scavenger receptor), forkhead box 4 (FOXO4), and secretory carrier membrane protein 4 (SCAMP4). Senescent cells also express an inflammatory signature, the so-called senescence-associated secretory phenotype (SASP). Through SASP, the senescent cells produce a wide range of inflammatory cytokines (IL-6, IL-8), growth factors (TGF-β), chemokines (CCL-2), and matrix metalloproteinases (MMP-3, MMP-9) that operate in a cell-autonomous manner to reinforce senescence (autocrine effects) and communicate with and modify the microenvironment (paracrine effects). SASP factors can contribute to tumor suppression by triggering senescence surveillance, an immune-mediated clearance of senescent cells. However, chronic inflammation is also a known driver of tumorigenesis, and accumulating evidence indicates that chronic SASP can also boost cancer and aging-related diseases.

The secretion profile of senescent cells is context dependent. For instance, the mitochondrial dysfunction-associated senescence (MiDAS), induced by different mitochondrial dysfunction in human fibroblasts, led to the appearance of a SASP that was deficient in IL-1-dependent inflammatory factors. A decrease in the NAD/NADH ratio activated AMPK signaling which induced MiDAS through the activation of p53. As a result, p53 inhibited NF-κB signaling which is a crucial inducer of pro-inflammatory SASP. In contrast, the cellular senescence caused by persistent DNA damage in human cells induced an inflammatory SASP, which was dependent on the activation of ataxia-telangiectasia mutated (ATM) kinase but not on that of p53. In particular, the expression and secretion levels of IL-6 and IL-8 were increased. It was also demonstrated that cellular senescence caused by the ectopic expression p16INK4a and p21CIP1 induced the senescent phenotype in human fibroblasts without an inflammatory SASP indicating that the growth arrest itself did not stimulate SASP.

One of the most defining characteristics of senescence is stable growth arrest. This is achieved by two important pathways, the p16/Rb and the p53/p21, both of which are central in tumor suppression. DNA damage results in: (1) high deposition of γH2Ax (histone coding gene) and 53BP1 (involved in DNA damage response) in chromatin: this leads to activation of a kinase cascade eventually resulting in p53 activation, and (2) activation of p16INK4a and ARF (both encoded by CDKN2A) and P15INK4b (encoded by CDKN2B): p53 induces transcription of cyclin-dependent kinase inhibitor (p21) and along with both p16INK4a and p15INK4b block genes for cell cycle progression (CDK4 and CDK6). This eventually leads to hypophosphorylation of Retinoblastoma protein (Rb) and cell cycle arrest at the G1 phase.

Selectively killing senescent cells has been shown to significantly improve the health span of mice in the context of normal aging and ameliorates the consequences of age-related disease or cancer therapy (Ovadya et al., J. Clin. Invest. 128(4):1247-1254, 2018). In nature, the senescent cells are normally removed by the innate immune cells. Induction of senescence not only prevents the potential proliferation and transformation of damaged/altered cells, but also favors tissue repair through the production of SASP factors that function as chemoattractants mainly for .NK cells (such as IL-15 and CCL2) and macrophages (such as CFS-1 and CCL2). These innate immune cells mediate the immunosurveillance mechanism for eliminating stressed cells. Senescent cells usually up-regulate the NK-cell activating receptor NKG2D and DNAM-1 ligands, which belong to a family of stress-inducible ligands: an important component of the frontline immune defense against infectious diseases and malignancies. Upon receptor activation, NK cells can then specifically induce the death of senescent cells through their cytolytic machinery. A role for NK cells in the immune surveillance of senescent cells has been pointed out in liver fibrosis (Sagiv et al., Oncogene 32(15): 1971-1977, 2013), hepatocellular carcinoma (Iannello et al., J. Exp. Med. 210(10):2057-2069, 2013), multiple myeloma (Soriani et al., Blood 113(15):3503-3511, 2009), and glioma cells stressed by dysfunction of the mevalonate pathway (Ciaglia et al., Int. J. Cancer 142(1):176-190, 2018). Endometrial cells undergo acute cellular senescence and do not differentiate into decidual cells. The differentiated decidual cells secrete IL-15 and thereby recruit uterine NK cells to target and eliminate the undifferentiated senescent cells thus helping to re-model and rejuvenate the endometrium (Brighton et al., Elife 6: e31274, 2017). With a similar mechanism, during liver fibrosis, p53-expressing senescent liver satellite cells skewed the polarization of resident Kupfer macrophages and freshly infiltrated macrophages toward the pro-inflammatory M1 phenotype, which display senolytic activity. F4/80$^+$ macrophages have been shown to play a key role in the clearance of mouse uterine senescent cells to maintain postpartum uterine function.

Senescent cells recruit NK cells by mainly upregulating ligands to NKG2D (expressed on NK cells), chemokines, and other SASP factors. In vivo models of liver fibrosis have shown effective clearance of senescent cells by activated NK cells (Krizhanovsky et al., Cell 134(4):657-667, 2008). Studies have described various models to study senescence including liver fibrosis (Krizhanovsky et al., Cell 134(4): 657-667, 2008), osteoarthritis (Xu et al., J. Gerontol. A Biol. Sci. Med. Sci. 72(6):780-785, 2017), and Parkinson's disease (Chinta et al., Cell Rep. 22(4):930-940, 2018). Animal models for studying senescent cells are described in: Krizhanovsky et al., Cell 134(4):657-667, 2008; Baker et al., Nature 479(7372):232-236, 2011; Farr et al., Nat. Med. 23(9):1072-1079, 2017; Bourgeois et al., FEBS Lett. 592 (12):2083-2097, 2018; Xu et al., Nat. Med. 24(8):1246-1256, 2018.

Studies have also shown that CD26 plays a role in infectious diseases. Middle East Respiratory Syndrome (MERS) is a viral respiratory illness. It was caused by the infection of a coronavirus, MERS-COV. The mortality from MERS is approximately 30% (CDC coronavirus/MERS website). CD26 is the functional receptor for the entry of MERS-COV in humans (Raj et al., J. Virol. 88(3):1834-1838, 2014). The engagement of the MERS-CoA spike protein S with CD26 mediates viral attachment and internalization. The residues involved in the CD26 virus binding are identical to the ADA binding domain indicating a potential competition for CD26 binding (Lu et al., Nature 500(7461):227-231, 2013). It has been suggested that the S1 domain of COVID-19 spike glycoprotein also interacts with the human CD26 (Vankadari et al., Emerg. Microbes Infect. 9(1):601-604, 2020).

In summary, CD26 exerts its physiological roles either via its enzymatic activity by regulating many peptides or via its interactions with a variety of binding partners. Consequently, altered expression, and/or activity of CD26 have been implicated in several pathological processes, including inflammation, viral infection, immune-mediated diseases, tumor growth, cellular senescence, and metabolic diseases (Mentlein et al., Regul. Pept. 85(1):9-24, 1999; Lambeir et al., Crit. Rev. Clin. Lab. Sci. 40(3):209-294, 2003; Yu et al., FEBS J. 277(5):1126-1144, 2010; Kim et al., Genes Dev. 31(15):1529-1534, 2017; Deacon et al., Front. Endocrinol. 10:80, 2019). Thus, CD26 is a cell-surface targetable protein for drug development to treat a variety of diseases including viral infections and aging-related pathologies.

This application describes the identification of novel human-derived monoclonal antibodies and antigen-binding domains that specifically binding to human CD26. The data provided herein demonstrate that these antibodies and their derivatives can be used as full-length antibodies, scFvs, and scFvs in chimeric antigen receptors that specifically recognize CD26. These antibodies and their derivatives have applications in treating human diseases.

Proteins

Provided herein are proteins including an anti-CD26 antigen-binding domain, where the anti-CD26 antigen-binding domain comprises: (a) a heavy chain variable domain comprising a CDR1 comprising SEQ ID NO: 1, a CDR2 comprising SEQ ID NO: 2, and a CDR3 comprising SEQ ID NO: 3, and a light chain variable domain comprising a CDR1 comprising SEQ ID NO: 4, a CDR2 comprising SEQ ID NO: 5, and a CDR3 comprising SEQ ID NO: 6; (b) a heavy chain variable domain comprising a CDR1 comprising SEQ ID NO: 7, a CDR2 comprising SEQ ID NO: 8, and a CDR3 comprising SEQ ID NO: 9, and a light chain variable domain comprising a CDR1 comprising SEQ ID NO: 10, a CDR2 comprising SEQ ID NO: 11, and a CDR3 comprising SEQ ID NO: 12; (c) a heavy chain variable domain comprising a CDR1 comprising SEQ ID NO: 13, a CDR2 comprising SEQ ID NO: 14, and a CDR3 comprising SEQ ID NO: 15, and a light chain variable domain comprising a CDR1 comprising SEQ ID NO: 16, a CDR2 comprising SEQ ID NO: 17, and a CDR3 comprising SEQ ID NO: 18; (d) a heavy chain variable domain comprising a CDR1 comprising SEQ ID NO: 19, a CDR2 comprising SEQ ID NO: 20, and a CDR3 comprising SEQ ID NO: 21, and a light chain variable domain comprising a CDR1 comprising SEQ ID NO: 22, a CDR2 comprising SEQ ID NO: 23, and a CDR3 comprising SEQ ID NO: 24; or (e) a heavy chain variable domain comprising a CDR1 comprising SEQ ID NO: 25, a CDR2 comprising SEQ ID NO: 26, and a CDR3 comprising SEQ ID NO: 27, and a light chain variable domain comprising a CDR1 comprising SEQ ID NO: 28, a CDR2 comprising SEQ ID NO: 29, and a CDR3 comprising SEQ ID NO: 30; (f) a heavy chain variable domain comprising a CDR1 comprising SEQ ID NO: 31, a CDR2 comprising SEQ ID NO: 32, and a CDR3 comprising SEQ ID NO: 33, and a light chain variable domain comprising a CDR1 comprising SEQ ID NO: 34, a CDR2 comprising SEQ ID NO: 35, and a CDR3 comprising SEQ ID NO: 36; (g) a heavy chain variable domain comprising a CDR1 comprising SEQ ID NO: 37, a CDR2 comprising SEQ ID NO: 38, and a CDR3 comprising SEQ ID NO: 39, and a light chain variable domain comprising a CDR1 comprising SEQ ID NO: 40, a CDR2 comprising SEQ ID NO: 41, and a CDR3 comprising SEQ ID NO: 42; (h) a heavy chain variable domain comprising a CDR1 comprising SEQ ID NO: 43, a CDR2 comprising SEQ ID NO: 44, and a CDR3 comprising SEQ ID NO: 45, and a light chain variable domain comprising a CDR1 comprising SEQ ID NO: 46, a CDR2 comprising SEQ ID NO: 47, and a CDR3 comprising SEQ ID NO: 48; (i) a heavy chain variable domain comprising a CDR1 comprising SEQ ID NO: 49, a CDR2 comprising SEQ ID NO: 50, and a CDR3 comprising SEQ ID NO: 51, and a light chain variable domain comprising a CDR1 comprising SEQ ID NO: 52, a CDR2 comprising SEQ ID NO: 53, and a CDR3 comprising SEQ ID NO: 54; or (j) a heavy chain variable domain comprising a CDR1 comprising SEQ ID NO: 55, a CDR2 comprising SEQ ID NO: 56, and a CDR3 comprising SEQ ID NO: 57, and a light chain variable domain comprising a CDR1 comprising SEQ ID NO: 58, a CDR2 comprising SEQ ID NO: 59, and a CDR3 comprising SEQ ID NO: 60.

In some examples of any of the proteins described herein, the antigen-binding domain comprises a heavy chain variable domain comprising a CDR1 comprising SEQ ID NO: 1, a CDR2 comprising SEQ ID NO: 2, and a CDR3 comprising SEQ ID NO: 3, and a light chain variable domain comprising a CDR1 comprising SEQ ID NO: 4, a CDR2 comprising SEQ ID NO: 5, and a CDR3 comprising SEQ ID NO: 6. In some examples of any of the proteins described herein, the heavy chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 61. In some examples of any of the proteins described herein, the light chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 62.

In some examples of any of the proteins described herein, the antigen-binding domain comprises a heavy chain variable domain comprising a CDR1 comprising SEQ ID NO: 7, a CDR2 comprising SEQ ID NO: 8, and a CDR3 comprising SEQ ID NO: 9, and a light chain variable domain comprising a CDR1 comprising SEQ ID NO: 10, a CDR2 comprising SEQ ID NO: 11, and a CDR3 comprising SEQ ID NO: 12. In some examples of any of the proteins described herein, the heavy chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 63. In some examples of any of the proteins described herein, the light chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 64.

In some examples of any of the proteins described herein, the antigen-binding domain comprises a heavy chain variable domain comprising a CDR1 comprising SEQ ID NO: 13, a CDR2 comprising SEQ ID NO: 14, and a CDR3 comprising SEQ ID NO: 15, and a light chain variable domain comprising a CDR1 comprising SEQ ID NO: 16, a CDR2 comprising SEQ ID NO: 17, and a CDR3 comprising SEQ ID NO: 18. In some examples of any of the proteins described herein, the heavy chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 65. In some examples of any of the proteins described herein, the light chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 66.

In some examples of any of the proteins described herein, the antigen-binding domain comprises a heavy chain variable domain comprising a CDR1 comprising SEQ ID NO: 19, a CDR2 comprising SEQ ID NO: 20, and a CDR3 comprising SEQ ID NO: 21, and a light chain variable domain comprising a CDR1 comprising SEQ ID NO: 22, a CDR2 comprising SEQ ID NO: 23, and a CDR3 comprising SEQ ID NO: 24. In some examples of any of the proteins described herein, the heavy chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 67. In some examples of any of the proteins described herein, the light chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 68.

In some examples of any of the proteins described herein, the antigen-binding domain comprises a heavy chain variable domain comprising a CDR1 comprising SEQ ID NO: 25, a CDR2 comprising SEQ ID NO: 26, and a CDR3 comprising SEQ ID NO: 27, and a light chain variable domain comprising a CDR1 comprising SEQ ID NO: 28, a CDR2 comprising SEQ ID NO: 29, and a CDR3 comprising SEQ ID NO: 30. In some examples of any of the proteins described herein, the heavy chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 69. In some examples of any of the proteins described herein, the light chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 70.

In some examples of any of the proteins described herein, the antigen-binding domain comprises a heavy chain variable domain comprising a CDR1 comprising SEQ ID NO: 31, a CDR2 comprising SEQ ID NO: 32, and a CDR3 comprising SEQ ID NO: 33, and a light chain variable domain comprising a CDR1 comprising SEQ ID NO: 34, a CDR2 comprising SEQ ID NO: 35, and a CDR3 comprising SEQ ID NO: 36. In some examples of any of the proteins described herein, the heavy chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 71. In some examples of any of the proteins described herein, the light chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 72.

In some examples of any of the proteins described herein, the antigen-binding domain comprises a heavy chain variable domain comprising a CDR1 comprising SEQ ID NO: 37, a CDR2 comprising SEQ ID NO: 38, and a CDR3 comprising SEQ ID NO: 39, and a light chain variable domain comprising a CDR1 comprising SEQ ID NO: 40, a CDR2 comprising SEQ ID NO: 41, and a CDR3 comprising SEQ ID NO: 42. In some examples of any of the proteins described herein, the heavy chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 73. In some examples of any of the proteins described herein, the light chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 74.

In some examples of any of the proteins described herein, the antigen-binding domain comprises a heavy chain variable domain comprising a CDR1 comprising SEQ ID NO: 43, a CDR2 comprising SEQ ID NO: 44, and a CDR3 comprising SEQ ID NO: 45, and a light chain variable domain comprising a CDR1 comprising SEQ ID NO: 46, a CDR2 comprising SEQ ID NO: 47, and a CDR3 comprising SEQ ID NO: 48. In some examples of any of the proteins described herein, the heavy chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 75. In some examples of any of the proteins described herein, the light chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 76.

In some examples of any of the proteins described herein, the antigen-binding domain comprises a heavy chain variable domain comprising a CDR1 comprising SEQ ID NO: 49, a CDR2 comprising SEQ ID NO: 50, and a CDR3 comprising SEQ ID NO: 51, and a light chain variable domain comprising a CDR1 comprising SEQ ID NO: 52, a CDR2 comprising SEQ ID NO: 53, and a CDR3 comprising SEQ ID NO: 54. In some examples of any of the proteins described herein, the heavy chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 77. In some examples of any of the proteins described herein, the light chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 78.

In some examples of any of the proteins described herein, the antigen-binding domain comprises a heavy chain variable domain comprising a CDR1 comprising SEQ ID NO: 55, a CDR2 comprising SEQ ID NO: 56, and a CDR3 comprising SEQ ID NO: 57, and a light chain variable domain comprising a CDR1 comprising SEQ ID NO: 58, a CDR2 comprising SEQ ID NO: 59, and a CDR3 comprising SEQ ID NO: 60. In some examples of any of the proteins described herein, the heavy chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 79. In some examples of any of the proteins described herein, the light chain variable domain comprises a sequence that is at least 80% (e.g., at least 85%, at least 90%, at least 92%, at least 94%, at least 95%, at least 96%, at least 97%, at least 98%, at least 99%, or 100%) identical to SEQ ID NO: 80.

CD26 Ab-01D Heavy Chain Variable Domain CDR1 (SEQ ID NO: 1) TINDSYIH

CD26 Ab-01D Heavy Chain Variable Domain CDR2 (SEQ ID NO: 2) WIWPYGGFTY

CD26 Ab-01D Heavy Chain Variable Domain CDR3 (SEQ ID NO: 3) ARFLGSSSIMDY

CD26 Ab-01D Light Chain Variable Domain CDR1 (SEQ ID NO: 4) RASQDVNSNVA

CD26 Ab-01D Light Chain Variable Domain CDR2 (SEQ ID NO: 5) FGSGGLYS

CD26 Ab-01D Light Chain Variable Domain CDR3 (SEQ ID NO: 6) QQYSSYPL

CD26 Ab-04A Heavy Chain Variable Domain CDR1 (SEQ ID NO: 7) AINNYSIH

CD26 Ab-04A Heavy Chain Variable Domain CDR2 (SEQ ID NO: 8) SIWPYGGFTS

CD26 Ab-04A Heavy Chain Variable Domain CDR3 (SEQ ID NO: 9) ARFFSSYGDMDY

CD26 Ab-04A Light Chain Variable Domain CDR1 (SEQ ID NO: 10) RASQDVSGGVA

CD26 Ab-04A Light Chain Variable Domain CDR2 (SEQ ID NO: 11) YGTSGLYS

CD26 Ab-04A Light Chain Variable Domain CDR3 (SEQ ID NO: 12) QQGGWPI

CD26 Ab-10B Heavy Chain Variable Domain CDR1 (SEQ ID NO: 13) TISDYSIH

CD26 Ab-10B Heavy Chain Variable Domain CDR2 (SEQ ID NO: 14) SIWPGGFTS

CD26 Ab-10B Heavy Chain Variable Domain CDR3 (SEQ ID NO: 15) ARFHSSSGDMDY

CD26 Ab-10B Light Chain Variable Domain CDR1 (SEQ ID NO: 16) RASQDVWGYVA

CD26 Ab-10B Light Chain Variable Domain CDR2 (SEQ ID NO: 17) FASGALYS

CD26 Ab-10B Light Chain Variable Domain CDR3 (SEQ ID NO: 18) QQYFNWPI

CD26 Ab-12D Heavy Chain Variable Domain CDR1 (SEQ ID NO: 19) TINSSYIH

CD26 Ab-12D Heavy Chain Variable Domain CDR2 (SEQ ID NO: 20) GIGPYWGFTS

CD26 Ab-12D Heavy Chain Variable Domain CDR3 (SEQ ID NO: 21) ARFYSSYGFMDY

CD26 Ab-12D Light Chain Variable Domain CDR1 (SEQ ID NO: 22) RASQDVYSWVA

CD26 Ab-12D Light Chain Variable Domain CDR2 (SEQ ID NO: 23) YGPGSLYS

CD26 Ab-12D Light Chain Variable Domain CDR3 (SEQ ID NO: 24) QQYYNYPL

CD26 Ab-03B Heavy Chain Variable Domain CDR1 (SEQ ID NO: 25) TIGNSYIH

CD26 Ab-03B Heavy Chain Variable Domain CDR2 (SEQ ID NO: 26) GIGPYWGFTS

CD26 Ab-03B Heavy Chain Variable Domain CDR3 (SEQ ID NO: 27) ARFNGSSGFMDY

CD26 Ab-03B Light Chain Variable Domain CDR1 (SEQ ID NO: 28) RASQDVYYFVA

CD26 Ab-03B Light Chain Variable Domain CDR2 (SEQ ID NO: 29) SWPTGLYS

CD26 Ab-03B Light Chain Variable Domain CDR3 (SEQ ID NO: 30) QQYFSYPI

CD26 Ab-07H Heavy Chain Variable Domain CDR1 (SEQ ID NO: 31) KASGYTFARFGMY

CD26 Ab-07H Heavy Chain Variable Domain CDR2 (SEQ ID NO: 32) FIAPNHGYTF

CD26 Ab-07H Heavy Chain Variable Domain CDR3 (SEQ ID NO: 33) ARGHWYHGYMDY

CD26 Ab-07H Light Chain Variable Domain CDR1 (SEQ ID NO: 34) KSNQNLLYSHGRTYLN

CD26 Ab-07H Light Chain Variable Domain CDR2 (SEQ ID NO: 35) FGTSHLYS

CD26 Ab-07H Light Chain Variable Domain CDR3 (SEQ ID NO: 36) YQGYHVPF

CD26 Ab-01G Heavy Chain Variable Domain CDR1 (SEQ ID NO: 37) AASGFTIGNYGIH

CD26 Ab-01G Heavy Chain Variable Domain CDR2 (SEQ ID NO: 38) WIGPSGGYTF

CD26 Ab-01G Heavy Chain Variable Domain CDR3 (SEQ ID NO: 39) ARFDVHGFHGMDY

CD26 Ab-01G Light Chain Variable Domain CDR1 (SEQ ID NO: 40) RASQDVNNSVA

CD26 Ab-01G Light Chain Variable Domain CDR2 (SEQ ID NO: 41) FSPTGLYS

CD26 Ab-01G Light Chain Variable Domain CDR3 (SEQ ID NO: 42) QQYFDFPL

CD26 Ab-04E Heavy Chain Variable Domain CDR1 (SEQ ID NO: 43) AASGFTINDGFIH

CD26 Ab-04E Heavy Chain Variable Domain CDR2 (SEQ ID NO: 44) GIWPFGGSTS

CD26 Ab-04E Heavy Chain Variable Domain CDR3 (SEQ ID NO: 45) ARFDVVDWGVMDY

CD26 Ab-04E Light Chain Variable Domain CDR1 (SEQ ID NO: 46) RASQDVNDGVA

CD26 Ab-04E Light Chain Variable Domain CDR2 (SEQ ID NO: 47) YWASYLYS

CD26 Ab-04E Light Chain Variable Domain CDR3 (SEQ ID NO: 48) QQSWNFPL

CD26 Ab-03G Heavy Chain Variable Domain CDR1 (SEQ ID NO: 49) AASGFTIGNYGIH

CD26 Ab-03G Heavy Chain Variable Domain CDR2 (SEQ ID NO: 50) WIGPYGGYTF

CD26 Ab-03G Heavy Chain Variable Domain CDR3 (SEQ ID NO: 51) ARFNNLLWNGMDY

CD26 Ab-03G Light Chain Variable Domain CDR1 (SEQ ID NO: 52) RASQDVSSSVA

CD26 Ab-03G Light Chain Variable Domain CDR2 (SEQ ID NO: 53) SYPGWLYS

CD26 Ab-03G Light Chain Variable Domain CDR3 (SEQ ID NO: 54) QQFGDFPM

CD26 Ab-01F Heavy Chain Variable Domain CDR1 (SEQ ID NO: 55) AASGFTISDYSIH

CD26 Ab-01F Heavy Chain Variable Domain CDR2 (SEQ ID NO: 56) SIWPYGGFTS

CD26 Ab-01F Heavy Chain Variable Domain CDR3 (SEQ ID NO: 57) ARFHSSSGDMDY

CD26 Ab-01F Light Chain Variable Domain CDR1 (SEQ ID NO: 58) RASQDVWGYVA

CD26 Ab-01F Light Chain Variable Domain CDR2 (SEQ ID NO: 59) FSSRSLYS

CD26 Ab-01F Light Chain Variable Domain CDR3 (SEQ ID NO: 60) QQYFNWPI

In some embodiments, any of the proteins described herein can include an antigen-binding domain that includes a heavy chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 61, and a light chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 62.

```
CD26 Ab-01D Heavy Chain Variable Domain
                                        (SEQ ID NO: 61)
EVQLVESGGGLVQPGGSLRLSCAASGFTINDSYIHWVRQAPGKGLEWVA

WIWPYGGFTYYADSVKGRFTISADTSKNTAYLQMNSLRAEDTAVYYCAR

FLGSSSIMDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK
```

```
CD26 Ab-01D Light Chain Variable Domain
                                        (SEQ ID NO: 62)
DIQMTQSPSSLSASVGDRVTITCRASQDVNSNVAWYQQKPGKAPKLLIF

GSGGLYSGVPSRFSGSGSGTDFTLTISSLQPEDFATYYCQQYSSYPLTF

GQGTKVETKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

In some embodiments, any of the proteins described herein can include an antigen-binding domain that includes a heavy chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 63, and a light chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 64.

```
CD26 Ab-04A Heavy Chain Variable Domain
                                        (SEQ ID NO: 63)
EVQLVESGGGLVQPGGSLRLSCAASGFAINNYSIHWVRQAPGKGLEWVA

SIWPYGGFTSYADSVKGRFTISADTSKNTAYLQMNSLRAEDTAVYYCAR

FFSSYGDMDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHED PEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK
```

CD26 Ab-04A Light Chain Variable Domain
(SEQ ID NO: 64)
DIQMTQSPSSLSASVGDRVTITCRASQDVSGGVAWYQQKPGKAPKLLIY

GTSGLYSGVPSRFSGSGSGTDFTLTISSLQPEDFATYYCQQGGDWPITF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

In some embodiments, any of the proteins described herein can include an antigen-binding domain that includes a heavy chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 65, and a light chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 66.

CD26 Ab-10B Heavy Chain Variable Domain
(SEQ ID NO: 65)
EVQLVESGGGLVQPGGSLRLSCAASGFTISDYSIHWVRQAPGKGLEWVA

SIWPYGGFTSYADSVKGRFTISADTSKNTAYLQMNSLRAEDTAVYYCAR

FHSSSGDMDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK

CD26 Ab-10B Light Chain Variable Domain
(SEQ ID NO: 66)
DIQMTQSPSSLSASVGDRVTITCRASQDVWGYVAWYQQKPGKAPKLLIF

ASGALYSGVPSRFSGSGSGTDFTLTISSLQPEDFATYYCQQYFNWPITF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

In some embodiments, any of the proteins described herein can include an antigen-binding domain that includes a heavy chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 67, and a light chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 68).

CD26 Ab-12D Heavy Chain Variable Domain
(SEQ ID NO: 67)
EVQLVESGGGLVQPGGSLRLSCAASGFTINSSYIHWVRQAPGKGLEWVA

GIGPYWGFTSYADSVKGRFTISADTSKNTAYLQMNSLRAEDTAVYYCAR

FYSSYGFMDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK

CD26 Ab-12D Light Chain Variable Domain
(SEQ ID NO: 68)
DIQMTQSPSSLSASVGDRVTITCRASQDVYSWVAWYQQKPGKAPKLLIY

GPGSLYSGVPSRFSGSGSGTDFTLTISSLQPEDFATYYCQQYYNYPLTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

In some embodiments, any of the proteins described herein can include an antigen-binding domain that includes a heavy chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 69, and a light chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 70.

CD26 Ab-03B Heavy Chain Variable Domain
(SEQ ID NO: 69)
EVQLVESGGGLVQPGGSLRLSCAASGFTIGNSYIHWVRQAPGKGLEWVA

GIGPYWGFTSYADSVKGRFTISADTSKNTAYLQMNSLRAEDTAVYYCAR

FNGSSGFMDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK

CD26 Ab-03B Light Chain Variable Domain
(SEQ ID NO: 70)
DIQMTQSPSSLSASVGDRVTITCRASQDVYYFVAWYQQKPGKAPKLLIS

WPTGLYSGVPSRFSGSGSGTDFTLTISSLQPEDFATYYCQQYFSYPITF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

In some embodiments, any of the proteins described herein can include an antigen-binding domain that includes a heavy chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 71, and a light chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 72.

CD26 Ab-07H Heavy Chain Variable Domain
(SEQ ID NO: 71)
EVQLVESGGGLVQPGGSLRLSCKASGYTFARFGMYWVRQAPGKGLEWVA

FIAPNHGYTFYADSVKGRFTISADTSKNTAYLQMNSLRAEDTAVYYCAR

GHWYHGYMDYWGQGTLVTVSSAS

CD26 Ab-07H Light Chain Variable Domain
(SEQ ID NO: 72)
DIQMTQSPSSLSASVGDRVTITCKSNQNLLYSHGRTYLNWYQQKPGKAP

KLLIFGTSHLYSGVPSRFSGSGSGTDFTLTISSLQPEDFATYYCYQGYH

VPFTFGQGTKVEIKR

In some embodiments, any of the proteins described herein can include an antigen-binding domain that includes a heavy chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 73, and a light chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 74.

CD26 Ab-01G Heavy Chain Variable Domain
(SEQ ID NO: 73)
EVQLVESGGGLVQPGGSLRLSCAASGFTIGNYGIHWVRQAPGKGLEWVA

WIGPSGGYTFYADSVKGRFTISADTSKNTAYLQMNSLRAEDTAVYYCAR

FDVHGFHGMDYWGQGTLVTVSSAS

CD26 Ab-01G Light Chain Variable Domain
(SEQ ID NO: 74)
DIQMTQSPSSLSASVGDRVTITCRASQDVNNSVAWYQQKPGKAPKLLIF

SPTGLYSGVPSRFSGSGSGTDFTLTISSLQPEDFATYYCQQYFDFPLTF

GQGTKVEIKR

In some embodiments, any of the proteins described herein can include an antigen-binding domain that includes a heavy chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 75, and a light chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 76).

CD26 Ab-04E Heavy Chain Variable Domain
(SEQ ID NO: 75)
EVQLVESGGGLVQPGGSLRLSCAASGFTINDGFIHWVRQAPGKGLEWVA

GIWPFGGSTSYADSVKGRFTISADTSKNTAYLQMNSLRAEDTAVYYCAR

FDVVDWGVMDYWGQGTLVTVSSAS

CD26 Ab-04E Light Chain Variable Domain
(SEQ ID NO: 76)
DIQMTQSPSSLSASVGDRVTITCRASQDVNDGVAWYQQKPGKAPKLLIY

WASYLYSGVPSRFSGSGSGTDFTLTISSLQPEDFATYYCQQSWNFPLTF

GQGTKVEIKR

In some embodiments, any of the proteins described herein can include an antigen-binding domain that includes a heavy chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 77, and a light chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 78.

CD26 Ab-03G Heavy Chain Variable Domain
(SEQ ID NO: 77)
EVQLVESGGGLVQPGGSLRLSCAASGFTIGNYGIHWVRQAPGKGLEWVA

WIGPYGGYTFYADSVKGRFTISADTSKNTAYLQMNSLRAEDTAVYYCAR

FNNLLWNGMDYWGQGTLVTVSSAS

CD26 Ab-03G Light Chain Variable Domain
(SEQ ID NO: 78)
DIQMTQSPSSLSASVGDRVTITCRASQDVSSSVAWYQQKPGKAPKLLIS

YPGWLYSGVPSRFSGSGSGTDFTLTISSLQPEDFATYYCQQFGDFPMTF

GQGTKVEIKR

In some embodiments, any of the proteins described herein can include an antigen-binding domain that includes a heavy chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 79, and a light chain variable domain that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 80.

```
CD26 Ab-01F Heavy Chain Variable Domain
                                                    (SEQ ID NO: 79)
EVQLVESGGGLVQPGGSLRLSCAASGFTISDYSIHWVRQAPGKGLEWVA

SIWPYGGFTSYADSVKGRFTISADTSKNTAYLQMNSLRAEDTAVYYCAR

FHSSSGDMDYWGQGTLVTVSSAS
```

```
CD26 Ab-01F Light Chain Variable Domain
                                                    (SEQ ID NO: 80)
DIQMTQSPSSLSASVGDRVTITCRASQDVWGYVAWYQQKPGKAPKLLIF

SSRSLYSGVPSRFSGSGSGTDFTLTISSLQPEDFATYYCQQYFNWPITF

GQGTKVEIKR
```

In some embodiments, any of the proteins described herein can include an antigen-binding domain that includes a heavy chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 81, and a light chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 82.

```
CD26 Ab-01D-DNA Heavy Chain Variable Domain
                                                    (SEQ ID NO: 81)
GAAGTGCAGCTGGTGGAATCGGGAGGCGGTCTGGTGCAACCTGGCGGCA

GCCTTCGTCTGAGCTGTGCGGCGAGCGGGTTCACCATTAACGACTCTTA

TATTCATTGGGTGCGTCAAGCTCCCGGCAAGGGGCTGGAGTGGGTCGCG

TGGATTTGGCCCTACGGGGGTTTTACATATTATGCCGACAGCGTGAAAG

GTCGCTTTACGATTAGTGCGGACACCAGCAAAAATACCGCGTACCTGCA

GATGAATAGCCTGCGTGCGGAAGACACAGCGGTGTATTATTGCGCGCGT

TTCCTCGGTTCCTCCAGCATTATGGATTATTGGGGGCAGGGCACCCTTG

TTACCGTGAGCTCGGCGTCAGCGGCC
```

```
CD26 Ab-01D-DNA Light Chain Variable Domain
                                                    (SEQ ID NO: 82)
GATATTCAAATGACCCAGAGCCCGAGCAGCCTGAGCGCGAGCGTGGGAG

ATCGCGTGACCATTACCTGCCGTGCGAGCCAGGATGTTAATAGTAATGT

CGCATGGTATCAGCAGAAACCAGGCAAAGCGCCGAAACTTCTGATATTT

GGGTCTGGTGGGCTGTATAGCGGCGTGCCGTCGCGTTTTTCGGGCAGTG
```

-continued

```
GCAGCGGCACGGACTTTACCCTGACGATATCTTCCTTACAACCGGAGGA

TTTTGCGACCTACTACTGTCAACAGTATTCTAGCTACCCGTTAACCTTC

GGTCAAGGCACCAAAGTGGAAACCAAACGC
```

In some embodiments, any of the proteins described herein can include an antigen-binding domain that includes a heavy chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 83, and a light chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 84.

```
CD26 Ab-04A-DNA Heavy Chain Variable Domain
                                                    (SEQ ID NO: 83)
GAAGTGCAGCTGGTGGAATCGGGAGGCGGTCTGGTGCAACCTGGCGGCA

GCCTTCGTCTGAGCTGTGCGGCGAGCGGGTTCGCCATTAACAATTACTC

CATTCATTGGGTGCGTCAAGCTCCCGGCAAGGGGCTGGAGTGGGTCGCG

TCTATTTGGCCCTATGGGGGTTTTACATCTTATGCCGACAGCGTGAAAG

GTCGCTTTACGATTAGTGCGGACACCAGCAAAAATACCGCGTACCTGCA

GATGAATAGCCTGCGTGCGGAAGACACAGCGGTGTATTATTGCGCGCGT

TTCTTTAGCTCCTATGGCGATATGGATTATTGGGGGCAGGGCACCCTTG

TTACCGTGAGCTCGGCGTCAGCGGCC
```

```
CD26 Ab-04A-DNA Light Chain Variable Domain
                                                    (SEQ ID NO: 84)
GATATTCAAATGACCCAGAGCCCGAGCAGCCTGAGCGCGAGCGTGGGAG

ATCGCGTGACCATTACCTGCCGTGCGAGCCAGGATGTTAGTGGCGGGGT

CGCATGGTATCAGCAGAAACCAGGCAAAGCGCCGAAACTTCTGATATAT

GGGACAAGTGGGCTGTATAGCGGCGTGCCGTCGCGTTTTTCGGGCAGTG

GCAGCGGCACGGACTTTACCCTGACGATATCTTCCTTACAACCGGAGGA

TTTTGCGACCTACTACTGTCAACAGGGGGGGGGATTGGCCGATAACCTTC

GGTCAAGGCACCAAAGTGGAAATCAAACGC
```

In some embodiments, any of the proteins described herein can include an antigen-binding domain that includes a heavy chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 85, and a light chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 86.

CD26 Ab-10B-DNA Heavy Chain Variable Domain
(SEQ ID NO: 85)
GAAGTGCAGCTGGTGGAATCGGGAGGCGGTCTGGTGCAACCTGGCGGCA
GCCTTCGTCTGAGCTGTGCGGCGAGCGGGTTCACCATTAGTGACTATTC
TATTCATTGGGTGCGTCAAGCTCCCGGCAAGGGGCTGGAGTGGGTCGCG
TCTATTTGGCCCTATGGGGGTTTTACATCTTATGCCGACAGCGTGAAAG
GTCGCTTTACGATTAGTGCGGACACCAGCAAAAATACCGCGTACCTGCA
GATGAATAGCCTGCGTGCGGAAGACACAGCGGTGTATTATTGCGCGCGT
TTCCACAGCTCCTCCGGCGACATGGATTATTGGGGGCAGGGCACCCTTG
TTACCGTGAGCTCGGCGTCAGCGGCC CD26 Ab-10B-DNA Light Chain Variable Domain
(SEQ ID NO: 86)
GATATTCAAATGACCCAGAGCCCGAGCAGCCTGAGCGCGAGCGTGGGAG
ATCGCGTGACCATTACCTGCCGTGCGAGCCAGGATGTTTGGGGGTACGT
CGCATGGTATCAGCAGAAACCAGGCAAAGCGCCGAAACTTCTGATATTT
GCCTCCGGCGCCCTGTATAGCGGCGTGCCGTCGCGTTTTTCGGGCAGTG
GCAGCGGCACGGACTTTACCCTGACGATATCTTCCTTACAACCGGAGGA
TTTTGCGACCTACTACTGTCAACAGTACTTTAATTGGCCGATTACCTTC
GGTCAAGGCACCAAAGTGGAAATCAAACGC In some embodiments, any of the proteins described herein can include an antigen-binding domain that includes a heavy chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 87, and a light chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 88.

CD26 Ab-12D-DNA Heavy Chain Variable Domain
(SEQ ID NO: 87)
GAAGTGCAGCTGGTGGAATCGGGAGGCGGTCTGGTGCAACCTGGCGGCA
GCCTTCGTCTGAGCTGTGCGGCGAGCGGGTTCACCATTAACAGTTCCTA
CATTCATTGGGTGCGTCAAGCTCCCGGCAAGGGGCTGGAGTGGGTCGCG
GGGATTGGGCCCTATTGGGGTTTCACATCTTATGCCGACAGCGTAAAAG
GTCGCTTTACGATTAGTGCGGACACCAGCAAAAATACCGCGTACCTGCA
GATGAATAGCCTGCGTGCGGAAGACACAGCGGTGTATTATTGCGCGCGT
TTCTATAGCTCCTATGGCTTCATGGATTATTGGGGGCAGGGCACCCTTG
TTACCGTGAGCTCGGCGTCAGCGGCC CD26 Ab-12D-DNA Light Chain Variable Domain
(SEQ ID NO: 88)
GATATTCAAATGACCCAGAGCCCGAGCAGCCTGAGCGCGAGCGTGGGAG
ATCGCGTGACCATTACCTGCCGTGCGAGCCAGGATGTTTACTCCTGGGT -continued CGCATGGTATCAGCAGAAACCAGGCAAAGCGCCGAAACTTCTGATATAC
GGGCCCGGTTCCCTGTATAGCGGCGTGCCGTCGCGTTTTTCGGGCAGTG
GCAGCGGCACGGACTTTACCCTGACGATATCTTCCTTACAACCGGAGGA
TTTTGCGACCTACTACTGTCAACAGTACTATAATTATCCGCTCACCTTC
GGTCAAGGCACCAAAGTGGAAATCAAACGC In some embodiments, any of the proteins described herein can include an antigen-binding domain that includes a heavy chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 89, and a light chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 90.

CD26 Ab-03B-DNA Heavy Chain Variable Domain
(SEQ ID NO: 89)
GAAGTGCAGCTGGTGGAATCGGGAGGCGGTCTGGTGCAACCTGGCGGCA
GCCTTCGTCTGAGCTGTGCGGCGAGCGGGTTCACCATTGGTAATTCTTA
TATTCATTGGGTGCGTCAAGCTCCCGGCAAGGGGCTGGAGTGGGTCGCG
GGGATTGGGCCCTATTGGGGTTTCACATCTTATGCCGACAGCGTGAAAG
GTCGCTTTACGATTAGTGCGGACACCAGCAAAAATACCGCGTACCTGCA
GATGAATAGCCTGCGTGCGGAAGACACAGCGGTGTATTATTGCGCGCGT
TTCAACGGCTCTTCTGGTTTTATGGATTATTGGGGGCAGGGCACCCTTG
TTACCGTGAGCTCGGCGTCAGCGGCC CD26 Ab-03B-DNA Light Chain Variable Domain
(SEQ ID NO: 90)
GATATTCAAATGACCCAGAGCCCGAGCAGCCTGAGCGCGAGCGTGGGAG
ATCGCGTGACCATTACCTGCCGTGCGAGCCAGGATGTTTATTATTTTGT
CGCATGGTATCAGCAGAAACCAGGCAAAGCGCCGAAACTTCTGATATCC
TGGCCTACCGGGCTGTATAGCGGCGTGCCGTCGCGTTTTTCGGGCAGTG
GCAGCGGCACGGACTTTACCCTGACGATATCTTCCTTACAACCGGAGGA
TTTTGCGACCTACTACTGTCAACAGTATTTTAGTTATCCGATAACCTTC
GGTCAAGGCACCAAAGTGGAAATCAAACGC In some embodiments, any of the proteins described herein can include an antigen-binding domain that includes a heavy chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 91, and a light chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 92.

CD26 Ab-07H-DNA Heavy Chain Variable Domain
(SEQ ID NO: 91)
GAAGTGCAGCTGGTGGAATCGGGAGGCGGTCTGGTGCAACCTGGCGGCA
GCCTTCGTCTGAGCTGTAAGGCGTCTGGCTATACCTTCGCCCGCTTTGG
GATGTATTGGGTGCGTCAAGCTCCCGGCAAGGGGCTGGAGTGGGTCGCG
TTTATCGCTCCAAATCATGGCTATACATTTTATGCCGACAGCGTGAAAG
GTCGCTTTACGATTAGTGCGGACACCAGCAAAAATACCGCGTACCTGCA
GATGAATAGCCTGCGTGCGGAAGACACAGCGGTGTATTATTGCGCGCGT
GGGCACTGGTACCATGGGTATATGGATTATTGGGGGCAGGGCACCCTTG
TTACCGTGAGCTCGGCGTCAGCGGCC CD26 Ab-07H-DNA Light Chain Variable Domain
(SEQ ID NO: 92)
GATATTCAAATGACCCAGAGCCCGAGCAGCCTGAGCGCGAGCGTGGGAG
ATCGCGTGACCATTACCTGCAAAAGTAACCAGAACCTGCTGTACTCTCA
CGGCCGGACCTATCTGAATTGGTATCAGCAGAAACCAGGCAAAGCGCCG
AAACTTCTGATATTTGGGACGTCTCATCTGTATAGTGGCGTGCCGTCGC
GTTTTTCGGGCAGTGGCAGCGGCACGGACTTTACCCTGACGATATCTTC
CTTACAACCGGAGGATTTTGCGACCTACTACTGTTATCAGGGCTATCAT
GTTCCCTTCACCTTCGGTCAAGGCACCAAAGTGGAAATCAAACGC In some embodiments, any of the proteins described herein can include an antigen-binding domain that includes a heavy chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 93, and a light chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 94.

CD26 Ab-01G-DNA Heavy Chain Variable Domain
(SEQ ID NO: 93)
GAAGTGCAGCTGGTGGAATCGGGAGGCGGTCTGGTGCAACCTGGCGGCA
GCCTTCGTCTGAGCTGTGCGGCGAGCGGGTTCACCATTGGCAATTACGG
GATTCATTGGGTGCGTCAAGCTCCCGGCAAGGGGCTGGAGTGGGTCGCG
TGGATTGGGCCCTCCGGGGGTTATACATTCTATGCCGACAGCGTGAAAG
GTCGCTTTACGATTAGTGCGGACACCAGCAAAAATACCGCGTACCTGCA
GATGAATAGCCTGCGTGCGGAAGACACAGCGGTGTATTATTGCGCGCGT
TTCGACGTTCACGGGTTCCACGGGATGGATTATTGGGGGCAGGGCACCC
TTGTTACCGTGAGCTCGGCGTCAGCGGCC CD26 Ab-01G-DNA Light Chain Variable Domain
(SEQ ID NO: 94)
GATATTCAAATGACCCAGAGCCCGAGCAGCCTGAGCGCGAGCGTGGGAG
ATCGCGTGACCATTACCTGCCGTGCGAGCCAGGATGTTAACAACAGTGT -continued CGCATGGTATCAGCAGAAACCAGGCAAAGCGCCGAAACTTCTGATATTT
TCCCCTACTGGGCTGTATAGCGGCGTGCCGTCGCGTTTTTCGGGCAGTG
GCAGCGGCACGGACTTTACCCTGACGATATCTTCCTTACAACCGGAGGA
TTTTGCGACCTACTACTGTCAACAGTACTTCGACTTCCCGTTAACCTTC
GGTCAAGGCACCAAAGTGGAAATCAAACGT In some embodiments, any of the proteins described herein can include an antigen-binding domain that includes a heavy chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 95, and a light chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 96.

CD26 Ab-04E-DNA Heavy Chain Variable Domain
(SEQ ID NO: 95)
GAAGTGCAGCTGGTGGAATCGGGAGGCGGTCTGGTGCAACCTGGCGGCA
GCCTTCGTCTGAGCTGTGCGGCGAGCGGGTTCACCATTAACGACGGGTT
CATTCATTGGGTGCGTCAAGCTCCCGGCAAGGGGCTGGAGTGGGTCGCG
GGGATTTGGCCCTTTGGGGGTTCCACATCCTATGCCGACAGCGTGAAAG
GTCGCTTTACGATTAGTGCGGACACCAGCAAAAATACCGCGTACCTGCA
GATGAATAGCCTGCGTGCGGAAGACACAGCGGTGTATTATTGCGCGCGT
TTCGATGTCGTCGATTGGGGGGTCATGGATTATTGGGGGCAGGGCACCC
TTGTTACCGTGAGCTCGGCGTCAGCGGCC CD26 Ab-04E-DNA Light Chain Variable Domain
(SEQ ID NO: 96)
GATATTCAAATGACCCAGAGCCCGAGCAGCCTGAGCGCGAGCGTGGGAG
ATCGCGTGACCATTACCTGCCGTGCGAGCCAGGATGTTAATGATGGCGT
CGCATGGTATCAGCAGAAACCAGGCAAAGCGCCGAAACTTCTGATATAT
TGGGCGAGTTACCTGTATAGCGGCGTGCCGTCGCGTTTTTCGGGCAGTG
GCAGCGGCACGGACTTTACCCTGACGATATCTTCCTTACAACCGGAGGA
TTTTGCGACCTACTACTGTCAACAGTCCTGGAATTTTCCGCTCACCTTC
GGTCAAGGCACCAAAGTGGAAATCAAACGC In some embodiments, any of the proteins described herein can include an antigen-binding domain that includes a heavy chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 97, and a light chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 98.

CD26 Ab-03G-DNA Heavy Chain Variable Domain
(SEQ ID NO: 97)

GAAGTGCAGCTGGTGGAATCGGGAGGCGGTCTGGTGCAACCTGGCGGCA

GCCTTCGTCTGAGCTGTGCGGCGAGCGGGTTCACCATTGGTAATTACGG

GATTCATTGGGTGCGTCAAGCTCCCGGCAAGGGGCTGGAGTGGGTCGCG

TGGATTGGGCCCTATGGGGGTTACACATTCTATGCCGACAGCGTGAAAG

GTCGCTTTACGATTAGTGCGGACACCAGCAAAAATACCGCGTACCTGCA

GATGAATAGCCTGCGTGCGGAAGACACAGCGGTGTATTATTGCGCGCGT

TTCAATAACCTTCTTTGGAATGGGATGGATTATTGGGGGCAGGGCACCC

TTGTTACCGTGAGCTCGGCGTCAGCGGCC

CD26 Ab-03G-DNA Light Chain Variable Domain
(SEQ ID NO: 98)

GATATTCAAATGACCCAGAGCCCGAGCAGCCTGAGCGCGAGCGTGGGAG

ATCGCGTGACCATTACCTGCCGTGCGAGCCAGGATGTTTCCTCTTCCGT

CGCATGGTATCAGCAGAAACCAGGCAAAGCGCCGAAACTTCTGATATCC

TATCCTGGTTGGCTGTATAGCGGCGTGCCGTCGCGTTTTTCGGGCAGTG

GCAGCGGCACGGACTTTACCCTGACGATATCTTCCTTACAACCGGAGGA

TTTTGCGACCTACTACTGTCAACAGTTTGGGGATTTTCCGATGACCTTC

GGTCAAGGCACCAAAGTGGAAATCAAACGC

In some embodiments, any of the proteins described herein can include an antigen-binding domain that includes a heavy chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 99, and a light chain variable domain encoded by a nucleic acid that comprises a sequence that is at least 80% identical (e.g., at least 85% identical, at least 90% identical, at least 92% identical, at least 94% identical, at least 96% identical, at least 98% identical, at least 99% identical, or 100% identical) to SEQ ID NO: 100.

CD26 Ab-01F-DNA Heavy Chain Variable Domain
(SEQ ID NO: 99)

GAAGTGCAGCTGGTGGAATCGGGAGGCGGTCTGGTGCAACCTGGCGGCA

GCCTTCGTCTGAGCTGTGCGGCGAGCGGGTTCACCATTAGTGACTATTC

TATTCATTGGGTGCGTCAAGCTCCCGGCAAGGGGCTGGAGTGGGTCGCG

TCTATTTGGCCCTATGGGGGTTTTACATCTTATGCCGACAGCGTGAAAG

GTCGCTTTACGATTAGTGCGGACACCAGCAAAAATACCGCGTACCTGCA

GATGAATAGCCTGCGTGCGGAAGACACAGCGGTGTATTATTGCGCGCGT

TTCCACAGCTCCTCCGGCGACATGGATTATTGGGGGCAGGGCACCCTTG

TTACCGTGAGCTCGGCGTCAGCGGCC

CD26 Ab-01F-DNA Light Chain Variable Domain
(SEQ ID NO: 100)

GATATTCAAATGACCCAGAGCCCGAGCAGCCTGAGCGCGAGCGTGGGAG

ATCGCGTGACCATTACCTGCCGTGCGAGCCAGGATGTTTGGGGGTACGT

-continued

CGCATGGTATCAGCAGAAACCAGGCAAAGCGCCGAAACTTCTGATATTT

TCCTCCCGCTCCCTGTATAGCGGCGTGCCGTCGCGTTTTTCGGGCAGTG

GCAGCGGCACGGACTTTACCCTGACGATATCTTCCTTACAACCGGAGGA

TTTTGCGACCTACTACTGTCAACAGTACTTTAATTGGCCGATTACCTTC

GGTCAAGGCACCAAAGTGGAAATCAAACGC

In some embodiments, the proteins can be single-chain polypeptides. In some embodiments, the proteins can be multi-chain polypeptides. In some examples, the proteins described herein can be an antibody, antigen-binding antibody fragment, or a chimeric antigen receptor.

Antigen-Binding Domains

The antigen-binding domains present in any of the proteins described herein (e.g., single- or multi-chain proteins) described herein are each independently selected from the group consisting of: a VHH domain, a VNAR domain, and a scFv. In some embodiments, any of the antigen-binding domains described herein is a BiTe, a $(scFv)_2$, a nanobody, a nanobody-HSA, a DART, a TandAb, a scDiabody, a scDiabody-CH3, scFv-CH-CL-scFv, a HSAbody, scDiabody-HAS, or a tandem-scFv. Additional examples of antigen-binding domains that can be used in any of the proteins described herein are known in the art.

A VHH domain is a single monomeric variable antibody domain that can be found in camelids. A VNAR domain is a single monomeric variable antibody domain that can be found in cartilaginous fish. Non-limiting aspects of VHH domains and VNAR domains are described in, e.g., Cromie et al., Curr. Top. Med. Chem. 15:2543-2557, 2016; De Genst et al., Dev. Comp. Immunol. 30:187-198, 2006; De Meyer et al., Trends Biotechnol. 32:263-270, 2014; Kijanka et al., Nanomedicine 10:161-174, 2015; Kovaleva et al., Expert. Opin. Biol. Ther. 14:1527-1539, 2014; Krah et al., Immunopharmacol. Immunotoxicol. 38:21-28, 2016; Mujic-Delic et al., Trends Pharmacol. Sci. 35:247-255, 2014; Muyldermans, J. Biotechnol. 74:277-302, 2001; Muyldermans et al., Trends Biochem. Sci. 26:230-235, 2001; Muyldermans, Ann. Rev. Biochem. 82:775-797, 2013; Rahbarizadeh et al., Immunol. Invest. 40:299-338, 2011; Van Audenhove et al., EBioMedicine 8:40-48, 2016; Van Bockstaele et al., Curr. Opin. Investig. Drugs 10:1212-1224, 2009; Vincke et al., Methods Mol. Biol. 911:15-26, 2012; and Wesolowski et al., Med. Microbiol. Immunol. 198:157-174, 2009.

In some embodiments, two or more of polypeptides present in the multi-chain protein can assemble (e.g., non-covalently assemble) to form any of the antigen-binding domains described herein, e.g., an antigen-binding fragment of an antibody (e.g., any of the antigen-binding fragments of an antibody described herein), a VHH-scAb, a VHH-Fab, a Dual scFab, a $F(ab')_2$, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a κλ-body, an orthogonal Fab, a DVD-IgG, a IgG(H)-scFv, a scFv-(H)IgG, IgG(L)-scFv, scFv-(L) IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a $F(ab')_2$-$scFv_2$, a scFv-KIH, a Fab-scFv-Fc, a tetravalent HCAb, a scDiabody-Fc, a Diabody-Fc, a tandem scFv-Fc, an Intrabody, a dock and lock, a 1 mmTAC, an IgG-IgG conjugate, a Cov-X-Body, and a scFv1-PEG-$scFv_2$.

See, e.g., Spiess et al., Mol. Immunol. 67:95-106, 2015, incorporated in its entirety herewith, for a description of these elements. Non-limiting examples of an antigen-binding fragment of an antibody include an Fv fragment, a Fab fragment, a $F(ab')_2$ fragment, and a Fab' fragment. Additional examples of an antigen-binding fragment of an antibody is an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

An "Fv" fragment includes a non-covalently-linked dimer of one heavy chain variable domain and one light chain variable domain.

A "Fab" fragment includes, the constant domain of the light chain and the first constant domain ($C_{H1}$) of the heavy chain, in addition to the heavy and light chain variable domains of the Fv fragment.

A "$F(ab')_2$" fragment includes two Fab fragments joined, near the hinge region, by disulfide bonds.

A "dual variable domain immunoglobulin" or "DVD-Ig" refers to multivalent and multispecific binding proteins as described, e.g., in DiGiammarino et al., Methods Mol. Biol. 899:145-156, 2012; Jakob et al., MABs 5:358-363, 2013; and U.S. Pat. Nos. 7,612,181; 8,258,268; 8,586,714; 8,716,450; 8,722,855; 8,735,546; and 8,822,645, each of which is incorporated by reference in its entirety.

DARTs are described in, e.g., Garber, Nature Reviews Drug Discovery 13:799-801, 2014.

Antibodies

In some embodiments, a protein described herein can be an antibody (e.g., a human or humanized antibody). In some embodiments, an antibody can be a human or humanized IgG, e.g., a human or humanized IgG1, IgG2, IgG3, or IgG4. In some embodiments, an antibody can be a human or humanized IgA (e.g., a human or humanized IgA1 or IgA2). In some embodiments, an antibody can be a human or humanized IgD, a human or humanized IgE, or a human or humanized IgM.

In some embodiments, any of the proteins described herein can include an Fc receptor (e.g., an Fc receptor including three substitutions of S239D, A330L, and I332E).

Chimeric Antigen Receptors

In some embodiments, the proteins described herein can be a chimeric antigen receptor. Chimeric antigen receptors include an extracellular antigen-binding domain (e.g., any of the anti-CD26 antigen-binding domains described herein), a transmembrane domain, a costimulatory domain (e.g., an intracellular CD28 domain), and a CD3zeta signaling domain. In some examples, a chimeric antigen receptor can include an extracellular antigen-binding domain (e.g., any of the anti-CD26 antigen-binding domains described herein), a transmembrane domain (e.g., a CD8 alpha transmembrane domain), a CD28 intracellular signaling domain, and a CD3zeta intracellular signaling domain. In some embodiments, a chimeric antigen receptor can include a hinge region (e.g., a CD8 alpha hinge region) disposed between the extracellular antigen-binding domain and the transmembrane domain.

In some embodiments, a hinge region can comprise a sequence that is at least 80% identical (e.g., at least 85%, at least 90%, at least 92%, at least 94%, at least 96%, at least 98%, at least 99%, or 100% identical) to SEQ ID NO: 254. In some embodiments, a hinge region can be encoded by a sequence that is at least 80% identical (e.g., at least 85%, at least 90%, at least 92%, at least 94%, at least 96%, at least 98%, at least 99%, or 100% identical) to SEQ ID NO: 255.

```
Human CD8 alpha hinge
                                              (SEQ ID NO: 254)
ALSNSIMYFSHFVPVFLPAKPTTTPAPRPPTPAPTIASQPLSLRPEASR
PAAGGAVHTRGLD
```

```
Human CD8 alpha hinge
                                              (SEQ ID NO: 255)
GCTTTAAGCAACTCCATCATGTACTTCTCCCACTTCGTGCCCGTTTTTT

TACCCGCTAAGCCCACCACAACCCCCGCTCCCAGACCCCCTACCCCCGC

TCCTACCATCGCCTCCCAGCCTTTATCTTTAAGACCCGAAGCCTCTCGT

CCCGCTGCCGGCGGCGCCGTGCACACAAGGGGTTTAGAC
```

For example, a transmembrane domain can include a sequence that is at least 80%, at least 85%, at least 90%, at least 95%, at least 99%, or 100% identical to SEQ ID NO: 101 (FWVLVVVGGVLACYSLLVTVAFIIFWV). For example, a transmembrane domain can be a transmembrane domain from CD28 (e.g., human CD28). In some embodiments, a chimeric antigen receptor can include a transmembrane and cytoplasmic signaling domain from CD28 that includes a sequence that is at least 80% identical (e.g., at least 85%, at least 90%, at least 92%, at least 94%, at least 96%, at least 98%, at least 99%, or 100% identical) to SEQ ID NO: 256. In some embodiments, the transmembrane and cytoplasmic signaling domain from CD28 can be encoded by a sequence that is at least 80% identical (e.g., at least 85%, at least 90%, at least 92%, at least 94%, at least 96%, at least 98%, at least 99%, or 100% identical) to SEQ ID NO: 257.

```
Human CD28 Transmembrane Domain
                                              (SEQ ID NO: 256)
KPFWVLVVVGGVLACYSLLVTVAFIIFWVRSKRSRLLHSDYMNMTPRRP
GPTRKHYQPYAPPRDFAAYRS
```

```
Human CD28 Transmembrane Domain
                                              (SEQ ID NO: 257)
AAGCCTTTTTGGGTTTTAGTGGTGGTGGGCGGCGTGCTGGCTTGTTACT

CTTTACTGGTGACCGTGGCCTTCATCATCTTCTGGGTTCGTTCCAAGAG

GTCTCGTCTGCTGCACTCCGACTATATGAACATGACCCCTAGGAGGCCC

GGCCCTACCAGAAAACACTATCAGCCCTATGCCCCTCCTCGTGACTTTG

CCGCTTATCGTTCT
```

For example, a costimulatory domain can include a sequence that is at least 80%, at least 85%, at least 90%, at least 95%, at least 99%, or 100% identical to SEQ ID NO: 102 (RSKRSRLLHSDYMNMTPRRPGPTRKHYQPYAPPRDFAAYRS).

For example, a CD3zeta signaling domain can include a sequence that is at least 80%, at least 85%, at least 90%, at least 95%, at least 99%, or 100% identical to SEQ ID NO: 103

(RVKFSRSADAPAYQQGQNQLYNELNLGRREEYDVLDKRRGRDPEMGGK

PQRRKNPQEGLYNELQKDKMAEAYSEIGMKGERRRGKGHDGLYQGLSTA

TKDTYDALHMQALPPR).

For example, a CD3zeta signaling domain can include a sequence that is at least 80% (e.g., at least 85%, at least 90%, at least 92%, at least 94%, at least 96%, at least 98%, at least 99%, or 100% identical) to SEQ ID NO: 258. For example, a CD3zeta signaling domain is encoded by a sequence that is at least 80% identical (e.g., at least 85%, at least 90%, at least 92%, at least 94%, at least 96%, at least 98%, at least 99%, or 100% identical) to SEQ ID NO: 259.

Human CD3zeta Signaling Domain
(SEQ ID NO: 258)
RVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTAT

KDTYDALHMQALPPR

Human CD3zeta Signaling Domain
(SEQ ID NO: 259)
CGTGTGAAGTTCTCCAGATCCGCCGATGCCCCCGCTTACCAGCAAGGTC

AAAACCAGCTCTATAACGAGCTGAATTTAGGTCGTAGAGAGGAGTACGA

CGTGCTGGATAAAAGAAGGGGCAGAGACCCCGAAATGGGAGGCAAACCC

CAGAGAAGGAAGAACCCCCAAGAAGGACTGTACAACGAACTGCAGAAGG

ATAAGATGGCCGAGGCCTACTCCGAGATTGGCATGAAAGGCGAGAGGAG

GAGGGGCAAGGGCCATGATGGTTTATACCAAGGTTTATCCACAGCTACA

AAGGACACCTACGACGCTTTACACATGCAAGCTTTACCTCCTAGA

In some embodiments, a chimeric antigen receptor can include a sequence that is at least 80% identical (e.g., at least 85%, at least 90%, at least 92%, at least 94%, at least 96%, at least 98%, at least 99%, or 100% identical) to SEQ ID NO: 253. In some embodiments, a chimeric antigen receptor can be encoded by a sequence that is at least 80% identical (e.g., at least 85%, at least 90%, at least 92%, at least 94%, at least 96%, at least 98%, at least 99% or 100% identical) to SEQ ID NO: 252.

Exemplary Anti-CD26 Chimeric Antigen Receptor
(with Signal Sequence)
(SEQ ID NO: 253)
MDRLTSSFLLLIVPAYVLSDIQMTQSPSSLSASVGDRVTITCRASQDVNS

NVAWYQQKPGKAPKLLIFGSGGLYSGVPSRFSGSGSGTDFTLTISSLQPE

DFATYYCQQYSSYPLTFGQGTKVETKGGGGSGGGGSGGGGSEVQLVESGG

GLVQPGGSLRLSCAASGFTINDSYIHWVRQAPGKGLEWVAWIWPYGGFTY

YADSVKGRFTISADTSKNTAYLQMNSLRAEDTAVYYCARFLGSSSIMDYW

GQGTLVTVSSAEQKLISEEDLALSNSIMYFSHFVPVFLPAKPTTTPAPRP

PTPAPTIASQPLSLRPEASRPAAGGAVHTRGLDKPFWVLVVVGGVLACYS

LLVTVAFIIFWVRSKRSRLLHSDYMNMTPRRPGPTRKHYQPYAPPRDFAA

-continued

YRSRVKFSRSADAPAYQQGQNQLYNELNLGRREEYDVLDKRRGRDPEMGG

KPQRRKNPQEGLYNELQKDKMAEAYSEIGMKGERRRGKGHDGLYQGLSTA

TKDTYDALHMQALPPR

Exemplary Anti-CD26 Chimeric Antigen Receptor
(with Signal Sequence)
(SEQ ID NO: 252)
ATGGACAGACTTACTTCTTCATTCCTGCTCCTGATTGTCCCTGCGTACGT

CTTGTCCGACATCCAGATGACCCAGTCTCCATCCTCCCTGTCTGCATCTG

TAGGAGACAGAGTCACCATCACTTGCCGGGCGAGTCAGGACGTGAACTCC

AACGTGGCCTGGTATCAGCAGAAACCAGGGAAAGCCCCTAAGCTCCTGAT

CTTCGGCTCCGGCGGCCTGTACAGTGGGGTCCCATCAAGGTTCAGCGGCA

GTGGATCTGGGACAGATTTCACTCTCACTATCAGCAGCCTGCAGCCTGAA

GATTTTGCAACTTACTATTGTCAGCAGTACTCCTCCTACCCCCTGACGTT

CGGCCAAGGGACCAAGGTGGAAACCAAAGGTGGAGGTGGCAGCGGAGGAG

GTGGGTCCGGCGGTGGAGGAAGCGAGGTGCAGCTGGTGGAGTCTGGGGGA

GGCTTGGTCCAGCCTGGGGGGTCCCTGAGACTCTCCTGTGCAGCCTCTGG

ATTCACCATCAACGACTCCTACATCCACTGGGTCCGCCAGGCTCCAGGGA

AGGGGCTGGAGTGGGTGGCCTGGATCTGGCCCTACGGCGGCTTCACCTAC

TATGCAGACTCCGTGAAGGGCCGATTCACCATCTCCGCCGACACCTCCAA

GAACACGGCCTATCTGCAAATGAACAGCCTGAGAGCTGAGGACACGGCTG

TGTATTACTGTGCCAGGTTCCTGGGCTCCTCCTCCATCATGGACTACTGG

GGCCAAGGAACCCTGGTCACCGTCTCCTCAGCCGAGCAGAAGCTGATTAG

CGAGGAGGATCTGGCTTTAAGCAACTCCATCATGTACTTCTCCCACTTCG

TGCCCGTTTTTTTACCCGCTAAGCCCACCACAACCCCCGCTCCCAGACCC

CCTACCCCCGCTCCTACCATCGCCTCCCAGCCTTTATCTTTAAGACCCGA

AGCCTCTCGTCCCGCTGCCGGCGGCGCCGTGCACACAAGGGGTTTAGACA

AGCCTTTTTGGGTTTTAGTGGTGGTGGGCGGCGTGCTGGCTTGTTACTCT

TTACTGGTGACCGTGGCCTTCATCATCTTCTGGGTTCGTTCCAAGAGGTC

TCGTCTGCTGCACTCCGACTATATGAACATGACCCCTAGGAGGCCCGGCC

CTACCAGAAAACACTATCAGCCCTATGCCCCTCCTCGTGACTTTGCCGCT

TATCGTTCTCGTGTGAAGTTCTCCAGATCCGCCGATGCCCCCGCTTACCA

GCAAGGTCAAAACCAGCTCTATAACGAGCTGAATTTAGGTCGTAGAGAGG

AGTACGACGTGCTGGATAAAAGAAGGGGCAGAGACCCCGAAATGGGAGGC

AAACCCCAGAGAAGGAAGAACCCCCAAGAAGGACTGTACAACGAACTGCA

GAAGGATAAGATGGCCGAGGCCTACTCCGAGATTGGCATGAAAGGCGAGA

GGAGGAGGGGCAAGGGCCATGATGGTTTATACCAAGGTTTATCCACAGCT

ACAAAGGACACCTACGACGCTTTACACATGCAAGCTTTACCTCCTAGA

In some embodiments, a chimeric antigen receptor can include a sequence that is at least 80% identical (e.g., at least 85%, at least 90%, at least 92%, at least 94%, at least 96%, at least 98%, at least 99%, or 100% identical) to SEQ ID NO: 260. In some embodiments, a chimeric antigen receptor can be encoded by a sequence that is at least 80% identical (e.g., at least 85%, at least 90%, at least 92%, at least 94%, at least 96%, at least 98%, at least 99% or 100% identical) to SEQ ID NO: 261.

Exemplary Anti-CD26 Chimeric Antigen Receptor (without Signal Sequence)

(SEQ ID NO: 260)

```
DIQMTQSPSSLSASVGDRVTITCRASQDVNSNVAWYQQKPGKAPKLLIFG
SGGLYSGVPSRFSGSGSGTDFTLTISSLQPEDFATYYCQQYSSYPLTFGQ
GTKVETKGGGGSGGGGSGGGGSEVQLVESGGGLVQPGGSLRLSCAASGFT
INDSYIHWVRQAPGKGLEWVAWIWPYGGFTYYADSVKGRFTISADTSKNT
AYLQMNSLRAEDTAVYYCARFLGSSSIMDYWGQGTLVTVSSAEQKLISEE
DLALSNSIMYFSHFVPVFLPAKPTTTPAPRPPTPAPTIASQPLSLRPEAS
RPAAGGAVHTRGLDKPFWVLVVVGGVLACYSLLVTVAFIIFWVRSKRSRL
LHSDYMNMTPRRPGPTRKHYQPYAPPRDFAAYRSRVKFSRSADAPAYQQG
QNQLYNELNLGRREEYDVLDKRRGRDPEMGGKPQRRKNPQEGLYNELQKD
KMAEAYSEIGMKGERRRGKGHDGLYQGLSTATKDTYDALHMQALPPR
```

Exemplary Anti-CD26 Chimeric Antigen Receptor (without Signal Sequence)

(SEQ ID NO: 261)

```
GACATCCAGATGACCCAGTCTCCATCCTCCCTGTCTGCATCTGTAGGAGA
CAGAGTCACCATCACTTGCCGGGCGAGTCAGGACGTGAACTCCAACGTGG
CCTGGTATCAGCAGAAACCAGGGAAAGCCCCTAAGCTCCTGATCTTCGGC
TCCGGCGGCCTGTACAGTGGGGTCCCATCAAGGTTCAGCGGCAGTGGATC
TGGGACAGATTTCACTCTCACTATCAGCAGCCTGCAGCCTGAAGATTTTG
CAACTTACTATTGTCAGCAGTACTCCTCCTACCCCCTGACGTTCGGCCAA
GGGACCAAGGTGGAAACCAAAGGTGGAGGTGGCAGCGGAGGAGGTGGGTC
CGGCGGTGGAGGAAGCGAGGTGCAGCTGGTGGAGTCTGGGGGAGGCTTGG
TCCAGCCTGGGGGGTCCCTGAGACTCTCCTGTGCAGCCTCTGGATTCACC
ATCAACGACTCCTACATCCACTGGGTCCGCCAGGCTCCAGGGAAGGGGCT
GGAGTGGGTGGCCTGGATCTGGCCCTACGGCGGCTTCACCTACTATGCAG
ACTCCGTGAAGGGCCGATTCACCATCTCCGCCGACACCTCCAAGAACACG
GCCTATCTGCAAATGAACAGCCTGAGAGCTGAGGACACGGCTGTGTATTA
CTGTGCCAGGTTCCTGGGCTCCTCCTCCATCATGGACTACTGGGGCCAAG
GAACCCTGGTCACCGTCTCCTCAGCCGAGCAGAAGCTGATTAGCGAGGAG
GATCTGGCTTTAAGCAACTCCATCATGTACTTCTCCCACTTCGTGCCCGT
TTTTTTACCCGCTAAGCCCACCACAACCCCCGCTCCCAGACCCCCTACCC
CCGCTCCTACCATCGCCTCCCAGCCTTTATCTTTAAGACCCGAAGCCTCT
CGTCCCGCTGCCGGCGGCGCCGTGCACACAAGGGGTTTAGACAAGCCTTT
TTGGGTTTTAGTGGTGGTGGGCGGCGTGCTGGCTTGTTACTCTTTACTGG
TGACCGTGGCCTTCATCATCTTCTGGGTTCGTTCCAAGAGGTCTCGTCTG
CTGCACTCCGACTATATGAACATGACCCCTAGGAGGCCCGGCCCTACCAG
AAAACACTATCAGCCCTATGCCCCTCCTCGTGACTTTGCCGCTTATCGTT
CTCGTGTGAAGTTCTCCAGATCCGCCGATGCCCCCGCTTACCAGCAAGGT
```

-continued

```
CAAAACCAGCTCTATAACGAGCTGAATTTAGGTCGTAGAGAGGAGTACGA
CGTGCTGGATAAAAGAAGGGGCAGAGACCCCGAAATGGGAGGCAAACCCC
AGAGAAGGAAGAACCCCCAAGAAGGACTGTACAACGAACTGCAGAAGGAT
AAGATGGCCGAGGCCTACTCCGAGATTGGCATGAAAGGCGAGAGGAGGAG
GGGCAAGGGCCATGATGGTTTATACCAAGGTTTATCCACAGCTACAAAGG
ACACCTACGACGCTTTACACATGCAAGCTTTACCTCCTAGA
```

Nucleic Acids

Also provided herein are nucleic acids that include a sequence that encodes any of the proteins described herein. Also provided herein is a set of nucleic acids that together include sequences that encode any of the multi-chain proteins described herein.

Also provided herein are vectors that include a sequence that encode any of the proteins described herein. Also provided herein are sets of vectors that together include sequences that encode any of the multi-chain proteins described herein. Non-limiting examples of vectors include expression vectors. Examples of expression vectors include viral vectors (e.g., a lentivirus vector, an adeno-associated virus vector, or a retrovirus vector).

Some embodiments of any of the vectors or nucleic acids described herein can further include a promoter operably linked to a sequence or sequences encoding the protein.

Cells

Also provided herein are cells including a nucleic acid encoding any of the proteins described herein, or a vector comprising any of the nucleic acids described herein. In some examples of any of the cells described herein, the cell is an immune cell. Alternatively, the cell is a production cell line, including by not limited to Chinese Hamster ovary (CHO) cells (e.g., CHO.K1, CD-CHO, CHO-S, GS CHO, CHO-DG44, etc.), HEK293, Cos, NSO, Sp2/0, and PerC6 cells.

As used herein, an "immune cell" refers to a cell of the immune system which can be categorized as lymphocytes (e.g., T cells, B cells, and NK cells), neutrophils, and monocytes/macrophages. In some examples of any of the cells described herein, the immune cell is a T cell, a B cell, or a natural killer (NK) cell. In some examples of any of the cells described herein, the immune cell can be a T cell, e.g., a CD4+ T cell, a CD8+ T cell, a Treg cell, a Th1 T cell, a Th2 T cell, a Th17 T cell, an unspecific T cell, or a population of T cells that comprises a combination thereof.

Compositions

Also provided herein are compositions (e.g., pharmaceutical compositions) that include at least one of any of the proteins described herein or any of the cells described herein. Also provided herein are compositions (e.g., pharmaceutical compositions) that include at least one of any of the nucleic acids described herein or any of the vectors described herein. In some embodiments, the compositions (e.g., pharmaceutical compositions) can be disposed in a sterile vial or a pre-loaded syringe.

In some embodiments, the compositions (e.g., pharmaceutical compositions) are formulated for different routes of administration (e.g., intravenous, subcutaneous, intramuscular, or intratumoral). In some embodiments, the compositions (e.g., pharmaceutical compositions) can include a pharmaceutically acceptable carrier (e.g., phosphate buffered saline). Single or multiple administrations of any of the pharmaceutical compositions described herein can be given to a subject depending on, for example: the dosage and frequency as required and tolerated by the patient. A dosage of the pharmaceutical composition should provide a sufficient quantity of the protein, nucleic acid, vector, or cell to effectively treat or ameliorate conditions, diseases, or symptoms.

Also provided herein are methods of treating a subject having a cancer (e.g., any of the cancers described herein) that include administering a therapeutically effective amount of at least one of any of the compositions or pharmaceutical compositions provided herein.

Kits

Also provided herein are kits that include any of the pharmaceutical compositions described herein. In some embodiments, the kits can include instructions for performing any of the methods described herein. In some embodiments, the kits can include at least one dose of any of the compositions (e.g., pharmaceutical compositions) described herein. In some embodiments, the kits can provide a syringe for administering any of the pharmaceutical compositions described herein Methods of Treating Age-Related and Inflammatory Disease in a Subject Provided herein are methods of treating an age-related disease or an inflammatory disease in a subject, that include administering a therapeutically effective amount of any of the proteins described herein or any of the pharmaceutical compositions described herein. Also provided herein are methods of treating an age-related disease or an inflammatory disease in a subject, that include administering a therapeutically effective amount of any of the nucleic acids described herein or any of the pharmaceutical compositions described herein. Also provided herein are methods of treating an age-related disease or an inflammatory disease in a subject, that include administering a therapeutically effective amount of any of the cells described herein or any of the pharmaceutical compositions described herein.

In some embodiments, the methods further include administering: (i) a therapeutically effective amount of an NK cell activating agent and/or an NK cell and/or monoclonal antibody; and (ii) a therapeutically effective amount of a Treg cell activating agent and/or a Treg cell and/or a monoclonal antibody and/or an advanced glycation end product (AGE) inhibitor. In some embodiments, the age-related disease is inflamm-aging related.

Also provided herein are methods of treating an age-related disease or an inflammatory disease that include administering: (i) a therapeutically effective amount of an NK cell activating agent and/or an NK cell and/or monoclonal antibody; and (ii) a therapeutically effective amount of a Treg cell activating agent and/or a Treg cell and/or a monoclonal antibody and/or an advanced glycation end product (AGE) inhibitor.

In some embodiments of any of the methods described herein, (i) is administered to the subject at substantially the same time as (ii). In some embodiments of any of the methods described herein, (i) is administered to the subject prior to administration of (ii) to the subject. In some embodiments of any of the methods described herein, (ii) is administered to the subject prior to administration of (i) to the subject. In some embodiments, the subject is administered the protein, the cell, or the nucleic acid at substantially the same time as (i) and (ii). In some embodiments, the subject is administered the protein, the cell, or the nucleic acid prior to the administration of (i) and (ii). In some embodiments, the subject is administered the protein, the cell, or the nucleic acid after the administration of (i) and (ii).

In some embodiments of any of the methods described herein, the method includes administering a therapeutically effective amount of an NK cell to the subject. In some embodiments, the NK cell is an autologous NK cell. In some embodiments, the method can further include: isolating the NK cell from the subject; and culturing the isolated NK cell in a liquid culture medium under conditions sufficient to induce or increase proliferation of the NK cell, where following the isolating and culturing steps, the NK cell is administered to the subject. In some embodiments, the liquid culture medium includes one or more multi-chain chimeric polypeptide(s) (e.g., any of the exemplary multi-chain chimeric polypeptide(s) described herein).

In some embodiments, the NK cell includes a chimeric antigen receptor (e.g., a chimeric antigen receptor comprises an extracellular domain that binds specifically to tissue factor or CD26) (e.g., any of the chimeric antigen receptors described herein that include any of the anti-CD26 antigen-binding domains described herein).

In some embodiments, the method can include administering a therapeutically effective amount of an NK cell activating agent to the subject. In some embodiments, the NK cell activating agent is one or more multi-chain chimeric polypeptide(s) (e.g., one or more of any of the multi-chain chimeric polypeptides described herein). In some embodiments, the NK cell activating agent is one or more of an anti-tissue factor antibody, an anti-CD26 antibody (e.g., any of the anti-CD26 antibodies described herein), and/or an anti-CD36 antibody. In some embodiments, the NK cell activating agent includes one or more multi-chain chimeric polypeptide(s) and one or more of an anti-tissue factor antibody, an anti-CD26 antibody (e.g., any of the anti-CD26 antibodies described herein), and/or an anti-CD36 antibody.

In some embodiments, the method includes administering a therapeutically effective amount of a Treg cell to the subject. In some embodiments, the Treg cell is an autologous Treg cell. In some embodiments, the method further includes: isolating the Treg cell from the subject; culturing the isolated Treg cell in a liquid culture medium under conditions sufficient to induce or increase proliferation of the Treg cell, where following the isolating and culturing steps, the Treg cell is administered to the subject. In some embodiments, the liquid culture medium includes one or more single-chain chimeric polypeptide(s).

In some embodiments, the Treg cell includes a chimeric antigen receptor (e.g., a chimeric antigen receptor including an extracellular domain that binds specifically to tissue factor, CD26 (e.g., any of the anti-CD26 antibodies described herein), and/or CD36).

In some embodiments, the method includes administering a therapeutically effective amount of a Treg cell activating agent to the subject. In some embodiments, the Treg cell activating agent is one or more single-chain chimeric polypeptide(s) (e.g., one or more of any of the single-chain chimeric polypeptides described herein). In some embodiments, the Treg cell activating agent is one or both of an anti-tissue factor antibody, anti-CD26 antibody (e.g., any of the anti-CD26 antibodies described herein), and/or an anti-CD36 antibody. In some embodiments, the Treg cell activating agent is a soluble RAGE trap.

In some embodiments, the Treg cell activating agent includes one or more single-chain chimeric polypeptide(s) and one or more of an anti-tissue factor antibody, an anti-CD26 antibody (e.g., any of the anti-CD26 antibodies described herein), an anti-CD36 antibody, and a soluble RAGE trap.

In some embodiments, the method includes administering a therapeutically effective amount of a monoclonal antibody to the subject. In some embodiments, a monoclonal antibody comprises one or more of an anti-tissue factor antibody, anti-CD26 antibody (e.g., any of the anti-CD26 antibodies described herein), and/or anti-CD36 antibody that can directly or indirectly reduce inflammasome or senescent cell activity.

In some embodiments, the method includes administering a therapeutically effective amount of an advanced glycation end product (AGE) inhibitor to the subject. In some embodiments, an advanced glycation end product (AGE) inhibitor comprises one or more of soluble RAGE trap that can directly or indirectly reduce inflammasome or senescent cell activity.

In some embodiments of any of the methods described herein, the aging-related disease is inflamm-aging related. Non-limiting examples of aging-related disease is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, neurodegeneration, stroke, cancer, dementia, vascular disease, infection susceptibility, chronic inflammation, and renal dysfunction.

Non-limiting examples of inflammatory diseases include: rheumatoid arthritis, inflammatory bowel disease, lupus erythematosus, lupus nephritis, amyotrophic lateral sclerosis, diabetic nephropathy, CNS injury, Alzheimer's disease, Parkinson's disease, Crohn's disease, multiple sclerosis, Guillain-Barre syndrome, psoriasis, Grave's disease, ulcerative colitis, nonalcoholic steatohepatitis, and mood disorders.

In some embodiments, the age-related disease is a cancer. Non-limiting examples of cancer are selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments, the subject can be a subject identified or diagnosed as having an age-related disease or having chronic inflammation.

Also provided herein are methods of treating cancer in a subject, including administering to the subject a therapeutically effective amount of any one of the proteins described herein. Also provided herein are methods of treating an infectious disease in a subject, including administering to the subject a therapeutically effective amount of any one of the proteins described herein. Also provided herein are methods of treating an infectious disease in a subject, including administering to the subject a therapeutically effective amount of any one of the proteins described herein or any one of the pharmaceutical compositions described herein.

Non-limiting examples of infectious disease include: anthrax, arboviral disease, babesiosis, botulism, brucellosis, campylobacteriosis, cholera, congenital syphilis, covid-19, dengue virus infections, diphtheria, ehrlichiosis and anaplasmosis, gonorrhea, Hansen's disease, hantavirus infection, hepatitis, HIV infection, invasive pneumococcal disease, legionellosis, listeriosis, lyme disease, malaria, measles, meningococcal disease, pertussis, rubella, *salmonellosis*, smallpox, tetanus, tuberculosis, viral hemorrhagic fever, and zika virus disease.

In some embodiments, these methods can result in a reduction in the number, severity, or frequency of one or more symptoms of the age-related disease in the subject (e.g., as compared to the number, severity, or frequency of the one or more symptoms of the cancer in the subject prior to treatment).

In some examples, the methods can result in a decrease (e.g., about 1% decrease to about 99% decrease, an about 1% decrease to about 95% decrease, about 1% decrease to about 90% decrease, about 1% decrease to about 85% decrease, about 1% decrease to about 80% decrease, about 1% decrease to about 75% decrease, about 1% to about 70% decrease, about 1% decrease to about 65% decrease, about 1% decrease to about 60% decrease, about 1% decrease to about 55% decrease, about 1% decrease to about 50% decrease, about 1% decrease to about 45% decrease, about 1% decrease to about 40% decrease, about 1% decrease to about 35% decrease, about 1% decrease to about 30% decrease, about 1% decrease to about 25% decrease, about 1% decrease to about 20% decrease, about 1% decrease to about 15% decrease, about 1% decrease to about 10% decrease, about 1% decrease to about 5% decrease, about 5% decrease to about 99% decrease, an about 5% decrease to about 95% decrease, about 5% decrease to about 90% decrease, about 5% decrease to about 85% decrease, about 5% decrease to about 80% decrease, about 5% decrease to about 75% decrease, about 5% to about 70% decrease, about 5% decrease to about 65% decrease, about 5% decrease to about 60% decrease, about 5% decrease to about 55% decrease, about 5% decrease to about 50% decrease, about 5% decrease to about 45% decrease, about 5% decrease to about 40% decrease, about 5% decrease to about 35% decrease, about 5% decrease to about 30% decrease, about 5% decrease to about 25% decrease, about 5% decrease to about 20% decrease, about 5% decrease to about 15% decrease, about 5% decrease to about 10% decrease, about 10% decrease to about 99% decrease, an about 10% decrease to about 95% decrease, about 10% decrease to about 90% decrease, about 10% decrease to about 85% decrease, about 10% decrease to about 80% decrease, about 10% decrease to about 75% decrease, about 10% to about 70% decrease, about 10% decrease to about 65% decrease, about 10% decrease to about 60% decrease, about 10% decrease to about 55% decrease, about 10% decrease to about 50% decrease, about 10% decrease to about 45% decrease, about 10% decrease to about 40% decrease, about 10% decrease to about 35% decrease, about 10% decrease to about 30% decrease, about 10% decrease to about 25% decrease, about 10% decrease to about 20% decrease, about 10% decrease to about 15% decrease, about 15% decrease to about 99% decrease, an about 15% decrease to about 95% decrease, about 15% decrease to about 90% decrease, about 15% decrease to about 85% decrease, about 15% decrease to about 80% decrease, about 15% decrease to about 75% decrease, about 15% to about 70% decrease, about 15% decrease to about 65% decrease, about 15% decrease to about 60% decrease, about 15% decrease to about 55% decrease, about 15% decrease to about 50% decrease, about 15% decrease to about 45% decrease, about 15% decrease to about 40% decrease, about 15% decrease to about 35% decrease, about 15% decrease to about 30% decrease, about 15% decrease to about 25% decrease, about 15% decrease to about 20% decrease, about 20% decrease to about 99% decrease, an about 20% decrease to about 95% decrease, about 20% decrease to about 90% decrease, about 20% decrease to about 85% decrease, about 20% decrease to about 80% decrease, about 20% decrease to about 75% decrease, about 20% to about 70% decrease, about 20% decrease to about 65% decrease, about 20% decrease to about 60% decrease, about 20% decrease to about 55% decrease, about 20% decrease to about 50% decrease, about 20% decrease to about 45% decrease, about 20% decrease to about 40% decrease, about 20% decrease to about 35% decrease, about 20% decrease to about 30% decrease, about 20% decrease to about 25% decrease, about 25% decrease to about 99% decrease, an about 25% decrease to about 95% decrease, about 25% decrease to about 90% decrease, about 25% decrease to about 85% decrease, about 25% decrease to about 80% decrease, about 25% decrease to about 75% decrease, about 25% to about 70% decrease, about 25% decrease to about 65% decrease, about 25% decrease to about 60% decrease, about 25% decrease to about 55% decrease, about 25% decrease to about 50% decrease, about 25% decrease to about 45% decrease, about 25% decrease to about 40% decrease, about 25% decrease to about 35% decrease, about 25% decrease to about 30% decrease, about 30% decrease to about 99% decrease, an about 30% decrease to about 95% decrease, about 30% decrease to about 90% decrease, about 30% decrease to about 85% decrease, about 30% decrease to about 80% decrease, about 30% decrease to about 75% decrease, about 30% to about 70% decrease, about 30% decrease to about 65% decrease, about 30% decrease to about 60% decrease, about 30% decrease to about 55% decrease, about 30% decrease to about 50% decrease, about 30% decrease to about 45% decrease, about 30% decrease to about 40% decrease, about 30% decrease to about 35% decrease, about 35% decrease to about 99% decrease, an about 35% decrease to about 95% decrease, about 35% decrease to about 90% decrease, about 35% decrease to about 85% decrease, about 35% decrease to about 80% decrease, about 35% decrease to about 75% decrease, about 35% to about 70% decrease, about 35% decrease to about 65% decrease, about 35% decrease to about 60% decrease, about 35% decrease to about 55% decrease, about 35% decrease to about 50% decrease, about 35% decrease to about 45% decrease, about 35% decrease to about 40% decrease, about 40% decrease to about 99% decrease, an about 40% decrease to about 95% decrease, about 40% decrease to about 90% decrease, about 40% decrease to about 85% decrease, about 40% decrease to about 80% decrease, about 40% decrease to about 75% decrease, about 40% to about 70% decrease, about 40% decrease to about 65% decrease, about 40% decrease to about 60% decrease, about 40% decrease to about 55% decrease, about 40% decrease to about 50% decrease, about 40% decrease to about 45% decrease, about 45% decrease to about 99% decrease, an about 45% decrease to about 95% decrease, about 45% decrease to about 90% decrease, about 45% decrease to about 85% decrease, about 45% decrease to about 80% decrease, about 45% decrease to about 75% decrease, about 45% to about 70% decrease, about 45% decrease to about 65% decrease, about 45% decrease to about 60% decrease, about 45% decrease to about 55% decrease, about 45% decrease to about 50% decrease, about 50% decrease to about 99% decrease, an about 50% decrease to about 95% decrease, about 50% decrease to about 90% decrease, about 50% decrease to about 85% decrease, about 50% decrease to about 80% decrease, about 50% decrease to about 75% decrease, about 50% to about 70% decrease, about 50% decrease to about 65% decrease, about 50% decrease to about 60% decrease, about 50% decrease to about 55% decrease, about 55% decrease to about 99% decrease, an about 55% decrease to about 95% decrease, about 55% decrease to about 90% decrease, about 55% decrease to about 85% decrease, about 55% decrease to about 80% decrease, about 55% decrease to about 75% decrease, about 55% to about 70% decrease, about 55% decrease to about 65% decrease, about 55% decrease to about 60% decrease, about 60% decrease to about 99% decrease, an about 60% decrease to about 95% decrease, about 60% decrease to about 90% decrease, about 60% decrease to about 85% decrease, about 60% decrease to about 80% decrease, about 60% decrease to about 75% decrease, about 60% to about 70% decrease, about 60% decrease to about 65% decrease, about 65% decrease to about 99% decrease, an about 65% decrease to about 95% decrease, about 65% decrease to about 90% decrease, about 65% decrease to about 85% decrease, about 65% decrease to about 80% decrease, about 65% decrease to about 75% decrease, about 65% to about 70% decrease, about 70% decrease to about 99% decrease, an about 70% decrease to about 95% decrease, about 70% decrease to about 90% decrease, about 70% decrease to about 85% decrease, about 70% decrease to about 80% decrease, about 70% decrease to about 75% decrease, about 75% decrease to about 99% decrease, an about 75% decrease to about 95% decrease, about 75% decrease to about 90% decrease, about 75% decrease to about 85% decrease, about 75% decrease to about 80% decrease, about 80% decrease to about 99% decrease, an about 80% decrease to about 95% decrease, about 80% decrease to about 90% decrease, about 80% decrease to about 85% decrease, about 85% decrease to about 99% decrease, an about 85% decrease to about 95% decrease, about 85% decrease to about 90% decrease, about 90% decrease to about 99% decrease, an about 90% decrease to about 95% decrease, or about 95% decrease to about 99% decrease) in the number of senescent cells in the subject (e.g., a decrease in the number of senescent cells in one or more specific tissues involved and/or implicated in the aging-related disease or disorder in the subject), e.g., as compared to the number of senescent cells in the subject prior to treatment.

The term "subject" refers to any mammal. In some embodiments, the subject or "subject in need of treatment" may be a canine (e.g., a dog), feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon) or a human; or rodent (e.g., a mouse, a guinea pig, a hamster, or a rat). In some embodiments, the subject or "subject in need of treatment" may be a non-human mammal, especially mammals that are conventionally used as models for demonstrating therapeutic efficacy in humans (e.g., murine, lapine, porcine, canine or primate animals) may be employed.

Treg Cells

In some embodiments, a Treg cell can be administered to the subject. In some embodiments, a Treg cell administered to the subject can be an autologous Treg cell, haploidentical Treg cell, or allogenic Treg cell isolated from peripheral blood or umbilical cord blood. In some embodiments, the methods described herein can further include isolating a Treg cell from a subject, culturing the isolated Treg cell in a liquid culture medium, and administering the Treg cell back to the subject. In some embodiments, a Treg cell can be isolated using a commercially available kit (see, e.g., EasySep™ Human $CD4^+CD127^{low}CD25^+$ Regulatory T Cell Isolation Kit or Dynabeads Regulatory $CD4^+CD25^+$ T Cell Kit). In some embodiments, the liquid culture medium can include one or more of a single-chain chimeric polypeptide (e.g., any of the exemplary single-chain chimeric polypeptides described herein, e.g., 2t2 or 3t28). In some embodiments, the liquid culture medium can include the use of a bead having on its surface CD3 and CD28, and recombinant IL-2 or 2t2.

In some embodiments, the Treg cell can comprise a chimeric antigen receptor (e.g., a chimeric antigen receptor that includes an extracellular domain that binds specifically to tissue factor, CD26 (e.g., any of the anti-CD26 antigen-binding domains described herein), or CD36). Non-limiting examples of extracellular domains that can bind to tissue factor, CD26 or CD36 are scFvs. Non-limiting examples of anti-CD36 antibodies are commercially available from Invitrogen, Abcam, GeneTex, Novus Biologicals, Proteintech, and EMD Millipore. Non-limiting examples of anti-tissue factor heavy chain variable domain and light chain variable domains are described in U.S. Pat. Nos. 7,968,094 and 8,007,795.

Treg Cell Activating Agents

In some embodiments, one or more Treg cell activating agents can be administered to the subject. In some embodiments, the Treg cell activating agent can be a single-chain chimeric polypeptide (e.g., any of the exemplary single-chain chimeric polypeptides described herein), an anti-tissue factor antibody (e.g., the anti-tissue factor antibodies described in U.S. Pat. Nos. 7,968,094 and 8,007,795), a soluble RAGE protein, an anti-CD26 antibody (e.g, any of the anti-CD26 antibodies described herein), or an anti-CD36 antibody.

A soluble RAGE protein can have a sequence that is at least 80%, at least 85%, at least 90%, at least 95%, at least 99%, or 100% identical to SEQ ID NO: 104 or SEQ ID NO: 105.

```
Soluble Human RAGE Variant 1
                                     (SEQ ID NO: 104)
maagtavgaw vlvlslwgav vgaqnitari geplvlkckg

apkkppqrle wklntgrtea wkvlspqggg pwdsvarvlp

ngslflpavg iqdegifrcq amnrngketk snyrvrvyrk

nsrvfskasl lpkkkpstpa lahegl
```

```
Soluble Human RAGE Variant 2
                                     (SEQ ID NO: 105)
maagtavgaw vlvlslwgav vgaqnitari geplvlkckg

apkkppqrle wklntgrtea wkvlspqggg pwdsvarvlp
```

-continued

```
ngslflpavg iqdegifrcq amnrngketk snyrvrvyqi

pgkpeivdsa seltagvpnk vgtcvsegsy pagtlswhld

gkplvpnekg es
```

In some examples, a soluble RAGE protein is encoded by a nucleic acid having a sequence that is at least 80%, at least 85%, at least 90%, at least 95%, at least 99%, or 100% identical to SEQ ID NO: 106 or SEQ ID NO: 107.

```
Soluble Human RAGE Variant 1 cDNA
                                     (SEQ ID NO: 106)
atggcagccg gaacagcagt tggagcctgg gtgctggtcc

tcagtctgtg gggggcagta gtaggtgctc aaaacatcac

agcccggatt ggcgagccac tggtgctgaa gtgtaagggg

gcccccaaga aaccacccca gcggctggaa tggaaactga

acacaggccg gacagaagct tggaaggtcc tgtctcccca

gggaggaggc cctgggaca gtgtggctcg tgtccttccc

aacggctccc tcttccttcc ggctgtcggg atccaggatg

aggggatttt ccggtgccag gcaatgaaca ggaatggaaa

ggagaccaag tccaactacc gagtccgtgt ctaccgtaag

aattccaggg tcttctccaa ggcctccctc ttacctaaga

aaaagccttc aaccccagcc ttggcccatg agggcctctg a
```

```
Mouse RAGE cDNA
                                     (SEQ ID NO: 107)
atggcagccg gaacagcagt tggagcctgg gtgctggtcc

tcagtctgtg gggggcagta gtaggtgctc aaaacatcac

agcccggatt ggcgagccac tggtgctgaa gtgtaagggg

gcccccaaga aaccacccca gcggctggaa tggaaactga

acacaggccg gacagaagct tggaaggtcc tgtctcccca

gggaggaggc cctgggaca gtgtggctcg tgtccttccc

aacggctccc tcttccttcc ggctgtcggg atccaggatg

aggggatttt ccggtgccag gcaatgaaca ggaatggaaa

ggagaccaag tccaactacc gagtccgtgt ctaccagatt

cctgggaagc cagaaattgt agattctgcc tctgaactca

cggctggtgt tcccaataag gtggggacat gtgtgtcaga

gggaagctac cctgcaggga ctcttagctg gcacttggat

gggaagcccc tggtgcctaa tgagaagggt gagtcctaa
```

As can be appreciated by those in the art, substitutions/mutations that are made at positions that are not conserved between different species are less likely to have a negative impact on the activity of the protein/nucleic acid, whereas substitutions/mutations that are made at positions that are conserved between species are more likely to have a negative impact on the activity of the protein/nucleic acid.

NK Cells

In some embodiments, a NK cell can be administered to the subject. In some embodiments, a NK cell administered to the subject can be an autologous NK cell, haploidentical NK cells, or allogeneic NK cells isolated from peripheral blood, umbilical cord blood, or isolated and differentiated from iPSC. In some embodiments, the methods described herein can further include isolating a NK cell from a subject, culturing the isolated NK cell in a liquid culture medium, and administering the NK cell back to the subject. In some embodiments, a NK cell can be isolated using a commercially available kit (see, e.g., EasySep™ Human NK Cell Isolation Kit, MojoSort Human NK Cell Isolation Kit, and Novus Biologicals Human NK Cell Isolation Kit). In some embodiments, the liquid culture medium can include one or more of a multi-chain chimeric polypeptide (e.g., any of the exemplary multi-chain chimeric polypeptides described herein, e.g., 18t15-12s and/or 7t15-21s).

In some embodiments, the NK cell can comprise a chimeric antigen receptor (e.g., a chimeric antigen receptor that includes an extracellular domain that binds specifically to tissue factor or CD26). Non-limiting examples of extracellular domains that can bind to tissue factor or CD26 are scFvs. Non-limiting examples of an anti-CD26 antibodies are commercially available from Abcam, Invitrogen, and GeneTex. Additional examples of anti-CD26 antibodies are the anti-CD26 antibodies described herein. Non-limiting examples of anti-tissue factor heavy chain variable domain and light chain variable domains are described in U.S. Pat. Nos. 7,968,094 and 8,007,795. Chimeric antigen receptors include a transmembrane domain, a costimulatory domain (e.g., an intracellular CD28 domain), and a CD3zeta signaling domain. For example, a transmembrane domain can include a sequence that is at least 80%, at least 85%, at least 90%, at least 95%, at least 99%, or 100% identical to SEQ ID NO: 101. For example, a costimulatory domain can include a sequence that is at least 80%, at least 85%, at least 90%, at least 95%, at least 99%, or 100% identical to SEQ ID NO: 102. For example, a CD3zeta signaling domain can include a sequence that is at least 80%, at least 85%, at least 90%, at least 95%, at least 99%, or 100% identical to SEQ ID NO: 103.

NK Cell Activating Agents

In some embodiments, one or more NK cell activating agents can be administered to the subject. In some embodiments, the NK cell activating agent can be one or more multi-chain chimeric polypeptide (e.g., any of the exemplary multi-chain chimeric polypeptides described herein), an anti-tissue factor antibody (e.g., the anti-tissue factor antibodies described in U.S. Pat. Nos. 7,968,094 and 8,007,795), an anti-CD36 antibody (e.g., the anti-CD36 antibodies commercially available from Invitrogen, Abcam, GeneTex, Novus Biologicals, Proteintech, and EMD Millipore), and an anti-CD26 antibody (e.g., the anti-CD26 antibodies commercially available from Abcam, Invitrogen, and GeneTex). NK cell activating agents, such as cytokine-based agents, can act by directing activating NK cells or can enhance NK cell activity, such as antibodies mediating antibody-dependent cellular cytotoxicity (ADCC) of NK cells.

Multi-Chain Chimeric Polypeptides

Provided herein are multi-chain chimeric polypeptides that include (a) a first chimeric polypeptide comprising: (i) a first target-binding domain; (ii) a soluble tissue factor domain; and (iii) a first domain of a pair of affinity domains; (b) a second chimeric polypeptide comprising: (i) a second domain of a pair of affinity domains; and (ii) a second target-binding domain, where the first chimeric polypeptide and the second chimeric polypeptide associate through the binding of the first domain and the second domain of the pair of affinity domains.

In some embodiments of any of the multi-chain chimeric polypeptides described herein, the first target-binding domain (e.g., any of the first target-binding domains described herein) and the soluble tissue factor domain (e.g., any of the exemplary soluble tissue factor domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the first target-binding domain (e.g., any of the exemplary first target-binding domains described herein) and the soluble tissue factor domain (e.g., any of the exemplary soluble tissue factor domains described herein) in the first chimeric polypeptide.

In some embodiments of any of the multi-chain chimeric polypeptides described herein, the soluble tissue factor domain (e.g., any of the exemplary soluble tissue factor domains described herein) and the first domain of the pair of affinity domains (e.g., any of the exemplary first domains of any of the exemplary pairs of affinity domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the soluble tissue factor domain (e.g., any of the exemplary soluble tissue factor domains described herein) and the first domain of the pair of affinity domains (e.g., any of the exemplary first domains of any of the exemplary pairs of affinity domains described herein) in the first chimeric polypeptide.

In some embodiments of any of the multi-chain chimeric polypeptides described herein, the second domain of the pair of affinity domains (e.g., any of the exemplary second domains of any of the exemplary pairs of affinity domains described herein) and the second target-binding domain (e.g., any of the exemplary second target-binding domains described herein) directly abut each other in the second chimeric polypeptide. In some embodiments of any of the multi-chain chimeric polypeptides described herein, the second chimeric polypeptide further comprises a linker sequence (e.g., any of the exemplary linker sequences described herein or known in the art) between the second domain of the pair of affinity domains (e.g., any of the exemplary second domains of any of the exemplary pairs of affinity domains described herein) and the second target-binding domain (e.g., any of the exemplary second target-binding domains described herein) in the second chimeric polypeptide.

Tissue Factor

Human tissue factor is a 263 amino-acid transmembrane protein containing three domains: (1) a 219-amino acid N-terminal extracellular domain (residues 1-219); (2) a 22-amino acid transmembrane domain (residues 220-242); and (3) a 21-amino acid cytoplasmic C-terminal tail (residues 242-263) ((UniProtKB Identifier Number: P13726). The cytoplasmic tail contains two phosphorylation sites at Ser253 and Ser258, and one S-palmitoylation site at Cys245. Deletion or mutation of the cytoplasmic domain was not found to affect tissue factor coagulation activity. Tissue factor has one S-palmitoylation site in the intracellular domain of the protein at Cys245. The Cys245 is located at the amino acid terminus of the intracellular domain and close to the membrane surface. The tissue factor transmembrane domain is composed of a single-spanning a-helix.

The extracellular domain of tissue factor, composed of two fibronectin type III domains, is connected to the transmembrane domain through a six-amino acid linker. This linker provides conformational flexibility to decouple the tissue factor extracellular domain from its transmembrane and cytoplasmic domains. Each tissue factor fibronectin type III module is composed of two overlapping β sheets with the top sheet domain containing three antiparallel β-strands and the bottom sheet containing four β-strands. The β-strands are connected by β-loops between strand βA and βB, βC and βD, and βE and βF, all of which are conserved in conformation in the two modules. There are three short α-helix segments connecting the β-strands. A unique feature of tissue factor is a 17-amino acid β-hairpin between strand β10 and strand β11, which is not a common element of the fibronectin superfamily. The N-terminal domain also contains a 12 amino acid loop between β6F and β7G that is not present in the C-terminal domain and is unique to tissue factor. Such a fibronectin type III domain structure is a feature of the immunoglobulin-like family of protein folds and is conserved among a wide variety of extracellular proteins.

The zymogen FVII is rapidly converted to FVIIa by limited proteolysis once it binds to tissue to form the active tissue factor-FVIIa complex. The FVIIa, which circulates as an enzyme at a concentration of approximately 0.1 nM (1% of plasma FVII), can also bind directly to tissue factor. The allosteric interaction between tissue factor and FVIIa on the tissue factor-FVIIa complex greatly increases the enzymatic activity of FVIIa: an approximate 20- to 100-fold increase in the rate of hydrolysis of small, chromogenic peptidyl substrates, and nearly a million-fold increase in the rate of activation of the natural macromolecular substrates FIX and FX. In concert with allosteric activation of the active site of FVIIa upon binding to tissue factor, the formation of tissue factor-FVIIa complex on phospholipid bilayer (i.e., upon exposure of phosphatidyl-L-serine on membrane surfaces) increases the rate of FIX or FX activation, in a $Ca^{2+}$-dependent manner, an additional 1,000-fold. The roughly million-fold overall increase in FX activation by tissue factor-FVIIa-phospholipid complex relative to free FVIIa is a critical regulatory point for the coagulation cascade.

FVII is a ~50 kDa, single-chain polypeptide consisting of 406 amino acid residues, with an N-terminal γ-carboxyglutamate-rich (GLA) domain, two epidermal growth factor-like domains (EGF1 and EFG2), and a C-terminal serine protease domain. FVII is activated to FVIIa by a specific proteolytic cleavage of the $Ile\text{-}^{154}\text{-}Arg^{152}$ bond in the short linker region between the EGF2 and the protease domain. This cleavage results in the light and heavy chains being held together by a single disulfide bond of $Cys^{135}$ and $Cys^{262}$. FVIIa binds phospholipid membrane in a $Ca^{2+}$-dependent manner through its N-terminal GLA-domain. Immediately C-terminal to the GLA domain is an aromatic stack and two EGF domains. The aromatic stack connects the GLA to EGF1 domain which binds a single $Ca^{2+}$ ion. Occupancy of this $Ca^{2+}$-binding site increases FVIIa amidolytic activity and tissue factor association. The catalytic triad consist of $His^{193}$, $Asp^{242}$, and $Ser^{344}$, and binding of a single $Ca^{2+}$: ion within the FVIIa protease domain is critical for its catalytic activity. Proteolytic activation of FVII to FVIIa frees the newly formed amino terminus at $Ile^{153}$ to fold back and be inserted into the activation pocket forming a salt bridge with the carboxylate of $Asp^{343}$ to generate the oxyanion hole. Formation of this salt bridge is critical for FVIIa activity. However, oxyanion hole formation does not occur in free FVIIa upon proteolytic activation. As a result, FVIIa circulates in a zymogen-like state that is poorly recognized by plasma protease inhibitors, allowing it to circulate with a half-life of approximately 90 minutes.

Tissue factor-mediated positioning of the FVIIa active site above the membrane surface is important for FVIIa towards cognate substrates. Free FVIIa adopts a stable, extended structure when bound to the membrane with its active site positioned ~80 Å above the membrane surface. Upon FVIIa binding to tissue factor, the FVa active site is repositioned ~6 Å closer to the membrane. This modulation may aid in a proper alignment of the FVIIa catalytic triad with the target substrate cleavage site. Using GLA-domainless FVIIa, it has been shown that the active site was still positioned a similar distance above the membrane, demonstrating that tissue factor is able to fully support FVIIa active site positioning even in the absence of FVIIa-membrane interaction. Additional data showed that tissue factor supported full FVIIa proteolytic activity as long as the tissue factor extracellular domain was tethered in some way to the membrane surface. However, raising the active site of FVIIa greater than 80 Å above the membrane surface greatly reduced the ability of the tissue factor-FVIIa complex to activate FX but did not diminish tissue factor-FVIIa amidolytic activity.

Alanine scanning mutagenesis has been used to assess the role of specific amino acid side chains in the tissue factor extracellular domain for interaction with FVIIa (Gibbs et al., Biochemistry 33 (47): 14003-14010, 1994; Schullek et al., J Biol Chem 269 (30): 19399-19403, 1994). Alanine substitution identified a limited number of residue positions at which alanine replacements cause 5- to 10-fold lower affinity for FVIIa binding. Most of these residue side chains were found to be well-exposed to solvent in the crystal structure, concordant with macromolecular ligand interaction. The FVIIa ligand-binding site is located over an extensive region at the boundary between the two modules. In the C-module, residues $Arg^{135}$ and $Phe^{140}$ located on the protruding B-C loop provide an independent contact with FVIIa. $Leu^{133}$ is located at the base of the fingerlike structure and packed into the cleft between the two modules. This provides continuity to a major cluster of important binding residues consisting of $Lys^{20}$, $Thr^{60}$, $Asp^{58}$, and $Ile^{22}$. $Thr^{60}$ is only partially solvent-exposed and may play a local structural role rather than making a significant contact with ligand. The binding site extends onto the concave side of the intermodule angle involving $Glu^{24}$ and $Gln^{110}$, and potentially the more distant residue $Val^{207}$. The binding region extends from Asp58 onto a convex surface area formed by $Lys^{48}$, $Lys^{46}$, $Gln^{37}$, $Asp^{44}$, and $Trp^{45}$. $Trp^{45}$ and $Asp^{44}$ do not interact independently with FVIIa, indicating that the mutational effect at the $Trp^{45}$ position may reflect a structural importance of this side chain for the local packing of the adjacent $Asp^{44}$ and $Gln^{37}$ side chain. The interactive area further includes two surface-exposed aromatic residues, $Phe^{76}$ and $Tyr^{78}$, which form part of the hydrophobic cluster in the N-module.

The known physiologic substrates of tissue factor-FVIIa are FVII, FIX, and FX and certain proteinase-activated receptors. Mutational analysis has identified a number of residues that, when mutated, support full FVIIa amidolytic activity towards small peptidyl substrates but are deficient in their ability to support macromolecular substrate (i.e., FVII, FIX, and FX) activation (Ruf et al., J Biol Chem 267(31): 22206-22210, 1992; Ruf et al., J Biol Chem 267(9):6375-6381, 1992; Huang et al., J Biol Chem 271(36): 21752-21757, 1996; Kirchhofer et al., Biochemistry 39(25):7380-7387, 2000). The tissue factor loop region at residues 159-165, and residues in or adjacent to this flexible loop have been shown to be critical for the proteolytic activity of the tissue factor-FVIIa complex. This defines the proposed substrate-binding exosite region of tissue factor that is quite distant from the FVIIa active site. A substitution of the glycine residue by a marginally bulkier residue alanine, significantly impairs tissue factor-FVIIa proteolytic activity. This suggests that the flexibility afforded by glycine is critical for the loop of residues 159-165 for tissue factor macromolecular substrate recognition.

The residues $Lys^{165}$ and $Lys^{166}$ have also been demonstrated to be important for substrate recognition and binding. Mutation of either of these residues to alanine results in a significant decrease in the tissue factor co-factor function. $Lys^{165}$ and $Lys^{166}$ face away from each other, with $Lys^{165}$ pointing towards FVIIa in most tissue factor-FVIIa structures, and $Lys^{166}$ pointing into the substrate binding exosite region in the crystal structure. Putative salt bridge formation between $Lys^{165}$ of and $Gla^{35}$ of FVIIa would support the notion that tissue factor interaction with the GLA domain of FVIIa modulates substrate recognition. These results suggest that the C-terminal portion of the tissue factor ectodomain directly interacts with the GLA-domain, the possible adjacent EGF1 domains, of FIX and FX, and that the presence of the FVIIa GLA-domain may modulate these interactions either directly or indirectly.

Soluble Tissue Factor Domain

In some embodiments of any of the polypeptides described herein, the soluble tissue factor domain can be a wildtype tissue factor polypeptide lacking the signal sequence, the transmembrane domain, and the intracellular domain. In some examples, the soluble tissue factor domain can be a tissue factor mutant, wherein a wildtype tissue factor polypeptide lacking the signal sequence, the transmembrane domain, and the intracellular domain, and has been further modified at selected amino acids. In some examples, the soluble tissue factor domain can be a soluble human tissue factor domain. In some examples, the soluble tissue factor domain can be a soluble mouse tissue factor domain. In some examples, the soluble tissue factor domain can be a soluble rat tissue factor domain. Non-limiting examples of soluble human tissue factor domains, a mouse soluble tissue factor domain, a rat soluble tissue factor domain, and mutant soluble tissue factor domains are shown below.

```
Exemplary Soluble Human Tissue Factor Domain
                                    (SEQ ID NO: 120)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE
```

```
Exemplary Nucleic Acid Encoding Soluble Human
Tissue Factor Domain
                                    (SEQ ID NO: 121)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG
```

-continued

```
AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG
```

```
Exemplary Mutant Soluble Human Tissue Factor
Domain
                                    (SEQ ID NO: 122)
SGTTNTVAAYNLTWKSTNFATALEWEPKPVNQVYTVQISTKSGDWKSKCF

YTTDTECALTDEIVKDVKQTYLARVFSYPAGNVESTGSAGEPLYENSPEF

TPYLETNLGQPTIQSFEQVGTKVNVTVEDERTLVARNNTALSLRDVFGKD

LIYTLYYWKSSSSGKKTAKTNTNEFLIDVDKGENYCFSVQAVIPSRTVNR

KSTDSPVECMGQEKGEFRE
```

```
Exemplary Mutant Soluble Human Tissue Factor
Domain
                                    (SEQ ID NO: 123)
SGTTNTVAAYNLTWKSTNFATALEWEPKPVNQVYTVQISTKSGDAKSKCF

YTTDTECALTDEIVKDVKQTYLARVFSYPAGNVESTGSAGEPLAENSPEF

TPYLETNLGQPTIQSFEQVGTKVNVTVEDERTLVARNNTALSLRDVFGKD

LIYTLYYWKSSSSGKKTAKTNTNEFLIDVDKGENYCFSVQAVIPSRTVNR

KSTDSPVECMGQEKGEFRE
```

```
Exemplary Soluble Mouse Tissue Factor Domain
                                    (SEQ ID NO: 124)
AGIPEKAFNLTWISTDFKTILEWQPKPTNYTYTVQISDRSRNWKNKCFST

TDTECDLTDEIVKDVTWAYEAKVLSVPRRNSVHGDGDQLVIHGEEPPFTN

APKFLPYRDTNLGQPVIQQFEQDGRKLNVVVKDSLTLVRKNGTFLTLRQV

FGKDLGYIITYRKGSSTGKKTNITNTNEFSIDVEEGVSYCFFVQAMIFSR

KTNQNSPGSSTVCTEQWKSFLGE
```

```
Exemplary Soluble Rat Tissue Factor Domain
                                    (SEQ ID NO: 125)
AGTPPGKAFNLTWISTDFKTILEWQPKPTNYTYTVQISDRSRNWKYKCTG

TTDTECDLTDEIVKDVNWTYEARVLSVPWRNSTHGKETLFGTHGEEPPFT

NARKFLPYRDTKIGQPVIQKYEQGGTKLKVTVKDSFTLVRKNGTFLTLRQ

VFGNDLGYILTYRKDSSTGRKTNTTHTNEFLIDVEKGVSYCFFAQAVIFS

RKTNHKSPESITKCTEQWKSVLGE
```

In some embodiments, a soluble tissue factor domain can include a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 120, 122, 123, 124, or 125. In some embodiments, a soluble tissue factor domain can include a sequence of SEQ ID NO: 120, 122, 123, 124, or 125, with one to twenty amino acids (e.g., 2, 3, 4, 5, 6, 7, 8, 9, 10, 11, 12, 13, 14, 15, 16, 17, 18, 19, or 20) amino acids removed from its N-terminus and/or one to twenty amino acids (e.g., 2, 3, 4, 5, 6, 7, 8, 9, 10, 11, 12, 13, 14, 15, 16, 17, 18, 19, or 20) amino acids removed from its C-terminus.

As can be appreciated in the art, one skilled in the art would understand that mutation of amino acids that are conserved between different mammalian species is more likely to decrease the activity and/or structural stability of the protein, while mutation of amino acids that are not conserved between different mammalian species is less likely to decrease the activity and/or structural stability of the protein.

In some examples of any of the single- or multi-chain chimeric polypeptides described herein, the soluble tissue factor domain is not capable of binding to Factor VIIa. In some examples of any of the single- or multi-chain chimeric polypeptides described herein, the soluble tissue factor domain does not convert inactive Factor X into Factor Xa. In some embodiments of any of the single- or multi-chain chimeric polypeptides described herein, the single- or multi-chain chimeric polypeptide does not stimulate blood coagulation in a mammal.

In some examples, the soluble tissue factor domain can be a soluble human tissue factor domain. In some embodiments, the soluble tissue factor domain can be a soluble mouse tissue factor domain. In some embodiments, the soluble tissue factor domain can be a soluble rat tissue factor domain.

In some examples, the soluble tissue factor domain does not include one or more (e.g., two, three, four, five, six, or seven) of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the mutant soluble tissue factor possesses the amino acid sequence of SEQ ID NO: 122 or SEQ ID NO: 123.

In some examples, the soluble tissue factor domain can be encoded by a nucleic acid including a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 121.

Linker Sequences

In some embodiments, the linker sequence can be a flexible linker sequence. Non-limiting examples of linker sequences that can be used are described in Klein et al., Protein Engineering, Design & Selection 27(10):325-330, 2014; Priyanka et al., Protein Sci. 22(2):153-167, 2013. In some examples, the linker sequence is a synthetic linker sequence.

In some embodiments of any of the multi-chain chimeric polypeptides described herein, the first chimeric polypeptide can include one, two, three, four, five, six, seven, eight, nine, or ten linker sequence(s) (e.g., the same or different linker sequences, e.g., any of the exemplary linker sequences described herein or known in the art). In some embodiments of any of the multi-chain chimeric polypeptides described herein, the second chimeric polypeptide can include one, two, three, four, five, six, seven, eight, nine, or ten linker sequence(s) (e.g., the same or different linker sequences, e.g., any of the exemplary linker sequences described herein or known in the art).

In some embodiments, a linker sequence can have a total length of 1 amino acid to about 100 amino acids, 1 amino acid to about 90 amino acids, 1 amino acid to about 80 amino acids, 1 amino acid to about 70 amino acids, 1 amino acid to about 60 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, about 2 amino acids to about 100 amino acids, about 2 amino acids to about 90 amino acids, about 2 amino acids to about 80 amino acids, about 2 amino acids to about 70 amino acids, about 2 amino acids to about 60 amino acids, about 2 amino acids to about 50 amino acids, about 2 amino acids to about 45 amino acids, about 2 amino acids to about 40 amino acids, about 2 amino acids to about 35 amino acids, about 2 amino acids to about 30 amino acids, about 2 amino acids to about 25 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 100 amino acids, about 4 amino acids to about 90 amino acids, about 4 amino acids to about 80 amino acids, about 4 amino acids to about 70 amino acids, about 4 amino acids to about 60 amino acids, about 4 amino acids to about 50 amino acids, about 4 amino acids to about 45 amino acids, about 4 amino acids to about 40 amino acids, about 4 amino acids to about 35 amino acids, about 4 amino acids to about 30 amino acids, about 4 amino acids to about 25 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 100 amino acids, about 6 amino acids to about 90 amino acids, about 6 amino acids to about 80 amino acids, about 6 amino acids to about 70 amino acids, about 6 amino acids to about 60 amino acids, about 6 amino acids to about 50 amino acids, about 6 amino acids to about 45 amino acids, about 6 amino acids to about 40 amino acids, about 6 amino acids to about 35 amino acids, about 6 amino acids to about 30 amino acids, about 6 amino acids to about 25 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 100 amino acids, about 8 amino acids to about 90 amino acids, about 8 amino acids to about 80 amino acids, about 8 amino acids to about 70 amino acids, about 8 amino acids to about 60 amino acids, about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 100 amino acids, about 10 amino acids to about 90 amino acids, about 10 amino acids to about 80 amino acids, about 10 amino acids to about 70 amino acids, about 10 amino acids to about 60 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 100 amino acids, about 12 amino acids to about 90 amino acids, about 12 amino acids to about 80 amino acids, about 12 amino acids to about 70 amino acids, about 12 amino acids to about 60 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 100 amino acids, about 14 amino acids to about 90 amino acids, about 14 amino acids to about 80 amino acids, about 14 amino acids to about 70 amino acids, about 14 amino acids to about 60 amino acids, about 14 amino acids to about 50 amino acids, about 14 amino acids to about 45 amino acids, about 14 amino acids to about 40 amino acids, about 14 amino acids to about 35 amino acids, about 14 amino acids to about 30 amino acids, about 14 amino acids to about 25 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 100 amino acids, about 16 amino acids to about 90 amino acids, about 16 amino acids to about 80 amino acids, about 16 amino acids to about 70 amino acids, about 16 amino acids to about 60 amino acids, about 16 amino acids to about 50 amino acids, about 16 amino acids to about 45 amino acids, about 16 amino acids to about 40 amino acids, about 16 amino acids to about 35 amino acids, about 16 amino acids to about 30 amino acids, about 16 amino acids to about 25 amino acids, about 16 amino acids to about 24 amino acids, about 16 amino acids to about 22 amino acids, about 16 amino acids to about 20 amino acids, about 16 amino acids to about 18 amino acids, about 18 amino acids to about 100 amino acids, about 18 amino acids to about 90 amino acids, about 18 amino acids to about 80 amino acids, about 18 amino acids to about 70 amino acids, about 18 amino acids to about 60 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 24 amino acids, about 18 amino acids to about 22 amino acids, about 18 amino acids to about 20 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 24 amino acids, about 20 amino acids to about 22 amino acids, about 22 amino acids to about 100 amino acids, about 22 amino acids to about 90 amino acids, about 22 amino acids to about 80 amino acids, about 22 amino acids to about 70 amino acids, about 22 amino acids to about 60 amino acids, about 22 amino acids to about 50 amino acids, about 22 amino acids to about 45 amino acids, about 22 amino acids to about 40 amino acids, about 22 amino acids to about 35 amino acids, about 22 amino acids to about 30 amino acids, about 22 amino acids to about 25 amino acids, about 22 amino acids to about 24 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 100 amino acids, about 60 amino acids to about 90 amino acids, about 60 amino acids to about 80 amino acids, about 60 amino acids to about 70 amino acids, about 70 amino acids to about 100 amino acids, about 70 amino acids to about 90 amino acids, about 70 amino acids to about 80 amino acids, about 80 amino acids to about 100 amino acids, about 80 amino acids to about 90 amino acids, or about 90 amino acids to about 100 amino acids.

In some embodiments, the linker is rich in glycine (Gly or G) residues. In some embodiments, the linker is rich in serine (Ser or S) residues. In some embodiments, the linker is rich in glycine and serine residues. In some embodiments, the linker has one or more glycine-serine residue pairs (GS), e.g., 1, 2, 3, 4, 5, 6, 7, 8, 9, or 10 or more GS pairs. In some embodiments, the linker has one or more Gly-Gly-Gly-Ser (GGGS) sequences, e.g., 1, 2, 3, 4, 5, 6, 7, 8, 9, or 10 or more GGGS sequences. In some embodiments, the linker has one or more Gly-Gly-Gly-Gly-Ser (GGGGS) sequences, e.g., 1, 2, 3, 4, 5, 6, 7, 8, 9, or 10 or more GGGGS sequences. In some embodiments, the linker has one or more Gly-Gly-Ser-Gly (GGSG) sequences, e.g., 1, 2, 3, 4, 5, 6, 7, 8, 9, or 10 or more GGSG sequences.

In some embodiments, the linker sequence can comprise or consist of GGGGSGGGGSGGGGS (SEQ ID NO: 126). In some embodiments, the linker sequence can be encoded by a nucleic acid comprising or consisting of: GGCGGTGGAGGATCCGGAGGAGGTGGCTCCGGCGGCGGAGGATCT (SEQ ID NO: 127). In some embodiments, the linker sequence can comprise or consist of: GGGSGGGS (SEQ ID NO: 128).

Target-Binding Domains

In some embodiments of any of the single- or multi-chain chimeric polypeptides described herein, the first target-binding domain, the second target-binding domain, and/or the additional one or more target-binding domains can be an antigen-binding domain (e.g., any of the exemplary antigen-binding domains described herein or known in the art), a soluble interleukin or cytokine protein (e.g., any of the exemplary soluble interleukin proteins or soluble cytokine proteins described herein), and a soluble interleukin or cytokine receptor (e.g., any of the exemplary soluble interleukin receptors or soluble cytokine receptors described herein).

In some embodiments of any of the single- or multi-chain chimeric polypeptides described herein, one or more of the first target-binding domain (e.g., any of the exemplary first target binding domains described herein or known in the art), the second target-binding domain (e.g., any of the exemplary second target binding domains described herein or known in the art), and the one or more additional target binding domains can each, independently, bind specifically to a target selected from the group of: bind specifically to a target selected from the group consisting of: CD16a, CD28, CD3 (e.g., one or more of CD3α, CD3β, CD3δ, CD3M, and CD3K), CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein (e.g., ULBP1, ULBP2, ULBP3, ULBP4, ULBP5, and ULBP6), HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the single- or multi-chain chimeric polypeptides described herein, the first target-binding domain, the second target-binding domain, and/or the one or more additional target-binding domains can each independent have a total number of amino acids of about 5 amino acids to about 1000 amino acids, about 5 amino acids to about 950 amino acids, about 5 amino acids to about 900 amino acids, about 5 amino acids to about 850 amino acids, about 5 amino acids to about 800 amino acids, about 5 amino acids to about 750 amino acids, about 5 amino acids to about 700 amino acids, about 5 amino acids to about 650 amino acids, about 5 amino acids to about 600 amino acids, about 5 amino acids to about 550 amino acids, about 5 amino acids to about 500 amino acids, about 5 amino acids to about 450 amino acids, about 5 amino acids to about 400 amino acids, about 5 amino acids to about 350 amino acids, about 5 amino acids to about 300 amino acids, about 5 amino acids to about 280 amino acids, about 5 amino acids to about 260 amino acids, about 5 amino acids to about 240 amino acids, about 5 amino acids to about 220 amino acids, about 5 amino acids to about 200 amino acids, about 5 amino acids to about 195 amino acids, about 5 amino acids to about 190 amino acids, about 5 amino acids to about 185 amino acids, about 5 amino acids to about 180 amino acids, about 5 amino acids to about 175 amino acids, about 5 amino acids to about 170 amino acids, about 5 amino acids to about 165 amino acids, about 5 amino acids to about 160 amino acids, about 5 amino acids to about 155 amino acids, about 5 amino acids to about 150 amino acids, about 5 amino acids to about 145 amino acids, about 5 amino acids to about 140 amino acids, about 5 amino acids to about 135 amino acids, about 5 amino acids to about 130 amino acids, about 5 amino acids to about 125 amino acids, about 5 amino acids to about 120 amino acids, about 5 amino acids to about 115 amino acids, about 5 amino acids to about 110 amino acids, about 5 amino acids to about 105 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 10 amino acids to about 1000 amino acids, about 10 amino acids to about 950 amino acids, about 10 amino acids to about 900 amino acids, about 10 amino acids to about 850 amino acids, about 10 amino acids to about 800 amino acids, about 10 amino acids to about 750 amino acids, about 10 amino acids to about 700 amino acids, about 10 amino acids to about 650 amino acids, about 10 amino acids to about 600 amino acids, about 10 amino acids to about 550 amino acids, about 10 amino acids to about 500 amino acids, about 10 amino acids to about 450 amino acids, about 10 amino acids to about 400 amino acids, about 10 amino acids to about 350 amino acids, about 10 amino acids to about 300 amino acids, about 10 amino acids to about 280 amino acids, about 10 amino acids to about 260 amino acids, about 10 amino acids to about 240 amino acids, about 10 amino acids to about 220 amino acids, about 10 amino acids to about 200 amino acids, about 10 amino acids to about 195 amino acids, about 10 amino acids to about 190 amino acids, about 10 amino acids to about 185 amino acids, about 10 amino acids to about 180 amino acids, about 10 amino acids to about 175 amino acids, about 10 amino acids to about 170 amino acids, about 10 amino acids to about 165 amino acids, about 10 amino acids to about 160 amino acids, about 10 amino acids to about 155 amino acids, about 10 amino acids to about 150 amino acids, about 10 amino acids to about 145 amino acids, about 10 amino acids to about 140 amino acids, about 10 amino acids to about 135 amino acids, about 10 amino acids to about 130 amino acids, about 10 amino acids to about 125 amino acids, about 10 amino acids to about 120 amino acids, about 10 amino acids to about 115 amino acids, about 10 amino acids to about 110 amino acids, about 10 amino acids to about 105 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 15 amino acids to about 1000 amino acids, about 15 amino acids to about 950 amino acids, about 15 amino acids to about 900 amino acids, about 15 amino acids to about 850 amino acids, about 15 amino acids to about 800 amino acids, about 15 amino acids to about 750 amino acids, about 15 amino acids to about 700 amino acids, about 15 amino acids to about 650 amino acids, about 15 amino acids to about 600 amino acids, about 15 amino acids to about 550 amino acids, about 15 amino acids to about 500 amino acids, about 15 amino acids to about 450 amino acids, about 15 amino acids to about 400 amino acids, about 15 amino acids to about 350 amino acids, about 15 amino acids to about 300 amino acids, about 15 amino acids to about 280 amino acids, about 15 amino acids to about 260 amino acids, about 15 amino acids to about 240 amino acids, about 15 amino acids to about 220 amino acids, about 15 amino acids to about 200 amino acids, about 15 amino acids to about 195 amino acids, about 15 amino acids to about 190 amino acids, about 15 amino acids to about 185 amino acids, about 15 amino acids to about 180 amino acids, about 15 amino acids to about 175 amino acids, about 15 amino acids to about 170 amino acids, about 15 amino acids to about 165 amino acids, about 15 amino acids to about 160 amino acids, about 15 amino acids to about 155 amino acids, about 15 amino acids to about 150 amino acids, about 15 amino acids to about 145 amino acids, about 15 amino acids to about 140 amino acids, about 15 amino acids to about 135 amino acids, about 15 amino acids to about 130 amino acids, about 15 amino acids to about 125 amino acids, about 15 amino acids to about 120 amino acids, about 15 amino acids to about 115 amino acids, about 15 amino acids to about 110 amino acids, about 15 amino acids to about 105 amino acids, about 15 amino acids to about 100 amino acids, about 15 amino acids to about 95 amino acids, about 15 amino acids to about 90 amino acids, about 15 amino acids to about 85 amino acids, about 15 amino acids to about 80 amino acids, about 15 amino acids to about 75 amino acids, about 15 amino acids to about 70 amino acids, about 15 amino acids to about 65 amino acids, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 1000 amino acids, about 20 amino acids to about 950 amino acids, about 20 amino acids to about 900 amino acids, about 20 amino acids to about 850 amino acids, about 20 amino acids to about 800 amino acids, about 20 amino acids to about 750 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 280 amino acids, about 20 amino acids to about 260 amino acids, about 20 amino acids to about 240 amino acids, about 20 amino acids to about 220 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 1000 amino acids, about 25 amino acids to about 950 amino acids, about 25 amino acids to about 900 amino acids, about 25 amino acids to about 850 amino acids, about 25 amino acids to about 800 amino acids, about 25 amino acids to about 750 amino acids, about 25 amino acids to about 700 amino acids, about 25 amino acids to about 650 amino acids, about 25 amino acids to about 600 amino acids, about 25 amino acids to about 550 amino acids, about 25 amino acids to about 500 amino acids, about 25 amino acids to about 450 amino acids, about 25 amino acids to about 400 amino acids, about 25 amino acids to about 350 amino acids, about 25 amino acids to about 300 amino acids, about 25 amino acids to about 280 amino acids, about 25 amino acids to about 260 amino acids, about 25 amino acids to about 240 amino acids, about 25 amino acids to about 220 amino acids, about 25 amino acids to about 200 amino acids, about 25 amino acids to about 195 amino acids, about 25 amino acids to about 190 amino acids, about 25 amino acids to about 185 amino acids, about 25 amino acids to about 180 amino acids, about 25 amino acids to about 175 amino acids, about 25 amino acids to about 170 amino acids, about 25 amino acids to about 165 amino acids, about 25 amino acids to about 160 amino acids, about 25 amino acids to about 155 amino acids, about 25 amino acids to about 150 amino acids, about 25 amino acids to about 145 amino acids, about 25 amino acids to about 140 amino acids, about 25 amino acids to about 135 amino acids, about 25 amino acids to about 130 amino acids, about 25 amino acids to about 125 amino acids, about 25 amino acids to about 120 amino acids, about 25 amino acids to about 115 amino acids, about 25 amino acids to about 110 amino acids, about 25 amino acids to about 105 amino acids, about 25 amino acids to about 100 amino acids, about 25 amino acids to about 95 amino acids, about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 280 amino acids, about 30 amino acids to about 260 amino acids, about 30 amino acids to about 240 amino acids, about 30 amino acids to about 220 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 1000 amino acids, about 35 amino acids to about 950 amino acids, about 35 amino acids to about 900 amino acids, about 35 amino acids to about 850 amino acids, about 35 amino acids to about 800 amino acids, about 35 amino acids to about 750 amino acids, about 35 amino acids to about 700 amino acids, about 35 amino acids to about 650 amino acids, about 35 amino acids to about 600 amino acids, about 35 amino acids to about 550 amino acids, about 35 amino acids to about 500 amino acids, about 35 amino acids to about 450 amino acids, about 35 amino acids to about 400 amino acids, about 35 amino acids to about 350 amino acids, about 35 amino acids to about 300 amino acids, about 35 amino acids to about 280 amino acids, about 35 amino acids to about 260 amino acids, about 35 amino acids to about 240 amino acids, about 35 amino acids to about 220 amino acids, about 35 amino acids to about 200 amino acids, about 35 amino acids to about 195 amino acids, about 35 amino acids to about 190 amino acids, about 35 amino acids to about 185 amino acids, about 35 amino acids to about 180 amino acids, about 35 amino acids to about 175 amino acids, about 35 amino acids to about 170 amino acids, about 35 amino acids to about 165 amino acids, about 35 amino acids to about 160 amino acids, about 35 amino acids to about 155 amino acids, about 35 amino acids to about 150 amino acids, about 35 amino acids to about 145 amino acids, about 35 amino acids to about 140 amino acids, about 35 amino acids to about 135 amino acids, about 35 amino acids to about 130 amino acids, about 35 amino acids to about 125 amino acids, about 35 amino acids to about 120 amino acids, about 35 amino acids to about 115 amino acids, about 35 amino acids to about 110 amino acids, about 35 amino acids to about 105 amino acids, about 35 amino acids to about 100 amino acids, about 35 amino acids to about 95 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 1000 amino acids, about 40 amino acids to about 950 amino acids, about 40 amino acids to about 900 amino acids, about 40 amino acids to about 850 amino acids, about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 280 amino acids, about 40 amino acids to about 260 amino acids, about 40 amino acids to about 240 amino acids, about 40 amino acids to about 220 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 1000 amino acids, about 45 amino acids to about 950 amino acids, about 45 amino acids to about 900 amino acids, about 45 amino acids to about 850 amino acids, about 45 amino acids to about 800 amino acids, about 45 amino acids to about 750 amino acids, about 45 amino acids to about 700 amino acids, about 45 amino acids to about 650 amino acids, about 45 amino acids to about 600 amino acids, about 45 amino acids to about 550 amino acids, about 45 amino acids to about 500 amino acids, about 45 amino acids to about 450 amino acids, about 45 amino acids to about 400 amino acids, about 45 amino acids to about 350 amino acids, about 45 amino acids to about 300 amino acids, about 45 amino acids to about 280 amino acids, about 45 amino acids to about 260 amino acids, about 45 amino acids to about 240 amino acids, about 45 amino acids to about 220 amino acids, about 45 amino acids to about 200 amino acids, about 45 amino acids to about 195 amino acids, about 45 amino acids to about 190 amino acids, about 45 amino acids to about 185 amino acids, about 45 amino acids to about 180 amino acids, about 45 amino acids to about 175 amino acids, about 45 amino acids to about 170 amino acids, about 45 amino acids to about 165 amino acids, about 45 amino acids to about 160 amino acids, about 45 amino acids to about 155 amino acids, about 45 amino acids to about 150 amino acids, about 45 amino acids to about 145 amino acids, about 45 amino acids to about 140 amino acids, about 45 amino acids to about 135 amino acids, about 45 amino acids to about 130 amino acids, about 45 amino acids to about 125 amino acids, about 45 amino acids to about 120 amino acids, about 45 amino acids to about 115 amino acids, about 45 amino acids to about 110 amino acids, about 45 amino acids to about 105 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 1000 amino acids, about 55 amino acids to about 950 amino acids, about 55 amino acids to about 900 amino acids, about 55 amino acids to about 850 amino acids, about 55 amino acids to about 800 amino acids, about 55 amino acids to about 750 amino acids, about 55 amino acids to about 700 amino acids, about 55 amino acids to about 650 amino acids, about 55 amino acids to about 600 amino acids, about 55 amino acids to about 550 amino acids, about 55 amino acids to about 500 amino acids, about 55 amino acids to about 450 amino acids, about 55 amino acids to about 400 amino acids, about 55 amino acids to about 350 amino acids, about 55 amino acids to about 300 amino acids, about 55 amino acids to about 280 amino acids, about 55 amino acids to about 260 amino acids, about 55 amino acids to about 240 amino acids, about 55 amino acids to about 220 amino acids, about 55 amino acids to about 200 amino acids, about 55 amino acids to about 195 amino acids, about 55 amino acids to about 190 amino acids, about 55 amino acids to about 185 amino acids, about 55 amino acids to about 180 amino acids, about 55 amino acids to about 175 amino acids, about 55 amino acids to about 170 amino acids, about 55 amino acids to about 165 amino acids, about 55 amino acids to about 160 amino acids, about 55 amino acids to about 155 amino acids, about 55 amino acids to about 150 amino acids, about 55 amino acids to about 145 amino acids, about 55 amino acids to about 140 amino acids, about 55 amino acids to about 135 amino acids, about 55 amino acids to about 130 amino acids, about 55 amino acids to about 125 amino acids, about 55 amino acids to about 120 amino acids, about 55 amino acids to about 115 amino acids, about 55 amino acids to about 110 amino acids, about 55 amino acids to about 105 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 1000 amino acids, about 60 amino acids to about 950 amino acids, about 60 amino acids to about 900 amino acids, about 60 amino acids to about 850 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 280 amino acids, about 60 amino acids to about 260 amino acids, about 60 amino acids to about 240 amino acids, about 60 amino acids to about 220 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 1000 amino acids, about 65 amino acids to about 950 amino acids, about 65 amino acids to about 900 amino acids, about 65 amino acids to about 850 amino acids, about 65 amino acids to about 800 amino acids, about 65 amino acids to about 750 amino acids, about 65 amino acids to about 700 amino acids, about 65 amino acids to about 650 amino acids, about 65 amino acids to about 600 amino acids, about 65 amino acids to about 550 amino acids, about 65 amino acids to about 500 amino acids, about 65 amino acids to about 450 amino acids, about 65 amino acids to about 400 amino acids, about 65 amino acids to about 350 amino acids, about 65 amino acids to about 300 amino acids, about 65 amino acids to about 280 amino acids, about 65 amino acids to about 260 amino acids, about 65 amino acids to about 240 amino acids, about 65 amino acids to about 220 amino acids, about 65 amino acids to about 200 amino acids, about 65 amino acids to about 195 amino acids, about 65 amino acids to about 190 amino acids, about 65 amino acids to about 185 amino acids, about 65 amino acids to about 180 amino acids, about 65 amino acids to about 175 amino acids, about 65 amino acids to about 170 amino acids, about 65 amino acids to about 165 amino acids, about 65 amino acids to about 160 amino acids, about 65 amino acids to about 155 amino acids, about 65 amino acids to about 150 amino acids, about 65 amino acids to about 145 amino acids, about 65 amino acids to about 140 amino acids, about 65 amino acids to about 135 amino acids, about 65 amino acids to about 130 amino acids, about 65 amino acids to about 125 amino acids, about 65 amino acids to about 120 amino acids, about 65 amino acids to about 115 amino acids, about 65 amino acids to about 110 amino acids, about 65 amino acids to about 105 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 1000 amino acids, about 70 amino acids to about 950 amino acids, about 70 amino acids to about 900 amino acids, about 70 amino acids to about 850 amino acids, about 70 amino acids to about 800 amino acids, about 70 amino acids to about 750 amino acids, about 70 amino acids to about 700 amino acids, about 70 amino acids to about 650 amino acids, about 70 amino acids to about 600 amino acids, about 70 amino acids to about 550 amino acids, about 70 amino acids to about 500 amino acids, about 70 amino acids to about 450 amino acids, about 70 amino acids to about 400 amino acids, about 70 amino acids to about 350 amino acids, about 70 amino acids to about 300 amino acids, about 70 amino acids to about 280 amino acids, about 70 amino acids to about 260 amino acids, about 70 amino acids to about 240 amino acids, about 70 amino acids to about 220 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 1000 amino acids, about 75 amino acids to about 950 amino acids, about 75 amino acids to about 900 amino acids, about 75 amino acids to about 850 amino acids, about 75 amino acids to about 800 amino acids, about 75 amino acids to about 750 amino acids, about 75 amino acids to about 700 amino acids, about 75 amino acids to about 650 amino acids, about 75 amino acids to about 600 amino acids, about 75 amino acids to about 550 amino acids, about 75 amino acids to about 500 amino acids, about 75 amino acids to about 450 amino acids, about 75 amino acids to about 400 amino acids, about 75 amino acids to about 350 amino acids, about 75 amino acids to about 300 amino acids, about 75 amino acids to about 280 amino acids, about 75 amino acids to about 260 amino acids, about 75 amino acids to about 240 amino acids, about 75 amino acids to about 220 amino acids, about 75 amino acids to about 200 amino acids, about 75 amino acids to about 195 amino acids, about 75 amino acids to about 190 amino acids, about 75 amino acids to about 185 amino acids, about 75 amino acids to about 180 amino acids, about 75 amino acids to about 175 amino acids, about 75 amino acids to about 170 amino acids, about 75 amino acids to about 165 amino acids, about 75 amino acids to about 160 amino acids, about 75 amino acids to about 155 amino acids, about 75 amino acids to about 150 amino acids, about 75 amino acids to about 145 amino acids, about 75 amino acids to about 140 amino acids, about 75 amino acids to about 135 amino acids, about 75 amino acids to about 130 amino acids, about 75 amino acids to about 125 amino acids, about 75 amino acids to about 120 amino acids, about 75 amino acids to about 115 amino acids, about 75 amino acids to about 110 amino acids, about 75 amino acids to about 105 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 1000 amino acids, about 80 amino acids to about 950 amino acids, about 80 amino acids to about 900 amino acids, about 80 amino acids to about 850 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 280 amino acids, about 80 amino acids to about 260 amino acids, about 80 amino acids to about 240 amino acids, about 80 amino acids to about 220 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 80 amino acids to about 85 amino acids, about 85 amino acids to about 1000 amino acids, about 85 amino acids to about 950 amino acids, about 85 amino acids to about 900 amino acids, about 85 amino acids to about 850 amino acids, about 85 amino acids to about 800 amino acids, about 85 amino acids to about 750 amino acids, about 85 amino acids to about 700 amino acids, about 85 amino acids to about 650 amino acids, about 85 amino acids to about 600 amino acids, about 85 amino acids to about 550 amino acids, about 85 amino acids to about 500 amino acids, about 85 amino acids to about 450 amino acids, about 85 amino acids to about 400 amino acids, about 85 amino acids to about 350 amino acids, about 85 amino acids to about 300 amino acids, about 85 amino acids to about 280 amino acids, about 85 amino acids to about 260 amino acids, about 85 amino acids to about 240 amino acids, about 85 amino acids to about 220 amino acids, about 85 amino acids to about 200 amino acids, about 85 amino acids to about 195 amino acids, about 85 amino acids to about 190 amino acids, about 85 amino acids to about 185 amino acids, about 85 amino acids to about 180 amino acids, about 85 amino acids to about 175 amino acids, about 85 amino acids to about 170 amino acids, about 85 amino acids to about 165 amino acids, about 85 amino acids to about 160 amino acids, about 85 amino acids to about 155 amino acids, about 85 amino acids to about 150 amino acids, about 85 amino acids to about 145 amino acids, about 85 amino acids to about 140 amino acids, about 85 amino acids to about 135 amino acids, about 85 amino acids to about 130 amino acids, about 85 amino acids to about 125 amino acids, about 85 amino acids to about 120 amino acids, about 85 amino acids to about 115 amino acids, about 85 amino acids to about 110 amino acids, about 85 amino acids to about 105 amino acids, about 85 amino acids to about 100 amino acids, about 85 amino acids to about 95 amino acids, about 85 amino acids to about 90 amino acids, about 90 amino acids to about 1000 amino acids, about 90 amino acids to about 950 amino acids, about 90 amino acids to about 900 amino acids, about 90 amino acids to about 850 amino acids, about 90 amino acids to about 800 amino acids, about 90 amino acids to about 750 amino acids, about 90 amino acids to about 700 amino acids, about 90 amino acids to about 650 amino acids, about 90 amino acids to about 600 amino acids, about 90 amino acids to about 550 amino acids, about 90 amino acids to about 500 amino acids, about 90 amino acids to about 450 amino acids, about 90 amino acids to about 400 amino acids, about 90 amino acids to about 350 amino acids, about 90 amino acids to about 300 amino acids, about 90 amino acids to about 280 amino acids, about 90 amino acids to about 260 amino acids, about 90 amino acids to about 240 amino acids, about 90 amino acids to about 220 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 90 amino acids to about 95 amino acids, about 95 amino acids to about 1000 amino acids, about 95 amino acids to about 950 amino acids, about 95 amino acids to about 900 amino acids, about 95 amino acids to about 850 amino acids, about 95 amino acids to about 800 amino acids, about 95 amino acids to about 750 amino acids, about 95 amino acids to about 700 amino acids, about 95 amino acids to about 650 amino acids, about 95 amino acids to about 600 amino acids, about 95 amino acids to about 550 amino acids, about 95 amino acids to about 500 amino acids, about 95 amino acids to about 450 amino acids, about 95 amino acids to about 400 amino acids, about 95 amino acids to about 350 amino acids, about 95 amino acids to about 300 amino acids, about 95 amino acids to about 280 amino acids, about 95 amino acids to about 260 amino acids, about 95 amino acids to about 240 amino acids, about 95 amino acids to about 220 amino acids, about 95 amino acids to about 200 amino acids, about 95 amino acids to about 195 amino acids, about 95 amino acids to about 190 amino acids, about 95 amino acids to about 185 amino acids, about 95 amino acids to about 180 amino acids, about 95 amino acids to about 175 amino acids, about 95 amino acids to about 170 amino acids, about 95 amino acids to about 165 amino acids, about 95 amino acids to about 160 amino acids, about 95 amino acids to about 155 amino acids, about 95 amino acids to about 150 amino acids, about 95 amino acids to about 145 amino acids, about 95 amino acids to about 140 amino acids, about 95 amino acids to about 135 amino acids, about 95 amino acids to about 130 amino acids, about 95 amino acids to about 125 amino acids, about 95 amino acids to about 120 amino acids, about 95 amino acids to about 115 amino acids, about 95 amino acids to about 110 amino acids, about 95 amino acids to about 105 amino acids, about 95 amino acids to about 100 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 100 amino acids to about 105 amino acids, about 105 amino acids to about 1000 amino acids, about 105 amino acids to about 950 amino acids, about 105 amino acids to about 900 amino acids, about 105 amino acids to about 850 amino acids, about 105 amino acids to about 800 amino acids, about 105 amino acids to about 750 amino acids, about 105 amino acids to about 700 amino acids, about 105 amino acids to about 650 amino acids, about 105 amino acids to about 600 amino acids, about 105 amino acids to about 550 amino acids, about 105 amino acids to about 500 amino acids, about 105 amino acids to about 450 amino acids, about 105 amino acids to about 400 amino acids, about 105 amino acids to about 350 amino acids, about 105 amino acids to about 300 amino acids, about 105 amino acids to about 280 amino acids, about 105 amino acids to about 260 amino acids, about 105 amino acids to about 240 amino acids, about 105 amino acids to about 220 amino acids, about 105 amino acids to about 200 amino acids, about 105 amino acids to about 195 amino acids, about 105 amino acids to about 190 amino acids, about 105 amino acids to about 185 amino acids, about 105 amino acids to about 180 amino acids, about 105 amino acids to about 175 amino acids, about 105 amino acids to about 170 amino acids, about 105 amino acids to about 165 amino acids, about 105 amino acids to about 160 amino acids, about 105 amino acids to about 155 amino acids, about 105 amino acids to about 150 amino acids, about 105 amino acids to about 145 amino acids, about 105 amino acids to about 140 amino acids, about 105 amino acids to about 135 amino acids, about 105 amino acids to about 130 amino acids, about 105 amino acids to about 125 amino acids, about 105 amino acids to about 120 amino acids, about 105 amino acids to about 115 amino acids, about 105 amino acids to about 110 amino acids, about 110 amino acids to about 1000 amino acids, about 110 amino acids to about 950 amino acids, about 110 amino acids to about 900 amino acids, about 110 amino acids to about 850 amino acids, about 110 amino acids to about 800 amino acids, about 110 amino acids to about 750 amino acids, about 110 amino acids to about 700 amino acids, about 110 amino acids to about 650 amino acids, about 110 amino acids to about 600 amino acids, about 110 amino acids to about 550 amino acids, about 110 amino acids to about 500 amino acids, about 110 amino acids to about 450 amino acids, about 110 amino acids to about 400 amino acids, about 110 amino acids to about 350 amino acids, about 110 amino acids to about 300 amino acids, about 110 amino acids to about 280 amino acids, about 110 amino acids to about 260 amino acids, about 110 amino acids to about 240 amino acids, about 110 amino acids to about 220 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 1000 amino acids, about 115 amino acids to about 950 amino acids, about 115 amino acids to about 900 amino acids, about 115 amino acids to about 850 amino acids, about 115 amino acids to about 800 amino acids, about 115 amino acids to about 750 amino acids, about 115 amino acids to about 700 amino acids, about 115 amino acids to about 650 amino acids, about 115 amino acids to about 600 amino acids, about 115 amino acids to about 550 amino acids, about 115 amino acids to about 500 amino acids, about 115 amino acids to about 450 amino acids, about 115 amino acids to about 400 amino acids, about 115 amino acids to about 350 amino acids, about 115 amino acids to about 300 amino acids, about 115 amino acids to about 280 amino acids, about 115 amino acids to about 260 amino acids, about 115 amino acids to about 240 amino acids, about 115 amino acids to about 220 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 1000 amino acids, about 120 amino acids to about 950 amino acids, about 120 amino acids to about 900 amino acids, about 120 amino acids to about 850 amino acids, about 120 amino acids to about 800 amino acids, about 120 amino acids to about 750 amino acids, about 120 amino acids to about 700 amino acids, about 120 amino acids to about 650 amino acids, about 120 amino acids to about 600 amino acids, about 120 amino acids to about 550 amino acids, about 120 amino acids to about 500 amino acids, about 120 amino acids to about 450 amino acids, about 120 amino acids to about 400 amino acids, about 120 amino acids to about 350 amino acids, about 120 amino acids to about 300 amino acids, about 120 amino acids to about 280 amino acids, about 120 amino acids to about 260 amino acids, about 120 amino acids to about 240 amino acids, about 120 amino acids to about 220 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 1000 amino acids, about 125 amino acids to about 950 amino acids, about 125 amino acids to about 900 amino acids, about 125 amino acids to about 850 amino acids, about 125 amino acids to about 800 amino acids, about 125 amino acids to about 750 amino acids, about 125 amino acids to about 700 amino acids, about 125 amino acids to about 650 amino acids, about 125 amino acids to about 600 amino acids, about 125 amino acids to about 550 amino acids, about 125 amino acids to about 500 amino acids, about 125 amino acids to about 450 amino acids, about 125 amino acids to about 400 amino acids, about 125 amino acids to about 350 amino acids, about 125 amino acids to about 300 amino acids, about 125 amino acids to about 280 amino acids, about 125 amino acids to about 260 amino acids, about 125 amino acids to about 240 amino acids, about 125 amino acids to about 220 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 1000 amino acids, about 130 amino acids to about 950 amino acids, about 130 amino acids to about 900 amino acids, about 130 amino acids to about 850 amino acids, about 130 amino acids to about 800 amino acids, about 130 amino acids to about 750 amino acids, about 130 amino acids to about 700 amino acids, about 130 amino acids to about 650 amino acids, about 130 amino acids to about 600 amino acids, about 130 amino acids to about 550 amino acids, about 130 amino acids to about 500 amino acids, about 130 amino acids to about 450 amino acids, about 130 amino acids to about 400 amino acids, about 130 amino acids to about 350 amino acids, about 130 amino acids to about 300 amino acids, about 130 amino acids to about 280 amino acids, about 130 amino acids to about 260 amino acids, about 130 amino acids to about 240 amino acids, about 130 amino acids to about 220 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 1000 amino acids, about 135 amino acids to about 950 amino acids, about 135 amino acids to about 900 amino acids, about 135 amino acids to about 850 amino acids, about 135 amino acids to about 800 amino acids, about 135 amino acids to about 750 amino acids, about 135 amino acids to about 700 amino acids, about 135 amino acids to about 650 amino acids, about 135 amino acids to about 600 amino acids, about 135 amino acids to about 550 amino acids, about 135 amino acids to about 500 amino acids, about 135 amino acids to about 450 amino acids, about 135 amino acids to about 400 amino acids, about 135 amino acids to about 350 amino acids, about 135 amino acids to about 300 amino acids, about 135 amino acids to about 280 amino acids, about 135 amino acids to about 260 amino acids, about 135 amino acids to about 240 amino acids, about 135 amino acids to about 220 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 1000 amino acids, about 140 amino acids to about 950 amino acids, about 140 amino acids to about 900 amino acids, about 140 amino acids to about 850 amino acids, about 140 amino acids to about 800 amino acids, about 140 amino acids to about 750 amino acids, about 140 amino acids to about 700 amino acids, about 140 amino acids to about 650 amino acids, about 140 amino acids to about 600 amino acids, about 140 amino acids to about 550 amino acids, about 140 amino acids to about 500 amino acids, about 140 amino acids to about 450 amino acids, about 140 amino acids to about 400 amino acids, about 140 amino acids to about 350 amino acids, about 140 amino acids to about 300 amino acids, about 140 amino acids to about 280 amino acids, about 140 amino acids to about 260 amino acids, about 140 amino acids to about 240 amino acids, about 140 amino acids to about 220 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 1000 amino acids, about 145 amino acids to about 950 amino acids, about 145 amino acids to about 900 amino acids, about 145 amino acids to about 850 amino acids, about 145 amino acids to about 800 amino acids, about 145 amino acids to about 750 amino acids, about 145 amino acids to about 700 amino acids, about 145 amino acids to about 650 amino acids, about 145 amino acids to about 600 amino acids, about 145 amino acids to about 550 amino acids, about 145 amino acids to about 500 amino acids, about 145 amino acids to about 450 amino acids, about 145 amino acids to about 400 amino acids, about 145 amino acids to about 350 amino acids, about 145 amino acids to about 300 amino acids, about 145 amino acids to about 280 amino acids, about 145 amino acids to about 260 amino acids, about 145 amino acids to about 240 amino acids, about 145 amino acids to about 220 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 1000 amino acids, about 155 amino acids to about 950 amino acids, about 155 amino acids to about 900 amino acids, about 155 amino acids to about 850 amino acids, about 155 amino acids to about 800 amino acids, about 155 amino acids to about 750 amino acids, about 155 amino acids to about 700 amino acids, about 155 amino acids to about 650 amino acids, about 155 amino acids to about 600 amino acids, about 155 amino acids to about 550 amino acids, about 155 amino acids to about 500 amino acids, about 155 amino acids to about 450 amino acids, about 155 amino acids to about 400 amino acids, about 155 amino acids to about 350 amino acids, about 155 amino acids to about 300 amino acids, about 155 amino acids to about 280 amino acids, about 155 amino acids to about 260 amino acids, about 155 amino acids to about 240 amino acids, about 155 amino acids to about 220 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 1000 amino acids, about 160 amino acids to about 950 amino acids, about 160 amino acids to about 900 amino acids, about 160 amino acids to about 850 amino acids, about 160 amino acids to about 800 amino acids, about 160 amino acids to about 750 amino acids, about 160 amino acids to about 700 amino acids, about 160 amino acids to about 650 amino acids, about 160 amino acids to about 600 amino acids, about 160 amino acids to about 550 amino acids, about 160 amino acids to about 500 amino acids, about 160 amino acids to about 450 amino acids, about 160 amino acids to about 400 amino acids, about 160 amino acids to about 350 amino acids, about 160 amino acids to about 300 amino acids, about 160 amino acids to about 280 amino acids, about 160 amino acids to about 260 amino acids, about 160 amino acids to about 240 amino acids, about 160 amino acids to about 220 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 1000 amino acids, about 165 amino acids to about 950 amino acids, about 165 amino acids to about 900 amino acids, about 165 amino acids to about 850 amino acids, about 165 amino acids to about 800 amino acids, about 165 amino acids to about 750 amino acids, about 165 amino acids to about 700 amino acids, about 165 amino acids to about 650 amino acids, about 165 amino acids to about 600 amino acids, about 165 amino acids to about 550 amino acids, about 165 amino acids to about 500 amino acids, about 165 amino acids to about 450 amino acids, about 165 amino acids to about 400 amino acids, about 165 amino acids to about 350 amino acids, about 165 amino acids to about 300 amino acids, about 165 amino acids to about 280 amino acids, about 165 amino acids to about 260 amino acids, about 165 amino acids to about 240 amino acids, about 165 amino acids to about 220 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 1000 amino acids, about 170 amino acids to about 950 amino acids, about 170 amino acids to about 900 amino acids, about 170 amino acids to about 850 amino acids, about 170 amino acids to about 800 amino acids, about 170 amino acids to about 750 amino acids, about 170 amino acids to about 700 amino acids, about 170 amino acids to about 650 amino acids, about 170 amino acids to about 600 amino acids, about 170 amino acids to about 550 amino acids, about 170 amino acids to about 500 amino acids, about 170 amino acids to about 450 amino acids, about 170 amino acids to about 400 amino acids, about 170 amino acids to about 350 amino acids, about 170 amino acids to about 300 amino acids, about 170 amino acids to about 280 amino acids, about 170 amino acids to about 260 amino acids, about 170 amino acids to about 240 amino acids, about 170 amino acids to about 220 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 1000 amino acids, about 175 amino acids to about 950 amino acids, about 175 amino acids to about 900 amino acids, about 175 amino acids to about 850 amino acids, about 175 amino acids to about 800 amino acids, about 175 amino acids to about 750 amino acids, about 175 amino acids to about 700 amino acids, about 175 amino acids to about 650 amino acids, about 175 amino acids to about 600 amino acids, about 175 amino acids to about 550 amino acids, about 175 amino acids to about 500 amino acids, about 175 amino acids to about 450 amino acids, about 175 amino acids to about 400 amino acids, about 175 amino acids to about 350 amino acids, about 175 amino acids to about 300 amino acids, about 175 amino acids to about 280 amino acids, about 175 amino acids to about 260 amino acids, about 175 amino acids to about 240 amino acids, about 175 amino acids to about 220 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 1000 amino acids, about 180 amino acids to about 950 amino acids, about 180 amino acids to about 900 amino acids, about 180 amino acids to about 850 amino acids, about 180 amino acids to about 800 amino acids, about 180 amino acids to about 750 amino acids, about 180 amino acids to about 700 amino acids, about 180 amino acids to about 650 amino acids, about 180 amino acids to about 600 amino acids, about 180 amino acids to about 550 amino acids, about 180 amino acids to about 500 amino acids, about 180 amino acids to about 450 amino acids, about 180 amino acids to about 400 amino acids, about 180 amino acids to about 350 amino acids, about 180 amino acids to about 300 amino acids, about 180 amino acids to about 280 amino acids, about 180 amino acids to about 260 amino acids, about 180 amino acids to about 240 amino acids, about 180 amino acids to about 220 amino acids, about 180 amino acids to about 200 amino acids, about 180 amino acids to about 195 amino acids, about 180 amino acids to about 190 amino acids, about 180 amino acids to about 185 amino acids, about 185 amino acids to about 1000 amino acids, about 185 amino acids to about 950 amino acids, about 185 amino acids to about 900 amino acids, about 185 amino acids to about 850 amino acids, about 185 amino acids to about 800 amino acids, about 185 amino acids to about 750 amino acids, about 185 amino acids to about 700 amino acids, about 185 amino acids to about 650 amino acids, about 185 amino acids to about 600 amino acids, about 185 amino acids to about 550 amino acids, about 185 amino acids to about 500 amino acids, about 185 amino acids to about 450 amino acids, about 185 amino acids to about 400 amino acids, about 185 amino acids to about 350 amino acids, about 185 amino acids to about 300 amino acids, about 185 amino acids to about 280 amino acids, about 185 amino acids to about 260 amino acids, about 185 amino acids to about 240 amino acids, about 185 amino acids to about 220 amino acids, about 185 amino acids to about 200 amino acids, about 185 amino acids to about 195 amino acids, about 185 amino acids to about 190 amino acids, about 190 amino acids to about 1000 amino acids, about 190 amino acids to about 950 amino acids, about 190 amino acids to about 900 amino acids, about 190 amino acids to about 850 amino acids, about 190 amino acids to about 800 amino acids, about 190 amino acids to about 750 amino acids, about 190 amino acids to about 700 amino acids, about 190 amino acids to about 650 amino acids, about 190 amino acids to about 600 amino acids, about 190 amino acids to about 550 amino acids, about 190 amino acids to about 500 amino acids, about 190 amino acids to about 450 amino acids, about 190 amino acids to about 400 amino acids, about 190 amino acids to about 350 amino acids, about 190 amino acids to about 300 amino acids, about 190 amino acids to about 280 amino acids, about 190 amino acids to about 260 amino acids, about 190 amino acids to about 240 amino acids, about 190 amino acids to about 220 amino acids, about 190 amino acids to about 200 amino acids, about 190 amino acids to about 195 amino acids, about 195 amino acids to about 1000 amino acids, about 195 amino acids to about 950 amino acids, about 195 amino acids to about 900 amino acids, about 195 amino acids to about 850 amino acids, about 195 amino acids to about 800 amino acids, about 195 amino acids to about 750 amino acids, about 195 amino acids to about 700 amino acids, about 195 amino acids to about 650 amino acids, about 195 amino acids to about 600 amino acids, about 195 amino acids to about 550 amino acids, about 195 amino acids to about 500 amino acids, about 195 amino acids to about 450 amino acids, about 195 amino acids to about 400 amino acids, about 195 amino acids to about 350 amino acids, about 195 amino acids to about 300 amino acids, about 195 amino acids to about 280 amino acids, about 195 amino acids to about 260 amino acids, about 195 amino acids to about 240 amino acids, about 195 amino acids to about 220 amino acids, about 195 amino acids to about 200 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 450 amino acids, about 220 amino acids to about 400 amino acids, about 220 amino acids to about 350 amino acids, about 220 amino acids to about 300 amino acids, about 220 amino acids to about 280 amino acids, about 220 amino acids to about 260 amino acids, about 220 amino acids to about 240 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 450 amino acids, about 240 amino acids to about 400 amino acids, about 240 amino acids to about 350 amino acids, about 240 amino acids to about 300 amino acids, about 240 amino acids to about 280 amino acids, about 240 amino acids to about 260 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 450 amino acids, about 260 amino acids to about 400 amino acids, about 260 amino acids to about 350 amino acids, about 260 amino acids to about 300 amino acids, about 260 amino acids to about 280 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 450 amino acids, about 280 amino acids to about 400 amino acids, about 280 amino acids to about 350 amino acids, about 280 amino acids to about 300 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1000 amino acids, about 850 amino acids to about 950 amino acids, about 850 amino acids to about 900 amino acids, about 900 amino acids to about 1000 amino acids, about 900 amino acids to about 950 amino acids, or about 950 amino acids to about 1000 amino acids.

Any of the target-binding domains described herein can bind to its target with a dissociation equilibrium constant ($K_D$) of less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In some embodiments, the antigen-binding protein construct provided herein can bind to an identifying antigen with a $K_D$ of about $1\times10^{-3}$ M to about $1\times10^{-5}$ M, about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, or about $1\times10^{-9}$ M to about $1\times10^{-11}$ M (inclusive).

Any of the target-binding domains described herein can bind to its target with a $K_D$ of between about 1 pM to about 30 nM (e.g., about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 90 pM, about 2 pM to about 80 pM, about 2 pM to about 70 pM, about 2 pM to about 60 pM, about 2 pM to about 50 pM, about 2 pM to about 40 pM, about 2 pM to about 30 pM, about 2 pM to about 20 pM, about 2 pM to about 10 pM, about 2 pM to about 5 pM, about 2 pM to about 4 pM, about 2 pM to about 3 pM, about 5 pM to about 30 nM, about 5 pM to about 25 nM, about 5 pM to about 20 nM, about 5 pM to about 15 nM, about 5 pM to about 10 nM, about 5 pM to about 5 nM, about 5 PM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 90 pM, about 5 pM to about 80 pM, about 5 pM to about 70 pM, about 5 pM to about 60 pM, about 5 pM to about 50 pM, about 5 pM to about 40 pM, about 5 pM to about 30 pM, about 5 pM to about 20 pM, about 5 pM to about 10 pM, about 10 pM to about 30 nM, about 10 pM to about 25 nM, about 10 pM to about 20 nM, about 10 pM to about 15 nM, about 10 pM to about 10 nM, about 10 pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about 10 pM to about 200 pM, about 10 pM to about 150 pM, about 10 pM to about 100 pM, about 10 pM to about 90 pM, about 10 pM to about 80 pM, about 10 pM to about 70 pM, about 10 pM to about 60 pM, about 10 pM to about 50 pM, about 10 pM to about 40 pM, about 10 pM to about 30 pM, about 10 pM to about 20 pM, about 15 pM to about 30 nM, about 15 pM to about 25 nM, about 15 pM to about 20 nM, about 15 pM to about 15 nM, about 15 pM to about 10 nM, about 15 pM to about 5 nM, about 15 PM to about 2 nM, about 15 pM to about 1 nM, about 15 pM to about 950 pM, about 15 pM to about 900 pM, about 15 pM to about 850 pM, about 15 pM to about 800 pM, about 15 pM to about 750 pM, about 15 pM to about 700 pM, about 15 pM to about 650 pM, about 15 pM to about 600 pM, about 15 pM to about 550 pM, about 15 pM to about 500 pM, about 15 pM to about 450 pM, about 15 pM to about 400 pM, about 15 pM to about 350 pM, about 15 pM to about 300 pM, about 15 pM to about 250 pM, about 15 pM to about 200 pM, about 15 pM to about 150 pM, about 15 pM to about 100 pM, about 15 pM to about 90 pM, about 15 pM to about 80 pM, about 15 pM to about 70 pM, about 15 pM to about 60 pM, about 15 pM to about 50 pM, about 15 pM to about 40 pM, about 15 pM to about 30 pM, about 15 pM to about 20 pM, about 20 pM to about 30 nM, about 20 pM to about 25 nM, about 20 pM to about 20 nM, about 20 pM to about 15 nM, about 20 pM to about 10 nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about 20 pM to about 400 pM, about 20 pM to about 350 pM, about 20 pM to about 300 pM, about 20 pM to about 250 pM, about 20 pM to about 20 pM, about 200 pM to about 150 pM, about 20 pM to about 100 pM, about 20 pM to about 90 pM, about 20 pM to about 80 pM, about 20 pM to about 70 pM, about 20 pM to about 60 pM, about 20 pM to about 50 pM, about 20 pM to about 40 pM, about 20 pM to about 30 pM, about 30 pM to about 30 nM, about 30 pM to about 25 nM, about 30 pM to about 30 nM, about 30 pM to about 15 nM, about 30 pM to about 10 nM, about 30 PM to about 5 nM, about 30 PM to about 2 nM, about 30 pM to about 1 nM, about 30 pM to about 950 pM, about 30 pM to about 900 pM, about 30 pM to about 850 pM, about 30 pM to about 800 pM, about 30 pM to about 750 pM, about 30 pM to about 700 pM, about 30 pM to about 650 pM, about 30 pM to about 600 pM, about 30 pM to about 550 pM, about 30 pM to about 500 pM, about 30 pM to about 450 pM, about 30 pM to about 400 pM, about 30 pM to about 350 pM, about 30 pM to about 300 pM, about 30 pM to about 250 pM, about 30 PM to about 200 pM, about 30 pM to about 150 pM, about 30 pM to about 100 pM, about 30 pM to about 90 pM, about 30 pM to about 80 pM, about 30 pM to about 70 pM, about 30 pM to about 60 pM, about 30 pM to about 50 pM, about 30 pM to about 40 pM, about 40 pM to about 30 nM, about 40 pM to about 25 nM, about 40 pM to about 30 nM, about 40 pM to about 15 nM, about 40 pM to about 10 nM, about 40 pM to about 5 nM, about 40 pM to about 2 nM, about 40 pM to about 1 nM, about 40 pM to about 950 pM, about 40 pM to about 900 pM, about 40 pM to about 850 pM, about 40 pM to about 800 pM, about 40 pM to about 750 pM, about 40 pM to about 700 pM, about 40 pM to about 650 pM, about 40 pM to about 600 pM, about 40 pM to about 550 pM, about 40 pM to about 500 pM, about 40 pM to about 450 pM, about 40 pM to about 400 pM, about 40 pM to about 350 pM, about 40 pM to about 300 pM, about 40 pM to about 250 pM, about 40 pM to about 200 pM, about 40 pM to about 150 pM, about 40 pM to about 100 pM, about 40 pM to about 90 pM, about 40 pM to about 80 pM, about 40 pM to about 70 pM, about 40 pM to about 60 pM, about 40 pM to about 50 pM, about 50 pM to about 30 nM, about 50 pM to about 25 nM, about 50 pM to about 30 nM, about 50 pM to about 15 nM, about 50 pM to about 10 nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about 50 pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 90 pM, about 50 pM to about 80 pM, about 50 pM to about 70 pM, about 50 pM to about 60 pM, about 60 pM to about 30 nM, about 60 pM to about 25 nM, about 60 pM to about 30 nM, about 60 pM to about 15 nM, about 60 pM to about 10 nM, about 60 pM to about 5 nM, about 60 pM to about 2 nM, about 60 pM to about 1 nM, about 60 pM to about 950 pM, about 60 pM to about 900 pM, about 60 pM to about 850 pM, about 60 pM to about 800 pM, about 60 pM to about 750 pM, about 60 pM to about 700 pM, about 60 pM to about 650 pM, about 60 pM to about 600 pM, about 60 pM to about 550 pM, about 60 pM to about 500 pM, about 60 pM to about 450 pM, about 60 pM to about 400 pM, about 60 pM to about 350 pM, about 60 pM to about 300 pM, about 60 pM to about 250 pM, about 60 pM to about 200 pM, about 60 pM to about 150 pM, about 60 pM to about 100 pM, about 60 pM to about 90 pM, about 60 pM to about 80 pM, about 60 pM to about 70 pM, about 70 pM to about 30 nM, about 70 pM to about 25 nM, about 70 pM to about 30 nM, about 70 pM to about 15 nM, about 70 pM to about 10 nM, about 70 pM to about 5 nM, about 70 pM to about 2 nM, about 70 pM to about 1 nM, about 70 pM to about 950 pM, about 70 pM to about 900 pM, about 70 pM to about 850 pM, about 70 pM to about 800 pM, about 70 pM to about 750 pM, about 70 pM to about 700 pM, about 70 pM to about 650 pM, about 70 pM to about 600 pM, about 70 pM to about 550 pM, about 70 pM to about 500 pM, about 70 pM to about 450 pM, about 70 pM to about 400 pM, about 70 pM to about 350 pM, about 70 pM to about 300 pM, about 70 pM to about 250 pM, about 70 pM to about 200 pM, about 70 pM to about 150 pM, about 70 pM to about 100 pM, about 70 pM to about 90 pM, about 70 pM to about 80 pM, about 80 pM to about 30 nM, about 80 pM to about 25 nM, about 80 pM to about 30 nM, about 80 pM to about 15 nM, about 80 pM to about 10 nM, about 80 pM to about 5 nM, about 80 pM to about 2 nM, about 80 pM to about 1 nM, about 80 pM to about 950 pM, about 80 pM to about 900 pM, about 80 pM to about 850 pM, about 80 pM to about 800 pM, about 80 pM to about 750 pM, about 80 pM to about 700 pM, about 80 pM to about 650 pM, about 80 pM to about 600 pM, about 80 pM to about 550 pM, about 80 pM to about 500 pM, about 80 pM to about 450 pM, about 80 pM to about 400 pM, about 80 pM to about 350 pM, about 80 pM to about 300 pM, about 80 pM to about 250 pM, about 80 pM to about 200 pM, about 80 pM to about 150 pM, about 80 pM to about 100 pM, about 80 pM to about 90 pM, about 90 pM to about 30 nM, about 90 pM to about 25 nM, about 90 pM to about 30 nM, about 90 pM to about 15 nM, about 90 pM to about 10 nM, about 90 pM to about 5 nM, about 90 pM to about 2 nM, about 90 pM to about 1 nM, about 90 pM to about 950 pM, about 90 pM to about 900 pM, about 90 pM to about 850 pM, about 90 pM to about 800 pM, about 90 pM to about 750 pM, about 90 pM to about 700 pM, about 90 pM to about 650 pM, about 90 pM to about 600 pM, about 90 pM to about 550 pM, about 90 pM to about 500 pM, about 90 pM to about 450 pM, about 90 pM to about 400 pM, about 90 pM to about 350 pM, about 90 pM to about 300 pM, about 90 pM to about 250 pM, about 90 pM to about 200 pM, about 90 pM to about 150 pM, about 90 pM to about 100 pM, about 100 pM to about 30 nM, about 100 pM to about 25 nM, about 100 pM to about 30 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 150 pM to about 30 nM, about 150 pM to about 25 nM, about 150 pM to about 30 nM, about 150 pM to about 15 nM, about 150 pM to about 10 nM, about 150 pM to about 5 nM, about 150 pM to about 2 nM, about 150 pM to about 1 nM, about 150 pM to about 950 pM, about 150 pM to about 900 pM, about 150 pM to about 850 pM, about 150 pM to about 800 pM, about 150 pM to about 750 pM, about 150 pM to about 700 pM, about 150 pM to about 650 pM, about 150 pM to about 600 pM, about 150 pM to about 550 pM, about 150 pM to about 500 pM, about 150 pM to about 450 pM, about 150 pM to about 400 pM, about 150 pM to about 350 pM, about 150 pM to about 300 pM, about 150 pM to about 250 pM, about 150 pM to about 200 pM, about 200 pM to about 30 nM, about 200 pM to about 25 nM, about 200 pM to about 30 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 30 nM, about 300 pM to about 25 nM, about 300 pM to about 30 nM, about 300 pM to about 15 nM, about 300 pM to about 10 nM, about 300 pM to about 5 nM, about 300 pM to about 2 nM, about 300 PM to about 1 nM, about 300 pM to about 950 pM, about 300 pM to about 900 pM, about 300 pM to about 850 pM, about 300 pM to about 800 pM, about 300 pM to about 750 pM, about 300 PM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 30 nM, about 400 pM to about 25 nM, about 400 pM to about 30 nM, about 400 pM to about 15 nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 500 pM to about 30 nM, about 500 pM to about 25 nM, about 500 pM to about 30 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 30 nM, about 600 pM to about 25 nM, about 600 pM to about 30 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 30 nM, about 700 pM to about 25 nM, about 700 pM to about 30 nM, about 700 pM to about 15 nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 30 nM, about 800 pM to about 25 nM, about 800 pM to about 30 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 30 nM, about 900 pM to about 25 nM, about 900 pM to about 30 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 30 nM, about 1 nM to about 25 nM, about 1 nM to about 20 nM, about 1 nM to about 15 nM, about 1 nM to about 10 nM, about 1 nM to about 5 nM, about 2 nM to about 30 nM, about 2 nM to about 25 nM, about 2 nM to about 20 nM, about 2 nM to about 15 nM, about 2 nM to about 10 nM, about 2 nM to about 5 nM, about 4 nM to about 30 nM, about 4 nM to about 25 nM, about 4 nM to about 20 nM, about 4 nM to about 15 nM, about 4 nM to about 10 nM, about 4 nM to about 5 nM, about 5 nM to about 30 nM, about 5 nM to about 25 nM, about 5 nM to about 20 nM, about 5 nM to about 15 nM, about 5 nM to about 10 nM, about 10 nM to about 30 nM, about 10 nM to about 25 nM, about 10 nM to about 20 nM, about 10 nM to about 15 nM, about 15 nM to about 30 nM, about 15 nM to about 25 nM, about 15 nM to about 20 nM, about 20 nM to about 30 nM, and about 20 nM to about 25 nM).

Any of the target-binding domains described herein can bind to its target with a $K_D$ of between about 1 nM to about 10 nM (e.g., about 1 nM to about 9 nM, about 1 nM to about 8 nM, about 1 nM to about 7 nM, about 1 nM to about 6 nM, about 1 nM to about 5 nM, about 1 nM to about 4 nM, about 1 nM to about 3 nM, about 1 nM to about 2 nM, about 2 nM to about 10 nM, about 2 nM to about 9 nM, about 2 nM to about 8 nM, about 2 nM to about 7 nM, about 2 nM to about 6 nM, about 2 nM to about 5 nM, about 2 nM to about 4 nM, about 2 nM to about 3 nM, about 3 nM to about 10 nM, about 3 nM to about 9 nM, about 3 nM to about 8 nM, about 3 nM to about 7 nM, about 3 nM to about 6 nM, about 3 nM to about 5 nM, about 3 nM to about 4 nM, about 4 nM to about 10 nM, about 4 nM to about 9 nM, about 4 nM to about 8 nM, about 4 nM to about 7 nM, about 4 nM to about 6 nM, about 4 nM to about 5 nM, about 5 nM to about 10 nM, about 5 nM to about 9 nM, about 5 nM to about 8 nM, about 5 nM to about 7 nM, about 5 nM to about 6 nM, about 6 nM to about 10 nM, about 6 nM to about 9 nM, about 6 nM to about 8 nM, about 6 nM to about 7 nM, about 7 nM to about 10 nM, about 7 nM to about 9 nM, about 7 nM to about 8 nM, about 8 nM to about 10 nM, about 8 nM to about 9 nM, and about 9 nM to about 10 nM).

A variety of different methods known in the art can be used to determine the $K_D$ values of any of the polypeptides described herein (e.g., an electrophoretic mobility shift assay, a filter binding assay, surface plasmon resonance, and a biomolecular binding kinetics assay, etc.).

Antigen-Binding Domains

In some embodiments of any of the single- or multi-chain chimeric polypeptides described herein, the first target-binding domain and the second target-binding domain bind specifically to the same antigen. In some embodiments of these single- or multi-chain chimeric polypeptides, the first target-binding domain and the second target-binding domain bind specifically to the same epitope. In some embodiments of these single- or multi-chain chimeric polypeptides, the first target-binding domain and the second target-binding domain include the same amino acid sequence.

In some embodiments of any of the single- or multi-chain chimeric polypeptides described herein, the first target-binding domain and the second target-binding domain bind specifically to different antigens.

In some embodiments of any of the single- or multi-chain chimeric polypeptides described herein, one or both of the first target-binding domain and the second target-binding domain is an antigen-binding domain. In some embodiments of any of the single- or multi-chain chimeric polypeptides described herein, the first target-binding domain and the second target-binding domain are each antigen-binding domains.

In some embodiments of any of the single- or multi-chain chimeric polypeptides described herein, the antigen-binding domain includes or is a scFv or a single domain antibody (e.g., a VHH or a VNAR domain).

In some examples, an antigen-binding domain (e.g., any of the antigen-binding domains described herein) can bind specifically to any one of CD16a (see, e.g., those described in U.S. Pat. No. 9,035,026), CD28 (see, e.g., those described in U.S. Pat. No. 7,723,482), CD3 (see, e.g., those described in U.S. Pat. No. 9,226,962), CD33 (see, e.g., those described in U.S. Pat. No. 8,759,494), CD20 (see, e.g., those described in WO 2014/026054), CD19 (see, e.g., those described in U.S. Pat. No. 9,701,758), CD22 (see, e.g., those described in WO 2003/104425), CD123 (see, e.g., those described in WO 2014/130635), IL-1R (see, e.g., those described in U.S. Pat. No. 8,741,604), IL-1 (see, e.g., those described in WO 2014/095808), VEGF (see, e.g., those described in U.S. Pat. No. 9,090,684), IL-6R (see, e.g., those described in U.S. Pat. No. 7,482,436), IL-4 (see, e.g., those described in U.S. Patent Application Publication No. 2012/0171197), IL-10 (see, e.g., those described in U.S. Patent Application Publication No. 2016/0340413), PDL-1 (see, e.g., those described in Drees et al., Protein Express. Purif. 94:60-66, 2014), TIGIT (see, e.g., those described in U.S. Patent Application Publication No. 2017/0198042), PD-1 (see, e.g., those described in U.S. Pat. No. 7,488,802), TIM3 (see, e.g., those described in U.S. Pat. No. 8,552,156), CTLA4 (see, e.g., those described in WO 2012/120125), MICA (see, e.g., those described in WO 2016/154585), MICB (see, e.g., those described in U.S. Pat. No. 8,753,640), IL-6 (see, e.g., those described in Gejima et al., Human Antibodies 11 (4): 121-129, 2002), IL-8 (see, e.g., those described in U.S. Pat. No. 6,117,980), TNFα (see, e.g., those described in Geng et al., Immunol. Res. 62 (3): 377-385, 2015), CD26a (see, e.g., those described in WO 2017/189526), CD36 (see, e.g., those described in U.S. Patent Application Publication No. 2015/0259429), ULBP2 (see, e.g., those described in U.S. Pat. No. 9,273,136), CD30 (see, e.g., those described in Homach et al., Scand. J. Immunol. 48 (5): 497-501, 1998), CD200 (see, e.g., those described in U.S. Pat. No. 9,085,623), IGF-1R (see, e.g., those described in U.S. Patent Application Publication No. 2017/0051063), MUC4AC (see, e.g., those described in WO 2012/170470), MUC5AC (see, e.g., those described in U.S. Pat. No. 9,238,084), Trop-2 (see, e.g., those described in WO 2013/068946), CMET (see, e.g., those described in Edwardraja et al., Biotechnol. Bioeng. 106 (3): 367-375, 2010), EGFR (see, e.g., those described in Akbari et al., Protein Expr. Purif. 127:8-15, 2016), HER1 (see, e.g., those described in U.S. Patent Application Publication No. 2013/0274446), HER2 (see, e.g., those described in Cao et al., Biotechnol. Lett. 37 (7): 1347-1354, 2015), HER3 (see, e.g., those described in U.S. Pat. No. 9,505,843), PSMA (see, e.g., those described in Parker et al., Protein Expr. Purif. 89 (2): 136-145, 2013), CEA (see, e.g., those described in WO 1995/015341), B7H3 (see, e.g., those described in U.S. Pat. No. 9,371,395), EPCAM (see, e.g., those described in WO 2014/159531), BCMA (see, e.g., those described in Smith et al., Mol. Ther. 26 (6): 1447-1456, 2018), P-cadherin (see, e.g., those described in U.S. Pat. No. 7,452,537), CEACAM5 (see, e.g., those described in U.S. Pat. No. 9,617,345), a UL16-binding protein (see, e.g., those described in WO 2017/083612), HLA-DR (see, e.g., Pistillo et al., Exp. Clin. Immunogenet. 14 (2): 123-130, 1997), DLL4 (see, e.g., those described in WO 2014/007513), TYRO3 (see, e.g., those described in WO 2016/166348), AXL (see, e.g., those described in WO 2012/175692), MER (see, e.g., those described in WO 2016/106221), CD122 (see, e.g., those described in U.S. Patent Application Publication No. 2016/0367664), CD155 (see, e.g., those described in WO 2017/149538), or PDGF-DD (see, e.g., those described in U.S. Pat. No. 9,441,034).

The antigen-binding domains present in any of the single- or multi-chain chimeric polypeptides described herein are each independently selected from the group consisting of: a VHH domain, a VNAR domain, and a scFv. In some embodiments, any of the antigen-binding domains described herein is a BiTe, a $(scFv)_2$, a nanobody, a nanobody-HSA, a DART, a TandAb, a scDiabody, a scDiabody-CH3, scFv-CH-CL-scFv, a HSAbody, scDiabody-HAS, or a tandem-scFv. Additional examples of antigen-binding domains that can be used in any of the single- or multi-chain chimeric polypeptide are known in the art.

A VHH domain is a single monomeric variable antibody domain that can be found in camelids. A VNAR domain is a single monomeric variable antibody domain that can be found in cartilaginous fish. Non-limiting aspects of VHH domains and VNAR domains are described in, e.g., Cromie et al., Curr. Top. Med. Chem. 15:2543-2557, 2016; De Genst et al., Dev. Comp. Immunol. 30:187-198, 2006; De Meyer et al., Trends Biotechnol. 32:263-270, 2014; Kijanka et al., Nanomedicine 10:161-174, 2015; Kovaleva et al., Expert. Opin. Biol. Ther. 14:1527-1539, 2014; Krah et al., Immunopharmacol. Immunotoxicol. 38:21-28, 2016; Mujic-Delic et al., Trends Pharmacol. Sci. 35:247-255, 2014; Muyldermans, J. Biotechnol. 74:277-302, 2001; Muyldermans et al., Trends Biochem. Sci. 26:230-235, 2001; Muyldermans, Ann. Rev. Biochem. 82:775-797, 2013; Rahbarizadeh et al., Immunol. Invest. 40:299-338, 2011; Van Audenhove et al., EBioMedicine 8:40-48, 2016; Van Bockstaele et al., Curr. Opin. Investig. Drugs 10:1212-1224, 2009; Vincke et al., Methods Mol. Biol. 911:15-26, 2012; and Wesolowski et al., Med. Microbiol. Immunol. 198:157-174, 2009.

In some embodiments, each of the antigen-binding domains in the single- or multi-chain chimeric polypeptides described herein are both VHH domains, or at least one antigen-binding domain is a VHH domain. In some embodiments, each of the antigen-binding domains in the single- or multi-chain chimeric polypeptides described herein are both VNAR domains, or at least one antigen-binding domain is a VNAR domain. In some embodiments, each of the antigen-binding domains in the single- or multi-chain chimeric polypeptides described herein are both scFv domains, or at least one antigen-binding domain is a scFv domain.

In some embodiments, two or more of polypeptides present in the single- or multi-chain chimeric polypeptide can assemble (e.g., non-covalently assemble) to form any of the antigen-binding domains described herein, e.g., an antigen-binding fragment of an antibody (e.g., any of the antigen-binding fragments of an antibody described herein), a VHH-scAb, a VHH-Fab, a Dual scFab, a $F(ab')_2$, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a κλ-body, an orthogonal Fab, a DVD-IgG, a IgG(H)-scFv, a scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fc, a Diabody-Fc, a tandem scFv-Fc, an Intrabody, a dock and lock, a 1 mmTAC, an IgG-IgG conjugate, a Cov-X-Body, and a scFv1-PEG-scFv2. See, e.g., Spiess et al., Mol. Immunol. 67:95-106, 2015, incorporated in its entirety herewith, for a description of these elements. Non-limiting examples of an antigen-binding fragment of an antibody include an Fv fragment, a Fab fragment, a $F(ab')_2$ fragment, and a Fab' fragment. Additional examples of an antigen-binding fragment of an antibody is an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

In some embodiments of any of the antigen-binding domains described herein can bind to an antigen selected from the group consisting of: a protein, a carbohydrate, a lipid, and a combination thereof.

Additional examples and aspects of antigen-binding domains are known in the art.

Soluble Interleukin or Cytokine Protein

In some embodiments of any of the single- or multi-chain chimeric polypeptides described herein, one or both of the first target-binding domain and the second target-binding domain can be a soluble interleukin protein or soluble cytokine protein. In some embodiments, the soluble interleukin or soluble cytokine protein is selected from the group of: IL-2, IL-3, IL-7, IL-8, IL-10, IL-12, IL-15, IL-17, IL-18, IL-21, PDGF-DD, SCF, and FLT3L. Non-limiting examples of soluble IL-2, IL-3, IL-7, IL-8, IL-10, IL-15, IL-17, IL-18, IL-21, PDGF-DD, SCF, and FLT3L are provided below.

```
Human Soluble IL-2
                                    (SEQ ID NO: 129)
aptssstkkt qlqlehllld lqmilnginn yknpkltrml

tfkfympkka telkhlqcle eelkpleevl nlaqsknfhl

rprdlisnin vivlelkgse ttfmceyade tativeflnr

witfcqsiis tlt
```

```
Human Soluble IL-3
                                    (SEQ ID NO: 130)
apmtqttplkt swvncsnmid eiithlkqpp lplldfnnln

gedqdilmen nlrrpnleaf nravkslqna saiesilknl

lpclplataa ptrhpihikd gdwnefrrkl tfylktlena

qaqqttlsla if
```

```
Human Soluble IL-7
                                    (SEQ ID NO: 131)
dcdiegkdgkqyesv lmvsidqlld smkeigsncl nnefnffkrh

icdankegmf lfraarklrq flkmnstgdf dlhllkvseg

ttillnctgq vkgrkpaalg eaqptkslee nkslkeqkkl

ndlcflkrll qeiktcwnki lmgtkeh
```

```
Human Soluble IL-8
                                    (SEQ ID NO: 132)
egavlprsak elrcqcikty skpfhpkfik elrviesgph

canteiivkl sdgrelcldp kenwvqrvve kflkraens
```

```
Human Soluble IL-10
                                    (SEQ ID NO: 133)
spgqgtqsensc thfpgnlpnm lrdlrdafsr vktffqmkdq

ldnlllkesl ledfkgylgc qalsemiqfy leevmpqaen

qdpdikahvn slgenlktlr lrlrrchrfl pcenkskave

qvknafnklq ekgiykamse fdifinyiea ymtmkirn
```

```
Human Soluble IL-15
                                    (SEQ ID NO: 134)
Nwvnvisdlkki edliqsmhid atlytesdvh psckvtamkc

fllelqvisl esgdasihdt venliilann slssngnvte

sgckeceele eknikeflqs fvhivqmfin ts
```

```
Human Soluble IL-17
                                    (SEQ ID NO: 135)
gitiprn pgcpnsedkn fprtvmvnln ihnrntntnp

krssdyynrs tspwnlhrne dperypsviw eakcrhlgci

nadgnvdyhm nsvpiqqeil vlrrepphcp nsfrlekilv

svgctcvtpi vhhva
```

Human Soluble IL-18
(SEQ ID NO: 136)
yfgklesklsvirn lndqvlfidq gnrplfedmt dsdcrdnapr
tifiismykd sqprgmavti svkcekistl scenkiisfk
emnppdnikd tksdiiffqr svpghdnkmq fesssyegyf
lacekerdlf klilkkedel gdrsimftvq ned Human Soluble PDGF-DD
(SEQ ID NO: 137)
rdtsatpqsasi kalrnanlrr desnhltdly rrdetiqvkg
ngyvqsprfp nsyprnlllt wrlhsqentr iqlvfdnqfg
leeaendicr ydfvevedis etstiirgrw cghkevppri
ksrtnqikit fksddyfvak pgfkiyysll edfqpaaase
tnwesvtssi sgvsynspsv tdptliadal dkkiaefdtv
edllkyfnpe swqedlenmy ldtpryrgrs yhdrkskvdl
drlnddakry sctprnysvn ireelklanv vffprcllvq
rcggncgcgt vnwrsctens gktvkkyhev lqfepghikr
rgraktmalv diqldhherc dcicssrppr Human Soluble SCF
(SEQ ID NO: 138)
egicrnrvtnnvkdv tklvanlpkd ymitlkyvpg mdvlpshcwi
semvvqlsds ltdlldkfsn iseglsnysi idklvnivdd
lvecvkenss kdlkksfksp eprlftpeef frifnrsida
fkdfvvaset sdcvvsstls pekdsrvsvt kpfmlppvaa
sslrndssss nrkaknppgd sslhwaamal palfsliigf
afgalywkkr qpsltraven iqineednei smlqekeref qev Human Soluble FLT3L
(SEQ ID NO: 139)
tqdcsfqhspissd favkirelsd yllqdypvtv asnlqdeelc
gglwrlvlaq rwmerlktva gskmqgller vnteihfvtk
cafqpppscl rfvqtnisrl lqetseqlva lkpwitrqnf
srclelqcqp dsstlpppws prpleatapt apqppllll
llpvglllla aawclhwqrt rrrtprpgeq vppvpspqdl llveh Non-limiting examples of soluble MICA, MICB, ULBP1, ULBP2, ULBP3, ULBP4, ULBP5, and ULBP6 are provided below.

Human Soluble MICA
(SEQ ID NO: 140)
ephslry nltvlswdgs vqsgfltevh ldgqpflrcd
rqkcrakpqg qwaedvlgnk twdretrdlt gngkdlrmtl
ahikdqkegl hslqeirvce ihednstrss qhfyydgelf
lsqnletkew tmpqssraqt lamnvrnflk edamktkthy
hamhadclqe lrrylksgvv lrrtvppmvn vtrseasegn -continued itvtcrasgf ypwnitlswr qdgvslshdt qqwgdvlpdg
ngtyqtwvat ricqgeeqrf tcymehsgnh sthpvpsgkv
lvlqshwqtf hvsavaaaai fviiifyvrc ckkktsaaeg
pelvslqvld qhpvgtsdhr datqlgfqpl msdlgstgst ega Human Soluble MICB
(SEQ ID NO: 141)
aephslry nlmvlsqdes vqsgflaegh ldgqpflryd
rqkrrakpqg qwaedvlgak twdtetedlt engqdlrrtl
thikdqkggl hslqeirvce ihedsstrgs rhfyydgelf
lsqnletqes tvpqssraqt lamnvtnfwk edamktkthy
ramqadclqk lqrylksgva irrtvppmvn vtcsevsegn
itvtcrassf yprnitltwr qdgvslshnt qqwgdvlpdg
ngtyqtwvat rirqgeeqrf tcymehsgnh gthpvpsgkv
lvlqsqrtdf pyvsaampcf viiiilcvpc ckkktsaaeg
pelvslqvld qhpvgtgdhr daaqlgfqpl msatgstgst ega Human Soluble ULBP1
(SEQ ID NO: 142)
wvdthclcydfiit pksrpepqwc evqglvderp flhydcvnhk
akafaslgkk vnvtktweeq tetlrdvvdf lkgqlldiqv
enlipieplt lqarmscehe ahghgrgswq flingqkfll
fdsnnrkwta lhpgakkmte kweknrdvtm ffqkislgdc
kmwleeflmy weqmldptkp pslapg Human Soluble ULBP2
(SEQ ID NO: 143)
gradphslcyditvi pkfrpgprwc avqgqvdekt flhydcgnkt
vtpvsplgkk lnvttawkaq npvlrevvdi lteqlrdiql
enytpkeplt lqarmsceqk aeghssgswq fsfdgqifll
fdsekrmwtt vhpgarkmke kwendkvvam sfhyfsmgdc
igwledflmg mdstlepsag aplams Human Soluble ULBP3
(SEQ ID NO: 144)
dahslwynfti ihlprhgqqw cevqsqvdqk nflsydcgsd
kvlsmghlee qlyatdawgk qlemlrevgq rlrleladte
ledftpsgpl tlqvrmscec eadgyirgsw qfsfdgrkfl
lfdsnnrkwt vvhagarrmk ekwekdsglt tffkmvsmrd
ckswirdflm hrkkrlepta pptmapg Human Soluble ULBP4
(SEQ ID NO: 145)
hslcfnftik slsrpgqpwc eaqvflnknl flqynsdnnm
vkplgllgkk vyatstwgel tqtlgevgrd lrmllcdikp -continued

```
qiktsdpstl qvemfcqrea erctgaswqf atngeksllf

damnmtwtvi nheaskiket wkkdrgleky frklskgdcd

hwlreflghw eampeptvsp vnasdihwss sslpdrwiil

gafillvlmg ivlicvwwqn gewqaglwpl rts
```

Human Soluble ULBP5

(SEQ ID NO: 146)

```
gladp hslcyditvi pkfrpgprwc avqgqvdekt

flhydcgskt vtpvsplgkk lnvttawkaq npvlrevvdi

lteqlldiql enyipkeplt lqarmsceqk aeghgsgswq

lsfdgqifll fdsenrmwtt vhpgarkmke kwendkdmtm

sfhyismgdc tgwledflmg mdstlepsag apptmssg
```

Human Soluble ULBP6

(SEQ ID NO: 147)

```
rrddp hslcyditvi pkfrpgprwc avqgqvdekt flhydcgnkt

vtpvsplgkk lnvtmawkaq npvlrevvdi lteqlldiql

enytpkeplt lqarmsceqk aeghssgswq fsidgqtfll

fdsekrmwtt vhpgarkmke kwendkdvam sfhyismgdc

igwledflmg mdstlepsag aplamssg
```

Additional examples of soluble interleukin proteins and soluble cytokine proteins are known in the art.

Soluble Receptor

In some embodiments of any of the single- or multi-chain chimeric polypeptides described herein, one or both of the first target-binding domain and the second target-binding domain is a soluble interleukin receptor, a soluble cytokine receptor or a ligand receptor. In some embodiments, the soluble receptor is a soluble TGF-β receptor II (TGF-β RII) (see, e.g., those described in Yung et al., Am. J. Resp. Crit. Care Med. 194(9):1140-1151, 2016), a soluble TGF-βRIII (see, e.g., those described in Heng et al., Placenta 57:320, 2017), a soluble NKG2D (see, e.g., Cosman et al., Immunity 14(2):123-133, 2001; Costa et al., Front. Immunol., Vol. 9, Article 1150 May 29, 2018; doi: 10.3389/fimmu.2018.01150), a soluble NKp30 (see, e.g., Costa et al., Front. Immunol., Vol. 9, Article 1150 May 29, 2018; doi: 10.3389/fimmu.2018.01150), a soluble NKp44 (see, e.g., those described in Costa et al., Front. Immunol., Vol. 9, Article 1150 May 29, 2018; doi: 10.3389/fimmu.2018.01150), a soluble NKp46 (see, e.g., Mandelboim et al., Nature 409:1055-1060, 2001; Costa et al., Front. Immunol., Vol. 9, Article 1150 May 29, 2018; doi: 10.3389/fimmu.2018.01150), a soluble DNAM-1 (see, e.g., those described in Costa et al., Front. Immunol., Vol. 9, Article 1150 May 29, 2018; doi: 10.3389/fimmu.2018.01150), a scMHCI (see, e.g., those described in Washburn et al., PLOS One 6 (3): e18439, 2011), a scMHCII (see, e.g., those described in Bishwajit et al., Cellular Immunol. 170 (1): 25-33, 1996), a scTCR (see, e.g., those described in Weber et al., Nature 356 (6372): 793-796, 1992), a soluble CD155 (see, e.g., those described in Tahara-Hanaoka et al., Int. Immunol. 16 (4): 533-538, 2004), or a soluble CD28 (see, e.g., Hebbar et al., Clin. Exp. Immunol. 136:388-392, 2004).

Additional examples of soluble interleukin receptors and soluble cytokine receptors are known in the art.

Additional Antigen-Binding Domains

In some embodiments of any of the single- or multi-chain chimeric polypeptides, the first chimeric polypeptide further includes one or more (e.g., two, three, four, five, six, seven, eight, nine, or ten) additional target-binding domain(s) (e.g., any of the exemplary target-binding domains described herein or known in the art). In some embodiments of any of the multi-chain chimeric polypeptides, at least one of the one or more additional antigen-binding domain(s) can be positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein). In some embodiments, the first chimeric polypeptide can further include a linker sequence (e.g., any of the exemplary linker sequences described herein or known in the art) between the soluble tissue factor domain (e.g., any of the exemplary soluble tissue factor domains described herein) and the at least one of the one or more additional target-binding domain(s) (e.g., any of the exemplary target-binding domains described herein or known in the art), and/or a linker sequence (e.g., any of the exemplary linker sequences described herein or known in the art) between the at least one of the one or more additional target-binding domain(s) (e.g., any of the exemplary target-binding domains described herein or known in the art) and the first domain of the pair of affinity domains (e.g., any of the exemplary first domains described herein of any of the exemplary pairs of affinity domains described herein).

In some embodiments of any of the multi-chain chimeric polypeptides described herein, the first chimeric polypeptide further includes one or more (e.g., two, three, four, five, six, seven, eight, nine, or ten) additional target-binding domains at the N-terminal and/or C-terminal end of the first chimeric polypeptide. In some embodiments, at least one of the one or more additional target-binding domains (e.g., any of the exemplary target-binding domains described herein or known in the art) directly abuts the first domain of the pair of affinity domains (e.g., any of the exemplary first domains described herein of any of the exemplary pairs of affinity domains described herein) in the first chimeric polypeptide. In some embodiments, the first chimeric polypeptide further includes a linker sequence (e.g., any of the exemplary linker sequences described herein or known in the art) between the at least one of the one or more additional target-binding domains (e.g., any of the exemplary target-binding domains described herein or known in the art) and the first domain of the pair of affinity domains (e.g., any of the exemplary first domains described herein of any of the exemplary pairs of affinity domains described herein). In some embodiments, the at least one of the one or more additional target-binding domains (e.g., any of the exemplary target-binding domains described herein or known in the art) directly abuts the first target-binding domain (e.g., any of the exemplary target-binding domains described herein or known in the art) in the first chimeric polypeptide. In some embodiments, the first chimeric polypeptide further comprises a linker sequence (e.g., any of the exemplary linker sequences described herein or known in the art) between the at least one of the one or more additional target-binding domains (e.g., any of the exemplary target-binding domains described herein or known in the art) and the first target-binding domain (e.g., any of the exemplary target-binding domains described herein or known in the art).

In some embodiments of any of the multi-chain chimeric polypeptides described herein, at least one of the one or more additional target-binding domains (e.g., any of the exemplary target-binding domains described herein or known in the art) is disposed at the N- and/or C-terminus of the first chimeric polypeptide, and at least one of the one or more additional target-binding domains (e.g., any of the exemplary target-binding domains described herein or known in the art) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the N-terminus directly abuts the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the first chimeric polypeptide further comprises a linker sequence (e.g., any of the linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the C-terminus directly abuts the first target-binding domain (e.g., any of the exemplary target-binding domains described herein or known in the art) or the first domain of the pair of affinity domains (e.g., any of the exemplary first domains of any of the exemplary pairs of affinity domains described herein) in the first chimeric polypeptide. In some embodiments, the first chimeric polypeptide further includes a linker sequence (e.g., any of the exemplary linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the first domains described herein or any of the exemplary pairs of affinity domains described herein), directly abuts the soluble tissue factor domain and/or the first domain of the pair of affinity domains. In some embodiments, the first chimeric polypeptide further comprises a linker sequence (e.g., any of the exemplary linker sequences described herein or known in the art) disposed (i) between the soluble tissue factor domain (e.g., any of the exemplary soluble tissue factor domains described herein) and the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the exemplary first domains of any of the exemplary pairs of affinity domains described herein), and/or (ii) between the first domain of the pair of affinity domains and the at least one of the one or more additional target-binding domains positioned between the soluble tissue factor domain and the first domain of the pair of affinity domains.

In some embodiments of any of the multi-chain chimeric polypeptides described herein, the second chimeric polypeptide further includes one or more (e.g., two, three, four, five, six, seven, eight, nine, or ten) additional target-binding domains (e.g., any of the exemplary target-binding domains described herein or known in the art) at the N-terminal end and/or the C-terminal end of the second chimeric polypeptide. In some embodiments, at least one of the one or more additional target-binding domains (e.g., any of the exemplary target-binding domains described herein or known in the art) directly abuts the second domain of the pair of affinity domains (e.g., any of the exemplary second domains of any of the exemplary pairs of affinity domains described herein) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target-binding domains described herein or known in the art) and the second domain of the pair of affinity domains (e.g., any of the second domains described herein of any of the exemplary pairs of affinity domains described herein) in the second chimeric polypeptide. In some embodiments, at least one of the one or more additional target-binding domains (e.g., any of the exemplary target-binding domains described herein or known in the art) directly abuts the second target-binding domain (e.g., any of the target-binding domains described herein or known in the art) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target binding domains described herein or known in the art) and the second target-binding domain (e.g., any of the exemplary target binding domains described herein or known in the art) in the second chimeric polypeptide.

In some embodiments of any of the multi-chain chimeric polypeptides described herein, two or more (e.g., three or more, four or more, five or more, six or more, seven or more, eight or more, nine or more, or ten or more) of the first target-binding domain, the second target-binding domain, and the one or more additional target-binding domains bind specifically to the same antigen. In some embodiments, two or more (e.g., three or more, four or more, five or more, six or more, seven or more, eight or more, nine or more, or ten or more) of the first target-binding domain, the second target-binding domain, and the one or more additional target-binding domains bind specifically to the same epitope. In some embodiments, two or more (e.g., three or more, four or more, five or more, six or more, seven or more, eight or more, nine or more, or ten or more) of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence.

In some embodiments of any of the multi-chain chimeric polypeptides described herein, the first target-binding domain, the second target-binding domain, and the one or more additional target-binding domains bind specifically to different antigens. In some embodiments of any of the multi-chain chimeric polypeptides described herein, one or more (e.g., two or more, three or more, four or more, five or more, six or more, seven or more, eight or more, nine or more, or ten or more) of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain (e.g., a scFv or a single-domain antibody).

Pairs of Affinity Domains

In some embodiments, a multi-chain chimeric polypeptide includes: 1) a first chimeric polypeptide that includes a first domain of a pair of affinity domains, and 2) a second chimeric polypeptide that includes a second domain of a pair of affinity domains such that the first chimeric polypeptide and the second chimeric polypeptide associate through the binding of the first domain and the second domain of the pair of affinity domains. In some embodiments, the pair of affinity domains is a sushi domain from an alpha chain of human IL-15 receptor (IL15Rα) and a soluble IL-15. A sushi domain, also known as a short consensus repeat or type 1 glycoprotein motif, is a common motif in protein-protein interaction. Sushi domains have been identified on a number of protein-binding molecules, including complement components C1r, C1s, factor H, and C2m, as well as the nonimmunologic molecules factor XIII and B2-glycoprotein. A typical Sushi domain has approximately 60 amino acid residues and contains four cysteines (Ranganathan, Pac. Symp Biocomput. 2000:155-67). The first cysteine can form a disulfide bond with the third cysteine, and the second cysteine can form a disulfide bridge with the fourth cysteine. In some embodiments in which one member of the pair of affinity domains is a soluble IL-15, the soluble IL 15 has a D8N or D8A amino acid substitution. In some embodiments in which one member of the pair of affinity domains is an alpha chain of human IL-15 receptor (IL15Rα), the human IL15Rα is a mature full-length IL15Rα. In some embodiments, the pair of affinity domains is barnase and barnstar. In some embodiments, the pair of affinity domains is a PKA and an AKAP. In some embodiments, the pair of affinity domains is an adapter/docking tag module based on mutated RNase I fragments (Rossi, Proc Natl Acad Sci USA. 103: 6841-6846, 2006; Sharkey et al., Cancer Res. 68:5282-5290, 2008; Rossi et al., Trends Pharmacol Sci. 33:474-481, 2012) or SNARE modules based on interactions of the proteins syntaxin, synaptotagmin, synaptobrevin, and SNAP25 (Deyev et al., Nat Biotechnol. 1486-1492, 2003).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains and the second domain of the pair of affinity domains bind to each other with a dissociation equilibrium constant ($K_D$) of less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In some embodiments, the first domain of the pair of affinity domains and the second domain of the pair of affinity domains bind to each other with a $K_D$ of about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, about $1\times10^{-9}$ M to about $1\times10^{-11}$ M, about $1\times10^{-10}$ M to about $1\times10^{-12}$ M, about $1\times10^{-11}$ M to about $1\times10^{-13}$ M, about $1\times10^{-4}$ M to about $1\times10^{-5}$ M, about $1\times10^{-5}$ M to about $1\times10^{-6}$ M, about $1\times10^{-6}$ M to about $1\times10^{-7}$ M, about $1\times10^{-7}$ M to about $1\times10^{-8}$ M, about $1\times10^{-8}$ M to about $1\times10^{-9}$ M, about $1\times10^{-9}$ M to about $1\times10^{-10}$ M, about $1\times10^{-10}$ M to about $1\times10^{-11}$ M, about $1\times10^{-11}$ M to about $1\times10^{-12}$ M, or about $1\times10^{-12}$ M to about $1\times10^{-13}$ M (inclusive). Any of a variety of different methods known in the art can be used to determine the $K_D$ value of the binding of the first domain of the pair of affinity domains and the second domain of the pair of affinity domains (e.g., an electrophoretic mobility shift assay, a filter binding assay, surface plasmon resonance, and a biomolecular binding kinetics assay, etc.).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains, the second domain of the pair of affinity domains, or both is about 10 to 100 amino acids in length. For example, a first domain of a pair of affinity domains, a second domain of a pair of affinity domains, or both can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a first domain of a pair of affinity domains, a second domain of a pair of affinity domains, or both is about 10, 15, 20, 25, 30, 35, 40, 45, 50, 55, 60, 65, 70, 75, 80, 85, 90, 95, or 100 amino acids in length.

In some embodiments, any of the first and/or second domains of a pair of affinity domains disclosed herein can include one or more additional amino acids (e.g., 1, 2, 3, 5, 6, 7, 8, 9, 10, or more amino acids) at its N-terminus and/or C-terminus, so long as the function of the first and/or second domains of a pair of affinity domains remains intact. For example, a sushi domain from an alpha chain of human IL-15 receptor (IL15Rα) can include one or more additional amino acids at the N-terminus and/or the C-terminus, while still retaining the ability to bind to a soluble IL-15. Additionally or alternatively, a soluble IL-15 can include one or more additional amino acids at the N-terminus and/or the C-terminus, while still retaining the ability to bind to a sushi domain from an alpha chain of human IL-15 receptor (IL15Rα).

A non-limiting example of a sushi domain from an alpha chain of IL-15 receptor alpha (IL15Rα) can include a sequence that is at least 70% identical, at least 75% identical, at least 80% identical, at least 85% identical, at least 90% identical, at least 95% identical, at least 99% identical, or 100% identical to ITCPPPMSVEHADIWVKSYSLYSRERYICNSGFKRKAGTSSLTECVLNKATNVAH WTTPSLKCIR (SEQ ID NO: 148). In some embodiments, a sushi domain from an alpha chain of IL15Rα can be encoded by a nucleic acid including

```
                                        (SEQ ID NO: 149)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG.
```

In some embodiments, a soluble IL-15 can include a sequence that is at least 70% identical, at least 75% identical, at least 80% identical, at least 85% identical, at least 90% identical, at least 95% identical, at least 99% identical, or 100% identical to

```
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINT
```

S (SEQ ID NO: 134). In some embodiments, a soluble IL-15 can be encoded by a nucleic acid including the sequence of

```
                                        (SEQ ID NO: 150)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT
```

-continued

```
TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC.
```

Signal Sequence

In some embodiments, a multi-chain chimeric polypeptide includes a first chimeric polypeptide that includes a signal sequence at its N-terminal end. In some embodiments, a multi-chain chimeric polypeptide includes a second chimeric polypeptide that includes a signal sequence at its N-terminal end. In some embodiments, both the first chimeric polypeptide of a multi-chain chimeric polypeptide and a second chimeric polypeptide of the multi-chain chimeric polypeptide include a signal sequence. As will be understood by those of ordinary skill in the art, a signal sequence is an amino acid sequence that is present at the N-terminus of a number of endogenously produced proteins that directs the protein to the secretory pathway (e.g., the protein is directed to reside in certain intracellular organelles, to reside in the cell membrane, or to be secreted from the cell). Signal sequences are heterogeneous and differ greatly in their primary amino acid sequences. However, signal sequences are typically 16 to 30 amino acids in length and include a hydrophilic, usually positively charged N-terminal region, a central hydrophobic domain, and a C-terminal region that contains the cleavage site for signal peptidase.

In some embodiments, a first chimeric polypeptide of a multi-chain chimeric polypeptide, a second chimeric polypeptide of the multi-chain chimeric polypeptide, or both includes a signal sequence having an amino acid sequence MKWVTFISLLFLFSSAYS (SEQ ID NO: 151). In some embodiments, a first chimeric polypeptide of a multi-chain chimeric polypeptide, a second chimeric polypeptide of the multi-chain chimeric polypeptide, or both includes a signal sequence encoded by the nucleic acid sequence:

```
                                        (SEQ ID NO: 152)
ATGAAATGGGTGACCTTTATTTCTTTACTGTTCCTCTTTAGCAGCGCCT
ACTCC,

                                        (SEQ ID NO: 153)
ATGAAGTGGGTCACATTTATCTCTTTACTGTTCCTCTTCTCCAGCGCCT
ACAGC, or

                                        (SEQ ID NO: 154)
ATGAAATGGGTGACCTTTATTTCTTTACTGTTCCTCTTTAGCAGCGCCT
ACTCC.
```

In some embodiments, a first chimeric polypeptide of a multi-chain chimeric polypeptide, a second chimeric polypeptide of the multi-chain chimeric polypeptide, or both includes a signal sequence having an amino acid sequence MKCLLYLAFLFLGVNC (SEQ ID NO: 155). In some embodiments, a first chimeric polypeptide of a multi-chain chimeric polypeptide, a second chimeric polypeptide of the multi-chain chimeric polypeptide, or both includes a signal sequence having an amino acid sequence MGQIVTMFEALPHIIDEVINIVIIVLIIITSIKAVYNFATCGILALVSFLFLAGRSCG (SEQ ID NO: 156). In some embodiments, a first chimeric polypeptide of a multi-chain chimeric polypeptide, a second chimeric polypeptide of the multi-chain chimeric polypeptide, or both includes a signal sequence having an amino acid sequence (SEQ ID NO: 157)
MPNHQSGSPTGSSDLLLSGKKQRPHLALRRKRRREMRKINRKVRRMNLA
PIKEKTAWOHLQALISEAEEVLKTSQTPQNSLTLFLALLSVLGPPVTG.

In some embodiments, a first chimeric polypeptide of a multi-chain chimeric polypeptide, a second chimeric polypeptide of the multi-chain chimeric polypeptide, or both includes a signal sequence having an amino acid sequence MDSKGSSQKGSRLLLLLVVSNLLLCQGVVS (SEQ ID NO: 158). Those of ordinary skill in the art will be aware of other appropriate signal sequences for use in a first chimeric polypeptide and/or a second chimeric polypeptide of multi-chain chimeric polypeptides described herein.

In some embodiments, a first chimeric polypeptide of a multi-chain chimeric polypeptide, a second chimeric polypeptide of the multi-chain chimeric polypeptide, or both includes a signal sequence that is about 10 to 100 amino acids in length. For example, a signal sequence can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a signal sequence is about 10, 15, 20, 25, 30, 35, 40, 45, 50, 55, 60, 65, 70, 75, 80, 85, 90, 95, or 100 amino acids in length.

In some embodiments, any of the signal sequences disclosed herein can include one or more additional amino acids (e.g., 1, 2, 3, 5, 6, 7, 8, 9, 10, or more amino acids) at its N-terminus and/or C-terminus, so long as the function of the signal sequence remains intact. For example, a signal sequence having the amino acid sequence MKCLLYLAFLFLGVNC (SEQ ID NO: 155) can include one or more additional amino acids at the N-terminus or C-terminus, while still retaining the ability to direct a first chimeric polypeptide of a multi-chain chimeric polypeptide, a second chimeric polypeptide of the multi-chain chimeric polypeptide, or both to the secretory pathway.

In some embodiments, a first chimeric polypeptide of a multi-chain chimeric polypeptide, a second chimeric polypeptide of the multi-chain chimeric polypeptide, or both includes a signal sequence that directs the multi-chain chimeric polypeptide into the extracellular space. Such embodiments are useful in producing multi-chain chimeric polypeptides that are relatively easy to be isolated and/or purified.

Peptide Tags

In some embodiments, a multi-chain chimeric polypeptide includes a first chimeric polypeptide that includes a peptide tag (e.g., at the N-terminal end or the C-terminal end of the first chimeric polypeptide). In some embodiments, a multi-chain chimeric polypeptide includes a second chimeric polypeptide that includes a peptide tag (e.g., at the N-terminal end or the C-terminal end of the second chimeric polypeptide). In some embodiments, both the first chimeric polypeptide of a multi-chain chimeric polypeptide and a second chimeric polypeptide of the multi-chain chimeric polypeptide include a peptide tag. In some embodiments, a first chimeric polypeptide of a multi-chain chimeric polypeptide, a second chimeric polypeptide of the multi-chain chimeric polypeptide, or both include two or more peptide tags.

Exemplary peptide tags that can be included in a first chimeric polypeptide of a multi-chain chimeric polypeptide, a second chimeric polypeptide of the multi-chain chimeric polypeptide, or both include, without limitation, AviTag (GLNDIFEAQKIEWHE; SEQ ID NO: 159), a calmodulin-tag (KRRWKKNFIAVSAANRFKKISSSGAL; SEQ ID NO: 160), a polyglutamate tag (EEEEEE; SEQ ID NO: 161), an E-tag (GAPVPYPDPLEPR; SEQ ID NO: 162), a FLAG-tag (DYKDDDDK; SEQ ID NO: 163), an HA-tag, a peptide from hemagglutinin (YPYDVPDYA; SEQ ID NO: 164), a his-tag (HHHHH (SEQ ID NO: 165); HHHHHH (SEQ ID NO: 166); HHHHHHH (SEQ ID NO: 167); HHHHHHHH (SEQ ID NO: 168); HHHHHHHHH (SEQ ID NO: 169); or HHHHHHHHHH (SEQ ID NO: 170), a myc-tag (EQKLISEEDL; SEQ ID NO: 171), NE-tag (TKENPRSNQEESYDDNES; SEQ ID NO: 172), S-tag, (KETAAAKFERQHMDS; SEQ ID NO: 173), SBP-tag (MDEKTTGWRGGHVVEGLAGELEQLRARLEHHPQGQREP; SEQ ID NO: 174), Softag 1 (SLAELLNAGLGGS; SEQ ID NO: 175), Softag 3 (TQDPSRVG; SEQ ID NO: 176), Spot-tag (PDRVRAVSHWSS; SEQ ID NO: 177), Strep-tag (WSHPQFEK; SEQ ID NO: 178), TC tag (CCPGCC; SEQ ID NO: 179), Ty tag (EVHTNQDPLD; SEQ ID NO: 180), V5 tag (GKPIPNPLLGLDST; SEQ ID NO: 181), VSV-tag (YTDIEMNRLGK; SEQ ID NO: 182), and Xpress tag (DLYDDDDK; SEQ ID NO: 183). In some embodiments, tissue factor protein is a peptide tag.

Peptide tags that can be included in a first chimeric polypeptide of a multi-chain chimeric polypeptide, a second chimeric polypeptide of the multi-chain chimeric polypeptide, or both can be used in any of a variety of applications related to the multi-chain chimeric polypeptide. For example, a peptide tag can be used in the purification of a multi-chain chimeric polypeptide. As one non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both can include a myc tag; the multi-chain chimeric polypeptide that includes the myc-tagged first chimeric polypeptide, the myc-tagged second chimeric polypeptide, or both can be purified using an antibody that recognizes the myc tag(s). One non-limiting example of an antibody that recognizes a myc tag is 9E10, available from the non-commercial Developmental Studies Hybridoma Bank. As another non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both can include a histidine tag; the multi-chain chimeric polypeptide that includes the histidine-tagged first chimeric polypeptide, the histidine-tagged second chimeric polypeptide, or both can be purified using a nickel or cobalt chelate. Those of ordinary skill in the art will be aware of other suitable tags and agent that bind those tags for use in purifying multi-chain chimeric polypeptide. In some embodiments, a peptide tag is removed from the first chimeric polypeptide and/or the second chimeric polypeptide of the multi-chain chimeric polypeptide after purification. In some embodiments, a peptide tag is not removed from the first chimeric polypeptide and/or the second chimeric polypeptide of the multi-chain chimeric polypeptide after purification.

Peptide tags that can be included in a first chimeric polypeptide of a multi-chain chimeric polypeptide, a second chimeric polypeptide of the multi-chain chimeric polypeptide, or both can be used, for example, in immunoprecipitation of the multi-chain chimeric polypeptide, imaging of the multi-chain chimeric polypeptide (e.g., via Western blotting, ELISA, flow cytometry, and/or immunocytochemistry), and/or solubilization of the multi-chain chimeric polypeptide.

In some embodiments, a first chimeric polypeptide of a multi-chain chimeric polypeptide, a second chimeric polypeptide of the multi-chain chimeric polypeptide, or both includes a peptide tag that is about 10 to 100 amino acids in length. For example, a peptide tag can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a peptide tag is about 10, 15, 20, 25, 30, 35, 40, 45, 50, 55, 60, 65, 70, 75, 80, 85, 90, 95, or 100 amino acids in length.

Peptide tags included in a first chimeric polypeptide of a multi-chain chimeric polypeptide, a second chimeric polypeptide of the multi-chain chimeric polypeptide, or both can be of any suitable length. For example, peptide tags can be 5, 6, 7, 8, 9, 10, 11, 12, 13, 14, 15, 16, 17, 18, 19, 20, or more amino acids in length. In embodiments in which a multi-chain chimeric polypeptide includes two or more peptide tags, the two or more peptide tags can be of the same or different lengths. In some embodiments, any of the peptide tags disclosed herein may include one or more additional amino acids (e.g., 1, 2, 3, 5, 6, 7, 8, 9, 10, or more amino acids) at the N-terminus and/or C-terminus, so long as the function of the peptide tag remains intact. For example, a myc tag having the amino acid sequence EQKLISEEDL (SEQ ID NO: 171) can include one or more additional amino acids (e.g., at the N-terminus and/or the C-terminus of the peptide tag), while still retaining the ability to be bound by an antibody (e.g., 9E10).

Exemplary Multi-Chain Chimeric Polypeptides-Type A

In some embodiments of any of the multi-chain chimeric polypeptides described herein, the first target-binding domain and the second targeting-binding domain each independently bind specifically to a receptor of IL-18 or a receptor of IL-12. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is an agonistic antigen-binding domain. In some embodiments of these multi-chain chimeric polypeptides, the first target-binding domain and the second target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12.

In some embodiments of these multi-chain chimeric polypeptides, the first target-binding domain includes a soluble IL-18 (e.g., a soluble human IL-18).

In some embodiments of these multi-chain chimeric polypeptides, the soluble human IL-18 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 136)
YFGKLESKLSVIRNLNDQVLFIDQGNRPLFEDMTDSDCRDNAPRTIFII
SMYKDSQPRGMAVTISVKCEKISTLSCENKIISFKEMNPPDNIKDTKSD
IIFFQRSVPGHDNKMQFESSSYEGYFLACEKERDLFKLILKKEDELGDR
SIMFTVQNED.

In some embodiments of these multi-chain chimeric polypeptides, the soluble human IL-18 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
TACTTCGGCAAACTGGAATCCAAGCTGAGCGTGATCCGGAATTTAAACG
ACCAAGTTCTGTTTATCGATCAAGGTAACCGGCCTCTGTTCGAGGACAT
GACCGACTCCGATTGCCGGGACAATGCCCCCCGGACCATCTTCATTATC
TCCATGTACAAGGACAGCCAGCCCCGGGGCATGGCTGTGACAATTAGCG
TGAAGTGTGAGAAAATCAGCACTTTATCTTGTGAGAACAAGATCATCTC
CTTTAAGGAAATGAACCCCCCCGATAACATCAAGGACACCAAGTCCGAT
ATCATCTTCTTCCAGCGGTCCGTGCCCGGTCACGATAACAAGATGCAGT
TCGAATCCTCCTCCTACGAGGGCTACTTTTTAGCTTGTGAAAAGGAGAG
GGATTTATTCAAGCTGATCCTCAAGAAGGAGGACGAGCTGGGCGATCGT
TCCATCATGTTCACCGTCCAAAACGAGGAT.

In some embodiments of these multi-chain chimeric polypeptides, the second target-binding domain includes a soluble IL-12 (e.g., a soluble human IL-12). In some embodiments of these multi-chain chimeric polypeptides, the soluble human IL-15 includes a sequence of soluble human IL-12β (p40) and a sequence of soluble human IL-12α (p35). In some embodiments of these multi-chain chimeric polypeptides, the soluble IL-15 human IL-15 further includes a linker sequence (e.g., any of the exemplary linker sequences described herein) between the sequence of soluble IL-12β (p40) and the sequence of soluble human IL-12α (p35). In some examples of these multi-chain chimeric polypeptides, the linker sequence comprises GGGGSGGGGSGGGGS (SEQ ID NO: 126).

In some embodiments of these multi-chain chimeric polypeptides, the sequence of soluble human IL-12β (p40) comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)
IWELKKDVYVVELDWYPDAPGEMVVLTCDTPEEDGITWTLDQSSEVLGS
GKTLTIQVKEFGDAGQYTCHKGGEVLSHSLLLLHKKEDGIWSTDILKDQ
KEPKNKTFLRCEAKNYSGRFTCWWLTTISTDLTFSVKSSRGSSDPQGVT
CGAATLSAERVRGDNKEYEYSVECQEDSACPAAEESLPIEVMVDAVHKL
KYENYTSSFFIRDIIKPDPPKNLQLKPLKNSRQVEVSWEYPDTWSTPHS
YFSLTFCVQVQGKSKREKKDRVFTDKTSATVICRKNASISVRAQDRYYS
SSWSEWASVPCS.

In some embodiments of these multi-chain chimeric polypeptides, the soluble human IL-12β (p40) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)
ATTTGGGAACTGAAGAAGGACGTCTACGTGGTCGAACTGGACTGGTATC
CCGATGCTCCCGGCGAAATGGTGGTGCTCACTTGTGACACCCCCGAAGA
AGACGGCATCACTTGGACCCTCGATCAGAGCAGCGAGGTGCTGGGCTCC
GGAAAGACCCTCACAATCCAAGTTAAGGAGTTCGGAGACGCTGGCCAAT
ACACATGCCACAAGGGAGGCGAGGTGCTCAGCCATTCCTTATTATTATT
ACACAAGAAGGAAGACGGAATCTGGTCCACCGACATTTTAAAAGATCAG
AAGGAGCCCAAGAATAAGACCTTTTTAAGGTGTGAGGCCAAAAACTACA
GCGGTCGTTTCACTTGTTGGTGGCTGACCACCATTTCCACCGATTTAAC
CTTCTCCGTGAAAAGCAGCCGGGGAAGCTCCGACCCTCAAGGTGTGACA
TGTGGAGCCGCTACCCTCAGCGCTGAGAGGGTTCGTGGCGATAACAAGG
AATACGAGTACAGCGTGGAGTGCCAAGAAGATAGCGCTTGTCCCGCTGC
CGAAGAATCTTTACCCATTGAGGTGATGGTGGACGCCGTGCACAAACTC
AAGTACGAGAACTACACCTCCTCCTTCTTTATCCGGGACATCATTAAGC
CCGATCCTCCTAAGAATTTACAGCTGAAGCCTCTCAAAAATAGCCGGCA
AGTTGAGGTCTCTTGGGAATATCCCGACACTTGGAGCACACCCCACAGC
TACTTCTCTTTAACCTTTTGTGTGCAAGTTCAAGGTAAAAGCAAGCGGG
AGAAGAAAGACCGGGTGTTTACCGACAAAACCAGCGCCACCGTCATCTG

-continued

TCGGAAGAACGCCTCCATCAGCGTGAGGGCTCAAGATCGTTATTACTCC

AGCAGCTGGTCCGAGTGGGCCAGCGTGCCTTGTTCC.

In some embodiments of these multi-chain chimeric polypeptides, the soluble human IL-12α (p35) includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)
RNLPVATPDPGMFPCLHHSQNLLRAVSNMLQKARQTLEFYPCTSEEIDH

EDITKDKTSTVEACLPLELTKNESCLNSRETSFITNGSCLASRKTSFMM

ALCLSSIYEDLKMYQVEFKTMNAKLLMDPKRQIFLDQNMLAVIDELMQA

LNFNSETVPQKSSLEEPDFYKTKIKLCILLHAFRIRAVTIDRVMSYLNA

S.

In some embodiments of these multi-chain chimeric polypeptides, the soluble human IL-12α (p35) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 189)
CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC

CCGATTTTTACAAGACAAAGATCAAACTGTGCATTTTACTCCACGCCTT

TAGGATCCGGGCCGTGACCATTGACCGGGTCATGAGCTATTTAAACGCC

AGC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 190)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNEDSGTTNTVAAYNLTWKSTNFKTILEWEPKPVNQVYTVQIS

TKSGDWKSKCFYTTDTECDLTDEIVKDVKQTYLARVFSYPAGNVESTGS

AGEPLYENSPEFTPYLETNLGQPTIQSFEQVGTKVNVTVEDERTLVRRN

NTFLSLRDVFGKDLIYTLYYWKSSSSGKKTAKTNTNEFLIDVDKGENYC

FSVQAVIPSRTVNRKSTDSPVECMGQEKGEFRENWVNVISDLKKIEDLI

QSMHIDATLYTESDVHPSCKVTAMKCFLLELQVISLESGDASIHDTVEN

LIILANNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or (SEQ ID NO: 191)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGATAGCGGCACAACCAACACAG

TCGCTGCCTATAACCTCACTTGGAAGAGCACCAACTTCAAAACCATCCT

CGAATGGGAACCCAAACCCGTTAACCAAGTTTACACCGTGCAGATCAGC

ACCAAGTCCGGCGACTGGAAGTCCAAATGTTTCTATACCACCGACACCG

AGTGCGATCTCACCGATGAGATCGTGAAAGATGTGAAACAGACCTACCT

CGCCCGGGTGTTTAGCTACCCCGCCGGCAATGTGGAGAGCACTGGTTCC

GCTGGCGAGCCTTTATACGAGAACAGCCCCGAATTTACCCCTTACCTCG

AGACCAATTTAGGACAGCCCACCATCCAAAGCTTTGAGCAAGTTGGCAC

AAAGGTGAATGTGACAGTGGAGGACGAGCGGACTTTAGTGCGGCGGAAC

AACACCTTTCTCAGCCTCCGGGATGTGTTCGGCAAAGATTTAATCTACA

CACTGTATTACTGGAAGTCCTCTTCCTCCGGCAAGAAGACAGCTAAAAC

CAACACAAACGAGTTTTTAATCGACGTGGATAAAGGCGAAAACTACTGT

TTCAGCGTGCAAGCTGTGATCCCCTCCCGGACCGTGAATAGGAAAAGCA

CCGATAGCCCCGTTGAGTGCATGGGCCAAGAAAAGGGCGAGTTCCGGGA

GAACTGGGTGAACGTCATCAGCGATTTAAAGAAGATCGAAGATTTAATT

CAGTCCATGCATATCGACGCCACTTTATACACAGAATCCGACGTGCACC

-continued

```
CCTCTTGTAAGGTGACCGCCATGAAATGTTTTTACTGGAGCTGCAAGT

TATCTCTTTAGAGAGCGGAGACGCTAGCATCCACGACACCGTGGAGAAT

TTAATCATTTTAGCCAATAACTCTTTATCCAGCAACGGCAACGTGACAG

AGTCCGGCTGCAAGGAGTGCGAAGAGCTGGAGGAGAAGAACATCAAGGA

GTTTCTGCAATCCTTTGTGCACATTGTCCAGATGTTCATCAATACCTCC.
```

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or

```
                                        (SEQ ID NO: 192)
MKWVTFISLLFLFSSAYSYFGKLESKLSVIRNLNDQVLFIDQGNRPLFE

DMTDSDCRDNAPRTIFIISMYKDSQPRGMAVTISVKCEKISTLSCENKI

ISFKEMNPPDNIKDTKSDIIFFQRSVPGHDNKMQFESSSYEGYFLACEK

ERDLFKLILKKEDELGDRSIMFTVQNEDSGTTNTVAAYNLTWKSTNFKT

ILEWEPKPVNQVYTVQISTKSGDWKSKCFYTTDTECDLTDEIVKDVKQT

YLARVFSYPAGNVESTGSAGEPLYENSPEFTPYLETNLGQPTIQSFEQV

GTKVNVTVEDERTLVRRNNTFLSLRDVFGKDLIYTLYYWKSSSSGKKTA

KTNTNEFLIDVDKGENYCFSVQAVIPSRTVNRKSTDSPVECMGQEKGEF

RENWVNVISDLKKIEDLIQSMHIDATLYTESDVHPSCKVTAMKCFLLEL

QVISLESGDASIHDTVENLIILANNSLSSNGNVTESGCKECEELEEKNI

KEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 193)
ATGAAGTGGGTCACATTTATCTCTTTACTGTTCCTCTTCTCCAGCGCCT

ACAGCTACTTCGGCAAACTGGAATCCAAGCTGAGCGTGATCCGGAATTT

AAACGACCAAGTTCTGTTTATCGATCAAGGTAACCGGCCTCTGTTCGAG

GACATGACCGACTCCGATTGCCGGGACAATGCCCCCCGGACCATCTTCA

TTATCTCCATGTACAAGGACAGCCAGCCCCGGGGCATGGCTGTGACAAT

TAGCGTGAAGTGTGAGAAAATCAGCACTTTATCTTGTGAGAACAAGATC

ATCTCCTTTAAGGAAATGAACCCCCCCGATAACATCAAGGACACCAAGT

CCGATATCATCTTCTTCCAGCGGTCCGTGCCCGGTCACGATAACAAGAT

GCAGTTCGAATCCTCCTCCTACGAGGGCTACTTTTTAGCTTGTGAAAAG

GAGAGGGATTTATTCAAGCTGATCCTCAAGAAGGAGGACGAGCTGGGCG

ATCGTTCCATCATGTTCACCGTCCAAAACGAGGATAGCGGCACAACCAA

CACAGTCGCTGCCTATAACCTCACTTGGAAGAGCACCAACTTCAAAACC

ATCCTCGAATGGGAACCCAAACCCGTTAACCAAGTTTACACCGTGCAGA
```

-continued

```
TCAGCACCAAGTCCGGCGACTGGAAGTCCAAATGTTTCTATACCACCGA

CACCGAGTGCGATCTCACCGATGAGATCGTGAAAGATGTGAAACAGACC

TACCTCGCCCGGGTGTTTAGCTACCCCGCCGGCAATGTGGAGAGCACTG

GTTCCGCTGGCGAGCCTTTATACGAGAACAGCCCCGAATTTACCCCTTA

CCTCGAGACCAATTTAGGACAGCCCACCATCCAAAGCTTTGAGCAAGTT

GGCACAAAGGTGAATGTGACAGTGGAGGACGAGCGGACTTTAGTGCGGC

GGAACAACACCTTTCTCAGCCTCCGGGATGTGTTCGGCAAAGATTTAAT

CTACACACTGTATTACTGGAAGTCCTCTTCCTCCGGCAAGAAGACAGCT

AAAACCAACACAAACGAGTTTTTAATCGACGTGGATAAAGGCGAAAACT

ACTGTTTCAGCGTGCAAGCTGTGATCCCCTCCCGGACCGTGAATAGGAA

AAGCACCGATAGCCCCGTTGAGTGCATGGGCCAAGAAAAGGGCGAGTTC

CGGGAGAACTGGGTGAACGTCATCAGCGATTTAAAGAAGATCGAAGATT

TAATTCAGTCCATGCATATCGACGCCACTTTATACACAGAATCCGACGT

GCACCCCTCTTGTAAGGTGACCGCCATGAAATGTTTTTACTGGAGCTG

CAAGTTATCTCTTTAGAGAGCGGAGACGCTAGCATCCACGACACCGTGG

AGAATTTAATCATTTTAGCCAATAACTCTTTATCCAGCAACGGCAACGT

GACAGAGTCCGGCTGCAAGGAGTGCGAAGAGCTGGAGGAGAAGAACATC

AAGGAGTTTCTGCAATCCTTTGTGCACATTGTCCAGATGTTCATCAATA

CCTCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 194)
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCSGGGGSGGGGSGGGGSRNLPVATPDPGMFPCLHHSQNL

LRAVSNMLQKARQTLEFYPCTSEEIDHEDITKDKTSTVEACLPLELTKN

ESCLNSRETSFITNGSCLASRKTSFMMALCLSSIYEDLKMYQVEFKTMN

AKLLMDPKRQIFLDQNMLAVIDELMQALNFNSETVPQKSSLEEPDFYKT

KIKLCILLHAFRIRAVTIDRVMSYLNASITCPPPMSVEHADIWVKSYSL

YSRERYICNSGFKRKAGTSSLTECVLNKATNVAHWTTPSLKCIR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 195)
ATTTGGGAACTGAAGAAGGACGTCTACGTGGTCGAACTGGACTGGTATC
CCGATGCTCCCGGCGAAATGGTGGTGCTCACTTGTGACACCCCCGAAGA
AGACGGCATCACTTGGACCCTCGATCAGAGCAGCGAGGTGCTGGGCTCC
GGAAAGACCCTCACAATCCAAGTTAAGGAGTTCGGAGACGCTGGCCAAT
ACACATGCCACAAGGGAGGCGAGGTGCTCAGCCATTCCTTATTATTATT
ACACAAGAAGGAAGACGGAATCTGGTCCACCGACATTTTAAAAGATCAG
AAGGAGCCCAAGAATAAGACCTTTTTAAGGTGTGAGGCCAAAAACTACA
GCGGTCGTTTCACTTGTTGGTGGCTGACCACCATTTCCACCGATTTAAC
CTTCTCCGTGAAAAGCAGCCGGGGAAGCTCCGACCCTCAAGGTGTGACA
TGTGGAGCCGCTACCCTCAGCGCTGAGAGGGTTCGTGGCGATAACAAGG
AATACGAGTACAGCGTGGAGTGCCAAGAAGATAGCGCTTGTCCCGCTGC
CGAAGAATCTTTACCCATTGAGGTGATGGTGGACGCCGTGCACAAACTC
AAGTACGAGAACTACACCTCCTCCTTCTTTATCCGGGACATCATTAAGC
CCGATCCTCCTAAGAATTTACAGCTGAAGCCTCTCAAAAATAGCCGGCA
AGTTGAGGTCTCTTGGGAATATCCCGACACTTGGAGCACACCCCACAGC
TACTTCTCTTTAACCTTTTGTGTGCAAGTTCAAGGTAAAAGCAAGCGGG
AGAAGAAAGACCGGGTGTTTACCGACAAAACCAGCGCCACCGTCATCTG
TCGGAAGAACGCCTCCATCAGCGTGAGGGCTCAAGATCGTTATTACTCC
AGCAGCTGGTCCGAGTGGGCCAGCGTGCCTTGTTCCGGCGGTGGAGGAT
CCGGAGGAGGTGGCTCCGGCGGCGGAGGATCTCGTAACCTCCCCGTGGC
TACCCCCGATCCCGGAATGTTCCCTTGTTTACACCACAGCCAGAATTTA
CTGAGGGCCGTGAGCAACATGCTGCAGAAAGCTAGGCAGACTTTAGAAT
TTTACCCTTGCACCAGCGAGGAGATCGACCATGAAGATATCACCAAGGA
CAAGACATCCACCGTGGAGGCTTGTTTACCTCTGGAGCTGACAAAGAAC
GAGTCTTGTCTCAACTCTCGTGAAACCAGCTTCATCACAAATGGCTCTT
GTTTAGCTTCCCGGAAGACCTCCTTTATGATGGCTTTATGCCTCAGCTC
CATCTACGAGGATTTAAAGATGTACCAAGTGGAGTTCAAGACCATGAAC
GCCAAGCTGCTCATGGACCCTAAACGGCAGATCTTTTTAGACCAGAACA
TGCTGGCTGTGATTGATGAGCTGATGCAAGCTTTAAACTTCAACTCCGA
GACCGTCCCTCAGAAGTCCTCCCTCGAGGAGCCCGATTTTTACAAGACA
AAGATCAAACTGTGCATTTTACTCCACGCCTTTAGGATCCGGGCCGTGA
CCATTGACCGGGTCATGAGCTATTTAAACGCCAGCATTACATGCCCCCC
TCCCATGAGCGTGGAGCACGCCGACATCTGGGTGAAGAGCTATAGCCTC
TACAGCCGGGAGAGGTATATCTGTAACAGCGGCTTCAAGAGGAAGGCCG
GCACCAGCAGCCTCACCGAGTGCGTGCTGAATAAGGCTACCAACGTGGC
TCACTGGACAACACCCTCTTTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 196)
MKWVTFISLLFLFSSAYSIWELKKDVYVVELDWYPDAPGEMVVLTCDTP
EEDGITWTLDQSSEVLGSGKTLTIQVKEFGDAGQYTCHKGGEVLSHSLL
LLHKKEDGIWSTDILKDQKEPKNKTFLRCEAKNYSGRFTCWWLTTISTD
LTFSVKSSRGSSDPQGVTCGAATLSAERVRGDNKEYEYSVECQEDSACP
AAEESLPIEVMVDAVHKLKYENYTSSFFIRDIIKPDPPKNLQLKPLKNS
RQVEVSWEYPDTWSTPHSYFSLTFCVQVQGKSKREKKDRVFTDKTSATV
ICRKNASISVRAQDRYYSSSWSEWASVPCSGGGGSGGGGSGGGGSRNLP
VATPDPGMFPCLHHSQNLLRAVSNMLQKARQTLEFYPCTSEEIDHEDIT
KDKTSTVEACLPLELTKNESCLNSRETSFITNGSCLASRKTSFMMALCL
SSIYEDLKMYQVEFKTMNAKLLMDPKRQIFLDQNMLAVIDELMQALNEN
SETVPQKSSLEEPDFYKTKIKLCILLHAFRIRAVTIDRVMSYLNASITC
PPPMSVEHADIWVKSYSLYSRERYICNSGFKRKAGTSSLTECVLNKATN
VAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)
ATGAAATGGGTGACCTTTATTTCTTTACTGTTCCTCTTTAGCAGCGCCT
ACTCCATTTGGGAACTGAAGAAGGACGTCTACGTGGTCGAACTGGACTG
GTATCCCGATGCTCCCGGCGAAATGGTGGTGCTCACTTGTGACACCCCC
GAAGAAGACGGCATCACTTGGACCCTCGATCAGAGCAGCGAGGTGCTGG
GCTCCGGAAAGACCCTCACAATCCAAGTTAAGGAGTTCGGAGACGCTGG
CCAATACACATGCCACAAGGGAGGCGAGGTGCTCAGCCATTCCTTATTA
TTATTACACAAGAAGGAAGACGGAATCTGGTCCACCGACATTTTAAAAG
ATCAGAAGGAGCCCAAGAATAAGACCTTTTTAAGGTGTGAGGCCAAAAA
CTACAGCGGTCGTTTCACTTGTTGGTGGCTGACCACCATTTCCACCGAT
TTAACCTTCTCCGTGAAAAGCAGCCGGGGAAGCTCCGACCCTCAAGGTG
TGACATGTGGAGCCGCTACCCTCAGCGCTGAGAGGGTTCGTGGCGATAA
CAAGGAATACGAGTACAGCGTGGAGTGCCAAGAAGATAGCGCTTGTCCC
GCTGCCGAAGAATCTTTACCCATTGAGGTGATGGTGGACGCCGTGCACA
AACTCAAGTACGAGAACTACACCTCCTCCTTCTTTATCCGGGACATCAT
TAAGCCCGATCCTCCTAAGAATTTACAGCTGAAGCCTCTCAAAAATAGC
CGGCAAGTTGAGGTCTCTTGGGAATATCCCGACACTTGGAGCACACCCC
ACAGCTACTTCTCTTTAACCTTTTGTGTGCAAGTTCAAGGTAAAAGCAA
GCGGGAGAAGAAAGACCGGGTGTTTACCGACAAAACCAGCGCCACCGTC
ATCTGTCGGAAGAACGCCTCCATCAGCGTGAGGGCTCAAGATCGTTATT

-continued

```
ACTCCAGCAGCTGGTCCGAGTGGGCCAGCGTGCCTTGTTCCGGCGGTGG
AGGATCCGGAGGAGGTGGCTCCGGCGGCGGAGGATCTCGTAACCTCCCC
GTGGCTACCCCCGATCCCGGAATGTTCCCTTGTTTACACCACAGCCAGA
ATTTACTGAGGGCCGTGAGCAACATGCTGCAGAAAGCTAGGCAGACTTT
AGAATTTTACCCTTGCACCAGCGAGGAGATCGACCATGAAGATATCACC
AAGGACAAGACATCCACCGTGGAGGCTTGTTTACCTCTGGAGCTGACAA
AGAACGAGTCTTGTCTCAACTCTCGTGAAACCAGCTTCATCACAAATGG
CTCTTGTTTAGCTTCCCGGAAGACCTCCTTTATGATGGCTTTATGCCTC
AGCTCCATCTACGAGGATTTAAAGATGTACCAAGTGGAGTTCAAGACCA
TGAACGCCAAGCTGCTCATGGACCCTAAACGGCAGATCTTTTTAGACCA
GAACATGCTGGCTGTGATTGATGAGCTGATGCAAGCTTTAAACTTCAAC
TCCGAGACCGTCCCTCAGAAGTCCTCCCTCGAGGAGCCCGATTTTTACA
AGACAAAGATCAAACTGTGCATTTTACTCCACGCCTTTAGGATCCGGGC
CGTGACCATTGACCGGGTCATGAGCTATTTAAACGCCAGCATTACATGC
CCCCCTCCCATGAGCGTGGAGCACGCCGACATCTGGGTGAAGAGCTATA
GCCTCTACAGCCGGGAGAGGTATATCTGTAACAGCGGCTTCAAGAGGAA
GGCCGGCACCAGCAGCCTCACCGAGTGCGTGCTGAATAAGGCTACCAAC
GTGGCTCACTGGACAACACCCTCTTTAAAGTGCATCCGG.
```

Exemplary Multi-Chain Chimeric Polypeptides-Type B

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the first target-binding domain includes a soluble IL-21 (e.g., a soluble human IL-21).

In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 198)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS.
```

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 199)
CAAGGTCAAGATCGCCACATGATTAGAATGCGTCAACTTATAGATATTG
TTGATCAGCTGAAAAATTATGTGAATGACTTGGTCCCTGAATTTCTGCC
AGCTCCAGAAGATGTAGAGACAAACTGTGAGTGGTCAGCTTTTTCCTGT
TTTCAGAAGGCCCAACTAAAGTCAGCAAATACAGGAAACAATGAAAGGA
TAATCAATGTATCAATTAAAAAGCTGAAGAGGAAACCACCTTCCACAAA
TGCAGGGAGAAGACAGAAACACAGACTAACATGCCCTTCATGTGATTCT
```

-continued

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 200)

CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC.

In some embodiments of these multi-chain chimeric polypeptides, the sequence of soluble human IL-7 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 131)

DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 202)

GATTGTGATATTGAAGGTAAAGATGGCAAACAATATGAGAGTGTTCTA

ATGGTCAGCATCGATCAATTATTGGACAGCATGAAAGAAATTGGTAGC

AATTGCCTGAATAATGAATTTAACTTTTTTAAAAGACATATCTGTGAT

GCTAATAAGGAAGGTATGTTTTTATTCCGTGCTGCTCGCAAGTTGAGG

CAATTTCTTAAAATGAATAGCACTGGTGATTTTGATCTCCACTTATTA

-continued

AAAGTTTCAGAAGGCACAACAATACTGTTGAACTGCACTGGCCAGGTT

AAAGGAAGAAAACCAGCTGCCCTGGGTGAAGCCCAACCAACAAAGAGT

TTGGAAGAAAATAAATCTTTAAAGGAACAGAAAAAACTGAATGACTTG

TGTTTCCTAAAGAGACTATTACAAGAGATAAAAACTTGTTGGAATAAA

ATTTTGATGGGCACTAAAGAACAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 203)

QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDSSGTTNTVAAYNLTW

KSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPT

IQSFEQVGTKVNVTVEDERTLVRRNNTFLSLRDVFGKDLIYTLYYWKSS

SSGKKTAKTNTNEFLIDVDKGENYCFSVQAVIPSRTVNRKSTDSPVECM

GQEKGEFRENWVNVISDLKKIEDLIQSMHIDATLYTESDVHPSCKVTAM

KCFLLELQVISLESGDASIHDTVENLIILANNSLSSNGNVTESGCKECE

ELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or (SEQ ID NO: 204)

CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCCTCAGGCACTACAAATACTGTGGCAGCATATAATTTAACTTGG

AAATCAACTAATTTCAAGACAATTTTGGAGTGGGAACCCAAACCCGTCA

ATCAAGTCTACACTGTTCAAATAAGCACTAAGTCAGGAGATTGGAAAAG

CAAATGCTTTTACACAACAGACACAGAGTGTGACCTCACCGACGAGATT

GTGAAGGATGTGAAGCAGACGTACTTGGCACGGGTCTTCTCCTACCCGG

CAGGGAATGTGGAGAGCACCGGTTCTGCTGGGGAGCCTCTGTATGAGAA

-continued

```
CTCCCCAGAGTTCACACCTTACCTGGAGACAAACCTCGGACAGCCAACA
ATTCAGAGTTTTGAACAGGTGGGAACAAAAGTGAATGTGACCGTAGAAG
ATGAACGGACTTTAGTCAGAAGGAACAACACTTTCCTAAGCCTCCGGGA
TGTTTTTGGCAAGGACTTAATTTATACACTTTATTATTGGAAATCTTCA
AGTTCAGGAAAGAAAACAGCCAAAACAAACACTAATGAGTTTTTGATTG
ATGTGGATAAAGGAGAAAACTACTGTTTCAGTGTTCAAGCAGTGATTCC
CTCCCGAACAGTTAACCGGAAGAGTACAGACAGCCCGGTAGAGTGTATG
GGCCAGGAGAAAGGGGAATTCAGAGAAAACTGGGTGAACGTCATCAGCG
ATTTAAAGAAGATCGAAGATTTAATTCAGTCCATGCATATCGACGCCAC
TTTATACACAGAATCCGACGTGCACCCCTCTTGTAAGGTGACCGCCATG
AAATGTTTTTTACTGGAGCTGCAAGTTATCTCTTTAGAGAGCGGAGACG
CTAGCATCCACGACACCGTGGAGAATTTAATCATTTTAGCCAATAACTC
TTTATCCAGCAACGGCAACGTGACAGAGTCCGGCTGCAAGGAGTGCGAA
GAGCTGGAGGAGAAGAACATCAAGGAGTTTCTGCAATCCTTTGTGCACA
TTGTCCAGATGTTCATCAATACCTCC.
```

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
(SEQ ID NO: 205)
MGVKVLFALICIAVAEAQGQDRHMIRMRQLIDIVDQLKNYVNDLVPEFL
PAPEDVETNCEWSAFSCFQKAQLKSANTGNNERIINVSIKKLKRKPPST
NAGRRQKHRLTCPSCDSYEKKPPKEFLERFKSLLQKMIHQHLSSRTHGS
EDSSGTTNTVAAYNLTWKSTNFKTILEWEPKPVNQVYTVQISTKSGDWK
SKCFYTTDTECDLTDEIVKDVKQTYLARVFSYPAGNVESTGSAGEPLYE
NSPEFTPYLETNLGQPTIQSFEQVGTKVNVTVEDERTLVRRNNTFLSLR
DVFGKDLIYTLYYWKSSSSGKKTAKTNTNEFLIDVDKGENYCFSVQAVI
PSRTVNRKSTDSPVECMGQEKGEFRENWVNVISDLKKIEDLIQSMHIDA
TLYTESDVHPSCKVTAMKCFLLELQVISLESGDASIHDTVENLIILANN
SLSSNGNVTESGCKECEELEEKNIKEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or

```
(SEQ ID NO: 206)
ATGGGAGTGAAAGTTCTTTTTGCCCTTATTTGTATTGCTGTGGCCGAGG
CCCAAGGTCAAGATCGCCACATGATTAGAATGCGTCAACTTATAGATAT
TGTTGATCAGCTGAAAAATTATGTGAATGACTTGGTCCCTGAATTTCTG
CCAGCTCCAGAAGATGTAGAGACAAACTGTGAGTGGTCAGCTTTTTCCT
```

-continued

```
GTTTTCAGAAGGCCCAACTAAAGTCAGCAAATACAGGAAACAATGAAAG
GATAATCAATGTATCAATTAAAAAGCTGAAGAGGAAACCACCTTCCACA
AATGCAGGGAGAAGACAGAAACACAGACTAACATGCCCTTCATGTGATT
CTTATGAGAAAAAACCACCCAAAGAATTCCTAGAAAGATTCAAATCACT
TCTCCAAAAGATGATTCATCAGCATCTGTCCTCTAGAACACACGGAAGT
GAAGATTCCTCAGGCACTACAAATACTGTGGCAGCATATAATTTAACTT
GGAAATCAACTAATTTCAAGACAATTTTGGAGTGGGAACCCAAACCCGT
CAATCAAGTCTACACTGTTCAAATAAGCACTAAGTCAGGAGATTGGAAA
AGCAAATGCTTTTACACAACAGACACAGAGTGTGACCTCACCGACGAGA
TTGTGAAGGATGTGAAGCAGACGTACTTGGCACGGGTCTTCTCCTACCC
GGCAGGGAATGTGGAGAGCACCGGTTCTGCTGGGGAGCCTCTGTATGAG
AACTCCCCAGAGTTCACACCTTACCTGGAGACAAACCTCGGACAGCCAA
CAATTCAGAGTTTTGAACAGGTGGGAACAAAAGTGAATGTGACCGTAGA
AGATGAACGGACTTTAGTCAGAAGGAACAACACTTTCCTAAGCCTCCGG
GATGTTTTTGGCAAGGACTTAATTTATACACTTTATTATTGGAAATCTT
CAAGTTCAGGAAAGAAAACAGCCAAAACAAACACTAATGAGTTTTTGAT
TGATGTGGATAAAGGAGAAAACTACTGTTTCAGTGTTCAAGCAGTGATT
CCCTCCCGAACAGTTAACCGGAAGAGTACAGACAGCCCGGTAGAGTGTA
TGGGCCAGGAGAAAGGGGAATTCAGAGAAAACTGGGTGAACGTCATCAG
CGATTTAAAGAAGATCGAAGATTTAATTCAGTCCATGCATATCGACGCC
ACTTTATACACAGAATCCGACGTGCACCCCTCTTGTAAGGTGACCGCCA
TGAAATGTTTTTTACTGGAGCTGCAAGTTATCTCTTTAGAGAGCGGAGA
CGCTAGCATCCACGACACCGTGGAGAATTTAATCATTTTAGCCAATAAC
TCTTTATCCAGCAACGGCAACGTGACAGAGTCCGGCTGCAAGGAGTGCG
AAGAGCTGGAGGAGAAGAACATCAAGGAGTTTCTGCAATCCTTTGTGCA
CATTGTCCAGATGTTCATCAATACCTCC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
(SEQ ID NO: 207)
DCDIEGKDGKQYESVLMVSIDQLLDSMKEIGSNCLNNEFNFFKRHICDA
NKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILM
GTKEHITCPPPMSVEHADIWVKSYSLYSRERYICNSGFKRKAGTSSLTE
CVLNKATNVAHWTTPSLKCIR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 208)
GATTGTGATATTGAAGGTAAAGATGGCAAACAATATGAGAGTGTTCTAA
TGGTCAGCATCGATCAATTATTGGACAGCATGAAAGAAATTGGTAGCAA
TTGCCTGAATAATGAATTTAACTTTTTTAAAAGACATATCTGTGATGCT
AATAAGGAAGGTATGTTTTTATTCCGTGCTGCTCGCAAGTTGAGGCAAT
TTCTTAAAATGAATAGCACTGGTGATTTTGATCTCCACTTATTAAAAGT
TTCAGAAGGCACAACAATACTGTTGAACTGCACTGGCCAGGTTAAAGGA
AGAAAACCAGCTGCCCTGGGTGAAGCCCAACCAACAAAGAGTTTGGAAG
AAAATAAATCTTTAAAGGAACAGAAAAAACTGAATGACTTGTGTTTCCT
AAAGAGACTATTACAAGAGATAAAAACTTGTTGGAATAAAATTTTGATG
GGCACTAAAGAACACATCACGTGCCCTCCCCCCATGTCCGTGGAACACG
CAGACATCTGGGTCAAGAGCTACAGCTTGTACTCCAGGGAGCGGTACAT
TTGTAACTCTGGTTTCAAGCGTAAAGCCGGCACGTCCAGCCTGACGGAG
TGCGTGTTGAACAAGGCCACGAATGTCGCCCACTGGACAACCCCCAGTC
TCAAATGCATTAGA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 209)
MGVKVLFALICIAVAEADCDIEGKDGKQYESVLMVSIDQLLDSMKEIGS
NCLNNEFNFFKRHICDANKEGMFLFRAARKLRQFLKMNSTGDFDLHLLK
VSEGTTILLNCTGQVKGRKPAALGEAQPTKSLEENKSLKEQKKLNDLCF
LKRLLQEIKTCWNKILMGTKEHITCPPPMSVEHADIWVKSYSLYSRERY
ICNSGFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 210)
ATGGGAGTGAAAGTTCTTTTTGCCCTTATTTGTATTGCTGTGGCCGAGG
CCGATTGTGATATTGAAGGTAAAGATGGCAAACAATATGAGAGTGTTCT
AATGGTCAGCATCGATCAATTATTGGACAGCATGAAAGAAATTGGTAGC
AATTGCCTGAATAATGAATTTAACTTTTTTAAAAGACATATCTGTGATG
CTAATAAGGAAGGTATGTTTTTATTCCGTGCTGCTCGCAAGTTGAGGCA
ATTTCTTAAAATGAATAGCACTGGTGATTTTGATCTCCACTTATTAAAA
GTTTCAGAAGGCACAACAATACTGTTGAACTGCACTGGCCAGGTTAAAG
GAAGAAAACCAGCTGCCCTGGGTGAAGCCCAACCAACAAAGAGTTTGGA
AGAAAATAAATCTTTAAAGGAACAGAAAAAACTGAATGACTTGTGTTTC

-continued

CTAAAGAGACTATTACAAGAGATAAAAACTTGTTGGAATAAAATTTTGA
TGGGCACTAAAGAACACATCACGTGCCCTCCCCCCATGTCCGTGGAACA
CGCAGACATCTGGGTCAAGAGCTACAGCTTGTACTCCAGGGAGCGGTAC
ATTTGTAACTCTGGTTTCAAGCGTAAAGCCGGCACGTCCAGCCTGACGG
AGTGCGTGTTGAACAAGGCCACGAATGTCGCCCACTGGACAACCCCCAG
TCTCAAATGCATTAGA.

Exemplary Multi-Chain Chimeric Polypeptides-Type C

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 199)
CAAGGTCAAGATCGCCACATGATTAGAATGCGTCAACTTATAGATATTG
TTGATCAGCTGAAAAATTATGTGAATGACTTGGTCCCTGAATTTCTGCC
AGCTCCAGAAGATGTAGAGACAAACTGTGAGTGGTCAGCTTTTTCCTGT
TTTCAGAAGGCCCAACTAAAGTCAGCAAATACAGGAAACAATGAAAGGA
TAATCAATGTATCAATTAAAAAGCTGAAGAGGAAACCACCTTCCACAAA
TGCAGGGAGAAGACAGAAACACAGACTAACATGCCCTTCATGTGATTCT
TATGAGAAAAAACCACCCAAAGAATTCCTAGAAAGATTCAAATCACTTC
TCCAAAAGATGATTCATCAGCATCTGTCCTCTAGAACACACGGAAGTGA
AGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 200)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA

-continued
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCC.

In some embodiments of these multi-chain chimeric polypeptides, the sequence of soluble human IL-7 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 131)
DCDIEGKDGKQYESVLMVSIDQLLDSMKEIGSNCLNNEFNFFKRHICDA
NKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILM
GTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 202)
GATTGTGATATTGAAGGTAAAGATGGCAAACAATATGAGAGTGTTCTAA
TGGTCAGCATCGATCAATTATTGGACAGCATGAAAGAAATTGGTAGCAA
TTGCCTGAATAATGAATTTAACTTTTTTAAAAGACATATCTGTGATGCT
AATAAGGAAGGTATGTTTTTATTCCGTGCTGCTCGCAAGTTGAGGCAAT
TTCTTAAAATGAATAGCACTGGTGATTTTGATCTCCACTTATTAAAAGT
TTCAGAAGGCACAACAATACTGTTGAACTGCACTGGCCAGGTTAAAGGA
AGAAAACCAGCTGCCCTGGGTGAAGCCCAACCAACAAAGAGTTTGGAAG
AAAATAAATCTTTAAAGGAACAGAAAAAACTGAATGACTTGTGTTTCCT
AAAGAGACTATTACAAGAGATAAAAACTTGTTGGAATAAAATTTTGATG
GGCACTAAAGAACAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 216)
DCDIEGKDGKQYESVLMVSIDQLLDSMKEIGSNCLNNEFNFFKRHICDA
NKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILM

GTKEHSGTTNTVAAYNLTWKSTNFKTILEWEPKPVNQVYTVQISTKSGD
WKSKCFYTTDTECDLTDEIVKDVKQTYLARVFSYPAGNVESTGSAGEPL
YENSPEFTPYLETNLGQPTIQSFEQVGTKVNVTVEDERTLVRRNNTFLS
LRDVFGKDLIYTLYYWKSSSSGKKTAKTNTNEFLIDVDKGENYCFSVQA
VIPSRTVNRKSTDSPVECMGQEKGEFRENWVNVISDLKKIEDLIQSMHI
DATLYTESDVHPSCKVTAMKCFLLELQVISLESGDASIHDTVENLIILA
NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or (SEQ ID NO: 217)
GATTGCGACATCGAGGGCAAGGACGGCAAGCAGTACGAGAGCGTGCTGA
TGGTGTCCATCGACCAGCTGCTGGACAGCATGAAGGAGATCGGCTCCAA
CTGCCTCAACAACGAGTTCAACTTCTTCAAGCGGCACATCTGCGACGCC
AACAAGGAGGGCATGTTCCTGTTCAGGGCCGCCAGGAAACTGCGGCAGT
TCCTGAAGATGAACTCCACCGGCGACTTCGACCTGCACCTGCTGAAGGT
GTCCGAGGGCACCACCATCCTGCTGAACTGCACCGGACAGGTGAAGGGC
CGGAAACCTGCTGCTCTGGGAGAGGCCCAACCCACCAAGAGCCTGGAGG
AGAACAAGTCCCTGAAGGAGCAGAAGAAGCTGAACGACCTGTGCTTCCT
GAAGAGGCTGCTGCAGGAGATCAAGACCTGCTGGAACAAGATCCTGATG
GGCACCAAGGAGCATAGCGGCACAACCAACACAGTCGCTGCCTATAACC
TCACTTGGAAGAGCACCAACTTCAAAACCATCCTCGAATGGGAACCCAA
ACCCGTTAACCAAGTTTACACCGTGCAGATCAGCACCAAGTCCGGCGAC
TGGAAGTCCAAATGTTTCTATACCACCGACACCGAGTGCGATCTCACCG
ATGAGATCGTGAAAGATGTGAAACAGACCTACCTCGCCCGGGTGTTTAG
CTACCCCGCCGGCAATGTGGAGAGCACTGGTTCCGCTGGCGAGCCTTTA
TACGAGAACAGCCCCGAATTTACCCCTTACCTCGAGACCAATTTAGGAC
AGCCCACCATCCAAAGCTTTGAGCAAGTTGGCACAAAGGTGAATGTGAC
AGTGGAGGACGAGCGGACTTTAGTGCGGCGGAACAACACCTTTCTCAGC
CTCCGGGATGTGTTCGGCAAAGATTTAATCTACACACTGTATTACTGGA
AGTCCTCTTCCTCCGGCAAGAAGACAGCTAAAACCAACACAAACGAGTT
TTTAATCGACGTGGATAAAGGCGAAAACTACTGTTTCAGCGTGCAAGCT
GTGATCCCCTCCCGGACCGTGAATAGGAAAAGCACCGATAGCCCCGTTG
AGTGCATGGGCCAAGAAAAGGGCGAGTTCCGGGAGAACTGGGTGAACGT
CATCAGCGATTTAAAGAAGATCGAAGATTTAATTCAGTCCATGCATATC
GACGCCACTTTATACACAGAATCCGACGTGCACCCCTCTTGTAAGGTGA
CCGCCATGAAATGTTTTTTACTGGAGCTGCAAGTTATCTCTTTAGAGAG
CGGAGACGCTAGCATCCACGACACCGTGGAGAATTTAATCATTTTAGCC
AATAACTCTTTATCCAGCAACGGCAACGTGACAGAGTCCGGCTGCAAGG
AGTGCGAAGAGCTGGAGGAGAAGAACATCAAGGAGTTTCTGCAATCCTT
TGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 218)
MKWVTFISLLFLFSSAYSDCDIEGKDGKQYESVLMVSIDQLLDSMKEIG
SNCLNNEFNFFKRHICDANKEGMFLFRAARKLRQFLKMNSTGDFDLHLL
KVSEGTTILLNCTGQVKGRKPAALGEAQPTKSLEENKSLKEQKKLNDLC
FLKRLLQEIKTCWNKILMGTKEHSGTTNTVAAYNLTWKSTNFKTILEWE
PKPVNQVYTVQISTKSGDWKSKCFYTTDTECDLTDEIVKDVKQTYLARV
FSYPAGNVESTGSAGEPLYENSPEFTPYLETNLGQPTIQSFEQVGTKVN
VTVEDERTLVRRNNTFLSLRDVFGKDLIYTLYYWKSSSSGKKTAKTNTN
EFLIDVDKGENYCFSVQAVIPSRTVNRKSTDSPVECMGQEKGEFRENWV
NVISDLKKIEDLIQSMHIDATLYTESDVHPSCKVTAMKCFLLELQVISL
ESGDASIHDTVENLIILANNSLSSNGNVTESGCKECEELEEKNIKEFLQ
SFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or (SEQ ID NO: 219)
ATGAAGTGGGTGACCTTCATCAGCCTGCTGTTCCTGTTCTCCAGCGCCT
ACTCCGATTGCGACATCGAGGGCAAGGACGGCAAGCAGTACGAGAGCGT
GCTGATGGTGTCCATCGACCAGCTGCTGGACAGCATGAAGGAGATCGGC
TCCAACTGCCTCAACAACGAGTTCAACTTCTTCAAGCGGCACATCTGCG
ACGCCAACAAGGAGGGCATGTTCCTGTTCAGGGCCGCCAGGAAACTGCG
GCAGTTCCTGAAGATGAACTCCACCGGCGACTTCGACCTGCACCTGCTG
AAGGTGTCCGAGGGCACCACCATCCTGCTGAACTGCACCGGACAGGTGA
AGGGCCGGAAACCTGCTGCTCTGGGAGAGGCCCAACCCACCAAGAGCCT
GGAGGAGAACAAGTCCCTGAAGGAGCAGAAGAAGCTGAACGACCTGTGC
TTCCTGAAGAGGCTGCTGCAGGAGATCAAGACCTGCTGGAACAAGATCC
TGATGGGCACCAAGGAGCATAGCGGCACAACCAACACAGTCGCTGCCTA
TAACCTCACTTGGAAGAGCACCAACTTCAAAACCATCCTCGAATGGGAA
CCCAAACCCGTTAACCAAGTTTACACCGTGCAGATCAGCACCAAGTCCG
GCGACTGGAAGTCCAAATGTTTCTATACCACCGACACCGAGTGCGATCT
CACCGATGAGATCGTGAAAGATGTGAAACAGACCTACCTCGCCCGGGTG
TTTAGCTACCCCGCCGGCAATGTGGAGAGCACTGGTTCCGCTGGCGAGC -continued CTTTATACGAGAACAGCCCCGAATTTACCCCTTACCTCGAGACCAATTT
AGGACAGCCCACCATCCAAAGCTTTGAGCAAGTTGGCACAAAGGTGAAT
GTGACAGTGGAGGACGAGCGGACTTTAGTGCGGCGGAACAACACCTTTC
TCAGCCTCCGGGATGTGTTCGGCAAAGATTTAATCTACACACTGTATTA
CTGGAAGTCCTCTTCCTCCGGCAAGAAGACAGCTAAAACCAACACAAAC
GAGTTTTTAATCGACGTGGATAAAGGCGAAAACTACTGTTTCAGCGTGC
AAGCTGTGATCCCCTCCCGGACCGTGAATAGGAAAAGCACCGATAGCCC
CGTTGAGTGCATGGGCCAAGAAAAGGGCGAGTTCCGGGAGAACTGGGTG
AACGTCATCAGCGATTTAAAGAAGATCGAAGATTTAATTCAGTCCATGC
ATATCGACGCCACTTTATACACAGAATCCGACGTGCACCCCTCTTGTAA
GGTGACCGCCATGAAATGTTTTTTACTGGAGCTGCAAGTTATCTCTTTA
GAGAGCGGAGACGCTAGCATCCACGACACCGTGGAGAATTTAATCATTT
TAGCCAATAACTCTTTATCCAGCAACGGCAACGTGACAGAGTCCGGCTG
CAAGGAGTGCGAAGAGCTGGAGGAGAAGAACATCAAGGAGTTTCTGCAA
TCCTTTGTGCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 220)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDSITCPPPMSVEHADI
WVKSYSLYSRERYICNSGFKRKAGTSSLTECVLNKATNVAHWTTPSLKC
IR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 221)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA

-continued

GGACTCCATTACATGCCCCCCTCCCATGAGCGTGGAGCACGCCGACATC
TGGGTGAAGAGCTATAGCCTCTACAGCCGGGAGAGGTATATCTGTAACA
GCGGCTTCAAGAGGAAGGCCGGCACCAGCAGCCTCACCGAGTGCGTGCT
GAATAAGGCTACCAACGTGGCTCACTGGACAACACCCTCTTTAAAGTGC
ATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 222)
MKWVTFISLLFLFSSAYSQGQDRHMIRMRQLIDIVDQLKNYVNDLVPEF
LPAPEDVETNCEWSAFSCFQKAQLKSANTGNNERIINVSIKKLKRKPPS
TNAGRRQKHRLTCPSCDSYEKKPPKEFLERFKSLLQKMIHQHLSSRTHG
SEDSITCPPPMSVEHADIWVKSYSLYSRERYICNSGFKRKAGTSSLTEC
VLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 223)
ATGAAGTGGGTGACCTTCATCAGCCTGCTGTTCCTGTTCTCCAGCGCCT
ACTCCCAGGGCCAGGACAGGCACATGATCCGGATGAGGCAGCTCATCGA
CATCGTCGACCAGCTGAAGAACTACGTGAACGACCTGGTGCCCGAGTTT
CTGCCTGCCCCCGAGGACGTGGAGACCAACTGCGAGTGGTCCGCCTTCT
CCTGCTTTCAGAAGGCCCAGCTGAAGTCCGCCAACACCGGCAACAACGA
GCGGATCATCAACGTGAGCATCAAGAAGCTGAAGCGGAAGCCTCCCTCC
ACAAACGCCGGCAGGAGGCAGAAGCACAGGCTGACCTGCCCCAGCTGTG
ACTCCTACGAGAAGAAGCCCCCCAAGGAGTTCCTGGAGAGGTTCAAGTC
CCTGCTGCAGAAGATGATCCATCAGCACCTGTCCTCCAGGACCCACGGC
TCCGAGGACTCCATTACATGCCCCCCTCCCATGAGCGTGGAGCACGCCG
ACATCTGGGTGAAGAGCTATAGCCTCTACAGCCGGGAGAGGTATATCTG
TAACAGCGGCTTCAAGAGGAAGGCCGGCACCAGCAGCCTCACCGAGTGC
GTGCTGAATAAGGCTACCAACGTGGCTCACTGGACAACACCCTCTTTAA
AGTGCATCCGG.

Exemplary Multi-Chain Chimeric Polypeptides-Type D

In some embodiments of any of the multi-chain chimeric polypeptides described herein, the first target-binding domain and the second targeting-binding domain each independently bind specifically to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain and the second target-binding domain each independently bind specifically to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain is a soluble TGF-β receptor (e.g., a soluble TGFβRII receptor, e.g., a soluble human TGFβRII). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 126).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 224)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to: c (SEQ ID NO: 224).

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 225)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT.
```

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 226)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC.
```

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 227)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 228)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or (SEQ ID NO: 229)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPDSGTTNTV
AAYNLTWKSTNFKTILEWEPKPVNQVYTVQISTKSGDWKSKCFYTTDTE
CDLTDEIVKDVKQTYLARVFSYPAGNVESTGSAGEPLYENSPEFTPYLE
TNLGQPTIQSFEQVGTKVNVTVEDERTLVRRNNTFLSLRDVFGKDLIYT
LYYWKSSSSGKKTAKTNTNEFLIDVDKGENYCFSVQAVIPSRTVNRKST
DSPVECMGQEKGEFRENWVNVISDLKKIEDLIQSMHIDATLYTESDVHP
SCKVTAMKCFLLELQVISLESGDASIHDTVENLIILANNSLSSNGNVTE
SGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or (SEQ ID NO: 230)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGACAGCGGCACAACCAACACAGTC
GCTGCCTATAACCTCACTTGGAAGAGCACCAACTTCAAAACCATCCTCG
AATGGGAACCCAAACCCGTTAACCAAGTTTACACCGTGCAGATCAGCAC
CAAGTCCGGCGACTGGAAGTCCAAATGTTTCTATACCACCGACACCGAG
TGCGATCTCACCGATGAGATCGTGAAAGATGTGAAACAGACCTACCTCG -continued CCCGGGTGTTTAGCTACCCCGCCGGCAATGTGGAGAGCACTGGTTCCGC
TGGCGAGCCTTTATACGAGAACAGCCCCGAATTTACCCCTTACCTCGAG
ACCAATTTAGGACAGCCCACCATCCAAAGCTTTGAGCAAGTTGGCACAA
AGGTGAATGTGACAGTGGAGGACGAGCGGACTTTAGTGCGGCGGAACAA
CACCTTTCTCAGCCTCCGGGATGTGTTCGGCAAAGATTTAATCTACACA
CTGTATTACTGGAAGTCCTCTTCCTCCGGCAAGAAGACAGCTAAAACCA
ACACAAACGAGTTTTTAATCGACGTGGATAAAGGCGAAAACTACTGTTT
CAGCGTGCAAGCTGTGATCCCCTCCCGGACCGTGAATAGGAAAAGCACC
GATAGCCCCGTTGAGTGCATGGGCCAAGAAAAGGGCGAGTTCCGGGAGA
ACTGGGTGAACGTCATCAGCGATTTAAAGAAGATCGAAGATTTAATTCA
GTCCATGCATATCGACGCCACTTTATACACAGAATCCGACGTGCACCCC
TCTTGTAAGGTGACCGCCATGAAATGTTTTTTACTGGAGCTGCAAGTTA
TCTCTTTAGAGAGCGGAGACGCTAGCATCCACGACACCGTGGAGAATTT
AATCATTTTAGCCAATAACTCTTTATCCAGCAACGGCAACGTGACAGAG
TCCGGCTGCAAGGAGTGCGAAGAGCTGGAGGAGAAGAACATCAAGGAGT
TTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 231)

MKWVTFISLLFLFSSAYSIPPHVQKSVNNDMIVTDNNGAVKFPQLCKFC
DVRFSTCDNQKSCMSNCSITSICEKPQEVCVAVWRKNDENITLETVCHD
PKLPYHDFILEDAASPKCIMKEKKKPGETFFMCSCSSDECNDNIIFSEE
YNTSNPDGGGGSGGGGSGGGGSIPPHVQKSVNNDMIVTDNNGAVKFPQL
CKFCDVRFSTCDNQKSCMSNCSITSICEKPQEVCVAVWRKNDENITLET
VCHDPKLPYHDFILEDAASPKCIMKEKKKPGETFFMCSCSSDECNDNII
FSEEYNTSNPDSGTTNTVAAYNLTWKSTNFKTILEWEPKPVNQVYTVQI
STKSGDWKSKCFYTTDTECDLTDEIVKDVKQTYLARVFSYPAGNVESTG
SAGEPLYENSPEFTPYLETNLGQPTIQSFEQVGTKVNVTVEDERTLVRR
NNTFLSLRDVFGKDLIYTLYYWKSSSSGKKTAKTNTNEFLIDVDKGENY
CFSVQAVIPSRTVNRKSTDSPVECMGQEKGEFRENWVNVISDLKKIEDL
IQSMHIDATLYTESDVHPSCKVTAMKCFLLELQVISLESGDASIHDTVE
NLIILANNSLSSNGNVTESGCKECEELEEKNIKEFLQSFVHIVQMFINT
S.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or (SEQ ID NO: 232)

ATGAAGTGGGTGACCTTCATCAGCCTGCTGTTCCTGTTCTCCAGCGCCT
ACTCCATCCCCCCCCATGTGCAAAAGAGCGTGAACAACGATATGATCGT
GACCGACAACAACGGCGCCGTGAAGTTTCCCCAGCTCTGCAAGTTCTGC
GATGTCAGGTTCAGCACCTGCGATAATCAGAAGTCCTGCATGTCCAACT
GCAGCATCACCTCCATCTGCGAGAAGCCCCAAGAAGTGTGCGTGGCCGT
GTGGCGGAAAAATGACGAGAACATCACCCTGGAGACCGTGTGTCACGAC
CCCAAGCTCCCTTATCACGACTTCATTCTGGAGGACGCTGCCTCCCCCA
AATGCATCATGAAGGAGAAGAAGAAGCCCGGAGAGACCTTCTTTATGTG
TTCCTGTAGCAGCGACGAGTGTAACGACAACATCATCTTCAGCGAAGAG
TACAACACCAGCAACCCTGATGGAGGTGGCGGATCCGGAGGTGGAGGTT
CTGGTGGAGGTGGGAGTATTCCTCCCCACGTGCAGAAGAGCGTGAATAA
TGACATGATCGTGACCGATAACAATGGCGCCGTGAAATTTCCCCAGCTG
TGCAAATTCTGCGATGTGAGGTTTTCCACCTGCGACAACCAGAAGTCCT
GTATGAGCAACTGCTCCATCACCTCCATCTGTGAGAAGCCTCAGGAGGT
GTGCGTGGCTGTCTGGCGGAAGAATGACGAGAATATCACCCTGGAAACC
GTCTGCCACGATCCCAAGCTGCCCTACCACGATTTCATCCTGGAAGACG
CCGCCAGCCCTAAGTGCATCATGAAAGAGAAAAAGAAGCCTGGCGAGAC
CTTTTTCATGTGCTCCTGCAGCAGCGACGAATGCAACGACAATATCATC
TTTAGCGAGGAATACAATACCAGCAACCCCGACAGCGGCACAACCAACA
CAGTCGCTGCCTATAACCTCACTTGGAAGAGCACCAACTTCAAAACCAT
CCTCGAATGGGAACCCAAACCCGTTAACCAAGTTTACACCGTGCAGATC
AGCACCAAGTCCGGCGACTGGAAGTCCAAATGTTTCTATACCACCGACA
CCGAGTGCGATCTCACCGATGAGATCGTGAAAGATGTGAAACAGACCTA
CCTCGCCCGGGTGTTTAGCTACCCCGCCGGCAATGTGGAGAGCACTGGT
TCCGCTGGCGAGCCTTTATACGAGAACAGCCCCGAATTTACCCCTTACC
TCGAGACCAATTTAGGACAGCCCACCATCCAAAGCTTTGAGCAAGTTGG
CACAAAGGTGAATGTGACAGTGGAGGACGAGCGGACTTTAGTGCGGCGG
AACAACACCTTTCTCAGCCTCCGGGATGTGTTCGGCAAAGATTTAATCT
ACACACTGTATTACTGGAAGTCCTCTTCCTCCGGCAAGAAGACAGCTAA
AACCAACACAAACGAGTTTTTAATCGACGTGGATAAAGGCGAAAACTAC
TGTTTCAGCGTGCAAGCTGTGATCCCCTCCCGGACCGTGAATAGGAAAA
GCACCGATAGCCCCGTTGAGTGCATGGGCCAAGAAAAGGGCGAGTTCCG
GGAGAACTGGGTGAACGTCATCAGCGATTTAAAGAAGATCGAAGATTTA
ATTCAGTCCATGCATATCGACGCCACTTTATACACAGAATCCGACGTGC
ACCCCTCTTGTAAGGTGACCGCCATGAAATGTTTTTTACTGGAGCTGCA
AGTTATCTCTTTAGAGAGCGGAGACGCTAGCATCCACGACACCGTGGAG
AATTTAATCATTTTAGCCAATAACTCTTTATCCAGCAACGGCAACGTGA
CAGAGTCCGGCTGCAAGGAGTGCGAAGAGCTGGAGGAGAAGAACATCAA
GGAGTTTCTGCAATCCTTTGTGCACATTGTCCAGATGTTCATCAATACC
TCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 233)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPDITCPPPM
SVEHADIWVKSYSLYSRERYICNSGFKRKAGTSSLTECVLNKATNVAHW
TTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 234)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGACATTACATGCCCCCCTCCCATG

-continued
AGCGTGGAGCACGCCGACATCTGGGTGAAGAGCTATAGCCTCTACAGCC
GGGAGAGGTATATCTGTAACAGCGGCTTCAAGAGGAAGGCCGGCACCAG
CAGCCTCACCGAGTGCGTGCTGAATAAGGCTACCAACGTGGCTCACTGG
ACAACACCCTCTTTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 235)
MKWVTFISLLFLFSSAYSIPPHVQKSVNNDMIVTDNNGAVKFPQLCKFC
DVRFSTCDNQKSCMSNCSITSICEKPQEVCVAVWRKNDENITLETVCHD
PKLPYHDFILEDAASPKCIMKEKKKPGETFFMCSCSSDECNDNIIFSEE
YNTSNPDGGGGSGGGGSGGGGSIPPHVQKSVNNDMIVTDNNGAVKFPQL
CKFCDVRFSTCDNQKSCMSNCSITSICEKPQEVCVAVWRKNDENITLET
VCHDPKLPYHDFILEDAASPKCIMKEKKKPGETFFMCSCSSDECNDNII
FSEEYNTSNPDITCPPPMSVEHADIWVKSYSLYSRERYICNSGFKRKAG
TSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 236)
ATGAAGTGGGTGACCTTCATCAGCCTGCTGTTCCTGTTCTCCAGCGCCT
ACTCCATCCCCCCCCATGTGCAAAAGAGCGTGAACAACGATATGATCGT
GACCGACAACAACGGCGCCGTGAAGTTTCCCCAGCTCTGCAAGTTCTGC
GATGTCAGGTTCAGCACCTGCGATAATCAGAAGTCCTGCATGTCCAACT
GCAGCATCACCTCCATCTGCGAGAAGCCCCAAGAAGTGTGCGTGGCCGT
GTGGCGGAAAAATGACGAGAACATCACCCTGGAGACCGTGTGTCACGAC
CCCAAGCTCCCTTATCACGACTTCATTCTGGAGGACGCTGCCTCCCCCA
AATGCATCATGAAGGAGAAGAAGAAGCCCGGAGAGACCTTCTTTATGTG
TTCCTGTAGCAGCGACGAGTGTAACGACAACATCATCTTCAGCGAAGAG
TACAACACCAGCAACCCTGATGGAGGTGGCGGATCCGGAGGTGGAGGTT
CTGGTGGAGGTGGGAGTATTCCTCCCCACGTGCAGAAGAGCGTGAATAA
TGACATGATCGTGACCGATAACAATGGCGCCGTGAAATTTCCCCAGCTG
TGCAAATTCTGCGATGTGAGGTTTTCCACCTGCGACAACCAGAAGTCCT
GTATGAGCAACTGCTCCATCACCTCCATCTGTGAGAAGCCTCAGGAGGT
GTGCGTGGCTGTCTGGCGGAAGAATGACGAGAATATCACCCTGGAAACC
GTCTGCCACGATCCCAAGCTGCCCTACCACGATTTCATCCTGGAAGACG
CCGCCAGCCCTAAGTGCATCATGAAAGAGAAAAAGAAGCCTGGCGAGAC

-continued

```
CTTTTTCATGTGCTCCTGCAGCAGCGACGAATGCAACGACAATATCATC
TTTAGCGAGGAATACAATACCAGCAACCCCGACATTACATGCCCCCCTC
CCATGAGCGTGGAGCACGCCGACATCTGGGTGAAGAGCTATAGCCTCTA
CAGCCGGGAGAGGTATATCTGTAACAGCGGCTTCAAGAGGAAGGCCGGC
ACCAGCAGCCTCACCGAGTGCGTGCTGAATAAGGCTACCAACGTGGCTC
ACTGGACAACACCCTCTTTAAAGTGCATCCGG.
```

Single-Chain Chimeric Polypeptides

Provided herein are single-chain chimeric polypeptides that include: (i) a first target-binding domain (e.g., any of the target-binding domains described herein or known in the art), (ii) a soluble tissue factor domain (e.g., any of the exemplary soluble tissue factor domains described herein or known in the art), and (iii) as second target-binding domain (e.g., any of the target-binding domains described herein or known in the art).

In some embodiments of any of the single-chain chimeric polypeptides described herein, the first target-binding domain (e.g., any of the exemplary target-binding domains described herein or known in the art) and the soluble tissue factor domain (e.g., any of the exemplary soluble tissue factor domains described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the soluble tissue factor domain (e.g., any of the exemplary soluble tissue factor domains described herein). In some embodiments of any of the single-chain chimeric polypeptides described herein, the soluble tissue factor domain (e.g., any of the exemplary soluble tissue factor domains described herein) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the soluble tissue factor domain (e.g., any of the exemplary soluble tissue factor domains described herein) and the second target-binding domain (e.g., any of the exemplary target-binding domains described herein or known in the art).

In some embodiments of any of the single-chain chimeric polypeptides described herein, the first target-binding domain (e.g., any of the exemplary target-binding domains described herein or known in the art) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the second target-binding domain (e.g., any of the exemplary target-binding domains described herein or known in the art). In some embodiments of any of the single-chain chimeric polypeptides described herein, the second target-binding domain (e.g., any of the exemplary target-binding domains described herein or known in the art) and the soluble tissue factor domain (e.g., any of the exemplary soluble tissue factor domains described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the second target-binding domain (e.g., any of the exemplary target-binding domains described herein or known in the art) and the soluble tissue factor domain (e.g., any of the exemplary soluble tissue factor domains described herein or known in the art).

Exemplary Embodiments of Single-Chain Chimeric Polypeptides-Type A

In some embodiments of any of the single-chain chimeric polypeptides described herein, the first target-binding domain and/or the second target-binding domain can independently bind specifically to CD3 (e.g., human CD3) or CD28 (e.g., human CD28). In some embodiments, the first target-binding domain binds specifically to CD3 (e.g., human CD3) and the second target-binding domain binds specifically to CD28 (e.g., human CD28). In some embodiments, the first target-binding domain binds specifically to CD28 (e.g., human CD28) and the second target-binding domain binds specifically to CD3 (e.g., human CD3).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, one or both of the first target-binding domain and the second target-binding domain is an antigen-binding domain. In some embodiments of these single-chain chimeric polypeptides, the first target-binding domain and the second target-binding domain are each an antigen-binding domain (e.g., any of the exemplary antigen-binding domains described herein). In some embodiments of these single-chain chimeric polypeptides, the antigen-binding domain includes a scFv or a single domain antibody.

A non-limiting example of an scFv that binds specifically to CD3 can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 237)
QIVLTQSPAIMSASPGEKVTMTCSASSSVSYMNWYQQKSGTSPKRWIYD
TSKLASGVPAHFRGSGSGTSYSLTISGMEAEDAATYYCQQWSSNPFTFG
SGTKLEINRGGGGSGGGGSGGGGSQVQLQQSGAELARPGASVKMSCKAS
GYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSS.

In some embodiments, an scFv that binds specifically to CD3 can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 238)
CAGATCGTGCTGACCCAAAGCCCCGCCATCATGAGCGCTAGCCCCGGTG
AGAAGGTGACCATGACATGCTCCGCTTCCAGCTCCGTGTCCTACATGAA
CTGGTATCAGCAGAAAAGCGGAACCAGCCCCAAAAGGTGGATCTACGAC
ACCAGCAAGCTGGCCTCCGGAGTGCCCGCTCATTTCCGGGGCTCTGGAT
CCGGCACCAGCTACTCTTTAACCATTTCCGGCATGGAAGCTGAAGACGC
TGCCACCTACTATTGCCAGCAATGGAGCAGCAACCCCTTCACATTCGGA
TCTGGCACCAAGCTCGAAATCAATCGTGGAGGAGGTGGCAGCGGCGGCG
GTGGATCCGGCGGAGGAGGAAGCCAAGTTCAACTCCAGCAGAGCGGCGC
TGAACTGGCCCGGCCCGGCGCCTCCGTCAAGATGAGCTGCAAGGCTTCC
GGCTATACATTTACTCGTTACACAATGCATTGGGTCAAGCAGAGGCCCG
GTCAAGGTTTAGAGTGGATCGGATATATCAACCCTTCCCGGGGCTACAC
CAACTATAACCAAAAGTTCAAGGATAAAGCCACTTTAACCACTGACAAG
AGCTCCTCCACCGCCTACATGCAGCTGTCCTCTTTAACCAGCGAGGACT
CCGCTGTTTACTACTGCGCTAGGTATTACGACGACCACTACTGTTTAGA
CTATTGGGGACAAGGTACCACTTTAACCGTCAGCAGC

A non-limiting example of an scFv that binds specifically to CD28 can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 239)
VQLQQSGPELVKPGASVKMSCKASGYTFTSYVIQWVKQKPGQGLEWIGS
INPYNDYTKYNEKFKGKATLTSDKSSITAYMEFSSLTSEDSALYYCARW
GDGNYWGRGTTLTVSSGGGGSGGGGSGGGGSDIEMTQSPAIMSASLGER
VTMTCTASSSVSSSYFHWYQQKPGSSPKLCIYSTSNLASGVPPRFSGSG
STSYSLTISSMEAEDAATYFCHQYHRSPTFGGGTKLETKR.

In some embodiments, an scFv that binds specifically to CD28 can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 240)
GTCCAGCTGCAGCAGAGCGGACCCGAACTCGTGAAACCCGGTGCTTCCG
TGAAAATGTCTTGTAAGGCCAGCGGATACACCTTCACCTCCTATGTGAT
CCAGTGGGTCAAACAGAAGCCCGGACAAGGTCTCGAGTGGATCGGCAGC
ATCAACCCTTACAACGACTATACCAAATACAACGAGAAGTTTAAGGGAA
AGGCTACTTTAACCTCCGACAAAAGCTCCATCACAGCCTACATGGAGTT
CAGCTCTTTAACATCCGAGGACAGCGCTCTGTACTATTGCGCCCGGTGG
GGCGACGGCAATTACTGGGGACGGGGCACAACACTGACCGTGAGCAGCG
GAGGCGGAGGCTCCGGCGGAGGCGGATCTGGCGGTGGCGGCTCCGACAT
CGAGATGACCCAGTCCCCCGCTATCATGTCCGCCTCTTTAGGCGAGCGG
GTCACAATGACTTGTACAGCCTCCTCCAGCGTCTCCTCCTCCTACTTCC
ATTGGTACCAACAGAAACCCGGAAGCTCCCCTAAACTGTGCATCTACAG
CACCAGCAATCTCGCCAGCGGCGTGCCCCCTAGGTTTTCCGGAAGCGGA
AGCACCAGCTACTCTTTAACCATCTCCTCCATGGAGGCTGAGGATGCCG
CCACCTACTTTTGTCACCAGTACCACCGGTCCCCCACCTTCGGAGGCGG
CACCAAACTGGAGACAAAGAGG.

In some embodiments of these single-chain chimeric polypeptides, the first target-binding domain and/or the second target-binding domain is a soluble receptor (e.g., a soluble CD28 receptor or a soluble CD3 receptor). In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 241)
QIVLTQSPAIMSASPGEKVTMTCSASSSVSYMNWYQQKSGTSPKRWIYD
TSKLASGVPAHFRGSGSGTSYSLTISGMEAEDAATYYCQQWSSNPFTFG
SGTKLEINRGGGGSGGGGSGGGGSQVQLQQSGAELARPGASVKMSCKAS
GYTFTRYTMHWVKQRPGQGLEWIGYINPSRGYTNYNQKFKDKATLTTDK
SSSTAYMQLSSLTSEDSAVYYCARYYDDHYCLDYWGQGTTLTVSSSGTT
NTVAAYNLTWKSTNFKTILEWEPKPVNQVYTVQISTKSGDWKSKCFYTT
DTECDLTDEIVKDVKQTYLARVFSYPAGNVESTGSAGEPLYENSPEFTP
YLETNLGQPTIQSFEQVGTKVNVTVEDERTLVRRNNTFLSLRDVFGKDL
IYTLYYWKSSSSGKKTAKTNTNEFLIDVDKGENYCFSVQAVIPSRTVNR
KSTDSPVECMGQEKGEFREVQLQQSGPELVKPGASVKMSCKASGYTFTS
YVIQWVKQKPGQGLEWIGSINPYNDYTKYNEKFKGKATLTSDKSSITAY
MEFSSLTSEDSALYYCARWGDGNYWGRGTTLTVSSGGGGSGGGGSGGGG
SDIEMTQSPAIMSASLGERVTMTCTASSSVSSSYFHWYQQKPGSSPKLC
IYSTSNLASGVPPRFSGSGSTSYSLTISSMEAEDAATYFCHQYHRSPTF
GGGTKLETKR.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 242)
CAGATCGTGCTGACCCAAAGCCCCGCCATCATGAGCGCTAGCCCCGGTG
AGAAGGTGACCATGACATGCTCCGCTTCCAGCTCCGTGTCCTACATGAA
CTGGTATCAGCAGAAAAGCGGAACCAGCCCCAAAAGGTGGATCTACGAC
ACCAGCAAGCTGGCCTCCGGAGTGCCCGCTCATTTCCGGGGCTCTGGAT
CCGGCACCAGCTACTCTTTAACCATTTCCGGCATGGAAGCTGAAGACGC
TGCCACCTACTATTGCCAGCAATGGAGCAGCAACCCCTTCACATTCGGA
TCTGGCACCAAGCTCGAAATCAATCGTGGAGGAGGTGGCAGCGGCGGCG
GTGGATCCGGCGGAGGAGGAAGCCAAGTTCAACTCCAGCAGAGCGGCGC
TGAACTGGCCCGGCCCGGCGCCTCCGTCAAGATGAGCTGCAAGGCTTCC
GGCTATACATTTACTCGTTACACAATGCATTGGGTCAAGCAGAGGCCCG
GTCAAGGTTTAGAGTGGATCGGATATATCAACCCTTCCCGGGGCTACAC
CAACTATAACCAAAAGTTCAAGGATAAAGCCACTTTAACCACTGACAAG
AGCTCCTCCACCGCCTACATGCAGCTGTCCTCTTTAACCAGCGAGGACT
CCGCTGTTTACTACTGCGCTAGGTATTACGACGACCACTACTGTTTAGA
CTATTGGGGACAAGGTACCACTTTAACCGTCAGCAGCTCCGGCACCACC
AATACCGTGGCCGCTTATAACCTCACATGGAAGAGCACCAACTTCAAGA
CAATTCTGGAATGGGAACCCAAGCCCGTCAATCAAGTTTACACCGTGCA
GATCTCCACCAAATCCGGAGACTGGAAGAGCAAGTGCTTCTACACAACA
GACACCGAGTGTGATTTAACCGACGAAATCGTCAAGGACGTCAAGCAAA
CCTATCTGGCTCGGGTCTTTTCCTACCCCGCTGGCAATGTCGAGTCCAC
CGGCTCCGCTGGCGAGCCTCTCTACGAGAATTCCCCCGAATTCACCCCT
TATTTAGAGACCAATTTAGGCCAGCCTACCATCCAGAGCTTCGAGCAAG
TTGGCACCAAGGTGAACGTCACCGTCGAGGATGAAAGGACTTTAGTGCG
GCGGAATAACACATTTTTATCCCTCCGGGATGTGTTCGGCAAAGACCTC
ATCTACACACTGTACTATTGGAAGTCCAGCTCCTCCGGCAAAAAGACCG
CTAAGACCAACACCAACGAGTTTTTAATTGACGTGGACAAAGGCGAGAA
CTACTGCTTCAGCGTGCAAGCCGTGATCCCTTCTCGTACCGTCAACCGG
AAGAGCACAGATTCCCCCGTTGAGTGCATGGGCCAAGAAAAGGGCGAGT
TCCGGGAGGTCCAGCTGCAGCAGAGCGGACCCGAACTCGTGAAACCCGG
TGCTTCCGTGAAAATGTCTTGTAAGGCCAGCGGATACACCTTCACCTCC
TATGTGATCCAGTGGGTCAAACAGAAGCCCGGACAAGGTCTCGAGTGGA
TCGGCAGCATCAACCCTTACAACGACTATACCAAATACAACGAGAAGTT
TAAGGGAAAGGCTACTTTAACCTCCGACAAAAGCTCCATCACAGCCTAC
ATGGAGTTCAGCTCTTTAACATCCGAGGACAGCGCTCTGTACTATTGCG
CCCGGTGGGGCGACGGCAATTACTGGGGACGGGGCACAACACTGACCGT

-continued

GAGCAGCGGAGGCGGAGGCTCCGGCGGAGGCGGATCTGGCGGTGGCGGC
TCCGACATCGAGATGACCCAGTCCCCCGCTATCATGTCCGCCTCTTTAG
GCGAGCGGGTCACAATGACTTGTACAGCCTCCTCCAGCGTCTCCTCCTC
CTACTTCCATTGGTACCAACAGAAACCCGGAAGCTCCCCTAAACTGTGC
ATCTACAGCACCAGCAATCTCGCCAGCGGCGTGCCCCCTAGGTTTTCCG
GAAGCGGAAGCACCAGCTACTCTTTAACCATCTCCTCCATGGAGGCTGA
GGATGCCGCCACCTACTTTTGTCACCAGTACCACCGGTCCCCCACCTTC
GGAGGCGGCACCAAACTGGAGACAAAGAGG.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 243)
MKWVTFISLLFLFSSAYSQIVLTQSPAIMSASPGEKVTMTCSASSSVSY
MNWYQQKSGTSPKRWIYDTSKLASGVPAHFRGSGSGTSYSLTISGMEAE
DAATYYCQQWSSNPFTFGSGTKLEINRGGGGSGGGGSGGGGSQVQLQQS
GAELARPGASVKMSCKASGYTFTRYTMHWVKQRPGQGLEWIGYINPSRG
YTNYNQKFKDKATLTTDKSSSTAYMQLSSLTSEDSAVYYCARYYDDHYC
LDYWGQGTTLTVSSSGTTNTVAAYNLTWKSTNFKTILEWEPKPVNQVYT
VQISTKSGDWKSKCFYTTDTECDLTDEIVKDVKQTYLARVFSYPAGNVE
STGSAGEPLYENSPEFTPYLETNLGQPTIQSFEQVGTKVNVTVEDERTL
VRRNNTFLSLRDVFGKDLIYTLYYWKSSSSGKKTAKTNTNEFLIDVDKG
ENYCFSVQAVIPSRTVNRKSTDSPVECMGQEKGEFREVQLQQSGPELVK
PGASVKMSCKASGYTFTSYVIQWVKQKPGQGLEWIGSINPYNDYTKYNE
KFKGKATLTSDKSSITAYMEFSSLTSEDSALYYCARWGDGNYWGRGTTL
TVSSGGGGSGGGGSGGGGSDIEMTQSPAIMSASLGERVTMTCTASSSVS
SSYFHWYQQKPGSSPKLCIYSTSNLASGVPPRFSGSGSTSYSLTISSME
AEDAATYFCHQYHRSPTFGGGTKLETKR.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 244)
ATGAAGTGGGTGACCTTCATCAGCTTATTATTTTTATTCAGCTCCGCCT
ATTCCCAGATCGTGCTGACCCAAAGCCCCGCCATCATGAGCGCTAGCCC
CGGTGAGAAGGTGACCATGACATGCTCCGCTTCCAGCTCCGTGTCCTAC
ATGAACTGGTATCAGCAGAAAAGCGGAACCAGCCCCAAAAGGTGGATCT
ACGACACCAGCAAGCTGGCCTCCGGAGTGCCCGCTCATTTCCGGGGCTC
TGGATCCGGCACCAGCTACTCTTTAACCATTTCCGGCATGGAAGCTGAA

-continued

```
GACGCTGCCACCTACTATTGCCAGCAATGGAGCAGCAACCCCTTCACAT
TCGGATCTGGCACCAAGCTCGAAATCAATCGTGGAGGAGGTGGCAGCGG
CGGCGGTGGATCCGGCGGAGGAGGAAGCCAAGTTCAACTCCAGCAGAGC
GGCGCTGAACTGGCCCGGCCCGGCGCCTCCGTCAAGATGAGCTGCAAGG
CTTCCGGCTATACATTTACTCGTTACACAATGCATTGGGTCAAGCAGAG
GCCCGGTCAAGGTTTAGAGTGGATCGGATATATCAACCCTTCCCGGGGC
TACACCAACTATAACCAAAAGTTCAAGGATAAAGCCACTTTAACCACTG
ACAAGAGCTCCTCCACCGCCTACATGCAGCTGTCCTCTTTAACCAGCGA
GGACTCCGCTGTTTACTACTGCGCTAGGTATTACGACGACCACTACTGT
TTAGACTATTGGGGACAAGGTACCACTTTAACCGTCAGCAGCTCCGGCA
CCACCAATACCGTGGCCGCTTATAACCTCACATGGAAGAGCACCAACTT
CAAGACAATTCTGGAATGGGAACCCAAGCCCGTCAATCAAGTTTACACC
GTGCAGATCTCCACCAAATCCGGAGACTGGAAGAGCAAGTGCTTCTACA
CAACAGACACCGAGTGTGATTTAACCGACGAAATCGTCAAGGACGTCAA
GCAAACCTATCTGGCTCGGGTCTTTTCCTACCCCGCTGGCAATGTCGAG
TCCACCGGCTCCGCTGGCGAGCCTCTCTACGAGAATTCCCCCGAATTCA
CCCCTTATTTAGAGACCAATTTAGGCCAGCCTACCATCCAGAGCTTCGA
GCAAGTTGGCACCAAGGTGAACGTCACCGTCGAGGATGAAAGGACTTTA
GTGCGGCGGAATAACACATTTTTATCCCTCCGGGATGTGTTCGGCAAAG
ACCTCATCTACACACTGTACTATTGGAAGTCCAGCTCCTCCGGCAAAAA
GACCGCTAAGACCAACACCAACGAGTTTTTAATTGACGTGGACAAAGGC
GAGAACTACTGCTTCAGCGTGCAAGCCGTGATCCCTTCTCGTACCGTCA
ACCGGAAGAGCACAGATTCCCCCGTTGAGTGCATGGGCCAAGAAAAGGG
CGAGTTCCGGGAGGTCCAGCTGCAGCAGAGCGGACCCGAACTCGTGAAA
CCCGGTGCTTCCGTGAAAATGTCTTGTAAGGCCAGCGGATACACCTTCA
CCTCCTATGTGATCCAGTGGGTCAAACAGAAGCCCGGACAAGGTCTCGA
GTGGATCGGCAGCATCAACCCTTACAACGACTATACCAAATACAACGAG
AAGTTTAAGGGAAAGGCTACTTTAACCTCCGACAAAAGCTCCATCACAG
CCTACATGGAGTTCAGCTCTTTAACATCCGAGGACAGCGCTCTGTACTA
TTGCGCCCGGTGGGGCGACGGCAATTACTGGGGACGGGGCACAACACTG
ACCGTGAGCAGCGGAGGCGGAGGCTCCGGCGGAGGCGGATCTGGCGGTG
GCGGCTCCGACATCGAGATGACCCAGTCCCCCGCTATCATGTCCGCCTC
TTTAGGCGAGCGGGTCACAATGACTTGTACAGCCTCCTCCAGCGTCTCC
TCCTCCTACTTCCATTGGTACCAACAGAAACCCGGAAGCTCCCCTAAAC
TGTGCATCTACAGCACCAGCAATCTCGCCAGCGGCGTGCCCCCTAGGTT
TTCCGGAAGCGGAAGCACCAGCTACTCTTTAACCATCTCCTCCATGGAG
GCTGAGGATGCCGCCACCTACTTTTGTCACCAGTACCACCGGTCCCCCA
CCTTCGGAGGCGGCACCAAACTGGAGACAAAGAGG.
```

Exemplary Embodiments of Single-Chain Chimeric Polypeptides-Type B

In some embodiments of any of the single-chain chimeric polypeptides described herein, the first target-binding domain and/or the second target-binding domain can independently bind specifically to an IL-2 receptor (e.g., human IL-2 receptor).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, the first target-binding domain and the second target-binding domain is a soluble human IL-2 protein. A non-limiting example of an IL-2 protein that binds specifically to an IL-2 receptor can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 129)
APTSSSTKKTQLQLEHLLLDLQMILNGINNYKNPKLTRMLTFKFYMPKK
ATELKHLQCLEEELKPLEEVLNLAQSKNFHLRPRDLISNINVIVLELKG
SETTFMCEYADETATIVEFLNRWITFCQSIISTLT.
```

In some embodiments, an IL-2 protein that binds specifically to an IL-2 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 246)
GCACCTACTTCAAGTTCTACAAAGAAAACACAGCTACAACTGGAGCATT
TACTGCTGGATTTACAGATGATTTTGAATGGAATTAATAATTACAAGAA
TCCCAAACTCACCAGGATGCTCACATTTAAGTTTTACATGCCCAAGAAG
GCCACAGAACTGAAACATCTTCAGTGTCTAGAAGAAGAACTCAAACCTC
TGGAGGAAGTGCTAAATTTAGCTCAAAGCAAAAACTTTCACTTAAGACC
CAGGGACTTAATCAGCAATATCAACGTAATAGTTCTGGAACTAAAGGGA
TCTGAAACAACATTCATGTGTGAATATGCTGATGAGACAGCAACCATTG
TAGAATTTCTGAACAGATGGATTACCTTTTGTCAAAGCATCATCTCAAC
ACTAACT.
```

In some embodiments, an IL-2 protein that binds specifically to an IL-2 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 247)
GCCCCCACCTCCTCCTCCACCAAGAAGACCCAGCTGCAGCTGGAGCATT

TACTGCTGGATTTACAGATGATTTTAAACGGCATCAACAACTACAAGAA

CCCCAAGCTGACTCGTATGCTGACCTTCAAGTTCTACATGCCCAAGAAG

GCCACCGAGCTGAAGCATTTACAGTGTTTAGAGGAGGAGCTGAAGCCCC

TCGAGGAGGTGCTGAATTTAGCCCAGTCCAAGAATTTCCATTTAAGGCC

CCGGGATTTAATCAGCAACATCAACGTGATCGTTTTAGAGCTGAAGGGC

TCCGAGACCACCTTCATGTGCGAGTACGCCGACGAGACCGCCACCATCG

TGGAGTTTTTAAATCGTTGGATCACCTTCTGCCAGTCCATCATCTCCAC

TTTAACC.

In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 248)
APTSSSTKKTQLQLEHLLLDLQMILNGINNYKNPKLTRMLTFKFYMPKK

ATELKHLQCLEEELKPLEEVLNLAQSKNFHLRPRDLISNINVIVLELKG

SETTFMCEYADETATIVEFLNRWITFCQSIISTLTSGTTNTVAAYNLTW

KSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPT

IQSFEQVGTKVNVTVEDERTLVRRNNTFLSLRDVFGKDLIYTLYYWKSS

SSGKKTAKTNTNEFLIDVDKGENYCFSVQAVIPSRTVNRKSTDSPVECM

GQEKGEFREAPTSSSTKKTQLQLEHLLLDLQMILNGINNYKNPKLTRML

TFKFYMPKKATELKHLQCLEEELKPLEEVLNLAQSKNFHLRPRDLISNI

NVIVLELKGSETTFMCEYADETATIVEFLNRWITFCQSIISTLT.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 249)
GCCCCCACCTCCTCCTCCACCAAGAAGACCCAGCTGCAGCTGGAGCATT

TACTGCTGGATTTACAGATGATTTTAAACGGCATCAACAACTACAAGAA

-continued

CCCCAAGCTGACTCGTATGCTGACCTTCAAGTTCTACATGCCCAAGAAG

GCCACCGAGCTGAAGCATTTACAGTGTTTAGAGGAGGAGCTGAAGCCCC

TCGAGGAGGTGCTGAATTTAGCCCAGTCCAAGAATTTCCATTTAAGGCC

CCGGGATTTAATCAGCAACATCAACGTGATCGTTTTAGAGCTGAAGGGC

TCCGAGACCACCTTCATGTGCGAGTACGCCGACGAGACCGCCACCATCG

TGGAGTTTTTAAATCGTTGGATCACCTTCTGCCAGTCCATCATCTCCAC

TTTAACCAGCGGCACAACCAACACAGTCGCTGCCTATAACCTCACTTGG

AAGAGCACCAACTTCAAAACCATCCTCGAATGGGAACCCAAACCCGTTA

ACCAAGTTTACACCGTGCAGATCAGCACCAAGTCCGGCGACTGGAAGTC

CAAATGTTTCTATACCACCGACACCGAGTGCGATCTCACCGATGAGATC

GTGAAAGATGTGAAACAGACCTACCTCGCCCGGGTGTTTAGCTACCCCG

CCGGCAATGTGGAGAGCACTGGTTCCGCTGGCGAGCCTTTATACGAGAA

CAGCCCCGAATTTACCCCTTACCTCGAGACCAATTTAGGACAGCCCACC

ATCCAAAGCTTTGAGCAAGTTGGCACAAAGGTGAATGTGACAGTGGAGG

ACGAGCGGACTTTAGTGCGGCGGAACAACACCTTTCTCAGCCTCCGGGA

TGTGTTCGGCAAAGATTTAATCTACACACTGTATTACTGGAAGTCCTCT

TCCTCCGGCAAGAAGACAGCTAAAACCAACACAAACGAGTTTTTAATCG

ACGTGGATAAAGGCGAAAACTACTGTTTCAGCGTGCAAGCTGTGATCCC

CTCCCGGACCGTGAATAGGAAAAGCACCGATAGCCCCGTTGAGTGCATG

GGCCAAGAAAAGGGCGAGTTCCGGGAGGCACCTACTTCAAGTTCTACAA

AGAAAACACAGCTACAACTGGAGCATTTACTGCTGGATTTACAGATGAT

TTTGAATGGAATTAATAATTACAAGAATCCCAAACTCACCAGGATGCTC

ACATTTAAGTTTTACATGCCCAAGAAGGCCACAGAACTGAAACATCTTC

AGTGTCTAGAAGAAGAACTCAAACCTCTGGAGGAAGTGCTAAATTTAGC

TCAAAGCAAAAACTTTCACTTAAGACCCAGGGACTTAATCAGCAATATC

AACGTAATAGTTCTGGAACTAAAGGGATCTGAAACAACATTCATGTGTG

AATATGCTGATGAGACAGCAACCATTGTAGAATTTCTGAACAGATGGAT

TACCTTTTGTCAAAGCATCATCTCAACACTAACT.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 250)
MKWVTFISLLFLFSSAYSAPTSSSTKKTQLQLEHLLLDLQMILNGINNY

KNPKLTRMLTFKFYMPKKATELKHLQCLEEELKPLEEVLNLAQSKNFHL

RPRDLISNINVIVLELKGSETTFMCEYADETATIVEFLNRWITFCQSII

STLTSGTTNTVAAYNLTWKSTNFKTILEWEPKPVNQVYTVQISTKSGDW

KSKCFYTTDTECDLTDEIVKDVKQTYLARVFSYPAGNVESTGSAGEPLY

ENSPEFTPYLETNLGQPTIQSFEQVGTKVNVTVEDERTLVRRNNTFLSL

-continued

RDVFGKDLIYTLYYWKSSSSGKKTAKTNTNEFLIDVDKGENYCFSVQAV
IPSRTVNRKSTDSPVECMGQEKGEFREAPTSSSTKKTQLQLEHLLLDLQ
MILNGINNYKNPKLTRMLTFKFYMPKKATELKHLQCLEEELKPLEEVLN
LAQSKNFHLRPRDLISNINVIVLELKGSETTFMCEYADETATIVEFLNR
WITFCQSIISTLT.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 251)
ATGAAGTGGGTGACCTTCATCAGCCTGCTGTTCCTGTTCTCCAGCGCCT
ACTCCGCCCCCACCTCCTCCTCCACCAAGAAGACCCAGCTGCAGCTGGA
GCATTTACTGCTGGATTTACAGATGATTTTAAACGGCATCAACAACTAC
AAGAACCCCAAGCTGACTCGTATGCTGACCTTCAAGTTCTACATGCCCA
AGAAGGCCACCGAGCTGAAGCATTTACAGTGTTTAGAGGAGGAGCTGAA
GCCCCTCGAGGAGGTGCTGAATTTAGCCCAGTCCAAGAATTTCCATTTA
AGGCCCCGGGATTTAATCAGCAACATCAACGTGATCGTTTTAGAGCTGA
AGGGCTCCGAGACCACCTTCATGTGCGAGTACGCCGACGAGACCGCCAC
CATCGTGGAGTTTTTAAATCGTTGGATCACCTTCTGCCAGTCCATCATC
TCCACTTTAACCAGCGGCACAACCAACACAGTCGCTGCCTATAACCTCA
CTTGGAAGAGCACCAACTTCAAAACCATCCTCGAATGGGAACCCAAACC
CGTTAACCAAGTTTACACCGTGCAGATCAGCACCAAGTCCGGCGACTGG
AAGTCCAAATGTTTCTATACCACCGACACCGAGTGCGATCTCACCGATG
AGATCGTGAAAGATGTGAAACAGACCTACCTCGCCCGGGTGTTTAGCTA
CCCCGCCGGCAATGTGGAGAGCACTGGTTCCGCTGGCGAGCCTTTATAC
GAGAACAGCCCCGAATTTACCCCTTACCTCGAGACCAATTTAGGACAGC
CCACCATCCAAAGCTTTGAGCAAGTTGGCACAAAGGTGAATGTGACAGT
GGAGGACGAGCGGACTTTAGTGCGGCGGAACAACACCTTTCTCAGCCTC
CGGGATGTGTTCGGCAAAGATTTAATCTACACACTGTATTACTGGAAGT
CCTCTTCCTCCGGCAAGAAGACAGCTAAAACCAACACAAACGAGTTTTT
AATCGACGTGGATAAAGGCGAAAACTACTGTTTCAGCGTGCAAGCTGTG
ATCCCCTCCCGGACCGTGAATAGGAAAAGCACCGATAGCCCCGTTGAGT
GCATGGGCCAAGAAAAGGGCGAGTTCCGGGAGGCACCTACTTCAAGTTC
TACAAAGAAAACACAGCTACAACTGGAGCATTTACTGCTGGATTTACAG
ATGATTTTGAATGGAATTAATAATTACAAGAATCCCAAACTCACCAGGA
TGCTCACATTTAAGTTTTACATGCCCAAGAAGGCCACAGAACTGAAACA
TCTTCAGTGTCTAGAAGAAGAACTCAAACCTCTGGAGGAAGTGCTAAAT
TTAGCTCAAAGCAAAAACTTTCACTTAAGACCCAGGGACTTAATCAGCA

-continued

ATATCAACGTAATAGTTCTGGAACTAAAGGGATCTGAAACAACATTCAT
GTGTGAATATGCTGATGAGACAGCAACCATTGTAGAATTTCTGAACAGA
TGGATTACCTTTTGTCAAAGCATCATCTCAACACTAACT.

EXAMPLES

The invention is further described in the following examples, which do not limit the scope of the invention described in the claims.

Example 1. Screening of Anti-CD26 scFv Clones

A plate of scFv clones were selected and their binding to CD26, Fc, and proA/L were tested. Controls include binding to Fc (IgG) representing non-specific binding and binding to proA/L (Protein A/L) representing detection of properly folded scFv.

For the Fc assays, the scFvs were tested to determine whether they bind specifically to the Fc portion of an antibody. The CD26 binding assays were performed using a CD26-Fc fusion protein, and therefore, the Fc assay was performed to ensure that each scFv does not bind specifically to the Fc portion of an antibody.

The proA/L assay is performed to determine whether each scFv has an intact structure with six CDRs and framework regions. The assay utilizes a proA and proL mixture.

DNA was also prepared for the scFv constructs and was sent for DNA sequencing to determine light chain (LC)/heavy chain (HC) region sequences (Figure. 1).

Example 2. Analysis of DNA Sequences of Selected scFvs

The DNA sequence of each selected clone was translated into an amino acid sequence and the light chain and heavy chain variable domain sequences were determined. The light chain (LC) and heavy chain (HC) amino acid sequences were analyzed to determine unique clone sequences and unique clone numbers. Then, the unique clone sequences were compared with their binding characteristics.

As a result, five unique clones with binding were identified (CD26-01D, CD26-04A, CD26-10B, CD26-12D, and CD26-03B). Sequencing results indicate that the light chain and heavy chain sequences for the five unique clones were intact and the sequences for the CDR-L1, CDR-L2, CDR-L3, CDR-H1, CDR-H2, and CDR-H3 were determined to be unique from each other (FIG. 2).

Complete scFv clone sequences were also converted into amino acid sequences and the complete scFv sequences are listed below, where each lower case x is used to indicate an amino acid in the hinge region of the scFv sequences linking the light chain variable domain and the heavy chain variable domain.

CD26-01D scFv amino acid sequence
(SEQ ID NO: 108)
DIQMTQSPSSLSASVGDRVTITCRASQDVNSNVAWYQQKPGKAPKLLIF
GSGGLYSGVPSRFSGSGSGTDFTLTISSLQPEDFATYYCQQYSSYPLTF
GQGTKVETKRxxxxxxxxxxxxxxxxxxEVQLVESGGGLVQPGGSLRLS -continued

CAASGFTINDSYIHWVRQAPGKGLEWVAWIWPYGGFTYYADSVKGRFTI

SADTSKNTAYLQMNSLRAEDTAVYYCARFLGSSSIMDYWGQGTLVTVSS

ASAA

CD26-04A scFv amino acid sequence (SEQ ID NO: 109)

DIQMTQSPSSLSASVGDRVTITCRASQDVSGGVAWYQQKPGKAPKLLIY

GTSGLYSGVPSRFSGSGSGTDFTLTISSLQPEDFATYYCQQGGDWPITF

GQGTKVEIKRxxxxxxxxxxxxxxxxxxEVQLVESGGGLVQPGGSLRLS

CAASGFAINNYSIHWVRQAPGKGLEWVASIWPYGGFTSYADSVKGRFTI

SADTSKNTAYLQMNSLRAEDTAVYYCARFFSSYGDMDYWGQGTLVTVSS

ASAA

CD26-10B scFv amino acid sequence (SEQ ID NO: 110)

DIQMTQSPSSLSASVGDRVTITCRASQDVWGYVAWYQQKPGKAPKLLIF

ASGALYSGVPSRFSGSGSGTDFTLTISSLQPEDFATYYCQQYFNWPITF

GQGTKVEIKRxxxxxxxxxxxxxxxxxxEVQLVESGGGLVQPGGSLRLS

CAASGFTISDYSIHWVRQAPGKGLEWVASIWPYGGFTSYADSVKGRFTI

SADTSKNTAYLQMNSLRAEDTAVYYCARFHSSSGDMDYWGQGTLVTVSS

ASAA

CD26-12D scFv amino acid sequence (SEQ ID NO: 111)

DIQMTQSPSSLSASVGDRVTITCRASQDVYSWVAWYQQKPGKAPKLLIY

GPGSLYSGVPSRFSGSGSGTDFTLTISSLQPEDFATYYCQQYYNYPLTF

GQGTKVEIKRxxxxxxxxxxxxxxxxxxEVQLVESGGGLVQPGGSLRLS

CAASGFTINSSYIHWVRQAPGKGLEWVAGIGPYWGFTSYADSVKGRFTI

SADTSKNTAYLQMNSLRAEDTAVYYCARFYSSYGFMDYWGQGTLVTVSS

ASAA

CD26-03B scFv amino acid sequence (SEQ ID NO: 112)

DIQMTQSPSSLSASVGDRVTITCRASQDVYYFVAWYQQKPGKAPKLLIS

WPTGLYSGVPSRFSGSGSGTDFTLTISSLQPEDFATYYCQQYFSYPITF

GQGTKVEIKRxxxxxxxxxxxxxxxxxxEVQLVESGGGLVQPGGSLRLS

CAASGFTIGNSYIHWVRQAPGKGLEWVAGIGPYWGFTSYADSVKGRFTI

SADTSKNTAYLQMNSLRAEDTAVYYCARFNGSSGFMDYWGQGTLVTVSS

ASAA

Example 3. Perform Serial Dilution of Each Unique Binding scFv Clone

Figure 4:
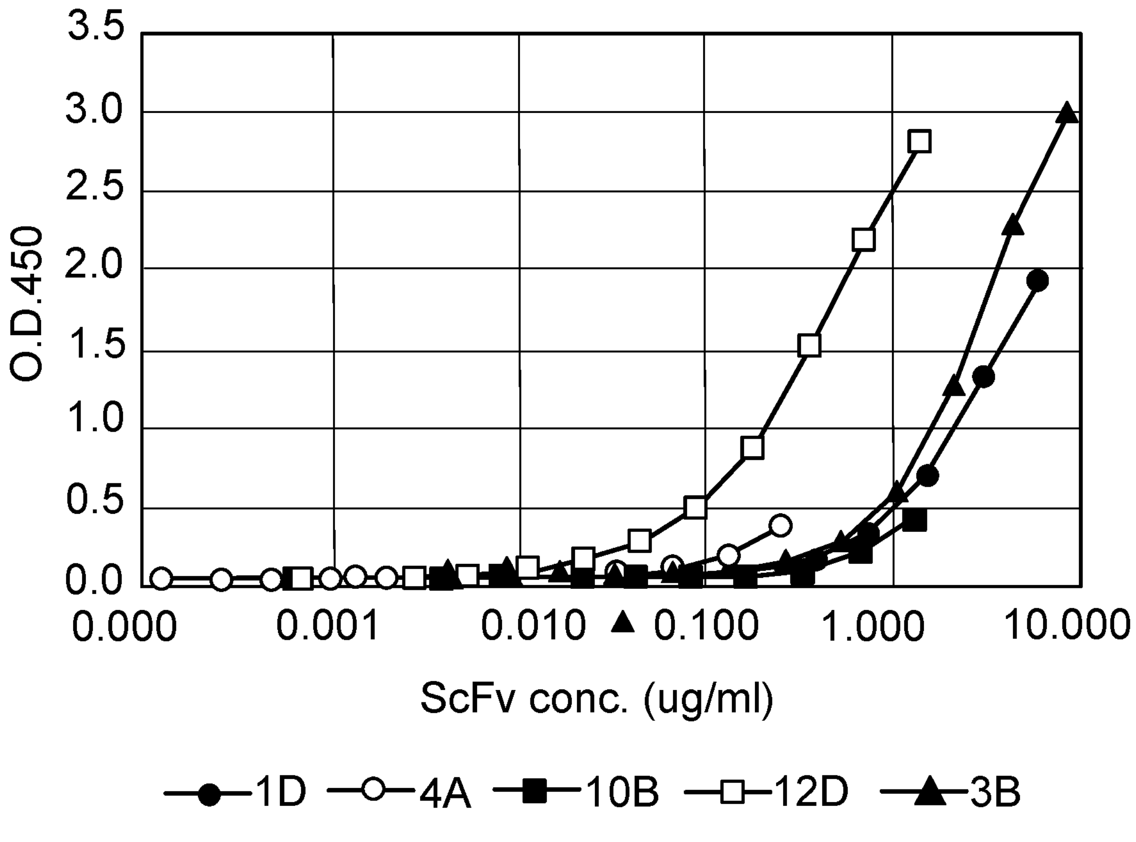
FIG. 4 shows binding of scFvs with CD26 corrected for concentration, where the concentration of the scFvs was determined and the ELISA binding data was corrected for concentration.

The relative binding affinity of the five scFv clones described in Example 2 was also assessed using serial dilution of the scFv supernatants. The supernatants were diluted ⅓ each time for 7 times and their binding affinity was determined using an ELISA assay (FIG. 3). The concentrations of the scFvs were also determined and ELISA binding data was corrected for the concentration of the individual scFvs (FIG. 4).

Example 4. Identification of Additional Anti-CD26 scFvs

Figure 6:
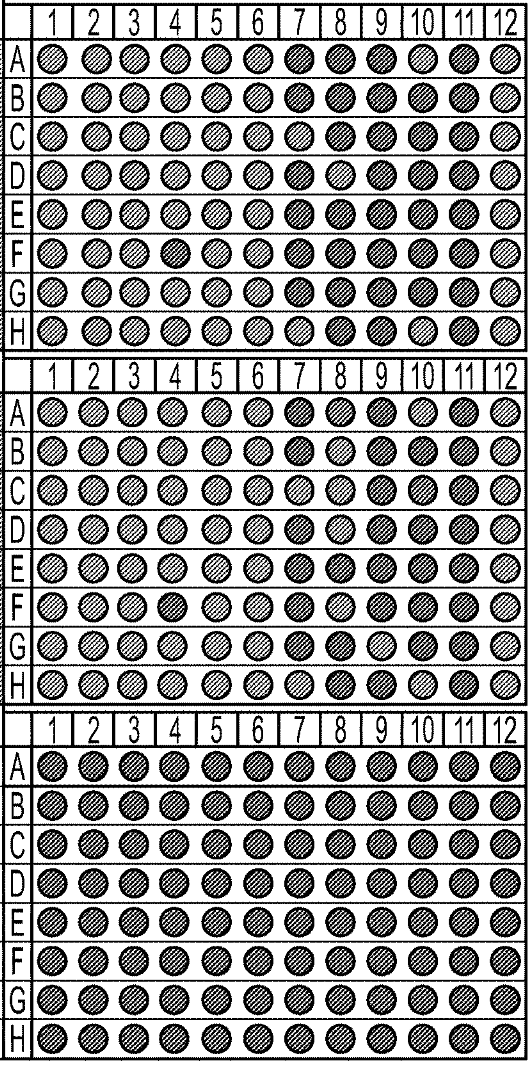
FIG. 6 shows screening of CD26-binding scFvs in a YCM screen, where scFv clones CD26-01F, CD26-01G, and CD26-07H are shown in circled spots.

Additional library screening was performed with new plate of scFv clones where additional clones were selected and their binding to CD26, Fc, and proA/L were tested (FIGS. 5 and 6). Supernatants were collected and tested using an ELISA to determine binding to CD26-Fc. Assay controls were conducted to assess non-specific binding to Fc (IgG) and binding to proA/L (Protein A/L) demonstrating proper folding of the scFv (as described in Example 1). In addition, DNA encoding each selected scFv was sent for DNA sequencing to determine light chain (LC)/heavy chain (HC) variable domain sequences.

Sequencing was conducted to determine the sequences of each selected scFv. ScFvs were also analyzed for how many times they were selected based on the ELISA results. ScFv clones 03G and 04E were selected and scFv clones 01F, 01G, and 07H were selected (FIG. 6) for further analysis.

Example 5. Determine DNA Sequences of Each Additional scFv Clone

The DNA sequence of each clone was translated into an amino acid sequence and the light chain and heavy chain variable domain sequences were determined. The light chain (LC) and heavy chain (HC) variable domain amino acid sequences were analyzed to determine unique clone sequences and unique clone numbers. Then, the unique clone sequences were compared with their binding characteristics to report final binder sequences.

As a result, five additional unique clones with anti-CD26 binding activity were identified (CD26-07H, CD26-01G, CD26-04E, CD26-03G, and CD26-01F). Sequencing results indicate that the light chain and heavy chain variable domains for the five unique clones are intact and the sequences for the CDR-L1, CDR-L2, CDR-L3, CDR-H1, CDR-H2, and CDR-H3 regions are unique from each other (FIG. 7).

Complete scFv clone sequences were also converted into amino acid sequences and the complete scFv sequences are listed below. The front portion of the sequence is the light chain (LC) variable domain (underlined), and the terminal portion of the sequence the heavy chain (HC) variable domain (underlined). The LC and HC variable domains are linked to each other with linker sequence, which is shown with place-holding Xs.

CD26-03G scFv (SEQ ID NO: 113)

DIQMTQSPSSLSASVGDRVTITCRASQDVSSSVAWYQQKPGKAPKLLIS

YPGWLYSGVPSRFSGSGSGTDFTLTISSLQPEDFATYYCQQFGDFPMTF

GQGTKVEIKRxxxxxxxxxxxxEVQLVESGGGLVQPGGSLRLSCAASGF

TIGNYGIHWVRQAPGKGLEWVAWIGPYGGYTFYADSVKGRFTISADTSK

NTAYLQMNSLRAEDTAVYYCARFNNLLWNGMDYWGQGTLVTVSSAS

CD26-04E scFv (SEQ ID NO: 114)

DIQMTQSPSSLSASVGDRVTITCRASQDVNDGVAWYQQKPGKAPKLLIY
WASYLYSGVPSRFSGSGSGTDFTLTISSLOPEDFATYYCQQSWNFPLTF
GQGTKVEIKRxxxxxxxxxxxxxxxxxxEVQLVESGGGLVQPGGSLRLS
CAASGFTINDGFIHWVRQAPGKGLEWVAGIWPFGGSTSYADSVKGRFTI
SADTSKNTAYLQMNSLRAEDTAVYYCARFDVVDWGVMDYWGQGTLVTVS
SAS CD26-01F scFv (SEQ ID NO: 115)

DIQMTQSPSSLSASVGDRVTITCRASQDVWGYVAWYQQKPGKAPKLLIF
SSRSLYSGVPSRFSGSGSGTDFTLTISSLQPEDFATYYCQQYFNWPITF
GQGTKVEIKRxxxxxxxxxxxxxxxxxxEVQLVESGGGLVQPGGSLRLS
CAASGFTISDYSIHWVRQAPGKGLEWVASIWPYGGFTSYADSVKGRFTI
SADTSKNTAYLQMNSLRAEDTAVYYCARFHSSSGDMDYWGQGTLVTVSS
AS CD26-01G scFv (SEQ ID NO: 116)

DIQMTQSPSSLSASVGDRVTITCRASQDVNNSVAWYQQKPGKAPKLLIF
SPTGLYSGVPSRFSGSGSGTDFTLTISSLQPEDFATYYCQQYFDFPLTF
GQGTKVEIKRxxxxxxxxxxxxxxxxxxEVQLVESGGGLVQPGGSLRLS
CAASGFTIGNYGIHWVRQAPGKGLEWVAWIGPSGGYTFYADSVKGRFTI
SADTSKNTAYLQMNSLRAEDTAVYYCARFDVHGFHGMDYWGQGTLVTVS
SAS CD26-07H scFv amino acid sequence (SEQ ID NO: 117)

DIQMTQSPSSLSASVGDRVTITCKSNQNLLYSHGRTYLNWYQQKPGKAP
KLLIFGTSHLYSGVPSRFSGSGSGTDFTLTISSLQPEDFATYYCYQGYH
VPFTFGQGTKVEIKRxxxxxxxxxxxxxxxEVQLVESGGGLVQPGGSLR
LSCKASGYTFARFGMYWVRQAPGKGLEWVAFIAPNHGYTFYADSVKGRF
TISADTSKNTAYLQMNSLRAEDTAVYYCARGHWYHGYMDYWGQGTLVTV
SSAS

Example 6. CD26-Binding of Anti-CD26 Antibodies

Anti-CD26 IgG1 monoclonal antibodies were constructed based on the scFv sequences provided above in Example 2. The CD26-binding of anti-CD26 monoclonal antibodies was determined with ELISA using either a human CD26-Fc fusion protein or goat anti-human IgG.

The CD26-Fc sequences were obtained from the UniProt website and DNA encoding these sequences was synthesized by Genewiz. The construct was made linking the C-terminal of CD26 sequence (N29-P766) with human IgG1 Fc. The nucleic acid and protein sequences of the construct are shown below.

The nucleic acid sequence of the CD26-Fc construct (including signal peptide sequence) is as follows (SEQ ID NO: 118):

(Signal peptide)

ATGAAGTGGGTGACCTTCATCAGCCTGCTGTTCCTGTTCTCCAGCGCCT
ACTCC (human CD26 N29-P766)

AACAAAGGCACAGATGATGCTACAGCTGACAGTCGCAAAACTTACACTC
TAACTGATTACTTAAAAAATACTTATAGACTGAAGTTATACTCCTTAAG
ATGGATTTCAGATCATGAATATCTCTACAAACAAGAAAATAATATCTTG
GTATTCAATGCTGAATATGGAAACAGCTCAGTTTTCTTGGAGAACAGTA
CATTTGATGAGTTTGGACATTCTATCAATGATTATTCAATATCTCCTGA
TGGGCAGTTTATTCTCTTAGAATACAACTACGTGAAGCAATGGAGGCAT
TCCTACACAGCTTCATATGACATTTATGATTTAAATAAAAGGCAGCTGA
TTACAGAAGAGAGGATTCCAAACAACACACAGTGGGTCACATGGTCACC
AGTGGGTCATAAATTGGCATATGTTTGGAACAATGACATTTATGTTAAA
ATTGAACCAAATTTACCAAGTTACAGAATCACATGGACGGGGAAAGAAG
ATATAATATATAATGGAATAACTGACTGGGTTTATGAAGAGGAAGTCTT
CAGTGCCTACTCTGCTCTGTGGTGGTCTCCAAACGGCACTTTTTTAGCA
TATGCCCAATTTAACGACACAGAAGTCCCACTTATTGAATACTCCTTCT
ACTCTGATGAGTCACTGCAGTACCCAAAGACTGTACGGGTTCCATATCC
AAAGGCAGGAGCTGTGAATCCAACTGTAAAGTTCTTTGTTGTAAATACA
GACTCTCTCAGCTCAGTCACCAATGCAACTTCCATACAAATCACTGCTC
CTGCTTCTATGTTGATAGGGGATCACTACTTGTGTGATGTGACATGGGC
AACACAAGAAAGAATTTCTTTGCAGTGGCTCAGGAGGATTCAGAACTAT
TCGGTCATGGATATTTGTGACTATGATGAATCCAGTGGAAGATGGAACT
GCTTAGTGGCACGGCAACACATTGAAATGAGTACTACTGGCTGGGTTGG
AAGATTTAGGCCTTCAGAACCTCATTTTACCCTTGATGGTAATAGCTTC
TACAAGATCATCAGCAATGAAGAAGGTTACAGACACATTTGCTATTTCC
AAATAGATAAAAAAGACTGCACATTTATTACAAAAGGCACCTGGGAAGT
CATCGGGATAGAAGCTCTAACCAGTGATTATCTATACTACATTAGTAAT
GAATATAAAGGAATGCCAGGAGGAAGGAATCTTTATAAAATCCAACTTA
GTGACTATACAAAAGTGACATGCCTCAGTTGTGAGCTGAATCCGGAAAG
GTGTCAGTACTATTCTGTGTCATTCAGTAAAGAGGCGAAGTATTATCAG
CTGAGATGTTCCGGTCCTGGTCTGCCCCTCTATACTCTACACAGCAGCG
TGAATGATAAAGGGCTGAGAGTCCTGGAAGACAATTCAGCTTTGGATAA
AATGCTGCAGAATGTCCAGATGCCCTCCAAAAAACTGGACTTCATTATT
TTGAATGAAACAAAATTTTGGTATCAGATGATCTTGCCTCCTCATTTTG
ATAAATCCAAGAAATATCCTCTACTATTAGATGTGTATGCAGGCCCATG
TAGTCAAAAAGCAGACACTGTCTTCAGACTGAACTGGGCCACTTACCTT
GCAAGCACAGAAAACATTATAGTAGCTAGCTTTGATGGCAGAGGAAGTG
GTTACCAAGGAGATAAGATCATGCATGCAATCAACAGAAGACTGGGAAC

-continued

```
ATTTGAAGTTGAAGATCAAATTGAAGCAGCCAGACAATTTTCAAAAATG

GGATTTGTGGACAACAAACGAATTGCAATTTGGGGCTGGTCATATGGAG

GGTACGTAACCTCAATGGTCCTGGGATCAGGAAGTGGCGTGTTCAAGTG

TGGAATAGCCGTGGCGCCTGTATCCCGGTGGGAGTACTATGACTCAGTG

TACACAGAACGTTACATGGGTCTCCCAACTCCAGAAGACAACCTTGACC

ATTACAGAAATTCAACAGTCATGAGCAGAGCTGAAAATTTTAAACAAGT

TGAGTACCTCCTTATTCATGGAACAGCAGATGATAACGTTCACTTTCAG

CAGTCAGCTCAGATCTCCAAAGCCCTGGTCGATGTTGGAGTGGATTTCC

AGGCAATGTGGTATACTGATGAAGACCATGGAATAGCTAGCAGCACAGC

ACACCAACATATATATACCCACATGAGCCACTTCATAAAACAATGTTTC

TCTTTACCT

(human IgG1 Fc)
GAGCCGAAATCTTGTGACAAAACTCACACATGCCCACCGTGCCCAGCAC

CTGAACTCCTGGGGGGACCGTCAGTCTTCCTCTTCCCCCCAAAACCCAA

GGACACCCTCATGATCTCCCGGACCCCTGAGGTCACATGCGTGGTGGTG

GACGTGAGCCACGAAGACCCTGAGGTCAAGTTCAACTGGTACGTGGACG

GCGTGGAGGTGCATAATGCCAAGACAAAGCCGCGGGAGGAGCAGTACAA

CAGCACGTACCGTGTGGTCAGCGTCCTCACCGTCCTGCACCAGGACTGG

CTGAATGGCAAGGAGTACAAGTGCAAGGTCTCCAACAAAGCCCTCCCAG

CCCCCATCGAGAAAACCATCTCCAAAGCCAAAGGGCAGCCCCGAGAACC

ACAGGTGTACACCCTGCCCCCATCCCGGGATGAGCTGACCAAGAACCAG

GTCAGCCTGACCTGCCTGGTCAAAGGCTTCTATCCCAGCGACATCGCCG

TGGAGTGGGAGAGCAATGGGCAGCCGGAGAACAACTACAAGACCACGCC

TCCCGTGCTGGACTCCGACGGCTCCTTCTTCCTCTACAGCAAGCTCACC

GTGGACAAGAGCAGGTGGCAGCAGGGGAACGTCTTCTCATGCTCCGTGA

TGCATGAGGCTCTGCACAACCACTACACGCAGAAGAGCCTCTCCCTGTC

TCCTGGTAAA
```

The amino acid sequence of the human CD26-Fc construct (including signal peptide sequence) is as follows (SEQ ID NO: 119):

```
(Signal peptide)
MKWVTFISLLFLFSSAYS

(human CD26 N29-P766)
NKGTDDATADSRKTYTLTDYLKNTYRLKLYSLRWISDHEYLYKQENNIL

VFNAEYGNSSVFLENSTFDEFGHSINDYSISPDGQFILLEYNYVKQWRH

SYTASYDIYDLNKRQLITEERIPNNTQWVTWSPVGHKLAYVWNNDIYVK

IEPNLPSYRITWTGKEDIIYNGITDWVYEEEVFSAYSALWWSPNGTFLA

YAQFNDTEVPLIEYSFYSDESLQYPKTVRVPYPKAGAVNPTVKFFVVNT

DSLSSVTNATSIQITAPASMLIGDHYLCDVTWATQERISLQWLRRIQNY

SVMDICDYDESSGRWNCLVARQHIEMSTTGWVGRFRPSEPHFTLDGNSF

YKIISNEEGYRHICYFQIDKKDCTFITKGTWEVIGIEALTSDYLYYISN

EYKGMPGGRNLYKIQLSDYTKVTCLSCELNPERCQYYSVSFSKEAKYYQ
```

-continued

```
LRCSGPGLPLYTLHSSVNDKGLRVLEDNSALDKMLQNVQMPSKKLDFII

LNETKFWYQMILPPHFDKSKKYPLLLDVYAGPCSQKADTVFRLNWATYL

ASTENIIVASFDGRGSGYQGDKIMHAINRRLGTFEVEDQIEAARQFSKM

GFVDNKRIAIWGWSYGGYVTSMVLGSGSGVFKCGIAVAPVSRWEYYDSV

YTERYMGLPTPEDNLDHYRNSTVMSRAENFKQVEYLLIHGTADDNVHFQ

QSAQISKALVDVGVDFQAMWYTDEDHGIASSTAHQHIYTHMSHFIKQCF

SLP

(human IgG1 Fc)
EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK
```

The CD26-Fc construct was cloned into a modified retrovirus expression vectors as described previously (Hughes et al., Hum. Gene Ther. 16:457-72, 2005), and the expression vectors were transfected into CHO-K1 cells. Expression of the construct in CHO-K1 cells allowed for secretion of the soluble CD26-Fc fusion protein (referred to as CD26-Fc), which can be purified by MabSelect protein A affinity and other chromatography methods.

Figure 8:
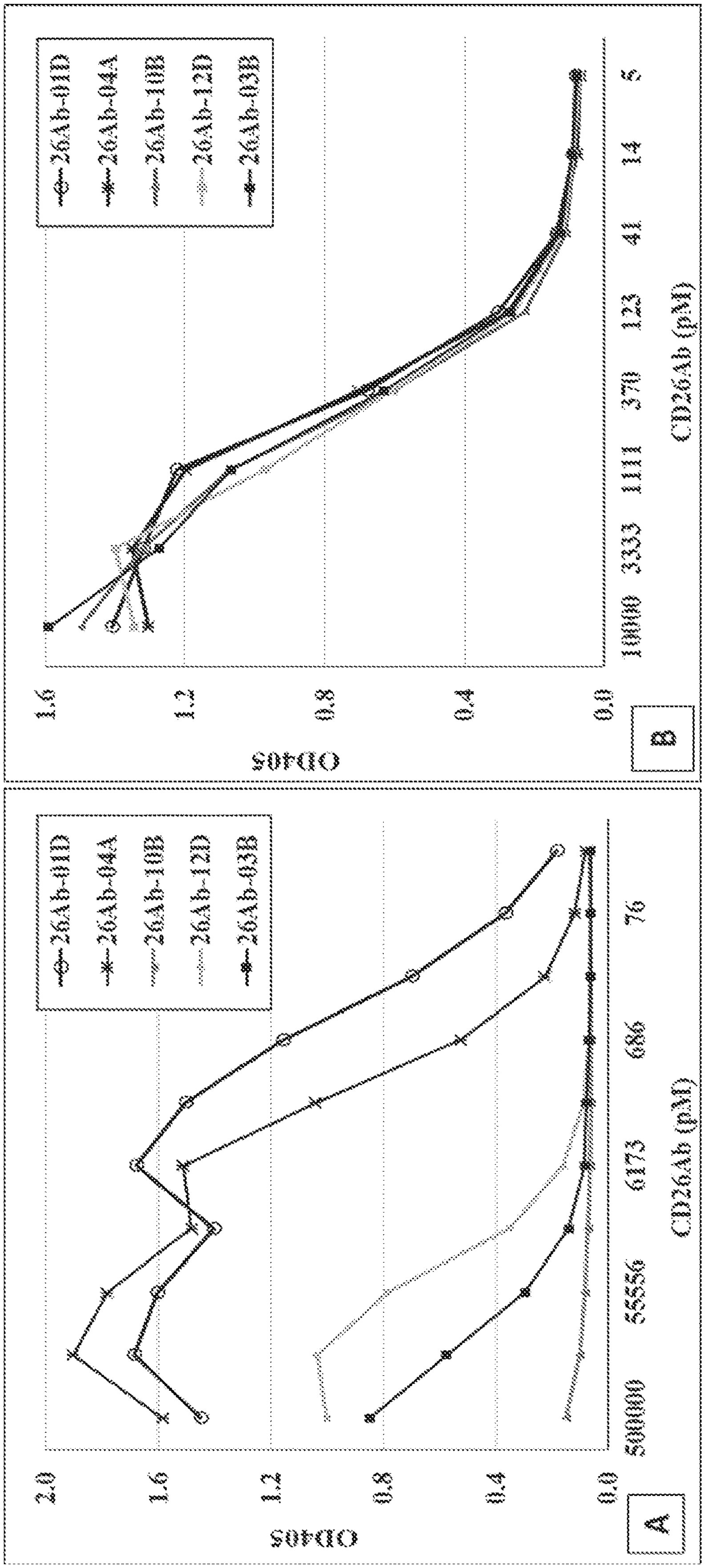
FIG. 8 shows human CD26-binding activity of anti-CD26 monoclonal antibodies. Anti-CD26 IgGIkappa monoclonal antibodies were constructed based on the selected scFv sequences. The CD26-binding of purified anti-CD26 monoclonal antibodies was determined with ELISA using (A) human CD26-Fc fusion protein-coated or (B) goat anti-human IgG-coated 96-well Maxisorp plates. The plates were blocked with blocking buffer. Purified anti-CD26 monoclonal antibodies were diluted in blocking buffer and added in the wells of CD26-Fc or goat anti-human IgG-coated plates. The anti-CD26 monoclonal antibodies were probed with goat anti-human kappa-HRP/ABTS and read by an ELISA plate reader at 405 nM. The results show that CD26Ab-01D and CD26Ab-04A are able to bind to CD26 and CD26Ab-01D has a better binding activity than CD26Ab-04A. CD26Ab-12D and CD26Ab-03B have weak CD26-binding activity. However, CD26Ab-10B has no significant CD26-binding activity.

Human CD26-Fc fusion protein (sequence shown above) or goat anti-human IgG was used to coat 96 well Maxisorp plates. The plates were blocked with blocking buffer. Purified anti-CD26 monoclonal antibodies were diluted in blocking buffer and added in the wells of CD26-Fc (FIG. 8A) or goat anti-human IgG-coated plates (FIG. 8B). The anti-CD26 monoclonal antibodies were probed with goat anti-human kappa-HRP/ABTS and read using an ELISA plate reader at 405 nM. The results show that CD26Ab-01D and CD26Ab-04A are able to bind to the CD26-Fc fusion protein and CD26Ab-01D has a better binding activity than CD26Ab-04A (FIG. 8A). CD26Ab-12D and CD26Ab-03B have weak CD26-binding activity. However, CD26Ab-10B has no significant CD26-binding activity.

Example 7. CD26-Binding of Anti-CD26 Antibodies

Figure 9:
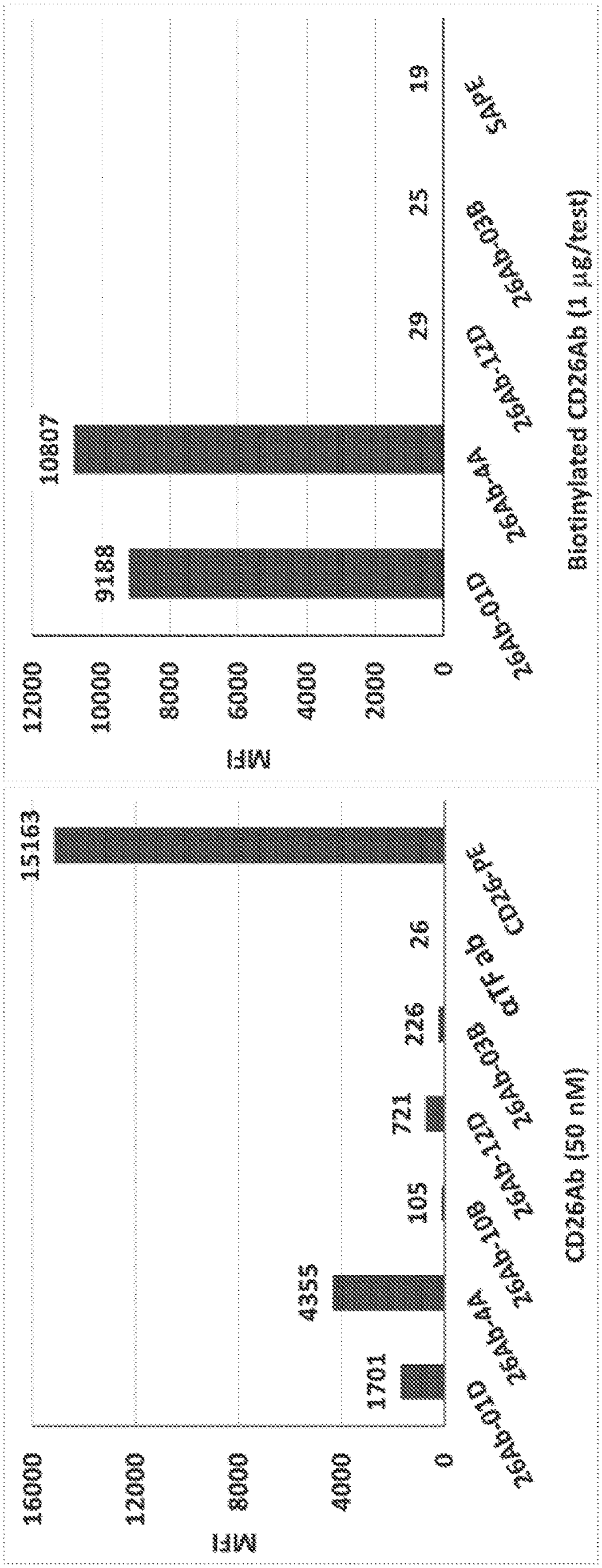
FIG. 9 shows human CD26-binding activity of anti-CD26 monoclonal antibodies. Human CD26-transfected CHO cells were stained with (A) five different anti-CD26 monoclonal antibodies at 50 nM or (B) five different biotinylated anti-CD26 antibodies at 1 μg/test (26Ab-10B had very low production and was not biotinylated) and then probed using goat anti-human IgG-PE for unbiotinylated antibodies or using streptavidin-PE for the biotinylated antibodies. The data was analyzed by BD FACSCelesta with BD FACSDiva Software. Anti-tissue factor antibody (anti-TF Ab) was used as a negative control and PE-conjugated anti-CD26 (BioLegend) was used as a positive control. The results demonstrate that CD26Ab-01D and CD26-04A bind well to cells expressing CD26 and the other three of five antibodies had weaker binding.

Human CD26 binding activity of anti-CD26 monoclonal antibodies was analyzed. Human CD26-transfected CHO cells were stained with 5 clones of anti-CD26 monoclonal antibodies at 50 nM (FIG. 9, left panel) or biotinylated anti-CD26 monoclonal antibodies at 1 μg/test (FIG. 9, right panel) (26Ab-10B had very low production and was not biotinylated) and then probed by goat anti-human IgG-PE for unbiotinylated antibodies or by streptavidin-PE for the biotinylated antibodies. The data was analyzed by BD FACSCelesta with BD FACSDiva Software. Anti-tissue factor antibody (Anti-TF Ab) was used as a negative control and PE-conjugated anti-CD26 (BioLegend) as a positive control. The results demonstrate that CD26Ab-01D and CD26-04A bind to CD26 well and the three tested antibodies have very weak binding (FIG. 9).

Example 8. ADCC Activities of Anti-CD26 Antibodies

Figure 10:
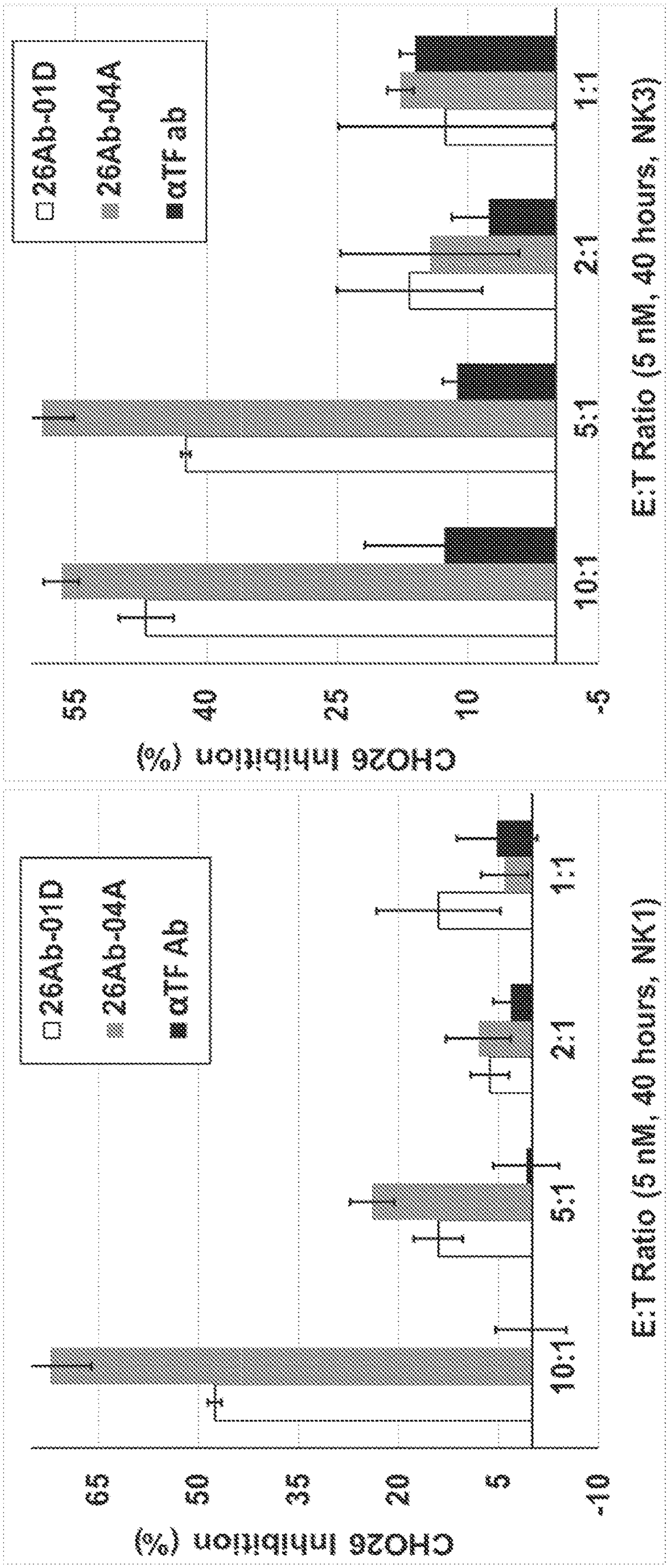
FIG. 10 shows ADCC activity of different anti-CD26 monoclonal antibodies. Human CD26-transfected CHO cells (CHO26) were labeled with CellTrace Violet and used as target cells, and fresh human NK cells (left: donor-1 and right: donor-2) were used as effector cells. The effector cells were plated with violet-labelled target cells at the indicated effector:target (E:T) ratios with 26Ab-01D or 26Ab-04A at a 5 nM concentration. Anti-tissue factor antibody (anti-TF Ab) was used as a control. Target cell inhibition (%) was calculated using a formula: (1-[viable CHO26 cell number in experimental sample/viable CHO26 cell number in the sample without splenocytes])×100 on day 2 as assessed by flow cytometry and represents anti-CD26 antibody-mediated ADCC. The results show CD26Ab-01D- and CD26Ab-04A-dependent and NK cell-mediated cytotoxicity against CD26-positive CHO cells.

ADCC activities of the anti-CD26 monoclonal antibodies were analyzed. Human CD26-transfected CHO cells (CHO26) were labeled with CellTrace Violet and used as target cells, and fresh human NK cells (left: donor-1 and right: donor-2) were used as effector cells. The effector cells were plated with violet-labeled target cells at the indicated effector:target (E:T) ratios with 26Ab-01D or 26Ab-04A at a 5 nM concentration. Anti-tissue factor antibody (Anti-TF Ab) was used as a control. Target cell inhibition (%) was calculated using a formula: (1-viable CHO26 cell number in experimental sample/viable CHO26 cell number in the sample without splenocytes)×100 on day 2 by flow cytometry. The results show CD26Ab-01D- and CD26Ab-04A-dependent and NK cell-mediated cytotoxicity against CD26 positive CHO cells (FIG. 10).

Example 9. Interaction of CD26 and ADA

Figure 11:
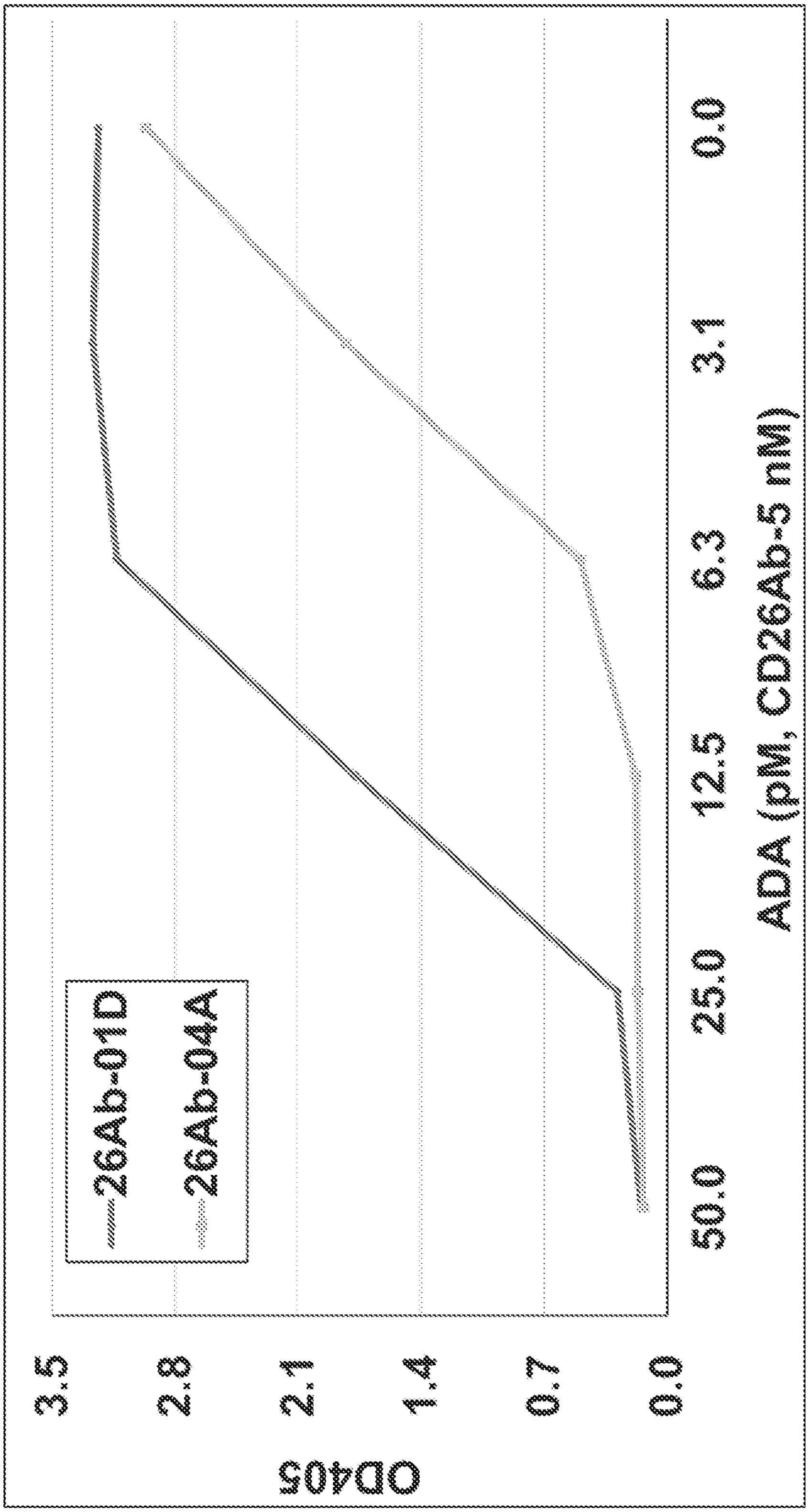
FIG. 11 shows interaction of human CD26 and adenosine deaminase (ADA). Human CD26-Fc fusion protein was used to coat 96-well Maxisorp plate. The plate was blocked with blocking buffer. Human ADA (R&D systems) was diluted in blocking buffer and added to the wells of a CD26-Fc coated plate. Two biotinylated anti-CD26 monoclonal antibodies (CD26Ab-01D and CD26Ab-04A) were added to the plate. The anti-CD26 monoclonal antibodies were probed with SAHRP/ABTS and read by an ELISA plate reader at 405 nM. The results show that ADA was able to block CD26Ab-01D and CD26Ab-04A binding to CD26.

Interaction of human CD26 and adenosine deaminase (ADA) was analyzed. Human CD26-Fc fusion protein (5 μg/mL) was used to coat 96-well Maxisorp plate. The plate was blocked with blocking buffer, 1%-BSA-PBS for 20 minutes. Human ADA (R&D systems) was diluted in blocking buffer and added to the wells of a CD26-Fc coated plate and then two biotinylated anti-CD26 monoclonal antibodies (CD26Ab-01D and CD26Ab-04A) were added in the plate (final concentration 5 nM) for 30 minutes. The anti-CD26 monoclonal antibodies were probed with SAHRP/ABTS and read using an ELISA plate reader at 405 nM. The results show that ADA was able to block CD26Ab-01D and CD26Ab-04A binding to CD26 molecule (FIG. 11).

Example 10. Anti-CD26 CAR Treg Cells

Figure 12:
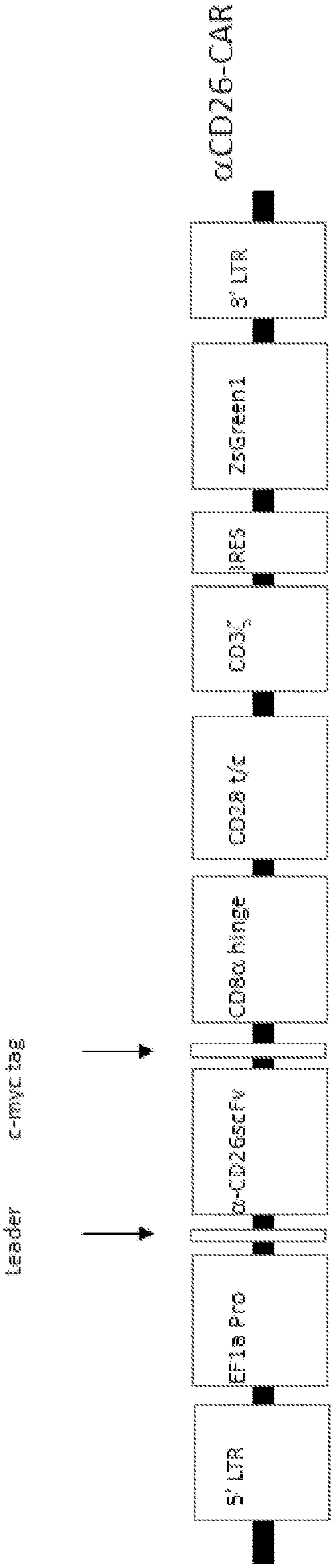
FIG. 12 is a schematic of a nucleic acid encoding an anti-CD26 CAR in a lentiviral vector.

An anti-human CD26 chimerical antigen receptor (CAR) was generated comprising a HC leader, anti-CD26 scFv, c-myc tag, CD8a hinge, CD28 transmembrane/cytoplasmic domain, and CD3 zeta cytoplasmic domain sequences obtained from our own data or the UniProt website and DNA for these sequences was synthesized by Genewiz. Specifically, constructs were made linking the anti-CD26 VL to anti-CD26 VH with a linker to generate a single chain version of anti-CD26 antibody and then directly linking the anti-CD26 scFv sequence to the c-myc tag, CD8a hinge, CD28 transmembrane/cytoplasmic domain, CD3 zeta cytoplasmic domain (FIG. 12). The nucleic acid and protein sequences of a construct comprising anti-CD26 CAR are shown below.

The nucleic acid sequence of the anti-CD26 CAR construct (including signal peptide sequence) is as follows (SEQ ID NO: 252):

```
(Signal peptide)
ATGGACAGACTTACTTCTTCATTCCTGCTCCTGATTGTCCCTGCGTACG

TCTTGTCC

(Human anti-human CD26 antibody VL)
GACATCCAGATGACCCAGTCTCCATCCTCCCTGTCTGCATCTGTAGGAG

ACAGAGTCACCATCACTTGCCGGGCGAGTCAGGACGTGAACTCCAACGT

GGCCTGGTATCAGCAGAAACCAGGGAAAGCCCCTAAGCTCCTGATCTTC

GGCTCCGGCGGCCTGTACAGTGGGGTCCCATCAAGGTTCAGCGGCAGTG

GATCTGGGACAGATTTCACTCTCACTATCAGCAGCCTGCAGCCTGAAGA

TTTTGCAACTTACTATTGTCAGCAGTACTCCTCCTACCCCCTGACGTTC

GGCCAAGGGACCAAGGTGGAAACCAAA
```

-continued

```
(Linker)
GGTGGAGGTGGCAGCGGAGGAGGTGGGTCCGGCGGTGGAGGAAGC

(Human anti-human CD26 antibody VH)
GAGGTGCAGCTGGTGGAGTCTGGGGGAGGCTTGGTCCAGCCTGGGGGGT

CCCTGAGACTCTCCTGTGCAGCCTCTGGATTCACCATCAACGACTCCTA

CATCCACTGGGTCCGCCAGGCTCCAGGGAAGGGGCTGGAGTGGGTGGCC

TGGATCTGGCCCTACGGCGGCTTCACCTACTATGCAGACTCCGTGAAGG

GCCGATTCACCATCTCCGCCGACACCTCCAAGAACACGGCCTATCTGCA

AATGAACAGCCTGAGAGCTGAGGACACGGCTGTGTATTACTGTGCCAGG

TTCCTGGGCTCCTCCTCCATCATGGACTACTGGGGCCAAGGAACCCTGG

TCACCGTCTCCTCAGCC

(Human c-myc tag)
GAGCAGAAGCTGATTAGCGAGGAGGATCTG

(Human CD8α hinge)
GCTTTAAGCAACTCCATCATGTACTTCTCCCACTTCGTGCCCGTTTTTT

TACCCGCTAAGCCCACCACAACCCCCGCTCCCAGACCCCCTACCCCCGC

TCCTACCATCGCCTCCCAGCCTTTATCTTTAAGACCCGAAGCCTCTCGT

CCCGCTGCCGGCGGCGCCGTGCACACAAGGGGTTTAGAC

(Human CD28 transmembrane/cytoplasmic domain)
AAGCCTTTTTGGGTTTTAGTGGTGGTGGGCGGCGTGCTGGCTTGTTACT

CTTTACTGGTGACCGTGGCCTTCATCATCTTCTGGGTTCGTTCCAAGAG

GTCTCGTCTGCTGCACTCCGACTATATGAACATGACCCCTAGGAGGCCC

GGCCCTACCAGAAAACACTATCAGCCCTATGCCCCTCCTCGTGACTTTG

CCGCTTATCGTTCT

(Human CD3 zeta cytoplasmic domain)
CGTGTGAAGTTCTCCAGATCCGCCGATGCCCCCGCTTACCAGCAAGGTC

AAAACCAGCTCTATAACGAGCTGAATTTAGGTCGTAGAGAGGAGTACGA

CGTGCTGGATAAAAGAAGGGGCAGAGACCCCGAAATGGGAGGCAAACCC

CAGAGAAGGAAGAACCCCCAAGAAGGACTGTACAACGAACTGCAGAAGG

ATAAGATGGCCGAGGCCTACTCCGAGATTGGCATGAAAGGCGAGAGGAG

GAGGGGCAAGGGCCATGATGGTTTATACCAAGGTTTATCCACAGCTACA

AAGGACACCTACGACGCTTTACACATGCAAGCTTTACCTCCTAGA
```

The amino acid sequence of the anti-CD26 CAR (including signal peptide sequence) is as follows (SEQ ID NO: 253) (CDRs shown in bold):

(Signal peptide)
MDRLTSSFLLLIVPAYVLS (Human anti-human CD26 antibody $V_L$)
DIQMTQSPSSLSASVGDRVTITCRASQDVNSNVAWYQQKPGKAPKLLIF

GSGGLYSGVPSRFSGSGSGTDFTLTISSLQPEDFATYYCQQYSSYPLTF

GQGTKVETK

-continued (Linker)
GGGGSGGGGSGGGGS (Human anti-human CD26 antibody $V_H$)
EVQLVESGGGLVQPGGSLRLSCAASGFTINDSYIHWVRQAPGKGLEWVA

WIWPYGGFTYYADSVKGRFTISADTSKNTAYLQMNSLRAEDTAVYYCAR

FLGSSSIMDYWGQGTLVTVSSA (Human c-myc tag)
EQKLISEEDL (Human CD8α hinge)
ALSNSIMYFSHFVPVFLPAKPTTTPAPRPPTPAPTIASQPLSLRPEASR

PAAGGAVHTRGLD (Human CD28 transmembrane/cytoplasmic domain)
KPFWVLVVVGGVLACYSLLVTVAFIIFWVRSKRSRLLHSDYMNMTPRRP

GPTRKHYQPYAPPRDFAAYRS (Human CD3 zeta cytoplasmic domain)
RVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTAT

KDTYDALHMQALPPR

The anti-CD26 CAR construct was cloned into a lentivirus expression vector pLVX-EF1a-IRES-ZsGreen1 (Cat #631982, Takara). The expression vector was mixed with *Lenti*-X Packaging Single Shots (Cat #631275, Takara) and transfected into *Lenti*-X 293T cells (Cat #632180, Takara). The lentiviral supernatants from the transfected *Lenti*-X 293T cells were collected after 3 days incubation at 37° C. in a CO2 incubator. An estimated titer of lentivirus was instantly evaluated with the *Lenti*-X GoStix™ Plus (Cat #631280, Takara). The actual lentivirus titers were further evaluated by transduction of *Lenti*-X 293T cells. Human Treg cells were isolated with a Miltenyi human Treg cell isolation kit (Cat #130-094-775, Miltenyi) from donor buffy coat PBMCs. The Treg cells were activated with Dynabeads human T-Activator CD3/CD28 (Cat #11131D, ThermoFisher) overnight, and transduced with the lentivirus carrying anti-CD26 CAR at a MOI of 40 measured by flow cytometry.

Figure 13:
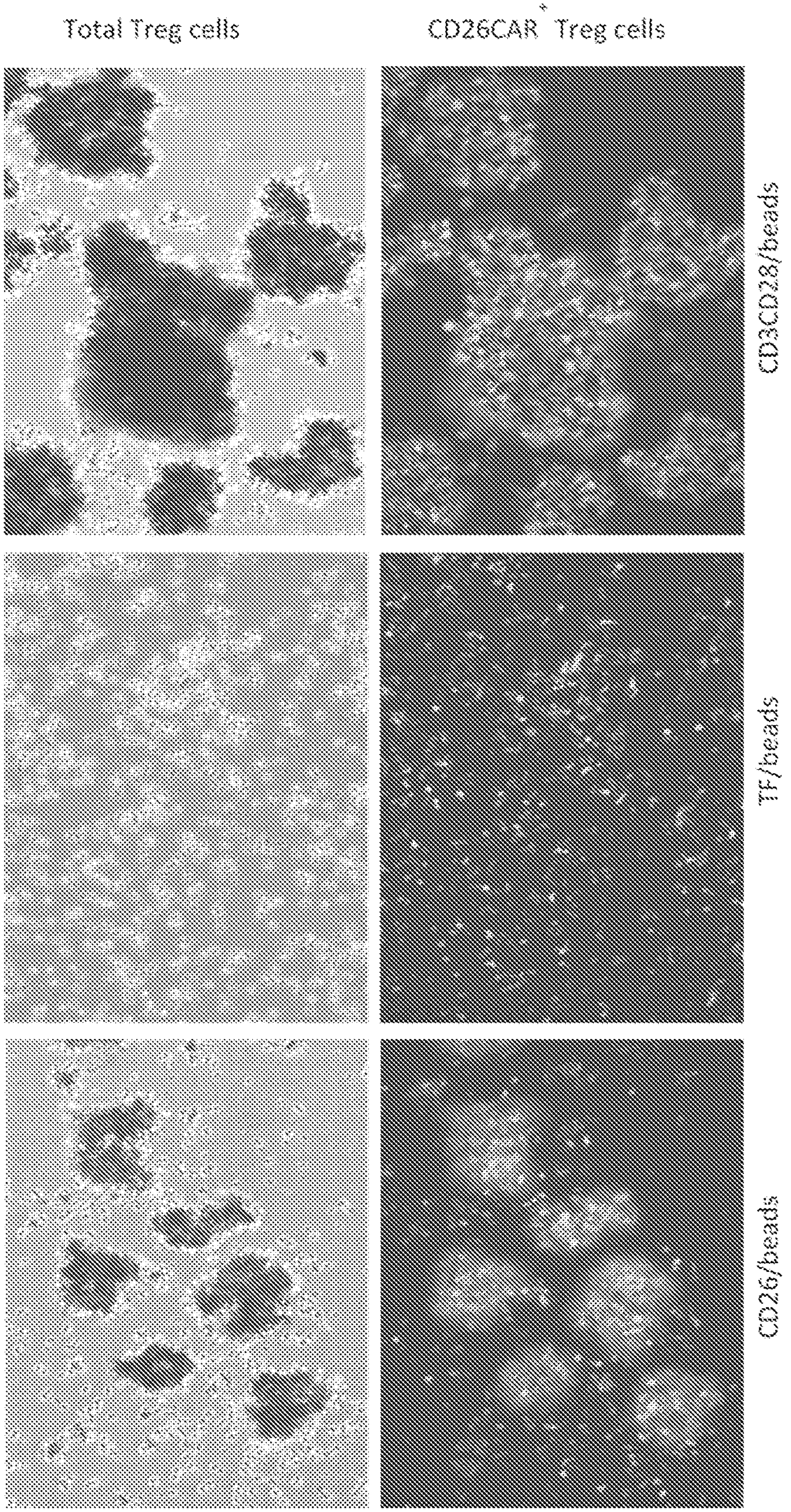
FIG. 13 is a set of images showing total Treg cells and anti-CD26 CAR Treg cells stimulated with the specific antigen (CD26/beads), non-specific antigen (TF/beads), or TCR (CD3/CD28/beads) for 3 days.
Figure 14:
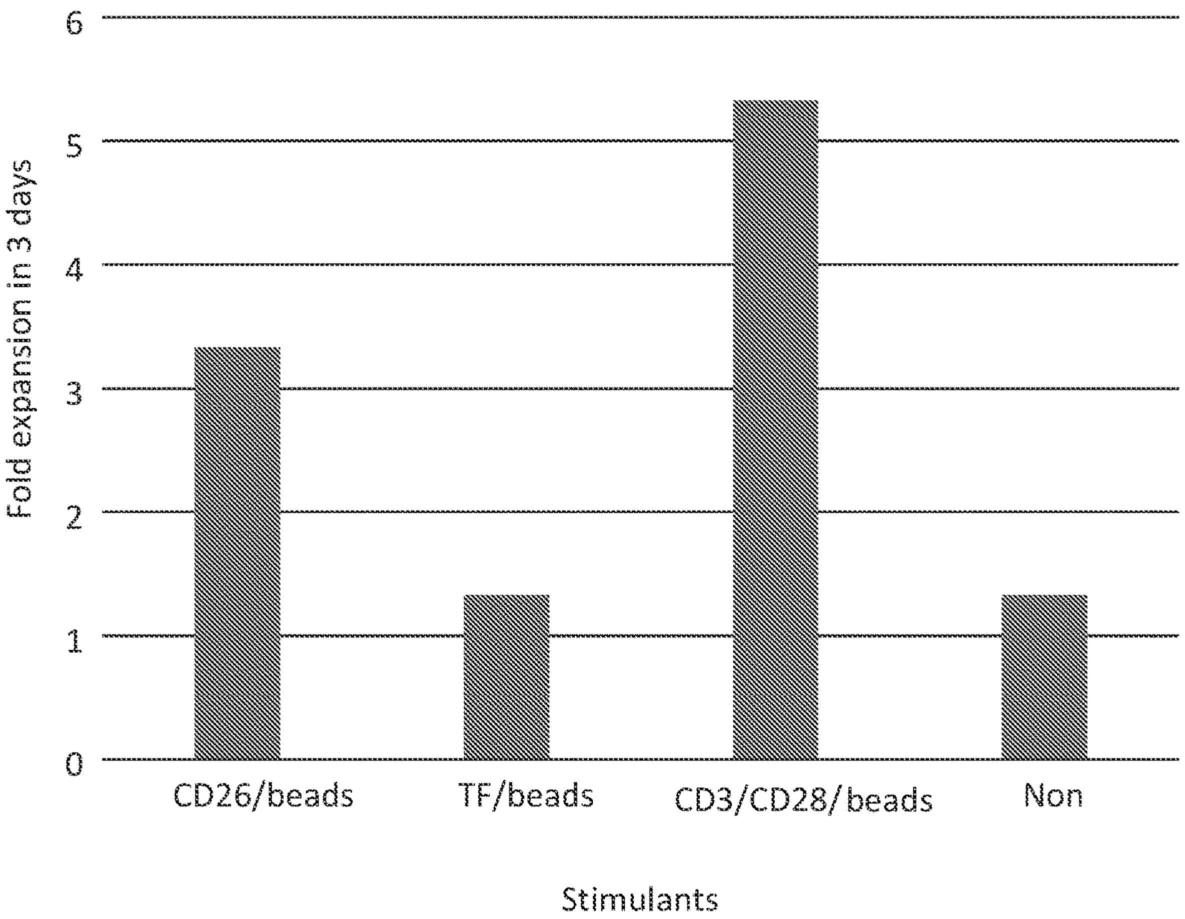
FIG. 14 is a graph showing the fold-expansion of anti-CD26 CAR Treg cells after three days of stimulation with the specific antigen (CD26/beads), non-specific antigen (TF/beads), or TCR (CD3/CD28/beads).

The αCD26 CAR-transduced Treg cells were verified by stimulation with biotinylated CD26-Fc conjugated Dynabeads M280 Streptavidin (Cat #11205D, ThermoFisher). The aCD26 CAR Treg cells were activated and expanded using antigen-specific CD26-beads (3-fold) or through the TCR using CD3/CD28 beads (5-fold), but not by non-specific tissue factor conjugated beads or medium only (FIG. 13 and FIG. 14). FIG. 13 shows images of total Treg cells (upper panels) and anti-CD26 CAR Treg cells (lower panels) stimulated with the specific antigen (CD26/beads), non-specific antigen (TF/beads), or TCR (CD3/CD28/beads) for 3 days, where the αCD26 CAR Treg cells were shown to be activated and expanded using antigen-specific CD26-beads (3-fold, lower left panel) or through the TCR using CD3/CD28 beads (5-fold, lower right panel), but not by non-specific tissue factor conjugated beads (lower middle panel).

Figure 15:
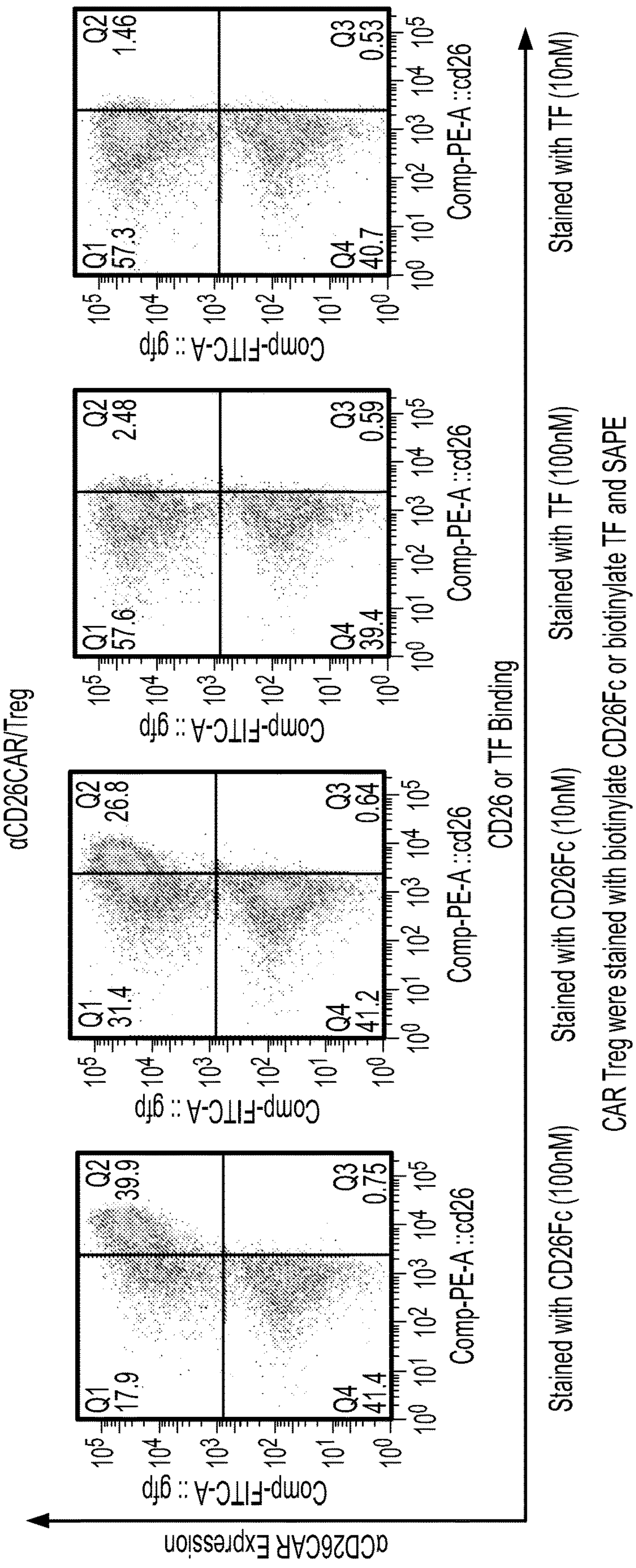
FIG. 15 is a set of fluorescence-assisted cell sorting (FACS) data showing the staining of anti-CD26 CAR Treg cells with CD26-Fc or tissue factor (TF).

To further verify if the anti-CD26 CAR displayed and functioned well on Treg cells, the CAR-transduced Treg cells and un-transduced Treg cells were stained with the specific antigen: biotinylated CD26-Fc or a non-specific antigen: biotinylated tissue factor (TF), and detected by R-Phycoerythrin (PE)-conjugated Streptavidin (Cat #016-110-084, Jackson ImmunoResearch). The αCD26 CAR Treg cells were specifically stained with CD26-Fc at 100 nM and 10 nM but not with TF, suggesting that anti-CD26 CAR was well displayed on the Treg cell surface and functionally interacts with the specific antigen at an affinity over 10 nM (FIG. 15).

Figure 16:
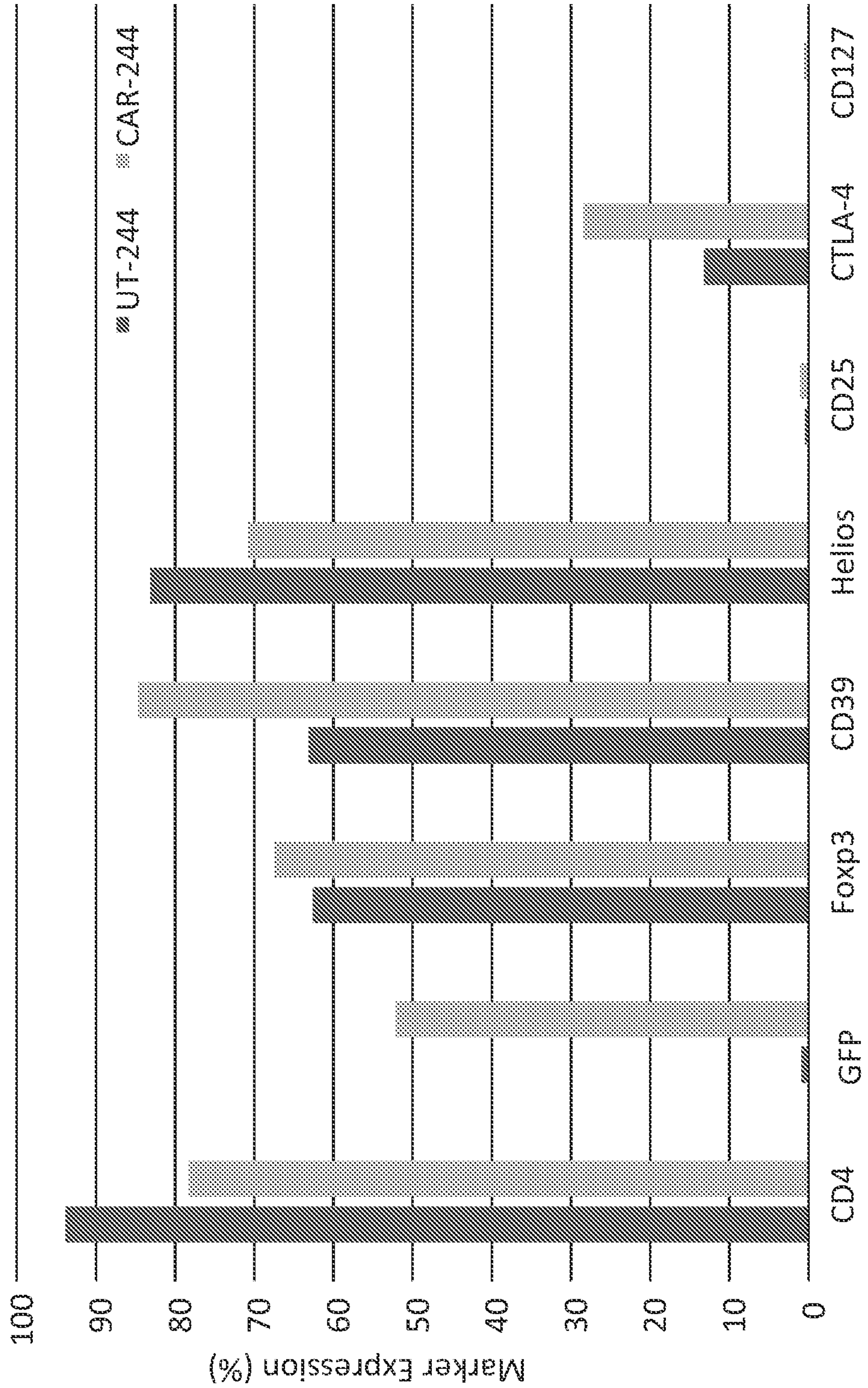
FIG. 16 is a graph showing cell marker expression in anti-CD26 CAR Treg cells and un-transduced Treg cells.

The αCD26 CAR-transduced Treg cells and un-transduced Treg cells were stained with the indicated antibodies shown in FIG. 16. The αCD26 CAR Treg cells expressed more CD39 and CTLA-4 compared to the un-transduced Treg cells. The higher CD39 and CTLA-4 expression might be related to a better suppression ability of the αCD26 CAR Treg cells than the untransduced Treg cells in the suppression assays.

Figure 17:
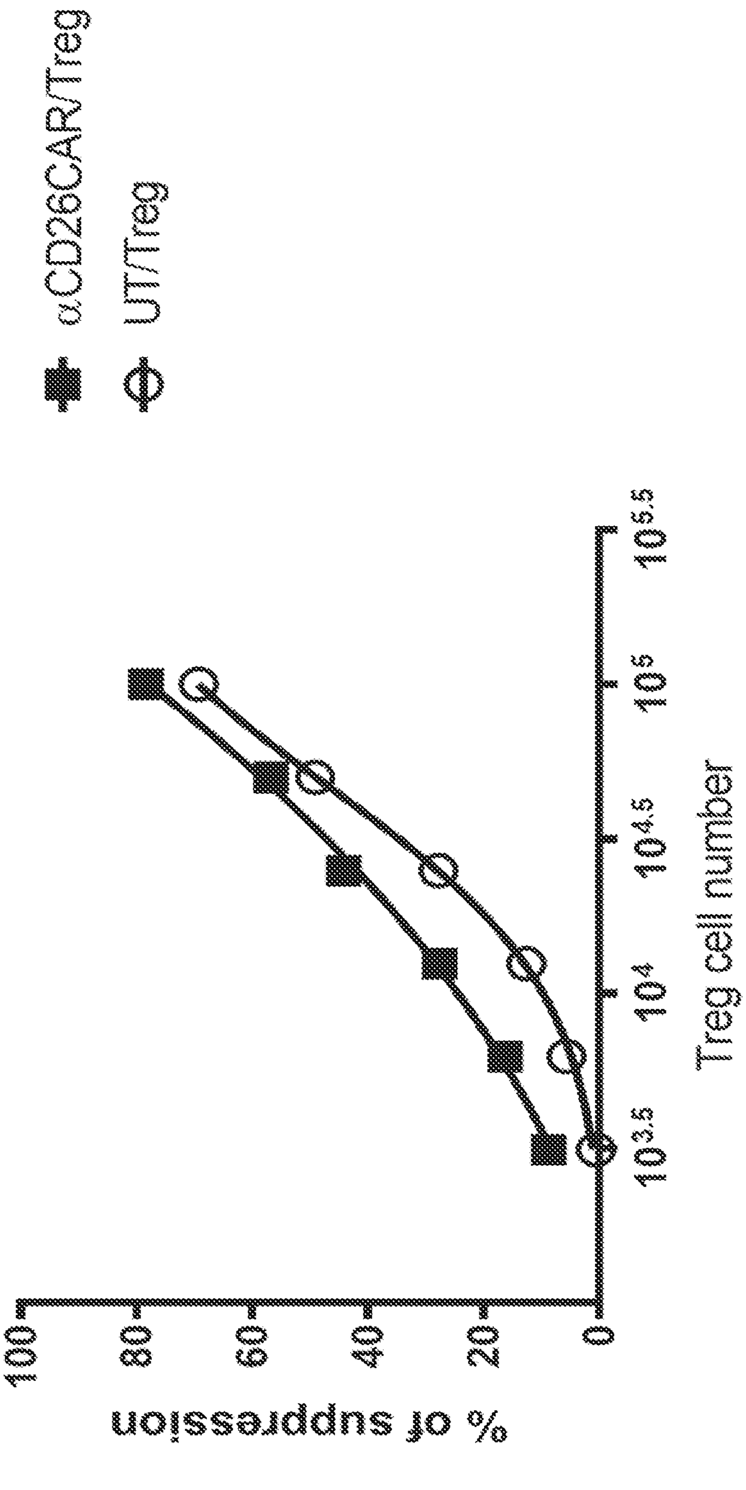
FIG. 17 is a graph of the suppression activity of anti-CD26 CAR Treg cells and un-transduced Treg cells.

In the suppression assays, «CD26 CAR Treg cells or untransduced Treg cells were incubated with the CellTrace violet cell proliferation kit (Cat #C34557, ThermoFisher)-labelled Tresp cells from the same donor for 5 days. The suppression of Tresp cell proliferation by αCD26 CAR Treg cells and untransduced Treg cells were analyzed by flow cytometry. The αCD26 CAR Treg cells suppressed Tresp proliferation better than the untransduced Treg cells did (FIG. 17).

Figure 18:
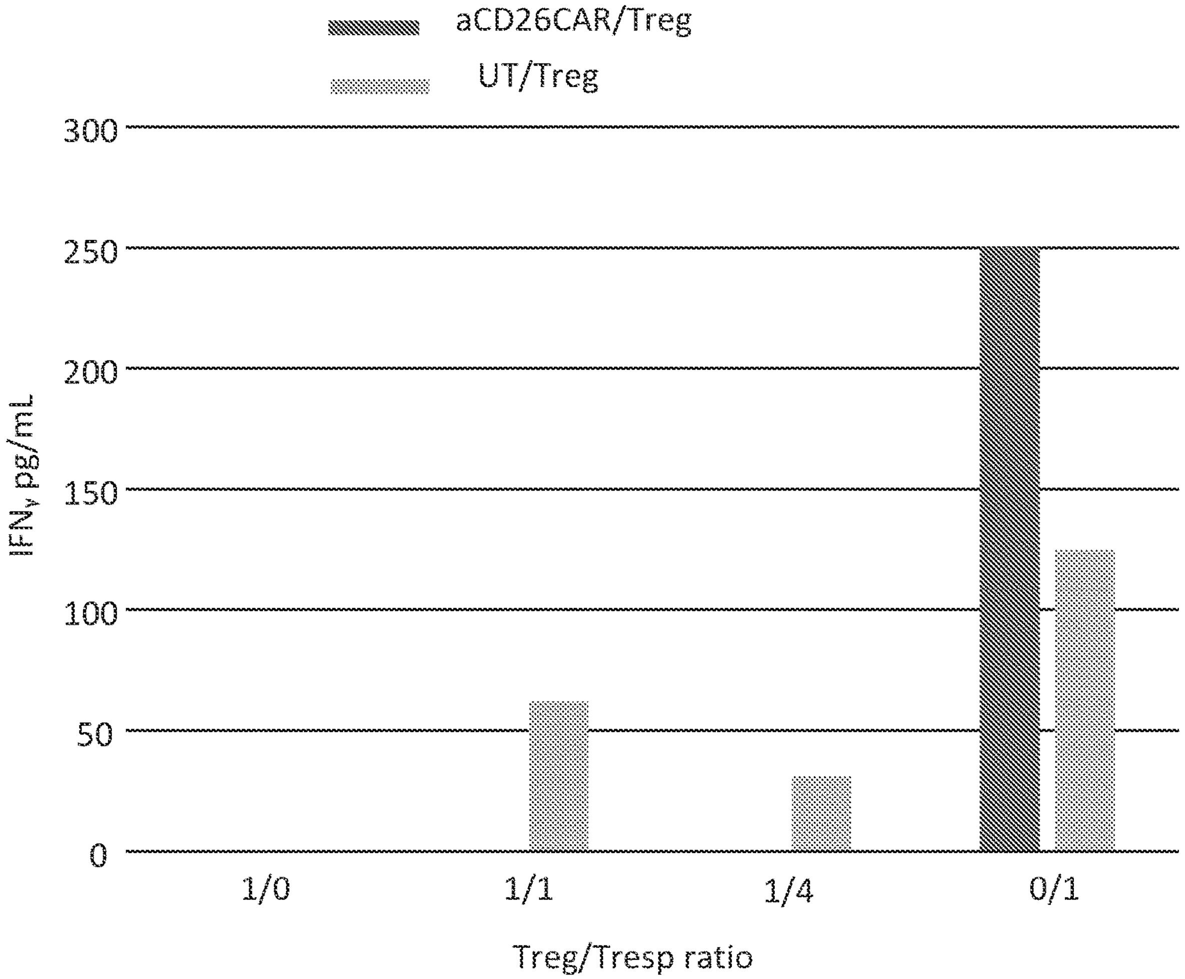
FIG. 18 is a graph showing the suppression of IFNg production by Tresp cells with anti-CD26 CAR Treg cells or untransduced Treg cells.
Figure 19:
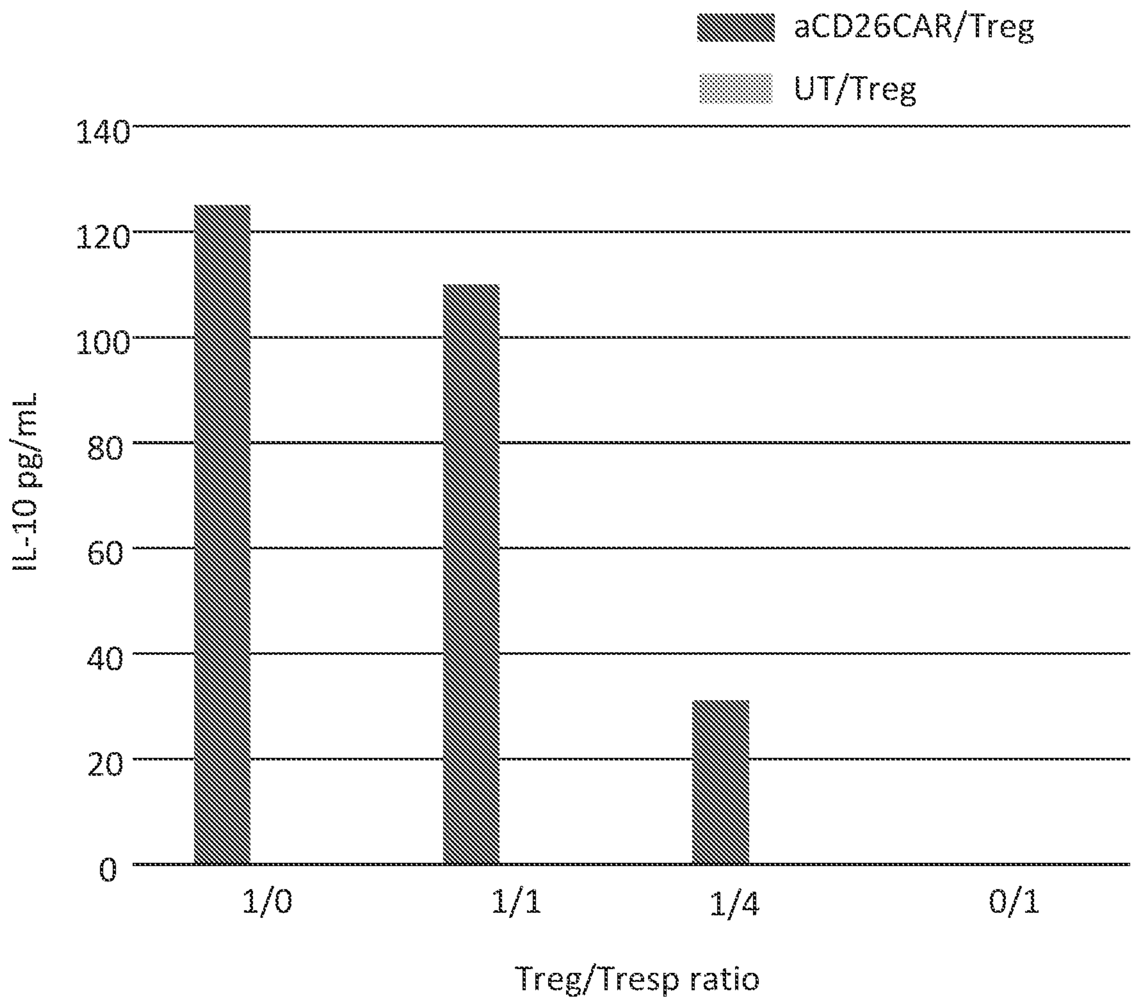
FIG. 19 is a graph showing the IL-10 production by anti-CD26 CAR Treg cells and untransduced Treg cells.

The culture supernatants from the suppression assays were collected for ELISA analysis of the interferon gamma and IL-10 produced by Treg or Tresp cells. The Tresp cells alone produced INFg around 125-250 pg/mL, while the Treg cells alone did not produce IFNg. The αCD26 CAR Treg cells suppressed Tresp cell production of interferon gamma better than the untransduced Treg cells did (FIG. 18). On the other hand, although Tresp cells did not produce IL-10, αCD26 CAR Treg cells produced more IL-10 than untransduced Treg cells did (FIG. 19).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A protein comprising an anti-CD26 antigen-binding domain, wherein the anti-CD26 antigen-binding domain comprises:
   - (a) a heavy chain variable domain comprising a CDR1 comprising SEQ ID NO: 1, a CDR2 comprising SEQ ID NO: 2, and a CDR3 comprising SEQ ID NO: 3, and a light chain variable domain comprising a CDR1 comprising SEQ ID NO: 4, a CDR2 comprising SEQ ID NO: 5, and a CDR3 comprising SEQ ID NO: 6;
   - (b) a heavy chain variable domain comprising a CDR1 comprising SEQ ID NO: 7, a CDR2 comprising SEQ ID NO: 8, and a CDR3 comprising SEQ ID NO: 9, and a light chain variable domain comprising a CDR1 comprising SEQ ID NO: 10, a CDR2 comprising SEQ ID NO: 11, and a CDR3 comprising SEQ ID NO: 12;
   - (c) a heavy chain variable domain comprising a CDR1 comprising SEQ ID NO: 13, a CDR2 comprising SEQ ID NO: 14, and a CDR3 comprising SEQ ID NO: 15, and a light chain variable domain comprising a CDR1 comprising SEQ ID NO: 16, a CDR2 comprising SEQ ID NO: 17, and a CDR3 comprising SEQ ID NO: 18;
   - (d) a heavy chain variable domain comprising a CDR1 comprising SEQ ID NO: 19, a CDR2 comprising SEQ ID NO: 20, and a CDR3 comprising SEQ ID NO: 21, and a light chain variable domain comprising a CDR1 comprising SEQ ID NO: 22, a CDR2 comprising SEQ ID NO: 23, and a CDR3 comprising SEQ ID NO: 24;
   - (e) a heavy chain variable domain comprising a CDR1 comprising SEQ ID NO: 25, a CDR2 comprising SEQ ID NO: 26, and a CDR3 comprising SEQ ID NO: 27, and a light chain variable domain comprising a CDR1 comprising SEQ ID NO: 28, a CDR2 comprising SEQ ID NO: 29, and a CDR3 comprising SEQ ID NO: 30;
   - (f) a heavy chain variable domain comprising a CDR1 comprising SEQ ID NO: 31, a CDR2 comprising SEQ ID NO: 32, and a CDR3 comprising SEQ ID NO: 33, and a light chain variable domain comprising a CDR1 comprising SEQ ID NO: 34, a CDR2 comprising SEQ ID NO: 35, and a CDR3 comprising SEQ ID NO: 36;
   - (g) a heavy chain variable domain comprising a CDR1 comprising SEQ ID NO: 37, a CDR2 comprising SEQ ID NO: 38, and a CDR3 comprising SEQ ID NO: 39, and a light chain variable domain comprising a CDR1 comprising SEQ ID NO: 40, a CDR2 comprising SEQ ID NO: 41, and a CDR3 comprising SEQ ID NO: 42;

(h) a heavy chain variable domain comprising a CDR1 comprising SEQ ID NO: 43, a CDR2 comprising SEQ ID NO: 44, and a CDR3 comprising SEQ ID NO: 45, and a light chain variable domain comprising a CDR1 comprising SEQ ID NO: 46, a CDR2 comprising SEQ ID NO: 47, and a CDR3 comprising SEQ ID NO: 48;

(i) a heavy chain variable domain comprising a CDR1 comprising SEQ ID NO: 49, a CDR2 comprising SEQ ID NO: 50, and a CDR3 comprising SEQ ID NO: 51, and a light chain variable domain comprising a CDR1 comprising SEQ ID NO: 52, a CDR2 comprising SEQ ID NO: 53, and a CDR3 comprising SEQ ID NO: 54; or (j) a heavy chain variable domain comprising a CDR1 comprising SEQ ID NO: 55, a CDR2 comprising SEQ ID NO: 56, and a CDR3 comprising SEQ ID NO: 57, and a light chain variable domain comprising a CDR1 comprising SEQ ID NO: 58, a CDR2 comprising SEQ ID NO: 59, and a CDR3 comprising SEQ ID NO: 60.

2. The protein of claim 1, wherein:

the heavy chain variable domain comprises a sequence that is at least 80% identical to SEQ ID NO: 61 and the light chain variable domain comprises a sequence that is at least 80% identical to SEQ ID NO: 62;

the heavy chain variable domain comprises a sequence that is at least 80% identical to SEQ ID NO: 63 and the light chain variable domain comprises a sequence that is at least 80% identical to SEQ ID NO: 64;

the heavy chain variable domain comprises a sequence that is at least 80% identical to SEQ ID NO: 65 and the light chain variable domain comprises a sequence that is at least 80% identical to SEQ ID NO: 66;

the heavy chain variable domain comprises a sequence that is at least 80% identical to SEQ ID NO: 67 and the light chain variable domain comprises a sequence that is at least 80% identical to SEQ ID NO: 68;

the heavy chain variable domain comprises a sequence that is at least 80% identical to SEQ ID NO: 69 and the light chain variable domain comprises a sequence that is at least 80% identical to SEQ ID NO: 70;

the heavy chain variable domain comprises a sequence that is at least 80% identical to SEQ ID NO: 71 and the light chain variable domain comprises a sequence that is at least 80% identical to SEQ ID NO: 72;

the heavy chain variable domain comprises a sequence that is at least 80% identical to SEQ ID NO: 73 and the light chain variable domain comprises a sequence that is at least 80% identical to SEQ ID NO: 74;

the heavy chain variable domain comprises a sequence that is at least 80% identical to SEQ ID NO: 75 and the light chain variable domain comprises a sequence that is at least 80% identical to SEQ ID NO: 76;

the heavy chain variable domain comprises a sequence that is at least 80% identical to SEQ ID NO: 77 and the light chain variable domain comprises a sequence that is at least 80% identical to SEQ ID NO: 78; or the heavy chain variable domain comprises a sequence that is at least 80% identical to SEQ ID NO: 79 and the light chain variable domain comprises a sequence that is at least 80% identical to SEQ ID NO: 80.

3. The protein of claim 1, wherein the protein is a multi-chain protein.

4. The protein of claim 1, wherein the protein is a single-chain protein.

5. The protein of claim 1, wherein the protein is an antibody or an antigen-binding antibody fragment.

6. The protein of claim 1, wherein the protein is a chimeric antigen receptor (CAR).

7. A pharmaceutical composition comprising a protein of claim 1 and a pharmaceutically acceptable carrier.

8. A kit comprising the pharmaceutical composition of claim 7.

9. A nucleic acid encoding a protein of claim 1.

10. A vector comprising the nucleic acid of claim 9.

11. A cell comprising the nucleic acid of claim 9.

12. The cell of claim 11, wherein the cell is an immune cell.

13. The cell of claim 12, wherein the immune cell is a T cell, a B cell, or a natural killer (NK) cell.

14. A pharmaceutical composition comprising a cell of claim 11 and a pharmaceutically acceptable carrier.

15. A method of treating an age-related disease or an inflammatory disease in a subject, the method comprising administering to the subject a therapeutically effective amount of the protein of claim 1.

16. A method of treating an age-related disease or an inflammatory disease in a subject, the method comprising administering to the subject a therapeutically effective amount of the nucleic acid of claim 9.

17. A method of treating an age-related disease or an inflammatory disease in a subject, the method comprising administering to the subject a therapeutically effective amount of the cell of claim 11.

18. The method of claim 15, wherein the subject is further administered:

(i) a therapeutically effective amount of an NK cell activating agent and/or an NK cell and/or a monoclonal antibody; and/or (ii) a therapeutically effective amount of a Treg cell activating agent and/or a Treg cell and/or a monoclonal antibody and/or an advanced glycation end product (AGE) inhibitor.

19. The method of claim 18, wherein the method comprises administering a therapeutically effective amount of an NK cell to the subject.

20. A method of treating cancer in a subject, the method comprising administering to the subject a therapeutically effective amount of the protein of claim 1.

21. A method of treating an infectious disease in a subject, the method comprising administering to the subject a therapeutically effective amount of the protein of claim 1.

* * * * *

SEQUENCE LISTING

<160> NUMBER OF SEQ ID NOS: 261

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Thr Ile Asn Asp Ser Tyr Ile His
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide

<400> SEQUENCE: 2

Trp Ile Trp Pro Tyr Gly Gly Phe Thr Tyr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide

<400> SEQUENCE: 3

Ala Arg Phe Leu Gly Ser Ser Ser Ile Met Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide

<400> SEQUENCE: 4

Arg Ala Ser Gln Asp Val Asn Ser Asn Val Ala
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Phe Gly Ser Gly Gly Leu Tyr Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

Gln Gln Tyr Ser Ser Tyr Pro Leu
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide

<400> SEQUENCE: 7

Ala Ile Asn Asn Tyr Ser Ile His
1 5

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Ser Ile Trp Pro Tyr Gly Gly Phe Thr Ser
1 5 10

<210> SEQ ID NO 9
<211> LENGTH: 12
<212> TYPE: PRT
<213> ORGANISM: Artificial Sequence
<220> FEATURE:
<223> OTHER INFORMATION: Synthetic peptide

<400> SEQUENCE: 9

Ala Arg Phe Phe Ser Ser Tyr Gly Asp Met Asp Tyr
1 5 10

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Arg Ala Ser Gln Asp Val Ser Gly Gly Val Ala
1 5 10

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Tyr Gly Thr Ser Gly Leu Tyr Ser
1 5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Gln Gln Gly Gly Trp Pro Ile
1 5

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

```
Thr Ile Ser Asp Tyr Ser Ile His
1               5


<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Ser Ile Trp Pro Gly Gly Phe Thr Ser
1               5


<210> SEQ ID NO 15
<211> LENGTH: 12
<212> TYPE: PRT
<213> ORGANISM: Artificial Sequence
<220> FEATURE:
<223> OTHER INFORMATION: Synthetic peptide

<400> SEQUENCE: 15

Ala Arg Phe His Ser Ser Ser Gly Asp Met Asp Tyr
1               5                   10


<210> SEQ ID NO 16
<211> LENGTH: 11
<212> TYPE: PRT
<213> ORGANISM: Artificial Sequence
<220> FEATURE:
<223> OTHER INFORMATION: Synthetic peptide

<400> SEQUENCE: 16

Arg Ala Ser Gln Asp Val Trp Gly Tyr Val Ala
1               5                   10


<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

Phe Ala Ser Gly Ala Leu Tyr Ser
1               5


<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Gln Gln Tyr Phe Asn Trp Pro Ile
1               5


<210> SEQ ID NO 19
<211> LENGTH: 8
<212> TYPE: PRT
<213> ORGANISM: Artificial Sequence
<220> FEATURE:
<223> OTHER INFORMATION: Synthetic peptide

<400> SEQUENCE: 19

Thr Ile Asn Ser Ser Tyr Ile His
```

1 5

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Gly Ile Gly Pro Tyr Trp Gly Phe Thr Ser
1 5 10

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide

<400> SEQUENCE: 21

Ala Arg Phe Tyr Ser Ser Tyr Gly Phe Met Asp Tyr
1 5 10

<210> SEQ ID NO 22
<211> LENGTH: 11
<212> TYPE: PRT
<213> ORGANISM: Artificial Sequence
<220> FEATURE:
<223> OTHER INFORMATION: Synthetic peptide

<400> SEQUENCE: 22

Arg Ala Ser Gln Asp Val Tyr Ser Trp Val Ala
1 5 10

<210> SEQ ID NO 23
<211> LENGTH: 8
<212> TYPE: PRT
<213> ORGANISM: Artificial Sequence
<220> FEATURE:
<223> OTHER INFORMATION: Synthetic peptide

<400> SEQUENCE: 23

Tyr Gly Pro Gly Ser Leu Tyr Ser
1 5

<210> SEQ ID NO 24
<211> LENGTH: 8
<212> TYPE: PRT
<213> ORGANISM: Artificial Sequence
<220> FEATURE:
<223> OTHER INFORMATION: Synthetic peptide

<400> SEQUENCE: 24

Gln Gln Tyr Tyr Asn Tyr Pro Leu
1 5

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide

<400> SEQUENCE: 25

Thr Ile Gly Asn Ser Tyr Ile His
1 5

<210> SEQ ID NO 26
<211> LENGTH: 10
<212> TYPE: PRT
<213> ORGANISM: Artificial Sequence
<220> FEATURE:
<223> OTHER INFORMATION: Synthetic peptide

<400> SEQUENCE: 26

Gly Ile Gly Pro Tyr Trp Gly Phe Thr Ser
1 5 10

<210> SEQ ID NO 27
<211> LENGTH: 12
<212> TYPE: PRT
<213> ORGANISM: Artificial Sequence
<220> FEATURE:
<223> OTHER INFORMATION: Synthetic peptide

<400> SEQUENCE: 27

Ala Arg Phe Asn Gly Ser Ser Gly Phe Met Asp Tyr
1 5 10

<210> SEQ ID NO 28
<211> LENGTH: 11
<212> TYPE: PRT
<213> ORGANISM: Artificial Sequence
<220> FEATURE:
<223> OTHER INFORMATION: Synthetic peptide

<400> SEQUENCE: 28

Arg Ala Ser Gln Asp Val Tyr Tyr Phe Val Ala
1 5 10

<210> SEQ ID NO 29
<211> LENGTH: 8
<212> TYPE: PRT
<213> ORGANISM: Artificial Sequence
<220> FEATURE:
<223> OTHER INFORMATION: Synthetic peptide

<400> SEQUENCE: 29

Ser Trp Pro Thr Gly Leu Tyr Ser
1 5

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide

<400> SEQUENCE: 30

Gln Gln Tyr Phe Ser Tyr Pro Ile
1 5

<210> SEQ ID NO 31
<211> LENGTH: 13
<212> TYPE: PRT
<213> ORGANISM: Artificial Sequence
<220> FEATURE:
<223> OTHER INFORMATION: Synthetic peptide

<400> SEQUENCE: 31

Lys Ala Ser Gly Tyr Thr Phe Ala Arg Phe Gly Met Tyr
1 5 10

<210> SEQ ID NO 32
<211> LENGTH: 10
<212> TYPE: PRT
<213> ORGANISM: Artificial Sequence
<220> FEATURE:
<223> OTHER INFORMATION: Synthetic peptide

<400> SEQUENCE: 32

Phe Ile Ala Pro Asn His Gly Tyr Thr Phe
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic peptide

<400> SEQUENCE: 33

Ala Arg Gly His Trp Tyr His Gly Tyr Met Asp Tyr
1               5                   10

<210> SEQ ID NO 34
<211> LENGTH: 16
<212> TYPE: PRT
<213> ORGANISM: Artificial Sequence
<220> FEATURE:
<223> OTHER INFORMATION: Synthetic peptide

<400> SEQUENCE: 34

Lys Ser Asn Gln Asn Leu Leu Tyr Ser His Gly Arg Thr Tyr Leu Asn
1               5                   10                  15

<210> SEQ ID NO 35
<211> LENGTH: 8
<212> TYPE: PRT
<213> ORGANISM: Artificial Sequence
<220> FEATURE:
<223> OTHER INFORMATION: Synthetic peptide

<400> SEQUENCE: 35

Phe Gly Thr Ser His Leu Tyr Ser
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic peptide

<400> SEQUENCE: 36

Tyr Gln Gly Tyr His Val Pro Phe
1               5

<210> SEQ ID NO 37
<211> LENGTH: 13
<212> TYPE: PRT
<213> ORGANISM: Artificial Sequence
<220> FEATURE:
<223> OTHER INFORMATION: Synthetic peptide

<400> SEQUENCE: 37

Ala Ala Ser Gly Phe Thr Ile Gly Asn Tyr Gly Ile His
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic peptide

<400> SEQUENCE: 38

Trp Ile Gly Pro Ser Gly Gly Tyr Thr Phe
1 5 10

<210> SEQ ID NO 39
<211> LENGTH: 13
<212> TYPE: PRT
<213> ORGANISM: Artificial Sequence
<220> FEATURE:
<223> OTHER INFORMATION: Synthetic peptide

<400> SEQUENCE: 39

Ala Arg Phe Asp Val His Gly Phe His Gly Met Asp Tyr
1 5 10

<210> SEQ ID NO 40
<211> LENGTH: 11
<212> TYPE: PRT
<213> ORGANISM: Artificial Sequence
<220> FEATURE:
<223> OTHER INFORMATION: Synthetic peptide

<400> SEQUENCE: 40

Arg Ala Ser Gln Asp Val Asn Asn Ser Val Ala
1 5 10

<210> SEQ ID NO 41
<211> LENGTH: 8
<212> TYPE: PRT
<213> ORGANISM: Artificial Sequence
<220> FEATURE:
<223> OTHER INFORMATION: Synthetic peptide

<400> SEQUENCE: 41

Phe Ser Pro Thr Gly Leu Tyr Ser
1 5

<210> SEQ ID NO 42
<211> LENGTH: 8
<212> TYPE: PRT
<213> ORGANISM: Artificial Sequence
<220> FEATURE:
<223> OTHER INFORMATION: Synthetic peptide

<400> SEQUENCE: 42

Gln Gln Tyr Phe Asp Phe Pro Leu
1 5

<210> SEQ ID NO 43
<211> LENGTH: 13
<212> TYPE: PRT
<213> ORGANISM: Artificial Sequence
<220> FEATURE:
<223> OTHER INFORMATION: Synthetic peptide

<400> SEQUENCE: 43

Ala Ala Ser Gly Phe Thr Ile Asn Asp Gly Phe Ile His
1 5 10

<210> SEQ ID NO 44

<211> LENGTH: 10
<212> TYPE: PRT
<213> ORGANISM: Artificial Sequence
<220> FEATURE:
<223> OTHER INFORMATION: Synthetic peptide

<400> SEQUENCE: 44

Gly Ile Trp Pro Phe Gly Gly Ser Thr Ser
1 5 10

<210> SEQ ID NO 45
<211> LENGTH: 13
<212> TYPE: PRT
<213> ORGANISM: Artificial Sequence
<220> FEATURE:
<223> OTHER INFORMATION: Synthetic peptide

<400> SEQUENCE: 45

Ala Arg Phe Asp Val Val Asp Trp Gly Val Met Asp Tyr
1 5 10

<210> SEQ ID NO 46
<211> LENGTH: 11
<212> TYPE: PRT
<213> ORGANISM: Artificial Sequence
<220> FEATURE:
<223> OTHER INFORMATION: Synthetic peptide

<400> SEQUENCE: 46

Arg Ala Ser Gln Asp Val Asn Asp Gly Val Ala
1 5 10

<210> SEQ ID NO 47
<211> LENGTH: 8
<212> TYPE: PRT
<213> ORGANISM: Artificial Sequence
<220> FEATURE:
<223> OTHER INFORMATION: Synthetic peptide

<400> SEQUENCE: 47

Tyr Trp Ala Ser Tyr Leu Tyr Ser
1 5

<210> SEQ ID NO 48
<211> LENGTH: 8
<212> TYPE: PRT
<213> ORGANISM: Artificial Sequence
<220> FEATURE:
<223> OTHER INFORMATION: Synthetic peptide

<400> SEQUENCE: 48

Gln Gln Ser Trp Asn Phe Pro Leu
1 5

<210> SEQ ID NO 49
<211> LENGTH: 13
<212> TYPE: PRT
<213> ORGANISM: Artificial Sequence
<220> FEATURE:
<223> OTHER INFORMATION: Synthetic peptide

<400> SEQUENCE: 49

Ala Ala Ser Gly Phe Thr Ile Gly Asn Tyr Gly Ile His
1 5 10

<210> SEQ ID NO 50
<211> LENGTH: 10

<212> TYPE: PRT
<213> ORGANISM: Artificial Sequence
<220> FEATURE:
<223> OTHER INFORMATION: Synthetic peptide

<400> SEQUENCE: 50

Trp Ile Gly Pro Tyr Gly Gly Tyr Thr Phe
1 5 10

<210> SEQ ID NO 51
<211> LENGTH: 13
<212> TYPE: PRT
<213> ORGANISM: Artificial Sequence
<220> FEATURE:
<223> OTHER INFORMATION: Synthetic peptide

<400> SEQUENCE: 51

Ala Arg Phe Asn Asn Leu Leu Trp Asn Gly Met Asp Tyr
1 5 10

<210> SEQ ID NO 52
<211> LENGTH: 11
<212> TYPE: PRT
<213> ORGANISM: Artificial Sequence
<220> FEATURE:
<223> OTHER INFORMATION: Synthetic peptide

<400> SEQUENCE: 52

Arg Ala Ser Gln Asp Val Ser Ser Ser Val Ala
1 5 10

<210> SEQ ID NO 53
<211> LENGTH: 8
<212> TYPE: PRT
<213> ORGANISM: Artificial Sequence
<220> FEATURE:
<223> OTHER INFORMATION: Synthetic peptide

<400> SEQUENCE: 53

Ser Tyr Pro Gly Trp Leu Tyr Ser
1 5

<210> SEQ ID NO 54
<211> LENGTH: 8
<212> TYPE: PRT
<213> ORGANISM: Artificial Sequence
<220> FEATURE:
<223> OTHER INFORMATION: Synthetic peptide

<400> SEQUENCE: 54

Gln Gln Phe Gly Asp Phe Pro Met
1 5

<210> SEQ ID NO 55
<211> LENGTH: 13
<212> TYPE: PRT
<213> ORGANISM: Artificial Sequence
<220> FEATURE:
<223> OTHER INFORMATION: Synthetic peptide

<400> SEQUENCE: 55

Ala Ala Ser Gly Phe Thr Ile Ser Asp Tyr Ser Ile His
1 5 10

<210> SEQ ID NO 56
<211> LENGTH: 10
<212> TYPE: PRT

<213> ORGANISM: Artificial Sequence
<220> FEATURE:
<223> OTHER INFORMATION: Synthetic peptide

<400> SEQUENCE: 56

Ser Ile Trp Pro Tyr Gly Gly Phe Thr Ser
1 5 10

<210> SEQ ID NO 57
<211> LENGTH: 12
<212> TYPE: PRT
<213> ORGANISM: Artificial Sequence
<220> FEATURE:
<223> OTHER INFORMATION: Synthetic peptide

<400> SEQUENCE: 57

Ala Arg Phe His Ser Ser Ser Gly Asp Met Asp Tyr
1 5 10

<210> SEQ ID NO 58
<211> LENGTH: 11
<212> TYPE: PRT
<213> ORGANISM: Artificial Sequence
<220> FEATURE:
<223> OTHER INFORMATION: Synthetic peptide

<400> SEQUENCE: 58

Arg Ala Ser Gln Asp Val Trp Gly Tyr Val Ala
1 5 10

<210> SEQ ID NO 59
<211> LENGTH: 8
<212> TYPE: PRT
<213> ORGANISM: Artificial Sequence
<220> FEATURE:
<223> OTHER INFORMATION: Synthetic peptide

<400> SEQUENCE: 59

Phe Ser Ser Arg Ser Leu Tyr Ser
1 5

<210> SEQ ID NO 60
<211> LENGTH: 8
<212> TYPE: PRT
<213> ORGANISM: Artificial Sequence
<220> FEATURE:
<223> OTHER INFORMATION: Synthetic peptide

<400> SEQUENCE: 60

Gln Gln Tyr Phe Asn Trp Pro Ile
1 5

<210> SEQ ID NO 61
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 61

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Ile Asn Asp Ser
20 25 30

Tyr Ile His Trp Val Arg Gln Ala Pro Gly Lys Gly Leu Glu Trp Val
35 40 45

-continued

```
Ala Trp Ile Trp Pro Tyr Gly Gly Phe Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Leu Gly Ser Ser Ser Ile Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 62
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 62

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Ser Asn
            20                  25                  30

Val Ala Trp Tyr Gln Gln Lys Pro Gly Lys Ala Pro Lys Leu Leu Ile
        35                  40                  45

Phe Gly Ser Gly Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Val Glu Thr Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 63
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 63

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Ile Asn Asn Tyr
            20                  25                  30

Ser Ile His Trp Val Arg Gln Ala Pro Gly Lys Gly Leu Glu Trp Val
        35                  40                  45

Ala Ser Ile Trp Pro Tyr Gly Gly Phe Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ala Arg Phe Phe Ser Ser Tyr Gly Asp Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 64
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 64

```
Asp Ile Gln Met Thr Gln Ser Pro Ser Ser Leu Ser Ala Ser Val Gly
```

```
1               5                   10                  15

Asp Arg Val Thr Ile Thr Cys Arg Ala Ser Gln Asp Val Ser Gly Gly
            20                  25                  30

Val Ala Trp Tyr Gln Gln Lys Pro Gly Lys Ala Pro Lys Leu Leu Ile
        35                  40                  45

Tyr Gly Thr Ser Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gly Asp Trp Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 65
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Ser Ile His Trp Val Arg Gln Ala Pro Gly Lys Gly Leu Glu Trp Val
        35                  40                  45

Ala Ser Ile Trp Pro Tyr Gly Gly Phe Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe His Ser Ser Ser Gly Asp Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

-continued

```
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 66
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Tyr
            20                  25                  30

Val Ala Trp Tyr Gln Gln Lys Pro Gly Lys Ala Pro Lys Leu Leu Ile
        35                  40                  45

Phe Ala Ser Gly Ala Leu Tyr Ser Gly Val Pro Ser Arg Phe Ser Gly
    50                  55                  60
```

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Phe Asn Trp Pro Ile
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 67
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 67

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Ile Asn Ser Ser
20 25 30

Tyr Ile His Trp Val Arg Gln Ala Pro Gly Lys Gly Leu Glu Trp Val
35 40 45

Ala Gly Ile Gly Pro Tyr Trp Gly Phe Thr Ser Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Phe Tyr Ser Ser Tyr Gly Phe Met Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

```
Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 68
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Tyr Ser Trp
            20                  25                  30

Val Ala Trp Tyr Gln Gln Lys Pro Gly Lys Ala Pro Lys Leu Leu Ile
        35                  40                  45

Tyr Gly Pro Gly Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Leu
                85                  90                  95

Thr Phe Gly Gln Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 69
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 69

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gly Asn Ser
            20                  25                  30

Tyr Ile His Trp Val Arg Gln Ala Pro Gly Lys Gly Leu Glu Trp Val
        35                  40                  45

Ala Gly Ile Gly Pro Tyr Trp Gly Phe Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Asn Gly Ser Ser Gly Phe Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 70
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 70

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Tyr Tyr Phe
20 25 30

Val Ala Trp Tyr Gln Gln Lys Pro Gly Lys Ala Pro Lys Leu Leu Ile
35 40 45

Ser Trp Pro Thr Gly Leu Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Phe Ser Tyr Pro Ile
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser

```
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 71
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Lys Ala Ser Gly Tyr Thr Phe Ala Arg Phe
            20                  25                  30

Gly Met Tyr Trp Val Arg Gln Ala Pro Gly Lys Gly Leu Glu Trp Val
        35                  40                  45

Ala Phe Ile Ala Pro Asn His Gly Tyr Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly His Trp Tyr His Gly Tyr Met Asp Tyr Trp Gly Gln Gly
            100                 105                 110

Thr Leu Val Thr Val Ser Ser Ala Ser
        115                 120


<210> SEQ ID NO 72
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Lys Ser Asn Gln Asn Leu Leu Tyr Ser
            20                  25                  30

His Gly Arg Thr Tyr Leu Asn Trp Tyr Gln Gln Lys Pro Gly Lys Ala
        35                  40                  45

Pro Lys Leu Leu Ile Phe Gly Thr Ser His Leu Tyr Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Tyr Gln Gly
                85                  90                  95

Tyr His Val Pro Phe Thr Phe Gly Gln Gly Thr Lys Val Glu Ile Lys
            100                 105                 110

Arg
```

<210> SEQ ID NO 73
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 73

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gly Asn Tyr
            20                  25                  30

Gly Ile His Trp Val Arg Gln Ala Pro Gly Lys Gly Leu Glu Trp Val
        35                  40                  45

Ala Trp Ile Gly Pro Ser Gly Gly Tyr Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Asp Val His Gly Phe His Gly Met Asp Tyr Trp Gly Gln
            100                 105                 110

Gly Thr Leu Val Thr Val Ser Ser Ala Ser
        115                 120
```

<210> SEQ ID NO 74
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 74

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asn Ser
            20                  25                  30

Val Ala Trp Tyr Gln Gln Lys Pro Gly Lys Ala Pro Lys Leu Leu Ile
        35                  40                  45

Phe Ser Pro Thr Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asp Phe Pro Leu
                85                  90                  95

Thr Phe Gly Gln Gly Thr Lys Val Glu Ile Lys Arg
            100                 105
```

<210> SEQ ID NO 75
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 75

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Asp Gly
            20                  25                  30
```

```
Phe Ile His Trp Val Arg Gln Ala Pro Gly Lys Gly Leu Glu Trp Val
        35                  40                  45

Ala Gly Ile Trp Pro Phe Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Asp Val Val Asp Trp Gly Val Met Asp Tyr Trp Gly Gln
            100                 105                 110

Gly Thr Leu Val Thr Val Ser Ser Ala Ser
        115                 120


<210> SEQ ID NO 76
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asp Gly
            20                  25                  30

Val Ala Trp Tyr Gln Gln Lys Pro Gly Lys Ala Pro Lys Leu Leu Ile
        35                  40                  45

Tyr Trp Ala Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Asn Phe Pro Leu
                85                  90                  95

Thr Phe Gly Gln Gly Thr Lys Val Glu Ile Lys Arg
            100                 105


<210> SEQ ID NO 77
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gly Asn Tyr
            20                  25                  30

Gly Ile His Trp Val Arg Gln Ala Pro Gly Lys Gly Leu Glu Trp Val
        35                  40                  45

Ala Trp Ile Gly Pro Tyr Gly Gly Tyr Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Asn Asn Leu Leu Trp Asn Gly Met Asp Tyr Trp Gly Gln
```

```
            100                 105                 110

Gly Thr Leu Val Thr Val Ser Ser Ala Ser
        115                 120


<210> SEQ ID NO 78
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Ser
            20                  25                  30

Val Ala Trp Tyr Gln Gln Lys Pro Gly Lys Ala Pro Lys Leu Leu Ile
        35                  40                  45

Ser Tyr Pro Gly Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Gly Asp Phe Pro Met
                85                  90                  95

Thr Phe Gly Gln Gly Thr Lys Val Glu Ile Lys Arg
            100                 105


<210> SEQ ID NO 79
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Ser Ile His Trp Val Arg Gln Ala Pro Gly Lys Gly Leu Glu Trp Val
        35                  40                  45

Ala Ser Ile Trp Pro Tyr Gly Gly Phe Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe His Ser Ser Ser Gly Asp Met Asp Tyr Trp Gly Gln Gly
            100                 105                 110

Thr Leu Val Thr Val Ser Ser Ala Ser
        115                 120


<210> SEQ ID NO 80
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 80
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Tyr
            20                  25                  30

Val Ala Trp Tyr Gln Gln Lys Pro Gly Lys Ala Pro Lys Leu Leu Ile
        35                  40                  45

Phe Ser Ser Arg Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Ile
                85                  90                  95

Thr Phe Gly Gln Gly Thr Lys Val Glu Ile Lys Arg
            100                 105


<210> SEQ ID NO 81
<211> LENGTH: 369
<212> TYPE: DNA
<213> ORGANISM: Artificial Sequence
<220> FEATURE:
<223> OTHER INFORMATION: Synthetic polynucleotide

<400> SEQUENCE: 81

gaagtgcagc tggtggaatc gggaggcggt ctggtgcaac ctggcggcag ccttcgtctg      60

agctgtgcgg cgagcgggtt caccattaac gactcttata ttcattgggt gcgtcaagct     120

cccggcaagg ggctggagtg ggtcgcgtgg atttggccct acgggggttt tacatattat     180

gccgacagcg tgaaaggtcg ctttacgatt agtgcggaca ccagcaaaaa taccgcgtac     240

ctgcagatga atagcctgcg tgcggaagac acagcggtgt attattgcgc gcgtttcctc     300

ggttcctcca gcattatgga ttattggggg cagggcaccc ttgttaccgt gagctcggcg     360

tcagcggcc                                                             369


<210> SEQ ID NO 82
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 82

gatattcaaa tgacccagag cccgagcagc ctgagcgcga gcgtgggaga tcgcgtgacc      60

attacctgcc gtgcgagcca ggatgttaat agtaatgtcg catggtatca gcagaaacca     120

ggcaaagcgc cgaaacttct gatatttggg tctggtgggc tgtatagcgg cgtgccgtcg     180

cgtttttcgg gcagtggcag cggcacggac tttaccctga cgatatcttc cttacaaccg     240

gaggattttg cgacctacta ctgtcaacag tattctagct acccgttaac cttcggtcaa     300

ggcaccaaag tggaaaccaa acgc                                            324


<210> SEQ ID NO 83
<211> LENGTH: 369
<212> TYPE: DNA
<213> ORGANISM: Artificial Sequence
<220> FEATURE:
<223> OTHER INFORMATION: Synthetic polynucleotide

<400> SEQUENCE: 83

gaagtgcagc tggtggaatc gggaggcggt ctggtgcaac ctggcggcag ccttcgtctg      60
```

agctgtgcgg cgagcgggtt cgccattaac aattactcca ttcattgggt gcgtcaagct 120
cccggcaagg ggctggagtg ggtcgcgtct atttggccct atgggggttt tacatcttat 180
gccgacagcg tgaaaggtcg ctttacgatt agtgcggaca ccagcaaaaa taccgcgtac 240
ctgcagatga atagcctgcg tgcggaagac acagcggtgt attattgcgc gcgtttcttt 300
agctcctatg gcgatatgga ttattggggg cagggcaccc ttgttaccgt gagctcggcg 360
tcagcggcc 369

<210> SEQ ID NO 84
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 84
gatattcaaa tgacccagag cccgagcagc ctgagcgcga gcgtgggaga tcgcgtgacc 60
attacctgcc gtgcgagcca ggatgttagt ggcggggtcg catggtatca gcagaaacca 120
ggcaaagcgc cgaaacttct gatatatggg acaagtgggc tgtatagcgg cgtgccgtcg 180
cgtttttcgg gcagtggcag cggcacggac tttaccctga cgatatcttc cttacaaccg 240
gaggattttg cgacctacta ctgtcaacag gggggggatt ggccgataac cttcggtcaa 300
ggcaccaaag tggaaatcaa acgc 324

<210> SEQ ID NO 85
<211> LENGTH: 369
<212> TYPE: DNA
<213> ORGANISM: Artificial Sequence
<220> FEATURE:
<223> OTHER INFORMATION: Synthetic polynucleotide

<400> SEQUENCE: 85
gaagtgcagc tggtggaatc gggaggcggt ctggtgcaac ctggcggcag ccttcgtctg 60
agctgtgcgg cgagcgggtt caccattagt gactattcta ttcattgggt gcgtcaagct 120
cccggcaagg ggctggagtg ggtcgcgtct atttggccct atgggggttt tacatcttat 180
gccgacagcg tgaaaggtcg ctttacgatt agtgcggaca ccagcaaaaa taccgcgtac 240
ctgcagatga atagcctgcg tgcggaagac acagcggtgt attattgcgc gcgtttccac 300
agctcctccg gcgacatgga ttattggggg cagggcaccc ttgttaccgt gagctcggcg 360
tcagcggcc 369

<210> SEQ ID NO 86
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 86
gatattcaaa tgacccagag cccgagcagc ctgagcgcga gcgtgggaga tcgcgtgacc 60
attacctgcc gtgcgagcca ggatgtttgg gggtacgtcg catggtatca gcagaaacca 120
ggcaaagcgc cgaaacttct gatatttgcc tccggcgccc tgtatagcgg cgtgccgtcg 180
cgtttttcgg gcagtggcag cggcacggac tttaccctga cgatatcttc cttacaaccg 240
gaggattttg cgacctacta ctgtcaacag tactttaatt ggccgattac cttcggtcaa 300
ggcaccaaag tggaaatcaa acgc 324

<210> SEQ ID NO 87
<211> LENGTH: 369
<212> TYPE: DNA
<213> ORGANISM: Artificial Sequence
<220> FEATURE:
<223> OTHER INFORMATION: Synthetic polynucleotide

<400> SEQUENCE: 87
gaagtgcagc tggtggaatc gggaggcggt ctggtgcaac ctggcggcag ccttcgtctg 60
agctgtgcgg cgagcgggtt caccattaac agttcctaca ttcattgggt gcgtcaagct 120
cccggcaagg ggctggagtg ggtcgcgggg attgggccct attggggttt cacatcttat 180
gccgacagcg taaaaggtcg ctttacgatt agtgcggaca ccagcaaaaa taccgcgtac 240
ctgcagatga atagcctgcg tgcggaagac acagcggtgt attattgcgc gcgtttctat 300
agctcctatg gcttcatgga ttattggggg cagggcaccc ttgttaccgt gagctcggcg 360
tcagcggcc 369

<210> SEQ ID NO 88
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 88
gatattcaaa tgacccagag cccgagcagc ctgagcgcga gcgtgggaga tcgcgtgacc 60
attacctgcc gtgcgagcca ggatgtttac tcctgggtcg catggtatca gcagaaacca 120
ggcaaagcgc cgaaacttct gatatacggg cccggttccc tgtatagcgg cgtgccgtcg 180
cgtttttcgg gcagtggcag cggcacggac tttaccctga cgatatcttc cttacaaccg 240
gaggattttg cgacctacta ctgtcaacag tactataatt atccgctcac cttcggtcaa 300
ggcaccaaag tggaaatcaa acgc 324

<210> SEQ ID NO 89
<211> LENGTH: 369
<212> TYPE: DNA
<213> ORGANISM: Artificial Sequence
<220> FEATURE:
<223> OTHER INFORMATION: Synthetic polynucleotide

<400> SEQUENCE: 89
gaagtgcagc tggtggaatc gggaggcggt ctggtgcaac ctggcggcag ccttcgtctg 60
agctgtgcgg cgagcgggtt caccattggt aattcttata ttcattgggt gcgtcaagct 120
cccggcaagg ggctggagtg ggtcgcgggg attgggccct attggggttt cacatcttat 180
gccgacagcg tgaaaggtcg ctttacgatt agtgcggaca ccagcaaaaa taccgcgtac 240
ctgcagatga atagcctgcg tgcggaagac acagcggtgt attattgcgc gcgtttcaac 300
ggctcttctg gttttatgga ttattggggg cagggcaccc ttgttaccgt gagctcggcg 360
tcagcggcc 369

<210> SEQ ID NO 90
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 90
gatattcaaa tgacccagag cccgagcagc ctgagcgcga gcgtgggaga tcgcgtgacc 60
attacctgcc gtgcgagcca ggatgtttat tattttgtcg catggtatca gcagaaacca 120
ggcaaagcgc cgaaacttct gatatcctgg cctaccgggc tgtatagcgg cgtgccgtcg 180
cgtttttcgg gcagtggcag cggcacggac tttaccctga cgatatcttc cttacaaccg 240
gaggattttg cgacctacta ctgtcaacag tattttagtt atccgataac cttcggtcaa 300
ggcaccaaag tggaaatcaa acgc 324

<210> SEQ ID NO 91
<211> LENGTH: 369
<212> TYPE: DNA
<213> ORGANISM: Artificial Sequence
<220> FEATURE:
<223> OTHER INFORMATION: Synthetic polynucleotide

<400> SEQUENCE: 91
gaagtgcagc tggtggaatc gggaggcggt ctggtgcaac ctggcggcag ccttcgtctg 60
agctgtaagg cgtctggcta taccttcgcc cgctttggga tgtattgggt gcgtcaagct 120
cccggcaagg ggctggagtg ggtcgcgttt atcgctccaa atcatggcta tacattttat 180
gccgacagcg tgaaaggtcg ctttacgatt agtgcggaca ccagcaaaaa taccgcgtac 240
ctgcagatga atagcctgcg tgcggaagac acagcggtgt attattgcgc gcgtgggcac 300
tggtaccatg ggtatatgga ttattggggg cagggcaccc ttgttaccgt gagctcggcg 360
tcagcggcc 369

<210> SEQ ID NO 92
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 92
gatattcaaa tgacccagag cccgagcagc ctgagcgcga gcgtgggaga tcgcgtgacc 60
attacctgca aaagtaacca gaacctgctg tactctcacg gccggaccta tctgaattgg 120
tatcagcaga aaccaggcaa agcgccgaaa cttctgatat ttgggacgtc tcatctgtat 180
agtggcgtgc cgtcgcgttt ttcgggcagt ggcagcggca cggactttac cctgacgata 240
tcttccttac aaccggagga ttttgcgacc tactactgtt atcagggcta tcatgttccc 300
ttcaccttcg gtcaaggcac caaagtggaa atcaaacgc 339

<210> SEQ ID NO 93
<211> LENGTH: 372
<212> TYPE: DNA
<213> ORGANISM: Artificial Sequence
<220> FEATURE:
<223> OTHER INFORMATION: Synthetic polynucleotide

<400> SEQUENCE: 93
gaagtgcagc tggtggaatc gggaggcggt ctggtgcaac ctggcggcag ccttcgtctg 60
agctgtgcgg cgagcgggtt caccattggc aattacggga ttcattgggt gcgtcaagct 120
cccggcaagg ggctggagtg ggtcgcgtgg attgggccct ccgggggtta tacattctat 180
gccgacagcg tgaaaggtcg ctttacgatt agtgcggaca ccagcaaaaa taccgcgtac 240

```
ctgcagatga atagcctgcg tgcggaagac acagcggtgt attattgcgc gcgtttcgac    300

gttcacgggt tccacgggat ggattattgg gggcagggca cccttgttac cgtgagctcg    360

gcgtcagcgg cc                                                        372


<210> SEQ ID NO 94
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 94

gatattcaaa tgacccagag cccgagcagc ctgagcgcga gcgtgggaga tcgcgtgacc     60

attacctgcc gtgcgagcca ggatgttaac aacagtgtcg catggtatca gcagaaacca    120

ggcaaagcgc cgaaacttct gatattttcc cctactgggc tgtatagcgg cgtgccgtcg    180

cgtttttcgg gcagtggcag cggcacggac tttaccctga cgatatcttc cttacaaccg    240

gaggattttg cgacctacta ctgtcaacag tacttcgact tcccgttaac cttcggtcaa    300

ggcaccaaag tggaaatcaa acgt                                           324


<210> SEQ ID NO 95
<211> LENGTH: 372
<212> TYPE: DNA
<213> ORGANISM: Artificial Sequence
<220> FEATURE:
<223> OTHER INFORMATION: Synthetic polynucleotide

<400> SEQUENCE: 95

gaagtgcagc tggtggaatc gggaggcggt ctggtgcaac ctggcggcag ccttcgtctg     60

agctgtgcgg cgagcgggtt caccattaac gacgggttca ttcattgggt gcgtcaagct    120

cccggcaagg ggctggagtg ggtcgcgggg atttggccct ttgggggttc cacatcctat    180

gccgacagcg tgaaaggtcg ctttacgatt agtgcggaca ccagcaaaaa taccgcgtac    240

ctgcagatga atagcctgcg tgcggaagac acagcggtgt attattgcgc gcgtttcgat    300

gtcgtcgatt ggggggtcat ggattattgg gggcagggca cccttgttac cgtgagctcg    360

gcgtcagcgg cc                                                        372


<210> SEQ ID NO 96
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 96

gatattcaaa tgacccagag cccgagcagc ctgagcgcga gcgtgggaga tcgcgtgacc     60

attacctgcc gtgcgagcca ggatgttaat gatggcgtcg catggtatca gcagaaacca    120

ggcaaagcgc cgaaacttct gatatattgg gcgagttacc tgtatagcgg cgtgccgtcg    180

cgtttttcgg gcagtggcag cggcacggac tttaccctga cgatatcttc cttacaaccg    240

gaggattttg cgacctacta ctgtcaacag tcctggaatt ttccgctcac cttcggtcaa    300

ggcaccaaag tggaaatcaa acgc                                           324


<210> SEQ ID NO 97
<211> LENGTH: 372
<212> TYPE: DNA
<213> ORGANISM: Artificial Sequence
```

<220> FEATURE:
<223> OTHER INFORMATION: Synthetic polynucleotide

<400> SEQUENCE: 97
gaagtgcagc tggtggaatc gggaggcggt ctggtgcaac ctggcggcag ccttcgtctg 60
agctgtgcgg cgagcgggtt caccattggt aattacggga ttcattgggt gcgtcaagct 120
cccggcaagg ggctggagtg ggtcgcgtgg attgggccct atgggggtta cacattctat 180
gccgacagcg tgaaaggtcg ctttacgatt agtgcggaca ccagcaaaaa taccgcgtac 240
ctgcagatga atagcctgcg tgcggaagac acagcggtgt attattgcgc gcgtttcaat 300
aaccttcttt ggaatgggat ggattattgg gggcagggca cccttgttac cgtgagctcg 360
gcgtcagcgg cc 372

<210> SEQ ID NO 98
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 98
gatattcaaa tgacccagag cccgagcagc ctgagcgcga gcgtgggaga tcgcgtgacc 60
attacctgcc gtgcgagcca ggatgtttcc tcttccgtcg catggtatca gcagaaacca 120
ggcaaagcgc cgaaacttct gatatcctat cctggttggc tgtatagcgg cgtgccgtcg 180
cgtttttcgg gcagtggcag cggcacggac tttaccctga cgatatcttc cttacaaccg 240
gaggattttg cgacctacta ctgtcaacag tttggggatt ttccgatgac cttcggtcaa 300
ggcaccaaag tggaaatcaa acgc 324

<210> SEQ ID NO 99
<211> LENGTH: 369
<212> TYPE: DNA
<213> ORGANISM: Artificial Sequence
<220> FEATURE:
<223> OTHER INFORMATION: Synthetic polynucleotide

<400> SEQUENCE: 99
gaagtgcagc tggtggaatc gggaggcggt ctggtgcaac ctggcggcag ccttcgtctg 60
agctgtgcgg cgagcgggtt caccattagt gactattcta ttcattgggt gcgtcaagct 120
cccggcaagg ggctggagtg ggtcgcgtct atttggccct atgggggttt tacatcttat 180
gccgacagcg tgaaaggtcg ctttacgatt agtgcggaca ccagcaaaaa taccgcgtac 240
ctgcagatga atagcctgcg tgcggaagac acagcggtgt attattgcgc gcgtttccac 300
agctcctccg gcgacatgga ttattggggg cagggcaccc ttgttaccgt gagctcggcg 360
tcagcggcc 369

<210> SEQ ID NO 100
<211> LENGTH: 324
<212> TYPE: DNA
<213> ORGANISM: Artificial Sequence
<220> FEATURE:
<223> OTHER INFORMATION: Synthetic polynucleotide

<400> SEQUENCE: 100
gatattcaaa tgacccagag cccgagcagc ctgagcgcga gcgtgggaga tcgcgtgacc 60
attacctgcc gtgcgagcca ggatgtttgg gggtacgtcg catggtatca gcagaaacca 120
ggcaaagcgc cgaaacttct gatattttcc tcccgctccc tgtatagcgg cgtgccgtcg 180
cgtttttcgg gcagtggcag cggcacggac tttaccctga cgatatcttc cttacaaccg 240
gaggattttg cgacctacta ctgtcaacag tactttaatt ggccgattac cttcggtcaa 300
ggcaccaaag tggaaatcaa acgc 324

<210> SEQ ID NO 101
<211> LENGTH: 27
<212> TYPE: PRT
<213> ORGANISM: Artificial Sequence
<220> FEATURE:
<223> OTHER INFORMATION: Synthetic peptide

<400> SEQUENCE: 101

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 102
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 102

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 103
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 103

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 104
<211> LENGTH: 146

<212> TYPE: PRT
<213> ORGANISM: Homo sapiens

<400> SEQUENCE: 104

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Arg Lys Asn Ser Arg Val Phe Ser Lys Ala
        115                 120                 125

Ser Leu Leu Pro Lys Lys Lys Pro Ser Thr Pro Ala Leu Ala His Glu
    130                 135                 140

Gly Leu
145

<210> SEQ ID NO 105
<211> LENGTH: 172
<212> TYPE: PRT
<213> ORGANISM: Homo sapiens

<400> SEQUENCE: 105

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Glu Ser
                165                 170

<210> SEQ ID NO 106
<211> LENGTH: 441

```
<212> TYPE: DNA
<213> ORGANISM: Homo sapiens

<400> SEQUENCE: 106

atggcagccg gaacagcagt tggagcctgg gtgctggtcc tcagtctgtg gggggcagta     60

gtaggtgctc aaaacatcac agcccggatt ggcgagccac tggtgctgaa gtgtaagggg    120

gcccccaaga aaccacccca gcggctggaa tggaaactga acacaggccg gacagaagct    180

tggaaggtcc tgtctcccca gggaggaggc ccctgggaca gtgtggctcg tgtccttccc    240

aacggctccc tcttccttcc ggctgtcggg atccaggatg aggggatttt ccggtgccag    300

gcaatgaaca ggaatggaaa ggagaccaag tccaactacc gagtccgtgt ctaccgtaag    360

aattccaggg tcttctccaa ggcctccctc ttacctaaga aaaagccttc aaccccagcc    420

ttggcccatg agggcctctg a                                              441


<210> SEQ ID NO 107
<211> LENGTH: 519
<212> TYPE: DNA
<213> ORGANISM: Mus sp.

<400> SEQUENCE: 107

atggcagccg gaacagcagt tggagcctgg gtgctggtcc tcagtctgtg gggggcagta     60

gtaggtgctc aaaacatcac agcccggatt ggcgagccac tggtgctgaa gtgtaagggg    120

gcccccaaga aaccacccca gcggctggaa tggaaactga acacaggccg gacagaagct    180

tggaaggtcc tgtctcccca gggaggaggc ccctgggaca gtgtggctcg tgtccttccc    240

aacggctccc tcttccttcc ggctgtcggg atccaggatg aggggatttt ccggtgccag    300

gcaatgaaca ggaatggaaa ggagaccaag tccaactacc gagtccgtgt ctaccagatt    360

cctgggaagc cagaaattgt agattctgcc tctgaactca cggctggtgt tcccaataag    420

gtggggacat gtgtgtcaga gggaagctac cctgcaggga ctcttagctg gcacttggat    480

gggaagcccc tggtgcctaa tgagaagggt gagtcctaa                           519


<210> SEQ ID NO 108
<211> LENGTH: 249
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (109)..(126)
<223> OTHER INFORMATION: Any amino acid

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Ser Asn
            20                  25                  30

Val Ala Trp Tyr Gln Gln Lys Pro Gly Lys Ala Pro Lys Leu Leu Ile
        35                  40                  45

Phe Gly Ser Gly Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95
```

Thr Phe Gly Gln Gly Thr Lys Val Glu Thr Lys Arg Xaa Xaa Xaa Xaa
100 105 110

Xaa Xaa Xaa Xaa Xaa Xaa Xaa Xaa Xaa Xaa Xaa Xaa Xaa Xaa Glu Val
115 120 125

Gln Leu Val Glu Ser Gly Gly Gly Leu Val Gln Pro Gly Gly Ser Leu
130 135 140

Arg Leu Ser Cys Ala Ala Ser Gly Phe Thr Ile Asn Asp Ser Tyr Ile
145 150 155 160

His Trp Val Arg Gln Ala Pro Gly Lys Gly Leu Glu Trp Val Ala Trp
165 170 175

Ile Trp Pro Tyr Gly Gly Phe Thr Tyr Tyr Ala Asp Ser Val Lys Gly
180 185 190

Arg Phe Thr Ile Ser Ala Asp Thr Ser Lys Asn Thr Ala Tyr Leu Gln
195 200 205

Met Asn Ser Leu Arg Ala Glu Asp Thr Ala Val Tyr Tyr Cys Ala Arg
210 215 220

Phe Leu Gly Ser Ser Ser Ile Met Asp Tyr Trp Gly Gln Gly Thr Leu
225 230 235 240

Val Thr Val Ser Ser Ala Ser Ala Ala
245

<210> SEQ ID NO 109
<211> LENGTH: 249
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (109)..(126)
<223> OTHER INFORMATION: Any amino acid

<400> SEQUENCE: 109

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Ser Gly Gly
20 25 30

Val Ala Trp Tyr Gln Gln Lys Pro Gly Lys Ala Pro Lys Leu Leu Ile
35 40 45

Tyr Gly Thr Ser Gly Leu Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Gly Gly Asp Trp Pro Ile
85 90 95

Thr Phe Gly Gln Gly Thr Lys Val Glu Ile Lys Arg Xaa Xaa Xaa Xaa
100 105 110

Xaa Xaa Xaa Xaa Xaa Xaa Xaa Xaa Xaa Xaa Xaa Xaa Xaa Xaa Glu Val
115 120 125

Gln Leu Val Glu Ser Gly Gly Gly Leu Val Gln Pro Gly Gly Ser Leu
130 135 140

Arg Leu Ser Cys Ala Ala Ser Gly Phe Ala Ile Asn Asn Tyr Ser Ile
145 150 155 160

His Trp Val Arg Gln Ala Pro Gly Lys Gly Leu Glu Trp Val Ala Ser
165 170 175

Ile Trp Pro Tyr Gly Gly Phe Thr Ser Tyr Ala Asp Ser Val Lys Gly
180 185 190

Arg Phe Thr Ile Ser Ala Asp Thr Ser Lys Asn Thr Ala Tyr Leu Gln
195 200 205

Met Asn Ser Leu Arg Ala Glu Asp Thr Ala Val Tyr Tyr Cys Ala Arg
210 215 220

Phe Phe Ser Ser Tyr Gly Asp Met Asp Tyr Trp Gly Gln Gly Thr Leu
225 230 235 240

Val Thr Val Ser Ser Ala Ser Ala Ala
245

<210> SEQ ID NO 110
<211> LENGTH: 249
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (109)..(126)
<223> OTHER INFORMATION: Any amino acid

<400> SEQUENCE: 110

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Trp Gly Tyr
20 25 30

Val Ala Trp Tyr Gln Gln Lys Pro Gly Lys Ala Pro Lys Leu Leu Ile
35 40 45

Phe Ala Ser Gly Ala Leu Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Phe Asn Trp Pro Ile
85 90 95

Thr Phe Gly Gln Gly Thr Lys Val Glu Ile Lys Arg Xaa Xaa Xaa Xaa
100 105 110

Xaa Xaa Xaa Xaa Xaa Xaa Xaa Xaa Xaa Xaa Xaa Xaa Xaa Xaa Glu Val
115 120 125

Gln Leu Val Glu Ser Gly Gly Gly Leu Val Gln Pro Gly Gly Ser Leu
130 135 140

Arg Leu Ser Cys Ala Ala Ser Gly Phe Thr Ile Ser Asp Tyr Ser Ile
145 150 155 160

His Trp Val Arg Gln Ala Pro Gly Lys Gly Leu Glu Trp Val Ala Ser
165 170 175

Ile Trp Pro Tyr Gly Gly Phe Thr Ser Tyr Ala Asp Ser Val Lys Gly
180 185 190

Arg Phe Thr Ile Ser Ala Asp Thr Ser Lys Asn Thr Ala Tyr Leu Gln
195 200 205

Met Asn Ser Leu Arg Ala Glu Asp Thr Ala Val Tyr Tyr Cys Ala Arg
210 215 220

Phe His Ser Ser Ser Gly Asp Met Asp Tyr Trp Gly Gln Gly Thr Leu
225 230 235 240

Val Thr Val Ser Ser Ala Ser Ala Ala
245

<210> SEQ ID NO 111
<211> LENGTH: 249
<212> TYPE: PRT

<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (109)..(126)
<223> OTHER INFORMATION: Any amino acid

<400> SEQUENCE: 111

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Tyr Ser Trp
20 25 30

Val Ala Trp Tyr Gln Gln Lys Pro Gly Lys Ala Pro Lys Leu Leu Ile
35 40 45

Tyr Gly Pro Gly Ser Leu Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Asn Tyr Pro Leu
85 90 95

Thr Phe Gly Gln Gly Thr Lys Val Glu Ile Lys Arg Xaa Xaa Xaa Xaa
100 105 110

Xaa Xaa Xaa Xaa Xaa Xaa Xaa Xaa Xaa Xaa Xaa Xaa Xaa Xaa Glu Val
115 120 125

Gln Leu Val Glu Ser Gly Gly Gly Leu Val Gln Pro Gly Gly Ser Leu
130 135 140

Arg Leu Ser Cys Ala Ala Ser Gly Phe Thr Ile Asn Ser Ser Tyr Ile
145 150 155 160

His Trp Val Arg Gln Ala Pro Gly Lys Gly Leu Glu Trp Val Ala Gly
165 170 175

Ile Gly Pro Tyr Trp Gly Phe Thr Ser Tyr Ala Asp Ser Val Lys Gly
180 185 190

Arg Phe Thr Ile Ser Ala Asp Thr Ser Lys Asn Thr Ala Tyr Leu Gln
195 200 205

Met Asn Ser Leu Arg Ala Glu Asp Thr Ala Val Tyr Tyr Cys Ala Arg
210 215 220

Phe Tyr Ser Ser Tyr Gly Phe Met Asp Tyr Trp Gly Gln Gly Thr Leu
225 230 235 240

Val Thr Val Ser Ser Ala Ser Ala Ala
245

<210> SEQ ID NO 112
<211> LENGTH: 249
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (109)..(126)
<223> OTHER INFORMATION: Any amino acid

<400> SEQUENCE: 112

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Tyr Tyr Phe
20 25 30

Val Ala Trp Tyr Gln Gln Lys Pro Gly Lys Ala Pro Lys Leu Leu Ile 35 40 45

Ser Trp Pro Thr Gly Leu Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Phe Ser Tyr Pro Ile
85 90 95

Thr Phe Gly Gln Gly Thr Lys Val Glu Ile Lys Arg Xaa Xaa Xaa Xaa
100 105 110

Xaa Xaa Xaa Xaa Xaa Xaa Xaa Xaa Xaa Xaa Xaa Xaa Xaa Xaa Glu Val
115 120 125

Gln Leu Val Glu Ser Gly Gly Gly Leu Val Gln Pro Gly Gly Ser Leu
130 135 140

Arg Leu Ser Cys Ala Ala Ser Gly Phe Thr Ile Gly Asn Ser Tyr Ile
145 150 155 160

His Trp Val Arg Gln Ala Pro Gly Lys Gly Leu Glu Trp Val Ala Gly
165 170 175

Ile Gly Pro Tyr Trp Gly Phe Thr Ser Tyr Ala Asp Ser Val Lys Gly
180 185 190

Arg Phe Thr Ile Ser Ala Asp Thr Ser Lys Asn Thr Ala Tyr Leu Gln
195 200 205

Met Asn Ser Leu Arg Ala Glu Asp Thr Ala Val Tyr Tyr Cys Ala Arg
210 215 220

Phe Asn Gly Ser Ser Gly Phe Met Asp Tyr Trp Gly Gln Gly Thr Leu
225 230 235 240

Val Thr Val Ser Ser Ala Ser Ala Ala
245

<210> SEQ ID NO 113
<211> LENGTH: 248
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (109)..(126)
<223> OTHER INFORMATION: Any amino acid

<400> SEQUENCE: 113

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Ser Ser Ser
20 25 30

Val Ala Trp Tyr Gln Gln Lys Pro Gly Lys Ala Pro Lys Leu Leu Ile
35 40 45

Ser Tyr Pro Gly Trp Leu Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Gly Asp Phe Pro Met
85 90 95

Thr Phe Gly Gln Gly Thr Lys Val Glu Ile Lys Arg Xaa Xaa Xaa Xaa
100 105 110

Xaa Xaa Xaa Xaa Xaa Xaa Xaa Xaa Xaa Xaa Xaa Xaa Xaa Xaa Glu Val
115 120 125

```
Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Gly Asn Tyr Gly Ile
145                 150                 155                 160

His Trp Val Arg Gln Ala Pro Gly Lys Gly Leu Glu Trp Val Ala Trp
                165                 170                 175

Ile Gly Pro Tyr Gly Gly Tyr Thr Phe Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe Asn Asn Leu Leu Trp Asn Gly Met Asp Tyr Trp Gly Gln Gly Thr
225                 230                 235                 240

Leu Val Thr Val Ser Ser Ala Ser
                245


<210> SEQ ID NO 114
<211> LENGTH: 248
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (109)..(126)
<223> OTHER INFORMATION: Any amino acid

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asp Gly
            20                  25                  30

Val Ala Trp Tyr Gln Gln Lys Pro Gly Lys Ala Pro Lys Leu Leu Ile
        35                  40                  45

Tyr Trp Ala Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Asn Phe Pro Leu
                85                  90                  95

Thr Phe Gly Gln Gly Thr Lys Val Glu Ile Lys Arg Xaa Xaa Xaa Xaa
            100                 105                 110

Xaa Xaa Xaa Xaa Xaa Xaa Xaa Xaa Xaa Xaa Xaa Xaa Xaa Xaa Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Asn Asp Gly Phe Ile
145                 150                 155                 160

His Trp Val Arg Gln Ala Pro Gly Lys Gly Leu Glu Trp Val Ala Gly
                165                 170                 175

Ile Trp Pro Phe Gly Gly Ser Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220
```

```
Phe Asp Val Val Asp Trp Gly Val Met Asp Tyr Trp Gly Gln Gly Thr
225                 230                 235                 240

Leu Val Thr Val Ser Ser Ala Ser
                245


<210> SEQ ID NO 115
<211> LENGTH: 247
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (109)..(126)
<223> OTHER INFORMATION: Any amino acid

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Trp Gly Tyr
            20                  25                  30

Val Ala Trp Tyr Gln Gln Lys Pro Gly Lys Ala Pro Lys Leu Leu Ile
        35                  40                  45

Phe Ser Ser Arg Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Asn Trp Pro Ile
                85                  90                  95

Thr Phe Gly Gln Gly Thr Lys Val Glu Ile Lys Arg Xaa Xaa Xaa Xaa
            100                 105                 110

Xaa Xaa Xaa Xaa Xaa Xaa Xaa Xaa Xaa Xaa Xaa Xaa Xaa Xaa Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Ser Asp Tyr Ser Ile
145                 150                 155                 160

His Trp Val Arg Gln Ala Pro Gly Lys Gly Leu Glu Trp Val Ala Ser
                165                 170                 175

Ile Trp Pro Tyr Gly Gly Phe Thr Ser Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Phe His Ser Ser Ser Gly Asp Met Asp Tyr Trp Gly Gln Gly Thr Leu
225                 230                 235                 240

Val Thr Val Ser Ser Ala Ser
                245


<210> SEQ ID NO 116
<211> LENGTH: 248
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (109)..(126)
```

<223> OTHER INFORMATION: Any amino acid

<400> SEQUENCE: 116

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Asn Ser
20 25 30

Val Ala Trp Tyr Gln Gln Lys Pro Gly Lys Ala Pro Lys Leu Leu Ile
35 40 45

Phe Ser Pro Thr Gly Leu Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Phe Asp Phe Pro Leu
85 90 95

Thr Phe Gly Gln Gly Thr Lys Val Glu Ile Lys Arg Xaa Xaa Xaa Xaa
100 105 110

Xaa Xaa Xaa Xaa Xaa Xaa Xaa Xaa Xaa Xaa Xaa Xaa Xaa Xaa Glu Val
115 120 125

Gln Leu Val Glu Ser Gly Gly Gly Leu Val Gln Pro Gly Gly Ser Leu
130 135 140

Arg Leu Ser Cys Ala Ala Ser Gly Phe Thr Ile Gly Asn Tyr Gly Ile
145 150 155 160

His Trp Val Arg Gln Ala Pro Gly Lys Gly Leu Glu Trp Val Ala Trp
165 170 175

Ile Gly Pro Ser Gly Gly Tyr Thr Phe Tyr Ala Asp Ser Val Lys Gly
180 185 190

Arg Phe Thr Ile Ser Ala Asp Thr Ser Lys Asn Thr Ala Tyr Leu Gln
195 200 205

Met Asn Ser Leu Arg Ala Glu Asp Thr Ala Val Tyr Tyr Cys Ala Arg
210 215 220

Phe Asp Val His Gly Phe His Gly Met Asp Tyr Trp Gly Gln Gly Thr
225 230 235 240

Leu Val Thr Val Ser Ser Ala Ser
245

<210> SEQ ID NO 117
<211> LENGTH: 249
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (114)..(128)
<223> OTHER INFORMATION: Any amino acid

<400> SEQUENCE: 117

Asp Ile Gln Met Thr Gln Ser Pro Ser Ser Leu Ser Ala Ser Val Gly
1 5 10 15

Asp Arg Val Thr Ile Thr Cys Lys Ser Asn Gln Asn Leu Leu Tyr Ser
20 25 30

His Gly Arg Thr Tyr Leu Asn Trp Tyr Gln Gln Lys Pro Gly Lys Ala
35 40 45

Pro Lys Leu Leu Ile Phe Gly Thr Ser His Leu Tyr Ser Gly Val Pro
50 55 60

Ser Arg Phe Ser Gly Ser Gly Ser Gly Thr Asp Phe Thr Leu Thr Ile

```
65                  70                  75                  80

Ser Ser Leu Gln Pro Glu Asp Phe Ala Thr Tyr Tyr Cys Tyr Gln Gly
                85                  90                  95

Tyr His Val Pro Phe Thr Phe Gly Gln Gly Thr Lys Val Glu Ile Lys
            100                 105                 110

Arg Xaa Xaa Xaa Xaa Xaa Xaa Xaa Xaa Xaa Xaa Xaa Xaa Xaa Xaa Xaa
        115                 120                 125

Glu Val Gln Leu Val Glu Ser Gly Gly Gly Leu Val Gln Pro Gly Gly
    130                 135                 140

Ser Leu Arg Leu Ser Cys Lys Ala Ser Gly Tyr Thr Phe Ala Arg Phe
145                 150                 155                 160

Gly Met Tyr Trp Val Arg Gln Ala Pro Gly Lys Gly Leu Glu Trp Val
                165                 170                 175

Ala Phe Ile Ala Pro Asn His Gly Tyr Thr Phe Tyr Ala Asp Ser Val
            180                 185                 190

Lys Gly Arg Phe Thr Ile Ser Ala Asp Thr Ser Lys Asn Thr Ala Tyr
        195                 200                 205

Leu Gln Met Asn Ser Leu Arg Ala Glu Asp Thr Ala Val Tyr Tyr Cys
    210                 215                 220

Ala Arg Gly His Trp Tyr His Gly Tyr Met Asp Tyr Trp Gly Gln Gly
225                 230                 235                 240

Thr Leu Val Thr Val Ser Ser Ala Ser
                245
```

<210> SEQ ID NO 118
<211> LENGTH: 2964
<212> TYPE: DNA
<213> ORGANISM: Homo sapiens

<400> SEQUENCE: 118

```
atgaagtggg tgaccttcat cagcctgctg ttcctgttct ccagcgccta ctccaacaaa     60

ggcacagatg atgctacagc tgacagtcgc aaaacttaca ctctaactga ttacttaaaa    120

aatacttata gactgaagtt atactcctta agatggattt cagatcatga atatctctac    180

aaacaagaaa ataatatctt ggtattcaat gctgaatatg gaaacagctc agttttcttg    240

gagaacagta catttgatga gtttggacat tctatcaatg attattcaat atctcctgat    300

gggcagttta ttctcttaga atacaactac gtgaagcaat ggaggcattc ctacacagct    360

tcatatgaca tttatgattt aaataaaagg cagctgatta cagaagagag gattccaaac    420

aacacacagt gggtcacatg gtcaccagtg ggtcataaat tggcatatgt ttggaacaat    480

gacatttatg ttaaaattga accaaattta ccaagttaca gaatcacatg gacggggaaa    540

gaagatataa tatataatgg aataactgac tgggtttatg aagaggaagt cttcagtgcc    600

tactctgctc tgtggtggtc tccaaacggc actttttag catatgccca atttaacgac     660

acagaagtcc cacttattga atactccttc tactctgatg agtcactgca gtacccaaag    720

actgtacggg ttccatatcc aaaggcagga gctgtgaatc caactgtaaa gttctttgtt    780

gtaaatacag actctctcag ctcagtcacc aatgcaactt ccatacaaat cactgctcct    840

gcttctatgt tgataggggga tcactacttg tgtgatgtga catgggcaac acaagaaaga    900

atttctttgc agtggctcag gaggattcag aactattcgg tcatggatat ttgtgactat    960

gatgaatcca gtggaagatg gaactgctta gtggcacggc aacacattga aatgagtact   1020

actggctggg ttggaagatt taggccttca gaacctcatt ttacccttga tggtaatagc   1080
```

ttctacaaga tcatcagcaa tgaagaaggt tacagacaca tttgctattt ccaaatagat 1140
aaaaaagact gcacatttat tacaaaaggc acctgggaag tcatcgggat agaagctcta 1200
accagtgatt atctatacta cattagtaat gaatataaag gaatgccagg aggaaggaat 1260
ctttataaaa tccaacttag tgactataca aaagtgacat gcctcagttg tgagctgaat 1320
ccggaaaggt gtcagtacta ttctgtgtca ttcagtaaag aggcgaagta ttatcagctg 1380
agatgttccg gtcctggtct gcccctctat actctacaca gcagcgtgaa tgataaaggg 1440
ctgagagtcc tggaagacaa ttcagctttg gataaaatgc tgcagaatgt ccagatgccc 1500
tccaaaaaac tggacttcat tattttgaat gaaacaaaat tttggtatca gatgatcttg 1560
cctcctcatt ttgataaatc caagaaatat cctctactat tagatgtgta tgcaggccca 1620
tgtagtcaaa aagcagacac tgtcttcaga ctgaactggg ccacttacct tgcaagcaca 1680
gaaaacatta tagtagctag ctttgatggc agaggaagtg gttaccaagg agataagatc 1740
atgcatgcaa tcaacagaag actgggaaca tttgaagttg aagatcaaat tgaagcagcc 1800
agacaatttt caaaaatggg atttgtggac aacaaacgaa ttgcaatttg gggctggtca 1860
tatggagggt acgtaacctc aatggtcctg ggatcaggaa gtggcgtgtt caagtgtgga 1920
atagccgtgg cgcctgtatc ccggtgggag tactatgact cagtgtacac agaacgttac 1980
atgggtctcc caactccaga agacaacctt gaccattaca gaaattcaac agtcatgagc 2040
agagctgaaa attttaaaca agttgagtac ctccttattc atggaacagc agatgataac 2100
gttcactttc agcagtcagc tcagatctcc aaagccctgg tcgatgttgg agtggatttc 2160
caggcaatgt ggtatactga tgaagaccat ggaatagcta gcagcacagc acaccaacat 2220
atatataccc acatgagcca cttcataaaa caatgtttct ctttacctga gccgaaatct 2280
tgtgacaaaa ctcacacatg cccaccgtgc ccagcacctg aactcctggg gggaccgtca 2340
gtcttcctct tccccccaaa acccaaggac accctcatga tctcccggac ccctgaggtc 2400
acatgcgtgg tggtggacgt gagccacgaa gaccctgagg tcaagttcaa ctggtacgtg 2460
gacggcgtgg aggtgcataa tgccaagaca aagccgcggg aggagcagta caacagcacg 2520
taccgtgtgg tcagcgtcct caccgtcctg caccaggact ggctgaatgg caaggagtac 2580
aagtgcaagg tctccaacaa agccctccca gcccccatcg agaaaaccat ctccaaagcc 2640
aaagggcagc cccgagaacc acaggtgtac accctgcccc catcccggga tgagctgacc 2700
aagaaccagg tcagcctgac ctgcctggtc aaaggcttct atcccagcga catcgccgtg 2760
gagtgggaga gcaatgggca gccggagaac aactacaaga ccacgcctcc cgtgctggac 2820
tccgacggct ccttcttcct ctacagcaag ctcaccgtgg acaagagcag gtggcagcag 2880
gggaacgtct tctcatgctc cgtgatgcat gaggctctgc acaaccacta cacgcagaag 2940
agcctctccc tgtctcctgg taaa 2964

<210> SEQ ID NO 119
<211> LENGTH: 988
<212> TYPE: PRT
<213> ORGANISM: Homo sapiens

<400> SEQUENCE: 119

Met Lys Trp Val Thr Phe Ile Ser Leu Leu Phe Leu Phe Ser Ser Ala
1 5 10 15

Tyr Ser Asn Lys Gly Thr Asp Asp Ala Thr Ala Asp Ser Arg Lys Thr
20 25 30

Tyr Thr Leu Thr Asp Tyr Leu Lys Asn Thr Tyr Arg Leu Lys Leu Tyr

```
        35                  40                  45

Ser Leu Arg Trp Ile Ser Asp His Glu Tyr Leu Tyr Lys Gln Glu Asn
    50                  55                  60

Asn Ile Leu Val Phe Asn Ala Glu Tyr Gly Asn Ser Ser Val Phe Leu
65                  70                  75                  80

Glu Asn Ser Thr Phe Asp Glu Phe Gly His Ser Ile Asn Asp Tyr Ser
                85                  90                  95

Ile Ser Pro Asp Gly Gln Phe Ile Leu Leu Glu Tyr Asn Tyr Val Lys
            100                 105                 110

Gln Trp Arg His Ser Tyr Thr Ala Ser Tyr Asp Ile Tyr Asp Leu Asn
        115                 120                 125

Lys Arg Gln Leu Ile Thr Glu Glu Arg Ile Pro Asn Asn Thr Gln Trp
    130                 135                 140

Val Thr Trp Ser Pro Val Gly His Lys Leu Ala Tyr Val Trp Asn Asn
145                 150                 155                 160

Asp Ile Tyr Val Lys Ile Glu Pro Asn Leu Pro Ser Tyr Arg Ile Thr
                165                 170                 175

Trp Thr Gly Lys Glu Asp Ile Ile Tyr Asn Gly Ile Thr Asp Trp Val
            180                 185                 190

Tyr Glu Glu Glu Val Phe Ser Ala Tyr Ser Ala Leu Trp Trp Ser Pro
        195                 200                 205

Asn Gly Thr Phe Leu Ala Tyr Ala Gln Phe Asn Asp Thr Glu Val Pro
    210                 215                 220

Leu Ile Glu Tyr Ser Phe Tyr Ser Asp Glu Ser Leu Gln Tyr Pro Lys
225                 230                 235                 240

Thr Val Arg Val Pro Tyr Pro Lys Ala Gly Ala Val Asn Pro Thr Val
                245                 250                 255

Lys Phe Phe Val Val Asn Thr Asp Ser Leu Ser Ser Val Thr Asn Ala
            260                 265                 270

Thr Ser Ile Gln Ile Thr Ala Pro Ala Ser Met Leu Ile Gly Asp His
        275                 280                 285

Tyr Leu Cys Asp Val Thr Trp Ala Thr Gln Glu Arg Ile Ser Leu Gln
    290                 295                 300

Trp Leu Arg Arg Ile Gln Asn Tyr Ser Val Met Asp Ile Cys Asp Tyr
305                 310                 315                 320

Asp Glu Ser Ser Gly Arg Trp Asn Cys Leu Val Ala Arg Gln His Ile
                325                 330                 335

Glu Met Ser Thr Thr Gly Trp Val Gly Arg Phe Arg Pro Ser Glu Pro
            340                 345                 350

His Phe Thr Leu Asp Gly Asn Ser Phe Tyr Lys Ile Ile Ser Asn Glu
        355                 360                 365

Glu Gly Tyr Arg His Ile Cys Tyr Phe Gln Ile Asp Lys Lys Asp Cys
    370                 375                 380

Thr Phe Ile Thr Lys Gly Thr Trp Glu Val Ile Gly Ile Glu Ala Leu
385                 390                 395                 400

Thr Ser Asp Tyr Leu Tyr Tyr Ile Ser Asn Glu Tyr Lys Gly Met Pro
                405                 410                 415

Gly Gly Arg Asn Leu Tyr Lys Ile Gln Leu Ser Asp Tyr Thr Lys Val
            420                 425                 430

Thr Cys Leu Ser Cys Glu Leu Asn Pro Glu Arg Cys Gln Tyr Tyr Ser
        435                 440                 445

Val Ser Phe Ser Lys Glu Ala Lys Tyr Tyr Gln Leu Arg Cys Ser Gly
    450                 455                 460
```

```
Pro Gly Leu Pro Leu Tyr Thr Leu His Ser Ser Val Asn Asp Lys Gly
465                 470                 475                 480

Leu Arg Val Leu Glu Asp Asn Ser Ala Leu Asp Lys Met Leu Gln Asn
                485                 490                 495

Val Gln Met Pro Ser Lys Lys Leu Asp Phe Ile Ile Leu Asn Glu Thr
            500                 505                 510

Lys Phe Trp Tyr Gln Met Ile Leu Pro Pro His Phe Asp Lys Ser Lys
        515                 520                 525

Lys Tyr Pro Leu Leu Leu Asp Val Tyr Ala Gly Pro Cys Ser Gln Lys
    530                 535                 540

Ala Asp Thr Val Phe Arg Leu Asn Trp Ala Thr Tyr Leu Ala Ser Thr
545                 550                 555                 560

Glu Asn Ile Ile Val Ala Ser Phe Asp Gly Arg Gly Ser Gly Tyr Gln
                565                 570                 575

Gly Asp Lys Ile Met His Ala Ile Asn Arg Arg Leu Gly Thr Phe Glu
            580                 585                 590

Val Glu Asp Gln Ile Glu Ala Ala Arg Gln Phe Ser Lys Met Gly Phe
        595                 600                 605

Val Asp Asn Lys Arg Ile Ala Ile Trp Gly Trp Ser Tyr Gly Gly Tyr
    610                 615                 620

Val Thr Ser Met Val Leu Gly Ser Gly Ser Gly Val Phe Lys Cys Gly
625                 630                 635                 640

Ile Ala Val Ala Pro Val Ser Arg Trp Glu Tyr Tyr Asp Ser Val Tyr
                645                 650                 655

Thr Glu Arg Tyr Met Gly Leu Pro Thr Pro Glu Asp Asn Leu Asp His
            660                 665                 670

Tyr Arg Asn Ser Thr Val Met Ser Arg Ala Glu Asn Phe Lys Gln Val
        675                 680                 685

Glu Tyr Leu Leu Ile His Gly Thr Ala Asp Asp Asn Val His Phe Gln
    690                 695                 700

Gln Ser Ala Gln Ile Ser Lys Ala Leu Val Asp Val Gly Val Asp Phe
705                 710                 715                 720

Gln Ala Met Trp Tyr Thr Asp Glu Asp His Gly Ile Ala Ser Ser Thr
                725                 730                 735

Ala His Gln His Ile Tyr Thr His Met Ser His Phe Ile Lys Gln Cys
            740                 745                 750

Phe Ser Leu Pro Glu Pro Lys Ser Cys Asp Lys Thr His Thr Cys Pro
        755                 760                 765

Pro Cys Pro Ala Pro Glu Leu Leu Gly Gly Pro Ser Val Phe Leu Phe
    770                 775                 780

Pro Pro Lys Pro Lys Asp Thr Leu Met Ile Ser Arg Thr Pro Glu Val
785                 790                 795                 800

Thr Cys Val Val Val Asp Val Ser His Glu Asp Pro Glu Val Lys Phe
                805                 810                 815

Asn Trp Tyr Val Asp Gly Val Glu Val His Asn Ala Lys Thr Lys Pro
            820                 825                 830

Arg Glu Glu Gln Tyr Asn Ser Thr Tyr Arg Val Val Ser Val Leu Thr
        835                 840                 845

Val Leu His Gln Asp Trp Leu Asn Gly Lys Glu Tyr Lys Cys Lys Val
    850                 855                 860

Ser Asn Lys Ala Leu Pro Ala Pro Ile Glu Lys Thr Ile Ser Lys Ala
865                 870                 875                 880
```

```
Lys Gly Gln Pro Arg Glu Pro Gln Val Tyr Thr Leu Pro Pro Ser Arg
                885                 890                 895

Asp Glu Leu Thr Lys Asn Gln Val Ser Leu Thr Cys Leu Val Lys Gly
            900                 905                 910

Phe Tyr Pro Ser Asp Ile Ala Val Glu Trp Glu Ser Asn Gly Gln Pro
        915                 920                 925

Glu Asn Asn Tyr Lys Thr Thr Pro Pro Val Leu Asp Ser Asp Gly Ser
    930                 935                 940

Phe Phe Leu Tyr Ser Lys Leu Thr Val Asp Lys Ser Arg Trp Gln Gln
945                 950                 955                 960

Gly Asn Val Phe Ser Cys Ser Val Met His Glu Ala Leu His Asn His
                965                 970                 975

Tyr Thr Gln Lys Ser Leu Ser Leu Ser Pro Gly Lys
            980                 985
```

<210> SEQ ID NO 120
<211> LENGTH: 219
<212> TYPE: PRT
<213> ORGANISM: Homo sapiens

<400> SEQUENCE: 120

```
Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215
```

<210> SEQ ID NO 121
<211> LENGTH: 657
<212> TYPE: DNA
<213> ORGANISM: Homo sapiens

<400> SEQUENCE: 121

```
agcggcacaa ccaacacagt cgctgcctat aacctcactt ggaagagcac caacttcaaa     60

accatcctcg aatgggaacc caaacccgtt aaccaagttt acaccgtgca gatcagcacc    120

aagtccggcg actggaagtc caaatgtttc tataccaccg acaccgagtg cgatctcacc    180

gatgagatcg tgaaagatgt gaaacagacc tacctcgccc gggtgtttag ctaccccgcc    240

ggcaatgtgg agagcactgg ttccgctggc gagcctttat acgagaacag ccccgaattt    300

accccttacc tcgagaccaa tttaggacag cccaccatcc aaagctttga gcaagttggc    360

acaaaggtga atgtgacagt ggaggacgag cggactttag tgcggcggaa caacaccttt    420

ctcagcctcc gggatgtgtt cggcaaagat ttaatctaca cactgtatta ctggaagtcc    480

tcttcctccg gcaagaagac agctaaaacc aacacaaacg agtttttaat cgacgtggat    540

aaaggcgaaa actactgttt cagcgtgcaa gctgtgatcc cctcccggac cgtgaatagg    600

aaaagcaccg atagccccgt tgagtgcatg ggccaagaaa agggcgagtt ccgggag       657
```

```
<210> SEQ ID NO 122
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 122

Ser Gly Thr Thr Asn Thr Val Ala Ala Tyr Asn Leu Thr Trp Lys Ser
1               5                   10                  15

Thr Asn Phe Ala Thr Ala Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Ala Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Ala Arg Asn Asn Thr Ala Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215


<210> SEQ ID NO 123
<211> LENGTH: 219
<212> TYPE: PRT
<213> ORGANISM: Artificial Sequence
```

<220> FEATURE:
<223> OTHER INFORMATION: Synthetic polypeptide

<400> SEQUENCE: 123

```
Ser Gly Thr Thr Asn Thr Val Ala Ala Tyr Asn Leu Thr Trp Lys Ser
1               5                   10                  15

Thr Asn Phe Ala Thr Ala Leu Glu Trp Glu Pro Lys Pro Val Asn Gln
            20                  25                  30

Val Tyr Thr Val Gln Ile Ser Thr Lys Ser Gly Asp Ala Lys Ser Lys
        35                  40                  45

Cys Phe Tyr Thr Thr Asp Thr Glu Cys Ala Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Ala Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Ala Arg Asn Asn Thr Ala Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215
```

<210> SEQ ID NO 124
<211> LENGTH: 223
<212> TYPE: PRT
<213> ORGANISM: Mus sp.

<400> SEQUENCE: 124

```
Ala Gly Ile Pro Glu Lys Ala Phe Asn Leu Thr Trp Ile Ser Thr Asp
1               5                   10                  15

Phe Lys Thr Ile Leu Glu Trp Gln Pro Lys Pro Thr Asn Tyr Thr Tyr
            20                  25                  30

Thr Val Gln Ile Ser Asp Arg Ser Arg Asn Trp Lys Asn Lys Cys Phe
        35                  40                  45

Ser Thr Thr Asp Thr Glu Cys Asp Leu Thr Asp Glu Ile Val Lys Asp
    50                  55                  60

Val Thr Trp Ala Tyr Glu Ala Lys Val Leu Ser Val Pro Arg Arg Asn
65                  70                  75                  80

Ser Val His Gly Asp Gly Asp Gln Leu Val Ile His Gly Glu Glu Pro
                85                  90                  95

Pro Phe Thr Asn Ala Pro Lys Phe Leu Pro Tyr Arg Asp Thr Asn Leu
            100                 105                 110

Gly Gln Pro Val Ile Gln Gln Phe Glu Gln Asp Gly Arg Lys Leu Asn
        115                 120                 125
```

```
Val Val Val Lys Asp Ser Leu Thr Leu Val Arg Lys Asn Gly Thr Phe
    130                 135                 140

Leu Thr Leu Arg Gln Val Phe Gly Lys Asp Leu Gly Tyr Ile Ile Thr
145                 150                 155                 160

Tyr Arg Lys Gly Ser Ser Thr Gly Lys Lys Thr Asn Ile Thr Asn Thr
                165                 170                 175

Asn Glu Phe Ser Ile Asp Val Glu Glu Gly Val Ser Tyr Cys Phe Phe
            180                 185                 190

Val Gln Ala Met Ile Phe Ser Arg Lys Thr Asn Gln Asn Ser Pro Gly
        195                 200                 205

Ser Ser Thr Val Cys Thr Glu Gln Trp Lys Ser Phe Leu Gly Glu
    210                 215                 220
```

<210> SEQ ID NO 125
<211> LENGTH: 224
<212> TYPE: PRT
<213> ORGANISM: Rattus sp.

<400> SEQUENCE: 125

```
Ala Gly Thr Pro Pro Gly Lys Ala Phe Asn Leu Thr Trp Ile Ser Thr
1               5                   10                  15

Asp Phe Lys Thr Ile Leu Glu Trp Gln Pro Lys Pro Thr Asn Tyr Thr
            20                  25                  30

Tyr Thr Val Gln Ile Ser Asp Arg Ser Arg Asn Trp Lys Tyr Lys Cys
        35                  40                  45

Thr Gly Thr Thr Asp Thr Glu Cys Asp Leu Thr Asp Glu Ile Val Lys
    50                  55                  60

Asp Val Asn Trp Thr Tyr Glu Ala Arg Val Leu Ser Val Pro Trp Arg
65                  70                  75                  80

Asn Ser Thr His Gly Lys Glu Thr Leu Phe Gly Thr His Gly Glu Glu
                85                  90                  95

Pro Pro Phe Thr Asn Ala Arg Lys Phe Leu Pro Tyr Arg Asp Thr Lys
            100                 105                 110

Ile Gly Gln Pro Val Ile Gln Lys Tyr Glu Gln Gly Gly Thr Lys Leu
        115                 120                 125

Lys Val Thr Val Lys Asp Ser Phe Thr Leu Val Arg Lys Asn Gly Thr
    130                 135                 140

Phe Leu Thr Leu Arg Gln Val Phe Gly Asn Asp Leu Gly Tyr Ile Leu
145                 150                 155                 160

Thr Tyr Arg Lys Asp Ser Ser Thr Gly Arg Lys Thr Asn Thr Thr His
                165                 170                 175

Thr Asn Glu Phe Leu Ile Asp Val Glu Lys Gly Val Ser Tyr Cys Phe
            180                 185                 190

Phe Ala Gln Ala Val Ile Phe Ser Arg Lys Thr Asn His Lys Ser Pro
        195                 200                 205

Glu Ser Ile Thr Lys Cys Thr Glu Gln Trp Lys Ser Val Leu Gly Glu
    210                 215                 220
```

<210> SEQ ID NO 126
<211> LENGTH: 15
<212> TYPE: PRT
<213> ORGANISM: Artificial Sequence
<220> FEATURE:
<223> OTHER INFORMATION: Synthetic peptide

<400> SEQUENCE: 126

```
Gly Gly Gly Gly Ser Gly Gly Gly Gly Ser Gly Gly Gly Gly Ser
```

1 5 10 15

<210> SEQ ID NO 127
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 127
ggcggtggag gatccggagg aggtggctcc ggcggcggag gatct 45

<210> SEQ ID NO 128
<211> LENGTH: 8
<212> TYPE: PRT
<213> ORGANISM: Artificial Sequence
<220> FEATURE:
<223> OTHER INFORMATION: Synthetic peptide

<400> SEQUENCE: 128

Gly Gly Gly Ser Gly Gly Gly Ser
1 5

<210> SEQ ID NO 129
<211> LENGTH: 133
<212> TYPE: PRT
<213> ORGANISM: Homo sapiens

<400> SEQUENCE: 129

Ala Pro Thr Ser Ser Ser Thr Lys Lys Thr Gln Leu Gln Leu Glu His
1 5 10 15

Leu Leu Leu Asp Leu Gln Met Ile Leu Asn Gly Ile Asn Asn Tyr Lys
20 25 30

Asn Pro Lys Leu Thr Arg Met Leu Thr Phe Lys Phe Tyr Met Pro Lys
35 40 45

Lys Ala Thr Glu Leu Lys His Leu Gln Cys Leu Glu Glu Glu Leu Lys
50 55 60

Pro Leu Glu Glu Val Leu Asn Leu Ala Gln Ser Lys Asn Phe His Leu
65 70 75 80

Arg Pro Arg Asp Leu Ile Ser Asn Ile Asn Val Ile Val Leu Glu Leu
85 90 95

Lys Gly Ser Glu Thr Thr Phe Met Cys Glu Tyr Ala Asp Glu Thr Ala
100 105 110

Thr Ile Val Glu Phe Leu Asn Arg Trp Ile Thr Phe Cys Gln Ser Ile
115 120 125

Ile Ser Thr Leu Thr
130

<210> SEQ ID NO 130
<211> LENGTH: 133
<212> TYPE: PRT
<213> ORGANISM: Homo sapiens

<400> SEQUENCE: 130

Ala Pro Met Thr Gln Thr Thr Pro Leu Lys Thr Ser Trp Val Asn Cys
1 5 10 15

Ser Asn Met Ile Asp Glu Ile Ile Thr His Leu Lys Gln Pro Pro Leu
20 25 30

Pro Leu Leu Asp Phe Asn Asn Leu Asn Gly Glu Asp Gln Asp Ile Leu
35 40 45

Met Glu Asn Asn Leu Arg Arg Pro Asn Leu Glu Ala Phe Asn Arg Ala
50 55 60

Val Lys Ser Leu Gln Asn Ala Ser Ala Ile Glu Ser Ile Leu Lys Asn
65 70 75 80

Leu Leu Pro Cys Leu Pro Leu Ala Thr Ala Ala Pro Thr Arg His Pro
85 90 95

Ile His Ile Lys Asp Gly Asp Trp Asn Glu Phe Arg Arg Lys Leu Thr
100 105 110

Phe Tyr Leu Lys Thr Leu Glu Asn Ala Gln Ala Gln Gln Thr Thr Leu
115 120 125

Ser Leu Ala Ile Phe
130

<210> SEQ ID NO 131
<211> LENGTH: 152
<212> TYPE: PRT
<213> ORGANISM: Homo sapiens

<400> SEQUENCE: 131

Asp Cys Asp Ile Glu Gly Lys Asp Gly Lys Gln Tyr Glu Ser Val Leu
1 5 10 15

Met Val Ser Ile Asp Gln Leu Leu Asp Ser Met Lys Glu Ile Gly Ser
20 25 30

Asn Cys Leu Asn Asn Glu Phe Asn Phe Phe Lys Arg His Ile Cys Asp
35 40 45

Ala Asn Lys Glu Gly Met Phe Leu Phe Arg Ala Ala Arg Lys Leu Arg
50 55 60

Gln Phe Leu Lys Met Asn Ser Thr Gly Asp Phe Asp Leu His Leu Leu
65 70 75 80

Lys Val Ser Glu Gly Thr Thr Ile Leu Leu Asn Cys Thr Gly Gln Val
85 90 95

Lys Gly Arg Lys Pro Ala Ala Leu Gly Glu Ala Gln Pro Thr Lys Ser
100 105 110

Leu Glu Glu Asn Lys Ser Leu Lys Glu Gln Lys Lys Leu Asn Asp Leu
115 120 125

Cys Phe Leu Lys Arg Leu Leu Gln Glu Ile Lys Thr Cys Trp Asn Lys
130 135 140

Ile Leu Met Gly Thr Lys Glu His
145 150

<210> SEQ ID NO 132
<211> LENGTH: 79
<212> TYPE: PRT
<213> ORGANISM: Homo sapiens

<400> SEQUENCE: 132

Glu Gly Ala Val Leu Pro Arg Ser Ala Lys Glu Leu Arg Cys Gln Cys
1 5 10 15

Ile Lys Thr Tyr Ser Lys Pro Phe His Pro Lys Phe Ile Lys Glu Leu
20 25 30

Arg Val Ile Glu Ser Gly Pro His Cys Ala Asn Thr Glu Ile Ile Val
35 40 45

Lys Leu Ser Asp Gly Arg Glu Leu Cys Leu Asp Pro Lys Glu Asn Trp
50 55 60

Val Gln Arg Val Val Glu Lys Phe Leu Lys Arg Ala Glu Asn Ser
65 70 75

<210> SEQ ID NO 133
<211> LENGTH: 160
<212> TYPE: PRT
<213> ORGANISM: Homo sapiens

<400> SEQUENCE: 133

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160
```

<210> SEQ ID NO 134
<211> LENGTH: 114
<212> TYPE: PRT
<213> ORGANISM: Homo sapiens

<400> SEQUENCE: 134

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 135
<211> LENGTH: 132
<212> TYPE: PRT
<213> ORGANISM: Homo sapiens

<400> SEQUENCE: 135

```
Gly Ile Thr Ile Pro Arg Asn Pro Gly Cys Pro Asn Ser Glu Asp Lys
1               5                   10                  15
```

Asn Phe Pro Arg Thr Val Met Val Asn Leu Asn Ile His Asn Arg Asn
20 25 30

Thr Asn Thr Asn Pro Lys Arg Ser Ser Asp Tyr Tyr Asn Arg Ser Thr
35 40 45

Ser Pro Trp Asn Leu His Arg Asn Glu Asp Pro Glu Arg Tyr Pro Ser
50 55 60

Val Ile Trp Glu Ala Lys Cys Arg His Leu Gly Cys Ile Asn Ala Asp
65 70 75 80

Gly Asn Val Asp Tyr His Met Asn Ser Val Pro Ile Gln Gln Glu Ile
85 90 95

Leu Val Leu Arg Arg Glu Pro Pro His Cys Pro Asn Ser Phe Arg Leu
100 105 110

Glu Lys Ile Leu Val Ser Val Gly Cys Thr Cys Val Thr Pro Ile Val
115 120 125

His His Val Ala
130

<210> SEQ ID NO 136
<211> LENGTH: 157
<212> TYPE: PRT
<213> ORGANISM: Homo sapiens

<400> SEQUENCE: 136

Tyr Phe Gly Lys Leu Glu Ser Lys Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

Ile Ser Met Tyr Lys Asp Ser Gln Pro Arg Gly Met Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Gln Arg Ser Val Pro Gly His Asp Asn Lys
100 105 110

Met Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 137
<211> LENGTH: 352
<212> TYPE: PRT
<213> ORGANISM: Homo sapiens

<400> SEQUENCE: 137

Arg Asp Thr Ser Ala Thr Pro Gln Ser Ala Ser Ile Lys Ala Leu Arg
1 5 10 15

Asn Ala Asn Leu Arg Arg Asp Glu Ser Asn His Leu Thr Asp Leu Tyr
20 25 30

Arg Arg Asp Glu Thr Ile Gln Val Lys Gly Asn Gly Tyr Val Gln Ser
35 40 45

```
Pro Arg Phe Pro Asn Ser Tyr Pro Arg Asn Leu Leu Leu Thr Trp Arg
    50                  55                  60

Leu His Ser Gln Glu Asn Thr Arg Ile Gln Leu Val Phe Asp Asn Gln
65                  70                  75                  80

Phe Gly Leu Glu Glu Ala Glu Asn Asp Ile Cys Arg Tyr Asp Phe Val
                85                  90                  95

Glu Val Glu Asp Ile Ser Glu Thr Ser Thr Ile Ile Arg Gly Arg Trp
            100                 105                 110

Cys Gly His Lys Glu Val Pro Pro Arg Ile Lys Ser Arg Thr Asn Gln
        115                 120                 125

Ile Lys Ile Thr Phe Lys Ser Asp Asp Tyr Phe Val Ala Lys Pro Gly
    130                 135                 140

Phe Lys Ile Tyr Tyr Ser Leu Leu Glu Asp Phe Gln Pro Ala Ala Ala
145                 150                 155                 160

Ser Glu Thr Asn Trp Glu Ser Val Thr Ser Ser Ile Ser Gly Val Ser
                165                 170                 175

Tyr Asn Ser Pro Ser Val Thr Asp Pro Thr Leu Ile Ala Asp Ala Leu
            180                 185                 190

Asp Lys Lys Ile Ala Glu Phe Asp Thr Val Glu Asp Leu Leu Lys Tyr
        195                 200                 205

Phe Asn Pro Glu Ser Trp Gln Glu Asp Leu Glu Asn Met Tyr Leu Asp
    210                 215                 220

Thr Pro Arg Tyr Arg Gly Arg Ser Tyr His Asp Arg Lys Ser Lys Val
225                 230                 235                 240

Asp Leu Asp Arg Leu Asn Asp Asp Ala Lys Arg Tyr Ser Cys Thr Pro
                245                 250                 255

Arg Asn Tyr Ser Val Asn Ile Arg Glu Glu Leu Lys Leu Ala Asn Val
            260                 265                 270

Val Phe Phe Pro Arg Cys Leu Leu Val Gln Arg Cys Gly Gly Asn Cys
        275                 280                 285

Gly Cys Gly Thr Val Asn Trp Arg Ser Cys Thr Cys Asn Ser Gly Lys
    290                 295                 300

Thr Val Lys Lys Tyr His Glu Val Leu Gln Phe Glu Pro Gly His Ile
305                 310                 315                 320

Lys Arg Arg Gly Arg Ala Lys Thr Met Ala Leu Val Asp Ile Gln Leu
                325                 330                 335

Asp His His Glu Arg Cys Asp Cys Ile Cys Ser Ser Arg Pro Pro Arg
            340                 345                 350


<210> SEQ ID NO 138
<211> LENGTH: 248
<212> TYPE: PRT
<213> ORGANISM: Homo sapiens

<400> SEQUENCE: 138

Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
            20                  25                  30

Val Pro Gly Met Asp Val Leu Pro Ser His Cys Trp Ile Ser Glu Met
        35                  40                  45

Val Val Gln Leu Ser Asp Ser Leu Thr Asp Leu Leu Asp Lys Phe Ser
    50                  55                  60

Asn Ile Ser Glu Gly Leu Ser Asn Tyr Ser Ile Ile Asp Lys Leu Val
```

```
65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
        115                 120                 125

Phe Val Val Ala Ser Glu Thr Ser Asp Cys Val Val Ser Ser Thr Leu
    130                 135                 140

Ser Pro Glu Lys Asp Ser Arg Val Ser Val Thr Lys Pro Phe Met Leu
145                 150                 155                 160

Pro Pro Val Ala Ala Ser Ser Leu Arg Asn Asp Ser Ser Ser Ser Asn
                165                 170                 175

Arg Lys Ala Lys Asn Pro Pro Gly Asp Ser Ser Leu His Trp Ala Ala
            180                 185                 190

Met Ala Leu Pro Ala Leu Phe Ser Leu Ile Ile Gly Phe Ala Phe Gly
        195                 200                 205

Ala Leu Tyr Trp Lys Lys Arg Gln Pro Ser Leu Thr Arg Ala Val Glu
    210                 215                 220

Asn Ile Gln Ile Asn Glu Glu Asp Asn Glu Ile Ser Met Leu Gln Glu
225                 230                 235                 240

Lys Glu Arg Glu Phe Gln Glu Val
                245


<210> SEQ ID NO 139
<211> LENGTH: 209
<212> TYPE: PRT
<213> ORGANISM: Homo sapiens

<400> SEQUENCE: 139

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Pro Thr Ala Pro Gln Pro Pro Leu
145                 150                 155                 160

Leu Leu Leu Leu Leu Leu Pro Val Gly Leu Leu Leu Leu Ala Ala Ala
                165                 170                 175

Trp Cys Leu His Trp Gln Arg Thr Arg Arg Arg Thr Pro Arg Pro Gly
            180                 185                 190
```

```
Glu Gln Val Pro Pro Val Pro Ser Pro Gln Asp Leu Leu Leu Val Glu
        195                 200                 205

His


<210> SEQ ID NO 140
<211> LENGTH: 360
<212> TYPE: PRT
<213> ORGANISM: Homo sapiens

<400> SEQUENCE: 140

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser Gly Lys Val Leu Val Leu Gln Ser His Trp Gln Thr Phe His
        275                 280                 285

Val Ser Ala Val Ala Ala Ala Ala Ile Phe Val Ile Ile Ile Phe Tyr
    290                 295                 300

Val Arg Cys Cys Lys Lys Lys Thr Ser Ala Ala Glu Gly Pro Glu Leu
305                 310                 315                 320

Val Ser Leu Gln Val Leu Asp Gln His Pro Val Gly Thr Ser Asp His
                325                 330                 335

Arg Asp Ala Thr Gln Leu Gly Phe Gln Pro Leu Met Ser Asp Leu Gly
            340                 345                 350
```

Ser Thr Gly Ser Thr Glu Gly Ala
355 360

<210> SEQ ID NO 141
<211> LENGTH: 361
<212> TYPE: PRT
<213> ORGANISM: Homo sapiens

<400> SEQUENCE: 141

Ala Glu Pro His Ser Leu Arg Tyr Asn Leu Met Val Leu Ser Gln Asp
1 5 10 15

Glu Ser Val Gln Ser Gly Phe Leu Ala Glu Gly His Leu Asp Gly Gln
20 25 30

Pro Phe Leu Arg Tyr Asp Arg Gln Lys Arg Arg Ala Lys Pro Gln Gly
35 40 45

Gln Trp Ala Glu Asp Val Leu Gly Ala Lys Thr Trp Asp Thr Glu Thr
50 55 60

Glu Asp Leu Thr Glu Asn Gly Gln Asp Leu Arg Arg Thr Leu Thr His
65 70 75 80

Ile Lys Asp Gln Lys Gly Gly Leu His Ser Leu Gln Glu Ile Arg Val
85 90 95

Cys Glu Ile His Glu Asp Ser Ser Thr Arg Gly Ser Arg His Phe Tyr
100 105 110

Tyr Asp Gly Glu Leu Phe Leu Ser Gln Asn Leu Glu Thr Gln Glu Ser
115 120 125

Thr Val Pro Gln Ser Ser Arg Ala Gln Thr Leu Ala Met Asn Val Thr
130 135 140

Asn Phe Trp Lys Glu Asp Ala Met Lys Thr Lys Thr His Tyr Arg Ala
145 150 155 160

Met Gln Ala Asp Cys Leu Gln Lys Leu Gln Arg Tyr Leu Lys Ser Gly
165 170 175

Val Ala Ile Arg Arg Thr Val Pro Pro Met Val Asn Val Thr Cys Ser
180 185 190

Glu Val Ser Glu Gly Asn Ile Thr Val Thr Cys Arg Ala Ser Ser Phe
195 200 205

Tyr Pro Arg Asn Ile Thr Leu Thr Trp Arg Gln Asp Gly Val Ser Leu
210 215 220

Ser His Asn Thr Gln Gln Trp Gly Asp Val Leu Pro Asp Gly Asn Gly
225 230 235 240

Thr Tyr Gln Thr Trp Val Ala Thr Arg Ile Arg Gln Gly Glu Glu Gln
245 250 255

Arg Phe Thr Cys Tyr Met Glu His Ser Gly Asn His Gly Thr His Pro
260 265 270

Val Pro Ser Gly Lys Val Leu Val Leu Gln Ser Gln Arg Thr Asp Phe
275 280 285

Pro Tyr Val Ser Ala Ala Met Pro Cys Phe Val Ile Ile Ile Ile Leu
290 295 300

Cys Val Pro Cys Cys Lys Lys Lys Thr Ser Ala Ala Glu Gly Pro Glu
305 310 315 320

Leu Val Ser Leu Gln Val Leu Asp Gln His Pro Val Gly Thr Gly Asp
325 330 335

His Arg Asp Ala Ala Gln Leu Gly Phe Gln Pro Leu Met Ser Ala Thr
340 345 350

Gly Ser Thr Gly Ser Thr Glu Gly Ala
355 360

<210> SEQ ID NO 142
<211> LENGTH: 190
<212> TYPE: PRT
<213> ORGANISM: Homo sapiens

<400> SEQUENCE: 142

Trp Val Asp Thr His Cys Leu Cys Tyr Asp Phe Ile Ile Thr Pro Lys
1 5 10 15

Ser Arg Pro Glu Pro Gln Trp Cys Glu Val Gln Gly Leu Val Asp Glu
20 25 30

Arg Pro Phe Leu His Tyr Asp Cys Val Asn His Lys Ala Lys Ala Phe
35 40 45

Ala Ser Leu Gly Lys Lys Val Asn Val Thr Lys Thr Trp Glu Glu Gln
50 55 60

Thr Glu Thr Leu Arg Asp Val Val Asp Phe Leu Lys Gly Gln Leu Leu
65 70 75 80

Asp Ile Gln Val Glu Asn Leu Ile Pro Ile Glu Pro Leu Thr Leu Gln
85 90 95

Ala Arg Met Ser Cys Glu His Glu Ala His Gly His Gly Arg Gly Ser
100 105 110

Trp Gln Phe Leu Phe Asn Gly Gln Lys Phe Leu Leu Phe Asp Ser Asn
115 120 125

Asn Arg Lys Trp Thr Ala Leu His Pro Gly Ala Lys Lys Met Thr Glu
130 135 140

Lys Trp Glu Lys Asn Arg Asp Val Thr Met Phe Phe Gln Lys Ile Ser
145 150 155 160

Leu Gly Asp Cys Lys Met Trp Leu Glu Glu Phe Leu Met Tyr Trp Glu
165 170 175

Gln Met Leu Asp Pro Thr Lys Pro Pro Ser Leu Ala Pro Gly
180 185 190

<210> SEQ ID NO 143
<211> LENGTH: 191
<212> TYPE: PRT
<213> ORGANISM: Homo sapiens

<400> SEQUENCE: 143

Gly Arg Ala Asp Pro His Ser Leu Cys Tyr Asp Ile Thr Val Ile Pro
1 5 10 15

Lys Phe Arg Pro Gly Pro Arg Trp Cys Ala Val Gln Gly Gln Val Asp
20 25 30

Glu Lys Thr Phe Leu His Tyr Asp Cys Gly Asn Lys Thr Val Thr Pro
35 40 45

Val Ser Pro Leu Gly Lys Lys Leu Asn Val Thr Thr Ala Trp Lys Ala
50 55 60

Gln Asn Pro Val Leu Arg Glu Val Val Asp Ile Leu Thr Glu Gln Leu
65 70 75 80

Arg Asp Ile Gln Leu Glu Asn Tyr Thr Pro Lys Glu Pro Leu Thr Leu
85 90 95

Gln Ala Arg Met Ser Cys Glu Gln Lys Ala Glu Gly His Ser Ser Gly
100 105 110

Ser Trp Gln Phe Ser Phe Asp Gly Gln Ile Phe Leu Leu Phe Asp Ser
115 120 125

Glu Lys Arg Met Trp Thr Thr Val His Pro Gly Ala Arg Lys Met Lys
130 135 140

```
Glu Lys Trp Glu Asn Asp Lys Val Val Ala Met Ser Phe His Tyr Phe
145                 150                 155                 160

Ser Met Gly Asp Cys Ile Gly Trp Leu Glu Asp Phe Leu Met Gly Met
                165                 170                 175

Asp Ser Thr Leu Glu Pro Ser Ala Gly Ala Pro Leu Ala Met Ser
            180                 185                 190


<210> SEQ ID NO 144
<211> LENGTH: 188
<212> TYPE: PRT
<213> ORGANISM: Homo sapiens

<400> SEQUENCE: 144

Asp Ala His Ser Leu Trp Tyr Asn Phe Thr Ile Ile His Leu Pro Arg
1               5                   10                  15

His Gly Gln Gln Trp Cys Glu Val Gln Ser Gln Val Asp Gln Lys Asn
            20                  25                  30

Phe Leu Ser Tyr Asp Cys Gly Ser Asp Lys Val Leu Ser Met Gly His
        35                  40                  45

Leu Glu Glu Gln Leu Tyr Ala Thr Asp Ala Trp Gly Lys Gln Leu Glu
    50                  55                  60

Met Leu Arg Glu Val Gly Gln Arg Leu Arg Leu Glu Leu Ala Asp Thr
65                  70                  75                  80

Glu Leu Glu Asp Phe Thr Pro Ser Gly Pro Leu Thr Leu Gln Val Arg
                85                  90                  95

Met Ser Cys Glu Cys Glu Ala Asp Gly Tyr Ile Arg Gly Ser Trp Gln
            100                 105                 110

Phe Ser Phe Asp Gly Arg Lys Phe Leu Leu Phe Asp Ser Asn Asn Arg
        115                 120                 125

Lys Trp Thr Val Val His Ala Gly Ala Arg Arg Met Lys Glu Lys Trp
    130                 135                 140

Glu Lys Asp Ser Gly Leu Thr Thr Phe Phe Lys Met Val Ser Met Arg
145                 150                 155                 160

Asp Cys Lys Ser Trp Leu Arg Asp Phe Leu Met His Arg Lys Lys Arg
                165                 170                 175

Leu Glu Pro Thr Ala Pro Pro Thr Met Ala Pro Gly
            180                 185


<210> SEQ ID NO 145
<211> LENGTH: 233
<212> TYPE: PRT
<213> ORGANISM: Homo sapiens

<400> SEQUENCE: 145

His Ser Leu Cys Phe Asn Phe Thr Ile Lys Ser Leu Ser Arg Pro Gly
1               5                   10                  15

Gln Pro Trp Cys Glu Ala Gln Val Phe Leu Asn Lys Asn Leu Phe Leu
            20                  25                  30

Gln Tyr Asn Ser Asp Asn Asn Met Val Lys Pro Leu Gly Leu Leu Gly
        35                  40                  45

Lys Lys Val Tyr Ala Thr Ser Thr Trp Gly Glu Leu Thr Gln Thr Leu
    50                  55                  60

Gly Glu Val Gly Arg Asp Leu Arg Met Leu Leu Cys Asp Ile Lys Pro
65                  70                  75                  80

Gln Ile Lys Thr Ser Asp Pro Ser Thr Leu Gln Val Glu Met Phe Cys
                85                  90                  95
```

```
Gln Arg Glu Ala Glu Arg Cys Thr Gly Ala Ser Trp Gln Phe Ala Thr
            100                 105                 110

Asn Gly Glu Lys Ser Leu Leu Phe Asp Ala Met Asn Met Thr Trp Thr
        115                 120                 125

Val Ile Asn His Glu Ala Ser Lys Ile Lys Glu Thr Trp Lys Lys Asp
    130                 135                 140

Arg Gly Leu Glu Lys Tyr Phe Arg Lys Leu Ser Lys Gly Asp Cys Asp
145                 150                 155                 160

His Trp Leu Arg Glu Phe Leu Gly His Trp Glu Ala Met Pro Glu Pro
                165                 170                 175

Thr Val Ser Pro Val Asn Ala Ser Asp Ile His Trp Ser Ser Ser Ser
            180                 185                 190

Leu Pro Asp Arg Trp Ile Ile Leu Gly Ala Phe Ile Leu Leu Val Leu
        195                 200                 205

Met Gly Ile Val Leu Ile Cys Val Trp Trp Gln Asn Gly Glu Trp Gln
    210                 215                 220

Ala Gly Leu Trp Pro Leu Arg Thr Ser
225                 230


<210> SEQ ID NO 146
<211> LENGTH: 193
<212> TYPE: PRT
<213> ORGANISM: Homo sapiens

<400> SEQUENCE: 146

Gly Leu Ala Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
            20                  25                  30

Glu Lys Thr Phe Leu His Tyr Asp Cys Gly Ser Lys Thr Val Thr Pro
        35                  40                  45

Val Ser Pro Leu Gly Lys Lys Leu Asn Val Thr Thr Ala Trp Lys Ala
    50                  55                  60

Gln Asn Pro Val Leu Arg Glu Val Val Asp Ile Leu Thr Glu Gln Leu
65                  70                  75                  80

Leu Asp Ile Gln Leu Glu Asn Tyr Ile Pro Lys Glu Pro Leu Thr Leu
                85                  90                  95

Gln Ala Arg Met Ser Cys Glu Gln Lys Ala Glu Gly His Gly Ser Gly
            100                 105                 110

Ser Trp Gln Leu Ser Phe Asp Gly Gln Ile Phe Leu Leu Phe Asp Ser
        115                 120                 125

Glu Asn Arg Met Trp Thr Thr Val His Pro Gly Ala Arg Lys Met Lys
    130                 135                 140

Glu Lys Trp Glu Asn Asp Lys Asp Met Thr Met Ser Phe His Tyr Ile
145                 150                 155                 160

Ser Met Gly Asp Cys Thr Gly Trp Leu Glu Asp Phe Leu Met Gly Met
                165                 170                 175

Asp Ser Thr Leu Glu Pro Ser Ala Gly Ala Pro Pro Thr Met Ser Ser
            180                 185                 190

Gly


<210> SEQ ID NO 147
<211> LENGTH: 193
<212> TYPE: PRT
<213> ORGANISM: Homo sapiens
```

<400> SEQUENCE: 147

Arg Arg Asp Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
            20                  25                  30

Glu Lys Thr Phe Leu His Tyr Asp Cys Gly Asn Lys Thr Val Thr Pro
        35                  40                  45

Val Ser Pro Leu Gly Lys Lys Leu Asn Val Thr Met Ala Trp Lys Ala
    50                  55                  60

Gln Asn Pro Val Leu Arg Glu Val Val Asp Ile Leu Thr Glu Gln Leu
65                  70                  75                  80

Leu Asp Ile Gln Leu Glu Asn Tyr Thr Pro Lys Glu Pro Leu Thr Leu
                85                  90                  95

Gln Ala Arg Met Ser Cys Glu Gln Lys Ala Glu Gly His Ser Ser Gly
            100                 105                 110

Ser Trp Gln Phe Ser Ile Asp Gly Gln Thr Phe Leu Leu Phe Asp Ser
        115                 120                 125

Glu Lys Arg Met Trp Thr Thr Val His Pro Gly Ala Arg Lys Met Lys
    130                 135                 140

Glu Lys Trp Glu Asn Asp Lys Asp Val Ala Met Ser Phe His Tyr Ile
145                 150                 155                 160

Ser Met Gly Asp Cys Ile Gly Trp Leu Glu Asp Phe Leu Met Gly Met
                165                 170                 175

Asp Ser Thr Leu Glu Pro Ser Ala Gly Ala Pro Leu Ala Met Ser Ser
            180                 185                 190

Gly

<210> SEQ ID NO 148
<211> LENGTH: 65
<212> TYPE: PRT
<213> ORGANISM: Artificial Sequence
<220> FEATURE:
<223> OTHER INFORMATION: Synthetic polypeptide

<400> SEQUENCE: 148

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 149
<211> LENGTH: 195
<212> TYPE: DNA
<213> ORGANISM: Artificial Sequence
<220> FEATURE:
<223> OTHER INFORMATION: Synthetic polynucleotide

<400> SEQUENCE: 149
attacatgcc cccctcccat gagcgtggag cacgccgaca tctgggtgaa gagctatagc      60
ctctacagcc gggagaggta tatctgtaac agcggcttca agaggaaggc cggcaccagc     120
agcctcaccg agtgcgtgct gaataaggct accaacgtgg ctcactggac aacaccctct 180
ttaaagtgca tccgg 195

<210> SEQ ID NO 150
<211> LENGTH: 342
<212> TYPE: DNA
<213> ORGANISM: Homo sapiens

<400> SEQUENCE: 150
aactgggtga acgtcatcag cgatttaaag aagatcgaag atttaattca gtccatgcat 60
atcgacgcca ctttatacac agaatccgac gtgcacccct cttgtaaggt gaccgccatg 120
aaatgttttt tactggagct gcaagttatc tctttagaga gcggagacgc tagcatccac 180
gacaccgtgg agaatttaat cattttagcc aataactctt tatccagcaa cggcaacgtg 240
acagagtccg gctgcaagga gtgcgaagag ctggaggaga agaacatcaa ggagtttctg 300
caatcctttg tgcacattgt ccagatgttc atcaatacct cc 342

<210> SEQ ID NO 151
<211> LENGTH: 18
<212> TYPE: PRT
<213> ORGANISM: Artificial Sequence
<220> FEATURE:
<223> OTHER INFORMATION: Synthetic peptide

<400> SEQUENCE: 151

Met Lys Trp Val Thr Phe Ile Ser Leu Leu Phe Leu Phe Ser Ser Ala
1 5 10 15

Tyr Ser

<210> SEQ ID NO 152
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 152
atgaaatggg tgacctttat ttctttactg ttcctcttta gcagcgccta ctcc 54

<210> SEQ ID NO 153
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 153
atgaagtggg tcacatttat ctctttactg ttcctcttct ccagcgccta cagc 54

<210> SEQ ID NO 154
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 154
atgaaatggg tgacctttat ttctttactg ttcctcttta gcagcgccta ctcc 54

<210> SEQ ID NO 155
<211> LENGTH: 16

<212> TYPE: PRT
<213> ORGANISM: Artificial Sequence
<220> FEATURE:
<223> OTHER INFORMATION: Synthetic peptide

<400> SEQUENCE: 155

Met Lys Cys Leu Leu Tyr Leu Ala Phe Leu Phe Leu Gly Val Asn Cys
1               5                   10                  15

<210> SEQ ID NO 156
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 156

Met Gly Gln Ile Val Thr Met Phe Glu Ala Leu Pro His Ile Ile Asp
1               5                   10                  15

Glu Val Ile Asn Ile Val Ile Ile Val Leu Ile Ile Ile Thr Ser Ile
            20                  25                  30

Lys Ala Val Tyr Asn Phe Ala Thr Cys Gly Ile Leu Ala Leu Val Ser
        35                  40                  45

Phe Leu Phe Leu Ala Gly Arg Ser Cys Gly
    50                  55

<210> SEQ ID NO 157
<211> LENGTH: 97
<212> TYPE: PRT
<213> ORGANISM: Artificial Sequence
<220> FEATURE:
<223> OTHER INFORMATION: Synthetic polypeptide

<400> SEQUENCE: 157

Met Pro Asn His Gln Ser Gly Ser Pro Thr Gly Ser Ser Asp Leu Leu
1               5                   10                  15

Leu Ser Gly Lys Lys Gln Arg Pro His Leu Ala Leu Arg Arg Lys Arg
            20                  25                  30

Arg Arg Glu Met Arg Lys Ile Asn Arg Lys Val Arg Arg Met Asn Leu
        35                  40                  45

Ala Pro Ile Lys Glu Lys Thr Ala Trp Gln His Leu Gln Ala Leu Ile
    50                  55                  60

Ser Glu Ala Glu Glu Val Leu Lys Thr Ser Gln Thr Pro Gln Asn Ser
65                  70                  75                  80

Leu Thr Leu Phe Leu Ala Leu Leu Ser Val Leu Gly Pro Pro Val Thr
                85                  90                  95

Gly

<210> SEQ ID NO 158
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 158

Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser
            20                  25                  30

<210> SEQ ID NO 159
<211> LENGTH: 15
<212> TYPE: PRT
<213> ORGANISM: Artificial Sequence
<220> FEATURE:
<223> OTHER INFORMATION: Synthetic peptide

<400> SEQUENCE: 159

Gly Leu Asn Asp Ile Phe Glu Ala Gln Lys Ile Glu Trp His Glu
1 5 10 15

<210> SEQ ID NO 160
<211> LENGTH: 26
<212> TYPE: PRT
<213> ORGANISM: Artificial Sequence
<220> FEATURE:
<223> OTHER INFORMATION: Synthetic peptide

<400> SEQUENCE: 160

Lys Arg Arg Trp Lys Lys Asn Phe Ile Ala Val Ser Ala Ala Asn Arg
1 5 10 15

Phe Lys Lys Ile Ser Ser Ser Gly Ala Leu
20 25

<210> SEQ ID NO 161
<211> LENGTH: 6
<212> TYPE: PRT
<213> ORGANISM: Artificial Sequence
<220> FEATURE:
<223> OTHER INFORMATION: Synthetic peptide

<400> SEQUENCE: 161

Glu Glu Glu Glu Glu Glu
1 5

<210> SEQ ID NO 162
<211> LENGTH: 13
<212> TYPE: PRT
<213> ORGANISM: Artificial Sequence
<220> FEATURE:
<223> OTHER INFORMATION: Synthetic peptide

<400> SEQUENCE: 162

Gly Ala Pro Val Pro Tyr Pro Asp Pro Leu Glu Pro Arg
1 5 10

<210> SEQ ID NO 163
<211> LENGTH: 8
<212> TYPE: PRT
<213> ORGANISM: Artificial Sequence
<220> FEATURE:
<223> OTHER INFORMATION: Synthetic peptide

<400> SEQUENCE: 163

Asp Tyr Lys Asp Asp Asp Asp Lys
1 5

<210> SEQ ID NO 164
<211> LENGTH: 9
<212> TYPE: PRT
<213> ORGANISM: Artificial Sequence
<220> FEATURE:
<223> OTHER INFORMATION: Synthetic peptide

<400> SEQUENCE: 164

Tyr Pro Tyr Asp Val Pro Asp Tyr Ala
1 5

<210> SEQ ID NO 165
<211> LENGTH: 5
<212> TYPE: PRT
<213> ORGANISM: Artificial Sequence
<220> FEATURE:
<223> OTHER INFORMATION: Synthetic 5xHis tag

<400> SEQUENCE: 165

His His His His His
1               5

<210> SEQ ID NO 166
<211> LENGTH: 6
<212> TYPE: PRT
<213> ORGANISM: Artificial Sequence
<220> FEATURE:
<223> OTHER INFORMATION: Synthetic 6xHis tag

<400> SEQUENCE: 166

His His His His His His
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic 7xHis tag

<400> SEQUENCE: 167

His His His His His His His
1               5

<210> SEQ ID NO 168
<211> LENGTH: 8
<212> TYPE: PRT
<213> ORGANISM: Artificial Sequence
<220> FEATURE:
<223> OTHER INFORMATION: Synthetic 8xHis tag

<400> SEQUENCE: 168

His His His His His His His His
1               5

<210> SEQ ID NO 169
<211> LENGTH: 9
<212> TYPE: PRT
<213> ORGANISM: Artificial Sequence
<220> FEATURE:
<223> OTHER INFORMATION: Synthetic 9xHis tag

<400> SEQUENCE: 169

His His His His His His His His His
1               5

<210> SEQ ID NO 170
<211> LENGTH: 10
<212> TYPE: PRT
<213> ORGANISM: Artificial Sequence
<220> FEATURE:
<223> OTHER INFORMATION: Synthetic 10xHis tag

<400> SEQUENCE: 170

His His His His His His His His His His
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Synthetic peptide

<400> SEQUENCE: 171

Glu Gln Lys Leu Ile Ser Glu Glu Asp Leu
1 5 10

<210> SEQ ID NO 172
<211> LENGTH: 18
<212> TYPE: PRT
<213> ORGANISM: Artificial Sequence
<220> FEATURE:
<223> OTHER INFORMATION: Synthetic peptide

<400> SEQUENCE: 172

Thr Lys Glu Asn Pro Arg Ser Asn Gln Glu Glu Ser Tyr Asp Asp Asn
1 5 10 15

Glu Ser

<210> SEQ ID NO 173
<211> LENGTH: 15
<212> TYPE: PRT
<213> ORGANISM: Artificial Sequence
<220> FEATURE:
<223> OTHER INFORMATION: Synthetic peptide

<400> SEQUENCE: 173

Lys Glu Thr Ala Ala Ala Lys Phe Glu Arg Gln His Met Asp Ser
1 5 10 15

<210> SEQ ID NO 174
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 174

Met Asp Glu Lys Thr Thr Gly Trp Arg Gly Gly His Val Val Glu Gly
1 5 10 15

Leu Ala Gly Glu Leu Glu Gln Leu Arg Ala Arg Leu Glu His His Pro
20 25 30

Gln Gly Gln Arg Glu Pro
35

<210> SEQ ID NO 175
<211> LENGTH: 13
<212> TYPE: PRT
<213> ORGANISM: Artificial Sequence
<220> FEATURE:
<223> OTHER INFORMATION: Synthetic peptide

<400> SEQUENCE: 175

Ser Leu Ala Glu Leu Leu Asn Ala Gly Leu Gly Gly Ser
1 5 10

<210> SEQ ID NO 176
<211> LENGTH: 8
<212> TYPE: PRT
<213> ORGANISM: Artificial Sequence
<220> FEATURE:

<223> OTHER INFORMATION: Synthetic peptide

<400> SEQUENCE: 176

Thr Gln Asp Pro Ser Arg Val Gly
1 5

<210> SEQ ID NO 177
<211> LENGTH: 12
<212> TYPE: PRT
<213> ORGANISM: Artificial Sequence
<220> FEATURE:
<223> OTHER INFORMATION: Synthetic peptide

<400> SEQUENCE: 177

Pro Asp Arg Val Arg Ala Val Ser His Trp Ser Ser
1 5 10

<210> SEQ ID NO 178
<211> LENGTH: 8
<212> TYPE: PRT
<213> ORGANISM: Artificial Sequence
<220> FEATURE:
<223> OTHER INFORMATION: Synthetic peptide

<400> SEQUENCE: 178

Trp Ser His Pro Gln Phe Glu Lys
1 5

<210> SEQ ID NO 179
<211> LENGTH: 6
<212> TYPE: PRT
<213> ORGANISM: Artificial Sequence
<220> FEATURE:
<223> OTHER INFORMATION: Synthetic peptide

<400> SEQUENCE: 179

Cys Cys Pro Gly Cys Cys
1 5

<210> SEQ ID NO 180
<211> LENGTH: 10
<212> TYPE: PRT
<213> ORGANISM: Artificial Sequence
<220> FEATURE:
<223> OTHER INFORMATION: Synthetic peptide

<400> SEQUENCE: 180

Glu Val His Thr Asn Gln Asp Pro Leu Asp
1 5 10

<210> SEQ ID NO 181
<211> LENGTH: 14
<212> TYPE: PRT
<213> ORGANISM: Artificial Sequence
<220> FEATURE:
<223> OTHER INFORMATION: Synthetic peptide

<400> SEQUENCE: 181

Gly Lys Pro Ile Pro Asn Pro Leu Leu Gly Leu Asp Ser Thr
1 5 10

<210> SEQ ID NO 182
<211> LENGTH: 11
<212> TYPE: PRT
<213> ORGANISM: Artificial Sequence
<220> FEATURE:
<223> OTHER INFORMATION: Synthetic peptide

<400> SEQUENCE: 182

Tyr Thr Asp Ile Glu Met Asn Arg Leu Gly Lys
1 5 10

<210> SEQ ID NO 183
<211> LENGTH: 8
<212> TYPE: PRT
<213> ORGANISM: Artificial Sequence
<220> FEATURE:
<223> OTHER INFORMATION: Synthetic peptide

<400> SEQUENCE: 183

Asp Leu Tyr Asp Asp Asp Asp Lys
1 5

<210> SEQ ID NO 184

<400> SEQUENCE: 184

000

<210> SEQ ID NO 185
<211> LENGTH: 471
<212> TYPE: DNA
<213> ORGANISM: Homo sapiens

<400> SEQUENCE: 185
tacttcggca aactggaatc caagctgagc gtgatccgga atttaaacga ccaagttctg 60
tttatcgatc aaggtaaccg gcctctgttc gaggacatga ccgactccga ttgccgggac 120
aatgcccccc ggaccatctt cattatctcc atgtacaagg acagccagcc ccggggcatg 180
gctgtgacaa ttagcgtgaa gtgtgagaaa atcagcactt tatcttgtga gaacaagatc 240
atctccttta aggaaatgaa ccccccccgat aacatcaagg acaccaagtc cgatatcatc 300
ttcttccagc ggtccgtgcc cggtcacgat aacaagatgc agttcgaatc ctcctcctac 360
gagggctact ttttagcttg tgaaaaggag agggatttat tcaagctgat cctcaagaag 420
gaggacgagc tgggcgatcg ttccatcatg ttcaccgtcc aaaacgagga t 471

<210> SEQ ID NO 186
<211> LENGTH: 306
<212> TYPE: PRT
<213> ORGANISM: Homo sapiens

<400> SEQUENCE: 186

Ile Trp Glu Leu Lys Lys Asp Val Tyr Val Val Glu Leu Asp Trp Tyr
1 5 10 15

Pro Asp Ala Pro Gly Glu Met Val Val Leu Thr Cys Asp Thr Pro Glu
20 25 30

Glu Asp Gly Ile Thr Trp Thr Leu Asp Gln Ser Ser Glu Val Leu Gly
35 40 45

Ser Gly Lys Thr Leu Thr Ile Gln Val Lys Glu Phe Gly Asp Ala Gly
50 55 60

Gln Tyr Thr Cys His Lys Gly Gly Glu Val Leu Ser His Ser Leu Leu
65 70 75 80

Leu Leu His Lys Lys Glu Asp Gly Ile Trp Ser Thr Asp Ile Leu Lys
85 90 95

Asp Gln Lys Glu Pro Lys Asn Lys Thr Phe Leu Arg Cys Glu Ala Lys
100 105 110

```
Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305
```

<210> SEQ ID NO 187
<211> LENGTH: 918
<212> TYPE: DNA
<213> ORGANISM: Homo sapiens

<400> SEQUENCE: 187

```
atttgggaac tgaagaagga cgtctacgtg gtcgaactgg actggtatcc cgatgctccc     60

ggcgaaatgg tggtgctcac ttgtgacacc cccgaagaag acggcatcac ttggaccctc    120

gatcagagca gcgaggtgct gggctccgga aagaccctca caatccaagt taaggagttc    180

ggagacgctg gccaatacac atgccacaag ggaggcgagg tgctcagcca ttccttatta    240

ttattacaca agaaggaaga cggaatctgg tccaccgaca ttttaaaaga tcagaaggag    300

cccaagaata agaccttttt aaggtgtgag gccaaaaact acagcggtcg tttcacttgt    360

tggtggctga ccaccatttc caccgattta accttctccg tgaaaagcag ccggggaagc    420

tccgaccctc aaggtgtgac atgtggagcc gctaccctca gcgctgagag ggttcgtggc    480

gataacaagg aatacgagta cagcgtggag tgccaagaag atagcgcttg tcccgctgcc    540

gaagaatctt tacccattga ggtgatggtg gacgccgtgc acaaactcaa gtacgagaac    600

tacacctcct ccttctttat ccgggacatc attaagcccg atcctcctaa gaatttacag    660

ctgaagcctc tcaaaaatag ccggcaagtt gaggtctctt gggaatatcc cgacacttgg    720

agcacacccc acagctactt ctctttaacc ttttgtgtgc aagttcaagg taaaagcaag    780

cgggagaaga aagaccgggt gtttaccgac aaaaccagcg ccaccgtcat ctgtcggaag    840

aacgcctcca tcagcgtgag ggctcaagat cgttattact ccagcagctg gtccgagtgg    900

gccagcgtgc cttgttcc                                                  918
```

<210> SEQ ID NO 188
<211> LENGTH: 197
<212> TYPE: PRT
<213> ORGANISM: Homo sapiens

<400> SEQUENCE: 188

```
Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195
```

<210> SEQ ID NO 189
<211> LENGTH: 591
<212> TYPE: DNA
<213> ORGANISM: Homo sapiens

<400> SEQUENCE: 189

```
cgtaacctcc ccgtggctac ccccgatccc ggaatgttcc cttgtttaca ccacagccag      60

aatttactga gggccgtgag caacatgctg cagaaagcta ggcagacttt agaattttac     120

ccttgcacca gcgaggagat cgaccatgaa gatatcacca aggacaagac atccaccgtg     180

gaggcttgtt tacctctgga gctgacaaag aacgagtctt gtctcaactc tcgtgaaacc     240

agcttcatca caaatggctc ttgtttagct tcccggaaga cctcctttat gatggcttta     300

tgcctcagct ccatctacga ggatttaaag atgtaccaag tggagttcaa gaccatgaac     360

gccaagctgc tcatggaccc taaacggcag atctttttag accagaacat gctggctgtg     420

attgatgagc tgatgcaagc tttaaacttc aactccgaga ccgtccctca gaagtcctcc     480

ctcgaggagc ccgattttta caagacaaag atcaaactgt gcattttact ccacgccttt     540

aggatccggg ccgtgaccat tgaccgggtc atgagctatt taaacgccag c              591
```

<210> SEQ ID NO 190
<211> LENGTH: 490
<212> TYPE: PRT

<213> ORGANISM: Artificial Sequence
<220> FEATURE:
<223> OTHER INFORMATION: Synthetic polypeptide

<400> SEQUENCE: 190

Tyr Phe Gly Lys Leu Glu Ser Lys Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

Ile Ser Met Tyr Lys Asp Ser Gln Pro Arg Gly Met Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Gln Arg Ser Val Pro Gly His Asp Asn Lys
100 105 110

Met Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp Ser Gly Thr
145 150 155 160

Thr Asn Thr Val Ala Ala Tyr Asn Leu Thr Trp Lys Ser Thr Asn Phe
165 170 175

Lys Thr Ile Leu Glu Trp Glu Pro Lys Pro Val Asn Gln Val Tyr Thr
180 185 190

Val Gln Ile Ser Thr Lys Ser Gly Asp Trp Lys Ser Lys Cys Phe Tyr
195 200 205

Thr Thr Asp Thr Glu Cys Asp Leu Thr Asp Glu Ile Val Lys Asp Val
210 215 220

Lys Gln Thr Tyr Leu Ala Arg Val Phe Ser Tyr Pro Ala Gly Asn Val
225 230 235 240

Glu Ser Thr Gly Ser Ala Gly Glu Pro Leu Tyr Glu Asn Ser Pro Glu
245 250 255

Phe Thr Pro Tyr Leu Glu Thr Asn Leu Gly Gln Pro Thr Ile Gln Ser
260 265 270

Phe Glu Gln Val Gly Thr Lys Val Asn Val Thr Val Glu Asp Glu Arg
275 280 285

Thr Leu Val Arg Arg Asn Asn Thr Phe Leu Ser Leu Arg Asp Val Phe
290 295 300

Gly Lys Asp Leu Ile Tyr Thr Leu Tyr Tyr Trp Lys Ser Ser Ser Ser
305 310 315 320

Gly Lys Lys Thr Ala Lys Thr Asn Thr Asn Glu Phe Leu Ile Asp Val
325 330 335

Asp Lys Gly Glu Asn Tyr Cys Phe Ser Val Gln Ala Val Ile Pro Ser
340 345 350

Arg Thr Val Asn Arg Lys Ser Thr Asp Ser Pro Val Glu Cys Met Gly
355 360 365

Gln Glu Lys Gly Glu Phe Arg Glu Asn Trp Val Asn Val Ile Ser Asp
370 375 380

Leu Lys Lys Ile Glu Asp Leu Ile Gln Ser Met His Ile Asp Ala Thr 385 390 395 400

Leu Tyr Thr Glu Ser Asp Val His Pro Ser Cys Lys Val Thr Ala Met
405 410 415

Lys Cys Phe Leu Leu Glu Leu Gln Val Ile Ser Leu Glu Ser Gly Asp
420 425 430

Ala Ser Ile His Asp Thr Val Glu Asn Leu Ile Ile Leu Ala Asn Asn
435 440 445

Ser Leu Ser Ser Asn Gly Asn Val Thr Glu Ser Gly Cys Lys Glu Cys
450 455 460

Glu Glu Leu Glu Glu Lys Asn Ile Lys Glu Phe Leu Gln Ser Phe Val
465 470 475 480

His Ile Val Gln Met Phe Ile Asn Thr Ser
485 490

<210> SEQ ID NO 191
<211> LENGTH: 1470
<212> TYPE: DNA
<213> ORGANISM: Artificial Sequence
<220> FEATURE:
<223> OTHER INFORMATION: Synthetic polynucleotide

<400> SEQUENCE: 191
tacttcggca aactggaatc caagctgagc gtgatccgga atttaaacga ccaagttctg 60
tttatcgatc aaggtaaccg gcctctgttc gaggacatga ccgactccga ttgccgggac 120
aatgcccccc ggaccatctt cattatctcc atgtacaagg acagccagcc ccggggcatg 180
gctgtgacaa ttagcgtgaa gtgtgagaaa atcagcactt tatcttgtga gaacaagatc 240
atctccttta aggaaatgaa cccccccgat aacatcaagg acaccaagtc cgatatcatc 300
ttcttccagc ggtccgtgcc cggtcacgat aacaagatgc agttcgaatc ctcctcctac 360
gagggctact tttagcttg tgaaaaggag agggatttat tcaagctgat cctcaagaag 420
gaggacgagc tgggcgatcg ttccatcatg ttcaccgtcc aaaacgagga tagcggcaca 480
accaacacag tcgctgccta taacctcact tggaagagca ccaacttcaa aaccatcctc 540
gaatgggaac ccaaacccgt taaccaagtt tacaccgtgc agatcagcac caagtccggc 600
gactggaagt ccaaatgttt ctataccacc gacaccgagt gcgatctcac cgatgagatc 660
gtgaaagatg tgaaacagac ctacctcgcc cgggtgttta gctaccccgc cggcaatgtg 720
gagagcactg gttccgctgg cgagccttta tacgagaaca gccccgaatt tacccccttac 780 ctcgagacca atttaggaca gcccaccatc caaagctttg agcaagttgg cacaaaggtg 840
aatgtgacag tggaggacga gcggacttta gtgcggcgga acaacacctt tctcagcctc 900
cgggatgtgt tcggcaaaga tttaatctac acactgtatt actggaagtc ctcttcctcc 960
ggcaagaaga cagctaaaac caacacaaac gagtttttaa tcgacgtgga taaaggcgaa 1020
aactactgtt tcagcgtgca agctgtgatc ccctcccgga ccgtgaatag gaaaagcacc 1080
gatagccccg ttgagtgcat gggccaagaa aagggcgagt tccgggagaa ctgggtgaac 1140
gtcatcagcg atttaaagaa gatcgaagat ttaattcagt ccatgcatat cgacgccact 1200
ttatacacag aatccgacgt gcacccctct tgtaaggtga ccgccatgaa atgtttttta 1260
ctggagctgc aagttatctc tttagagagc ggagacgcta gcatccacga caccgtggag 1320
aatttaatca ttttagccaa taactcttta tccagcaacg gcaacgtgac agagtccggc 1380
tgcaaggagt gcgaagagct ggaggagaag aacatcaagg agtttctgca atcctttgtg 1440
cacattgtcc agatgttcat caatacctcc 1470

<210> SEQ ID NO 192
<211> LENGTH: 508
<212> TYPE: PRT
<213> ORGANISM: Artificial Sequence
<220> FEATURE:
<223> OTHER INFORMATION: Synthetic polypeptide

<400> SEQUENCE: 192

```
Met Lys Trp Val Thr Phe Ile Ser Leu Leu Phe Leu Phe Ser Ser Ala
1               5                   10                  15

Tyr Ser Tyr Phe Gly Lys Leu Glu Ser Lys Leu Ser Val Ile Arg Asn
            20                  25                  30

Leu Asn Asp Gln Val Leu Phe Ile Asp Gln Gly Asn Arg Pro Leu Phe
        35                  40                  45

Glu Asp Met Thr Asp Ser Asp Cys Arg Asp Asn Ala Pro Arg Thr Ile
    50                  55                  60

Phe Ile Ile Ser Met Tyr Lys Asp Ser Gln Pro Arg Gly Met Ala Val
65                  70                  75                  80

Thr Ile Ser Val Lys Cys Glu Lys Ile Ser Thr Leu Ser Cys Glu Asn
                85                  90                  95

Lys Ile Ile Ser Phe Lys Glu Met Asn Pro Pro Asp Asn Ile Lys Asp
            100                 105                 110

Thr Lys Ser Asp Ile Ile Phe Phe Gln Arg Ser Val Pro Gly His Asp
        115                 120                 125

Asn Lys Met Gln Phe Glu Ser Ser Ser Tyr Glu Gly Tyr Phe Leu Ala
    130                 135                 140

Cys Glu Lys Glu Arg Asp Leu Phe Lys Leu Ile Leu Lys Lys Glu Asp
145                 150                 155                 160

Glu Leu Gly Asp Arg Ser Ile Met Phe Thr Val Gln Asn Glu Asp Ser
                165                 170                 175

Gly Thr Thr Asn Thr Val Ala Ala Tyr Asn Leu Thr Trp Lys Ser Thr
            180                 185                 190

Asn Phe Lys Thr Ile Leu Glu Trp Glu Pro Lys Pro Val Asn Gln Val
        195                 200                 205

Tyr Thr Val Gln Ile Ser Thr Lys Ser Gly Asp Trp Lys Ser Lys Cys
    210                 215                 220

Phe Tyr Thr Thr Asp Thr Glu Cys Asp Leu Thr Asp Glu Ile Val Lys
225                 230                 235                 240

Asp Val Lys Gln Thr Tyr Leu Ala Arg Val Phe Ser Tyr Pro Ala Gly
                245                 250                 255

Asn Val Glu Ser Thr Gly Ser Ala Gly Glu Pro Leu Tyr Glu Asn Ser
            260                 265                 270

Pro Glu Phe Thr Pro Tyr Leu Glu Thr Asn Leu Gly Gln Pro Thr Ile
        275                 280                 285

Gln Ser Phe Glu Gln Val Gly Thr Lys Val Asn Val Thr Val Glu Asp
    290                 295                 300

Glu Arg Thr Leu Val Arg Arg Asn Asn Thr Phe Leu Ser Leu Arg Asp
305                 310                 315                 320

Val Phe Gly Lys Asp Leu Ile Tyr Thr Leu Tyr Tyr Trp Lys Ser Ser
                325                 330                 335

Ser Ser Gly Lys Lys Thr Ala Lys Thr Asn Thr Asn Glu Phe Leu Ile
            340                 345                 350

Asp Val Asp Lys Gly Glu Asn Tyr Cys Phe Ser Val Gln Ala Val Ile
        355                 360                 365
```

```
Pro Ser Arg Thr Val Asn Arg Lys Ser Thr Asp Ser Pro Val Glu Cys
    370                 375                 380

Met Gly Gln Glu Lys Gly Glu Phe Arg Glu Asn Trp Val Asn Val Ile
385                 390                 395                 400

Ser Asp Leu Lys Lys Ile Glu Asp Leu Ile Gln Ser Met His Ile Asp
                405                 410                 415

Ala Thr Leu Tyr Thr Glu Ser Asp Val His Pro Ser Cys Lys Val Thr
            420                 425                 430

Ala Met Lys Cys Phe Leu Leu Glu Leu Gln Val Ile Ser Leu Glu Ser
        435                 440                 445

Gly Asp Ala Ser Ile His Asp Thr Val Glu Asn Leu Ile Ile Leu Ala
    450                 455                 460

Asn Asn Ser Leu Ser Ser Asn Gly Asn Val Thr Glu Ser Gly Cys Lys
465                 470                 475                 480

Glu Cys Glu Glu Leu Glu Glu Lys Asn Ile Lys Glu Phe Leu Gln Ser
                485                 490                 495

Phe Val His Ile Val Gln Met Phe Ile Asn Thr Ser
            500                 505
```

<210> SEQ ID NO 193
<211> LENGTH: 1524
<212> TYPE: DNA
<213> ORGANISM: Artificial Sequence
<220> FEATURE:
<223> OTHER INFORMATION: Synthetic polynucleotide

<400> SEQUENCE: 193

```
atgaagtggg tcacatttat ctctttactg ttcctcttct ccagcgccta cagctacttc     60

ggcaaactgg aatccaagct gagcgtgatc cggaatttaa acgaccaagt tctgtttatc    120

gatcaaggta accggcctct gttcgaggac atgaccgact ccgattgccg ggacaatgcc    180

ccccggacca tcttcattat ctccatgtac aaggacagcc agccccgggg catggctgtg    240

acaattagcg tgaagtgtga gaaaatcagc actttatctt gtgagaacaa gatcatctcc    300

tttaaggaaa tgaacccccc cgataacatc aaggacacca agtccgatat catcttcttc    360

cagcggtccg tgcccggtca cgataacaag atgcagttcg aatcctcctc ctacgagggc    420

tactttttag cttgtgaaaa ggagagggat ttattcaagc tgatcctcaa gaaggaggac    480

gagctgggcg atcgttccat catgttcacc gtccaaaacg aggatagcgg cacaaccaac    540

acagtcgctg cctataacct cacttggaag agcaccaact tcaaaaccat cctcgaatgg    600

gaacccaaac ccgttaacca agtttacacc gtgcagatca gcaccaagtc cggcgactgg    660

aagtccaaat gtttctatac caccgacacc gagtgcgatc tcaccgatga gatcgtgaaa    720

gatgtgaaac agacctacct cgcccgggtg tttagctacc ccgccggcaa tgtggagagc    780

actggttccg ctggcgagcc tttatacgag aacagccccg aatttacccc ttacctcgag    840

accaatttag gacagcccac catccaaagc tttgagcaag ttggcacaaa ggtgaatgtg    900

acagtggagg acgagcggac tttagtgcgg cggaacaaca cctttctcag cctccgggat    960

gtgttcggca aagatttaat ctacacactg tattactgga agtcctcttc ctccggcaag   1020

aagacagcta aaaccaacac aaacgagttt ttaatcgacg tggataaagg cgaaaactac   1080

tgtttcagcg tgcaagctgt gatcccctcc cggaccgtga ataggaaaag caccgatagc   1140

cccgttgagt gcatgggcca agaaaagggc gagttccggg agaactgggt gaacgtcatc   1200

agcgatttaa agaagatcga agatttaatt cagtccatgc atatcgacgc cactttatac   1260
```

```
acagaatccg acgtgcaccc ctcttgtaag gtgaccgcca tgaaatgttt tttactggag   1320

ctgcaagtta tctctttaga gagcggagac gctagcatcc acgacaccgt ggagaattta   1380

atcattttag ccaataactc tttatccagc aacggcaacg tgacagagtc cggctgcaag   1440

gagtgcgaag agctggagga gaagaacatc aaggagtttc tgcaatcctt tgtgcacatt   1500

gtccagatgt tcatcaatac ctcc                                          1524


<210> SEQ ID NO 194
<211> LENGTH: 583
<212> TYPE: PRT
<213> ORGANISM: Artificial Sequence
<220> FEATURE:
<223> OTHER INFORMATION: Synthetic polypeptide

<400> SEQUENCE: 194

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
```

```
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser Ile Thr Cys Pro Pro Pro Met Ser Val Glu
        515                 520                 525

His Ala Asp Ile Trp Val Lys Ser Tyr Ser Leu Tyr Ser Arg Glu Arg
    530                 535                 540

Tyr Ile Cys Asn Ser Gly Phe Lys Arg Lys Ala Gly Thr Ser Ser Leu
545                 550                 555                 560

Thr Glu Cys Val Leu Asn Lys Ala Thr Asn Val Ala His Trp Thr Thr
                565                 570                 575

Pro Ser Leu Lys Cys Ile Arg
            580
```

<210> SEQ ID NO 195
<211> LENGTH: 1749
<212> TYPE: DNA
<213> ORGANISM: Artificial Sequence
<220> FEATURE:
<223> OTHER INFORMATION: Synthetic polynucleotide

<400> SEQUENCE: 195

```
atttgggaac tgaagaagga cgtctacgtg gtcgaactgg actggtatcc cgatgctccc      60

ggcgaaatgg tggtgctcac ttgtgacacc cccgaagaag acggcatcac ttggaccctc     120

gatcagagca gcgaggtgct gggctccgga aagaccctca caatccaagt taaggagttc     180

ggagacgctg gccaatacac atgccacaag ggaggcgagg tgctcagcca ttccttatta     240

ttattacaca agaaggaaga cggaatctgg tccaccgaca ttttaaaaga tcagaaggag     300

cccaagaata agaccttttt aaggtgtgag gccaaaaact acagcggtcg tttcacttgt     360

tggtggctga ccaccatttc caccgattta accttctccg tgaaaagcag ccggggaagc     420

tccgaccctc aaggtgtgac atgtggagcc gctaccctca gcgctgagag ggttcgtggc     480
```

```
gataacaagg aatacgagta cagcgtggag tgccaagaag atagcgcttg tcccgctgcc    540
gaagaatctt tacccattga ggtgatggtg gacgccgtgc acaaactcaa gtacgagaac    600
tacacctcct ccttctttat ccgggacatc attaagcccg atcctcctaa gaatttacag    660
ctgaagcctc tcaaaaatag ccggcaagtt gaggtctctt gggaatatcc cgacacttgg    720
agcacacccc acagctactt ctctttaacc ttttgtgtgc aagttcaagg taaaagcaag    780
cgggagaaga aagaccgggt gtttaccgac aaaaccagcg ccaccgtcat ctgtcggaag    840
aacgcctcca tcagcgtgag ggctcaagat cgttattact ccagcagctg gtccgagtgg    900
gccagcgtgc cttgttccgg cggtggagga tccggaggag gtggctccgg cggcggagga    960
tctcgtaacc tccccgtggc tacccccgat cccggaatgt tcccttgttt acaccacagc   1020
cagaatttac tgagggccgt gagcaacatg ctgcagaaag ctaggcagac tttagaattt   1080
tacccttgca ccagcgagga gatcgaccat gaagatatca ccaaggacaa gacatccacc   1140
gtggaggctt gtttacctct ggagctgaca aagaacgagt cttgtctcaa ctctcgtgaa   1200
accagcttca tcacaaatgg ctcttgttta gcttcccgga agacctcctt tatgatggct   1260
ttatgcctca gctccatcta cgaggattta aagatgtacc aagtggagtt caagaccatg   1320
aacgccaagc tgctcatgga ccctaaacgg cagatctttt tagaccagaa catgctggct   1380
gtgattgatg agctgatgca agctttaaac ttcaactccg agaccgtccc tcagaagtcc   1440
tccctcgagg agcccgattt ttacaagaca aagatcaaac tgtgcatttt actccacgcc   1500
tttaggatcc gggccgtgac cattgaccgg gtcatgagct atttaaacgc cagcattaca   1560
tgcccccctc ccatgagcgt ggagcacgcc gacatctggg tgaagagcta tagcctctac   1620
agccgggaga ggtatatctg taacagcggc ttcaagagga aggccggcac cagcagcctc   1680
accgagtgcg tgctgaataa ggctaccaac gtggctcact ggacaacacc ctctttaaag   1740
tgcatccgg                                                           1749
```

<210> SEQ ID NO 196
<211> LENGTH: 601
<212> TYPE: PRT
<213> ORGANISM: Artificial Sequence
<220> FEATURE:
<223> OTHER INFORMATION: Synthetic polypeptide

<400> SEQUENCE: 196

```
Met Lys Trp Val Thr Phe Ile Ser Leu Leu Phe Leu Phe Ser Ser Ala
1               5                   10                  15

Tyr Ser Ile Trp Glu Leu Lys Lys Asp Val Tyr Val Val Glu Leu Asp
            20                  25                  30

Trp Tyr Pro Asp Ala Pro Gly Glu Met Val Val Leu Thr Cys Asp Thr
        35                  40                  45

Pro Glu Glu Asp Gly Ile Thr Trp Thr Leu Asp Gln Ser Ser Glu Val
    50                  55                  60

Leu Gly Ser Gly Lys Thr Leu Thr Ile Gln Val Lys Glu Phe Gly Asp
65                  70                  75                  80

Ala Gly Gln Tyr Thr Cys His Lys Gly Gly Glu Val Leu Ser His Ser
                85                  90                  95

Leu Leu Leu Leu His Lys Lys Glu Asp Gly Ile Trp Ser Thr Asp Ile
            100                 105                 110

Leu Lys Asp Gln Lys Glu Pro Lys Asn Lys Thr Phe Leu Arg Cys Glu
        115                 120                 125

Ala Lys Asn Tyr Ser Gly Arg Phe Thr Cys Trp Trp Leu Thr Thr Ile
```

```
    130                 135                 140

Ser Thr Asp Leu Thr Phe Ser Val Lys Ser Ser Arg Gly Ser Ser Asp
145                 150                 155                 160

Pro Gln Gly Val Thr Cys Gly Ala Ala Thr Leu Ser Ala Glu Arg Val
                165                 170                 175

Arg Gly Asp Asn Lys Glu Tyr Glu Tyr Ser Val Glu Cys Gln Glu Asp
            180                 185                 190

Ser Ala Cys Pro Ala Ala Glu Glu Ser Leu Pro Ile Glu Val Met Val
        195                 200                 205

Asp Ala Val His Lys Leu Lys Tyr Glu Asn Tyr Thr Ser Ser Phe Phe
    210                 215                 220

Ile Arg Asp Ile Ile Lys Pro Asp Pro Pro Lys Asn Leu Gln Leu Lys
225                 230                 235                 240

Pro Leu Lys Asn Ser Arg Gln Val Glu Val Ser Trp Glu Tyr Pro Asp
                245                 250                 255

Thr Trp Ser Thr Pro His Ser Tyr Phe Ser Leu Thr Phe Cys Val Gln
            260                 265                 270

Val Gln Gly Lys Ser Lys Arg Glu Lys Lys Asp Arg Val Phe Thr Asp
        275                 280                 285

Lys Thr Ser Ala Thr Val Ile Cys Arg Lys Asn Ala Ser Ile Ser Val
    290                 295                 300

Arg Ala Gln Asp Arg Tyr Tyr Ser Ser Ser Trp Ser Glu Trp Ala Ser
305                 310                 315                 320

Val Pro Cys Ser Gly Gly Gly Gly Ser Gly Gly Gly Gly Ser Gly Gly
                325                 330                 335

Gly Gly Ser Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
        355                 360                 365

Leu Gln Lys Ala Arg Gln Thr Leu Glu Phe Tyr Pro Cys Thr Ser Glu
    370                 375                 380

Glu Ile Asp His Glu Asp Ile Thr Lys Asp Lys Thr Ser Thr Val Glu
385                 390                 395                 400

Ala Cys Leu Pro Leu Glu Leu Thr Lys Asn Glu Ser Cys Leu Asn Ser
                405                 410                 415

Arg Glu Thr Ser Phe Ile Thr Asn Gly Ser Cys Leu Ala Ser Arg Lys
            420                 425                 430

Thr Ser Phe Met Met Ala Leu Cys Leu Ser Ser Ile Tyr Glu Asp Leu
        435                 440                 445

Lys Met Tyr Gln Val Glu Phe Lys Thr Met Asn Ala Lys Leu Leu Met
    450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
            500                 505                 510

Cys Ile Leu Leu His Ala Phe Arg Ile Arg Ala Val Thr Ile Asp Arg
        515                 520                 525

Val Met Ser Tyr Leu Asn Ala Ser Ile Thr Cys Pro Pro Pro Met Ser
    530                 535                 540

Val Glu His Ala Asp Ile Trp Val Lys Ser Tyr Ser Leu Tyr Ser Arg
545                 550                 555                 560
```

Glu Arg Tyr Ile Cys Asn Ser Gly Phe Lys Arg Lys Ala Gly Thr Ser
565 570 575

Ser Leu Thr Glu Cys Val Leu Asn Lys Ala Thr Asn Val Ala His Trp
580 585 590

Thr Thr Pro Ser Leu Lys Cys Ile Arg
595 600

<210> SEQ ID NO 197
<211> LENGTH: 1803
<212> TYPE: DNA
<213> ORGANISM: Artificial Sequence
<220> FEATURE:
<223> OTHER INFORMATION: Synthetic polynucleotide

<400> SEQUENCE: 197
atgaaatggg tgacctttat ttctttactg ttcctcttta gcagcgccta ctccatttgg 60
gaactgaaga aggacgtcta cgtggtcgaa ctggactggt atcccgatgc tcccggcgaa 120
atggtggtgc tcacttgtga cacccccgaa gaagacggca tcacttggac cctcgatcag 180
agcagcgagg tgctgggctc cggaaagacc ctcacaatcc aagttaagga gttcggagac 240
gctggccaat acacatgcca caagggaggc gaggtgctca gccattcctt attattatta 300
cacaagaagg aagacggaat ctggtccacc gacattttaa aagatcagaa ggagcccaag 360
aataagacct tttaaggtg tgaggccaaa aactacagcg gtcgtttcac ttgttggtgg 420
ctgaccacca tttccaccga tttaaccttc tccgtgaaaa gcagccgggg aagctccgac 480
cctcaaggtg tgacatgtgg agccgctacc ctcagcgctg agagggttcg tggcgataac 540
aaggaatacg agtacagcgt ggagtgccaa gaagatagcg cttgtcccgc tgccgaagaa 600
tctttaccca ttgaggtgat ggtggacgcc gtgcacaaac tcaagtacga gaactacacc 660
tcctccttct ttatccggga catcattaag cccgatcctc ctaagaattt acagctgaag 720
cctctcaaaa atagccggca agttgaggtc tcttgggaat atcccgacac ttggagcaca 780
ccccacagct acttctcttt aaccttttgt gtgcaagttc aaggtaaaag caagcgggag 840
aagaaagacc gggtgtttac cgacaaaacc agcgccaccg tcatctgtcg gaagaacgcc 900
tccatcagcg tgagggctca agatcgttat tactccagca gctggtccga gtgggccagc 960
gtgccttgtt ccggcggtgg aggatccgga ggaggtggct ccggcggcgg aggatctcgt 1020
aacctccccg tggctacccc cgatcccgga atgttccctt gtttacacca cagccagaat 1080
ttactgaggg ccgtgagcaa catgctgcag aaagctaggc agactttaga attttaccct 1140
tgcaccagcg aggagatcga ccatgaagat atcaccaagg acaagacatc caccgtggag 1200
gcttgtttac ctctggagct gacaaagaac gagtcttgtc tcaactctcg tgaaaccagc 1260
ttcatcacaa atggctcttg tttagcttcc cggaagacct cctttatgat ggctttatgc 1320
ctcagctcca tctacgagga tttaaagatg taccaagtgg agttcaagac catgaacgcc 1380
aagctgctca tggaccctaa acggcagatc tttttagacc agaacatgct ggctgtgatt 1440
gatgagctga tgcaagcttt aaacttcaac tccgagaccg tccctcagaa gtcctccctc 1500
gaggagcccg atttttacaa gacaaagatc aaactgtgca ttttactcca cgcctttagg 1560
atccgggccg tgaccattga ccgggtcatg agctatttaa acgccagcat tacatgcccc 1620
cctcccatga gcgtggagca cgccgacatc tgggtgaaga gctatagcct ctacagccgg 1680
gagaggtata tctgtaacag cggcttcaag aggaaggccg gcaccagcag cctcaccgag 1740
tgcgtgctga ataaggctac caacgtggct cactggacaa caccctcttt aaagtgcatc 1800
cgg 1803

<210> SEQ ID NO 198
<211> LENGTH: 133
<212> TYPE: PRT
<213> ORGANISM: Homo sapiens

<400> SEQUENCE: 198

Gln Gly Gln Asp Arg His Met Ile Arg Met Arg Gln Leu Ile Asp Ile
1 5 10 15

Val Asp Gln Leu Lys Asn Tyr Val Asn Asp Leu Val Pro Glu Phe Leu
20 25 30

Pro Ala Pro Glu Asp Val Glu Thr Asn Cys Glu Trp Ser Ala Phe Ser
35 40 45

Cys Phe Gln Lys Ala Gln Leu Lys Ser Ala Asn Thr Gly Asn Asn Glu
50 55 60

Arg Ile Ile Asn Val Ser Ile Lys Lys Leu Lys Arg Lys Pro Pro Ser
65 70 75 80

Thr Asn Ala Gly Arg Arg Gln Lys His Arg Leu Thr Cys Pro Ser Cys
85 90 95

Asp Ser Tyr Glu Lys Lys Pro Pro Lys Glu Phe Leu Glu Arg Phe Lys
100 105 110

Ser Leu Leu Gln Lys Met Ile His Gln His Leu Ser Ser Arg Thr His
115 120 125

Gly Ser Glu Asp Ser
130

<210> SEQ ID NO 199
<211> LENGTH: 399
<212> TYPE: DNA
<213> ORGANISM: Homo sapiens

<400> SEQUENCE: 199
caaggtcaag atcgccacat gattagaatg cgtcaactta tagatattgt tgatcagctg 60
aaaaattatg tgaatgactt ggtccctgaa tttctgccag ctccagaaga tgtagagaca 120
aactgtgagt ggtcagcttt ttcctgtttt cagaaggccc aactaaagtc agcaaataca 180
ggaaacaatg aaaggataat caatgtatca attaaaaagc tgaagaggaa accaccttcc 240
acaaatgcag ggagaagaca gaaacacaga ctaacatgcc cttcatgtga ttcttatgag 300
aaaaaaccac ccaaagaatt cctagaaaga ttcaaatcac ttctccaaaa gatgattcat 360
cagcatctgt cctctagaac acacggaagt gaagattcc 399

<210> SEQ ID NO 200
<211> LENGTH: 399
<212> TYPE: DNA
<213> ORGANISM: Homo sapiens

<400> SEQUENCE: 200
cagggccagg acaggcacat gatccggatg aggcagctca tcgacatcgt cgaccagctg 60
aagaactacg tgaacgacct ggtgcccgag tttctgcctg cccccgagga cgtggagacc 120
aactgcgagt ggtccgcctt ctcctgcttt cagaaggccc agctgaagtc cgccaacacc 180
ggcaacaacg agcggatcat caacgtgagc atcaagaagc tgaagcggaa gcctccctcc 240
acaaacgccg gcaggaggca gaagcacagg ctgacctgcc ccagctgtga ctcctacgag 300
aagaagcccc ccaaggagtt cctggagagg ttcaagtccc tgctgcagaa gatgatccat 360
cagcacctgt cctccaggac ccacggctcc gaggactcc 399

<210> SEQ ID NO 201

<400> SEQUENCE: 201

000

<210> SEQ ID NO 202
<211> LENGTH: 456
<212> TYPE: DNA
<213> ORGANISM: Homo sapiens

<400> SEQUENCE: 202
gattgtgata ttgaaggtaa agatggcaaa caatatgaga gtgttctaat ggtcagcatc 60
gatcaattat tggacagcat gaaagaaatt ggtagcaatt gcctgaataa tgaatttaac 120
ttttttaaaa gacatatctg tgatgctaat aaggaaggta tgtttttatt ccgtgctgct 180
cgcaagttga ggcaatttct taaaatgaat agcactggtg attttgatct ccacttatta 240
aaagtttcag aaggcacaac aatactgttg aactgcactg gccaggttaa aggaagaaaa 300
ccagctgccc tgggtgaagc ccaaccaaca aagagtttgg aagaaaataa atctttaaag 360
gaacagaaaa aactgaatga cttgtgtttc ctaaagagac tattacaaga gataaaaact 420
tgttggaata aaattttgat gggcactaaa gaacac 456

<210> SEQ ID NO 203
<211> LENGTH: 466
<212> TYPE: PRT
<213> ORGANISM: Artificial Sequence
<220> FEATURE:
<223> OTHER INFORMATION: Synthetic polypeptide

<400> SEQUENCE: 203

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ser Gly Thr Thr Asn Thr Val Ala Ala Tyr Asn
    130                 135                 140

Leu Thr Trp Lys Ser Thr Asn Phe Lys Thr Ile Leu Glu Trp Glu Pro
145                 150                 155                 160

Lys Pro Val Asn Gln Val Tyr Thr Val Gln Ile Ser Thr Lys Ser Gly
                165                 170                 175

Asp Trp Lys Ser Lys Cys Phe Tyr Thr Thr Asp Thr Glu Cys Asp Leu
            180                 185                 190

```
Thr Asp Glu Ile Val Lys Asp Val Lys Gln Thr Tyr Leu Ala Arg Val
        195                 200                 205

Phe Ser Tyr Pro Ala Gly Asn Val Glu Ser Thr Gly Ser Ala Gly Glu
    210                 215                 220

Pro Leu Tyr Glu Asn Ser Pro Glu Phe Thr Pro Tyr Leu Glu Thr Asn
225                 230                 235                 240

Leu Gly Gln Pro Thr Ile Gln Ser Phe Glu Gln Val Gly Thr Lys Val
                245                 250                 255

Asn Val Thr Val Glu Asp Glu Arg Thr Leu Val Arg Arg Asn Asn Thr
            260                 265                 270

Phe Leu Ser Leu Arg Asp Val Phe Gly Lys Asp Leu Ile Tyr Thr Leu
        275                 280                 285

Tyr Tyr Trp Lys Ser Ser Ser Ser Gly Lys Lys Thr Ala Lys Thr Asn
    290                 295                 300

Thr Asn Glu Phe Leu Ile Asp Val Asp Lys Gly Glu Asn Tyr Cys Phe
305                 310                 315                 320

Ser Val Gln Ala Val Ile Pro Ser Arg Thr Val Asn Arg Lys Ser Thr
                325                 330                 335

Asp Ser Pro Val Glu Cys Met Gly Gln Glu Lys Gly Glu Phe Arg Glu
            340                 345                 350

Asn Trp Val Asn Val Ile Ser Asp Leu Lys Lys Ile Glu Asp Leu Ile
        355                 360                 365

Gln Ser Met His Ile Asp Ala Thr Leu Tyr Thr Glu Ser Asp Val His
    370                 375                 380

Pro Ser Cys Lys Val Thr Ala Met Lys Cys Phe Leu Leu Glu Leu Gln
385                 390                 395                 400

Val Ile Ser Leu Glu Ser Gly Asp Ala Ser Ile His Asp Thr Val Glu
                405                 410                 415

Asn Leu Ile Ile Leu Ala Asn Asn Ser Leu Ser Ser Asn Gly Asn Val
            420                 425                 430

Thr Glu Ser Gly Cys Lys Glu Cys Glu Glu Leu Glu Glu Lys Asn Ile
        435                 440                 445

Lys Glu Phe Leu Gln Ser Phe Val His Ile Val Gln Met Phe Ile Asn
    450                 455                 460

Thr Ser
465
```

<210> SEQ ID NO 204
<211> LENGTH: 1398
<212> TYPE: DNA
<213> ORGANISM: Artificial Sequence
<220> FEATURE:
<223> OTHER INFORMATION: Synthetic polynucleotide

<400> SEQUENCE: 204

```
caaggtcaag atcgccacat gattagaatg cgtcaactta tagatattgt tgatcagctg     60

aaaaattatg tgaatgactt ggtccctgaa tttctgccag ctccagaaga tgtagagaca    120

aactgtgagt ggtcagcttt ttcctgtttt cagaaggccc aactaaagtc agcaaataca    180

ggaaacaatg aaaggataat caatgtatca attaaaaagc tgaagaggaa accaccttcc    240

acaaatgcag ggagaagaca gaaacacaga ctaacatgcc cttcatgtga ttcttatgag    300

aaaaaaccac ccaaagaatt cctagaaaga ttcaaatcac ttctccaaaa gatgattcat    360

cagcatctgt cctctagaac acacggaagt gaagattcct caggcactac aaatactgtg    420
```

```
gcagcatata atttaacttg gaaatcaact aatttcaaga caattttgga gtgggaaccc    480
aaacccgtca atcaagtcta cactgttcaa ataagcacta agtcaggaga ttggaaaagc    540
aaatgctttt acacaacaga cacagagtgt gacctcaccg acgagattgt gaaggatgtg    600
aagcagacgt acttggcacg ggtcttctcc tacccggcag ggaatgtgga gagcaccggt    660
tctgctgggg agcctctgta tgagaactcc ccagagttca caccttacct ggagacaaac    720
ctcggacagc caacaattca gagttttgaa caggtgggaa caaaagtgaa tgtgaccgta    780
gaagatgaac ggactttagt cagaaggaac aacactttcc taagcctccg ggatgttttt    840
ggcaaggact taatttatac actttattat tggaaatctt caagttcagg aaagaaaaca    900
gccaaaacaa acactaatga gtttttgatt gatgtggata aaggagaaaa ctactgtttc    960
agtgttcaag cagtgattcc ctcccgaaca gttaaccgga agagtacaga cagcccggta   1020
gagtgtatgg gccaggagaa aggggaattc agagaaaact gggtgaacgt catcagcgat   1080
ttaaagaaga tcgaagattt aattcagtcc atgcatatcg acgccacttt atacacagaa   1140
tccgacgtgc acccctcttg taaggtgacc gccatgaaat gtttttact ggagctgcaa    1200
gttatctctt tagagagcgg agacgctagc atccacgaca ccgtggagaa tttaatcatt   1260
ttagccaata actctttatc cagcaacggc aacgtgacag agtccggctg caaggagtgc   1320
gaagagctgg aggagaagaa catcaaggag tttctgcaat cctttgtgca cattgtccag   1380
atgttcatca atacctcc                                                 1398
```

<210> SEQ ID NO 205
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 205

```
Met Gly Val Lys Val Leu Phe Ala Leu Ile Cys Ile Ala Val Ala Glu
1               5                   10                  15

Ala Gln Gly Gln Asp Arg His Met Ile Arg Met Arg Gln Leu Ile Asp
            20                  25                  30

Ile Val Asp Gln Leu Lys Asn Tyr Val Asn Asp Leu Val Pro Glu Phe
        35                  40                  45

Leu Pro Ala Pro Glu Asp Val Glu Thr Asn Cys Glu Trp Ser Ala Phe
    50                  55                  60

Ser Cys Phe Gln Lys Ala Gln Leu Lys Ser Ala Asn Thr Gly Asn Asn
65                  70                  75                  80

Glu Arg Ile Ile Asn Val Ser Ile Lys Lys Leu Lys Arg Lys Pro Pro
                85                  90                  95

Ser Thr Asn Ala Gly Arg Arg Gln Lys His Arg Leu Thr Cys Pro Ser
            100                 105                 110

Cys Asp Ser Tyr Glu Lys Lys Pro Pro Lys Glu Phe Leu Glu Arg Phe
        115                 120                 125

Lys Ser Leu Leu Gln Lys Met Ile His Gln His Leu Ser Ser Arg Thr
    130                 135                 140

His Gly Ser Glu Asp Ser Ser Gly Thr Thr Asn Thr Val Ala Ala Tyr
145                 150                 155                 160

Asn Leu Thr Trp Lys Ser Thr Asn Phe Lys Thr Ile Leu Glu Trp Glu
                165                 170                 175

Pro Lys Pro Val Asn Gln Val Tyr Thr Val Gln Ile Ser Thr Lys Ser
            180                 185                 190
```

Gly Asp Trp Lys Ser Lys Cys Phe Tyr Thr Thr Asp Thr Glu Cys Asp
195 200 205

Leu Thr Asp Glu Ile Val Lys Asp Val Lys Gln Thr Tyr Leu Ala Arg
210 215 220

Val Phe Ser Tyr Pro Ala Gly Asn Val Glu Ser Thr Gly Ser Ala Gly
225 230 235 240

Glu Pro Leu Tyr Glu Asn Ser Pro Glu Phe Thr Pro Tyr Leu Glu Thr
245 250 255

Asn Leu Gly Gln Pro Thr Ile Gln Ser Phe Glu Gln Val Gly Thr Lys
260 265 270

Val Asn Val Thr Val Glu Asp Glu Arg Thr Leu Val Arg Arg Asn Asn
275 280 285

Thr Phe Leu Ser Leu Arg Asp Val Phe Gly Lys Asp Leu Ile Tyr Thr
290 295 300

Leu Tyr Tyr Trp Lys Ser Ser Ser Ser Gly Lys Lys Thr Ala Lys Thr
305 310 315 320

Asn Thr Asn Glu Phe Leu Ile Asp Val Asp Lys Gly Glu Asn Tyr Cys
325 330 335

Phe Ser Val Gln Ala Val Ile Pro Ser Arg Thr Val Asn Arg Lys Ser
340 345 350

Thr Asp Ser Pro Val Glu Cys Met Gly Gln Glu Lys Gly Glu Phe Arg
355 360 365

Glu Asn Trp Val Asn Val Ile Ser Asp Leu Lys Lys Ile Glu Asp Leu
370 375 380

Ile Gln Ser Met His Ile Asp Ala Thr Leu Tyr Thr Glu Ser Asp Val
385 390 395 400

His Pro Ser Cys Lys Val Thr Ala Met Lys Cys Phe Leu Leu Glu Leu
405 410 415

Gln Val Ile Ser Leu Glu Ser Gly Asp Ala Ser Ile His Asp Thr Val
420 425 430

Glu Asn Leu Ile Ile Leu Ala Asn Asn Ser Leu Ser Ser Asn Gly Asn
435 440 445

Val Thr Glu Ser Gly Cys Lys Glu Cys Glu Glu Leu Glu Glu Lys Asn
450 455 460

Ile Lys Glu Phe Leu Gln Ser Phe Val His Ile Val Gln Met Phe Ile
465 470 475 480

Asn Thr Ser

<210> SEQ ID NO 206
<211> LENGTH: 1449
<212> TYPE: DNA
<213> ORGANISM: Artificial Sequence
<220> FEATURE:
<223> OTHER INFORMATION: Synthetic polynucleotide

<400> SEQUENCE: 206
atgggagtga aagttctttt tgcccttatt tgtattgctg tggccgaggc ccaaggtcaa 60
gatcgccaca tgattagaat gcgtcaactt atagatattg ttgatcagct gaaaaattat 120
gtgaatgact tggtccctga atttctgcca gctccagaag atgtagagac aaactgtgag 180
tggtcagctt tttcctgttt tcagaaggcc caactaaagt cagcaaatac aggaaacaat 240
gaaaggataa tcaatgtatc aattaaaaag ctgaagagga aaccaccttc cacaaatgca 300
gggagaagac agaaacacag actaacatgc ccttcatgtg attcttatga gaaaaaacca 360

-continued

```
cccaaagaat tcctagaaag attcaaatca cttctccaaa agatgattca tcagcatctg    420

tcctctagaa cacacggaag tgaagattcc tcaggcacta caaatactgt ggcagcatat    480

aatttaactt ggaaatcaac taatttcaag acaattttgg agtgggaacc caaacccgtc    540

aatcaagtct acactgttca aataagcact aagtcaggag attggaaaag caaatgcttt    600

tacacaacag acacagagtg tgacctcacc gacgagattg tgaaggatgt gaagcagacg    660

tacttggcac gggtcttctc ctacccggca gggaatgtgg agagcaccgg ttctgctggg    720

gagcctctgt atgagaactc cccagagttc acaccttacc tggagacaaa cctcggacag    780

ccaacaattc agagttttga acaggtggga acaaaagtga atgtgaccgt agaagatgaa    840

cggactttag tcagaaggaa caacactttc ctaagcctcc gggatgtttt tggcaaggac    900

ttaatttata cactttatta ttggaaatct tcaagttcag gaaagaaaac agccaaaaca    960

aacactaatg agtttttgat tgatgtggat aaaggagaaa actactgttt cagtgttcaa   1020

gcagtgattc cctcccgaac agttaaccgg aagagtacag acagcccggt agagtgtatg   1080

ggccaggaga aaggggaatt cagagaaaac tgggtgaacg tcatcagcga tttaaagaag   1140

atcgaagatt taattcagtc catgcatatc gacgccactt tatacacaga atccgacgtg   1200

cacccctctt gtaaggtgac cgccatgaaa tgtttttac tggagctgca agttatctct   1260

ttagagagcg gagacgctag catccacgac accgtggaga atttaatcat tttagccaat   1320

aactctttat ccagcaacgg caacgtgaca gagtccggct gcaaggagtg cgaagagctg   1380

gaggagaaga acatcaagga gtttctgcaa tcctttgtgc acattgtcca gatgttcatc   1440

aatacctcc                                                            1449
```

```
<210> SEQ ID NO 207
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 207

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His Ile Thr Cys Pro Pro Pro Met Ser
145                 150                 155                 160

Val Glu His Ala Asp Ile Trp Val Lys Ser Tyr Ser Leu Tyr Ser Arg
```

165                 170                 175

Glu Arg Tyr Ile Cys Asn Ser Gly Phe Lys Arg Lys Ala Gly Thr Ser
            180                 185                 190

Ser Leu Thr Glu Cys Val Leu Asn Lys Ala Thr Asn Val Ala His Trp
        195                 200                 205

Thr Thr Pro Ser Leu Lys Cys Ile Arg
    210                 215

<210> SEQ ID NO 208
<211> LENGTH: 651
<212> TYPE: DNA
<213> ORGANISM: Artificial Sequence
<220> FEATURE:
<223> OTHER INFORMATION: Synthetic polynucleotide

<400> SEQUENCE: 208
gattgtgata ttgaaggtaa agatggcaaa caatatgaga gtgttctaat ggtcagcatc 60
gatcaattat tggacagcat gaaagaaatt ggtagcaatt gcctgaataa tgaatttaac 120
ttttttaaaa gacatatctg tgatgctaat aaggaaggta tgtttttatt ccgtgctgct 180
cgcaagttga ggcaatttct taaaatgaat agcactggtg attttgatct ccacttatta 240
aaagtttcag aaggcacaac aatactgttg aactgcactg gccaggttaa aggaagaaaa 300
ccagctgccc tgggtgaagc ccaaccaaca aagagtttgg aagaaaataa atctttaaag 360
gaacagaaaa aactgaatga cttgtgtttc ctaaagagac tattacaaga gataaaaact 420
tgttggaata aaattttgat gggcactaaa gaacacatca cgtgccctcc ccccatgtcc 480
gtggaacacg cagacatctg ggtcaagagc tacagcttgt actccaggga gcggtacatt 540
tgtaactctg gtttcaagcg taaagccggc acgtccagcc tgacggagtg cgtgttgaac 600
aaggccacga atgtcgccca ctggacaacc cccagtctca aatgcattag a 651

<210> SEQ ID NO 209
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 209

Met Gly Val Lys Val Leu Phe Ala Leu Ile Cys Ile Ala Val Ala Glu
1               5                   10                  15

Ala Asp Cys Asp Ile Glu Gly Lys Asp Gly Lys Gln Tyr Glu Ser Val
            20                  25                  30

Leu Met Val Ser Ile Asp Gln Leu Leu Asp Ser Met Lys Glu Ile Gly
        35                  40                  45

Ser Asn Cys Leu Asn Asn Glu Phe Asn Phe Phe Lys Arg His Ile Cys
    50                  55                  60

Asp Ala Asn Lys Glu Gly Met Phe Leu Phe Arg Ala Ala Arg Lys Leu
65                  70                  75                  80

Arg Gln Phe Leu Lys Met Asn Ser Thr Gly Asp Phe Asp Leu His Leu
                85                  90                  95

Leu Lys Val Ser Glu Gly Thr Thr Ile Leu Leu Asn Cys Thr Gly Gln
            100                 105                 110

Val Lys Gly Arg Lys Pro Ala Ala Leu Gly Glu Ala Gln Pro Thr Lys
        115                 120                 125

Ser Leu Glu Glu Asn Lys Ser Leu Lys Glu Gln Lys Lys Leu Asn Asp
    130                 135                 140

```
Leu Cys Phe Leu Lys Arg Leu Leu Gln Glu Ile Lys Thr Cys Trp Asn
145                 150                 155                 160

Lys Ile Leu Met Gly Thr Lys Glu His Ile Thr Cys Pro Pro Pro Met
                165                 170                 175

Ser Val Glu His Ala Asp Ile Trp Val Lys Ser Tyr Ser Leu Tyr Ser
            180                 185                 190

Arg Glu Arg Tyr Ile Cys Asn Ser Gly Phe Lys Arg Lys Ala Gly Thr
        195                 200                 205

Ser Ser Leu Thr Glu Cys Val Leu Asn Lys Ala Thr Asn Val Ala His
    210                 215                 220

Trp Thr Thr Pro Ser Leu Lys Cys Ile Arg
225                 230
```

<210> SEQ ID NO 210
<211> LENGTH: 702
<212> TYPE: DNA
<213> ORGANISM: Artificial Sequence
<220> FEATURE:
<223> OTHER INFORMATION: Synthetic polynucleotide

<400> SEQUENCE: 210

```
atgggagtga aagttctttt tgcccttatt tgtattgctg tggccgaggc cgattgtgat      60

attgaaggta aagatggcaa acaatatgag agtgttctaa tggtcagcat cgatcaatta     120

ttggacagca tgaaagaaat tggtagcaat tgcctgaata atgaatttaa ctttttttaaa     180

agacatatct gtgatgctaa taaggaaggt atgtttttat tccgtgctgc tcgcaagttg     240

aggcaatttc ttaaaatgaa tagcactggt gattttgatc tccacttatt aaaagtttca     300

gaaggcacaa caatactgtt gaactgcact ggccaggtta aaggaagaaa accagctgcc     360

ctgggtgaag cccaaccaac aaagagtttg gaagaaaata aatctttaaa ggaacagaaa     420

aaactgaatg acttgtgttt cctaaagaga ctattacaag agataaaaac ttgttggaat     480

aaaattttga tgggcactaa agaacacatc acgtgccctc cccccatgtc cgtggaacac     540

gcagacatct gggtcaagag ctacagcttg tactccaggg agcggtacat ttgtaactct     600

ggtttcaagc gtaaagccgg cacgtccagc ctgacggagt gcgtgttgaa caaggccacg     660

aatgtcgccc actggacaac ccccagtctc aaatgcatta ga                        702
```

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216
<211> LENGTH: 485
<212> TYPE: PRT
<213> ORGANISM: Artificial Sequence
<220> FEATURE:
<223> OTHER INFORMATION: Synthetic polypeptide

<400> SEQUENCE: 216

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His Ser Gly Thr Thr Asn Thr Val Ala
145                 150                 155                 160

Ala Tyr Asn Leu Thr Trp Lys Ser Thr Asn Phe Lys Thr Ile Leu Glu
                165                 170                 175

Trp Glu Pro Lys Pro Val Asn Gln Val Tyr Thr Val Gln Ile Ser Thr
            180                 185                 190

Lys Ser Gly Asp Trp Lys Ser Lys Cys Phe Tyr Thr Thr Asp Thr Glu
        195                 200                 205

Cys Asp Leu Thr Asp Glu Ile Val Lys Asp Val Lys Gln Thr Tyr Leu
    210                 215                 220

Ala Arg Val Phe Ser Tyr Pro Ala Gly Asn Val Glu Ser Thr Gly Ser
225                 230                 235                 240

Ala Gly Glu Pro Leu Tyr Glu Asn Ser Pro Glu Phe Thr Pro Tyr Leu
                245                 250                 255

Glu Thr Asn Leu Gly Gln Pro Thr Ile Gln Ser Phe Glu Gln Val Gly
            260                 265                 270

Thr Lys Val Asn Val Thr Val Glu Asp Glu Arg Thr Leu Val Arg Arg
        275                 280                 285

Asn Asn Thr Phe Leu Ser Leu Arg Asp Val Phe Gly Lys Asp Leu Ile
    290                 295                 300

Tyr Thr Leu Tyr Tyr Trp Lys Ser Ser Ser Ser Gly Lys Lys Thr Ala
305                 310                 315                 320
```

Lys Thr Asn Thr Asn Glu Phe Leu Ile Asp Val Asp Lys Gly Glu Asn
325 330 335

Tyr Cys Phe Ser Val Gln Ala Val Ile Pro Ser Arg Thr Val Asn Arg
340 345 350

Lys Ser Thr Asp Ser Pro Val Glu Cys Met Gly Gln Glu Lys Gly Glu
355 360 365

Phe Arg Glu Asn Trp Val Asn Val Ile Ser Asp Leu Lys Lys Ile Glu
370 375 380

Asp Leu Ile Gln Ser Met His Ile Asp Ala Thr Leu Tyr Thr Glu Ser
385 390 395 400

Asp Val His Pro Ser Cys Lys Val Thr Ala Met Lys Cys Phe Leu Leu
405 410 415

Glu Leu Gln Val Ile Ser Leu Glu Ser Gly Asp Ala Ser Ile His Asp
420 425 430

Thr Val Glu Asn Leu Ile Ile Leu Ala Asn Asn Ser Leu Ser Ser Asn
435 440 445

Gly Asn Val Thr Glu Ser Gly Cys Lys Glu Cys Glu Glu Leu Glu Glu
450 455 460

Lys Asn Ile Lys Glu Phe Leu Gln Ser Phe Val His Ile Val Gln Met
465 470 475 480

Phe Ile Asn Thr Ser
485

<210> SEQ ID NO 217
<211> LENGTH: 1455
<212> TYPE: DNA
<213> ORGANISM: Artificial Sequence
<220> FEATURE:
<223> OTHER INFORMATION: Synthetic polynucleotide

<400> SEQUENCE: 217
gattgcgaca tcgagggcaa ggacggcaag cagtacgaga gcgtgctgat ggtgtccatc 60
gaccagctgc tggacagcat gaaggagatc ggctccaact gcctcaacaa cgagttcaac 120
ttcttcaagc ggcacatctg cgacgccaac aaggagggca tgttcctgtt cagggccgcc 180
aggaaactgc ggcagttcct gaagatgaac tccaccggcg acttcgacct gcacctgctg 240
aaggtgtccg agggcaccac catcctgctg aactgcaccg gacaggtgaa gggccggaaa 300
cctgctgctc tgggagaggc ccaacccacc aagagcctgg aggagaacaa gtccctgaag 360
gagcagaaga agctgaacga cctgtgcttc ctgaagaggc tgctgcagga gatcaagacc 420
tgctggaaca agatcctgat gggcaccaag gagcatagcg gcacaaccaa cacagtcgct 480
gcctataacc tcacttggaa gagcaccaac ttcaaaacca tcctcgaatg ggaacccaaa 540
cccgttaacc aagtttacac cgtgcagatc agcaccaagt ccggcgactg gaagtccaaa 600
tgtttctata ccaccgacac cgagtgcgat ctcaccgatg agatcgtgaa agatgtgaaa 660
cagacctacc tcgcccgggt gtttagctac cccgccggca atgtggagag cactggttcc 720
gctggcgagc ctttatacga gaacagcccc gaatttaccc cttacctcga gaccaattta 780
ggacagccca ccatccaaag ctttgagcaa gttggcacaa aggtgaatgt gacagtggag 840
gacgagcgga ctttagtgcg gcggaacaac acctttctca gcctccggga tgtgttcggc 900
aaagatttaa tctacacact gtattactgg aagtcctctt cctccggcaa gaagacagct 960
aaaaccaaca caaacgagtt tttaatcgac gtggataaag gcgaaaacta ctgtttcagc 1020
gtgcaagctg tgatcccctc ccggaccgtg aataggaaaa gcaccgatag ccccgttgag 1080
tgcatgggcc aagaaaaggg cgagttccgg gagaactggg tgaacgtcat cagcgattta 1140
aagaagatcg aagatttaat tcagtccatg catatcgacg ccactttata cacagaatcc 1200
gacgtgcacc cctcttgtaa ggtgaccgcc atgaaatgtt ttttactgga gctgcaagtt 1260
atctctttag agagcggaga cgctagcatc cacgacaccg tggagaattt aatcatttta 1320
gccaataact ctttatccag caacggcaac gtgacagagt ccggctgcaa ggagtgcgaa 1380
gagctggagg agaagaacat caaggagttt ctgcaatcct ttgtgcacat tgtccagatg 1440
ttcatcaata cctcc 1455

<210> SEQ ID NO 218
<211> LENGTH: 503
<212> TYPE: PRT
<213> ORGANISM: Artificial Sequence
<220> FEATURE:
<223> OTHER INFORMATION: Synthetic polypeptide

<400> SEQUENCE: 218

Met Lys Trp Val Thr Phe Ile Ser Leu Leu Phe Leu Phe Ser Ser Ala
1 5 10 15

Tyr Ser Asp Cys Asp Ile Glu Gly Lys Asp Gly Lys Gln Tyr Glu Ser
20 25 30

Val Leu Met Val Ser Ile Asp Gln Leu Leu Asp Ser Met Lys Glu Ile
35 40 45

Gly Ser Asn Cys Leu Asn Asn Glu Phe Asn Phe Phe Lys Arg His Ile
50 55 60

Cys Asp Ala Asn Lys Glu Gly Met Phe Leu Phe Arg Ala Ala Arg Lys
65 70 75 80

Leu Arg Gln Phe Leu Lys Met Asn Ser Thr Gly Asp Phe Asp Leu His
85 90 95

Leu Leu Lys Val Ser Glu Gly Thr Thr Ile Leu Leu Asn Cys Thr Gly
100 105 110

Gln Val Lys Gly Arg Lys Pro Ala Ala Leu Gly Glu Ala Gln Pro Thr
115 120 125

Lys Ser Leu Glu Glu Asn Lys Ser Leu Lys Glu Gln Lys Lys Leu Asn
130 135 140

Asp Leu Cys Phe Leu Lys Arg Leu Leu Gln Glu Ile Lys Thr Cys Trp
145 150 155 160

Asn Lys Ile Leu Met Gly Thr Lys Glu His Ser Gly Thr Thr Asn Thr
165 170 175

Val Ala Ala Tyr Asn Leu Thr Trp Lys Ser Thr Asn Phe Lys Thr Ile
180 185 190

Leu Glu Trp Glu Pro Lys Pro Val Asn Gln Val Tyr Thr Val Gln Ile
195 200 205

Ser Thr Lys Ser Gly Asp Trp Lys Ser Lys Cys Phe Tyr Thr Thr Asp
210 215 220

Thr Glu Cys Asp Leu Thr Asp Glu Ile Val Lys Asp Val Lys Gln Thr
225 230 235 240

Tyr Leu Ala Arg Val Phe Ser Tyr Pro Ala Gly Asn Val Glu Ser Thr
245 250 255

Gly Ser Ala Gly Glu Pro Leu Tyr Glu Asn Ser Pro Glu Phe Thr Pro
260 265 270

Tyr Leu Glu Thr Asn Leu Gly Gln Pro Thr Ile Gln Ser Phe Glu Gln
275 280 285

Val Gly Thr Lys Val Asn Val Thr Val Glu Asp Glu Arg Thr Leu Val

```
    290                 295                 300

Arg Arg Asn Asn Thr Phe Leu Ser Leu Arg Asp Val Phe Gly Lys Asp
305                 310                 315                 320

Leu Ile Tyr Thr Leu Tyr Tyr Trp Lys Ser Ser Ser Ser Gly Lys Lys
                325                 330                 335

Thr Ala Lys Thr Asn Thr Asn Glu Phe Leu Ile Asp Val Asp Lys Gly
            340                 345                 350

Glu Asn Tyr Cys Phe Ser Val Gln Ala Val Ile Pro Ser Arg Thr Val
        355                 360                 365

Asn Arg Lys Ser Thr Asp Ser Pro Val Glu Cys Met Gly Gln Glu Lys
    370                 375                 380

Gly Glu Phe Arg Glu Asn Trp Val Asn Val Ile Ser Asp Leu Lys Lys
385                 390                 395                 400

Ile Glu Asp Leu Ile Gln Ser Met His Ile Asp Ala Thr Leu Tyr Thr
                405                 410                 415

Glu Ser Asp Val His Pro Ser Cys Lys Val Thr Ala Met Lys Cys Phe
            420                 425                 430

Leu Leu Glu Leu Gln Val Ile Ser Leu Glu Ser Gly Asp Ala Ser Ile
        435                 440                 445

His Asp Thr Val Glu Asn Leu Ile Ile Leu Ala Asn Asn Ser Leu Ser
    450                 455                 460

Ser Asn Gly Asn Val Thr Glu Ser Gly Cys Lys Glu Cys Glu Glu Leu
465                 470                 475                 480

Glu Glu Lys Asn Ile Lys Glu Phe Leu Gln Ser Phe Val His Ile Val
                485                 490                 495

Gln Met Phe Ile Asn Thr Ser
            500
```

<210> SEQ ID NO 219
<211> LENGTH: 1509
<212> TYPE: DNA
<213> ORGANISM: Artificial Sequence
<220> FEATURE:
<223> OTHER INFORMATION: Synthetic polynucleotide

<400> SEQUENCE: 219

```
atgaagtggg tgaccttcat cagcctgctg ttcctgttct ccagcgccta ctccgattgc     60

gacatcgagg gcaaggacgg caagcagtac gagagcgtgc tgatggtgtc catcgaccag    120

ctgctggaca gcatgaagga gatcggctcc aactgcctca acaacgagtt caacttcttc    180

aagcggcaca tctgcgacgc caacaaggag ggcatgttcc tgttcagggc cgccaggaaa    240

ctgcggcagt tcctgaagat gaactccacc ggcgacttcg acctgcacct gctgaaggtg    300

tccgagggca ccaccatcct gctgaactgc accggacagg tgaagggccg gaaacctgct    360

gctctgggag aggcccaacc caccaagagc ctggaggaga acaagtccct gaaggagcag    420

aagaagctga acgacctgtg cttcctgaag aggctgctgc aggagatcaa gacctgctgg    480

aacaagatcc tgatgggcac caaggagcat agcggcacaa ccaacacagt cgctgcctat    540

aacctcactt ggaagagcac caacttcaaa accatcctcg aatgggaacc caaacccgtt    600

aaccaagttt acaccgtgca gatcagcacc aagtccggcg actggaagtc caaatgtttc    660

tataccaccg acaccgagtg cgatctcacc gatgagatcg tgaaagatgt gaaacagacc    720

tacctcgccc gggtgtttag ctaccccgcc ggcaatgtgg agagcactgg ttccgctggc    780

gagcctttat acgagaacag ccccgaattt acccccttacc tcgagaccaa tttaggacag    840
```

```
cccaccatcc aaagctttga gcaagttggc acaaaggtga atgtgacagt ggaggacgag    900

cggactttag tgcggcggaa caacaccttt ctcagcctcc gggatgtgtt cggcaaagat    960

ttaatctaca cactgtatta ctggaagtcc tcttcctccg gcaagaagac agctaaaacc   1020

aacacaaacg agtttttaat cgacgtggat aaaggcgaaa actactgttt cagcgtgcaa   1080

gctgtgatcc cctcccggac cgtgaatagg aaaagcaccg atagccccgt tgagtgcatg   1140

ggccaagaaa agggcgagtt ccgggagaac tgggtgaacg tcatcagcga tttaaagaag   1200

atcgaagatt taattcagtc catgcatatc gacgccactt tatacacaga atccgacgtg   1260

cacccctctt gtaaggtgac cgccatgaaa tgtttttac tggagctgca agttatctct   1320

ttagagagcg gagacgctag catccacgac accgtggaga atttaatcat tttagccaat   1380

aactctttat ccagcaacgg caacgtgaca gagtccggct gcaaggagtg cgaagagctg   1440

gaggagaaga acatcaagga gtttctgcaa tcctttgtgc acattgtcca gatgttcatc   1500

aatacctcc                                                           1509
```

```
<210> SEQ ID NO 220
<211> LENGTH: 198
<212> TYPE: PRT
<213> ORGANISM: Artificial Sequence
<220> FEATURE:
<223> OTHER INFORMATION: Synthetic polypeptide

<400> SEQUENCE: 220

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ile Thr Cys Pro Pro Pro Met Ser Val Glu His
    130                 135                 140

Ala Asp Ile Trp Val Lys Ser Tyr Ser Leu Tyr Ser Arg Glu Arg Tyr
145                 150                 155                 160

Ile Cys Asn Ser Gly Phe Lys Arg Lys Ala Gly Thr Ser Ser Leu Thr
                165                 170                 175

Glu Cys Val Leu Asn Lys Ala Thr Asn Val Ala His Trp Thr Thr Pro
            180                 185                 190

Ser Leu Lys Cys Ile Arg
        195


<210> SEQ ID NO 221
<211> LENGTH: 594
<212> TYPE: DNA
<213> ORGANISM: Artificial Sequence
<220> FEATURE:
```

<223> OTHER INFORMATION: Synthetic polynucleotide

<400> SEQUENCE: 221
cagggccagg acaggcacat gatccggatg aggcagctca tcgacatcgt cgaccagctg 60
aagaactacg tgaacgacct ggtgcccgag tttctgcctg cccccgagga cgtggagacc 120
aactgcgagt ggtccgcctt ctcctgcttt cagaaggccc agctgaagtc cgccaacacc 180
ggcaacaacg agcggatcat caacgtgagc atcaagaagc tgaagcggaa gcctccctcc 240
acaaacgccg gcaggaggca gaagcacagg ctgacctgcc ccagctgtga ctcctacgag 300
aagaagcccc ccaaggagtt cctggagagg ttcaagtccc tgctgcagaa gatgatccat 360
cagcacctgt cctccaggac ccacggctcc gaggactcca ttacatgccc ccctcccatg 420
agcgtggagc acgccgacat ctgggtgaag agctatagcc tctacagccg ggagaggtat 480
atctgtaaca gcggcttcaa gaggaaggcc ggcaccagca gcctcaccga gtgcgtgctg 540
aataaggcta ccaacgtggc tcactggaca acaccctctt taaagtgcat ccgg 594

<210> SEQ ID NO 222
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 222

Met Lys Trp Val Thr Phe Ile Ser Leu Leu Phe Leu Phe Ser Ser Ala
1 5 10 15

Tyr Ser Gln Gly Gln Asp Arg His Met Ile Arg Met Arg Gln Leu Ile
20 25 30

Asp Ile Val Asp Gln Leu Lys Asn Tyr Val Asn Asp Leu Val Pro Glu
35 40 45

Phe Leu Pro Ala Pro Glu Asp Val Glu Thr Asn Cys Glu Trp Ser Ala
50 55 60

Phe Ser Cys Phe Gln Lys Ala Gln Leu Lys Ser Ala Asn Thr Gly Asn
65 70 75 80

Asn Glu Arg Ile Ile Asn Val Ser Ile Lys Lys Leu Lys Arg Lys Pro
85 90 95

Pro Ser Thr Asn Ala Gly Arg Arg Gln Lys His Arg Leu Thr Cys Pro
100 105 110

Ser Cys Asp Ser Tyr Glu Lys Lys Pro Pro Lys Glu Phe Leu Glu Arg
115 120 125

Phe Lys Ser Leu Leu Gln Lys Met Ile His Gln His Leu Ser Ser Arg
130 135 140

Thr His Gly Ser Glu Asp Ser Ile Thr Cys Pro Pro Pro Met Ser Val
145 150 155 160

Glu His Ala Asp Ile Trp Val Lys Ser Tyr Ser Leu Tyr Ser Arg Glu
165 170 175

Arg Tyr Ile Cys Asn Ser Gly Phe Lys Arg Lys Ala Gly Thr Ser Ser
180 185 190

Leu Thr Glu Cys Val Leu Asn Lys Ala Thr Asn Val Ala His Trp Thr
195 200 205

Thr Pro Ser Leu Lys Cys Ile Arg
210 215

<210> SEQ ID NO 223
<211> LENGTH: 648

<212> TYPE: DNA
<213> ORGANISM: Artificial Sequence
<220> FEATURE:
<223> OTHER INFORMATION: Synthetic polynucleotide

<400> SEQUENCE: 223

```
atgaagtggg tgaccttcat cagcctgctg ttcctgttct ccagcgccta ctcccagggc     60

caggacaggc acatgatccg gatgaggcag ctcatcgaca tcgtcgacca gctgaagaac    120

tacgtgaacg acctggtgcc cgagtttctg cctgcccccg aggacgtgga gaccaactgc    180

gagtggtccg ccttctcctg ctttcagaag gcccagctga agtccgccaa caccggcaac    240

aacgagcgga tcatcaacgt gagcatcaag aagctgaagc ggaagcctcc ctccacaaac    300

gccggcagga ggcagaagca caggctgacc tgccccagct gtgactccta cgagaagaag    360

ccccccaagg agttcctgga gaggttcaag tccctgctgc agaagatgat ccatcagcac    420

ctgtcctcca ggacccacgg ctccgaggac tccattacat gcccccctcc catgagcgtg    480

gagcacgccg acatctgggt gaagagctat agcctctaca gccgggagag gtatatctgt    540

aacagcggct tcaagaggaa ggccggcacc agcagcctca ccgagtgcgt gctgaataag    600

gctaccaacg tggctcactg gacaacaccc tctttaaagt gcatccgg                 648
```

<210> SEQ ID NO 224
<211> LENGTH: 136
<212> TYPE: PRT
<213> ORGANISM: Homo sapiens

<400> SEQUENCE: 224

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135
```

<210> SEQ ID NO 225
<211> LENGTH: 408
<212> TYPE: DNA
<213> ORGANISM: Homo sapiens

<400> SEQUENCE: 225

```
atcccccccc atgtgcaaaa gagcgtgaac aacgatatga tcgtgaccga caacaacggc     60

gccgtgaagt ttccccagct ctgcaagttc tgcgatgtca ggttcagcac ctgcgataat    120

cagaagtcct gcatgtccaa ctgcagcatc acctccatct gcgagaagcc ccaagaagtg    180

tgcgtggccg tgtggcggaa aaatgacgag aacatcaccc tggagaccgt gtgtcacgac    240
```

cccaagctcc cttatcacga cttcattctg gaggacgctg cctcccccaa atgcatcatg 300
aaggagaaga agaagcccgg agagaccttc tttatgtgtt cctgtagcag cgacgagtgt 360
aacgacaaca tcatcttcag cgaagagtac aacaccagca accctgat 408

<210> SEQ ID NO 226
<211> LENGTH: 408
<212> TYPE: DNA
<213> ORGANISM: Homo sapiens

<400> SEQUENCE: 226
attcctcccc acgtgcagaa gagcgtgaat aatgacatga tcgtgaccga taacaatggc 60
gccgtgaaat ttccccagct gtgcaaattc tgcgatgtga ggttttccac ctgcgacaac 120
cagaagtcct gtatgagcaa ctgctccatc acctccatct gtgagaagcc tcaggaggtg 180
tgcgtggctg tctggcggaa gaatgacgag aatatcaccc tggaaaccgt ctgccacgat 240
cccaagctgc cctaccacga tttcatcctg gaagacgccg ccagccctaa gtgcatcatg 300
aaagagaaaa agaagcctgg cgagaccttt ttcatgtgct cctgcagcag cgacgaatgc 360
aacgacaata tcatctttag cgaggaatac aataccagca accccgac 408

<210> SEQ ID NO 227
<211> LENGTH: 287
<212> TYPE: PRT
<213> ORGANISM: Artificial Sequence
<220> FEATURE:
<223> OTHER INFORMATION: Synthetic polypeptide

<400> SEQUENCE: 227

Ile Pro Pro His Val Gln Lys Ser Val Asn Asn Asp Met Ile Val Thr
1 5 10 15

Asp Asn Asn Gly Ala Val Lys Phe Pro Gln Leu Cys Lys Phe Cys Asp
20 25 30

Val Arg Phe Ser Thr Cys Asp Asn Gln Lys Ser Cys Met Ser Asn Cys
35 40 45

Ser Ile Thr Ser Ile Cys Glu Lys Pro Gln Glu Val Cys Val Ala Val
50 55 60

Trp Arg Lys Asn Asp Glu Asn Ile Thr Leu Glu Thr Val Cys His Asp
65 70 75 80

Pro Lys Leu Pro Tyr His Asp Phe Ile Leu Glu Asp Ala Ala Ser Pro
85 90 95

Lys Cys Ile Met Lys Glu Lys Lys Lys Pro Gly Glu Thr Phe Phe Met
100 105 110

Cys Ser Cys Ser Ser Asp Glu Cys Asn Asp Asn Ile Ile Phe Ser Glu
115 120 125

Glu Tyr Asn Thr Ser Asn Pro Asp Gly Gly Gly Gly Ser Gly Gly Gly
130 135 140

Gly Ser Gly Gly Gly Gly Ser Ile Pro Pro His Val Gln Lys Ser Val
145 150 155 160

Asn Asn Asp Met Ile Val Thr Asp Asn Asn Gly Ala Val Lys Phe Pro
165 170 175

Gln Leu Cys Lys Phe Cys Asp Val Arg Phe Ser Thr Cys Asp Asn Gln
180 185 190

Lys Ser Cys Met Ser Asn Cys Ser Ile Thr Ser Ile Cys Glu Lys Pro
195 200 205

Gln Glu Val Cys Val Ala Val Trp Arg Lys Asn Asp Glu Asn Ile Thr 210 215 220

Leu Glu Thr Val Cys His Asp Pro Lys Leu Pro Tyr His Asp Phe Ile
225 230 235 240

Leu Glu Asp Ala Ala Ser Pro Lys Cys Ile Met Lys Glu Lys Lys Lys
245 250 255

Pro Gly Glu Thr Phe Phe Met Cys Ser Cys Ser Ser Asp Glu Cys Asn
260 265 270

Asp Asn Ile Ile Phe Ser Glu Glu Tyr Asn Thr Ser Asn Pro Asp
275 280 285

<210> SEQ ID NO 228
<211> LENGTH: 861
<212> TYPE: DNA
<213> ORGANISM: Artificial Sequence
<220> FEATURE:
<223> OTHER INFORMATION: Synthetic polynucleotide

<400> SEQUENCE: 228
atcccccccc atgtgcaaaa gagcgtgaac aacgatatga tcgtgaccga caacaacggc 60
gccgtgaagt ttccccagct ctgcaagttc tgcgatgtca ggttcagcac ctgcgataat 120
cagaagtcct gcatgtccaa ctgcagcatc acctccatct gcgagaagcc ccaagaagtg 180
tgcgtggccg tgtggcggaa aaatgacgag aacatcaccc tggagaccgt gtgtcacgac 240
cccaagctcc cttatcacga cttcattctg gaggacgctg cctcccccaa atgcatcatg 300
aaggagaaga agaagcccgg agagaccttc tttatgtgtt cctgtagcag cgacgagtgt 360
aacgacaaca tcatcttcag cgaagagtac aacaccagca accctgatgg aggtggcgga 420
tccggaggtg gaggttctgg tggaggtggg agtattcctc cccacgtgca gaagagcgtg 480
aataatgaca tgatcgtgac cgataacaat ggcgccgtga aatttcccca gctgtgcaaa 540
ttctgcgatg tgaggttttc cacctgcgac aaccagaagt cctgtatgag caactgctcc 600
atcacctcca tctgtgagaa gcctcaggag gtgtgcgtgg ctgtctggcg gaagaatgac 660
gagaatatca ccctggaaac cgtctgccac gatcccaagc tgccctacca cgatttcatc 720
ctggaagacg ccgccagccc taagtgcatc atgaaagaga aaaagaagcc tggcgagacc 780
tttttcatgt gctcctgcag cagcgacgaa tgcaacgaca atatcatctt tagcgaggaa 840
tacaatacca gcaaccccga c 861

<210> SEQ ID NO 229
<211> LENGTH: 620
<212> TYPE: PRT
<213> ORGANISM: Artificial Sequence
<220> FEATURE:
<223> OTHER INFORMATION: Synthetic polypeptide

<400> SEQUENCE: 229

Ile Pro Pro His Val Gln Lys Ser Val Asn Asn Asp Met Ile Val Thr
1 5 10 15

Asp Asn Asn Gly Ala Val Lys Phe Pro Gln Leu Cys Lys Phe Cys Asp
20 25 30

Val Arg Phe Ser Thr Cys Asp Asn Gln Lys Ser Cys Met Ser Asn Cys
35 40 45

Ser Ile Thr Ser Ile Cys Glu Lys Pro Gln Glu Val Cys Val Ala Val
50 55 60

Trp Arg Lys Asn Asp Glu Asn Ile Thr Leu Glu Thr Val Cys His Asp
65 70 75 80

```
Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Gly Ser Gly Gly Gly
    130                 135                 140

Gly Ser Gly Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ser
        275                 280                 285

Gly Thr Thr Asn Thr Val Ala Ala Tyr Asn Leu Thr Trp Lys Ser Thr
    290                 295                 300

Asn Phe Lys Thr Ile Leu Glu Trp Glu Pro Lys Pro Val Asn Gln Val
305                 310                 315                 320

Tyr Thr Val Gln Ile Ser Thr Lys Ser Gly Asp Trp Lys Ser Lys Cys
                325                 330                 335

Phe Tyr Thr Thr Asp Thr Glu Cys Asp Leu Thr Asp Glu Ile Val Lys
            340                 345                 350

Asp Val Lys Gln Thr Tyr Leu Ala Arg Val Phe Ser Tyr Pro Ala Gly
        355                 360                 365

Asn Val Glu Ser Thr Gly Ser Ala Gly Glu Pro Leu Tyr Glu Asn Ser
    370                 375                 380

Pro Glu Phe Thr Pro Tyr Leu Glu Thr Asn Leu Gly Gln Pro Thr Ile
385                 390                 395                 400

Gln Ser Phe Glu Gln Val Gly Thr Lys Val Asn Val Thr Val Glu Asp
                405                 410                 415

Glu Arg Thr Leu Val Arg Arg Asn Asn Thr Phe Leu Ser Leu Arg Asp
            420                 425                 430

Val Phe Gly Lys Asp Leu Ile Tyr Thr Leu Tyr Tyr Trp Lys Ser Ser
        435                 440                 445

Ser Ser Gly Lys Lys Thr Ala Lys Thr Asn Thr Asn Glu Phe Leu Ile
    450                 455                 460

Asp Val Asp Lys Gly Glu Asn Tyr Cys Phe Ser Val Gln Ala Val Ile
465                 470                 475                 480

Pro Ser Arg Thr Val Asn Arg Lys Ser Thr Asp Ser Pro Val Glu Cys
                485                 490                 495

Met Gly Gln Glu Lys Gly Glu Phe Arg Glu Asn Trp Val Asn Val Ile
```

```
            500                 505                 510

Ser Asp Leu Lys Lys Ile Glu Asp Leu Ile Gln Ser Met His Ile Asp
        515                 520                 525

Ala Thr Leu Tyr Thr Glu Ser Asp Val His Pro Ser Cys Lys Val Thr
    530                 535                 540

Ala Met Lys Cys Phe Leu Leu Glu Leu Gln Val Ile Ser Leu Glu Ser
545                 550                 555                 560

Gly Asp Ala Ser Ile His Asp Thr Val Glu Asn Leu Ile Ile Leu Ala
                565                 570                 575

Asn Asn Ser Leu Ser Ser Asn Gly Asn Val Thr Glu Ser Gly Cys Lys
            580                 585                 590

Glu Cys Glu Glu Leu Glu Glu Lys Asn Ile Lys Glu Phe Leu Gln Ser
        595                 600                 605

Phe Val His Ile Val Gln Met Phe Ile Asn Thr Ser
    610                 615                 620


<210> SEQ ID NO 230
<211> LENGTH: 1860
<212> TYPE: DNA
<213> ORGANISM: Artificial Sequence
<220> FEATURE:
<223> OTHER INFORMATION: Synthetic polynucleotide

<400> SEQUENCE: 230

atcccccccc atgtgcaaaa gagcgtgaac aacgatatga tcgtgaccga caacaacggc     60

gccgtgaagt ttccccagct ctgcaagttc tgcgatgtca ggttcagcac ctgcgataat    120

cagaagtcct gcatgtccaa ctgcagcatc acctccatct gcgagaagcc ccaagaagtg    180

tgcgtggccg tgtggcggaa aaatgacgag aacatcaccc tggagaccgt gtgtcacgac    240

cccaagctcc cttatcacga cttcattctg gaggacgctg cctcccccaa atgcatcatg    300

aaggagaaga agaagcccgg agagaccttc tttatgtgtt cctgtagcag cgacgagtgt    360

aacgacaaca tcatcttcag cgaagagtac aacaccagca accctgatgg aggtggcgga    420

tccggaggtg gaggttctgg tggaggtggg agtattcctc cccacgtgca gaagagcgtg    480

aataatgaca tgatcgtgac cgataacaat ggcgccgtga aatttcccca gctgtgcaaa    540

ttctgcgatg tgaggttttc cacctgcgac aaccagaagt cctgtatgag caactgctcc    600

atcacctcca tctgtgagaa gcctcaggag gtgtgcgtgg ctgtctggcg gaagaatgac    660

gagaatatca ccctggaaac cgtctgccac gatcccaagc tgccctacca cgatttcatc    720

ctggaagacg ccgccagccc taagtgcatc atgaaagaga aaaagaagcc tggcgagacc    780

tttttcatgt gctcctgcag cagcgacgaa tgcaacgaca atatcatctt tagcgaggaa    840

tacaatacca gcaaccccga cagcggcaca accaacacag tcgctgccta taacctcact    900

tggaagagca ccaacttcaa aaccatcctc gaatgggaac ccaaacccgt taaccaagtt    960

tacaccgtgc agatcagcac caagtccggc gactggaagt ccaaatgttt ctataccacc   1020

gacaccgagt gcgatctcac cgatgagatc gtgaaagatg tgaaacagac ctacctcgcc   1080

cgggtgttta gctaccccgc cggcaatgtg gagagcactg gttccgctgg cgagccttta   1140

tacgagaaca gccccgaatt taccccttac ctcgagacca atttaggaca gcccaccatc   1200

caaagctttg agcaagttgg cacaaaggtg aatgtgacag tggaggacga gcggacttta   1260

gtgcggcgga acaacacctt tctcagcctc cgggatgtgt tcggcaaaga tttaatctac   1320

acactgtatt actggaagtc ctcttcctcc ggcaagaaga cagctaaaac caacacaaac   1380
```

```
gagtttttaa tcgacgtgga taaaggcgaa aactactgtt tcagcgtgca agctgtgatc   1440

ccctcccgga ccgtgaatag gaaaagcacc gatagccccg ttgagtgcat gggccaagaa   1500

aagggcgagt tccgggagaa ctgggtgaac gtcatcagcg atttaaagaa gatcgaagat   1560

ttaattcagt ccatgcatat cgacgccact ttatacacag aatccgacgt gcacccctct   1620

tgtaaggtga ccgccatgaa atgtttttta ctggagctgc aagttatctc tttagagagc   1680

ggagacgcta gcatccacga caccgtggag aatttaatca ttttagccaa taactcttta   1740

tccagcaacg gcaacgtgac agagtccggc tgcaaggagt gcgaagagct ggaggagaag   1800

aacatcaagg agtttctgca atcctttgtg cacattgtcc agatgttcat caatacctcc   1860
```

```
<210> SEQ ID NO 231
<211> LENGTH: 638
<212> TYPE: PRT
<213> ORGANISM: Artificial Sequence
<220> FEATURE:
<223> OTHER INFORMATION: Synthetic polypeptide

<400> SEQUENCE: 231

Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Gly Ser Gly
145                 150                 155                 160

Gly Gly Gly Ser Gly Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285
```

```
Cys Asn Asp Asn Ile Ile Phe Ser Glu Glu Tyr Asn Thr Ser Asn Pro
    290                 295                 300

Asp Ser Gly Thr Thr Asn Thr Val Ala Ala Tyr Asn Leu Thr Trp Lys
305                 310                 315                 320

Ser Thr Asn Phe Lys Thr Ile Leu Glu Trp Glu Pro Lys Pro Val Asn
                325                 330                 335

Gln Val Tyr Thr Val Gln Ile Ser Thr Lys Ser Gly Asp Trp Lys Ser
            340                 345                 350

Lys Cys Phe Tyr Thr Thr Asp Thr Glu Cys Asp Leu Thr Asp Glu Ile
        355                 360                 365

Val Lys Asp Val Lys Gln Thr Tyr Leu Ala Arg Val Phe Ser Tyr Pro
    370                 375                 380

Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
                405                 410                 415

Thr Ile Gln Ser Phe Glu Gln Val Gly Thr Lys Val Asn Val Thr Val
            420                 425                 430

Glu Asp Glu Arg Thr Leu Val Arg Arg Asn Asn Thr Phe Leu Ser Leu
        435                 440                 445

Arg Asp Val Phe Gly Lys Asp Leu Ile Tyr Thr Leu Tyr Tyr Trp Lys
    450                 455                 460

Ser Ser Ser Ser Gly Lys Lys Thr Ala Lys Thr Asn Thr Asn Glu Phe
465                 470                 475                 480

Leu Ile Asp Val Asp Lys Gly Glu Asn Tyr Cys Phe Ser Val Gln Ala
                485                 490                 495

Val Ile Pro Ser Arg Thr Val Asn Arg Lys Ser Thr Asp Ser Pro Val
            500                 505                 510

Glu Cys Met Gly Gln Glu Lys Gly Glu Phe Arg Glu Asn Trp Val Asn
        515                 520                 525

Val Ile Ser Asp Leu Lys Lys Ile Glu Asp Leu Ile Gln Ser Met His
    530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
                565                 570                 575

Glu Ser Gly Asp Ala Ser Ile His Asp Thr Val Glu Asn Leu Ile Ile
            580                 585                 590

Leu Ala Asn Asn Ser Leu Ser Ser Asn Gly Asn Val Thr Glu Ser Gly
        595                 600                 605

Cys Lys Glu Cys Glu Glu Leu Glu Glu Lys Asn Ile Lys Glu Phe Leu
    610                 615                 620

Gln Ser Phe Val His Ile Val Gln Met Phe Ile Asn Thr Ser
625                 630                 635
```

<210> SEQ ID NO 232
<211> LENGTH: 1914
<212> TYPE: DNA
<213> ORGANISM: Artificial Sequence
<220> FEATURE:
<223> OTHER INFORMATION: Synthetic polynucleotide

<400> SEQUENCE: 232

```
atgaagtggg tgaccttcat cagcctgctg ttcctgttct ccagcgccta ctccatcccc     60
```

```
ccccatgtgc aaaagagcgt gaacaacgat atgatcgtga ccgacaacaa cggcgccgtg    120

aagtttcccc agctctgcaa gttctgcgat gtcaggttca gcacctgcga taatcagaag    180

tcctgcatgt ccaactgcag catcacctcc atctgcgaga agccccaaga agtgtgcgtg    240

gccgtgtggc ggaaaaatga cgagaacatc accctggaga ccgtgtgtca cgaccccaag    300

ctcccttatc acgacttcat tctggaggac gctgcctccc ccaaatgcat catgaaggag    360

aagaagaagc ccggagagac cttctttatg tgttcctgta gcagcgacga gtgtaacgac    420

aacatcatct tcagcgaaga gtacaacacc agcaaccctg atggaggtgg cggatccgga    480

ggtggaggtt ctggtggagg tgggagtatt cctccccacg tgcagaagag cgtgaataat    540

gacatgatcg tgaccgataa caatggcgcc gtgaaatttc cccagctgtg caaattctgc    600

gatgtgaggt tttccacctg cgacaaccag aagtcctgta tgagcaactg ctccatcacc    660

tccatctgtg agaagcctca ggaggtgtgc gtggctgtct ggcggaagaa tgacgagaat    720

atcaccctgg aaaccgtctg ccacgatccc aagctgccct accacgattt catcctggaa    780

gacgccgcca gccctaagtg catcatgaaa gagaaaaaga agcctggcga gacctttttc    840

atgtgctcct gcagcagcga cgaatgcaac gacaatatca tctttagcga ggaatacaat    900

accagcaacc ccgacagcgg cacaaccaac acagtcgctg cctataacct cacttggaag    960

agcaccaact tcaaaaccat cctcgaatgg gaacccaaac ccgttaacca agtttacacc   1020

gtgcagatca gcaccaagtc cggcgactgg aagtccaaat gtttctatac caccgacacc   1080

gagtgcgatc tcaccgatga gatcgtgaaa gatgtgaaac agacctacct cgcccgggtg   1140

tttagctacc ccgccggcaa tgtggagagc actggttccg ctggcgagcc tttatacgag   1200

aacagccccg aatttacccc ttacctcgag accaatttag gacagcccac catccaaagc   1260

tttgagcaag ttggcacaaa ggtgaatgtg acagtggagg acgagcggac tttagtgcgg   1320

cggaacaaca cctttctcag cctccgggat gtgttcggca aagatttaat ctacacactg   1380

tattactgga agtcctcttc ctccggcaag aagacagcta aaaccaacac aaacgagttt   1440

ttaatcgacg tggataaagg cgaaaactac tgtttcagcg tgcaagctgt gatcccctcc   1500

cggaccgtga ataggaaaag caccgatagc cccgttgagt gcatgggcca agaaaagggc   1560

gagttccggg agaactgggt gaacgtcatc agcgatttaa agaagatcga agatttaatt   1620

cagtccatgc atatcgacgc cactttatac acagaatccg acgtgcaccc ctcttgtaag   1680

gtgaccgcca tgaaatgttt tttactggag ctgcaagtta tctctttaga gagcggagac   1740

gctagcatcc acgacaccgt ggagaattta atcattttag ccaataactc tttatccagc   1800

aacggcaacg tgacagagtc cggctgcaag gagtgcgaag agctggagga gaagaacatc   1860

aaggagtttc tgcaatcctt tgtgcacatt gtccagatgt tcatcaatac ctcc         1914
```

<210> SEQ ID NO 233
<211> LENGTH: 352
<212> TYPE: PRT
<213> ORGANISM: Artificial Sequence
<220> FEATURE:
<223> OTHER INFORMATION: Synthetic polypeptide

<400> SEQUENCE: 233

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
```

```
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Gly Ser Gly Gly Gly
    130                 135                 140

Gly Ser Gly Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp Ile
        275                 280                 285

Thr Cys Pro Pro Pro Met Ser Val Glu His Ala Asp Ile Trp Val Lys
    290                 295                 300

Ser Tyr Ser Leu Tyr Ser Arg Glu Arg Tyr Ile Cys Asn Ser Gly Phe
305                 310                 315                 320

Lys Arg Lys Ala Gly Thr Ser Ser Leu Thr Glu Cys Val Leu Asn Lys
                325                 330                 335

Ala Thr Asn Val Ala His Trp Thr Thr Pro Ser Leu Lys Cys Ile Arg
            340                 345                 350
```

<210> SEQ ID NO 234
<211> LENGTH: 1056
<212> TYPE: DNA
<213> ORGANISM: Artificial Sequence
<220> FEATURE:
<223> OTHER INFORMATION: Synthetic polynucleotide

<400> SEQUENCE: 234

```
atcccccccc atgtgcaaaa gagcgtgaac aacgatatga tcgtgaccga caacaacggc     60

gccgtgaagt ttccccagct ctgcaagttc tgcgatgtca ggttcagcac ctgcgataat    120

cagaagtcct gcatgtccaa ctgcagcatc acctccatct gcgagaagcc ccaagaagtg    180

tgcgtggccg tgtggcggaa aaatgacgag aacatcaccc tggagaccgt gtgtcacgac    240

cccaagctcc cttatcacga cttcattctg gaggacgctg cctcccccaa atgcatcatg    300
```

```
aaggagaaga agaagcccgg agagaccttc tttatgtgtt cctgtagcag cgacgagtgt    360

aacgacaaca tcatcttcag cgaagagtac aacaccagca accctgatgg aggtggcgga    420

tccggaggtg gaggttctgg tggaggtggg agtattcctc cccacgtgca gaagagcgtg    480

aataatgaca tgatcgtgac cgataacaat ggcgccgtga aatttcccca gctgtgcaaa    540

ttctgcgatg tgaggttttc cacctgcgac aaccagaagt cctgtatgag caactgctcc    600

atcacctcca tctgtgagaa gcctcaggag gtgtgcgtgg ctgtctggcg gaagaatgac    660

gagaatatca ccctggaaac cgtctgccac gatcccaagc tgccctacca cgatttcatc    720

ctggaagacg ccgccagccc taagtgcatc atgaaagaga aaaagaagcc tggcgagacc    780

tttttcatgt gctcctgcag cagcgacgaa tgcaacgaca atatcatctt tagcgaggaa    840

tacaatacca gcaaccccga cattacatgc ccccctccca tgagcgtgga gcacgccgac    900

atctgggtga agagctatag cctctacagc cgggagaggt atatctgtaa cagcggcttc    960

aagaggaagg ccggcaccag cagcctcacc gagtgcgtgc tgaataaggc taccaacgtg   1020

gctcactgga caacaccctc tttaaagtgc atccgg                             1056
```

<210> SEQ ID NO 235
<211> LENGTH: 370
<212> TYPE: PRT
<213> ORGANISM: Artificial Sequence
<220> FEATURE:
<223> OTHER INFORMATION: Synthetic polypeptide

<400> SEQUENCE: 235

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Gly Ser Gly
145                 150                 155                 160

Gly Gly Gly Ser Gly Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
```

```
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ile Thr Cys Pro Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
        355                 360                 365

Ile Arg
    370
```

<210> SEQ ID NO 236
<211> LENGTH: 1110
<212> TYPE: DNA
<213> ORGANISM: Artificial Sequence
<220> FEATURE:
<223> OTHER INFORMATION: Synthetic polynucleotide

<400> SEQUENCE: 236

```
atgaagtggg tgaccttcat cagcctgctg ttcctgttct ccagcgccta ctccatcccc      60

ccccatgtgc aaaagagcgt gaacaacgat atgatcgtga ccgacaacaa cggcgccgtg     120

aagtttcccc agctctgcaa gttctgcgat gtcaggttca gcacctgcga taatcagaag     180

tcctgcatgt ccaactgcag catcacctcc atctgcgaga agccccaaga agtgtgcgtg     240

gccgtgtggc ggaaaaatga cgagaacatc accctggaga ccgtgtgtca cgaccccaag     300

ctcccttatc acgacttcat tctggaggac gctgcctccc ccaaatgcat catgaaggag     360

aagaagaagc ccggagagac cttctttatg tgttcctgta gcagcgacga gtgtaacgac     420

aacatcatct tcagcgaaga gtacaacacc agcaaccctg atggaggtgg cggatccgga     480

ggtggaggtt ctggtggagg tgggagtatt cctccccacg tgcagaagag cgtgaataat     540

gacatgatcg tgaccgataa caatggcgcc gtgaaatttc cccagctgtg caaattctgc     600

gatgtgaggt tttccacctg cgacaaccag aagtcctgta tgagcaactg ctccatcacc     660

tccatctgtg agaagcctca ggaggtgtgc gtggctgtct ggcggaagaa tgacgagaat     720

atcaccctgg aaaccgtctg ccacgatccc aagctgccct accacgattt catcctggaa     780

gacgccgcca gccctaagtg catcatgaaa gagaaaaaga agcctggcga gaccttttttc     840

atgtgctcct gcagcagcga cgaatgcaac gacaatatca tctttagcga ggaatacaat     900

accagcaacc ccgacattac atgcccccct cccatgagcg tggagcacgc cgacatctgg     960

gtgaagagct atagcctcta cagccgggag aggtatatct gtaacagcgg cttcaagagg    1020

aaggccggca ccagcagcct caccgagtgc gtgctgaata aggctaccaa cgtggctcac    1080

tggacaacac cctctttaaa gtgcatccgg                                     1110
```

<210> SEQ ID NO 237

<211> LENGTH: 241
<212> TYPE: PRT
<213> ORGANISM: Artificial Sequence
<220> FEATURE:
<223> OTHER INFORMATION: Synthetic polypeptide

<400> SEQUENCE: 237

Gln Ile Val Leu Thr Gln Ser Pro Ala Ile Met Ser Ala Ser Pro Gly
1 5 10 15

Glu Lys Val Thr Met Thr Cys Ser Ala Ser Ser Ser Val Ser Tyr Met
20 25 30

Asn Trp Tyr Gln Gln Lys Ser Gly Thr Ser Pro Lys Arg Trp Ile Tyr
35 40 45

Asp Thr Ser Lys Leu Ala Ser Gly Val Pro Ala His Phe Arg Gly Ser
50 55 60

Gly Ser Gly Thr Ser Tyr Ser Leu Thr Ile Ser Gly Met Glu Ala Glu
65 70 75 80

Asp Ala Ala Thr Tyr Tyr Cys Gln Gln Trp Ser Ser Asn Pro Phe Thr
85 90 95

Phe Gly Ser Gly Thr Lys Leu Glu Ile Asn Arg Gly Gly Gly Gly Ser
100 105 110

Gly Gly Gly Gly Ser Gly Gly Gly Gly Ser Gln Val Gln Leu Gln Gln
115 120 125

Ser Gly Ala Glu Leu Ala Arg Pro Gly Ala Ser Val Lys Met Ser Cys
130 135 140

Lys Ala Ser Gly Tyr Thr Phe Thr Arg Tyr Thr Met His Trp Val Lys
145 150 155 160

Gln Arg Pro Gly Gln Gly Leu Glu Trp Ile Gly Tyr Ile Asn Pro Ser
165 170 175

Arg Gly Tyr Thr Asn Tyr Asn Gln Lys Phe Lys Asp Lys Ala Thr Leu
180 185 190

Thr Thr Asp Lys Ser Ser Ser Thr Ala Tyr Met Gln Leu Ser Ser Leu
195 200 205

Thr Ser Glu Asp Ser Ala Val Tyr Tyr Cys Ala Arg Tyr Tyr Asp Asp
210 215 220

His Tyr Cys Leu Asp Tyr Trp Gly Gln Gly Thr Thr Leu Thr Val Ser
225 230 235 240

Ser

<210> SEQ ID NO 238
<211> LENGTH: 723
<212> TYPE: DNA
<213> ORGANISM: Artificial Sequence
<220> FEATURE:
<223> OTHER INFORMATION: Synthetic polynucleotide

<400> SEQUENCE: 238
cagatcgtgc tgacccaaag ccccgccatc atgagcgcta gccccggtga gaaggtgacc 60
atgacatgct ccgcttccag ctccgtgtcc tacatgaact ggtatcagca gaaaagcgga 120
accagcccca aaaggtggat ctacgacacc agcaagctgg cctccggagt gcccgctcat 180
ttccggggct ctggatccgg caccagctac tctttaacca tttccggcat ggaagctgaa 240
gacgctgcca cctactattg ccagcaatgg agcagcaacc ccttcacatt cggatctggc 300
accaagctcg aaatcaatcg tggaggaggt ggcagcggcg gcggtggatc cggcggagga 360
ggaagccaag ttcaactcca gcagagcggc gctgaactgg cccggcccgg cgcctccgtc 420

```
aagatgagct gcaaggcttc cggctataca tttactcgtt acacaatgca ttgggtcaag    480

cagaggcccg gtcaaggttt agagtggatc ggatatatca acccttcccg gggctacacc    540

aactataacc aaaagttcaa ggataaagcc actttaacca ctgacaagag ctcctccacc    600

gcctacatgc agctgtcctc tttaaccagc gaggactccg ctgtttacta ctgcgctagg    660

tattacgacg accactactg tttagactat tggggacaag gtaccacttt aaccgtcagc    720

agc                                                                  723
```

<210> SEQ ID NO 239
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 239

```
Val Gln Leu Gln Gln Ser Gly Pro Glu Leu Val Lys Pro Gly Ala Ser
1               5                   10                  15

Val Lys Met Ser Cys Lys Ala Ser Gly Tyr Thr Phe Thr Ser Tyr Val
            20                  25                  30

Ile Gln Trp Val Lys Gln Lys Pro Gly Gln Gly Leu Glu Trp Ile Gly
        35                  40                  45

Ser Ile Asn Pro Tyr Asn Asp Tyr Thr Lys Tyr Asn Glu Lys Phe Lys
    50                  55                  60

Gly Lys Ala Thr Leu Thr Ser Asp Lys Ser Ser Ile Thr Ala Tyr Met
65                  70                  75                  80

Glu Phe Ser Ser Leu Thr Ser Glu Asp Ser Ala Leu Tyr Tyr Cys Ala
                85                  90                  95

Arg Trp Gly Asp Gly Asn Tyr Trp Gly Arg Gly Thr Thr Leu Thr Val
            100                 105                 110

Ser Ser Gly Gly Gly Gly Ser Gly Gly Gly Gly Ser Gly Gly Gly Gly
        115                 120                 125

Ser Asp Ile Glu Met Thr Gln Ser Pro Ala Ile Met Ser Ala Ser Leu
    130                 135                 140

Gly Glu Arg Val Thr Met Thr Cys Thr Ala Ser Ser Ser Val Ser Ser
145                 150                 155                 160

Ser Tyr Phe His Trp Tyr Gln Gln Lys Pro Gly Ser Ser Pro Lys Leu
                165                 170                 175

Cys Ile Tyr Ser Thr Ser Asn Leu Ala Ser Gly Val Pro Pro Arg Phe
            180                 185                 190

Ser Gly Ser Gly Ser Thr Ser Tyr Ser Leu Thr Ile Ser Ser Met Glu
        195                 200                 205

Ala Glu Asp Ala Ala Thr Tyr Phe Cys His Gln Tyr His Arg Ser Pro
    210                 215                 220

Thr Phe Gly Gly Gly Thr Lys Leu Glu Thr Lys Arg
225                 230                 235
```

<210> SEQ ID NO 240
<211> LENGTH: 708
<212> TYPE: DNA
<213> ORGANISM: Artificial Sequence
<220> FEATURE:
<223> OTHER INFORMATION: Synthetic polynucleotide

<400> SEQUENCE: 240

```
gtccagctgc agcagagcgg acccgaactc gtgaaacccg gtgcttccgt gaaaatgtct     60
```

```
tgtaaggcca gcggatacac cttcacctcc tatgtgatcc agtgggtcaa acagaagccc    120

ggacaaggtc tcgagtggat cggcagcatc aacccttaca acgactatac caaatacaac    180

gagaagttta agggaaaggc tactttaacc tccgacaaaa gctccatcac agcctacatg    240

gagttcagct ctttaacatc cgaggacagc gctctgtact attgcgcccg gtggggcgac    300

ggcaattact ggggacgggg cacaacactg accgtgagca gcggaggcgg aggctccggc    360

ggaggcggat ctggcggtgg cggctccgac atcgagatga cccagtcccc cgctatcatg    420

tccgcctctt taggcgagcg ggtcacaatg acttgtacag cctcctccag cgtctcctcc    480

tcctacttcc attggtacca acagaaaccc ggaagctccc ctaaactgtg catctacagc    540

accagcaatc tcgccagcgg cgtgccccct aggttttccg gaagcggaag caccagctac    600

tctttaacca tctcctccat ggaggctgag gatgccgcca cctacttttg tcaccagtac    660

caccggtccc ccaccttcgg aggcggcacc aaactggaga caaagagg                 708
```

<210> SEQ ID NO 241
<211> LENGTH: 696
<212> TYPE: PRT
<213> ORGANISM: Artificial Sequence
<220> FEATURE:
<223> OTHER INFORMATION: Synthetic polypeptide

<400> SEQUENCE: 241

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Gly Gly Gly Gly Ser
            100                 105                 110

Gly Gly Gly Gly Ser Gly Gly Gly Gly Ser Gln Val Gln Leu Gln Gln
        115                 120                 125

Ser Gly Ala Glu Leu Ala Arg Pro Gly Ala Ser Val Lys Met Ser Cys
    130                 135                 140

Lys Ala Ser Gly Tyr Thr Phe Thr Arg Tyr Thr Met His Trp Val Lys
145                 150                 155                 160

Gln Arg Pro Gly Gln Gly Leu Glu Trp Ile Gly Tyr Ile Asn Pro Ser
                165                 170                 175

Arg Gly Tyr Thr Asn Tyr Asn Gln Lys Phe Lys Asp Lys Ala Thr Leu
            180                 185                 190

Thr Thr Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Tyr Tyr Asp Asp
    210                 215                 220

His Tyr Cys Leu Asp Tyr Trp Gly Gln Gly Thr Thr Leu Thr Val Ser
225                 230                 235                 240

Ser Ser Gly Thr Thr Asn Thr Val Ala Ala Tyr Asn Leu Thr Trp Lys
                245                 250                 255
```

Ser Thr Asn Phe Lys Thr Ile Leu Glu Trp Glu Pro Lys Pro Val Asn
260 265 270

Gln Val Tyr Thr Val Gln Ile Ser Thr Lys Ser Gly Asp Trp Lys Ser
275 280 285

Lys Cys Phe Tyr Thr Thr Asp Thr Glu Cys Asp Leu Thr Asp Glu Ile
290 295 300

Val Lys Asp Val Lys Gln Thr Tyr Leu Ala Arg Val Phe Ser Tyr Pro
305 310 315 320

Ala Gly Asn Val Glu Ser Thr Gly Ser Ala Gly Glu Pro Leu Tyr Glu
325 330 335

Asn Ser Pro Glu Phe Thr Pro Tyr Leu Glu Thr Asn Leu Gly Gln Pro
340 345 350

Thr Ile Gln Ser Phe Glu Gln Val Gly Thr Lys Val Asn Val Thr Val
355 360 365

Glu Asp Glu Arg Thr Leu Val Arg Arg Asn Asn Thr Phe Leu Ser Leu
370 375 380

Arg Asp Val Phe Gly Lys Asp Leu Ile Tyr Thr Leu Tyr Tyr Trp Lys
385 390 395 400

Ser Ser Ser Ser Gly Lys Lys Thr Ala Lys Thr Asn Thr Asn Glu Phe
405 410 415

Leu Ile Asp Val Asp Lys Gly Glu Asn Tyr Cys Phe Ser Val Gln Ala
420 425 430

Val Ile Pro Ser Arg Thr Val Asn Arg Lys Ser Thr Asp Ser Pro Val
435 440 445

Glu Cys Met Gly Gln Glu Lys Gly Glu Phe Arg Glu Val Gln Leu Gln
450 455 460

Gln Ser Gly Pro Glu Leu Val Lys Pro Gly Ala Ser Val Lys Met Ser
465 470 475 480

Cys Lys Ala Ser Gly Tyr Thr Phe Thr Ser Tyr Val Ile Gln Trp Val
485 490 495

Lys Gln Lys Pro Gly Gln Gly Leu Glu Trp Ile Gly Ser Ile Asn Pro
500 505 510

Tyr Asn Asp Tyr Thr Lys Tyr Asn Glu Lys Phe Lys Gly Lys Ala Thr
515 520 525

Leu Thr Ser Asp Lys Ser Ser Ile Thr Ala Tyr Met Glu Phe Ser Ser
530 535 540

Leu Thr Ser Glu Asp Ser Ala Leu Tyr Tyr Cys Ala Arg Trp Gly Asp
545 550 555 560

Gly Asn Tyr Trp Gly Arg Gly Thr Thr Leu Thr Val Ser Ser Gly Gly
565 570 575

Gly Gly Ser Gly Gly Gly Gly Ser Gly Gly Gly Gly Ser Asp Ile Glu
580 585 590

Met Thr Gln Ser Pro Ala Ile Met Ser Ala Ser Leu Gly Glu Arg Val
595 600 605

Thr Met Thr Cys Thr Ala Ser Ser Ser Val Ser Ser Ser Tyr Phe His
610 615 620

Trp Tyr Gln Gln Lys Pro Gly Ser Ser Pro Lys Leu Cys Ile Tyr Ser
625 630 635 640

Thr Ser Asn Leu Ala Ser Gly Val Pro Pro Arg Phe Ser Gly Ser Gly
645 650 655

Ser Thr Ser Tyr Ser Leu Thr Ile Ser Ser Met Glu Ala Glu Asp Ala
660 665 670

```
Ala Thr Tyr Phe Cys His Gln Tyr His Arg Ser Pro Thr Phe Gly Gly
        675                 680                 685

Gly Thr Lys Leu Glu Thr Lys Arg
    690                 695


<210> SEQ ID NO 242
<211> LENGTH: 2088
<212> TYPE: DNA
<213> ORGANISM: Artificial Sequence
<220> FEATURE:
<223> OTHER INFORMATION: Synthetic polynucleotide

<400> SEQUENCE: 242

cagatcgtgc tgacccaaag ccccgccatc atgagcgcta gccccggtga gaaggtgacc     60

atgacatgct ccgcttccag ctccgtgtcc tacatgaact ggtatcagca gaaaagcgga    120

accagcccca aaaggtggat ctacgacacc agcaagctgg cctccggagt gcccgctcat    180

ttccggggct ctggatccgg caccagctac tctttaacca tttccggcat ggaagctgaa    240

gacgctgcca cctactattg ccagcaatgg agcagcaacc ccttcacatt cggatctggc    300

accaagctcg aaatcaatcg tggaggaggt ggcagcggcg gcggtggatc cggcggagga    360

ggaagccaag ttcaactcca gcagagcggc gctgaactgg cccggcccgg cgcctccgtc    420

aagatgagct gcaaggcttc cggctataca tttactcgtt acacaatgca ttgggtcaag    480

cagaggcccg gtcaaggttt agagtggatc ggatatatca acccttcccg gggctacacc    540

aactataacc aaaagttcaa ggataaagcc actttaacca ctgacaagag ctcctccacc    600

gcctacatgc agctgtcctc tttaaccagc gaggactccg ctgtttacta ctgcgctagg    660

tattacgacg accactactg tttagactat tggggacaag gtaccacttt aaccgtcagc    720

agctccggca ccaccaatac cgtggccgct tataacctca catggaagag caccaacttc    780

aagacaattc tggaatggga acccaagccc gtcaatcaag tttacaccgt gcagatctcc    840

accaaatccg gagactggaa gagcaagtgc ttctacacaa cagacaccga gtgtgattta    900

accgacgaaa tcgtcaagga cgtcaagcaa acctatctgg ctcgggtctt ttcctacccc    960

gctggcaatg tcgagtccac cggctccgct ggcgagcctc tctacgagaa ttcccccgaa   1020

ttcacccctt atttagagac caatttaggc cagcctacca tccagagctt cgagcaagtt   1080

ggcaccaagg tgaacgtcac cgtcgaggat gaaaggactt tagtgcggcg gaataacaca   1140

tttttatccc tccgggatgt gttcggcaaa gacctcatct acacactgta ctattggaag   1200

tccagctcct ccggcaaaaa gaccgctaag accaacacca acgagttttt aattgacgtg   1260

gacaaaggcg agaactactg cttcagcgtg caagccgtga tcccttctcg taccgtcaac   1320

cggaagagca cagattcccc cgttgagtgc atgggccaag aaaagggcga gttccgggag   1380

gtccagctgc agcagagcgg acccgaactc gtgaaacccg gtgcttccgt gaaaatgtct   1440

tgtaaggcca gcggatacac cttcacctcc tatgtgatcc agtgggtcaa acagaagccc   1500

ggacaaggtc tcgagtggat cggcagcatc aacccttaca acgactatac caaatacaac   1560

gagaagttta agggaaaggc tactttaacc tccgacaaaa gctccatcac agcctacatg   1620

gagttcagct ctttaacatc cgaggacagc gctctgtact attgcgcccg gtggggcgac   1680

ggcaattact ggggacgggg cacaacactg accgtgagca gcggaggcgg aggctccggc   1740

ggaggcggat ctggcggtgg cggctccgac atcgagatga cccagtcccc cgctatcatg   1800

tccgcctctt taggcgagcg ggtcacaatg acttgtacag cctcctccag cgtctcctcc   1860

tcctacttcc attggtacca acagaaaccc ggaagctccc ctaaactgtg catctacagc   1920
```

accagcaatc tcgccagcgg cgtgcccccct aggttttccg gaagcggaag caccagctac 1980
tctttaacca tctcctccat ggaggctgag gatgccgcca cctacttttg tcaccagtac 2040
caccggtccc ccaccttcgg aggcggcacc aaactggaga caaagagg 2088

<210> SEQ ID NO 243
<211> LENGTH: 714
<212> TYPE: PRT
<213> ORGANISM: Artificial Sequence
<220> FEATURE:
<223> OTHER INFORMATION: Synthetic polypeptide

<400> SEQUENCE: 243

Met Lys Trp Val Thr Phe Ile Ser Leu Leu Phe Leu Phe Ser Ser Ala
1 5 10 15

Tyr Ser Gln Ile Val Leu Thr Gln Ser Pro Ala Ile Met Ser Ala Ser
20 25 30

Pro Gly Glu Lys Val Thr Met Thr Cys Ser Ala Ser Ser Ser Val Ser
35 40 45

Tyr Met Asn Trp Tyr Gln Gln Lys Ser Gly Thr Ser Pro Lys Arg Trp
50 55 60

Ile Tyr Asp Thr Ser Lys Leu Ala Ser Gly Val Pro Ala His Phe Arg
65 70 75 80

Gly Ser Gly Ser Gly Thr Ser Tyr Ser Leu Thr Ile Ser Gly Met Glu
85 90 95

Ala Glu Asp Ala Ala Thr Tyr Tyr Cys Gln Gln Trp Ser Ser Asn Pro
100 105 110

Phe Thr Phe Gly Ser Gly Thr Lys Leu Glu Ile Asn Arg Gly Gly Gly
115 120 125

Gly Ser Gly Gly Gly Gly Ser Gly Gly Gly Gly Ser Gln Val Gln Leu
130 135 140

Gln Gln Ser Gly Ala Glu Leu Ala Arg Pro Gly Ala Ser Val Lys Met
145 150 155 160

Ser Cys Lys Ala Ser Gly Tyr Thr Phe Thr Arg Tyr Thr Met His Trp
165 170 175

Val Lys Gln Arg Pro Gly Gln Gly Leu Glu Trp Ile Gly Tyr Ile Asn
180 185 190

Pro Ser Arg Gly Tyr Thr Asn Tyr Asn Gln Lys Phe Lys Asp Lys Ala
195 200 205

Thr Leu Thr Thr Asp Lys Ser Ser Ser Thr Ala Tyr Met Gln Leu Ser
210 215 220

Ser Leu Thr Ser Glu Asp Ser Ala Val Tyr Tyr Cys Ala Arg Tyr Tyr
225 230 235 240

Asp Asp His Tyr Cys Leu Asp Tyr Trp Gly Gln Gly Thr Thr Leu Thr
245 250 255

Val Ser Ser Ser Gly Thr Thr Asn Thr Val Ala Ala Tyr Asn Leu Thr
260 265 270

Trp Lys Ser Thr Asn Phe Lys Thr Ile Leu Glu Trp Glu Pro Lys Pro
275 280 285

Val Asn Gln Val Tyr Thr Val Gln Ile Ser Thr Lys Ser Gly Asp Trp
290 295 300

Lys Ser Lys Cys Phe Tyr Thr Thr Asp Thr Glu Cys Asp Leu Thr Asp
305 310 315 320

Glu Ile Val Lys Asp Val Lys Gln Thr Tyr Leu Ala Arg Val Phe Ser
325 330 335

Tyr Pro Ala Gly Asn Val Glu Ser Thr Gly Ser Ala Gly Glu Pro Leu
340 345 350

Tyr Glu Asn Ser Pro Glu Phe Thr Pro Tyr Leu Glu Thr Asn Leu Gly
355 360 365

Gln Pro Thr Ile Gln Ser Phe Glu Gln Val Gly Thr Lys Val Asn Val
370 375 380

Thr Val Glu Asp Glu Arg Thr Leu Val Arg Arg Asn Asn Thr Phe Leu
385 390 395 400

Ser Leu Arg Asp Val Phe Gly Lys Asp Leu Ile Tyr Thr Leu Tyr Tyr
405 410 415

Trp Lys Ser Ser Ser Ser Gly Lys Lys Thr Ala Lys Thr Asn Thr Asn
420 425 430

Glu Phe Leu Ile Asp Val Asp Lys Gly Glu Asn Tyr Cys Phe Ser Val
435 440 445

Gln Ala Val Ile Pro Ser Arg Thr Val Asn Arg Lys Ser Thr Asp Ser
450 455 460

Pro Val Glu Cys Met Gly Gln Glu Lys Gly Glu Phe Arg Glu Val Gln
465 470 475 480

Leu Gln Gln Ser Gly Pro Glu Leu Val Lys Pro Gly Ala Ser Val Lys
485 490 495

Met Ser Cys Lys Ala Ser Gly Tyr Thr Phe Thr Ser Tyr Val Ile Gln
500 505 510

Trp Val Lys Gln Lys Pro Gly Gln Gly Leu Glu Trp Ile Gly Ser Ile
515 520 525

Asn Pro Tyr Asn Asp Tyr Thr Lys Tyr Asn Glu Lys Phe Lys Gly Lys
530 535 540

Ala Thr Leu Thr Ser Asp Lys Ser Ser Ile Thr Ala Tyr Met Glu Phe
545 550 555 560

Ser Ser Leu Thr Ser Glu Asp Ser Ala Leu Tyr Tyr Cys Ala Arg Trp
565 570 575

Gly Asp Gly Asn Tyr Trp Gly Arg Gly Thr Thr Leu Thr Val Ser Ser
580 585 590

Gly Gly Gly Gly Ser Gly Gly Gly Gly Ser Gly Gly Gly Gly Ser Asp
595 600 605

Ile Glu Met Thr Gln Ser Pro Ala Ile Met Ser Ala Ser Leu Gly Glu
610 615 620

Arg Val Thr Met Thr Cys Thr Ala Ser Ser Ser Val Ser Ser Ser Tyr
625 630 635 640

Phe His Trp Tyr Gln Gln Lys Pro Gly Ser Ser Pro Lys Leu Cys Ile
645 650 655

Tyr Ser Thr Ser Asn Leu Ala Ser Gly Val Pro Pro Arg Phe Ser Gly
660 665 670

Ser Gly Ser Thr Ser Tyr Ser Leu Thr Ile Ser Ser Met Glu Ala Glu
675 680 685

Asp Ala Ala Thr Tyr Phe Cys His Gln Tyr His Arg Ser Pro Thr Phe
690 695 700

Gly Gly Gly Thr Lys Leu Glu Thr Lys Arg
705 710

<210> SEQ ID NO 244
<211> LENGTH: 2142
<212> TYPE: DNA
<213> ORGANISM: Artificial Sequence
<220> FEATURE:

<223> OTHER INFORMATION: Synthetic polynucleotide

<400> SEQUENCE: 244
atgaagtggg tgaccttcat cagcttatta tttttattca gctccgccta ttcccagatc 60
gtgctgaccc aaagccccgc catcatgagc gctagccccg gtgagaaggt gaccatgaca 120
tgctccgctt ccagctccgt gtcctacatg aactggtatc agcagaaaag cggaaccagc 180
cccaaaaggt ggatctacga caccagcaag ctggcctccg gagtgcccgc tcatttccgg 240
ggctctggat ccggcaccag ctactcttta accatttccg gcatggaagc tgaagacgct 300
gccacctact attgccagca atggagcagc aaccccttca cattcggatc tggcaccaag 360
ctcgaaatca atcgtggagg aggtggcagc ggcggcggtg gatccggcgg aggaggaagc 420
caagttcaac tccagcagag cggcgctgaa ctggcccggc ccggcgcctc cgtcaagatg 480
agctgcaagg cttccggcta tacatttact cgttacacaa tgcattgggt caagcagagg 540
cccggtcaag gtttagagtg gatcggatat atcaaccctt cccggggcta caccaactat 600
aaccaaaagt tcaaggataa agccacttta accactgaca agagctcctc caccgcctac 660
atgcagctgt cctctttaac cagcgaggac tccgctgttt actactgcgc taggtattac 720
gacgaccact actgtttaga ctattgggga caaggtacca ctttaaccgt cagcagctcc 780
ggcaccacca ataccgtggc cgcttataac ctcacatgga agagcaccaa cttcaagaca 840
attctggaat gggaacccaa gcccgtcaat caagtttaca ccgtgcagat ctccaccaaa 900
tccggagact ggaagagcaa gtgcttctac acaacagaca ccgagtgtga tttaaccgac 960
gaaatcgtca aggacgtcaa gcaaacctat ctggctcggg tcttttccta ccccgctggc 1020
aatgtcgagt ccaccggctc cgctggcgag cctctctacg agaattcccc cgaattcacc 1080
ccttatttag agaccaattt aggccagcct accatccaga gcttcgagca agttggcacc 1140
aaggtgaacg tcaccgtcga ggatgaaagg actttagtgc ggcggaataa cacattttta 1200
tccctccggg atgtgttcgg caaagacctc atctacacac tgtactattg gaagtccagc 1260
tcctccggca aaaagaccgc taagaccaac accaacgagt ttttaattga cgtggacaaa 1320
ggcgagaact actgcttcag cgtgcaagcc gtgatccctt ctcgtaccgt caaccggaag 1380
agcacagatt cccccgttga gtgcatgggc caagaaaagg gcgagttccg ggaggtccag 1440
ctgcagcaga gcggacccga actcgtgaaa cccggtgctt ccgtgaaaat gtcttgtaag 1500
gccagcggat acaccttcac ctcctatgtg atccagtggg tcaaacagaa gcccggacaa 1560
ggtctcgagt ggatcggcag catcaaccct tacaacgact ataccaaata caacgagaag 1620
tttaagggaa aggctacttt aacctccgac aaaagctcca tcacagccta catggagttc 1680
agctctttaa catccgagga cagcgctctg tactattgcg cccggtgggg cgacggcaat 1740
tactggggac ggggcacaac actgaccgtg agcagcggag gcggaggctc cggcggaggc 1800
ggatctggcg gtggcggctc cgacatcgag atgacccagt cccccgctat catgtccgcc 1860
tctttaggcg agcgggtcac aatgacttgt acagcctcct ccagcgtctc ctcctcctac 1920
ttccattggt accaacagaa acccggaagc tcccctaaac tgtgcatcta cagcaccagc 1980
aatctcgcca gcggcgtgcc ccctaggttt tccggaagcg gaagcaccag ctactcttta 2040
accatctcct ccatggaggc tgaggatgcc gccacctact tttgtcacca gtaccaccgg 2100
tcccccacct tcggaggcgg caccaaactg gagacaaaga gg 2142

<210> SEQ ID NO 245

<400> SEQUENCE: 245

000

<210> SEQ ID NO 246
<211> LENGTH: 399
<212> TYPE: DNA
<213> ORGANISM: Homo sapiens

<400> SEQUENCE: 246
gcacctactt caagttctac aaagaaaaca cagctacaac tggagcattt actgctggat 60
ttacagatga ttttgaatgg aattaataat tacaagaatc ccaaactcac caggatgctc 120
acatttaagt tttacatgcc caagaaggcc acagaactga aacatcttca gtgtctagaa 180
gaagaactca aacctctgga ggaagtgcta aatttagctc aaagcaaaaa ctttcactta 240
agacccaggg acttaatcag caatatcaac gtaatagttc tggaactaaa gggatctgaa 300
acaacattca tgtgtgaata tgctgatgag acagcaacca ttgtagaatt tctgaacaga 360
tggattacct tttgtcaaag catcatctca acactaact 399

<210> SEQ ID NO 247
<211> LENGTH: 399
<212> TYPE: DNA
<213> ORGANISM: Homo sapiens

<400> SEQUENCE: 247
gcccccacct cctcctccac caagaagacc cagctgcagc tggagcattt actgctggat 60
ttacagatga ttttaaacgg catcaacaac tacaagaacc ccaagctgac tcgtatgctg 120
accttcaagt tctacatgcc caagaaggcc accgagctga agcatttaca gtgtttagag 180
gaggagctga agcccctcga ggaggtgctg aatttagccc agtccaagaa tttccattta 240
aggccccggg atttaatcag caacatcaac gtgatcgttt tagagctgaa gggctccgag 300
accaccttca tgtgcgagta cgccgacgag accgccacca tcgtggagtt tttaaatcgt 360
tggatcacct tctgccagtc catcatctcc actttaacc 399

<210> SEQ ID NO 248
<211> LENGTH: 485
<212> TYPE: PRT
<213> ORGANISM: Artificial Sequence
<220> FEATURE:
<223> OTHER INFORMATION: Synthetic polypeptide

<400> SEQUENCE: 248

Ala Pro Thr Ser Ser Ser Thr Lys Lys Thr Gln Leu Gln Leu Glu His
1 5 10 15

Leu Leu Leu Asp Leu Gln Met Ile Leu Asn Gly Ile Asn Asn Tyr Lys
20 25 30

Asn Pro Lys Leu Thr Arg Met Leu Thr Phe Lys Phe Tyr Met Pro Lys
35 40 45

Lys Ala Thr Glu Leu Lys His Leu Gln Cys Leu Glu Glu Glu Leu Lys
50 55 60

Pro Leu Glu Glu Val Leu Asn Leu Ala Gln Ser Lys Asn Phe His Leu
65 70 75 80

Arg Pro Arg Asp Leu Ile Ser Asn Ile Asn Val Ile Val Leu Glu Leu
85 90 95

Lys Gly Ser Glu Thr Thr Phe Met Cys Glu Tyr Ala Asp Glu Thr Ala
100 105 110

```
Thr Ile Val Glu Phe Leu Asn Arg Trp Ile Thr Phe Cys Gln Ser Ile
        115                 120                 125

Ile Ser Thr Leu Thr Ser Gly Thr Thr Asn Thr Val Ala Ala Tyr Asn
    130                 135                 140

Leu Thr Trp Lys Ser Thr Asn Phe Lys Thr Ile Leu Glu Trp Glu Pro
145                 150                 155                 160

Lys Pro Val Asn Gln Val Tyr Thr Val Gln Ile Ser Thr Lys Ser Gly
                165                 170                 175

Asp Trp Lys Ser Lys Cys Phe Tyr Thr Thr Asp Thr Glu Cys Asp Leu
            180                 185                 190

Thr Asp Glu Ile Val Lys Asp Val Lys Gln Thr Tyr Leu Ala Arg Val
        195                 200                 205

Phe Ser Tyr Pro Ala Gly Asn Val Glu Ser Thr Gly Ser Ala Gly Glu
    210                 215                 220

Pro Leu Tyr Glu Asn Ser Pro Glu Phe Thr Pro Tyr Leu Glu Thr Asn
225                 230                 235                 240

Leu Gly Gln Pro Thr Ile Gln Ser Phe Glu Gln Val Gly Thr Lys Val
                245                 250                 255

Asn Val Thr Val Glu Asp Glu Arg Thr Leu Val Arg Arg Asn Asn Thr
            260                 265                 270

Phe Leu Ser Leu Arg Asp Val Phe Gly Lys Asp Leu Ile Tyr Thr Leu
        275                 280                 285

Tyr Tyr Trp Lys Ser Ser Ser Ser Gly Lys Lys Thr Ala Lys Thr Asn
    290                 295                 300

Thr Asn Glu Phe Leu Ile Asp Val Asp Lys Gly Glu Asn Tyr Cys Phe
305                 310                 315                 320

Ser Val Gln Ala Val Ile Pro Ser Arg Thr Val Asn Arg Lys Ser Thr
                325                 330                 335

Asp Ser Pro Val Glu Cys Met Gly Gln Glu Lys Gly Glu Phe Arg Glu
            340                 345                 350

Ala Pro Thr Ser Ser Ser Thr Lys Lys Thr Gln Leu Gln Leu Glu His
        355                 360                 365

Leu Leu Leu Asp Leu Gln Met Ile Leu Asn Gly Ile Asn Asn Tyr Lys
    370                 375                 380

Asn Pro Lys Leu Thr Arg Met Leu Thr Phe Lys Phe Tyr Met Pro Lys
385                 390                 395                 400

Lys Ala Thr Glu Leu Lys His Leu Gln Cys Leu Glu Glu Glu Leu Lys
                405                 410                 415

Pro Leu Glu Glu Val Leu Asn Leu Ala Gln Ser Lys Asn Phe His Leu
            420                 425                 430

Arg Pro Arg Asp Leu Ile Ser Asn Ile Asn Val Ile Val Leu Glu Leu
        435                 440                 445

Lys Gly Ser Glu Thr Thr Phe Met Cys Glu Tyr Ala Asp Glu Thr Ala
    450                 455                 460

Thr Ile Val Glu Phe Leu Asn Arg Trp Ile Thr Phe Cys Gln Ser Ile
465                 470                 475                 480

Ile Ser Thr Leu Thr
                485
```

<210> SEQ ID NO 249
<211> LENGTH: 1455
<212> TYPE: DNA
<213> ORGANISM: Artificial Sequence
<220> FEATURE:
<223> OTHER INFORMATION: Synthetic polynucleotide

<400> SEQUENCE: 249
gcccccacct cctcctccac caagaagacc cagctgcagc tggagcattt actgctggat 60
ttacagatga ttttaaacgg catcaacaac tacaagaacc ccaagctgac tcgtatgctg 120
accttcaagt tctacatgcc caagaaggcc accgagctga agcatttaca gtgtttagag 180
gaggagctga agcccctcga ggaggtgctg aatttagccc agtccaagaa tttccattta 240
aggccccggg atttaatcag caacatcaac gtgatcgttt tagagctgaa gggctccgag 300
accaccttca tgtgcgagta cgccgacgag accgccacca tcgtggagtt tttaaatcgt 360
tggatcacct tctgccagtc catcatctcc actttaacca gcggcacaac caacacagtc 420
gctgcctata acctcacttg gaagagcacc aacttcaaaa ccatcctcga atgggaaccc 480
aaacccgtta accaagttta caccgtgcag atcagcacca agtccggcga ctggaagtcc 540
aaatgtttct ataccaccga caccgagtgc gatctcaccg atgagatcgt gaaagatgtg 600
aaacagacct acctcgcccg ggtgtttagc taccccgccg gcaatgtgga gagcactggt 660
tccgctggcg agcctttata cgagaacagc cccgaattta ccccttacct cgagaccaat 720
ttaggacagc ccaccatcca aagctttgag caagttggca caaaggtgaa tgtgacagtg 780
gaggacgagc ggactttagt gcggcggaac aacacctttc tcagcctccg ggatgtgttc 840
ggcaaagatt taatctacac actgtattac tggaagtcct cttcctccgg caagaagaca 900
gctaaaacca acacaaacga gtttttaatc gacgtggata aaggcgaaaa ctactgtttc 960
agcgtgcaag ctgtgatccc ctcccggacc gtgaatagga aaagcaccga tagccccgtt 1020
gagtgcatgg gccaagaaaa gggcgagttc cgggaggcac ctacttcaag ttctacaaag 1080
aaaacacagc tacaactgga gcatttactg ctggatttac agatgatttt gaatggaatt 1140
aataattaca agaatcccaa actcaccagg atgctcacat ttaagtttta catgcccaag 1200
aaggccacag aactgaaaca tcttcagtgt ctagaagaag aactcaaacc tctggaggaa 1260
gtgctaaatt tagctcaaag caaaaacttt cacttaagac ccagggactt aatcagcaat 1320
atcaacgtaa tagttctgga actaaaggga tctgaaacaa cattcatgtg tgaatatgct 1380
gatgagacag caaccattgt agaatttctg aacagatgga ttaccttttg tcaaagcatc 1440
atctcaacac taact 1455

<210> SEQ ID NO 250
<211> LENGTH: 503
<212> TYPE: PRT
<213> ORGANISM: Artificial Sequence
<220> FEATURE:
<223> OTHER INFORMATION: Synthetic polypeptide

<400> SEQUENCE: 250

Met Lys Trp Val Thr Phe Ile Ser Leu Leu Phe Leu Phe Ser Ser Ala
1 5 10 15

Tyr Ser Ala Pro Thr Ser Ser Ser Thr Lys Lys Thr Gln Leu Gln Leu
20 25 30

Glu His Leu Leu Leu Asp Leu Gln Met Ile Leu Asn Gly Ile Asn Asn
35 40 45

Tyr Lys Asn Pro Lys Leu Thr Arg Met Leu Thr Phe Lys Phe Tyr Met
50 55 60

Pro Lys Lys Ala Thr Glu Leu Lys His Leu Gln Cys Leu Glu Glu Glu
65 70 75 80

Leu Lys Pro Leu Glu Glu Val Leu Asn Leu Ala Gln Ser Lys Asn Phe

```
                85                  90                  95

His Leu Arg Pro Arg Asp Leu Ile Ser Asn Ile Asn Val Ile Val Leu
            100                 105                 110

Glu Leu Lys Gly Ser Glu Thr Thr Phe Met Cys Glu Tyr Ala Asp Glu
        115                 120                 125

Thr Ala Thr Ile Val Glu Phe Leu Asn Arg Trp Ile Thr Phe Cys Gln
    130                 135                 140

Ser Ile Ile Ser Thr Leu Thr Ser Gly Thr Thr Asn Thr Val Ala Ala
145                 150                 155                 160

Tyr Asn Leu Thr Trp Lys Ser Thr Asn Phe Lys Thr Ile Leu Glu Trp
                165                 170                 175

Glu Pro Lys Pro Val Asn Gln Val Tyr Thr Val Gln Ile Ser Thr Lys
            180                 185                 190

Ser Gly Asp Trp Lys Ser Lys Cys Phe Tyr Thr Thr Asp Thr Glu Cys
        195                 200                 205

Asp Leu Thr Asp Glu Ile Val Lys Asp Val Lys Gln Thr Tyr Leu Ala
    210                 215                 220

Arg Val Phe Ser Tyr Pro Ala Gly Asn Val Glu Ser Thr Gly Ser Ala
225                 230                 235                 240

Gly Glu Pro Leu Tyr Glu Asn Ser Pro Glu Phe Thr Pro Tyr Leu Glu
                245                 250                 255

Thr Asn Leu Gly Gln Pro Thr Ile Gln Ser Phe Glu Gln Val Gly Thr
            260                 265                 270

Lys Val Asn Val Thr Val Glu Asp Glu Arg Thr Leu Val Arg Arg Asn
        275                 280                 285

Asn Thr Phe Leu Ser Leu Arg Asp Val Phe Gly Lys Asp Leu Ile Tyr
    290                 295                 300

Thr Leu Tyr Tyr Trp Lys Ser Ser Ser Ser Gly Lys Lys Thr Ala Lys
305                 310                 315                 320

Thr Asn Thr Asn Glu Phe Leu Ile Asp Val Asp Lys Gly Glu Asn Tyr
                325                 330                 335

Cys Phe Ser Val Gln Ala Val Ile Pro Ser Arg Thr Val Asn Arg Lys
            340                 345                 350

Ser Thr Asp Ser Pro Val Glu Cys Met Gly Gln Glu Lys Gly Glu Phe
        355                 360                 365

Arg Glu Ala Pro Thr Ser Ser Ser Thr Lys Lys Thr Gln Leu Gln Leu
    370                 375                 380

Glu His Leu Leu Leu Asp Leu Gln Met Ile Leu Asn Gly Ile Asn Asn
385                 390                 395                 400

Tyr Lys Asn Pro Lys Leu Thr Arg Met Leu Thr Phe Lys Phe Tyr Met
                405                 410                 415

Pro Lys Lys Ala Thr Glu Leu Lys His Leu Gln Cys Leu Glu Glu Glu
            420                 425                 430

Leu Lys Pro Leu Glu Glu Val Leu Asn Leu Ala Gln Ser Lys Asn Phe
        435                 440                 445

His Leu Arg Pro Arg Asp Leu Ile Ser Asn Ile Asn Val Ile Val Leu
    450                 455                 460

Glu Leu Lys Gly Ser Glu Thr Thr Phe Met Cys Glu Tyr Ala Asp Glu
465                 470                 475                 480

Thr Ala Thr Ile Val Glu Phe Leu Asn Arg Trp Ile Thr Phe Cys Gln
                485                 490                 495

Ser Ile Ile Ser Thr Leu Thr
            500
```

<210> SEQ ID NO 251
<211> LENGTH: 1509
<212> TYPE: DNA
<213> ORGANISM: Artificial Sequence
<220> FEATURE:
<223> OTHER INFORMATION: Synthetic polynucleotide

<400> SEQUENCE: 251
atgaagtggg tgaccttcat cagcctgctg ttcctgttct ccagcgccta ctccgccccc 60
acctcctcct ccaccaagaa gacccagctg cagctggagc atttactgct ggatttacag 120
atgattttaa acggcatcaa caactacaag aaccccaagc tgactcgtat gctgaccttc 180
aagttctaca tgcccaagaa ggccaccgag ctgaagcatt tacagtgttt agaggaggag 240
ctgaagcccc tcgaggaggt gctgaattta gcccagtcca agaatttcca tttaaggccc 300
cgggatttaa tcagcaacat caacgtgatc gttttagagc tgaagggctc cgagaccacc 360
ttcatgtgcg agtacgccga cgagaccgcc accatcgtgg agtttttaaa tcgttggatc 420
accttctgcc agtccatcat ctccacttta accagcggca caaccaacac agtcgctgcc 480
tataacctca cttggaagag caccaacttc aaaaccatcc tcgaatggga acccaaaccc 540
gttaaccaag tttacaccgt gcagatcagc accaagtccg gcgactggaa gtccaaatgt 600
ttctatacca ccgacaccga gtgcgatctc accgatgaga tcgtgaaaga tgtgaaacag 660
acctacctcg cccgggtgtt tagctacccc gccggcaatg tggagagcac tggttccgct 720
ggcgagcctt tatacgagaa cagccccgaa tttacccctt acctcgagac caatttagga 780
cagcccacca tccaaagctt tgagcaagtt ggcacaaagg tgaatgtgac agtggaggac 840
gagcggactt tagtgcggcg gaacaacacc tttctcagcc tccgggatgt gttcggcaaa 900
gatttaatct acacactgta ttactggaag tcctcttcct ccggcaagaa gacagctaaa 960
accaacacaa acgagttttt aatcgacgtg gataaaggcg aaaactactg tttcagcgtg 1020
caagctgtga tcccctcccg gaccgtgaat aggaaaagca ccgatagccc cgttgagtgc 1080
atgggccaag aaaagggcga gttccgggag gcacctactt caagttctac aaagaaaaca 1140
cagctacaac tggagcattt actgctggat ttacagatga ttttgaatgg aattaataat 1200
tacaagaatc ccaaactcac caggatgctc acatttaagt tttacatgcc caagaaggcc 1260
acagaactga aacatcttca gtgtctagaa gaagaactca aacctctgga ggaagtgcta 1320
aatttagctc aaagcaaaaa ctttcactta agacccaggg acttaatcag caatatcaac 1380
gtaatagttc tggaactaaa gggatctgaa acaacattca tgtgtgaata tgctgatgag 1440
acagcaacca ttgtagaatt tctgaacaga tggattacct tttgtcaaag catcatctca 1500
acactaact 1509

<210> SEQ ID NO 252
<211> LENGTH: 1548
<212> TYPE: DNA
<213> ORGANISM: Artificial Sequence
<220> FEATURE:
<223> OTHER INFORMATION: Synthetic polynucleotide

<400> SEQUENCE: 252
atggacagac ttacttcttc attcctgctc ctgattgtcc ctgcgtacgt cttgtccgac 60
atccagatga cccagtctcc atcctccctg tctgcatctg taggagacag agtcaccatc 120
acttgccggg cgagtcagga cgtgaactcc aacgtggcct ggtatcagca gaaaccaggg 180

```
aaagccccta agctcctgat cttcggctcc ggcggcctgt acagtggggt cccatcaagg    240

ttcagcggca gtggatctgg gacagatttc actctcacta tcagcagcct gcagcctgaa    300

gattttgcaa cttactattg tcagcagtac tcctcctacc ccctgacgtt cggccaaggg    360

accaaggtgg aaaccaaagg tggaggtggc agcggaggag gtgggtccgg cggtggagga    420

agcgaggtgc agctggtgga gtctggggga ggcttggtcc agcctggggg gtccctgaga    480

ctctcctgtg cagcctctgg attcaccatc aacgactcct acatccactg ggtccgccag    540

gctccaggga aggggctgga gtgggtggcc tggatctggc cctacggcgg cttcacctac    600

tatgcagact ccgtgaaggg ccgattcacc atctccgccg acacctccaa gaacacggcc    660

tatctgcaaa tgaacagcct gagagctgag gacacggctg tgtattactg tgccaggttc    720

ctgggctcct cctccatcat ggactactgg ggccaaggaa ccctggtcac cgtctcctca    780

gccgagcaga agctgattag cgaggaggat ctggctttaa gcaactccat catgtacttc    840

tcccacttcg tgcccgtttt tttacccgct aagcccacca caacccccgc tcccagaccc    900

cctacccccg ctcctaccat cgcctcccag cctttatctt taagacccga agcctctcgt    960

cccgctgccg gcggcgccgt gcacacaagg ggtttagaca agcctttttg ggttttagtg   1020

gtggtgggcg gcgtgctggc ttgttactct ttactggtga ccgtggcctt catcatcttc   1080

tgggttcgtt ccaagaggtc tcgtctgctg cactccgact atatgaacat gacccctagg   1140

aggcccggcc ctaccagaaa acactatcag ccctatgccc ctcctcgtga ctttgccgct   1200

tatcgttctc gtgtgaagtt ctccagatcc gccgatgccc ccgcttacca gcaaggtcaa   1260

aaccagctct ataacgagct gaatttaggt cgtagagagg agtacgacgt gctggataaa   1320

agaaggggca gagaccccga aatgggaggc aaaccccaga gaaggaagaa cccccaagaa   1380

ggactgtaca acgaactgca gaaggataag atggccgagg cctactccga gattggcatg   1440

aaaggcgaga ggaggagggg caagggccat gatggtttat accaaggttt atccacagct   1500

acaaaggaca cctacgacgc tttacacatg caagctttac ctcctaga                1548
```

<210> SEQ ID NO 253
<211> LENGTH: 516
<212> TYPE: PRT
<213> ORGANISM: Artificial Sequence
<220> FEATURE:
<223> OTHER INFORMATION: Synthetic polypeptide

<400> SEQUENCE: 253

```
Met Asp Arg Leu Thr Ser Ser Phe Leu Leu Leu Ile Val Pro Ala Tyr
1               5                   10                  15

Val Leu Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
        35                  40                  45

Asn Ser Asn Val Ala Trp Tyr Gln Gln Lys Pro Gly Lys Ala Pro Lys
    50                  55                  60

Leu Leu Ile Phe Gly Ser Gly Gly Leu Tyr Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Ser Ser
            100                 105                 110

Tyr Pro Leu Thr Phe Gly Gln Gly Thr Lys Val Glu Thr Lys Gly Gly
        115                 120                 125
```

```
Gly Gly Ser Gly Gly Gly Gly Ser Gly Gly Gly Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Phe Thr Ile Asn Asp Ser Tyr Ile His
                165                 170                 175

Trp Val Arg Gln Ala Pro Gly Lys Gly Leu Glu Trp Val Ala Trp Ile
            180                 185                 190

Trp Pro Tyr Gly Gly Phe Thr Tyr Tyr Ala Asp Ser Val Lys Gly Arg
        195                 200                 205

Phe Thr Ile Ser Ala Asp Thr Ser Lys Asn Thr Ala Tyr Leu Gln Met
    210                 215                 220

Asn Ser Leu Arg Ala Glu Asp Thr Ala Val Tyr Tyr Cys Ala Arg Phe
225                 230                 235                 240

Leu Gly Ser Ser Ser Ile Met Asp Tyr Trp Gly Gln Gly Thr Leu Val
                245                 250                 255

Thr Val Ser Ser Ala Glu Gln Lys Leu Ile Ser Glu Glu Asp Leu Ala
            260                 265                 270

Leu Ser Asn Ser Ile Met Tyr Phe Ser His Phe Val Pro Val Phe Leu
        275                 280                 285

Pro Ala Lys Pro Thr Thr Thr Pro Ala Pro Arg Pro Pro Thr Pro Ala
    290                 295                 300

Pro Thr Ile Ala Ser Gln Pro Leu Ser Leu Arg Pro Glu Ala Ser Arg
305                 310                 315                 320

Pro Ala Ala Gly Gly Ala Val His Thr Arg Gly Leu Asp Lys Pro Phe
                325                 330                 335

Trp Val Leu Val Val Val Gly Gly Val Leu Ala Cys Tyr Ser Leu Leu
            340                 345                 350

Val Thr Val Ala Phe Ile Ile Phe Trp Val Arg Ser Lys Arg Ser Arg
        355                 360                 365

Leu Leu His Ser Asp Tyr Met Asn Met Thr Pro Arg Arg Pro Gly Pro
    370                 375                 380

Thr Arg Lys His Tyr Gln Pro Tyr Ala Pro Pro Arg Asp Phe Ala Ala
385                 390                 395                 400

Tyr Arg Ser Arg Val Lys Phe Ser Arg Ser Ala Asp Ala Pro Ala Tyr
                405                 410                 415

Gln Gln Gly Gln Asn Gln Leu Tyr Asn Glu Leu Asn Leu Gly Arg Arg
            420                 425                 430

Glu Glu Tyr Asp Val Leu Asp Lys Arg Arg Gly Arg Asp Pro Glu Met
        435                 440                 445

Gly Gly Lys Pro Gln Arg Arg Lys Asn Pro Gln Glu Gly Leu Tyr Asn
    450                 455                 460

Glu Leu Gln Lys Asp Lys Met Ala Glu Ala Tyr Ser Glu Ile Gly Met
465                 470                 475                 480

Lys Gly Glu Arg Arg Arg Gly Lys Gly His Asp Gly Leu Tyr Gln Gly
                485                 490                 495

Leu Ser Thr Ala Thr Lys Asp Thr Tyr Asp Ala Leu His Met Gln Ala
            500                 505                 510

Leu Pro Pro Arg
        515
```

<210> SEQ ID NO 254
<211> LENGTH: 62

<212> TYPE: PRT
<213> ORGANISM: Homo sapiens

<400> SEQUENCE: 254

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Ser
        35                  40                  45

Arg Pro Ala Ala Gly Gly Ala Val His Thr Arg Gly Leu Asp
    50                  55                  60

<210> SEQ ID NO 255
<211> LENGTH: 186
<212> TYPE: DNA
<213> ORGANISM: Homo sapiens

<400> SEQUENCE: 255
gctttaagca actccatcat gtacttctcc cacttcgtgc ccgttttttt acccgctaag     60
cccaccacaa cccccgctcc cagacccccct acccccgctc ctaccatcgc ctcccagcct    120
ttatctttaa gacccgaagc ctctcgtccc gctgccggcg gcgccgtgca cacaaggggt    180
ttagac                                                                186

<210> SEQ ID NO 256
<211> LENGTH: 70
<212> TYPE: PRT
<213> ORGANISM: Homo sapiens

<400> SEQUENCE: 256

Lys Pro Phe Trp Val Leu Val Val Val Gly Gly Val Leu Ala Cys Tyr
1               5                   10                  15

Ser Leu Leu Val Thr Val Ala Phe Ile Ile Phe Trp Val Arg Ser Lys
            20                  25                  30

Arg Ser Arg Leu Leu His Ser Asp Tyr Met Asn Met Thr Pro Arg Arg
        35                  40                  45

Pro Gly Pro Thr Arg Lys His Tyr Gln Pro Tyr Ala Pro Pro Arg Asp
    50                  55                  60

Phe Ala Ala Tyr Arg Ser
65                  70

<210> SEQ ID NO 257
<211> LENGTH: 210
<212> TYPE: DNA
<213> ORGANISM: Homo sapiens

<400> SEQUENCE: 257
aagccttttt gggttttagt ggtggtgggc ggcgtgctgg cttgttactc tttactggtg     60
accgtggcct tcatcatctt ctgggttcgt tccaagaggt ctcgtctgct gcactccgac    120
tatatgaaca tgacccctag gaggcccggc cctaccagaa aacactatca gccctatgcc    180
cctcctcgtg actttgccgc ttatcgttct                                      210

<210> SEQ ID NO 258
<211> LENGTH: 113
<212> TYPE: PRT
<213> ORGANISM: Homo sapiens

<400> SEQUENCE: 258

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg


<210> SEQ ID NO 259
<211> LENGTH: 339
<212> TYPE: DNA
<213> ORGANISM: Homo sapiens

<400> SEQUENCE: 259

cgtgtgaagt tctccagatc cgccgatgcc cccgcttacc agcaaggtca aaaccagctc      60

tataacgagc tgaatttagg tcgtagagag gagtacgacg tgctggataa aagaaggggc     120

agagaccccg aaatgggagg caaaccccag agaaggaaga acccccaaga aggactgtac     180

aacgaactgc agaaggataa gatggccgag gcctactccg agattggcat gaaaggcgag     240

aggaggaggg gcaagggcca tgatggttta taccaaggtt tatccacagc tacaaaggac     300

acctacgacg ctttacacat gcaagcttta cctcctaga                            339


<210> SEQ ID NO 260
<211> LENGTH: 497
<212> TYPE: PRT
<213> ORGANISM: Artificial Sequence
<220> FEATURE:
<223> OTHER INFORMATION: Synthetic polypeptide

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Ser Asn
            20                  25                  30

Val Ala Trp Tyr Gln Gln Lys Pro Gly Lys Ala Pro Lys Leu Leu Ile
        35                  40                  45

Phe Gly Ser Gly Gly Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Val Glu Thr Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
```

```
    130                 135                 140

Ala Ala Ser Gly Phe Thr Ile Asn Asp Ser Tyr Ile His Trp Val Arg
145                 150                 155                 160

Gln Ala Pro Gly Lys Gly Leu Glu Trp Val Ala Trp Ile Trp Pro Tyr
                165                 170                 175

Gly Gly Phe Thr Tyr Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ala Arg Phe Leu Gly Ser
    210                 215                 220

Ser Ser Ile Met Asp Tyr Trp Gly Gln Gly Thr Leu Val Thr Val Ser
225                 230                 235                 240

Ser Ala Glu Gln Lys Leu Ile Ser Glu Glu Asp Leu Ala Leu Ser Asn
                245                 250                 255

Ser Ile Met Tyr Phe Ser His Phe Val Pro Val Phe Leu Pro Ala Lys
            260                 265                 270

Pro Thr Thr Thr Pro Ala Pro Arg Pro Pro Thr Pro Ala Pro Thr Ile
        275                 280                 285

Ala Ser Gln Pro Leu Ser Leu Arg Pro Glu Ala Ser Arg Pro Ala Ala
    290                 295                 300

Gly Gly Ala Val His Thr Arg Gly Leu Asp Lys Pro Phe Trp Val Leu
305                 310                 315                 320

Val Val Val Gly Gly Val Leu Ala Cys Tyr Ser Leu Leu Val Thr Val
                325                 330                 335

Ala Phe Ile Ile Phe Trp Val Arg Ser Lys Arg Ser Arg Leu Leu His
            340                 345                 350

Ser Asp Tyr Met Asn Met Thr Pro Arg Arg Pro Gly Pro Thr Arg Lys
        355                 360                 365

His Tyr Gln Pro Tyr Ala Pro Pro Arg Asp Phe Ala Ala Tyr Arg Ser
    370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Gln Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

<210> SEQ ID NO 261
<211> LENGTH: 1491
<212> TYPE: DNA
<213> ORGANISM: Artificial Sequence
<220> FEATURE:
<223> OTHER INFORMATION: Synthetic polynucleotide

<400> SEQUENCE: 261

-continued

```
gacatccaga tgacccagtc tccatcctcc ctgtctgcat ctgtaggaga cagagtcacc     60
atcacttgcc gggcgagtca ggacgtgaac tccaacgtgg cctggtatca gcagaaacca    120
gggaaagccc ctaagctcct gatcttcggc tccggcggcc tgtacagtgg ggtcccatca    180
aggttcagcg gcagtggatc tgggacagat ttcactctca ctatcagcag cctgcagcct    240
gaagattttg caacttacta ttgtcagcag tactcctcct accccctgac gttcggccaa    300
gggaccaagg tggaaaccaa aggtggaggt ggcagcggag gaggtgggtc cggcggtgga    360
ggaagcgagg tgcagctggt ggagtctggg ggaggcttgg tccagcctgg ggggtccctg    420
agactctcct gtgcagcctc tggattcacc atcaacgact cctacatcca ctgggtccgc    480
caggctccag ggaaggggct ggagtgggtg gcctggatct ggccctacgg cggcttcacc    540
tactatgcag actccgtgaa gggccgattc accatctccg ccgacacctc caagaacacg    600
gcctatctgc aaatgaacag cctgagagct gaggacacgg ctgtgtatta ctgtgccagg    660
ttcctgggct cctcctccat catggactac tggggccaag gaaccctggt caccgtctcc    720
tcagccgagc agaagctgat tagcgaggag gatctggctt taagcaactc catcatgtac    780
ttctcccact tcgtgcccgt ttttttaccc gctaagccca ccacaacccc cgctcccaga    840
ccccctaccc ccgctcctac catcgcctcc cagcctttat ctttaagacc cgaagcctct    900
cgtcccgctg ccggcggcgc cgtgcacaca aggggtttag acaagccttt ttgggtttta    960
gtggtggtgg gcggcgtgct ggcttgttac tctttactgg tgaccgtggc cttcatcatc   1020
ttctgggttc gttccaagag gtctcgtctg ctgcactccg actatatgaa catgacccct   1080
aggaggcccg gccctaccag aaaacactat cagccctatg cccctcctcg tgactttgcc   1140
gcttatcgtt ctcgtgtgaa gttctccaga tccgccgatg cccccgctta ccagcaaggt   1200
caaaaccagc tctataacga gctgaattta ggtcgtagag aggagtacga cgtgctggat   1260
aaaagaaggg gcagagaccc cgaaatggga ggcaaacccc agagaaggaa gaacccccaa   1320
gaaggactgt acaacgaact gcagaaggat aagatggccg aggcctactc cgagattggc   1380
atgaaaggcg agaggaggag gggcaagggc catgatggtt tataccaagg tttatccaca   1440
gctacaaagg acacctacga cgctttacac atgcaagctt tacctcctag a            1491
```